US011591372B2

(12) United States Patent
Collins et al.

(10) Patent No.: US 11,591,372 B2
(45) Date of Patent: Feb. 28, 2023

(54) RECOMBINANT HUMAN/BOVINE PARAINFLUENZA VIRUS 1 (HPIV1) EXPRESSING A CHIMERIC RSV/HPIV1 F PROTEIN AND USES THEREOF

(71) Applicant: The United States of America, as represented by the Secretary, Department of Health and Human Services, Bethesda, MD (US)

(72) Inventors: Peter Collins, Silver Spring, MD (US); Bo Liang, Boyds, MD (US); Shirin Munir, Potomac, MD (US); Anne Schaap Nutt, Austin, TX (US); Ursula Buchholz, Silver Spring, MD (US); Natalie Mackow, East Setauket, NY (US); Peter Kwong, Washington, DC (US); Barney Graham, Rockville, MD (US); Jason McLellan, Austin, TX (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 190 days.

(21) Appl. No.: 16/877,319

(22) Filed: May 18, 2020

(65) Prior Publication Data

US 2020/0277338 A1 Sep. 3, 2020

Related U.S. Application Data

(63) Continuation of application No. 15/545,218, filed as application No. PCT/US2016/014154 on Jan. 20, 2016, now Pat. No. 10,654,898.

(60) Provisional application No. 62/105,667, filed on Jan. 20, 2015.

(51) Int. Cl.

| | |
|---|---|
| *C07K 14/005* | (2006.01) |
| *A61K 39/12* | (2006.01) |
| *A61P 31/14* | (2006.01) |
| *A61K 39/155* | (2006.01) |
| *A61K 39/00* | (2006.01) |

(52) U.S. Cl.

CPC ............ *C07K 14/005* (2013.01); *A61K 39/12* (2013.01); *A61K 39/155* (2013.01); *A61P 31/14* (2018.01); *A61K 2039/5254* (2013.01); *A61K 2039/5256* (2013.01); *A61K 2039/575* (2013.01); *A61K 2039/70* (2013.01); *C07K 2319/03* (2013.01); *C07K 2319/033* (2013.01); *C12N 2760/00022* (2013.01); *C12N 2760/18534* (2013.01); *C12N 2760/18571* (2013.01); *C12N 2760/18622* (2013.01); *C12N 2760/18634* (2013.01); *C12N 2760/18641* (2013.01); *C12N 2760/18643* (2013.01); *C12N 2760/18671* (2013.01); *C12N 2760/18722* (2013.01); *C12N 2760/18734* (2013.01); *C12N 2760/18741* (2013.01); *C12N 2760/18743* (2013.01); *C12N 2760/18771* (2013.01)

(58) Field of Classification Search
None
See application file for complete search history.

(56) References Cited

U.S. PATENT DOCUMENTS

| | | | | |
|---|---|---|---|---|
| 5,993,824 | A | 11/1999 | Murphy et al. | |
| 6,410,023 | B1 | 6/2002 | Durbin et al. | |
| 7,192,593 | B2 | 3/2007 | Murphy et al. | |
| 7,201,907 | B1 | 4/2007 | Schmidt et al. | |
| 7,208,161 | B1 | 4/2007 | Murphy et al. | |
| 7,250,171 | B1 | 7/2007 | Tao et al. | |
| 7,314,631 | B1 | 1/2008 | Murphy et al. | |
| 7,425,618 | B2 * | 9/2008 | Oliver ................ | C07K 16/1027 530/389.1 |
| 7,465,574 | B2 | 12/2008 | Jin et al. | |
| 7,622,123 | B2 | 11/2009 | Skiadopoulos et al. | |
| 7,632,508 | B2 | 12/2009 | Schmidt et al. | |
| 7,704,509 | B2 | 4/2010 | Murphy et al. | |
| 7,820,182 | B2 | 10/2010 | Buchholz et al. | |
| 7,842,798 | B2 | 11/2010 | Buchholz et al. | |
| 7,846,455 | B2 | 12/2010 | Collins et al. | |

(Continued)

FOREIGN PATENT DOCUMENTS

| | | |
|---|---|---|
| WO | WO 2004/027037 | 1/2004 |
| WO | WO 2010/039224 | 4/2010 |

(Continued)

OTHER PUBLICATIONS

Seq alignment of Geneseq db access No. ADJ97205 in WO2004010935 with instant SEQ ID 31, 2004.*
Seq alignment of Geneseq db access No. BBN47168 in USPgPub 2014271699 with instant SEQ ID 135, Nov. 2014.*
Lamb, R. A., and Parks, G. D. ((2013). "Paramyxoviridae," in Fields virology, 6th Edn, eds D. M. Knipe and P. M. Howley (Philadelphia, PA: Lippincott, Williams & Wilkins), 957-995).*

(Continued)

*Primary Examiner* — Shanon A. Foley
(74) *Attorney, Agent, or Firm* — Klarquist Sparkman, LLP

(57) ABSTRACT

Recombinant paramyxoviruses including a viral genome encoding a heterologous gene are provided. In several embodiments, the recombinant paramyxovirus is a recombinant parainfluenza virus, such as a recombinant PIV3 including a viral genome encoding a heterologous respiratory syncytial virus F ectodomain linked to the transmembrane domain and the cytoplasmic tail of the F protein from the PIV3. Nucleic acid molecules including the genome of a recombinant paramyxoviruses are also provided. The recombinant viruses may advantageously be used in vaccine formulations, such as for vaccines against parainfluenza virus and respiratory syncytial virus.

15 Claims, 62 Drawing Sheets

Specification includes a Sequence Listing.

(56) References Cited

U.S. PATENT DOCUMENTS

| | | | |
|---|---|---|---|
| 7,951,383 | B2 | 5/2011 | Murphy et al. |
| 8,084,037 | B2 | 12/2011 | Haller et al. |
| 8,367,074 | B1 | 2/2013 | Skiadopoulos et al. |
| 8,372,963 | B2 | 2/2013 | Grunwald et al. |
| 2006/0099226 | A1 | 5/2006 | Schmidt et al. |
| 2009/0017517 | A1 | 1/2009 | Schickli et al. |
| 2009/0263883 | A1 | 10/2009 | Haller et al. |
| 2011/0081708 | A1 | 4/2011 | Liu et al. |
| 2012/0045471 | A1 | 2/2012 | Haller et al. |
| 2012/0064112 | A1 | 3/2012 | Samal et al. |
| 2013/0052718 | A1 | 2/2013 | Skiadopoulos et al. |
| 2014/0186397 | A1 | 7/2014 | Hurwitz et al. |
| 2014/0248314 | A1 | 9/2014 | Swanson et al. |
| 2014/0271699 | A1 | 9/2014 | Kwong et al. |
| 2016/0046675 | A1 | 2/2016 | Kwong et al. |
| 2018/0312544 | A1 | 11/2018 | Collins et al. |

FOREIGN PATENT DOCUMENTS

| | | | |
|---|---|---|---|
| WO | WO 2014/160463 | | 10/2014 |
| WO | WO 2014160463 | * | 10/2014 |

OTHER PUBLICATIONS

Seq alignment of Geneseq db access No. ADJ97204 in WO2004010935, 2007, with instant SEQ ID No. 24.*

Whitehead et al., "Recombinant Respiratory Syncytial Virus (RSV) Bearing a Set of Mutations from Cold-Passaged RSV is Attenuated in Chimpanzees," *J Virol.* 72.5: 4467-4471, 1998.

Yang et al., "Implication of Respiratory Syncytial Virus (RSV) F Transgene Sequence Heterogeneity Observed in Phase 1 Evaluation of MEDI-534, a Live Attenuated Parainfluenza Type 3 Vectored RSV Vaccine," *Vaccine* 31.26: 2822-2827, 2013.

Zimmer et al., "A Chimeric Respiratory Syncytial Virus Fusion Protein Functionally Replaces the F and HN Glycoproteins in Recombinant Sendai Virus," *J Virol.* 79.16: 10467-10477, 2005.

Fath et al., "Multiparameter RNA and Codon Optimization: A Standardized Tool to Assess and Enhance Autologous Mammalian Gene Expression," *PLoS One* 6.3: e17596, Mar. 2011 (14 pages).

Bailly et al., "Sequence Determination and Molecular Analysis of Two Strains of Bovine Parainfluenza Virus Type 3 that are Attenuated for Primates," *Virus Genes* 20.2: 173-182, 2000.

Bailly et al. Alignment of SEQ ID 43. Geneseq, db acc No. Q9J7E1_PI3B, Oct. 2000.

Bailly et al. Alignment of SEQ ID 48. UniProt, db acc No. Q9J7E0_PI3B, Oct. 2000.

Bailly et al. Alignment of SEQ ID 49. UniProt, db acc No. Q9J7D9_PI3B, Oct. 2000.

Bailly et al. Alignment of SEQ ID 53. UniProt, db acc No. Q9J7D8_PI3B, Oct. 2000.

Bartlett et al., "Attenuation and Efficacy of Human Parainfluenza Virus Type 1 (HPIV1) Vaccine Candidates Containing Stabilized Mutations in the P/C and L Genes," *Virol J.* 4: 67 (13 pages).

Basavarajappa et al., "A Recombinant Newcastle Disease Virus (NDV) Expressing Infectious Laryngotracheitis Virus (ILTV) Surface Glycoprotein D Protects Against Highly Virulent ILTV and NDV Challenges in Chickens," *Vaccine* 32.28: 3555-3563, Jun. 2014.

Bernstein et al., "Phase 1 Study of the Safety and Immunogenicity of a Live, Attenuated Respiratory Syncytial Virus and Parainfluenza Virus Type 3 Vaccine in Seronegative Children," *Pediatr Infect Dis J.* 31.2: 109-114, Feb. 2012.

Clements et al., "Evaluation of Bovine, Cold-Adapted Human, and Wild-Type Human Parainfluenza Type 3 Viruses in Adult Volunteers and in Chimpanzees," *J Clin Microbiol.* 29.6: 1175-1182, Jun. 1991.

Connors et al., "A Cold-Passaged, Attenuated Strain of Human Respiratory Syncytial Virus Contains Mutations in the F and L Genes," *Virology* 208.2: 478-484, Apr. 1995.

Collins et al. Alignment of SEQ ID 52. Geneseq, db acc No. ADV68236, Jun. 2007.

Cullen et al., "Cotton Rat Immune Responses to Virus-Like Particles Containing the Pre-Fusion Form of Respiratory Syncytial Virus Fusion Protein," *J Transl Med.* 13: 350, Nov. 2015 (13 pages).

Durbin et al., "Mutations in the C, D, and V Open Reading Frames of Human Parainfluenza Virus Type 3 Attenuate Replication in Rodents and Primates," *Virology* 261.2: 319-330, Sep. 1999.

Fu et al., "Intranasal Immunization with a Helper-Dependent Adenoviral Vector Expressing the Codon-Optimized Fusion Glycoprotein of Human Respiratory Syncytial Virus Elicits Protective Immunity in BALB/c Mice," *Virol J.* 10: 183, Jun. 2013 (8 pages).

Graham et al., "Challenges and Opportunities for Respiratory Syncytial Virus Vaccines," *Challenges and Opportunities for Respiratory Syncytial Virus Vaccines.* Springer Berlin Heidelberg, 2013: 391-404.

Graham et al., "Novel Antigens for RSV Vaccines," *Current Opinion in Immunology* 35: 30-38, Aug. 2015.

International Search Report and Written Opinion for International Application No. PCT/US2016/014154, mailed by the European Patent Office acting as International Searching Authority dated Apr. 26, 2016.

Jones et al., "Sendai Virus-Based RSV Vaccine Protects African Green Monkeys from RSV Infection," *Vaccine* 30.5: 959-968, Jan. 2012.

Joyce et al., "Iterative Structure-Based Improvement of a Fusion-Glycoprotein Vaccine Against RSV," *Nat Struct Mol Biol.* 23.9: 811-820, Sep. 2016.

Karron et al., "Evaluation of Two Chimeric Bovine-Human Parainfluenza Virus Type 3 Vaccines in Infants and Young Children," *Vaccine* 30.26: 3975-3981, Jun. 2012.

Kohlmann, et al. "Protective efficacy and immunogenicity of an adenoviral vector vaccine encoding the codon-optimized F protein of respiratory syncytial virus." *Journal of Virology* 83.23 (2009): 12601-12610.

Kwon et al. Alignment of SEQ ID 21. Geneseq, db acc No. BBN47168, Nov. 2014.

Lawlor et al., "A Single Amino Acid in the F2 Subunit of Respiratory Syncytial Virus Fusion Protein Alters Growth and Fusogenicity," *J Gen Virol. 94.Pt 12*: 2627-2635, Dec. 2013.

Liang et al., "Chimeric Bovine/Human Parainfluenza Virus Type 3 Expressing Respiratory Syncytial Virus (RSV) F Glycoprotein: Effect of Insert Position on Expression, Replication, Immunogenicity, Stability, and Protection Against RSV Infection," *J Virol.* 88.8: 4237-4250, Apr. 2014/.

Liang et al., "Enhanced Neutralizing Antibody Response Induced by Respiratory Syncytial Virus Prefusion F Protein Expressed by a Vaccine Candidate," *J Virol.* 89.18: 9499-9510, Sep. 2015.

Liang et al., "Packaging and Prefusion Stabilization Separately and Additively Increase the Quantity and Quality of Respiratory Syncytial Virus (RSV)—Neutralizing Antibodies Induced by an RSV Fusion Protein Expressed by a Parainfluenza Virus Vector," *J Virol.* 90.21: 10022-10038, Oct. 2016.

Maykowski et al., "Seasonality and Clinical Impact of Human Parainfluenza Viruses," *Influenza and Other Respir Viruses* 12.6: 706-716, Nov. 2018.

McAuliffe et al., "Codon Substitution Mutations at Two Positions in the L Polymerase Protein of Human Parainfluenza Virus Type 1 Yield Viruses with a Spectrum of Attenuation In Vivo and Increased Phenotypic Stability In Vitro," *J Virol* 78.4: 2029-2036, Feb. 2004.

McGinnes et al., "Assembly and Immunological Properties of Newcastle Disease Virus-Like Particles Containing the Respiratory Syncytial Virus F and G Proteins," *J Virol.* 85.1: 366-377, Jan. 2011.

McLellan et al., "Structure of RSV Fusion Glycoprotein Trimer Bound to a Prefusion-Specific Neutralizing Antibody," *Science*, 340.6136: 1113-1117, May 2013.

McLellan et al., "Structure-Based Design of a Fusion Glycoprotein Vaccine for Respiratory Syncytial Virus," *Science* 342.6158: 592-598, Nov. 2013, including supplementary information.

Nelson et al., "Genetic Stability of RSV-F Expression and the Restricted Growth Phenotype of a Live Attenuated PIV3 Vectored RSV Vaccine Candidate (MEDI-534) Following Restrictive Growth in Human Lung Cells," *Vaccine* 31.36: 3756-3762, Aug. 2013.

Newman et al., "Generation of Recombinant Human Parainfluenza Virus Type 1 Vaccine Candidates by Importation of Temperature-

(56) References Cited

OTHER PUBLICATIONS

Sensitive and Attenuating Mutations from Heterologous Paramyxoviruses," *J Virol.* 78.4: 2017-2028, Feb. 2004.
Newman et al., "Sequence Analysis of the Washington/1964 Strain of Human Parainfluenza Virus Type 1 (HPIV1) and Recovery and Characterization of Wild-Type Recombinant HPIV1 Produced by Reverse Genetics," *Virus Genes* 24.1: 77-92, 2002.
Park et al., "Engineered Viral Vaccine Constructs with Dual Specificity: Avian Influenza and Newcastle Disease," *Proc Natl Acad Sci U.S.A.* 103.21: 8203-8208, May 2006.
Quiñones-Kochs et al., "Mechanisms of Loss of Foreign Gene Expression in Recombinant Vesicular Stomatitis Viruses," *Virology* 287.2: 427-435, Sep. 2001.
Ray et al. Alignment of SEQ ID 101. Geneseq, db acc No. AAB08627, Dec. 2000.
Schmidt et al., "Bovine Parainfluenza Virus Type 3 (BPIV3) Fusion and Hemagglutinin-Neuraminidase Glycoproteins make an Important Contribution to the Restricted Replication of BPIV3 in Primates," *J Virol.* 74.19: 8922-8929, Oct. 2000.
Schmidt et al., "Long-Term and Memory Immune Responses in Mice Against Newcastle Disease Virus-Like Particles Containing Respiratory Syncytial Virus Glycoprotein Ectodomains," *J Virol.* 86.21: 11654-11662, Nov. 2012.
Schmidt et al., "Modification of the Respiratory Syncytial Virus F Protein in Virus-Like Particles Impacts Generation of B Cell Memory," *J Virol.* 88.17: 10165-10176, Sep. 2014.
Schmidt et al., "Mucosal Immunization of Rhesus Monkeys against Respiratory Syncytial Virus Subgroups A and B and Human Parainfluenza Virus Type 3 by using a Live cDNA-Derived Vaccine Based on a Host Range-Attenuated Bovine Parainfluenza Virus Type 3 Vector Backbone," *J Virol.* 76.3: 1089-1099, Feb. 2002.
Schmidt et al., "Progress in the Development of Human Parainfluenza Virus Vaccines," *Expert Rev Respir Med.* 5.4: 515-526, Aug. 2011.
Schmidt et al., "Recombinant Bovine/Human Parainfluenza Virus Type 3 (B/HPIV3) Expressing the Respiratory Syncytial Virus (RSV) G and F Proteins can be used to Achieve Simultaneous Mucosal Immunization against RSV and HPIV3," *J Virol.* 75.10: 4594-4603, May 2001.
Skiadopoulos et al., "Determinants of the Host Range Restriction of Replication of Bovine Parainfluenza Virus Type 3 in Rhesus Monkeys are Polygenic," *J Virol.* 77.2: 1141-1148, Jan. 2003.
Skiadopoulos et al., "Evaluation of the Replication and Immunogenicity of Recombinant Human Parainfluenza Virus Type 3 Vectors Expressing Up to Three Foreign Glycoproteins," *Virology* 297.1: 136-152, May 2002.
Skiadopoulos et al., "Identification of Mutations Contributing to the Temperature-Sensitive, Cold-Adapted, and Attenuation Phenotypes of the Live-Attenuated Cold-Passage 45 (cp45) Human Parainfluenza Virus 3 Candidate Vaccine," *J Virol.* 73.2: 1374-1381, Feb. 1999.
Tang et al., "Effects of Human Metapneumovirus and Respiratory Syncytial Virus Antigen Insertion in Two 3' Proximal Genome Positions of Bovine/Human Parainfluenza Virus Type 3 on Virus Replication and Immunogenicity," *J Virol.* 77.20: 10819-10828, Oct. 2003.
Tang et al., "Parainfluenza Virus Type 3 Expressing the Native or Soluble Fusion (F) Protein of Respiratory Syncytial Virus (RSV) Confers Protection from RSV Infection in African Green Monkeys," *J Virol.* 78.20: 11198-11207, Oct. 2004.
Tang et al. Alignment of SEQ ID 43. Geneseq, db acc No. AZY46953, Sep. 2012.
Ternette et al., "Immunogenicity and Efficacy of Codon Optimized DNA Vaccines Encoding the F-Protein of Respiratory Syncytial Virus," *Vaccine* 25.41: 7271-7279, Oct. 2007.
Whitehead et al., "Addition of a Missense Mutation Present in the L Gene of Respiratory Syncytial Virus (RSV) cpts530/1030 to RSV Vaccine Candidate cpts248/404 Increases Its Attenuation and Temperature Sensitivity," *J Virol.* 73.2: 871-877, Feb. 1999.

* cited by examiner

Non-HEK/GA-opt

HEK/GA-opt

™

Nasal turbinates

Lungs

Lungs

Nasal turbinates

LLC-MK2 cells

Vero cells
MOI=0.01
Virus Titer (log10TCID50/ml)
Days P.I.
Empty B/H3
HEK/GA-opt *
Ecto *
Post-fusion *
DS *
* HEK and GA codon-optimized Post-fusion form of RSV F
32°C
Post-fusion *
Ecto *
HEK/GA-opt *
RSV (A2)
Mock
RSV F1
RSV F0
RSV F1
HPIV3 HN
Medium supernatant
Cell lysate
Vero cells
MOI=10
48h p.i.

Pre-fusion form of RSV F
37°C
Empty B/H3
Non-HEK/non-opt
HEK/GA-opt *
DS *
DS-Cav1 *
RSV F0
RSV F1
GAPDH
HPIV3 HN
Cell lysate
* HEK and GA codon-optimized FIG. 15B *w/o complement*
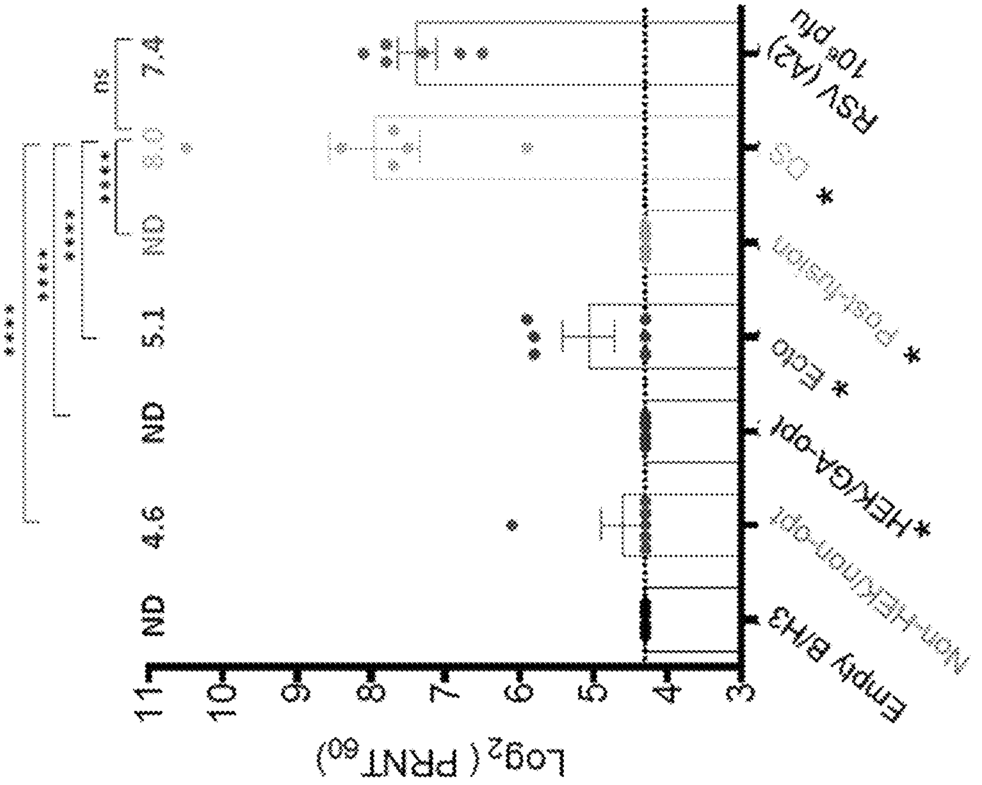
FIG. 15A *with complement*
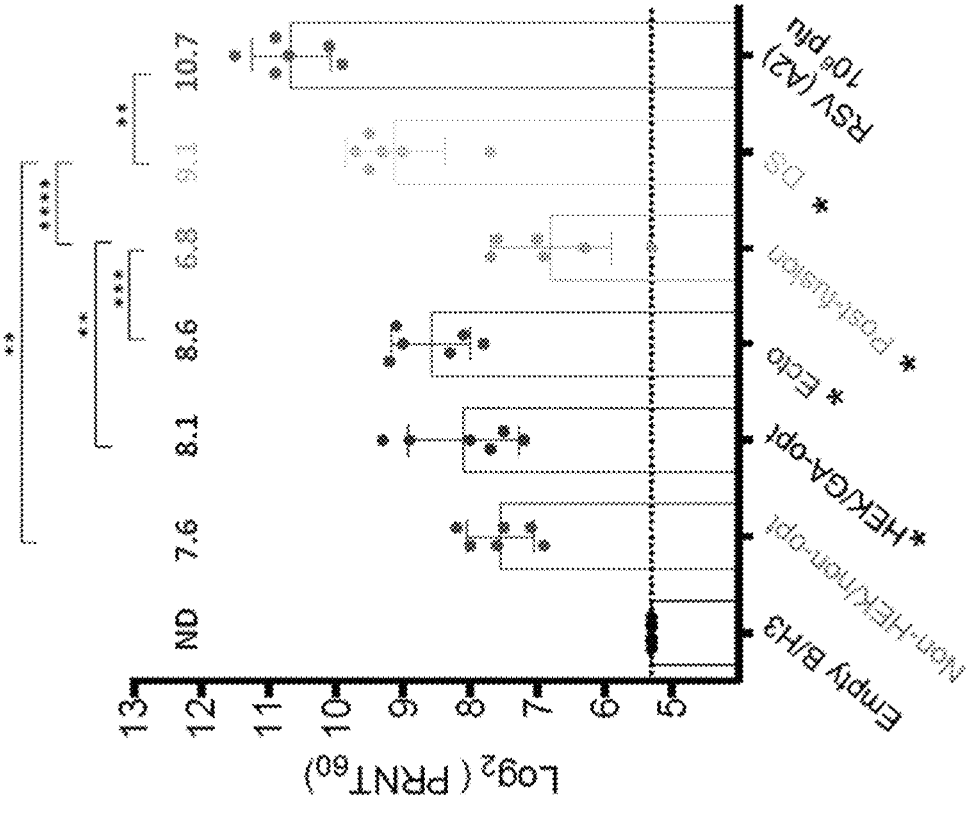

*Nasal turbinates*

*Lungs*

FIG. 17B

| | Ectodomain | TM | CT |
|---|---|---|---|
| RSV(A2)F | 510 DELLHNVNAGKSTTNIMITT 530 | IIIVIIVILLSLIAVGLLLYC 551 | KARSTPVTLSKDQLSGINNIAFSN 574 |
| BPIV3 F | 478 **NQKLDSVGSWYQSSAT** 494 | **ITIIIVMIIILVIINITIIVV** 515 | **IIKFHRIQGKDQNDKNSEPYILTNRQ** 540 |
| B3CT | 510 DELLHNVNAGKSTTNIMITT 530 | IIIVIIVILLSLIAVGLLLYC 551 | **IIKFHRIQGKDQNDKNSEPYILTNRQ** 576 |
| B3TMCT | 510 DELLHNVNAGKSTTNIMITT 530 | **ITIIIVMIIILVIINITIIVV** 551 | **IIKFHRIQGKDQNDKNSEPYILTNRQ** 576 |

FIG. 18A

~ 0.5ug of sucrose purified viruses were loaded each lane

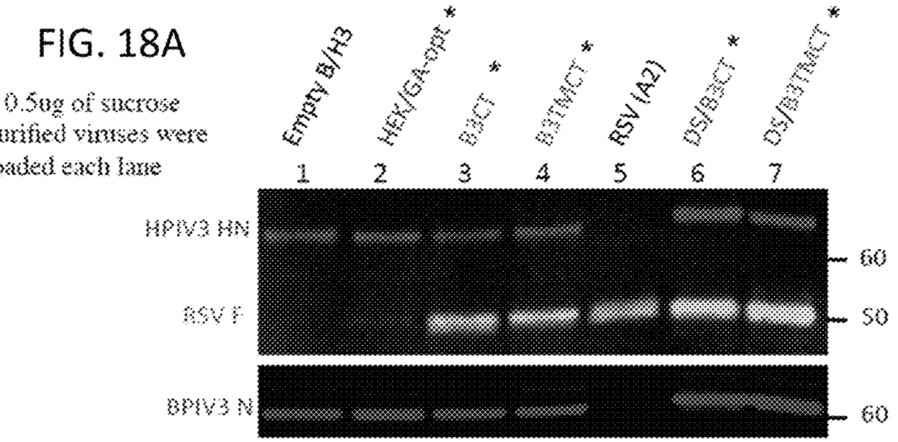

➢ B3CT, B3TMCT packaging efficiency similar to RSV

FIG. 18B

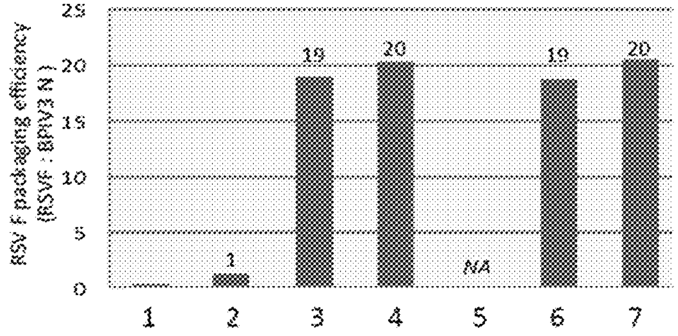

* HEK and GA codon-optimized

FIG. 19A
➢ Observed surface labeling
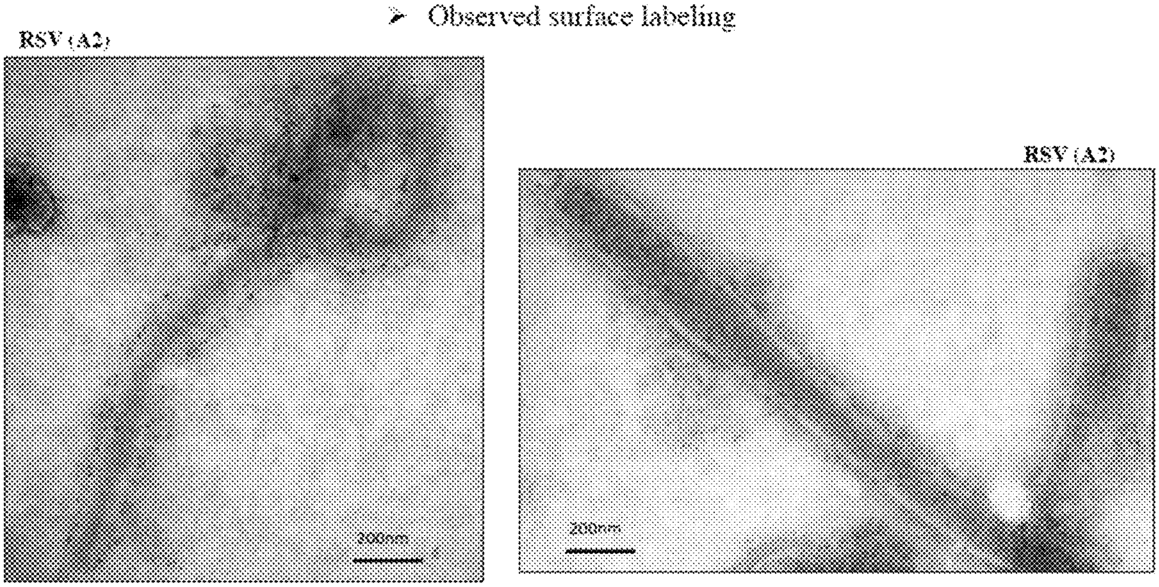
FIG. 19B
➢ No surface labeling
FIG. 19C
➢ Very little surface labeling
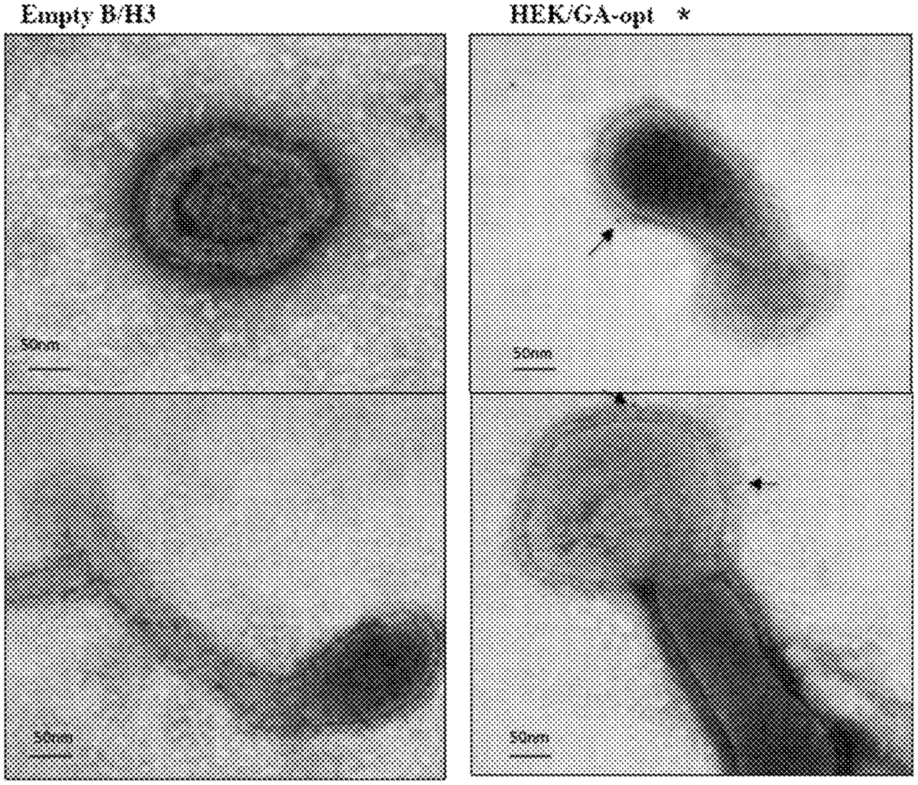
* HEK and GA codon-optimized B3CT * FIG. 19D
B3TMCT * FIG. 19E
DS/B3TMCT * FIG. 19F
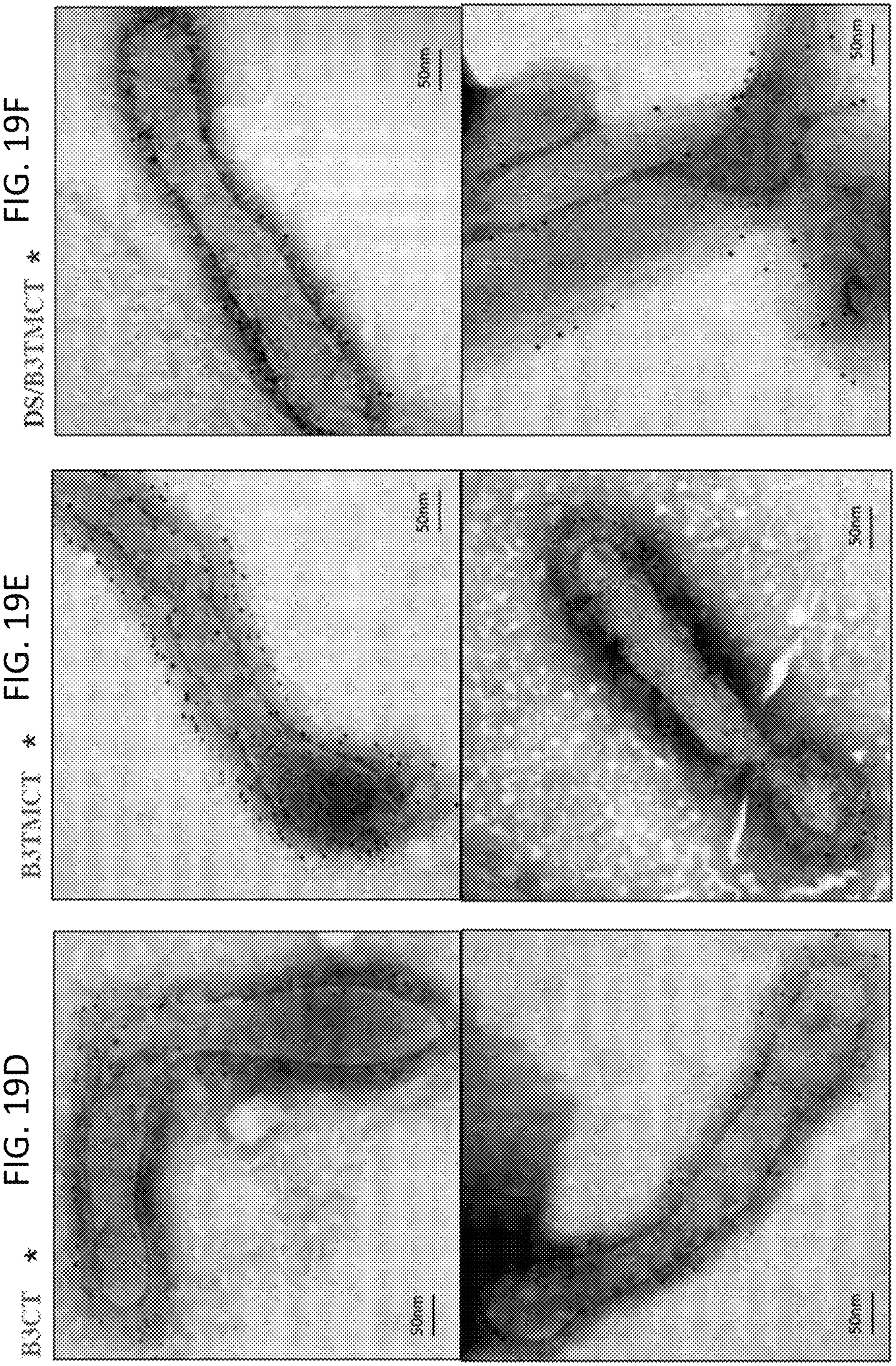
* HEK and GA codon-optimized

*with complement*

*w/o complement*

* HEK and GA codon-optimized

* HEK and GA codon-optimized

FIG. 26

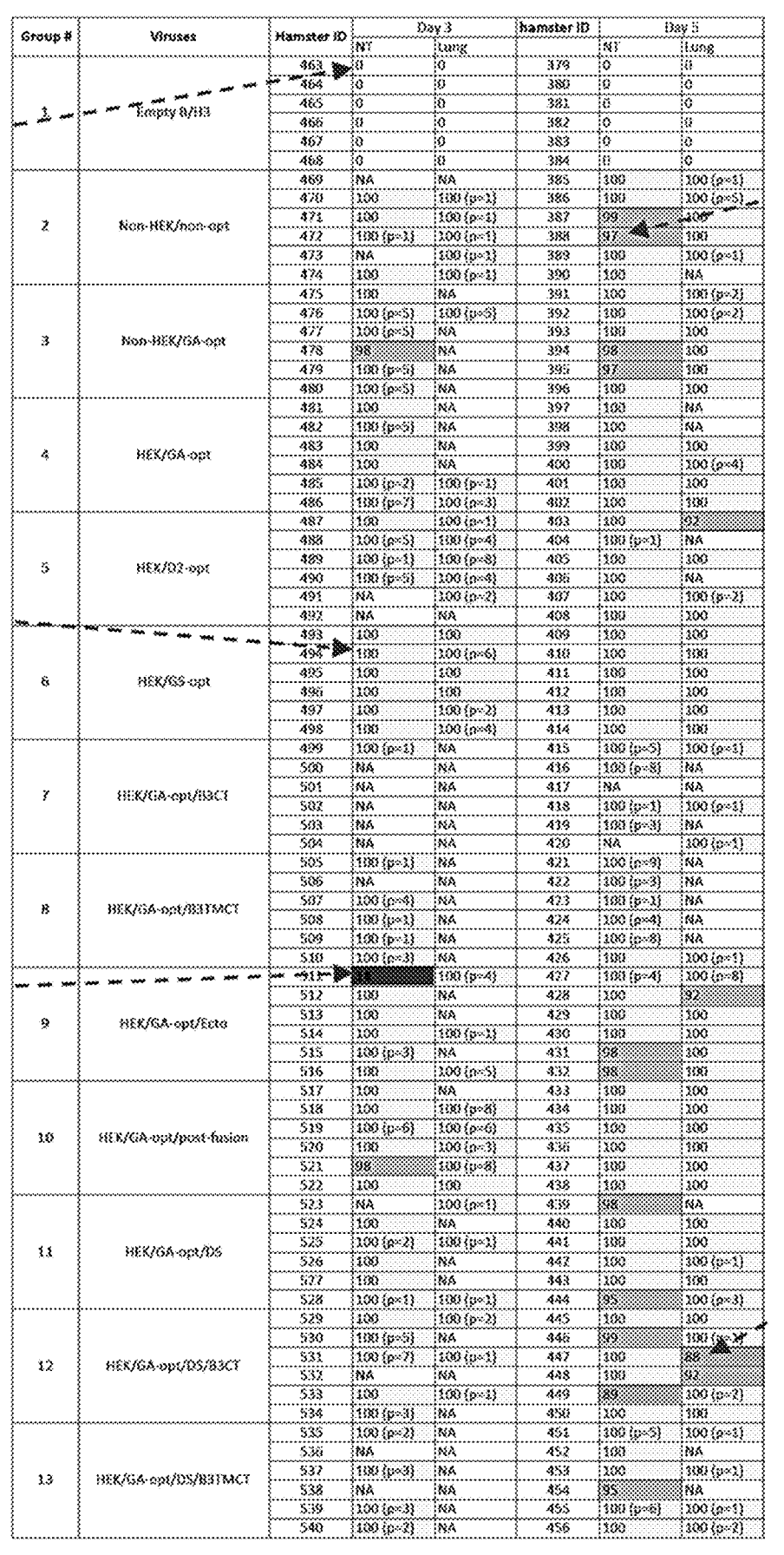

| Group # | Viruses | Hamster ID | Day 3 | | hamster ID | Day 5 | |
|---|---|---|---|---|---|---|---|
| | | | NT | Lung | | NT | Lung |
| 1 | Empty 8/H3 | 463 | 0 | 0 | 379 | 0 | 0 |
| | | 464 | 0 | 0 | 380 | 0 | 0 |
| | | 465 | 0 | 0 | 381 | 0 | 0 |
| | | 466 | 0 | 0 | 382 | 0 | 0 |
| | | 467 | 0 | 0 | 383 | 0 | 0 |
| | | 468 | 0 | 0 | 384 | 0 | 0 |
| 2 | Non-HEK/non-opt | 469 | NA | NA | 385 | 100 | 100 (p=1) |
| | | 470 | 100 | 100 (p=1) | 386 | 100 | 100 (p=5) |
| | | 471 | 100 | 100 (p=1) | 387 | 99 | 100 |
| | | 472 | 100 (p=1) | 100 (p=1) | 388 | 97 | 100 |
| | | 473 | NA | 100 (p=1) | 389 | 100 | 100 (p=1) |
| | | 474 | 100 | 100 (p=1) | 390 | 100 | NA |
| 3 | Non-HEK/GA-opt | 475 | 100 | NA | 391 | 100 | 100 (p=2) |
| | | 476 | 100 (p=5) | 100 (p=5) | 392 | 100 | 100 (p=2) |
| | | 477 | 100 (p=5) | NA | 393 | 100 | 100 |
| | | 478 | 98 | NA | 394 | 98 | 100 |
| | | 479 | 100 (p=5) | NA | 395 | 97 | 100 |
| | | 480 | 100 (p=5) | NA | 396 | 100 | 100 |
| 4 | HEK/GA-opt | 481 | 100 | NA | 397 | 100 | NA |
| | | 482 | 100 (p=5) | NA | 398 | 100 | NA |
| | | 483 | 100 | NA | 399 | 100 | 100 |
| | | 484 | 100 | NA | 400 | 100 | 100 (p=4) |
| | | 485 | 100 (p=2) | 100 (p=1) | 401 | 100 | 100 |
| | | 486 | 100 (p=7) | 100 (p=3) | 402 | 100 | 100 |
| 5 | HEK/D2-opt | 487 | 100 | 100 (p=1) | 403 | 100 | 92 |
| | | 488 | 100 (p=5) | 100 (p=4) | 404 | 100 (p=1) | NA |
| | | 489 | 100 (p=1) | 100 (p=8) | 405 | 100 | 100 |
| | | 490 | 100 (p=5) | 100 (p=4) | 406 | 100 | NA |
| | | 491 | NA | 100 (p=2) | 407 | 100 | 100 (p=2) |
| | | 492 | NA | NA | 408 | 100 | 100 |
| 6 | HEK/GS-opt | 493 | 100 | 100 | 409 | 100 | 100 |
| | | 494 | 100 | 100 (p=6) | 410 | 100 | 100 |
| | | 495 | 100 | 100 | 411 | 100 | 100 |
| | | 496 | 100 | 100 | 412 | 100 | 100 |
| | | 497 | 100 | 100 (p=2) | 413 | 100 | 100 |
| | | 498 | 100 | 100 (p=4) | 414 | 100 | 100 |
| 7 | HEK/GA-opt/B3CT | 499 | 100 (p=1) | NA | 415 | 100 (p=5) | 100 (p=1) |
| | | 500 | NA | NA | 416 | 100 (p=8) | NA |
| | | 501 | NA | NA | 417 | NA | NA |
| | | 502 | NA | NA | 418 | 100 (p=1) | 100 (p=1) |
| | | 503 | NA | NA | 419 | 100 (p=3) | NA |
| | | 504 | NA | NA | 420 | NA | 100 (p=1) |
| 8 | HEK/GA-opt/B3TMCT | 505 | 100 (p=1) | NA | 421 | 100 (p=9) | NA |
| | | 506 | NA | NA | 422 | 100 (p=3) | NA |
| | | 507 | 100 (p=4) | NA | 423 | 100 (p=1) | NA |
| | | 508 | 100 (p=1) | NA | 424 | 100 (p=4) | NA |
| | | 509 | 100 (p=1) | NA | 425 | 100 (p=8) | NA |
| | | 510 | 100 (p=3) | NA | 426 | 100 | 100 (p=1) |
| 9 | HEK/GA-opt/Ecto | 511 | [illegible] | 100 (p=4) | 427 | 100 (p=4) | 100 (p=8) |
| | | 512 | 100 | NA | 428 | 100 | 92 |
| | | 513 | 100 | NA | 429 | 100 | 100 |
| | | 514 | 100 | 100 (p=1) | 430 | 100 | 100 |
| | | 515 | 100 (p=3) | NA | 431 | 98 | 100 |
| | | 516 | 100 | 100 (p=5) | 432 | 98 | 100 |
| 10 | HEK/GA-opt/post-fusion | 517 | 100 | NA | 433 | 100 | 100 |
| | | 518 | 100 | 100 (p=8) | 434 | 100 | 100 |
| | | 519 | 100 (p=6) | 100 (p=6) | 435 | 100 | 100 |
| | | 520 | 100 | 100 (p=3) | 436 | 100 | 100 |
| | | 521 | 98 | 100 (p=8) | 437 | 100 | 100 |
| | | 522 | 100 | 100 | 438 | 100 | 100 |
| 11 | HEK/GA-opt/DS | 523 | NA | 100 (p=1) | 439 | 98 | NA |
| | | 524 | 100 | NA | 440 | 100 | 100 |
| | | 525 | 100 (p=2) | 100 (p=1) | 441 | 100 | 100 |
| | | 526 | 100 | NA | 442 | 100 | 100 (p=1) |
| | | 527 | 100 | NA | 443 | 100 | 100 |
| | | 528 | 100 (p=1) | 100 (p=1) | 444 | 95 | 100 (p=3) |
| 12 | HEK/GA-opt/DS/B3CT | 529 | 100 | 100 (p=2) | 445 | 100 | 100 |
| | | 530 | 100 (p=5) | NA | 446 | 99 | 100 (p=[illegible]) |
| | | 531 | 100 (p=7) | 100 (p=1) | 447 | 100 | 89 |
| | | 532 | NA | NA | 448 | 100 | 92 |
| | | 533 | 100 | 100 (p=1) | 449 | 89 | 100 (p=2) |
| | | 534 | 100 (p=3) | NA | 450 | 100 | 100 |
| 13 | HEK/GA-opt/DS/B3TMCT | 535 | 100 (p=2) | NA | 451 | 100 (p=5) | 100 (p=1) |
| | | 536 | NA | NA | 452 | 100 | NA |
| | | 537 | 100 (p=3) | NA | 453 | 100 | 100 (p=1) |
| | | 538 | NA | NA | 454 | 95 | NA |
| | | 539 | 100 (p=3) | NA | 455 | 100 (p=6) | 100 (p=1) |
| | | 540 | 100 (p=2) | NA | 456 | 100 | 100 (p=2) |

| Group # | Viruses | Virus titer at permissive temp of 32°C (log10 PFU/ml) | Virus titer ($log_{10}$ PFU/ml) at increasing temperature | | | | | |
|---|---|---|---|---|---|---|---|---|
| | | | 35°C | 36°C | 37°C | 38°C | 39°C | 40°C |
| 1 | Empty B/H3 | 6.3 | 6.4 | 6.3 | 6 | 5.7 | 5.4 | 2.2 |
| 2 | Non-HEK/non-opt | 7.7 | 7 | 7.2 | 6.4 | 5.3 | 3.6 | <1.7 |
| 3 | Non-HEK/GA-opt | 7.2 | 6.5 | 6 | 5.3 | 4.2 | <1.7 | <1.7 |
| 4 | HEK/GA-opt | 6.9 | 6.5 | 6 | 5.4 | 3.7 | 3.3 | <1.7 |
| 5 | HEK/D2-opt | 7.4 | 7 | 6.6 | 6.5 | 4.9 | <1.7 | <1.7 |
| 6 | HEK/GS-opt | 7.8 | 7.6 | 7.2 | 6.8 | 5.7 | 3.3 | <1.7 |
| 7 | HEK/GA-opt/B3CT | 7.3 | 6.7 | 5.6 | 4.9 | <1.7 | <1.7 | <1.7 |
| 8 | HEK/GA-opt/B3TMCT | 7.7 | 6.8 | 6.1 | 4.9 | <1.7 | <1.7 | <1.7 |
| 9 | HEK/GA-opt/Ecto | 7.3 | 6.8 | 6.6 | 5.2 | 4.7 | <1.7 | <1.7 |
| 10 | HEK/GA-opt/post-fusion | 7.6 | 6.9 | 6.8 | 5.9 | 5.4 | <1.7 | <1.7 |
| 11 | HEK/GA-opt/DS | 7.2 | 6.8 | 6.3 | 5.9 | 3.7 | <1.7 | <1.7 |
| 12 | HEK/GA-opt/DS/B3CT | 6.8 | 6.6 | 5.9 | 5.2 | <1.7 | <1.7 | <1.7 |
| 13 | HEK/GA-opt/DS/B3TMCT | 6.5 | 5.9 | 5.3 | 5 | 3.6 | <1.7 | <1.7 |

FIG. 33

| Viruses | Monkey ID | % of viruses in NP swab expressing RSVF | | |
|---|---|---|---|---|
| | | Day 4 | Day 5 | Day 6 |
| Non-HEK/non-opt | RH37033 | 100 | ≥ 97 | ≥ 98 |
| | RH37051 | 91 | 93 | 93 |
| | RH37057 | 97 | ≥ 99 | ≥ 98 |
| | RH37063 | ≥ 99 | 92 | ≥ 98 |
| | RH37380 | ≥ 98 | ≥ 98 | ≥ 99 |
| HEK/GA-opt/DS | RH37034 | ≥ 98 | 94 | 100 |
| | RH37073 | ≥ 99 | ≥ 99 | 100 |
| | RH37078 | 93 | ≥ 98 | 96 |
| | RH37103 | ≥ 98 | ≥ 98 | ≥ 98 |
| | RH37760 | ≥ 99 | 95 | 96 |
| HEK/GA-opt/DS/B3TMCT | RH38487 | NA | NA | NA |
| | RH37324 | ≥ 98 | ≥ 99 | 100 |
| | RH37140 | 100 | 93 | 100 |
| | RH37360 | 100 | ≥ 98 | ≥ 99 |

Indicates 100% viruses in this sample expressed RSV F

Indicates 90-99% viruses in this sample expressed RSV F

Samples with ≥98 or ≥99 % of viruses expressing RSV F indicates that only 1-2 out of more than 50 overlapping plaques did not have RSV F expression (an example shown in Figure 33 D-F).

"NA" means no plaque was developed with that sample.

Examples of plaque images were shown with arrows pointing to corresponding tissue specimens. All plaques were derived directly from tissue without further passaging.

FIG. 35

| | Viruses | 1st hamster study | 1st NHP study (14RSV02) | 2nd hamster study | 2nd NHP study (15PIV06) |
|---|---|---|---|---|---|
| 1 | Non-HEK/non-opt | X | X | X | |
| 2 | Non-HEK/GA-opt | | | | |
| 3 | HEK/GA-opt | X | | | |
| 4 | HEK/DNA2.0-opt | | | | |
| 5 | HEK/GS-opt | X | | X | |
| 6 | HEK/GA-opt/B3CT | X | | | |
| 7 | HEK/GA-opt/B3TMCT | X | | X | |
| 8 | HEK/GA-opt/Ecto | X | | | |
| 9 | HEK/GA-opt/Postfusion | X | | | |
| 10 | HEK/GA-opt/DS | X | X | X | X |
| 11 | HEK/GA-opt/DS/B3CT | X | | | |
| 12 | HEK/GA-opt/DS/B3TMCT | X | X | X | |
| 13 | HEK/GA-opt/DS-Cav1 | | | X | |
| 14 | HEK/GA-opt/DS-Cav1/B3CT | | | | |
| 15 | HEK/GA-opt/DS-Cav1/B3TMCT | | | X | X |
| 16 | HEK/GS-opt/DS-Cav1 | | | X | |
| 17 | HEK/GS-opt/DS-Cav1/B3CT | | | | |
| 18 | HEK/GS-opt/DS-Cav1/B3TMCT | | | X | X |
| 19 | HEK/GS-opt/DS-Cav1/(1-513) Foldon | | | X | |

rHPIV1 $C^{\Delta 170}$-F1 rHPIV1 $C^{\Delta 170}$-F2 rHPIV1 $C^{\Delta 170}$-F3 rHPIV1 $C^{\Delta 170}$ rHPIV1 $L^{Y942A}$-F1 rHPIV1 $L^{Y942A}$-F2 rHPIV1 $L^{Y942A}$-F3 rHPIV1 $L^{Y942A}$ wt HPIV1

FIG. 42

Attenuating mutations introduced in the HPIV1 backbone in the P/C or the L ORF

| Gene | Mutation | ORF | Nucleotide changes → mutant | Type of mutation | Codon position | Amino acid change | # of nucleotide changes needed for reversion to wt |
|---|---|---|---|---|---|---|---|
| P/C | Δ170 | C | AG**G GAT TTC** → AGC | deletion | 168-170 | RDF → S (D Deletion; 3 nt deletions in the flanking R-F codons resulting in an S substitution) | 6 (insertions) |
| L | Y942A | L | **TAT** → **GCG** | Substitution | 942 | Y → A | 3 |

FIG. 43

Temperature sensitivity of recombinant viruses on LLC-MK2 cell monolayers

| | Virus Titer ($log_{10}$ $TCID_{50}$/ml) at | | | | | | |
|---|---|---|---|---|---|---|---|
| Virus | 32°C | 35°C | 36°C | 37°C | 38°C | 39°C | 40°C |
| wt rHPIV1 | 7.7 | 8.5 | 7.5 | 7.5 | 8.0 | 7.2 | 6.2 |
| rHPIV1 $C^{\Delta170}$ | 7.0 | 7.0 | 6.5 | 6.2 | 6.7 | 6.5 | **3.2** |
| rHPIV1 $L^{Y942A}$ | 8.0 | 7.2 | **5.2** | 4.5 | 2.2 | ≤1.2 | ≤1.2 |
| rHPIV1 $C^{\Delta170}$-F1 | 7.0 | 6.7 | 7.0 | 6.2 | 6.2 | **3.2** | 1.5 |
| rHPIV1 $C^{\Delta170}$-F2 | 8.2 | 6.5 | 7.7 | 7.0 | 7.7 | 6.5 | **2.2** |
| rHPIV1 $C^{\Delta170}$-F3 | 8.0 | 8.0 | 7.5 | 8.0 | 7.7 | 6.7 | **2.0** |
| rHPIV1 $L^{Y942A}$-F1 | 7.0 | **4.7** | 4.7 | 1.5 | 1.5 | ≤1.2 | ≤1.2 |
| rHPIV1 $L^{Y942A}$-F2 | 5.5 | **3.2** | ≤1.2 | ≤1.2 | ≤1.2 | ≤1.2 | ≤1.2 |
| rHPIV1 $L^{Y942A}$-F3 | 8.2 | 7.2 | **5.5** | 4.2 | ≤1.2 | ≤1.2 | ≤1.2 |

FIG. 44

Percentage of virus population expressing RSV F after *in vivo* replication

| | % PFU expressing RSV F | |
|---|---|---|
| | Day 3 | Day 5 |
| Virus | Nasal Turbinate | Nasal Turbinate |
| rHPIV1 $C^{\Delta 170}$-F1 | 100 (6/6) | 100 (5/6)<br>98 (1/6) |
| rHPIV1 $C^{\Delta 170}$-F2 | 100 (6/6) | ND |
| rHPIV1 $C^{\Delta 170}$-F3 | 100 (6/6) | 100 (6/6) |

FIG. 45

Immunization of hamsters with rHPIV1 expressing RSV F induces serum neutralizing antibodies against RSV

| | Neutralizing serum antibody response (mean reciprocal $\log_2 \pm$ SE) to: | | | |
|---|---|---|---|---|
| | RSV | | HPIV1 | |
| Immunizing Virus | Pre | Day 28 | Pre | Day 28 |
| rHPIV1 $C^{\Delta 170}$ | ≤ 3.3 | ≤ 3.3 (A) | ≤ 1 | 3.9 ± 0.3 (A) |
| rHPIV1 $L^{Y942A}$ | ≤ 3.3 | ≤ 3.3 (A) | ≤ 1 | ≤ 1 (B) |
| rHPIV1 $C^{\Delta 170}$-F1 | ≤ 3.3 | 7.3 ± 0.3 (B, C) | ≤ 1 | 2.8 ± 0.5 (A) |
| rHPIV1 $C^{\Delta 170}$-F2 | ≤ 3.3 | 4.7 ± 0.7 (C) | ≤ 1 | ≤ 1 (B) |
| rHPIV1 $C^{\Delta 170}$-F3 | ≤ 3.3 | 6.7 ± 0.8 (C, B) | ≤ 1 | ≤ 1 (B) |
| rHPIV1 $L^{Y942A}$-F1 | ≤ 3.3 | ≤ 3.3 (A) | ≤ 1 | ≤ 1 (B) |
| rHPIV1 $L^{Y942A}$-F2 | ≤ 3.3 | ≤ 3.3 (A) | ≤ 1 | ≤ 1 (B) |
| rHPIV1 $L^{Y942A}$-F3 | ≤ 3.3 | ≤ 3.3 (A) | ≤ 1 | ≤ 1 (B) |
| rB/HPIV3-F2 | ≤ 3.3 | 9.7 ± 0.4 (D) | ≤ 1 | ≤ 1 (B) |
| wt RSV | ≤ 3.3 | 11.3 ± 0.4 (D) | ≤ 1 | ≤ 1 (B) |

B/HPIV3-wtHN-RSVF (HEK/GS-opt/DS-Cav1/B3TMCT/pre-N)

Correction of HN assignments (aa 263 and 370) to wt HPIV3 HN in B/HPIV3

*"mutant HN" = the assignments in the original recombinant HPIV3 (Durbin et al Virology 235:323-332 1997)

FIG. 59A
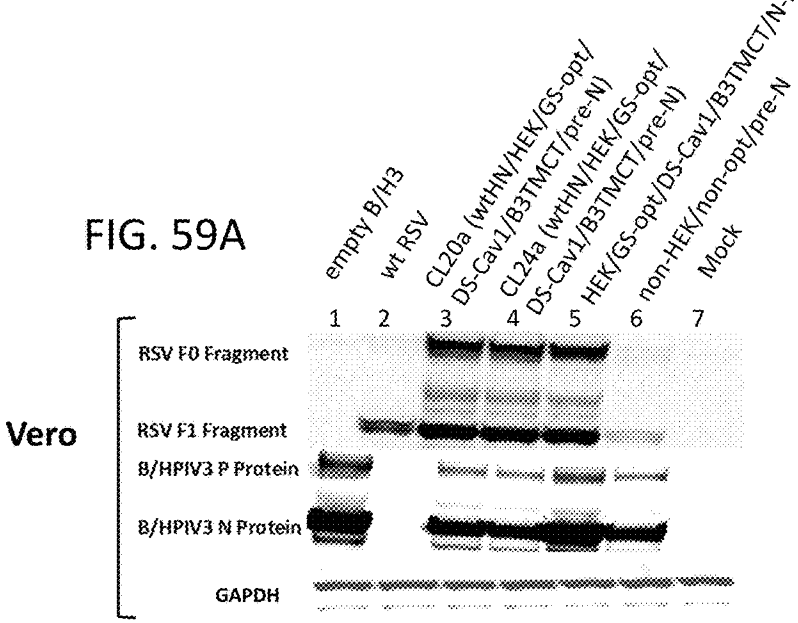
FIG. 59B
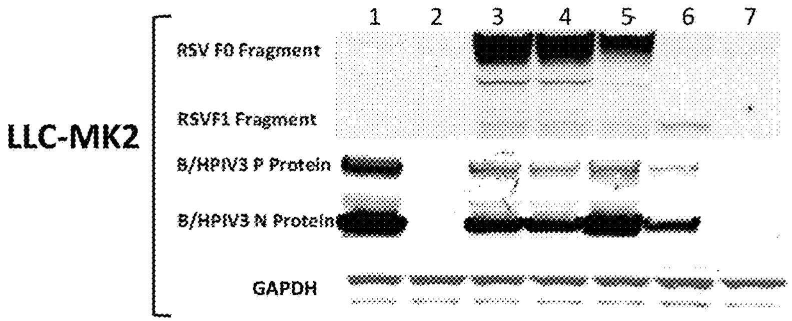
FIG. 60
TM and CT Domains of RSV F protein and HPIV1 F protein
| | Ectodomain | | TM | | CT |
|---|---|---|---|---|---|
| RSV A2 F 510 | DELLHNVNAGKSTTNIMITT | 530 | IIIVIIVILLSLIAVGLLLYC | 551 | KARSTPVTLSKDQLSGINNIAFSN |
| HPIV1 F 477 | LMKARAIISAVGGWHNTEST | 497 | QIIMIIIVCILIIIICGILYYLY | 520 | RVRRLLVMINSTHNSPVNAYTLESRMRNPYMGNNSN |
| RSV F-TMCT 510 | DELLHNVNAGKSTTNIMITT | 530 | QIIMIIIVCILIIIICGILYYLY | 553 | RVRRLLVMINSTHNSPVNAYTLESRMRNPYMGNNSN |

FIG. 66

RSV F and HPIV3 F TM and CT Domains

| | Ectodomain | | TM | | CT |
|---|---|---|---|---|---|
| RSV A2 F | 510 DELLHNVNAGKSTTNIMITT | 530 | IIIVIIVILLSLIAVGLLLYC | 551 | KARSTPVTLSKDQLSGINNIAFSN |
| HPIV3 F | 474 IRRSNQKLDSIGNWHQSSTT | 494 | IIIILIMIIILFIINITIITIAI | 517 | KYYRIQKRNRVDQNDKPYVLTNK |
| RSV F-H3TMCT | 510 DELLHNVNAGKSTTNIMITT | 530 | IIIILIMIIILFIINITIITIAI | 553 | KYYRIQKRNRVDQNDKPYVLTNK |

RECOMBINANT HUMAN/BOVINE PARAINFLUENZA VIRUS 1 (HPIV1) EXPRESSING A CHIMERIC RSV/HPIV1 F PROTEIN AND USES THEREOF

CROSS REFERENCE TO RELATED APPLICATIONS

This application is a continuation of U.S. application Ser. No. 15/545,218, filed Jul. 20, 2017, which is the U.S. National Stage of International Application No. PCT/US2016/014154, filed Jan. 20, 2016, which was published in English under PCT Article 21(2), which in turn claims the benefit of U.S. Provisional Application No. 62/105,667, filed Jan. 20, 2015. The contents of each of these applications is incorporated by reference herein in their entirety.

FIELD

This disclosure relates to recombinant paramyxoviruses that include a viral genome including a heterologous gene encoding an antigen of a heterologous virus. For example, the recombinant paramyxovirus can be a recombinant parainfluenza virus (PIV) that includes a genome including a heterologous gene encoding a respiratory syncytial virus (RSV) fusion (F) protein.

BACKGROUND

Paramyxoviruses are a family of negative-sense single stranded RNA viruses that account for many animal and human deaths worldwide each year. The paramyxoviruses include sub-families Paramyxovirinae and Pneumovirinae. Respiratory syncytial virus (RSV) is an enveloped non-segmented negative-strand RNA virus in the family Paramyxoviridae, genus *Pneumovirinae.* It is the most common cause of bronchiolitis and pneumonia among children in their first year of life. RSV also causes repeated infections including severe lower respiratory tract disease, which may occur at any age, especially among the elderly or those with compromised cardiac, pulmonary, or immune systems. Passive immunization currently is used to prevent severe illness caused by RSV infection, especially in infants with prematurity, bronchopulmonary dysplasia, or congenital heart disease. Despite the burden of RSV infection in certain populations, development of an effective RSV vaccine remains elusive.

Parainfluenza virus (PIV) is another enveloped non-segmented negative-strand RNA virus that, like RSV, is in the paramyxovirus family. However, PIVs are in subfamily Paramyxovirinae. PIVs include members of the genus *Respirovirus* (including PIV1, PIV3, Sendai virus) and rubulavirus (including PIV2, PIV4, PIV5). In addition the members of genus *Avulavirus* (including Newcastle disease virus NDV) historically were termed PIVs and operationally can be considered the same. The human parainfluenza viruses (HPIVs, serotypes 1, 2, and 3) are second only to RSV in causing severe respiratory infections in infants and children worldwide, with HPIV3 being the most important of the HPIVs in terms of disease impact. The HPIV genome is approximately 15.5 kb, including a gene order of 3'-N-P-M-F-HN-L. Each gene encoding a separate mRNA that encodes a major protein: N, nucleoprotein; P, phosphoprotein; M, matrix protein; F, fusion glycoprotein; HN, hemagglutinin-neuramindase glycoprotein; L, large polymerase protein. The P gene contains one or more additional open reading frames (ORFs) encoding accessory proteins. Similar to RSV, development of an effective HPIV vaccine remains elusive.

SUMMARY

Recombinant paramyxoviruses including a viral genome encoding a heterologous gene are provided. In several embodiments, the recombinant paramyxovirus can be a recombinant parainfluenza virus comprising a viral genome comprising a heterologous gene encoding a type I membrane protein comprising a recombinant RSV F ectodomain linked to a cytoplasmic tail (CT), or a transmembrane domain (TM) and a CT, of an F protein of the paramyxovirus. The paramyxovirus can be, for example, a recombinant human/bovine parainfluenza virus 3 (B/HPIV3), a recombinant human parainfluenza virus 1 (HPIV1), a recombinant human parainfluenza virus 2 (HPIV2), a recombinant human parainfluenza virus 3 (HPIV3), or a recombinant bovine parainfluenza virus 3 (BPIV3).

Surprisingly, swapping the TM and CT of the heterologous RSV F protein for the corresponding TM and CT of the paramyxovirus F protein provided a multi-fold increase in RSV F ectodomain incorporation in the envelope of recombinant paramyxovirus, and dramatically increased the elicitation of an immune response to the ectodomain when the recombinant paramyxovirus was administered to a subject. Further, the induction of virus-neutralizing serum antibodies was dramatically increased both in quantity and in quality. Accordingly, in several embodiments, the disclosed recombinant paramyxoviruses can be included in immunogenic compositions for eliciting a bivalent immune response to the paramyxovirus and the heterologous RSV F protein.

The RSV F ectodomain encoded by the heterologous gene can be from a human RSV F protein. In several embodiments the RSV F ectodomain can include one or more amino acid substitutions (such as the "DS-Cav1" substitutions, S155C, S290C, S190F, and V207L) to stabilize the ectodomain in a RSV F prefusion conformation. In additional embodiments, the RSV F ectodomain can include one more amino acid substitutions to increase ectodomain expression or incorporation in the viral envelope (such as the "HEK" substitutions, K66E and Q101P).

In a non-limiting embodiment, the recombinant paramyxovirus can be a recombinant B/HPIV3 and the RSV F ectodomain is linked to a TM and CT from a BPIV3 F protein. In some such embodiments, the RSV F ectodomain linked to the TM and CT from the BPIV3 F protein comprises the amino acid sequence set forth as SEQ ID NO: 21, or an amino acid sequence at least 90% identical to SEQ ID NO: 21.

In several embodiments, the recombinant paramyxovirus is a recombinant PIV comprising a viral genome comprising, from upstream to downstream: a PIV genomic promoter followed by the N, P, M, F, HN, and L genes. In some such embodiments, the heterologous gene included in the viral genome can be located between the genomic promoter and the gene encoding the N protein, or between the genes encoding the N and the P protein.

In additional embodiments, the heterologous gene included in the viral genome of the recombinant paramyxovirus can be codon-optimized for expression in human cells. In more embodiments, the recombinant paramyxovirus can be an attenuated virus. In other embodiments, the added gene and its encoded protein can provide attenuation needed for a vaccine candidate.

Immunogenic compositions including the recombinant paramyxovirus are also provided. The compositions can further include an adjuvant. Methods of generating an immune response in a subject by administering an effective amount of a disclosed recombinant paramyxovirus to the subject are also disclosed. Further provided are isolated nucleic acid molecules including the viral genome of any of the recombinant paramyxoviruses disclosed herein.

The foregoing and other features and advantages of this disclosure will become more apparent from the following detailed description of several embodiments which proceeds with reference to the accompanying figures.

BRIEF DESCRIPTION OF THE FIGURES

FIGS. 15A and 15B. Serum RSV-neutralizing antibody titers from hamsters infected with rB/HPIV3 vectors expressing secreted (Ecto), post-fusion, and stabilized pre-fusion forms of the RSV F protein. Hamsters (n=6 animals per virus) were inoculated IN with $10^5$ $TCID_{50}$ of the indicated rB/HPIV3 vectors or $10^6$ PFU of wt RSV in a 0.1 ml inoculum. Serum samples were collected at 28 days post-immunization, and RSV-neutralizing antibody titers were determined by a 60% plaque reduction neutralization test ($PRNT_{60}$) performed on Vero cells at 32° C. (A) with and (B) without added guinea pig complement. The height of each bar represents the mean titer. The values of mean titers are shown above the bars. The standard error of the mean is shown by the horizontal lines. The detection limit for the neutralization assay is indicated with a dotted line. ND means neutralization titer is below the detection limit. The statistical significance of difference among groups was determined by Tukey-Kramer test and indicated by asterisks; *, $P \leq 0.05$; , $P \leq 0.01$; or *, $P \leq 0.001$; or ns, $P > 0.05$.

FIGS. 17A and 17B. Construction of rB/HPIV3 vectors expressing versions of RSV F protein engineered in an attempt to increase incorporation into the vector particle. (A) Structures of F proteins. (B) Sequences of the cytoplasmic tails (CT), transmembrane (TM) domains, and adjoining regions of the ectodomains of the RSV F protein (amino acid assignments in black) and BPIV3 F protein (boldface), with amino acid sequence positions indicated. Each of these modified proteins contained the HEK assignments and was expressed from a GA-optimized ORF. The HEK/GA-opt construct expressed full-length RSV F protein. "B3CT" has the CT of RSV F protein (amino acid sequence positions 551-574) replaced by the CT of BPIV3 F protein (positions 515-540, boldface). "B3TMCT" has both the TM and CT of RSV F protein (positions 530-574) replaced by the TM and CT of BPIV3 F protein (positions 494-540, boldface). "DS/B3CT", "DS/B3TMCT", "DS-Cav1/B3CT", and "DS-Cav1/B3TMCT" are versions of B3CT and B3TMCT containing the DS or DS-Cav1 mutations designed to stabilize the pre-fusion conformation. The ORFs encoding these various forms of RSV F protein were inserted into the rB/HPIV3 vector at the same position and with the same vector signals as described in FIGS. 1, 4, and 11. The sequences shown are as follows: RSV(A2)F (SEQ ID NO: 1, residues 510-574), BPIV3 F (SEQ ID NO: 151), B3CT (SEQ ID NO: 14, residues 510-576), B3TMCT (SEQ ID NO: 12, residues 510-576).

FIGS. 18A and 18B. Incorporation into the rB/HPIV3 vector particle of B3CT and B3TMCT versions of the RSV F protein. LLC-MK2 cells were infected with the indicated rB/HPIV3 vectors at an MOI of 0.01 $TCID_{50}$ at 32° C. The medium supernatants were harvested 6-7 days post-infection, clarified by low speed centrifugation, and subjected to centrifugation on 10%-30% sucrose gradients to obtain partially-purified vector particles. Additional Vero cells were infected with wt RSV at an MOI of 0.01 PFU and processed in the same way. The protein concentrations of the sucrose-purified preparations were determined by a standard commercial kit. (A) Western blot evaluation of the packaging efficiency of the RSV F protein into the rB/HPIV3 particles. To compare the relative amounts of RSV F in the particles, 0.5 μg of sucrose-purified particles were lysed, denatured, reduced and subjected to Western blot analyses. The HPIV3 HN and BPIV3 N proteins of the vector particle were quantified for comparison. (B) The packaging efficiency of each form of RSV F into its respective vector particle was calculated by normalizing its band density against that of the BPIV3 N protein. The order of the lanes is the same as in part A. The packaging efficiencies of various forms of RSV F are shown relative to the native F protein set at "1". The packaging efficiency of the B3CT and B3TMCT forms of RSV F into the vector particle was judged to be similar to that of RSV F into the RSV particle because the amount of modified RSV F protein per 0.5 μg of vector particles (lanes 3, 4, 6, 7) was similar to the amount of native RSV F protein per 0.5 μg of RSV particles (lane 5). The constructs indicated by asterisk * contained the HEK assignments and were GA-codon-optimized for human expression.

FIGS. 19A-19F. Visualization of the incorporation of B3CT and B3TMCT versions of the RSV F protein into rB/HPIV3 particles by transmission electron microscopy (TEM). Sucrose purified viruses were labeled with an RSV F-specific murine monoclonal antibody and mouse-IgG-specific second antibodies that were labeled with 6 nm gold particles. Virions and gold particles were visualized with TEM. Representative images of (A) RSV, (B) empty rB/HPIV3 vector (empty B/H3), (C) vector expressing HEK/GA-opt, (D) vector expressing B3CT, (E) vector expressing B3TMCT, and (F) vector expressing DS/B3TMCT are shown. Arrows point to sporadic gold particles in HEK/GA-opt virions (C). Substantially greater amounts of gold particles associated with the vector particles are evident in D, E, and F.

FIG. 26. Stability of expression of RSV F by rB/HPIV3 vectors during replication in hamsters. The percentage of recovered vector expressing RSV F in the nasal turbinates and lungs at day 3 and 5 post-immunization was determined by double-staining plaque assay of vector recovered directly from the tissue homogenates. The results are expressed for the individual animals. The percentages of rB/HPIV3 expressing RSV F protein in the tested specimens are indicated. Specimens with 100% expression of RSV F protein were colored in yellow; those with 90-99% expression of RSV F were colored in green; those with 80-89% expression of RSV F were colored in orange; those with less than 79% expression of RSV F were colored in red. Specimens that did not generate plaques due to low titer were marked as "NA". If the total number of the plaques developed with a sample was less than 10, the number of plaques was recorded as "p=X" (X equals to the number of plaques) in the bracket.

(FIG. 31) RSV neutralizing antibody titers at all time points were determined by a 60% plaque reduction neutralization test ($PRNT_{60}$) in the presence of added guinea pig complement. (FIG. 32) RSV neutralizing antibody titers at day 28 post-immunization were determined by a 60% plaque reduction neutralization test ($PRNT_{60}$) in the absence of added complement. The detection limit for the neutralization assay is indicated with a dotted line. The statistical significance of difference in mean titers was determined by Tukey-Kramer test and indicated by asterisks (, P≤0.01; *, P≤0.001). The day of RSV challenge is indicated.

FIG. 33. Stability of expression of RSV F by rB/HPIV3 vectors during replication in rhesus macaques. The percentage of recovered vector expressing RSV F in nasal pharyngeal swabs from day 4, 5 and 6 post-immunization was determined by double-staining plaque assay. The percentages of rB/HPIV3 expressing RSV F in the tested specimens are indicated. Specimens with 100% of viruses expressing RSV F were colored in yellow; those with 99-90% of viruses expressing RSV F were colored in green; those that did not generate plaques due to low titer were marked as "NA".

FIG. 35. Summary of exemplary rB/HPIV3 vectors expressing RSV F, annotated to indicate constructs that have been evaluated in two different studies in hamsters and two different studies in rhesus monkeys in Example 1.

FIG. 42 shows a table illustrating the attenuating mutations introduced in the HPIV1 backbone in the P/C or the L ORF. Nucleotide changes (deletion or substitution) in the wt sequence are underlined.

FIG. 43 shows a table illustrating temperature sensitivity of recombinant viruses on LLC-MK2 cell monolayers. For temperature sensitivity, the underlined values in boldface indicate the virus shut-off temperature indicating a temperature sensitive phenotype defined as the lowest restrictive temperature at which the mean $log_{10}$ reduction in virus titer at a given temperature vs. 32° C. was 2.0 $log_{10}$ or greater than that of the wt rHPIV1 at the same two temperatures. For monolayers, serial dilutions of each of the indicated viruses on LLC-MK2 cells were incubated at various temperatures for 7 days. Virus titers were determined by hemadsorption with guinea pig erythrocytes and reported as $Log_{10}$ $TCID_{50}$/ml with a detection limit of 1.2.

FIG. 44 shows a table illustrating the percentage of virus population expressing RSV F after in vivo replication. The percentage of virus population expressing RSV F after in vivo replication (stability) was determined by an immunofluorescent double-staining plaque assay. Vero cells were infected with serially diluted tissue homogenates of the nasal turbinates or lungs of infected hamsters (n=6 per virus) collected on day 3 and 5 p.i. (total 144 samples) and incubated for 6 days under methylcellulose overlay. Virus plaques were stained with mouse monoclonal anti-RSV F and goat polyclonal anti-HPIV1 specific antibodies followed by detection with the corresponding infrared dye conjugated secondary antibodies. Percentage of plaques expressing both RSV F and HPIV1 antigens are shown. The stability of HPIV1 $C^{\Delta 170}$-F1, -F2, and F3 for lung samples and that for HPIV1 $L^{Y942A}$-F1, -F2, and F3 in the URT and lungs could not be tested due to their lack of replication in these tissues. Numbers in parenthesis indicate the RSV F expression status for the number of hamsters of the total 6 hamsters per virus. ND, no plaques were detected.

FIG. 45 shows a table listing results indicating that immunization of hamsters with rHPIV1 expressing RSV F induces serum neutralizing antibodies against RSV. Groups of six-week old hamsters (n=6) were intranasally immunized with $10^5$ $TCID_{50}$ of each indicated virus in 0.1 ml inoculum. Serum samples were collected prior to immunization and at 28 days post immunization. Antibody titers against RSV and HPIV1 were determined by using a 60% plaque reduction neutralization test ($PRNT_{60}$) using green fluorescent protein (GFP)- or enhanced GFP (eGFP) expressing viruses (rRSV-eGFPM or HPIV1-GFP), and neutralizing antibody titers were presented as mean reciprocal $log_2$±SE. Based on the initial serum dilutions used in the assay, the $PRNT_{60}$ assay has a titer detection limit of 3.3 and 1.0 reciprocal $log_2$ $PRNT_{60}$ for RSV and HPIV1, respectively. Statistical significance of difference among the groups for RSV antibody titers was determined by one-way ANOVA with Tukey's multiple comparisons test ($p<0.05$) and that for HPIV1 antibody titers was determined by Unpaired t-test. Mean neutralizing antibody titers were categorized into groups (indicated in parenthesis as A, B, C, and D). Mean antibody titers of treatment groups with different letters are statistically different from each other; titers shown with two letters are not statistically different from those indicated with either letter.

(FIG. 46) Vero and (FIG. 47) LLC-MK2 cells were infected in triplicate at 32° C. at an MOI of 0.01 $TCID_{50}$ with empty rB/HPIV3 vector (empty B/H3) or vector expressing the RSV F ORF that was HEK-containing, GA-opt, and containing the DS-Cav1 prefusion stabilizing mutations (HEK/GA-opt/DS-Cav1) or was HEK-containing, GA-opt, and containing the DS-Cav1 mutations and BPIV3-specific TM and CT domains as potential packaging signals (HEK/GA-opt/DS-Cav1/B3TMCT). Aliquots of medium supernatants were collected at 24 h intervals for 6 days and viral titers were determined by limiting dilution assay on LLC-MK2 cells at 32° C. and reported as $TCID_{50}$/ml. Mean titers±SEM from three independent experiments are shown.

FIGS. 49A and 49B: (A) Vero and (B) LLC-MK2 cells were infected in triplicate at 32° C. at an MOI of 0.01 $TCID_{50}$ with empty rB/HPIV3 vector (empty B/H3) or vector expressing RSV F ORF that was HEK-containing, GS-opt, and bearing the DS-Cav1 mutations (HEK/GS-opt/DS-Cav1), or was HEK-containing, GA-opt, and bearing the DS-Cav1 mutations (HEK/GA-opt/DS-Cav1). FIGS. 49C and 49D: (C) Vero and (D) LLC-MK2 cells were infected at 32° C. at an MOI of 0.01 $TCID_{50}$ with empty rB/HPIV3 vector (empty B/H3) or vector expressing RSV F ORF that was HEK-containing, GS-opt, and bearing the DS-Cav1 and B3TMCT modifications (HEK/GS-opt/DS-Cav1/B3TMCT), or was HEK-containing, GA-opt, and contained the DS-Cav1 and B3TMCT modifications (HEK/GA-opt/DS-Cav1/B3TMCT). Aliquots of medium supernatant were collected at 24 h intervals for 6 days and viral titers were determined by limiting dilution assay on LLC-MK2 cells at 32° C. and reported as $TCID_{50}$/ml. Mean titers±SEM from three independent experiments are shown.

FIG. 57A: RSV neutralizing antibody titers at the indicated time points were determined by a 60% plaque reduction neutralization test ($PRNT_{60}$) in the presence of added guinea pig complement. The statistical significance of difference in mean titers of each time point was determined by pairwise student-t test (ns, $P>0.05$). FIG. 57A: RSV neutralizing antibody titers at day 28 post-immunization were determined by $PRNT_{60}$ in the absence of added complement. The detection limit for the neutralization assay is indicated with a dotted line. The statistical significance of difference in mean titers of each time point was determined by pairwise student-t test (ns, $P>0.05$).

FIG. 58A: Insertion of the HEK/GS-opt/DS-Cav1/B3TMCT insert into the first gene position of rB/HPIV3. FIG. 58A: Corrections of the HPIV3 HN gene that conferred increased phenotypic stability. The HN gene in the original recombinant HPIV3 made by reverse genetics (Durbin et al Virology 235:323-332 1997) had two engineered nucleotide substitutions in the HN gene at antigenome positions 7913 and 7915 that resulted in the amino acid substitution P370T, and an adventitious mutation at antigenome position 7593 that resulted in the amino acid substitution T2631. Here, these mutations were changed back to the "wild-type" assignments, i.e., that found in biologically derived HPIV3 strain JS (Genbank Z11575.1; Stokes et al Virus Res 25:91-103. 1992).

FIGS. 59A and 59B. Intracellular expression of RSV F and vector proteins by vectors expressing various versions of RSV F protein in the first gene position (pre-N) or in the second gene position (N-P). Analysis of rB/HPIV3-wt HN-HEK/GS-opt/DS-Cav1/B3TMCT/pre-N, the construct diagrammed in FIG. 58A. Vero (FIG. 59A) and LLC-MK2 (FIG. 59B) cells were infected with empty rB/HPIV3 vector (empty B/H3, lane 1), or the wtHN/HEK/GS-opt/DS-Cav1/B3TMCT/pre-N construct (pools CL20a, CL24a, lanes 3 and 4), or vector with the same version of RSV F inserted in the second (N-P) position (HEK/GS-opt/DS-Cav1/B3TMCT/N-P, lane 5), or vector with Non-HEK/non-opt version of RSV F inserted in the pre-N position (lane 6), or wt RSV (lane 2), or mock-infected (lane 7). The vectors were infected at an MOI of 10 $TCID_{50}$/cell, and wt RSV at MOI of 3 PFU/cell. Infected monolayers were incubated at 32° C. Cell lysates were collected at 48 hpi and subjected to Western blot analysis. RSV F in the forms of cleaved $F_1$ and/or uncleaved $F_0$ were detected. BPIV3 N and P proteins were used to evaluate effects on vector protein expression. GAPDH was used as a loading control.

FIG. 60. HPIV1 vector: sequences of the cytoplasmic tails (CT), transmembrane (TM) domains, and adjoining regions of the ectodomains of the RSV F protein (strain A2, amino acid assignments) and HPIV1 F protein (boldface), with the amino acid sequence positions indicated. RSV-F-TMCT is a chimeric protein consisting of the ectodomain of RSV F protein attached to the TM and CT domains of HPIV1 F protein. The sequences shown are as follows: RSV(A2)F (SEQ ID NO: 1, residues 510-574), HPIV1 F (SEQ ID NO: 152), RSV F-TMCT (SEQ ID NO: 135, residues 510-588).

FIG. 66. Sequences of the cytoplasmic tails (CT), transmembrane (TM) domains, and adjoining regions of the ectodomains of the RSV F protein (amino acid assignments) and HPIV3 F protein (boldface), with the amino acid sequence positions indicated. RSV-F-H3TMCT is a chimeric protein consisting of the ectodomain of RSV F protein attached to the TM and CT domains of HPIV3 F protein. The sequences shown are as follows: RSV(A2)F (SEQ ID NO: 1, residues 510-574), HPIV3 F (SEQ ID NO: 153), RSV F-H3TMCT (SEQ ID NO: 10, residues 510-575).

SEQUENCE LISTING

Figure 1:
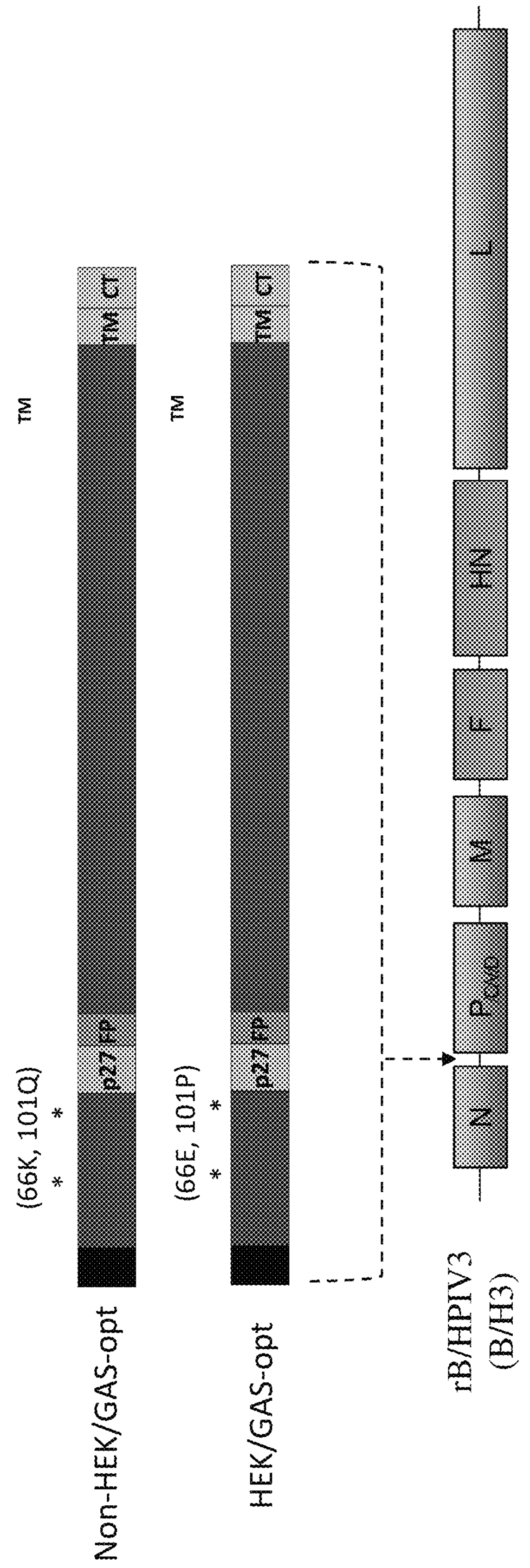
FIG. 1. Construction of rB/HPIV3 vectors expressing versions of the RSV F protein containing the non-HEK or HEK amino acid assignments. The F ORFs were codon-optimized for human expression using the GeneArt (GA) algorithm. The constructs were called non-HEK/GA-opt and HEK/GA-opt. The HEK (66E, 101P) and non-HEK (66K, 101Q) amino acid assignments are indicated by asterisks. Other annotations: S, signal sequence; p27, 27k protein fragment liberated by cleavage-activation; FP, fusion peptide; TM, transmembrane; CT, cytoplasmic tail. The RSV F ORFs were placed under the control of BPIV3 gene-start and gene-end transcription signals and inserted into the $2^{nd}$ genome position between the N and P genes of the B/HPIV3 vector. The rB/HPIV3 vector includes N, P, M, and L genes from BPIV3, and F and NH genes from HPIV3. The same vector genome position and vector transcription signals were used for all of the other rB/HPIV3 vectors expressing RSV F protein described in FIGS. 1-35.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file in the form of the file named "Sequence.txt" (~348 kb), which was created on May 18, 2020 which is incorporated by reference herein. In the accompanying sequence listing:

DETAILED DESCRIPTION

A previous study (Zimmer et al J Virol 2005 79:10467-77) evaluated the expression of RSV F protein from a heterologous gene in the Sendai virus, which is a murine relative of HPIV1 and also is closely related to HPIV3. That study showed that very little RSV F protein was incorporated into the Sendai virus vector particle. The investigators replaced the CT or CT plus TM of the RSV F protein with the corresponding sequences from the Sendai F protein on the premise that this would improve the efficiency of interaction of the foreign RSV F protein with the vector particle. These modifications indeed increased incorporation of the engineered RSV F into the Sendai particle, but only if the Sendai F protein gene was also deleted. The requirement to delete the vector F protein is incompatible with the generation of infectious, attenuated viruses for vaccination and also would remove one of the vector protective antigens, which are believed to be needed to generate a bivalent vaccine.

As disclosed herein, when expressed by rB/HPIV3, HPIV3, or HPIV1, the RSV F protein including RSV F TM and CT is incorporated into the vector particle only in trace amounts. However, swapping the TM and CT of the heterologous RSV F protein for the corresponding TM and CT of the paramyxovirus F protein provided a multi-fold increase in RSV F ectodomain incorporation in the envelope of recombinant paramyxovirus, such that the packaging of RSV F into the vector was as efficient (e.g. B/HPIV3) or more efficient (e.g. HPIV1) per μg of purified virion than that of RSV itself. This was effective when the TM and CT were swapped together, or when the CT was swapped alone. However, unexpected effects of increased fusogenicity of the chimeric RSV F specific to CT alone provide guidance that TMCT is preferred.

Efficient packaging of RSV F into the vector particle dramatically increased the elicitation of an immune response to the ectodomain (bearing all of the neutralization epitopes) when the recombinant paramyxovirus was administered to a subject. Unexpectedly, the virus-neutralizing serum antibody response was dramatically increased in quality, which was assessed by comparing RSV-neutralization activity in vitro in the absence of complement (which measures strongly-neutralizing antibodies) or in its presence (which augments neutralization by weak or non-neutralizing antibodies). This unanticipated increase in antibody quality is of particular importance for RSV, which is noted for inducing incomplete immune protection. The expression and efficient packaging of a foreign glycoprotein bearing the TMCT domains of a vector glycoprotein had the obvious potential to disrupt vector replication and morphogenesis: however, constructs are provided in which this effect was minimal.

To further increase immunogenicity, stabilization of the RSV F protein in the pre-fusion conformation was evaluated. On its own, pre-fusion stabilization also resulted in an increase in titers of strongly-neutralizing antibodies, suggestive of stabilization of neutralization epitopes. In the hamster model, the effect of pre-fusion stabilization on increased immunogenicity and protection appeared to be additive to that of efficient packaging conferred by TMCT. However, when evaluated in non-human primates, the effect of packaging appeared to be greater than that of pre-fusion stabilization.

Given the challenge of achieving protection against RSV, maximal immunogenicity is desired. Extensive experimentation uncovered other aspects of vector and insert construction (e.g., use of various insertion sites, use of codon-optimization, and use of an early-passage RSV F protein sequence) that provided increased expression of RSV F and reduced the cytopathic effects of syncytia formation mediated by the highly fusogenic RSV F protein.

It is noteworthy that a prototype vaccine virus based on rB/HPIV3 expressing an unmodified RSV F protein, which in clinical trials had disappointing RSV immunogenicity (Bernstein, et al. 2012. Pediatric Infectious Disease Journal 31:109-114), was confirmed by the methods of the present disclosure to induce RSV-neutralizing serum antibodies that were of poor quality, possessing neutralization activity in vitro only in the presence of added complement. In contrast, disclosed constructs induced, in African green monkeys, high titers of serum antibodies capable of efficiently neutralizing RSV in vitro in the absence of complement.

I. Summary of Terms

Unless otherwise noted, technical terms are used according to conventional usage. Definitions of common terms in molecular biology may be found in Benjamin Lewin, Genes X, published by Jones & Bartlett Publishers, 2009; and Meyers et al. (eds.), *The Encyclopedia of Cell Biology and Molecular Medicine*, published by Wiley-VCH in 16 volumes, 2008; and other similar references.

As used herein, the singular forms "a," "an," and "the," refer to both the singular as well as plural, unless the context clearly indicates otherwise. For example, the term "an antigen" includes single or plural antigens and can be considered equivalent to the phrase "at least one antigen." As used herein, the term "comprises" means "includes." It is further to be understood that any and all base sizes or amino acid sizes, and all molecular weight or molecular mass values, given for nucleic acids or polypeptides are approximate, and are provided for descriptive purposes, unless otherwise indicated. Although many methods and materials similar or equivalent to those described herein can be used, particular suitable methods and materials are described herein. In case of conflict, the present specification, including explanations of terms, will control. In addition, the materials, methods, and examples are illustrative only and not intended to be limiting. To facilitate review of the various embodiments, the following explanations of terms are provided:

Adjuvant: A vehicle used to enhance antigenicity. Adjuvants include a suspension of minerals (alum, aluminum hydroxide, or phosphate) on which antigen is adsorbed; or water-in-oil emulsion, for example, in which antigen solution is emulsified in mineral oil (Freund incomplete adjuvant), sometimes with the inclusion of killed mycobacteria (Freund's complete adjuvant) to further enhance antigenicity (inhibits degradation of antigen and/or causes influx of macrophages) Immunostimulatory oligonucleotides (such as those including a CpG motif) can also be used as adjuvants. Adjuvants include biological molecules (a "biological adjuvant"), such as costimulatory molecules. Exemplary adjuvants include IL-2, RANTES, GM-CSF, TNF-α, IFN-γ, G-CSF, LFA-3, CD72, B7-1, B7-2, OX-40L, 4-1BBL, immune stimulating complex (ISCOM) matrix, and toll-like receptor (TLR) agonists, such as TLR-9 agonists, Poly I:C, or PolyICLC. The person of ordinary skill in the art is familiar with adjuvants (see, e.g., Singh (ed.) Vaccine Adjuvants and Delivery Systems. Wiley-Interscience, 2007). Adjuvants can be used in combination with the disclosed recombinant.

Administration: The introduction of a composition into a subject by a chosen route. Administration can be local or systemic. For example, if the chosen route is intranasal, the composition (such as a composition including a disclosed recombinant paramyxovirus) is administered by introducing the composition into the nasal passages of the subject. Exemplary routes of administration include, but are not limited to, oral, injection (such as subcutaneous, intramuscular, intradermal, intraperitoneal, and intravenous), sublingual, rectal, transdermal (for example, topical), intranasal, vaginal, and inhalation routes.

Amino acid substitution: The replacement of one amino acid in a polypeptide with a different amino acid or with no amino acid (i.e., a deletion). In some examples, an amino acid in a polypeptide is substituted with an amino acid from a homologous polypeptide, for example, and amino acid in a recombinant group A RSV F polypeptide can be substituted with the corresponding amino acid from a group B RSV F polypeptide. Reference to a "66E" amino acid in a RSV F protein refers to an RSV F protein comprising a glutamate residue at position 66. The amino acid can be present due to substitution from a reference sequence. Reference to a "K66E" substitution in an RSV F protein refers to an RSV F protein comprising a glutamate residue at position 66 that has been substituted for a lysine residue in a reference (e.g., native) sequence.

Attenuated: A paramyxovirus that is "attenuated" or has an "attenuated phenotype" refers to a paramyxovirus that has decreased virulence compared to a reference wild type paramyxovirus under similar conditions of infection. Attenuation usually is associated with decreased virus replication as compared to replication of a reference wild-type paramyxovirus under similar conditions of infection, and thus "attenuation" and "restricted replication" often are used synonymously. In some hosts (typically non-natural hosts, including experimental animals), disease is not evident during infection with a reference paramyxovirus in question, and restriction of virus replication can be used as a surrogate marker for attenuation. In some embodiments, a recombinant paramyxovirus (e.g., RSV, PIV3) that is attenuated exhibits at least about 10-fold or greater decrease, such as at least about 100-fold or greater decrease in virus titer in the upper or lower respiratory tract of a mammal compared to non-attenuated, wild type virus titer in the upper or lower respiratory tract, respectively, of a mammal of the same species under the same conditions of infection. Examples of mammals include, but are not limited to, humans, mice, rabbits, rats, hamsters, such as for example *Mesocricetus auratus*, and non-human primates, such as for example *Ceroptihecus aethiops*. An attenuated paramyxovirus may display different phenotypes including without limitation altered growth, temperature sensitive growth, host range restricted growth, or plaque size alteration.

Cytoplasmic Tail (CT): A contiguous region of a transmembrane protein that includes a terminus (either N- or C-terminus) of the protein and extends into the cytoplasm of a cell or enveloped virus from the cytoplasmic surface of the cell membrane or viral envelope. In the case of a type I transmembrane protein, the CT includes the C-terminus of the protein. In the case of a type II transmembrane protein, the CT includes the N-terminus of the protein.

Degenerate variant: In the context of the present disclosure, a "degenerate variant" refers to a polynucleotide encoding a polypeptide that includes a sequence that is degenerate as a result of the genetic code. There are 20 natural amino acids, most of which are specified by more than one codon. Therefore, all degenerate nucleotide sequences encoding a peptide are included as long as the amino acid sequence of the peptide encoded by the nucleotide sequence is unchanged.

Gene: A nucleic acid sequence, typically a DNA sequence, that comprises control and coding sequences necessary for the transcription of an RNA, whether an mRNA or otherwise. For instance, a gene may comprise a promoter, one or more enhancers or silencers, a nucleic acid sequence that encodes a RNA and/or a polypeptide, downstream regulatory sequences and, possibly, other nucleic acid sequences involved in regulation of the expression of an mRNA.

Heterologous: Originating from a different genetic source. A heterologous gene included in a recombinant viral genome is a gene that does not originate from that viral genome. In one specific, non-limiting example, a heterologous gene encoding an ectodomain of a RSV F protein is included in the genome of a recombinant PIV vector. Methods for introducing a heterologous gene in a viral vector are well known in the art and also described herein.

Host cells: Cells in which a vector can be propagated and its nucleic acid expressed. The cell may be prokaryotic or eukaryotic. The term also includes any progeny of the subject host cell. It is understood that all progeny may not be identical to the parental cell since there may be mutations that occur during replication. However, such progeny are included when the term "host cell" is used.

Immune response: A response of a cell of the immune system, such as a B cell, T cell, or monocyte, to a stimulus. In one embodiment, the response is specific for a particular antigen (an "antigen-specific response"). In one embodiment, an immune response is a T cell response, such as a CD4+ response or a CD8+ response. In another embodiment, the response is a B cell response, and results in the production of specific antibodies.

Immunogen: A compound, composition, or substance that can stimulate the production of antibodies or a T cell response in an animal, including compositions that are injected or absorbed into an animal. An immunogen reacts with the products of specific humoral or cellular immunity, including those induced by heterologous antigens, such as a disclosed recombinant paramyxovirus. Administration of an immunogen to a subject can lead to protective immunity against a pathogen of interest.

Immunogenic composition: A composition comprising an immunogen that induces a measurable T cell response against an antigen, or induces a measurable B cell response (such as production of antibodies) against an antigen, included on the immunogen or encoded by a nucleic acid molecule included in the immunogen. In one example, an immunogenic composition is a composition that includes a disclosed recombinant paramyxovirus that induces a measurable CTL response against RSV and/or PIV, or induces a measurable B cell response (such as production of antibodies) against RSV and/or PIV, when administered to a subject. An immunogenic composition can include an isolated recombinant paramyxovirus as disclosed herein. For in vivo use, the immunogenic composition will typically include a recombinant paramyxovirus in a pharmaceutically acceptable carrier and may also include other agents, such as an adjuvant.

Isolated: An "isolated" biological component has been substantially separated or purified away from other biological components, such as other biological components in which the component naturally occurs, such as other chromosomal and extrachromosomal DNA, RNA, and proteins. Proteins, peptides, nucleic acids, and viruses that have been "isolated" include those purified by standard purification methods. Isolated does not require absolute purity, and can include protein, peptide, nucleic acid, or virus molecules that are at least 50% isolated, such as at least 75%, 80%, 90%, 95%, 98%, 99%, or even 99.9% isolated.

Linked: The terms "linked," "linkage," and "linking" refer to making two molecules into one contiguous molecule; for example, linking two polypeptides into one contiguous polypeptide by recombinant means. Reference to a gene encoding a type I membrane protein comprising a RSV F ectodomain "linked" to a TM and CT of a heterologous F protein refers to genetic linkage between the nucleic acid sequence encoding the RSV F ectodomain and the nucleic acid sequence encoding the TM and CT of the heterologous F protein in the gene by recombinant means, such that expression of the gene leads to production of a protein including, in the N- to C-terminal direction, the RSV F ectodomain, the TM, and the CT. In some embodiments, the C-terminal residue of the RSV F ectodomain can be directly linked (by peptide bond) to the N-terminal residue of the TM. In some embodiments, the C-terminal residue of the RSV F ectodomain can be indirectly linked to the N-terminal residue of the TM via a peptide linker (such as a glycine-serine linker).

Linker: A bi-functional molecule that can be used to link two molecules into one contiguous molecule. Non-limiting examples of peptide linkers include glycine-serine linkers.

Native protein, sequence, or di-sulfide bond: A polypeptide, sequence or di-sulfide bond that has not been modified, for example by selective mutation. For example, selective mutation to focus the antigenicity of the antigen to a target epitope, or to introduce a di-sulfide bond into a protein that does not occur in the native protein. Native protein or native sequence are also referred to as wild-type protein or wild-type sequence. A non-native di-sulfide bond is a disulfide bond that is not present in a native protein, for example a di-sulfide bond that forms in a protein due to introduction of one or more cysteine residues into the protein by genetic engineering.

Nucleic acid molecule: A polymeric form of nucleotides, which may include both sense and anti-sense strands of RNA, cDNA, genomic DNA, and synthetic forms and mixed polymers of the above. A nucleotide refers to a ribonucleotide, deoxynucleotide or a modified form of either type of nucleotide. The term "nucleic acid molecule" as used herein is synonymous with "nucleic acid" and "polynucleotide." A nucleic acid molecule is usually at least 10 bases in length, unless otherwise specified. The term includes single- and double-stranded forms of DNA. A polynucleotide may include either or both naturally occurring and modified nucleotides linked together by naturally occurring and/or non-naturally occurring nucleotide linkages.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked nucleic acid sequences are contiguous and, where necessary to join two protein-coding regions, in the same reading frame.

Paramyxovirus: A family of enveloped non-segmented negative-sense single-stranded RNA viruses. Examples of paramyxoviruses include, but are not limited to, human parainfluenza virus (HPIV) including types 1, 2, 3, 4A, and 4B (HPIV1, HPIV2, HPIV3, HPIV4A, and HPIV4B, respectively), mouse parainfluenza type 1 (Sendai virus, MPIV1), bovine parainfluenza virus type 3 (BPIV3), parainfluenza virus 5 (PIV5, previously called simian virus 5, SV5), simian virus 41 (SV41), and mumps virus. HPIV1, HPIV3, MPIV1, and BPIV3 are classified in the genus *Respirovirus*. HPIV2, HPIV4, SV5, SV41, and mumps virus are classified in the genus *Rubulavirus*. MPIV1, PIV5, and BPIV3 are animal relatives of HPIV1, HPIV2, and HPIV3, respectively (Chancock et al., Parainfluenza Viruses, Knipe et al. (Eds.), pp. 1341-1379, Lippincott Williams & Wilkins, Philadelphia, 2001). HPIV1, HPIV2, and HPIV3 represent distinct serotypes and do not elicit significant cross immunity. HPIVs are etiological agents of respiratory infections such as croup, pneumonia, or bronchitis.

Parainfluenza virus (PIV): A number of enveloped non-segmented negative-sense single-stranded RNA viruses from family Paramyxoviridae that are descriptively grouped together. This includes all of the members of genus *Respirovirus* (e.g., HPIV1, HPIV3) and a number of members of genus *Rubulavirus* (e.g. HPIV2, HPIV4, PIV5). Members of genus *Avulavirus* (e.g., NDV) historically have been called PIVs and can be considered as part of this group. HPIV serotypes 1, 2, and 3 are second only to RSV in causing severe respiratory infections in infants and children worldwide, with HPIV3 being the most important of the HPIVs in terms of disease impact. PIVs are made up of two structural modules: (1) an internal ribonucleoprotein core, or nucleocapsid, containing the viral genome, and (2) an outer, roughly spherical lipoprotein envelope. The PIV viral genome is approximately 15,000 nucleotides in length and encodes at least eight polypeptides. These proteins include the nucleocapsid structural protein (NP, NC, or N depending on the genera), the phosphoprotein (P), the matrix protein (M), the fusion glycoprotein (F), the hemagglutinin-neuraminidase glycoprotein (HN), the large polymerase protein (L), and the C and D proteins. The P gene contains one or more additional open reading frames (ORFs) encoding accessory proteins. The gene order is 3'-N-P-M-F-HN-L-5', and each gene encodes a separate protein encoding mRNA. Exemplary PIV strain sequences are known to the person of ordinary skill in the art, such as the sequences of the HPIV1, HPIV2, HPIV3, and BPIV3 viruses.

Pharmaceutically acceptable carriers: The pharmaceutically acceptable carriers of use are conventional. *Remington's Pharmaceutical Sciences*, by E. W. Martin, Mack Publishing Co., Easton, Pa., 19th Edition, 1995, describes compositions and formulations suitable for pharmaceutical delivery of the disclosed immunogens.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate. In particular embodiments, suitable for administration to a subject the carrier may be sterile, and/or suspended or otherwise contained in a unit dosage form containing one or more measured doses of the composition suitable to induce the desired immune response. It may also be accompanied by medications for its use for treatment purposes. The unit dosage form may be, for example, in a sealed vial that contains sterile contents or a syringe for injection into a subject, or lyophilized for subsequent solubilization and administration or in a solid or controlled release dosage.

Polypeptide: Any chain of amino acids, regardless of length or post-translational modification (e.g., glycosylation or phosphorylation). "Polypeptide" applies to amino acid polymers including naturally occurring amino acid polymers and non-naturally occurring amino acid polymer as well as in which one or more amino acid residue is a non-natural amino acid, for example an artificial chemical mimetic of a corresponding naturally occurring amino acid. A "residue"

refers to an amino acid or amino acid mimetic incorporated in a polypeptide by an amide bond or amide bond mimetic. A polypeptide has an amino terminal (N-terminal) end and a carboxy terminal (C-terminal) end. "Polypeptide" is used interchangeably with peptide or protein, and is used herein to refer to a polymer of amino acid residues.

Prime-boost vaccination: An immunotherapy including administration of a first immunogenic composition (the primer vaccine) followed by administration of a second immunogenic composition (the booster vaccine) to a subject to induce an immune response. The booster vaccine is administered to the subject after the primer vaccine; the skilled artisan will understand a suitable time interval between administration of the primer vaccine and the booster vaccine, and examples of such timeframes are disclosed herein. Additional administrations can be included in the prime-boost protocol, for example a second boost.

Recombinant: A recombinant nucleic acid molecule is one that has a sequence that is not naturally occurring: for example, includes one or more nucleic acid substitutions, deletions or insertions, and/or has a sequence that is made by an artificial combination of two otherwise separated segments of sequence. This artificial combination can be accomplished by chemical synthesis or, more commonly, by the artificial manipulation of isolated segments of nucleic acids, for example, by genetic engineering techniques.

A recombinant virus is one that includes a genome that includes a recombinant nucleic acid molecule.

A recombinant protein is one that has a sequence that is not naturally occurring or has a sequence that is made by an artificial combination of two otherwise separated segments of sequence. In several embodiments, a recombinant protein is encoded by a heterologous (for example, recombinant) nucleic acid that has been introduced into a host cell, such as a bacterial or eukaryotic cell, or into the genome of a recombinant virus.

Respiratory Syncytial Virus (RSV): An enveloped non-segmented negative-sense single-stranded RNA virus of the family Paramyxoviridae. The RSV genome is ~15,000 nucleotides in length and includes 10 genes encoding 11 proteins, including the glycoproteins SH, G and F. The F protein mediates fusion, allowing entry of the virus into the cell cytoplasm and also promoting the formation of syncytia. Two antigenic subgroups of human RSV strains have been described, the A and B subgroups, based primarily on differences in the antigenicity of the G glycoprotein. RSV strains for other species are also known, including bovine RSV. Exemplary RSV strain sequences are known to the person of ordinary skill in the art. Further, several models of human RSV infection are available, including model organisms infected with hRSV, as well as model organisms infected with species specific RSV, such as use of bRSV infection in cattle (see, e.g., Bern et al., *Am J. Physiol. Lung Cell Mol. Physiol.,* 301: L148-L156, 2011; and Nam and Kun (Eds.). Respiratory Syncytial Virus: Prevention, Diagnosis and Treatment. Nova Biomedical Nova Science Publisher, 2011; and Cane (Ed.) Respiratory Syncytial Virus. Elsevier Science, 2007.)

RSV Fusion (F) protein: An RSV envelope glycoprotein that facilitates fusion of viral and cellular membranes. In nature, the RSV F protein is initially synthesized as a single polypeptide precursor approximately 574 amino acids in length, designated $F_0$. $F_0$ includes an N-terminal signal peptide that directs localization to the endoplasmic reticulum, where the signal peptide (approximately the first 22 residues of $F_0$) is proteolytically cleaved. The remaining $F_0$ residues oligomerize to form a trimer which is again proteolytically processed by a cellular protease at two conserved furin consensus cleavage sequences (approximately $F_0$ positions 109/110 and 136/137; for example, $RARR_{109}$ (SEQ ID NO: 1, residues 106-109) and $RKRR_{136}$ (SEQ ID NO: 1, residues 133-136) to excise the pep27 polypeptide and generate two disulfide-linked fragments, $F_1$ and $F_2$. The smaller of these fragments, $F_2$, originates from the N-terminal portion of the $F_0$ precursor and includes approximately residues 26-109 of $F_0$. The larger of these fragments, $F_1$, includes the C-terminal portion of the $F_0$ precursor (approximately residues 137-574) including an extracellular/lumenal region (~residues 137-529), a TM (residues 530-550), and a CT (residues 551-574) at the C-terminus.

Three $F_2$-$F_1$ protomers oligomerize in the mature F protein, which adopts a metastable "prefusion" conformation that is triggered to undergo a conformational change (to a "postfusion" conformation) upon contact with a target cell membrane. This conformational change exposes a hydrophobic sequence, known as the fusion peptide, which is located at the N-terminus of the $F_1$ polypeptide, and which associates with the host cell membrane and promotes fusion of the membrane of the virus, or an infected cell, with the target cell membrane.

The extracellular portion of the RSV F protein is the RSV F ectodomain, which includes the $F_2$ protein and the $F_1$ ectodomain. An RSV F ectodomain trimer includes a protein complex of three RSV F ectodomains.

The RSV F protein adopts a "prefusion" conformation prior to triggering of the fusogenic event that leads to transition of RSV F to the postfusion conformation and following processing into a mature RSV F protein in the secretory system. The three-dimensional structure of an exemplary RSV F protein in a prefusion conformation is known, and disclosed for example in WO2014160463, which is incorporated by reference herein. In the prefusion state, the RSV F protein includes an antigenic site at its membrane distal apex termed "antigenic site Ø," that includes RSV F residues 62-69 and 196-209, and also includes the epitopes of the D25 and AM22 monoclonal antibodies. Thus, a recombinant RSV F protein stabilized in a prefusion conformation can be specifically bound by an antibody that binds the pre- but not post-fusion conformation of the RSV F protein, such as an antibody that specifically binds to an epitope within antigenic site Ø, for example, the D25 or AM22 antibody. Additional RSV F prefusion specific antibodies include the 5C4 and MPE8 antibodies.

Sequence identity: The similarity between amino acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs, orthologs, or variants of a polypeptide will possess a relatively high degree of sequence identity when aligned using standard methods.

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene,* 73:237-44, 1988; Higgins & Sharp, *CABIOS* 5:151-3, 1989; Corpet et al., *Nuc. Acids Res.* 16:10881-90, 1988; Huang et al. *Computer Appls. in the Biosciences* 8, 155-65, 1992; and Pearson et al., *Meth. Mol. Bio.* 24:307-31, 1994. Altschul et al., *J.*

*Mol. Biol.* 215:403-10, 1990, presents a detailed consideration of sequence alignment methods and homology calculations.

Once aligned, the number of matches is determined by counting the number of positions where an identical nucleotide or amino acid residue is present in both sequences. The percent sequence identity is determined by dividing the number of matches either by the length of the sequence set forth in the identified sequence, or by an articulated length (such as 100 consecutive nucleotides or amino acid residues from a sequence set forth in an identified sequence), followed by multiplying the resulting value by 100. For example, a peptide sequence that has 1166 matches when aligned with a test sequence having 1554 amino acids is 75.0 percent identical to the test sequence (1166÷1554*100=75.0). The percent sequence identity value is rounded to the nearest tenth. For example, 75.11, 75.12, 75.13, and 75.14 are rounded down to 75.1, while 75.15, 75.16, 75.17, 75.18, and 75.19 are rounded up to 75.2. The length value will always be an integer.

The NCBI Basic Local Alignment Search Tool (BLAST) (Altschul et al., *J. Mol. Biol.* 215:403, 1990) is available from several sources, including the National Center for Biotechnology Information (NCBI, Bethesda, Md.) and on the internet, for use in connection with the sequence analysis programs blastp, blastn, blastx, tblastn and tblastx. A description of how to determine sequence identity using this program is available on the NCBI website on the internet.

Homologs and variants of a polypeptide (such as a RSV F ectodomain) are typically characterized by possession of at least about 75%, for example at least about 80%, 85%, 90%, 91%, 92%, 93%, 94%, 95%, 96%, 97%, 98% or 99% sequence identity counted over the full length alignment with the amino acid sequence of interest. Proteins with even greater similarity to the reference sequences will show increasing percentage identities when assessed by this method, such as at least 80%, at least 85%, at least 90%, at least 95%, at least 98%, or at least 99% sequence identity. When less than the entire sequence is being compared for sequence identity, homologs and variants will typically possess at least 80% sequence identity over short windows of 10-20 amino acids, and may possess sequence identities of at least 85% or at least 90% or 95% depending on their similarity to the reference sequence. Methods for determining sequence identity over such short windows are available at the NCBI website on the internet. One of skill in the art will appreciate that these sequence identity ranges are provided for guidance only; it is entirely possible that strongly significant homologs could be obtained that fall outside of the ranges provided.

For sequence comparison of nucleic acid sequences, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters are used. Methods of alignment of sequences for comparison are well known in the art. Optimal alignment of sequences for comparison can be conducted, e.g., by the local homology algorithm of Smith & Waterman, *Adv. Appl. Math.* 2:482, 1981, by the homology alignment algorithm of Needleman & Wunsch, *J. Mol. Biol.* 48:443, 1970, by the search for similarity method of Pearson & Lipman, *Proc. Nat'l. Acad. Sci. USA* 85:2444, 1988, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Sambrook et al. (Molecular Cloning: A Laboratory Manual, $4^{th}$ ed, Cold Spring Harbor, N.Y., 2012) and Ausubel et al. (In Current Protocols in Molecular Biology, John Wiley & Sons, New York, through supplement 104, 2013). One example of a useful algorithm is PILEUP. PILEUP uses a simplification of the progressive alignment method of Feng & Doolittle, *J. Mol. Evol.* 35:351-360, 1987. The method used is similar to the method described by Higgins & Sharp, *CABIOS* 5:151-153, 1989. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, e.g., version 7.0 (Devereaux et al., *Nuc. Acids Res.* 12:387-395, 1984.

Another example of algorithms that are suitable for determining percent sequence identity and sequence similarity are the BLAST and the BLAST 2.0 algorithm, which are described in Altschul et al., *J. Mol. Biol.* 215:403-410, 1990 and Altschul et al., *Nucleic Acids Res.* 25:3389-3402, 1977. Software for performing BLAST analyses is publicly available through the National Center for Biotechnology Information (ncbi.nlm.nih.gov). The BLASTN program (for nucleotide sequences) uses as defaults a word length (W) of 11, alignments (B) of 50, expectation (E) of 10, M=5, N=−4, and a comparison of both strands. The BLASTP program (for amino acid sequences) uses as defaults a word length (W) of 3, and expectation (E) of 10, and the BLOSUM62 scoring matrix (see Henikoff & Henikoff, *Proc. Natl. Acad. Sci. USA* 89:10915, 1989). An oligonucleotide is a linear polynucleotide sequence of up to about 100 nucleotide bases in length.

As used herein, reference to "at least 90% identity" refers to "at least 90%, at least 91%, at least 92%, at least 93%, at least 94%, at least 95%, at least 96%, at least 97%, at least 98%, at least 99%, or even 100% identity" to a specified reference sequence.

Subject: Living multi-cellular vertebrate organisms, a category that includes human and non-human mammals. In an example, a subject is a human. In a particular example, the subject is a newborn infant. In an additional example, a subject is selected that is in need of inhibiting of an RSV infection. For example, the subject is either uninfected and at risk of RSV infection or is infected in need of treatment.

Transmembrane domain (TM): An amino acid sequence that spans a lipid bilayer, such as the lipid bilayer of a cell or virus or virus-like particle. A transmembrane domain can be used to anchor an antigen to a membrane. In some examples a transmembrane domain is a RSV F transmembrane domain.

Vaccine: A preparation of immunogenic material capable of stimulating an immune response, administered for the prevention, amelioration, or treatment of infectious or other types of disease. The immunogenic material may include attenuated or killed microorganisms (such as bacteria or viruses), or antigenic proteins, peptides or DNA derived from them. An attenuated vaccine is a virulent organism that has been modified to produce a less virulent form, but nevertheless retains the ability to elicit antibodies and cell-mediated immunity against the virulent form. An inactivated (killed) vaccine is a previously virulent organism that has been inactivated with chemicals, heat, or other treatment, but elicits antibodies against the organism. Vaccines may elicit both prophylactic (preventative or protective) and therapeutic responses. Methods of administration vary according to the vaccine, but may include inoculation, ingestion, inhalation or other forms of administration. Vaccines may be administered with an adjuvant to boost the immune response.

Vector: An entity containing a DNA or RNA molecule bearing a promoter(s) that is operationally linked to the coding sequence of an antigen(s) of interest and can express the coding sequence. Non-limiting examples include a naked or packaged (lipid and/or protein) DNA, a naked or packaged RNA, a subcomponent of a virus or bacterium or other microorganism that may be replication-incompetent, or a virus or bacterium or other microorganism that may be replication-competent. A vector is sometimes referred to as a construct. Recombinant DNA vectors are vectors having recombinant DNA. A vector can include nucleic acid sequences that permit it to replicate in a host cell, such as an origin of replication. A vector can also include one or more selectable marker genes and other genetic elements known in the art. Viral vectors are recombinant nucleic acid vectors having at least some nucleic acid sequences derived from one or more viruses.

II. Recombinant Viral Vectors

Recombinant paramyxoviruses are provided that include antigens from multiple viral pathogens, and can be used to induce an immune response to those viral pathogens. The recombinant paramyxoviruses include a genome encoding a heterologous gene. The recombinant paramyxoviruses comprise a genome comprising a heterologous gene encoding the ectodomain of a transmembrane protein (e.g., a viral glycoprotein) of a heterologous viral pathogen. The ectodomain can be linked to a CT, or a TM and a CT of an envelope protein from the paramyxovirus to allow for expression of the ectodomain of the transmembrane protein from the heterologous virus on the paramyxovirus envelope. For example, the recombinant paramyxovirus can be a recombinant PIV comprising a genome comprising a heterologous gene encoding the ectodomain of an RSV F protein linked to the TM and CT of the F protein from the PIV. Additional description of the recombinant paramyxovirus and modifications thereof is provided herein.

The paramyxovirus genome includes genes encoding N, P, M, F, HN, and L proteins. The genome also includes a genomic promoter and anti-promoter, with the order of promoter-N, P, M, F, HN, L-antipromoter. The heterologous gene included in the genome of the recombinant paramyxovirus can be located at any position between genes of the paramyxovirus genome, or between the promoter and the N gene, or the L gene and the antipromoter. The heterologous gene can be flanked by appropriate gene start and gene-end sequences to facilitate expression from the viral genome. In a preferred embodiment, the heterologous gene can be located between the promoter and the N gene, or between the N gene and the P gene.

In an embodiment, the heterologous gene included in the genome of the recombinant paramyxovirus encodes the ectodomain of a type I transmembrane protein (e.g., a type I viral glycoprotein) linked to a CT, or TM and CT, of the F protein of the paramyxovirus. In other embodiments, the heterologous gene included in the genome of the recombinant paramyxovirus encodes the ectodomain of a type II transmembrane protein (e.g., a type II viral glycoprotein) linked to a CT, or TM and CT, of the HN protein of the paramyxovirus.

The recombinant paramyxovirus can be a recombinant HPIV1, a HPIV2, a HPIV3, a BPIV3, a PIV5, a Sendai virus, or a NDV, or a chimera thereof, for example. Additional description of such recombinant paramyxovirus is provided below.

General methods of generating a recombinant paramyxovirus including a genome including a heterologous gene are known to the person of ordinary skill in the art, as are viral sequences and reagents for use in such methods. Non-limiting examples of methods of generating a recombinant PIV vector (such as a recombinant HPIV1, HPIV2, HPIV3, or H/BPIV3 vector) including a heterologous gene, methods of attenuating the vectors (e.g., by recombinant or chemical means), as well as viral sequences and reagents for use in such methods are provided in US Patent Publications 2012/0045471; 2010/0119547; 2009/0263883; 2009/0017517; 8084037; 6,410,023; 8,367,074; 7,951,383; 7,820,182; 7704509; 7632508; 7622123; 7250171; 7208161; 7201907; 7192593, and Newman et al. 2002. Virus genes 24:77-92, Tang et al., 2003. J Virol, 77(20):10819-10828; each of which is incorporated by reference herein in its entirety. Non-limiting examples of methods of generating a recombinant NDV vector including a heterologous gene, as well as viral sequences and reagents for use in such methods are provided in US Patent Publications 2012/0064112; and Basavarajappa et al. 2014 Vaccine, 32: 3555-3563, and McGinnes et al., J. Virol., 85: 366-377, 2011, each of which is incorporated by reference herein in its entirety. Non-limiting examples of methods of generating a recombinant Sendai vector including a heterologous gene, as well as viral sequences and reagents for use in such methods are provided in US Patent Publications 20140186397, and Jones et al., Vaccine, 30:959-968, 2012, each of which is incorporated by reference herein in its entirety.

A. HPIV1 Vectors

In some embodiments, the recombinant paramyxovirus can be a recombinant HPIV1 including a viral genome encoding HPIV1 N, P, C, M, F, HN, and L proteins. Nucleic acid sequences of HPIV1 genomes, and the genes therein, are known in the art, as are structural and functional genetic elements that control gene expression, such as gene start and gene end sequences and viral genome and anti-genome promoters. An exemplary HPIV1 Washington/1964 strain genome sequence is provided as GenBank Acc. No. AF457102.1, which is incorporated by reference herein in its entirety. This exemplary HPIV1 Washington/1964 strain genome sequence encodes N, P, C, M, F, HN, and L proteins set forth as: HPIV1 N, SEQ ID NO: 24 (GenBank protein ID #AAL89400.1, incorporated by reference herein) HPIV1 P, SEQ ID NO: 25 (GenBank protein ID #AAL89402.1, incorporated by reference herein) HPIV1 C, SEQ ID NO: 26 (ORF of P, GenBank protein ID #AAL89403.1, incorporated by reference herein) HPIV1 M, SEQ ID NO: 27 (GenBank protein ID #AAL89406.1, incorporated by reference herein) HPIV1 F, SEQ ID NO: 28 (GenBank protein ID #AAL89407.1, incorporated by reference herein) HPIV1 HN, SEQ ID NO: 29 (GenBank protein ID #AAL89408.1, incorporated by reference herein) HPIV1 L, SEQ ID NO: 30 (GenBank protein ID #AAL89409.1, incorporated by reference herein)

The corresponding gene-start and gene-end sequences for these HPIV1 genes are provided below:

| Gene | Gene start | SEQ ID | Gene end | SEQ ID | Intergenic |
|---|---|---|---|---|---|
| N | agggttaaag | 54 | aagtaagaaaaa | 55 | ctt |
| P | agggtgaatg | 56 | Aattaagaaaaa | 57 | ctt |
| M | agggtcaaag | 58 | Aaataagaaaaa | 59 | ctt |

-continued

| Gene | Gene start | SEQ ID | Gene end | SEQ ID | Intergenic |
|---|---|---|---|---|---|
| F | agggacaaag | 60 | Aagtaagaaaaa | 55 | ctt |
| HN | agggttaaag | 61 | Gaataagaaaaa | 62 | ctt |
| L | agggttaatg | 63 | Tagtaagaaaaa | 64 | ctt |

Further, viral leader/genome promoter and trailer/antigenome promoter of the HPIV2 V94 strain as set forth in GenBank Acc. No. AF457102.1 as nucleotides 1-96 and 15544-15600, respectively.

The recombinant paramyxovirus can be a recombinant HPIV1 including a viral genome encoding HPIV1 N, P, C, M, F, HN, and L proteins as set forth above, or encoding HPIV1 N, P, C, M, F, HN, and L proteins individually having at least 90% (such as at least 95%) sequence identity to the HPIV1 N, P, C, M, F, HN, and L proteins set forth above.

In some embodiments the recombinant paramyxovirus can be a recombinant HPIV1 including a genome including a heterologous gene encoding a recombinant viral glycoprotein ectodomain from a type I membrane protein (such as RSV F ectodomain) linked to a HPIV1 F protein TM and CT as set forth below, or encoding a recombinant viral glycoprotein ectodomain from a type I membrane protein (such as RSV F ectodomain) linked to a HPIV1 F protein TM and CT having at least 90% (such as at least 95%) sequence identity to the HPIV1 F protein TM and CT as set forth below. In some embodiments the recombinant paramyxovirus can be a recombinant HPIV1 including a genome including a heterologous gene encoding a recombinant viral glycoprotein ectodomain from a type I membrane protein (such as RSV F ectodomain) linked to a HPIV1 F protein CT as set forth below, or encoding a recombinant viral glycoprotein ectodomain from a type I membrane protein (such as RSV F ectodomain) linked to a HPIV1 F protein CT having at least 90% (such as at least 95%) sequence identity to the HPIV1 F protein CT as set forth below. HPIV1 F protein TM and CT sequences are known (see, e.g., GenBank accession # AF457102.1, incorporated by reference herein). Exemplary HPIV1 F protein TM and CT sequences are set forth as:

```
HPIV1 F TM:
QIIMIIIVCILIIIICGILYYLY, residues 1-23 of
SEQ ID NO: 31
```

-continued

```
HPIV1 F CT:
RVRRLLVMINSTHNSPVNAYTLESRMRNPYMGNNSN, residues
24-59 of SEQ ID NO: 31

HPIV1 F TM + CT:
QIIMIIIVCILIIIICGILYYLYRVRRLLVMINSTHNSPVNAYTLESRMRN
PYMGNNSN, SEQ ID NO: 31
```

B. HPIV2 Vectors

In some embodiments the recombinant paramyxovirus vector can be a recombinant HPIV2 including a viral genome encoding HPIV2 N, P, V, M, F, HN, and L proteins. The nucleic acid sequences of the gene encoding these HPIV2 proteins are known in the art, as are structural and functional genetic elements that control gene expression, such as gene start and gene-end sequences and viral genome and anti-genome promoters. An exemplary HPIV2 V94 strain genome sequence is provided as GenBank Acc. No. AF533010.1, which is incorporated by reference herein in its entirety. This exemplary HPIV2 V94 strain genome sequence encodes N, P, V, M, F, HN, and L proteins set forth as:

HPIV2 N, SEQ ID NO: 32 (encoded by GenBank No. AF533010.1, incorporated by reference herein)

HPIV2 P, SEQ ID NO: 33 (encoded by GenBank No. AF533010.1, incorporated by reference herein)

HPIV2 V, SEQ ID NO: 34 (ORF of P, encoded by GenBank No. AF533010.1, incorporated by reference herein)

HPIV2 M, SEQ ID NO: 35 (encoded by GenBank No. AF533010.1, incorporated by reference herein)

HPIV2 F, SEQ ID NO: 36 (encoded by GenBank No. AF533010.1, incorporated by reference herein)

HPIV2 HN, SEQ ID NO: 37 (encoded by GenBank No. AF533010.1, incorporated by reference herein)

HPIV2 L, SEQ ID NO: 38 (encoded by GenBank No. AF533010.1, incorporated by reference herein)

The corresponding gene-start and gene end sequences for these HPIV2 genes are provided below:

| Gene | Gene start | SEQ ID | Gene end | SEQ ID | Intergenic | SEQ ID |
|---|---|---|---|---|---|---|
| N | Agattccggtgccg | 65 | aatttaagaaaaaa | 66 | acat | |
| P | aggcccggacgggttag | 67 | aatttaataaaaaa | 68 | ttaaaagaagttaagtaaaatttaaagaacacaat agagaaaacct | 117 |
| M | Aggtccgaaagc | 69 | aatctaacaaaaaaa | 70 | ctaaacattcaataataaatcaaagttc | 118 |
| F | Aggccaaattat | 71 | aatttaagaaaaaa | 72 | cctaaaat | 119 |
| HN | Aagcacgaaccc | 73 | tatttaagaaaaaa | 74 | taatctttatataatgtaacaatactactaagattata atat | 120 |
| L | Aggccaga | 75 | tatttaagaaaaa | 76 | | |

Further, viral leader/genome promoter and trailer/antigenome promoter of the HPIV2 V94 strain as set forth in GenBank Acc. No. AF533010.1 are set forth as nucleotides 1-175 and 15565-15654, respectively.

The recombinant paramyxovirus can be a recombinant HPIV2 including a viral genome encoding HPIV2 N, P, V, M, F, HN, and L proteins as set forth above, or encoding HPIV2 N, P, V, M, F, HN, and L proteins individually having at least 90% (such as at least 95%) sequence identity to the HPIV2 N, P, V, M, F, HN, and L proteins set forth above.

In some embodiments the recombinant paramyxovirus can be a recombinant HPIV2 including a genome including a heterologous gene encoding a recombinant viral glycoprotein ectodomain from a type I membrane protein (such as RSV F ectodomain) linked to a HPIV2 F protein TM and CT as set forth below, or encoding a recombinant viral glycoprotein ectodomain from a type I membrane protein (such as RSV F ectodomain) linked to a HPIV2 F protein TM and CT having at least 90% (such as at least 95%) sequence identity to the HPIV2 F protein TM and CT as set forth below. In some embodiments the recombinant paramyxovirus can be a recombinant HPIV2 including a genome including a heterologous gene encoding a recombinant viral glycoprotein ectodomain from a type I membrane protein (such as RSV F ectodomain) linked to a HPIV2 F protein CT as set forth below, or encoding a recombinant viral glycoprotein ectodomain from a type I membrane protein (such as RSV F ectodomain) linked to a HPIV2 F protein CT having at least 90% (such as at least 95%) sequence identity to the HPIV2 F protein CT as set forth below. HPIV2 F protein TM and CT sequences are known (see, e.g., GenBank accession #AF533010.1, incorporated by reference herein). Exemplary HPIV2 F protein TM and CT sequences from the HPIV3 JS strain are set forth as:

```
HPIV2 F TM domain:
TLYSLSAIALILSVITLVVVGLLIAYII, residues 1-28
of SEQ ID NO: 39

HPIV2 F CT:
KLVSQIHQFRALAATTMFHRENPAVFSKNNHGNIYGIS, residues
29-66 of SEQ ID NO: 39

HPIV2 F TM+CT:
TLYSLSAIALILSVITLVVVGLLIAYIIKLVSQIHQFRALAATTMFHREN
PAVFSKNNHGNIYGIS, SEQ ID NO: 39
```

C. HPIV3 Vectors

In some embodiments the recombinant paramyxovirus can be a recombinant HPIV3 including a viral genome encoding HPIV3 N, P, C, M, F, HN, and L proteins. The nucleic acid sequences of the gene encoding these HPIV3 proteins are known in the art, as are structural and functional genetic elements that control gene expression, such as gene start and gene end sequences and viral genome and antigenome promoters. An exemplary HPIV3 JS strain genome sequence is provided as GenBank Acc. No. Z11575, which is incorporated by reference herein in its entirety. For this exemplary HPIV3 JS strain genome sequence nucleic acid sequences encoding the N, P, C, M, F, HN, and L proteins are set forth below.

HPIV3 N, SEQ ID NO: 40 (encoded by nucleotides 111-1658 of GenBank No. Z11575, incorporated by reference herein)

HPIV3 P, SEQ ID NO: 41 (encoded by nucleotides 1784-3595 of GenBank No. Z11575, incorporated by reference herein)

HPIV3 C, SEQ ID NO: 114 (encoded by nucleotides 1794-2393 of GenBank No. Z11575, incorporated by reference herein)

HPIV3 M, SEQ ID NO: 42 (encoded by nucleotides 3753-4814 of GenBank No. Z11575, incorporated by reference herein), HPIV3 F, SEQ ID NO: 43 (encoded by nucleotides 5072-6691 of GenBank No. Z11575, incorporated by reference herein), HPIV3 HN, SEQ ID NO: 44 (encoded by nucleotides 6806-8524 of GenBank No. Z11575, incorporated by reference herein)

HPIV3 L, SEQ ID NO: 45 (encoded by nucleotides 8646-15347 of GenBank No. Z11575, incorporated by reference herein)

In some embodiments, the HN gene in HPIV3 vector encodes a HPIV3 HN protein comprising the amino acid sequence set forth as

```
                                          (SEQ ID NO: 101)
MEYWKHTNHGKDAGNELETSMATHGNKLTNKIIYILWTIILVLLSIVFII

VLINSIKSEKAHESLLQDINNEFMEITEKIQMASDNTNDLIQSGVNTRLL

TIQSHVQNYIPISLTQQMSDLRKFISEITIRNDNQEVLPQRITHDVGIKP

LNPDDFWRCTSGLPSLMKTPKIRLMPGPGLLAMPTTVDGCVRTPSLVIND

LIYAYTSNLITRGCQDIGKSYQVLQIGIITVNSDLVPDLNPRISHTFNIN

DNRKSCSLALLNIDVYQLCSTPKVDERSDYASSGIEDIVLDIVNYDGSIS

TTRFKNNNISFDQPYAALYPSVGPGIYYKGKIIFLGYGGLEHPINENVIC

NTTGCPGKTQRDCNQASHSTWFSDRRMVNSIIVVDKGLNSIPKLKVWTIS

MRQNYWGSEGRLLLLGNKIYIYTRSTSWHSKLQLGIIDITDYSDIRIKWT

WHNVLSRPGNNECPWGHSCPDGCITGVYTDAYPLNPTGSIVSSVILDSQK

SRVNPVITYSTATERVNELAILNRTLSAGYTTTSCITHYNKGYCFHIVEI

NHKSLNTFQPMLFKTEIPKSCS
```

An exemplary DNA sequence encoding SEQ ID NO: 101 is provided as follows:

```
                                          (SEQ ID NO: 102)
atggaatactggaagcataccaatcacggaaaggatgctggtaatgagctg

gagacgtctatggctactcatggcaacaagctcactaataagataatatac

atattatggacaataatcctggtgttattatcaatagtcttcatcatagtg

ctaattaattccatcaaaagtgaaaaggcccacgaatcattgctgcaagac

ataaataatgagtttatggaaattacagaaaagatccaaatggcatcggat

aataccaatgatctaatacagtcaggagtgaatacaaggcttcttacaatt

cagagtcatgtccagaattacataccaatatcattgacacaacagatgtca

gatcttaggaaattcattagtgaaattacaattagaaatgataatcaagaa

gtgctgccacaaagaataacacatgatgtaggtataaaacctttaaatcca

gatgatttttggagatgcacgtctggtcttccatctttaatgaaaactcca

aaaataaggttaatgccagggccgggattattagctatgccaacgactgtt

gatggctgtgttagaactccgtctttagttataaatgatctgatttatgct

tatacctcaaatctaattactcgaggttgtcaggatataggaaaatcatat

caagtcttacagatagggataataactgtaaactcagacttggtacctgac

ttaaatcctaggatctctcatacctttaacataaatgacaataggaagtca

tgttctctagcactcctaaatatagatgtatatcaactgtgttcaactccc

aaagttgatgaaagatcagattatgcatcatcaggcatagaagatattgta

cttgatattgtcaattatgatggttcaatctcaacaacaagatttaagaat

aataacataagctttgatcaaccatatgctgcactatacccatctgttgga

ccagggatatactacaaaggcaaaataatatttctcgggtatggaggtctt

gaacatccaataaatgagaatgtaatctgcaacacaactgggtgccccggg

aaaacacagagagactgtaatcaagcatctcatagtacttggttttcagat

aggaggatggtcaactccatcattgttgttgacaaaggcttaaactcaatt
```

-continued

```
ccaaaattgaaagtatggacgatatctatgcgacaaaattactggggtca

gaaggaaggttacttctactaggtaacaagatctatatatatacaagatct

acaagttggcatagcaagttacaattaggaataattgatattactgattac

agtgatataaggataaaatggacatggcataatgtgctatcaagaccagga

aacaatgaatgtccatggggacattcatgtccagatggatgtataacagga

gtatatactgatgcatatccactcaatcccacagggagcattgtgtcatct

gtcatattagactcacaaaaatcgagagtgaacccagtcataacttactca

acagcaaccgaaagagtaaacgagctggccatcctaaacagaacactctca

gctggatatacaacaacaagctgcattacacactataacaaaggatattgt

tttcatatagtagaaataaatcataaaagcttaaacacatttcaacccatg

ttgttcaaaacagagattccaaaaagctgcagttaa
```

The corresponding gene-start and gene end sequences for these HPIV3 genes are provided below:

| Gene | Gene start | SEQ ID | Gene end | SEQ ID |
|---|---|---|---|---|
| N | aggattaaa-gac | 77 | aaataagaaaaa | 78 |
| P | Aggattaaag | 79 | aaataagaaaaa | 80 |
| M | Aggattaaag | 81 | aaataaaggataatcaaaaa | 82 |
| F | Aggacaaaag | 83 | aattataaaaaa | 84 |
| HN | Aggagtaaag | 85 | aaatataaaaaa | 86 |
| L | Aggagcaaag | 87 | aaagtaagaaaaa | 88 |

Further, viral genome and anti-genome promoters of the HPIV3 JS strain as set forth in GenBank Acc. No. Z11575 are provided as nucleotides 1-96 (genomic promoter) and nucleotides 15367-15462 (antigenomic promoter), respectively.

The recombinant paramyxovirus can be a recombinant HPIV3 including a viral genome encoding HPIV3 N, P, C, M, F, HN, and L proteins as set forth above, or encoding HPIV3 N, P, C, M, F, HN, and L proteins individually having at least 90% (such as at least 95%) sequence identity to the HPIV3 N, P, C, M, F, HN, and L proteins set forth above.

In some embodiments the recombinant paramyxovirus can be a recombinant HPIV3 including a genome including a heterologous gene encoding a recombinant viral glycoprotein ectodomain from a type I membrane protein (such as RSV F ectodomain) linked to a HPIV3 F protein TM and CT as set forth below, or encoding a recombinant viral glycoprotein ectodomain from a type I membrane protein (such as RSV F ectodomain) linked to a HPIV3 F protein TM and CT having at least 90% (such as at least 95%) sequence identity to the HPIV3 F protein TM and CT as set forth below. In some embodiments the recombinant paramyxovirus can be a recombinant HPIV3 including a genome including a heterologous gene encoding a recombinant viral glycoprotein ectodomain from a type I membrane protein (such as RSV F ectodomain) linked to a HPIV3 F protein CT as set forth below, or encoding a recombinant viral glycoprotein ectodomain from a type I membrane protein (such as RSV F ectodomain) linked to a HPIV3 F protein CT having at least 90% (such as at least 95%) sequence identity to the HPIV3 F protein CT as set forth below. HPIV3 F protein TM and CT sequences are known (see, e.g., protein encoded by nucleotides 5072-6691 of GenBank No. Z11575). Exemplary HPIV3 F protein TM and CT sequences from the HPIV3 JS strain are set forth as:

```
HPIV3 F TM domain:
IIIILIMIIILFIINITIITIAI, residues 1-23 of
SEQ ID NO: 46

HPIV3 F CT:
KYYRIQKRNRVDQNDKPYVLTNK, residues 24-46 of
SEQ ID NO: 46

HPIV3 F TM+CT:
IIIILIMIIILFIINITIITIAIKYYRIQKRNRVDQNDKPYVLTNK,
SEQ ID NO: 46
```

D. Bovine PIV3 and Chimeric Human/Bovine PIV3 Vectors

In some embodiments the recombinant paramyxovirus can be bovine PIV3 (BPIV3) or a chimeric paramyxovirus including a viral genome encoding a combination of N, P, C, V, M, F, HN, and L proteins from BPIV3 and HPIV3. For example, the chimeric viral genome can encode HPIV3 F and HN proteins and BPIV3 N, P, C, V, M, and L proteins. The nucleic acid sequences of the genes encoding these HPIV3 and BPIV3 proteins are known in the art, as are structural and functional genetic elements that control gene expression, such as gene start and gene end sequences and viral genome and anti-genome promoters. An exemplary BPIV3 Kansas genome sequence is provided as GenBank Acc. No. AF178654, which is incorporated by reference herein in its entirety. This exemplary BPIV3 Kansas strain genome sequence encodes N, P, C, V, M, F, HN, and L proteins set forth below:

BPIV3 N, SEQ ID NO: 47 (GenBank Acc. No.: AAF28254, encoded by nucleotides 111-1658 of GenBank No. AF178654, each of which is incorporated by reference herein)

BPIV3 P, SEQ ID NO: 48 (GenBank Acc. No.: AAF28255, encoded by nucleotides 1784-3574 of GenBank No. AF178654, each of which is incorporated by reference herein)

BPIV3 C, SEQ ID NO: 115 (encoded by nucleotide 1794-2399 of GenBank No. AF178654, incorporated by reference herein)

BPIV3 V, SEQ ID NO: 116 (encoded by nucleotide 1784-3018 of GenBank No. AF178654 with an inserted nucleotide g between nucleotide 2505-2506 at a gene editing site located at nucleotide 2500-2507)

BPIV3 M, SEQ ID NO: 49 (GenBank Acc. No.: AAF28256, encoded by nucleotides 3735-4790 of GenBank No. AF178654, each of which is incorporated by reference herein)

BPIV3 F, SEQ ID NO: 50 (GenBank Acc. No.: AAF28257, encoded by nucleotides 5066-6688 of GenBank No. AF178654, each of which is incorporated by reference herein)

BPIV3 HN, SEQ ID NO: 51 (GenBank Acc. No.: AAF28258, encoded by nucleotides 6800-8518 of GenBank No. AF178654, each of which is incorporated by reference herein)

BPIV3 L, SEQ ID NO: 52 (GenBank Acc. No.: AAF28259, encoded by nucleotides 8640-15341 of GenBank No. AF178654, each of which is incorporated by reference herein)

In some embodiments, the HPIV3 HN gene included in chimeric B/HPIV3 vector encodes a HPIV3 HN protein comprising the amino acid sequence set forth as SEQ ID NO: 101 or SEQ ID NO: 44, or a variant thereof. An exemplary DNA sequence encoding SEQ ID NO: 101 is provided SEQ ID NO: 102.

In some embodiments, the chimeric B/HPIV3 vector can include a HPIV3 F gene in place of the BPIV3 F gene, for example a gene encoding a HPIV3 F amino acid sequence set forth as SEQ ID NO: 43, or a variant thereof.

The corresponding gene-start and gene end sequences for these BPIV3 genes are provided below:

| Gene | Gene start | SEQ ID | Gene end | SEQ ID |
|---|---|---|---|---|
| N | Aggattaaagaa | 89 | caagtaagaaaaa | 90 |
| P | Aggattaatgga | 91 | tgattaagaaaaa | 92 |
| M | Aggatgaaagga | 93 | gaaaaatcaaaaa | 94 |
| F | Aggatcaaaggg | 95 | aaaagtacaaaaaa | 96 |
| HN | Aggaacaaagtt | 97 | gaaataataaaaaa | 98 |
| L | Aggagaaaagtg | 99 | aaagtaagaaaaa | 100 |

Further, viral genome and anti-genome promoters of the BPIV3 Kansas strain as set forth in GenBank Acc. No. AF178654 are provided as nucleotides 1-96 (genomic promoter) and nucleotides 15361-15456 (antigenomic promoter), respectively.

The recombinant paramyxovirus including a viral genome encoding N, P, C, V, M, F, HN, and L proteins from HPIV3 and BPIV3 viruses can encode a mixture of the HPIV3 and BPIV3 N, P, C, V, M, F, HN, and L proteins as set forth above, or can encode a mixture of the BPIV3 and HPIV3 N, P, C, V, M, F, HN, and L proteins individually having at least 90% (such as at least 95%) sequence identity to the BPIV3 or HPIV3 N, P, C, V, M, F, HN, and L proteins set forth above.

In some embodiments, the recombinant paramyxovirus can include a viral genome encoding HPIV3 F and HN proteins and BPIV3 N, P, C, V, M, and L proteins as set forth above, or encoding HPIV3 F and HN proteins and BPIV3 N, P, C, V, M, and L proteins individually having at least 90% (such as at least 95%) sequence identity to the corresponding HPIV3 F and HN protein or BPIV3 N, P, C, V, M, and L protein set forth above.

In some embodiments, the recombinant paramyxovirus including a genome encoding N, P, C, V, M, F, HN, and L proteins from BPIV3 can further include a heterologous gene encoding a recombinant viral glycoprotein ectodomain from a type I membrane protein (such as RSV F ectodomain) linked to a TM and CT of the BPIV3 F protein as set forth below, or linked to a TM and CT having at least 90% (such as at least 95%) sequence identity to the TM and CT of the BPIV3 F protein as set forth below. In some embodiments, the recombinant paramyxovirus including a genome encoding N, P, C, V, M, F, HN, and L proteins from BPIV3 can further include a heterologous gene encoding a recombinant viral glycoprotein ectodomain from a type I membrane protein (such as RSV F ectodomain) linked to a CT of the BPIV3 F protein as set forth below, or linked to a CT having at least 90% (such as at least 95%) sequence identity to the CT of the BPIV3 F protein as set forth below.

In some embodiments, the recombinant paramyxovirus including a genome encoding N, P, C, V, M, F, HN, and L proteins from HPIV3 and BPIV3 viruses (such as HPIV3 F and HN proteins and BPIV3 N, P, C, V, M, and L proteins) can further include a heterologous gene encoding a recombinant viral glycoprotein ectodomain from a type I membrane protein (such as RSV F ectodomain) linked to a TM and CT of the BPIV3 F protein as set forth below, or linked to a TM and CT having at least 90% (such as at least 95%) sequence identity to the TM and CT of the BPIV3 F protein as set forth below. In some embodiments, the recombinant paramyxovirus including a genome encoding N, P, C, V, M, F, HN, and L proteins from HPIV3 and BPIV3 viruses can further include a heterologous gene encoding a recombinant viral glycoprotein ectodomain from a type I membrane protein (such as RSV F ectodomain) linked to a CT of the BPIV3 F protein as set forth below, or linked to a CT having at least 90% (such as at least 95%) sequence identity to the CT of the BPIV3 F protein as set forth below. Exemplary BPIV3 F protein TM and CT sequences from the BPIV3 Kansas strain are set forth as:

```
BPIV3 F TM domain:
ITIIIVMIIILVIINITIIVV, residues 1-21 of SEQ ID
NO: 53

BPIV3 F CT:
IIKFHRIQGKDQNDKNSEPYILTNRQ, residues 22-57 of SEQ
ID NO: 53

BPIV3 F TM+CT:
ITIIIVMIIILVIINITIIVVIIKFHRIQGKDQNDKNSEPYILTNRQ,
SEQ ID NO: 53
```

In some embodiments, the recombinant paramyxovirus including a genome encoding N, P, C, V, M, F, HN, and L proteins from HPIV3 and BPIV3 viruses (such as HPIV3 F and HN proteins and BPIV3 N, P, C, V, M, and L proteins) can further include a heterologous gene encoding a recombinant viral glycoprotein ectodomain from a type I membrane protein (such as RSV F ectodomain) linked to a TM and CT of the HPIV3 F protein as set forth above, or linked to a TM and CT having at least 90% (such as at least 95%) sequence identity to the TM and CT of the HPIV3 F protein as set forth above. In some embodiments, the recombinant paramyxovirus including a genome encoding N, P, C, V, M, F, HN, and L proteins from HPIV3 and BPIV3 viruses can further include a heterologous gene encoding a recombinant viral glycoprotein ectodomain from a type I membrane protein (such as RSV F ectodomain) linked to a CT of the HPIV3 F protein as set forth below, or linked to a CT having at least 90% (such as at least 95%) sequence identity to the CT of the HPIV3 F protein as set forth below.

E. Sendai Virus

In an embodiment, the recombinant paramyxovirus can be a recombinant Sendai virus including a recombinant viral genome encoding Sendai virus N, P, C, V, M, F, HN, and L proteins including a heterologous gene encoding a recombinant viral glycoprotein ectodomain from a type I membrane protein (such as RSV F ectodomain) linked to a TM and CT of the Sendai virus F protein, or linked to a TM and CT having at least 90% (such as at least 95%) sequence identity to the CT of the Sendai virus F protein. In an embodiment, the recombinant paramyxovirus can be a recombinant Sendai virus including a recombinant viral genome encoding Sendai virus N, P, C, V, M, F, HN, and L proteins including a heterologous gene encoding a recombinant viral glycoprotein ectodomain from a type I membrane protein (such as RSV F ectodomain) linked to a CT of the Sendai virus F protein, or linked to a CT having at least 90% (such as at least 95%) sequence identity to the CT of the Sendai virus F protein. Sendai virus F protein TM and CT sequences are known (see, e.g., GenBank accession

#BAN84670, incorporated by reference herein). Exemplary Sendai virus F protein TM and CT sequences are set forth as:

```
Sendai F TM domain:
VITIIVVMVVILVVIIVIIIV (residues 1-21 of SEQ ID
NO: 103)

Sendai F CT:
LYRLRRSMLMGNPDDRIPRDTYTLEPKIRHMYTNGGFDAMAEKR
(residues 22-65 of SEQ ID NO: 103)

Sendai F TM+CT:
VITIIVVMVVILVVIIVIIIVLYRLRRSMLMGNPDDRIPRDTYTLEPKIR
HMYTNGGFDAMAEKR, SEQ ID NO: 103
```

F. NDV

In some embodiments the recombinant paramyxovirus can be a recombinant NDV virus including a recombinant viral genome encoding NDV N, P, V, M, F, HN, and L proteins including a heterologous gene encoding a recombinant viral glycoprotein ectodomain from a type I membrane protein (such as RSV F ectodomain) linked to a TM and CT of the NDV F protein as set forth below, or linked to a TM and CT having at least 90% (such as at least 95%) sequence identity to the TM and CT of the NDV F protein as set forth below. In some embodiments the recombinant paramyxovirus can be a recombinant NDV virus including a recombinant viral genome encoding NDV N, P, V, M, F, HN, and L proteins including a heterologous gene encoding a recombinant viral glycoprotein ectodomain from a type I membrane protein (such as RSV F ectodomain) linked to a CT of the NDV F protein as set forth below, or linked to a CT having at least 90% (such as at least 95%) sequence identity to the CT of the NDV F protein as set forth below. NDV virus F protein TM and CT sequences are known (see, e.g., GenBank accession #AAC28374, incorporated by reference herein). Exemplary NDV virus F protein TM and CT sequences are set forth as:

```
NDV F TM domain:
IVLTIISLVFGILSLILACYL (residues 1-21 of
SEQ ID NO: 104)

NDV F CT:
MYKQKAQQKTLLWLGNNTLDQMRATTKM (residues 22-49 of
SEQ ID NO: 104)

NDV F TM+CT:
IVLTIISLVFGILSLILACYLMYKQKAQQKTLLWLGNNTLDQMRATTKM,
SEQ ID NO: 104
```

G. Heterologous Genes

The recombinant paramyxovirus vector includes a recombinant genome including one or more heterologous genes encoding an ectodomain of one or more heterologous envelope proteins (or antigenic fragment thereof) of a heterologous viral pathogen, wherein the ectodomain is linked to a TM and CT of an envelope protein from the recombinant paramyxovirus. For example, one or more heterologous envelope proteins (or antigenic fragment thereof) from measles virus, subgroup A or subgroup B respiratory syncytial viruses, mumps virus, human papilloma viruses, type 1 or type 2 human immunodeficiency viruses, herpes simplex viruses, cytomegalovirus, rabies virus, Epstein Barr virus, filoviruses, bunyaviruses, flaviviruses, alphaviruses, human metapneumovirus, ebola virues (such as Zaire ebola virus), influenza viruses, or highly pathogenic coronaviruses (SARS, MERS) can be expressed by the disclosed recombinant paramyxovirus. Examples of useful envelope proteins include, but are not limited to, measles virus HA and F proteins, subgroup A or subgroup B respiratory syncytial virus F, G, and SH proteins, mumps virus HN and F proteins, human papilloma virus L1 protein, type 1 or type 2 human immunodeficiency virus gp160 protein, herpes simplex virus and cytomegalovirus gB, gC, gD, gE, gG, gH, gI, gJ, gK, gL, and gM proteins, rabies virus G protein, Epstein Barr Virus gp350 protein, filovirus G protein, bunyavirus G protein, flavivirus pre E, and NS1 proteins, human metapneuomovirus (HMPV) G and F proteins, Ebola virus GP protein, alphavirus E protein, and SARS and MERS S protein, and antigenic domains, fragments and epitopes thereof. Exemplary methods of inserting one or more heterologous genes or transcriptional units into a paramyxovirus viral genome or antigenome are described in WO04/027037 and US2013/0052718, each of which is incorporated by reference herein.

In several embodiments, the heterologous gene included in the recombinant paramyxovirus genome encodes the ectodomain of a RSV F protein, such as a bovine RSV F protein or a human RSV F protein. Human RSV can be classified into two groups: A and B. Groups A and B include subgroups A1, A2, B1, and B2, based mainly on sequence variability of the attachment (G) and fusion (F) proteins. The RSV F ectodomain can be derived from any RSV group (such as Group A or Group B) or subgroup of RSV, such as subgroup A1, A2, B1, or B2.

Exemplary human RSV F protein sequence from subgroup A2 and corresponding GenBank reference (which is incorporated by reference herein in its entirety) are set forth below:

RSV F A2 HEK Protein Sequence:

```
                                      (SEQ ID NO: 1)
MELLILKANAITTILTAVTFCFASGQNITEEFYQSTCSAVSKGYLSALRT
GWYTSVITIELSNIKENKCNGTDAKVKLIKQELDKYKNAVTELQLLMQST
PATNNRARRELPRFMNYTLNNAKKTNVTLSKKRKRRFLGFLLGVGSAIAS
GVAVSKVLHLEGEVNKIKSALLSTNKAVVSLSNGVSVLTSKVLDLKNYID
KQLLPIVNKQSCSISNIETVIEFQQKNNRLLEITREFSVNAGVTTPVSTY
MLTNSELLSLINDMPITNDQKKLMSNNVQIVRQQSYSIMSIIKEEVLAYV
VQLPLYGVIDTPCWKLHTSPLCTTNTKEGSNICLTRTDRGWYCDNAGSVS
FFPQAETCKVQSNRVFCDTMNSLTLPSEVNLCNVDIFNPKYDCKIMTSKT
DVSSSVITSLGAIVSCYGKTKCTASNKNRGIIKTFSNGCDYVSNKGVDTV
SVGNTLYYVNKQEGKSLYVKGEPIINFYDPLVFPSDEFDASISQVNEKIN
QSLAFIRKSDELLHNVNAGKSTTNIMITTIIIVIIVILLSLIAVGLLLYC
KARSTPVTLSKDQLSGINNIAFSN
```

RSV F B1 HEK Protein Sequence, Accession No. AAB82436:

```
auggagcugcugauccacagguuaagugcaaucuuccuaacucuugcuauu
aaugcauuguaccucaccucaagucagaacauaacugaggaguuuuaccaa
ucgacauguagugcaguuagcagagguuauuuuagugcuuuaagaacaggu
ugguauaccagugucauaacaauagaauuaaguaauauaaaagaaaccaaa
ugcaauggaacugacacuaaaguaaaacuuauaaaacaagaauuagauaag
uauaagaaugcagugacagaauuacagcuacuuaugcaaaacacaccagcu
gccaacaaccgggccagaagagaagcaccacaguauaugaacuauacaauc
aauaccacuaaaaaccuaaauguaucaauaagcaagaagaggaaacgaaga
```

-continued uuucugggcuucuuguuagguguaggaucugcaauagcaagugguauagcu guauccaaaguucuacaccuugaaggagaagugaacaagaucaaaaaugcu uuguuaucuacaaacaaagcuguagucagucuaucaaauggggucaguguu uuaaccagcaaaguguuagaucucaagaauuacauaaauaaccaauuauua cccauaguaaaucaacagagcugucgcaucuccaacauugaaacaguuaua gaauuccagcagaagaacagcagauuguuggaaaucaacagagaauucagu gucaaugcagguguaacaacaccuuuaagcacuuacauguuaacaaacagu gaguuacuaucauugaucaaugauaugccuauaacaaaugaucagaaaaaa uuaaugucaagcaauguucagauaguaaggcaacaaaguuauucuaucaug ucuauaauaaaggaagaaguccuugcauauguuguacagcuaccuaucuau gguguaauagauacaccuugcuggaaauuacacacaucaccucuaugcacc accaacaucaaagaaggaucaaauauuuguuuaacaaggacugauagagga ugguauugugauaaugcaggaucaguauccuucuuuccacaggcugacacu uguaaaguacaguccaaucgaguauuuugugacacuaugaacaguuugaca uuaccaagugaagucagccuuuguaacacugacauauucaauuccaaguau gacugcaaaauuaugacaucaaaaacagacauaagcagcucaguaauuacu ucucuuggagcuauagugucaugcuaugguaaaacuaaaugcacugcaucc aacaaaaaucgugggauuauaaagacauuuucuaugguugugacuaugug ucaaacaaaggaguagauacugugucagugggcaacacuuuauacuaugua aacaagcuggaaggcaagaaccuuuauguaaaaggggaaccuauaauaaau uacuaugacccucuaguguuuccuucugaugaguuugaugcaucaauaucu caagucaaugaaaaaaucaaucaaaguuuagcuuuuauucguagaucugau gaauuacuacauaauguaaauacuggcaaaucuacuacaaauauuaugaua acuacaauuauuauaguaaucauuguaguauuguuaucauuaauagcuauu gguuugcuguuguauugcaaagccaaaaacacaccaguuacacuaagcaaa gaccaacuaaguggaaucaauaauauugcauucagcaaauag (SEQ ID NO: 3, GenBank Accession No.: AF013254.1, nucleotides 5666-7390, incorporated by reference herein in its entirety)

RSV F B1 HEK Nucleic Acid Sequence:

MELLIHRLSAIFLTLAINALYLTSSQNITEEFYQSTCSAVSRGYFSALRTG

WYTSVITIELSNIKETKCNGTDTKVKLIKQELDKYKNAVTELQLLMQNTPA

ANNRARREAPQYMNYTINTTKNLNVSISKKRKRRFLGFLLGVGSAIASGIA

VSKVLHLEGEVNKIKNALLSTNKAVVSLSNGVSVLTSKVLDLKNYINNQLL

PIVNQQSCRISNIETVIEFQQKNSRLLEINREFSVNAGVTTPLSTYMLTNS

ELLSLINDMPITNDQKKLMSSNVQIVRQQSYSIMSIIKEEVLAYVVQLPIY

GVIDTPCWKLHTSPLCTTNIKEGSNICLTRTDRGWYCDNAGSVSFFPQADT

CKVQSNRVFCDTMNSLTLPSEVSLCNTDIFNSKYDCKIMTSKTDISSSVIT

SLGAIVSCYGKTKCTASNKNRGIIKTFSNGCDYVSNKGVDTVSVGNTLYYV

-continued

NKLEGKNLYVKGEPIINYYDPLVFPSDEFDASISQVNEKINQSLAFIRRSD

ELLHNVNTGKSTTNIMITTIIIVIIVVLLSLIAIGLLLYCKAKNTPVTLSK

DQLSGINNIAFSK (SEQ ID NO: 2, GenBank Accession No. AAB82436, incorporated by reference herein in its entirety)

As illustrated by the sequences above, the hRSV F protein exhibits remarkable sequence conservation, with sequence identity of more than 85% across hRSV subgroups. In view of the conservation and breadth of knowledge of RSV F sequences, the person of ordinary skill in the art can easily identify corresponding RSV F amino acid positions between different RSV F strains and subgroups. The numbering of amino acid substitutions disclosed herein is made with reference to the exemplary hRSV F protein sequence from the A2 stain set forth as SEQ ID NO: 1, unless context indicates otherwise.

For illustration purposes, the signal peptide, F2 polypeptide, pep27, $F_1$, $F_1$ ectodomain, transmembrane domain, and cytosolic domain of the RSV F protein from an A2 strain (SEQ ID NO: 1), are set forth as follows:

Signal peptide (SEQ ID NO: 1, residues 1-22):
MELLILKANAITTILTAVTFCF $F_2$ polypeptide (SEQ ID NO: 1, residues 23-109):
ASGQNITEEFYQSTCSAVSKGYLSALRTGWYTSVITIELSNIKENKCNGT

DAKVKLIKQELDKYKNAVTELQLLMQSTPATNNRARR

Pep27 (SEQ ID NO: 1, residues 110-136):
ELPRFMNYTLNNAKKTNVTLSKKRKRR $F_1$ (SEQ ID NO: 1, residues 137-574):
FLGFLLGVGSAIASGVAVSKVLHLEGEVNKIKSALLSTNKAVVSLSNGVS

VLTSKVLDLKNYIDKQLLPIVNKQSCSISNIETVIEFQQKNNRLLEITRE

FSVNAGVTTPVSTYMLTNSELLSLINDMPITNDQKKLMSNNVQIVRQQSY

SIMSIIKEEVLAYVVQLPLYGVIDTPCWKLHTSPLCTTNTKEGSNICLTR

TDRGWYCDNAGSVSFFPQAETCKVQSNRVFCDTMNSLTLPSEVNLCNVDI

FNPKYDCKIMTSKTDVSSSVITSLGAIVSCYGKTKCTASNKNRGIIKTFS

NGCDYVSNKGVDTVSVGNTLYYVNKQEGKSLYVKGEPIINFYDPLVFPSD

EFDASISQVNEKINQSLAFIRKSDELLHNVNAGKSTTNIMITTIIIVIIV

ILLSLIAVGLLLYCKARSTPVTLSKDQLSGINNIAFSN $F_1$ ectodomain of mature protein (SEQ ID NO: 1, residues 137-529):
FLGFLLGVGSAIASGVAVSKVLHLEGEVNKIKSALLSTNKAVVSLSNGVS

VLTSKVLDLKNYIDKQLLPIVNKQSCSISNIETVIEFQQKNNRLLEITRE

FSVNAGVTTPVSTYMLTNSELLSLINDMPITNDQKKLMSNNVQIVRQQSY

SIMSIIKEEVLAYVVQLPLYGVIDTPCWKLHTSPLCTTNTKEGSNICLTR

TDRGWYCDNAGSVSFFPQAETCKVQSNRVFCDTMNSLTLPSEVNLCNVDI

FNPKYDCKIMTSKTDVSSSVITSLGAIVSCYGKTKCTASNKNRGIIKTFS

NGCDYVSNKGVDTVSVGNTLYYVNKQEGKSLYVKGEPIINFYDPLVFPSD

EFDASISQVNEKINQSLAFIRKSDELLHNVNAGKSTTNIMITT $F_1$ Transmembrane domain (SEQ ID NO: 1, residues 530-550):
IIIVIIVILLSLIAVGLLLYC $F_1$ CT (SEQ ID NO: 1, residues 551-574):
KARSTPVTLSKDQLSGINNIAFSN In some embodiments, the heterologous gene included in the recombinant paramyxovirus genome encodes the ectodomain of a human RSF F protein, wherein the RSV F ectodomain comprises an amino acid sequence at least 85% (such as at least 90%, or at least 95%) identical to the RSV ectodomain of one of SEQ ID NOs: 1 (WT RSV F A), 2 (WT RSV F B), 12 (A2 HEK), 14 (A2 HEK+DS), or 19 (A2 HEK+DS-Cav1), or comprises the amino acid sequence of the RSV ectodomain of SEQ ID NO: 12, 14, or 19.

In some embodiments the recombinant paramyxovirus can include a genome including a heterologous gene encoding a recombinant hRSV F protein that has been codon-optimized for expression in a human cell. For example, the gene encoding the recombinant hRSV F protein can be codon-optimized for human expression using a GA, DNA2.0 (D2), or GenScript (GS) optimization algorithm (see Example 1). Non-limiting examples of nucleic acid sequences encoding the RSV F protein that have been codon-optimized for expression in a human cell are provided as follows:

GeneArt Optimized RSV F A2 HEK DNA Sequence:

```
                                                (SEQ ID NO: 4)
atggaactgctgatcctgaaggccaacgccatcacaacaatcctgaccgcc

gtgaccttctgcttcgccagcggccagaacatcaccgaggaattctaccag

agcacctgtagcgccgtgtccaagggctacctgagcgccctgagaaccggc

tggtacaccagcgtgatcaccatcgagctgtccaacatcaaagaaaacaag

tgcaacggcaccgacgccaaagtgaagctgatcaagcaggaactggacaag

tacaagaacgccgtgaccgagctgcagctgctgatgcagtccacccccgcc

accaacaaccgggccagaagagaactgccccggttcatgaactacaccctc

aacaacgccaaaaagaccaacgtgaccctgagcaagaagcggaagcggcgg

ttcctgggcttcctgctgggcgtgggcagcgccattgcctctggcgtggcc

gtgtctaaggtgctgcacctggaaggcgaagtgaacaagatcaagagcgcc

ctgctgtccacaaacaaggccgtggtgtccctgagcaacggcgtgtccgtg

ctgacctccaaggtgctggatctgaagaactacatcgacaagcagctgctg

cccatcgtgaacaagcagagctgcagcatcagcaacatcgagacagtgatc

gagttccagcagaagaacaaccggctgctggaaatcacccgcgagttcagc

gtgaacgccggcgtgaccacccccgtgtccacctacatgctgaccaacagc

gagctgctgtccctgatcaatgacatgcccatcaccaacgaccagaaaaag

ctgatgagcaacaacgtgcagatcgtgcggcagcagagctactccatcatg

agcatcatcaaagaagaggtgctggcctacgtggtgcagctgcccctgtac

ggcgtgatcgacacccccctgctggaagctgcacaccagcccccctgtgcacc

accaacacaaaagagggcagcaacatctgcctgacccggaccgaccggggc

tggtactgcgataatgccggcagcgtgtcattctttccacaggccgagaca

tgcaaggtgcagagcaaccgggtgttctgcgacaccatgaacagcctgacc

ctgccctccgaagtgaacctgtgcaacgtggacatcttcaaccctaagtac

gactgcaagatcatgaccagcaagaccgacgtgtccagctccgtgatcacc

tccctgggcgccatcgtgtcctgctacggcaagaccaagtgcaccgccagc

aacaagaaccggggcatcatcaagaccttcagcaacggctgcgactacgtg
```

-continued

```
tccaacaagggggtggacaccgtgtccgtgggcaacaccctgtactacgtg

aacaaacaggaaggcaagagcctgtacgtgaagggcgagcccatcatcaac

ttctacgacccccctggtgttccccagcgacgagttcgacgccagcatcagc

caggtcaacgagaagatcaaccagagcctggccttcatcagaaagagcgac

gagctgctgcacaatgtgaatgccggcaagagcaccacaaacatcatgatc

accactatcatcatcgtgatcatcgtcatcctgctgagtctgatcgccgtg

ggcctgctgctgtactgcaaggccagatccacccctgtgaccctgtccaag

gatcagctgtccggcatcaacaatatcgccttctccaactga
```

GenScript Optimized RSV F A2 HEK DNA Sequence:

```
                                                (SEQ ID NO: 5)
atggaactgctgatcctgaaagccaacgctattactactatcctgaccgc

cgtgacattttgcttcgcatctggacagaacattactgaggaattctacc

agtcaacatgcagcgccgtgtccaaaggatacctgagcgccctgcggacc

ggctggtatacatcagtgattactatcgagctgtccaacatcaaggaaaa

caaatgtaatgggaccgacgcaaaggtgaaactgatcaagcaggagctgg

ataagtacaaaaatgccgtgacagaactgcagctgctgatgcagtccaca

ccagcaactaacaatcgcgcccggagagagctgccccggttcatgaacta

taccctgaacaatgctaagaaaaccaatgtgacactgtccaagaaacgca

agaggcgcttcctgggatttctgctgggcgtggggtctgccatcgctagt

ggagtggccgtctctaaagtcctgcacctggagggcgaagtgaacaagat

caaaagcgccctgctgtccactaacaaggcagtggtcagtctgtcaaatg

gcgtgtccgtcctgacctctaaggtgctggacctgaaaaattatattgat

aagcagctgctgcctatcgtcaacaaacagagctgctccatttctaatat

cgagacagtgatcgaattccagcagaagaacaatagactgctggagatta

ccagagagttcagcgtgaacgccggcgtcaccacacccgtgtccacctac

atgctgacaaatagtgagctgctgtcactgattaacgacatgcctatcac

caatgatcagaagaaactgatgtccaacaatgtgcagatcgtcagacagc

agagttactcaatcatgtctatcattaaggaggaagtcctggcctacgtg

gtccagctgccactgtatggcgtgatcgacacccccctgctggaaactgca

tacatctcctctgtgcactaccaacacaaaggaaggaagtaatatctgcc

tgactcgaaccgaccggggatggtactgtgataacgcaggcagcgtgtcc

ttctttccacaggccgagacctgcaaggtccagagcaacagggtgttctg

tgacactatgaatagcctgaccctgccttccgaagtcaacctgtgcaatg

tggacatctttaatccaaagtacgattgtaagatcatgactagcaagacc

gatgtcagctcctctgtgattacttctctgggggccatcgtgagttgcta

cggaaagacaaaatgtactgccagcaacaaaaatcgcggcatcattaaga

ccttctccaacgggtgcgactatgtctctaacaagggcgtggatacagtg

agtgtcgggaacactctgtactatgtcaataagcaggagggaaaaagcct

gtacgtgaagggcgaacccatcattaacttctatgacccccctggtgttcc

cttccgacgagtttgatgcatctattagtcaggtgaacgaaaaaatcaat
```

-continued

```
cagagtctggcctttattcggaagtcagatgagctgctgcacaacgtgaa
tgctggcaaatctacaactaacatcatgatcaccacaatcatcatcgtga
ttatcgtcattctgctgtcactgatcgctgtggggctgctgctgtactgt
aaggcaagaagcaccccagtcactctgtcaaaagaccagctgtcaggqat
taacaacattgccttcagtaactga
```

Additional examples of codon-optimized (for human expression) sequences are provided below.

The RSV F protein encoded by the heterologous gene can include one or more amino acid substitutions that improve expression of the RSV F protein, availability of the RSV F protein on the virion envelope, or stability of the RSV F protein, for example, in a prefusion conformation. In some embodiments, the RSV F protein can include a glutamic acid substitution at position 66, a proline substitution at position 101, or both. For example the RSV F protein can include the "HEK" substitutions of a K66E substitution and a Q101P substitution. Exemplary DNA and protein sequences for a RSV F protein from the A2 subgroup including the HEK amino acid substitutions are set forth below.

RSV F A2 Protein with HEK Substitutions (RSV F_A2_HEK): SEQ ID NO: 1

GeneArt Optimized RSV F_A2_HEK DNA Sequence:

```
                                          (SEQ ID NO: 6)
atggaactgctgatcctgaaggccaacgccatcacaacaatcctgaccgc
cgtgaccttctgcttcgccagcggccagaacatcaccgaggaattctacc
agagcacctgtagcgccgtgtccaagggctacctgagcgccctgagaacc
ggctggtacaccagcgtgatcaccatcgagctgtccaacatcaaagaaaa
caagtgcaacggcaccgacgccaaagtgaagctgatcaagcaggaactgg
acaagtacaagaacgccgtgaccgagctgcagctgctgatgcagtccacc
cccgccaccaacaaccgggccagaagagaactgccccggttcatgaacta
caccctcaacaacgccaaaaagaccaacgtgaccctgagcaagaagcgga
agcggcggttcctgggcttcctgctgggcgtgggcagcgccattgcctct
ggcgtggccgtgtctaaggtgctgcacctggaaggcgaagtgaacaagat
caagagcgccctgctgtccacaaacaaggccgtggtgtccctgagcaacg
gcgtgtccgtgctgacctccaaggtgctggatctgaagaactacatcgac
aagcagctgctgcccatcgtgaacaagcagagctgcagcatcagcaacat
cgagacagtgatcgagttccagcagaagaacaaccggctgctggaaatca
cccgcgagttcagcgtgaacgccggcgtgaccacccccgtgtccacctac
atgctgaccaacagcgagctgctgtccctgatcaatgacatgcccatcac
caacgaccagaaaaagctgatgagcaacaacgtgcagatcgtgcggcagc
agagctactccatcatgagcatcatcaaagaagaggtgctggcctacgtg
gtgcagctgcccctgtacggcgtgatcgacacccccctgctggaagctgca
caccagcccccctgtgcaccaccaacacaaaagagggcagcaacatctgcc
tgacccggaccgaccggggctggtactgcgataatgccggcagcgtgtca
ttctttccacaggccgagacatgcaaggtgcagagcaaccgggtgttctg
cgacaccatgaacagcctgaccctgccctccgaagtgaacctgtgcaacg
```

-continued

```
tggacatcttcaaccctaagtacgactgcaagatcatgaccagcaagacc
gacgtgtccagctccgtgatcacctccctgggcgccatcgtgtcctgcta
cggcaagaccaagtgcaccgccagcaacaagaaccggggcatcatcaaga
ccttcagcaacggctgcgactacgtgtccaacaagggggtggacaccgtg
tccgtgggcaacaccctgtactacgtgaacaaacaggaaggcaagagcct
gtacgtgaagggcgagcccatcatcaacttctacgacccccctggtgttcc
ccagcgacgagttcgacgccagcatcagccaggtcaacgagaagatcaac
cagagcctggccttcatcagaaagagcgacgagctgctgcacaatgtgaa
tgccggcaagagcaccacaaacatcatgatcaccactatcatcatcgtga
tcatcgtcatcctgctgagtctgatcgccgtgggcctgctgctgtactgc
aaggccagatccacccctgtgaccctgtccaaggatcagctgtccggcat
caacaatatcgccttctccaactga
```

GenScript Optimized RSV F_A2_HEK DNA Sequence:

```
                                          (SEQ ID NO: 7)
atggaactgctgatcctgaaagccaacgctattactactatcctgaccgc
cgtgacattttgcttcgcatctggacagaacattactgaggaattctacc
agtcaacatgcagcgccgtgtccaaaggatacctgagcgccctgcggacc
ggctggtatacatcagtgattactatcgagctgtccaacatcaaggaaaa
caaatgtaatgggaccgacgcaaaggtgaaactgatcaagcaggagctgg
ataagtacaaaaatgccgtgacagaactgcagctgctgatgcagtccaca
ccagcaactaacaatcgcgcccggagagagctgccccggttcatgaacta
taccctgaacaatgctaagaaaaccaatgtgacactgtccaagaaacgca
agaggcgcttcctgggatttctgctgggcgtggggtctgccatcgctagt
ggagtggccgtctctaaagtcctgcacctggagggcgaagtgaacaagat
caaaagcgccctgctgtccactaacaaggcagtggtcagtctgtcaaatg
gcgtgtccgtcctgacctctaaggtgctggacctgaaaaattatattgat
aagcagctgctgcctatcgtcaacaaacagagctgctccatttctaatat
cgagacagtgatcgaattccagcagaagaacaatagactgctggagatta
ccagagagttcagcgtgaacgccggcgtcaccacacccgtgtccacctac
atgctgacaaatagtgagctgctgtcactgattaacgacatgcctatcac
caatgatcagaagaaactgatgtccaacaatgtgcagatcgtcagacagc
agagttactcaatcatgtctatcattaaggaggaagtcctggcctacgtg
gtccagctgccactgtatggcgtgatcgacacccccctgctggaaactgca
tacatctcctctgtgcactaccaacacaaaggaaggaagtaatatctgcc
tgactcgaaccgaccggggatggtactgtgataacgcaggcagcgtgtcc
ttctttccacaggccgagacctgcaaggtccagagcaacagggtgttctg
tgacactatgaatagcctgaccctgccttccgaagtcaacctgtgcaatg
tggacatctttaatccaaagtacgattgtaagatcatgactagcaagacc
gatgtcagctcctctgtgattacttctctgggggccatcgtgagttgcta
cggaaagacaaaatgtactgccagcaacaaaaatcgcggcatcattaaga
```

-continued
```
ccttctccaacgggtgcgactatgtgtctctaacaagggcgtggatacagtg

agtgtcgggaacactctgtactatgtcaataagcaggagggaaaaagcct

gtacgtgaagggcgaacccatcattaacttctatgaccccctggtgttcc

cttccgacgagtttgatgcatctattagtcaggtgaacgaaaaaatcaat

cagagtctggcctttattcggaagtcagatgagctgctgcacaacgtgaa

tgctggcaaatctacaactaacatcatgatcaccacaatcatcatcgtga

ttatcgtcattctgctgtcactgatcgctgtggggctgctgctgtactgt

aaggcaagaagcaccccagtcactctgtcaaaagaccagctgtcagggat

taacaacattgccttcagtaactga
```

In additional embodiments, the RSV F protein can include one or more amino acid substitutions that stabilize the ectodomain of the RSV F protein in a prefusion conformation. For example, the RSV F protein can include the "DS" substitution of a pair of cysteine substitutions at positions 155 and 290 that form a non-natural disulfide bond to stabilize the RSV F protein in its prefusion conformation. In some embodiments, the RSV F protein can include one or more cavity filling amino acid substitutions at positions 190 and/or 207 to stabilize the protein in a prefusion conformation. For example, the RSV F protein can include a 190F substitution and/or a 207L substitution. In some embodiments, the RSV F protein can include the "Cav1" substitutions of S190F and a F207L. In some embodiments, the RSV F protein can include the DS-Cav1 substitutions of S155C, S290C, S190F, and V207L to stabilize the protein in a prefusion conformation. Exemplary DNA and protein sequences for an RSV F protein (with a chimeric TM and/or CT domain) from the A2 subgroup including the DS-Cav1 amino acid substitutions are set forth as SEQ ID NOs: 10-11 and 21-23.

Additional amino acid substitutions and protein modifications that can be used to stabilize the RSV F ectodomain in a prefusion conformation are disclosed, for example, in WO2014160463, which is incorporated by reference in its entirety. The HEK substitutions can be combined with any of the amino acid substitutions for stabilizing the RSV F protein in a prefusion conformation.

In several embodiments, the heterologous gene included in the recombinant paramyxovirus genome encodes a recombinant RSV F ectodomain linked to a TM and CT of the F protein of the recombinant paramyxovirus.

In an embodiment, the recombinant paramyxovirus is a recombinant HPIV1 including a recombinant HPIV1 genome including a heterologous gene encoding a recombinant hRSV F ectodomain. The RSV F ectodomain can be linked to a TM and CT from HPIV1 F protein, for example as set forth as residues 1-23 of SEQ ID NO 31 (TM), residues 24-59 of SEQ ID NO: 31 (CT), or SEQ ID NO: 31 (TM+CT). Exemplary sequences are provided below:

hRSV F protein from an A2 strain including HEK and DS-Cav1 substitutions, and HPIV1 F CT domain (RSV F A2_HEK_DS-Cav1_H1CT) is provided as SEQ ID NO: 133
GenScript optimized RSV F A2_HEK_DS-Cav1_H1CT DNA sequence is provided as SEQ ID NO: 134
hRSV F Protein from an A2 Strain Including HEK and DS-Cav1 Substitutions, and HPIV1 F TM and CT Domains (RSV F A2_HEK_DS-Cav1_H1TMCT):

```
                                        (SEQ ID NO: 135)
MELLILKANAITTILTAVTFCFASGQNITEEFYQSTCSAVSKGYLSALRT

GWYTSVITIELSNIKENKCNGTDAKVKLIKQELDKYKNAVTELQLLMQST

PATNNRARRELPRFMNYTLNNAKKTNVTLSKKRKRRFLGFLLGVGSAIAS

GVAVCKVLHLEGEVNKIKSALLSTNKAVVSLSNGVSVLTFKVLDLKNYID

KQLLPILNKQSCSISNIETVIEFQQKNNRLLEITREFSVNAGVTTPVSTY

MLTNSELLSLINDMPITNDQKKLMSNNVQIVRQQSYSIMCIIKEEVLAYV

VQLPLYGVIDTPCWKLHTSPLCTTNTKEGSNICLTRTDRGWYCDNAGSVS

FFPQAETCKVQSNRVFCDTMNSLTLPSEVNLCNVDIFNPKYDCKIMTSKT

DVSSSVITSLGAIVSCYGKTKCTASNKNRGIIKTFSNGCDYVSNKGVDTV

SVGNTLYYVNKQEGKSLYVKGEPIINFYDPLVFPSDEFDASISQVNEKIN

QSLAFIRKSDELLHNVNAGKSTTNIMITTQIIMIIIVCILIIIICGILYY

LYRVRRLLVMINSTHNSPVNAYTLESRMRNPYMGNNSN
```

GenScript Optimized RSV F A2_HEK_DS-Cav1_H1TMCT DNA Sequence:

```
                                        (SEQ ID NO: 136)
atggaactgctgatcctgaaagccaacgctattactactatcctgaccgc

cgtgacattttgcttcgcatctggacagaacattactgaggaattctacc

agtcaacatgcagcgccgtgtccaaaggatacctgagcgccctgcggacc

ggctggtatacatcagtgattactatcgagctgtccaacatcaaggaaaa

caaatgtaatgggaccgacgcaaaggtgaaactgatcaagcaggagctgg

ataagtacaaaaatgccgtgacagaactgcagctgctgatgcagtccaca

ccagcaactaacaatcgcgcccggagagagctgccccggttcatgaacta

taccctgaacaatgctaagaaaaccaatgtgacactgtccaagaaacgca

agaggcgcttcctgggatttctgctgggcgtggggtctgccatcgctagt

ggagtggccgtctgcaaagtcctgcacctggagggcgaagtgaacaagat

caaaagcgccctgctgtccactaacaaggcagtggtcagtctgtcaaatg

gcgtgtccgtcctgaccttcaaggtgctggacctgaaaaattatattgat

aagcagctgctgcctatcctgaacaaacagagctgctccatttctaatat

cgagacagtgatcgaattccagcagaagaacaatagactgctggagatta

ccagagagttcagcgtgaacgccggcgtcaccacacccgtgtccacctac

atgctgacaaatagtgagctgctgtcactgattaacgacatgcctatcac

caatgatcagaagaaactgatgtccaacaatgtgcagatcgtcagacagc

agagttactcaatcatgtgcatcattaaggaggaagtcctggcctacgtg

gtccagctgccactgtatggcgtgatcgacacccctgctggaaactgca

tacatctcctctgtgcactaccaacacaaaggaaggaagtaatatctgcc

tgactcgaaccgaccggggatggtactgtgataacgcaggcagcgtgtcc

ttctttccacaggccgagacctgcaaggtccagagcaacagggtgttctg

tgacactatgaatagcctgaccctgccttccgaagtcaacctgtgcaatg

tggacatctttaatccaaagtacgattgtaagatcatgactagcaagacc

gatgtcagctcctctgtgattacttctctgggggccatcgtgagttgcta
```

```
-continued
cggaaagacaaaatgtactgccagcaacaaaaatcgcggcatcattaaga

ccttctccaacgggtgcgactatgtctctaacaagggcgtggatacagtg

agtgtcgggaacactctgtactatgtcaataagcaggagggaaaaagcct

gtacgtgaagggcgaacccatcattaacttctatgaccccctggtgttcc

cttccgacgagtttgatgcatctattagtcaggtgaacgaaaaaatcaat

cagagtctggcctttattcggaagtcagatgagctgctgcacaacgtgaa

tgctggcaaatctacaactaacatcatgatcaccacacagatcattatga

tcattatcgtgtgcattctgattatcattatctgtggcatcctgtactat

ctgtaccgagtgcggagactgctggtcatgattaacagcacccacaattc

ccccgtcaacgcctacacactggagtctaggatgcgcaatccttatatgg

ggaacaatagcaactgatag
```

In an embodiment, the recombinant paramyxovirus is a recombinant HPIV2 including a recombinant HPIV2 genome including a heterologous gene encoding a recombinant hRSV F ectodomain. The RSV F ectodomain can be linked to a TM and CT from a HPIV2 F protein, for example as set forth as residues 1-28 of SEQ ID NO: 39 (TM), residues 29-66 of SEQ ID NO: 39 (CT), or SEQ ID NO: 39 (TM+CT).

In an embodiment, the recombinant paramyxovirus can be a recombinant HPIV3 including a genome including a heterologous gene encoding a recombinant hRSV F ectodomain. The recombinant RSV F ectodomain can be linked to a TM and CT from a HPIV3 F protein, for example as set forth as residues 1-23 of SEQ ID NO 46 (TM), residues 24-46 of SEQ ID NO: 46 (CT), or SEQ ID NO: 46 (TM+CT). Exemplary sequences are provided below:

hRSV F protein from an A2 strain including HEK and DS-Cav1 substitutions, and HPIV3 F CT domain (RSV F_HEK_DS-Cav1_H3CT) protein sequence is provided as SEQ ID NO: 8

GenScript optimized RSV F_HEK_DS-Cav1_H3CT DNA sequence is provided as SEQ ID NO: 9 hRSV F Protein from an A2 Strain Including HEK and DS-Cav1 Substitutions, and HPIV3 F TM and CT Domains (RSV F_HEK_DS-Cav1_H3TMCT) Protein Sequence:

```
                                                 (SEQ ID NO: 10)
MELLILKANAITTILTAVTFCFASGQNITEEFYQSTCSAVSKGYLSALRT

GWYTSVITIELSNIKENKCNGTDAKVKLIKQELDKYKNAVTELQLLMQST

PATNNRARRELPRFMNYTLNNAKKTNVTLSKKRKRRFLGFLLGVGSAIAS

GVAVCKVLHLEGEVNKIKSALLSTNKAVVSLSNGVSVLTFKVLDLKNYID

KQLLPILNKQSCSISNIETVIEFQQKNNRLLEITREFSVNAGVTTPVSTY

MLTNSELLSLINDMPITNDQKKLMSNNVQIVRQQSYSIMCIIKEEVLAYV

VQLPLYGVIDTPCWKLHTSPLCTTNTKEGSNICLTRTDRGWYCDNAGSVS

FFPQAETCKVQSNRVFCDTMNSLTLPSEVNLCNVDIFNPKYDCKIMTSKT

DVSSSVITSLGAIVSCYGKTKCTASNKNRGIIKTFSNGCDYVSNKGVDTV

SVGNTLYYVNKQEGKSLYVKGEPIINFYDPLVFPSDEFDASISQVNEKIN

QSLAFIRKSDELLHNVNAGKSTTNIMITTIIIILIMIIILFIINITIITI

AIKYYRIQKRNRVDQNDKPYVLTNK
```

GenScript Optimized RSV F_HEK_DS-Cav1_H3TMCT DNA Sequence:

```
                                                 (SEQ ID NO: 11)
atggaactgctgatcctgaaagccaacgctattactactatcctgaccgc

cgtgacattttgcttcgcatctggacagaacattactgaggaattctacc

agtcaacatgcagcgccgtgtccaaaggatacctgagcgccctgcggacc

ggctggtatacatcagtgattactatcgagctgtccaacatcaaggaaaa

caaatgtaatgggaccgacgcaaaggtgaaactgatcaagcaggagctgg

ataagtacaaaaatgccgtgacagaactgcagctgctgatgcagtccaca

ccagcaactaacaatcgcgcccgagagagctgccccggttcatgaacta

taccctgaacaatgctaagaaaaccaatgtgacactgtccaagaaacgca

agaggcgcttcctgggatttctgctgggcgtggggtctgccatcgctagt

ggagtggccgtctgcaaagtcctgcacctggagggcgaagtgaacaagat

caaaagcgccctgctgtccactaacaaggcagtggtcagtctgtcaaatg

gcgtgtccgtcctgaccttcaaggtgctggacctgaaaaattatattgat

aagcagctgctgcctatcctgaacaaacagagctgctccatttctaatat

cgagacagtgatcgaattccagcagaagaacaatagactgctggagatta

ccagagagttcagcgtgaacgccggcgtcaccacacccgtgtccacctac

atgctgacaaatagtgagctgctgtcactgattaacgacatgcctatcac

caatgatcagaagaaactgatgtccaacaatgtgcagatcgtcagacagc

agagttactcaatcatgtgcatcattaaggaggaagtcctggcctacgtg

gtccagctgccactgtatggcgtgatcgacacccctgctggaaactgca

tacatctcctctgtgcactaccaacacaaaggaaggaagtaatatctgcc

tgactcgaaccgaccggggatggtactgtgataacgcaggcagcgtgtcc

ttctttccacaggccgagacctgcaaggtccagagcaacagggtgttctg

tgacactatgaatagcctgaccctgccttccgaagtcaacctgtgcaatg

tggacatctttaatccaaagtacgattgtaagatcatgactagcaagacc

gatgtcagctcctctgtgattacttctctggggccatcgtgagttgcta

cggaaagacaaaatgtactgccagcaacaaaaatcgcggcatcattaaga

ccttctccaacgggtgcgactatgtctctaacaagggcgtggatacagtg

agtgtcgggaacactctgtactatgtcaataagcaggagggaaaaagcct

gtacgtgaagggcgaacccatcattaacttctatgaccccctggtgttcc

cttccgacgagtttgatgcatctattagtcaggtgaacgaaaaaatcaat

cagagtctggcctttattcggaagtcagatgagctgctgcacaacgtgaa

tgctggcaaatctacaactaacatcatgatcaccacaatcatcatcatct

tgatcatgatcatcatcctgttcatcatcaacatcacaatcatcaccatc

gctatcaagtactaccgtatccagaagaggaacagagttgaccagaacga

taagccatacgtgctcactaacaagtga
```

In an embodiment, the recombinant paramyxovirus is a chimeric PIV including a recombinant viral genome encoding HPIV3 F and HN proteins and BPIV3 N, P, C, V, M, and L proteins, wherein the viral genome further includes a heterologous gene encoding a recombinant hRSV F ectodomain linked to a TM and/or CT from a BPIV3 F protein, for example as set forth as residues 1-21 of SEQ ID NO 53 (TM), residues 22-57 of SEQ ID NO: 53 (CT) or SEQ ID NO: 53 (TM+CT). Exemplary DNA and protein sequences for recombinant RSV F proteins of the A2 subgroup that include the HEK, DS, and/or Cav1 substitutions, as well as a heterologous TM and/or CT domains from BPIV3 F protein that can be used in a disclosed recombinant paramyxovirus are set forth below.

hRSV F Protein from an A2 Strain Including HEK Substitutions, and BPIV3 F TM and CT Domains (RSV F_A2_HEK_B3TMCT) Protein Sequence:

(SEQ ID NO: 12)

```
MELLILKANAITTILTAVTFCFASGQNITEEFYQSTCSAVSKGYLSALRT
GWYTSVITIELSNIKENKCNGTDAKVKLIKQELDKYKNAVTELQLLMQST
PATNNRARRELPRFMNYTLNNAKKTNVTLSKKRKRRFLGFLLGVGSAIAS
GVAVSKVLHLEGEVNKIKSALLSTNKAVVSLSNGVSVLTSKVLDLKNYID
KQLLPIVNKQSCSISNIETVIEFQQKNNRLLEITREFSVNAGVTTPVSTY
MLTNSELLSLINDMPITNDQKKLMSNNVQIVRQQSYSIMSIIKEEVLAYV
VQLPLYGVIDTPCWKLHTSPLCTTNTKEGSNICLTRTDRGWYCDNAGSVS
FFPQAETCKVQSNRVFCDTMNSLTLPSEVNLCNVDIFNPKYDCKIMTSKT
DVSSSVITSLGAIVSCYGKTKCTASNKNRGIIKTFSNGCDYVSNKGVDTV
SVGNTLYYVNKQEGKSLYVKGEPIINFYDPLVFPSDEFDASISQVNEKIN
QSLAFIRKSDELLHNVNAGKSTTNIMITTITIIIVMIIILVIINITIIVV
IIKFHRIQGKDQNDKNSEPYILTNRQ
```

GeneArt Optimized RSV F_A2_HEK_B3TMCT DNA Sequence:

(SEQ ID NO: 13)

```
atggaactgctgatcctgaaggccaacgccatcaccaccatcctgaccgc
cgtgaccttctgctttgccagcggccagaacatcaccgaggaattctacc
agagcacctgtagcgccgtgtccaagggctacctgagcgccctgagaacc
ggctggtacaccagcgtgatcaccatcgagctgagcaacatcaaagaaaa
caagtgcaacggcaccgacgccaaagtgaagctgatcaagcaggaactgg
acaagtacaagaatgccgtgaccgaactgcagctgctgatgcagagcacc
cccgccaccaacaaccgggccagaagagaactgcccagattcatgaacta
caccctgaacaacgccaaaaagaccaacgtgaccctgagcaagaagcgga
agcggcggttcctgggctttctgctgggagtgggaagcgccattgctagc
ggagtggccgtgtctaaggtgctgcacctggaaggcgaagtgaacaagat
caagtccgccctgctgagcaccaacaaggccgtggtgtctctgagcaacg
gcgtgtccgtgctgaccagcaaggtgctggatctgaagaactacatcgac
aaacagctgctgcccatcgtgaacaagcagagctgcagcatcagcaacat
cgagacagtgatcgagttccagcagaagaacaaccggctgctggaaatca
cccgcgagttcagcgtgaacgctggcgtgaccacccccgtgtccacctac
atgctgaccaacagcgagctgctgtccctgatcaacgacatgcccatcac
caacgaccagaaaaagctgatgagcaacaacgtgcagatcgtgcggcagc
agagctactccatcatgagcattatcaaagaagaggtgctggcctacgtg
gtgcagctgcctctgtacggcgtgatcgacaccccctgctggaagctgca
caccagccctctgtgcaccaccaacaccaaagagggctccaacatctgcc
tgacccggaccgacagaggctggtactgcgataatgccggctccgtctca
ttctttccacaagccgagacatgcaaggtgcagagcaaccgggtgttctg
cgacaccatgaacagcctgaccctgccctccgaagtgaatctgtgcaacg
tggacatcttcaaccctaagtacgactgcaagatcatgacctccaagacc
gacgtgtccagctccgtgatcacaagcctgggcgccatcgtgtcctgcta
cggcaagaccaagtgcaccgccagcaacaagaaccggggcatcatcaaga
ccttcagcaacggctgcgactacgtgtccaacaaggggtggacaccgtg
tctgtgggcaacaccctgtactacgtgaacaaacaggaaggcaagagcct
gtacgtgaagggcgagcccatcatcaacttctacgacccccctggtgttcc
ccagcgacgagttcgatgccagcatctcccaagtgaacgagaagatcaac
cagagcctggccttcatcagaaagtccgatgagctgctgcacaatgtgaa
cgccggcaagtccaccaccaatatcatgatcaccacaatcaccatcatca
ttgtgatgattatcatcctcgtgatcatcaacatcacaatcatcgtcgtg
attattaagttccaccggatccagggcaaggaccagaacgacaagaactc
cgagccctacatcctgacaaaccggcagtga
```

hRSV F protein from an A2 strain including HEK and DS substitutions, hRSV F TM domain and BPIV3 F CT domain (RSV F_A2_HEK_DS_B3CT) protein sequence is provided as SEQ ID NO: 14

GeneArt optimized RSV F_A2_HEK_DS_B3CT DNA sequence is provided as SEQ ID NO: 15:

hRSV F Protein from an A2 Strain Including HEK and DS-Cav1 Substitutions, hRSV F TM Domain and BPIV3 F CT Domain (RSV F_A2_HEK_DS-Cav1_B3CT) Protein Sequence:

(SEQ ID NO: 16)

```
MELLILKANAITTILTAVTFCFASGQNITEEFYQSTCSAVSKGYLSALRT
GWYTSVITIELSNIKENKCNGTDAKVKLIKQELDKYKNAVTELQLLMQST
PATNNRARRELPRFMNYTLNNAKKTNVTLSKKRKRRFLGFLLGVGSAIAS
GVAVCKVLHLEGEVNKIKSALLSTNKAVVSLSNGVSVLTFKVLDLKNYID
KQLLPILNKQSCSISNIETVIEFQQKNNRLLEITREFSVNAGVTTPVSTY
MLTNSELLSLINDMPITNDQKKLMSNNVQIVRQQSYSIMCIIKEEVLAYV
VQLPLYGVIDTPCWKLHTSPLCTTNTKEGSNICLTRTDRGWYCDNAGSVS
FFPQAETCKVQSNRVFCDTMNSLTLPSEVNLCNVDIFNPKYDCKIMTSKT
DVSSSVITSLGAIVSCYGKTKCTASNKNRGIIKTFSNGCDYVSNKGVDTV
SVGNTLYYVNKQEGKSLYVKGEPIINFYDPLVFPSDEFDASISQVNEKIN
QSLAFIRKSDELLHNVNAGKSTTNIMITTIIIVIIVILLSLIAVGLLLYC
IIKFHRIQGKDQNDKNSEPYILTNRQ
```

GeneArt Optimized RSV F_A2_HEK_DS-Cav1_B3CT DNA Sequence:

(SEQ ID NO: 17)
```
atggaactgctgatcctgaaggccaacgccatcaccaccatcctgaccgc
cgtgaccttctgctttgccagcggccagaacatcaccgaggaattctacc
agagcacctgtagcgccgtgtccaagggctacctgagcgccctgagaacc
ggctggtacaccagcgtgatcaccatcgagctgagcaacatcaaagaaaa
caagtgcaacggcaccgacgccaaagtgaagctgatcaagcaggaactgg
acaagtacaagaatgccgtgaccgaactgcagctgctgatgcagagcacc
cccgccaccaacaaccgggccagaagagaactgcccagattcatgaacta
caccctgaacaacgccaaaaagaccaacgtgaccctgagcaagaagcgga
agcggcggttcctgggctttctgctgggagtgggaagcgccattgctagc
ggagtggccgtgtgcaaggtgctgcacctggaaggcgaagtgaacaagat
caagtccgccctgctgagcaccaacaaggccgtggtgtctctgagcaacg
gcgtgtccgtgctgaccttcaaggtgctggatctgaagaactacatcgac
aaacagctgctgcccatcttgaacaagcagagctgcagcatcagcaacat
cgagacagtgatcgagttccagcagaagaacaaccggctgctggaaatca
cccgcgagttcagcgtgaacgctggcgtgaccacccccgtgtccacctac
atgctgaccaacagcgagctgctgtccctgatcaacgacatgcccatcac
caacgaccagaaaaagctgatgagcaacaacgtgcagatcgtgcggcagc
agagctactccatcatgtgcatcatcaaagaagaggtgctggcctacgtg
gtgcagctgcctctgtacggcgtgatcgacacccccctgctggaagctgca
caccagccctctgtgcaccaccaacaccaaagagggctccaacatctgcc
tgacccggaccgacagaggctggtactgcgataatgccggctccgtctca
ttctttccacaagccgagacatgcaaggtgcagagcaaccgggtgttctg
cgacaccatgaacagcctgaccctgccctccgaagtgaatctgtgcaacg
tggacatcttcaaccctaagtacgactgcaagatcatgacctccaagacc
gacgtgtccagctccgtgatcacaagcctgggcgccatcgtgtcctgcta
cggcaagaccaagtgcaccgccagcaacaagaaccggggcatcatcaaga
ccttcagcaacggctgcgactacgtgtccaacaagggggtggacaccgtg
tctgtgggcaacaccctgtactacgtgaacaaacaggaaggcaagagcct
gtacgtgaagggcgagcccatcatcaacttctacgacccccctggtgttcc
ccagcgacgagttcgatgccagcatctcccaagtgaacgagaagatcaac
cagagcctggccttcatcagaaagtccgatgagctgctgcacaatgtgaa
cgccggcaagtccaccaccaatatcatgatcaccacaatcatcatcgtga
ttatcgtgatcctgctgagcctgatcgccgtgggcctgctgctgtactgt
atcatcaagttccaccggatccagggcaaggaccagaacgacaagaactc
cgagccctacatcctgacaaaccggcagtga
```

GenScript Optimized RSV F_A2_HEK_DS-Cav1_B3CT DNA Sequence:

(SEQ ID NO: 18)
```
atggaactgctgatcctgaaagccaacgctattactactatcctgaccgc
cgtgacattttgcttcgcatctggacagaacattactgaggaattctacc
agtcaacatgcagcgccgtgtccaaaggatacctgagcgccctgcggacc
ggctggtatacatcagtgattactatcgagctgtccaacatcaaggaaaa
caaatgtaatgggaccgacgcaaaggtgaaactgatcaagcaggagctgg
ataagtacaaaaatgccgtgacagaactgcagctgctgatgcagtccaca
ccagcaactaacaatcgcgcccggagagagctgccccggttcatgaacta
taccctgaacaatgctaagaaaaccaatgtgacactgtccaagaaacgca
agaggcgcttcctgggatttctgctgggcgtggggtctgccatcgctagt
ggagtggccgtctgcaaagtcctgcacctggagggcgaagtgaacaagat
caaaagcgccctgctgtccactaacaaggcagtggtcagtctgtcaaatg
gcgtgtccgtcctgaccttcaaggtgctggacctgaaaaattatattgat
aagcagctgctgcctatcctgaacaaacagagctgctccatttctaatat
cgagacagtgatcgaattccagcagaagaacaatagactgctggagatta
ccagagagttcagcgtgaacgccggcgtcaccacacccgtgtccacctac
atgctgacaaatagtgagctgctgtcactgattaacgacatgcctatcac
caatgatcagaagaaactgatgtccaacaatgtgcagatcgtcagacagc
agagttactcaatcatgtgcatcattaaggaggaagtcctggcctacgtg
gtccagctgccactgtatggcgtgatcgacacccccctgctggaaactgca
tacatctcctctgtgcactaccaacacaaaggaaggaagtaatatctgcc
tgactcgaaccgaccggggatggtactgtgataacgcaggcagcgtgtcc
ttctttccacaggccgagacctgcaaggtccagagcaacagggtgttctg
tgacactatgaatagcctgaccctgccttccgaagtcaacctgtgcaatg
tggacatctttaatccaaagtacgattgtaagatcatgactagcaagacc
gatgtcagctcctctgtgattacttctctgggggccatcgtgagttgcta
cggaaagacaaaatgtactgccagcaacaaaaatcgcggcatcattaaga
ccttctccaacgggtgcgactatgtctctaacaagggcgtggatacagtg
agtgtcgggaacactctgtactatgtcaataagcaggagggaaaaagcct
gtacgtgaagggcgaacccatcattaacttctatgacccccctggtgttcc
cttccgacgagtttgatgcatctattagtcaggtgaacgaaaaaatcaat
cagagtctggcctttattcggaagtcagatgagctgctgcacaacgtgaa
tgctggcaaatctacaactaacatcatgatcaccacaatcatcatcgtga
ttatcgtcattctgctgtcactgatcgctgtggggctgctgctgtactgt
atcattaagttccaccggatccagggcaaggaccagaacgataaaaatag
cgagccctacattctgaccaacagacag
```

hRSV F Protein from an A2 Strain Including HEK and DS Substitutions, and BPIV3 F TM and CT Domains (RSV F_A2_HEK_DS_B3TMCT) Protein Sequence:

(SEQ ID NO: 19)

```
MELLILKANAITTILTAVTFCFASGQNITEEFYQSTCSAVSKGYLSALRT
GWYTSVITIELSNIKENKCNGTDAKVKLIKQELDKYKNAVTELQLLMQST
PATNNRARRELPRFMNYTLNNAKKTNVTLSKKRKRRFLGFLLGVGSAIAS
GVAVCKVLHLEGEVNKIKSALLSTNKAVVSLSNGVSVLTSKVLDLKNYID
KQLLPIVNKQSCSISNIETVIEFQQKNNRLLEITREFSVNAGVTTPVSTY
MLTNSELLSLINDMPITNDQKKLMSNNVQIVRQQSYSIMCIIKEEVLAYV
VQLPLYGVIDTPCWKLHTSPLCTTNTKEGSNICLTRTDRGWYCDNAGSVS
FFPQAETCKVQSNRVFCDTMNSLTLPSEVNLCNVDIFNPKYDCKIMTSKT
DVSSSVITSLGAIVSCYGKTKCTASNKNRGIIKTFSNGCDYVSNKGVDTV
SVGNTLYYVNKQEGKSLYVKGEPIINFYDPLVFPSDEFDASISQVNEKIN
QSLAFIRKSDELLHNVNAGKSTTNIMITTITIIIVMIIILVIINITIIVV
IIKFHRIQGKDQNDKNSEPYILTNRQ
```

GeneArt Optimized RSV F_A2_HEK_DS_B3TMCT DNA Sequence:

(SEQ ID NO: 20)

```
atggaactgctgatcctgaaggccaacgccatcaccaccatcctgaccgc
cgtgaccttctgctttgccagcggccagaacatcaccgaggaattctacc
agagcacctgtagcgccgtgtccaagggctacctgagcgccctgagaacc
ggctggtacaccagcgtgatcaccatcgagctgagcaacatcaaagaaaa
caagtgcaacggcaccgacgccaaagtgaagctgatcaagcaggaactgg
acaagtacaagaatgccgtgaccgaactgcagctgctgatgcagagcacc
cccgccaccaacaaccgggccagaagagaactgcccagattcatgaacta
caccctgaacaacgccaaaaagaccaacgtgaccctgagcaagaagcgga
agcggcggttcctgggctttctgctgggagtgggaagcgccattgctagc
ggagtggccgtgtgcaaggtgctgcacctggaaggcgaagtgaacaagat
caagtccgccctgctgagcaccaacaaggccgtggtgtctctgagcaacg
gcgtgtccgtgctgaccagcaaggtgctggatctgaagaactacatcgac
aaacagctgctgcccatcgtgaacaagcagagctgcagcatcagcaacat
cgagacagtgatcgagttccagcagaagaacaaccggctgctggaaatca
cccgcgagttcagcgtgaacgctggcgtgaccaccccccgtgtccacctac
atgctgaccaacagcgagctgctgtccctgatcaacgacatgcccatcac
caacgaccagaaaaagctgatgagcaacaacgtgcagatcgtgcggcagc
agagctactccatcatgtgcatcatcaaagaagaggtgctggcctacgtg
gtgcagctgcctctgtacggcgtgatcgacacccccctgctggaagctgca
caccagccctctgtgcaccaccaacaccaaagagggctccaacatctgcc
tgacccggaccgacagaggctggtactgcgataatgccggctccgtctca
ttctttccacaagccgagacatgcaaggtgcagagcaaccgggtgttctg
cgacaccatgaacagcctgaccctgccctccgaagtgaatctgtgcaacg
```

-continued

```
tggacatcttcaaccctaagtacgactgcaagatcatgacctccaagacc
gacgtgtccagctccgtgatcacaagcctgggcgccatcgtgtcctgcta
cggcaagaccaagtgcaccgccagcaacaagaaccggggcatcatcaaga
ccttcagcaacggctgcgactacgtgtccaacaagggggtggacaccgtg
tctgtgggcaacaccctgtactacgtgaacaaacaggaaggcaagagcct
gtacgtgaagggcgagcccatcatcaacttctacgacccccctggtgttcc
ccagcgacgagttcgatgccagcatctcccaagtgaacgagaagatcaac
cagagcctggccttcatcagaaagtccgatgagctgctgcacaatgtgaa
cgccggcaagtccaccaccaatatcatgatcaccacaatcaccatcatca
ttgtgatgattatcatcctcgtgatcatcaacatcacaatcatcgtcgtg
attattaagttccaccggatccagggcaaggaccagaacgacaagaactc
cgagccctacatcctgacaaaccggcagtga
```

Genescript Optimized RSV F_A2_HEK_DS_B3TMCT DNA Sequence:

(SEQ ID NO: 137)

```
atggaactgctgatcctgaaagccaacgctattactactatcctgaccgc
cgtgacattttgcttcgcatctggacagaacattactgaggaattctacc
agtcaacatgcagcgccgtgtccaaaggatacctgagcgccctgcggacc
ggctggtatacatcagtgattactatcgagctgtccaacatcaaggaaaa
caaatgtaatgggaccgacgcaaaggtgaaactgatcaagcaggagctgg
ataagtacaaaaatgccgtgacagaactgcagctgctgatgcagtccaca
ccagcaactaacaatcgcgcccggagagagctgccccggttcatgaacta
taccctgaacaatgctaagaaaaccaatgtgacactgtccaagaaacgca
agaggcgcttcctgggatttctgctgggcgtggggtctgccatcgctagt
ggagtggccgtctgcaaagtcctgcacctggagggcgaagtgaacaagat
caaaagcgccctgctgtccactaacaaggcagtggtcagtctgtcaaatg
gcgtgtccgtcctgacctccaaggtgctggacctgaaaaattatattgat
aagcagctgctgcctatcgtcaacaaacagagctgctccatttctaatat
cgagacagtgatcgaattccagcagaagaacaatagactgctggagatta
ccagagagttcagcgtgaacgccggcgtcaccacacccgtgtccacctac
atgctgacaaatagtgagctgctgtcactgattaacgacatgcctatcac
caatgatcagaagaaactgatgtccaacaatgtgcagatcgtcagacagc
agagttactcaatcatgtgcatcattaaggaggaagtcctggcctacgtg
gtccagctgccactgtatggcgtgatcgacacccccctgctggaaactgca
tacatctcctctgtgcactaccaacacaaaggaaggaagtaatatctgcc
tgactcgaaccgaccggggatggtactgtgataacgcaggcagcgtgtcc
ttctttccacaggccgagacctgcaaggtccagagcaacagggtgttctg
tgacactatgaatagcctgaccctgccttccgaagtcaacctgtgcaatg
tggacatctttaatccaaagtacgattgtaagatcatgactagcaagacc
gatgtcagctcctctgtgattacttctctgggggccatcgtgagttgcta
```

-continued cggaaagacaaaatgtactgccagcaacaaaaatcgcggcatcattaaga ccttctccaacgggtgcgactatgtctctaacaagggcgtggatacagtg agtgtcgggaacactctgtactatgtcaataagcaggagggaaaaagcct gtacgtgaagggcgaacccatcattaacttctatgacccccctggtgttcc cttccgacgagtttgatgcatctattagtcaggtgaacgaaaaaatcaat cagagtctggcctttattcggaagtcagatgagctgctgcacaacgtgaa tgctggcaaatctacaactaacatcatgatcaccacaatcaccatcatta tcgtgatgattatcattctggtcatcattaacatcacaatcattgtggtc atcattaagttccaccggattcagggcaaggaccagaacgataaaaatag cgagccctacatcctgaccaatagacagtga hRSV F Protein from an A2 Strain Including HEK and DS-Cav1 Substitutions, and BPIV3 F TM and CT Domains (RSV F_A2_HEK_DS-Cav1_B3TMCT) Protein Sequence:

(SEQ ID NO: 21)

MELLILKANAITTILTAVTFCFASGQNITEEFYQSTCSAVSKGYLSALRT

GWYTSVITIELSNIKENKCNGTDAKVKLIKQELDKYKNAVTELQLLMQST

PATNNRARRELPRFMNYTLNNAKKTNVTLSKKRKRRFLGFLLGVGSAIAS

GVAVCKVLHLEGEVNKIKSALLSTNKAVVSLSNGVSVLTFKVLDLKNYID

KQLLPILNKQSCSISNIETVIEFQQKNNRLLEITREFSVNAGVTTPVSTY

MLTNSELLSLINDMPITNDQKKLMSNNVQIVRQQSYSIMCIIKEEVLAYV

VQLPLYGVIDTPCWKLHTSPLCTTNTKEGSNICLTRTDRGWYCDNAGSVS

FFPQAETCKVQSNRVFCDTMNSLTLPSEVNLCNVDIFNPKYDCKIMTSKT

DVSSSVITSLGAIVSCYGKTKCTASNKNRGIIKTFSNGCDYVSNKGVDTV

SVGNTLYYVNKQEGKSLYVKGEPIINFYDPLVFPSDEFDASISQVNEKIN

QSLAFIRKSDELLHNVNAGKSTTNIMITTITIIIVMIIILVIINITIIVV

IIKFHRIQGKDQNDKNSEPYILTNRQ

GeneArt Optimized RSV F_A2_HEK_DS-Cav1_B3TMCT DNA Sequence:

(SEQ ID NO: 22)

atggaactgctgatcctgaaggccaacgccatcaccaccatcctgaccgc cgtgaccttctgctttgccagcggccagaacatcaccgaggaattctacc agagcacctgtagcgccgtgtccaagggctacctgagcgccctgagaacc ggctggtacaccagcgtgatcaccatcgagctgagcaacatcaaagaaaa caagtgcaacggcaccgacgccaaagtgaagctgatcaagcaggaactgg acaagtacaagaatgccgtgaccgaactgcagctgctgatgcagagcacc cccgccaccaacaaccgggccagaagagaactgcccagattcatgaacta caccctgaacaacgccaaaaagaccaacgtgaccctgagcaagaagcgga agcggcggttcctgggctttctgctgggagtgggaagcgccattgctagc ggagtggccgtgtgcaaggtgctgcacctggaaggcgaagtgaacaagat caagtccgccctgctgagcaccaacaaggccgtggtgtctctgagcaacg gcgtgtccgtgctgaccttcaaggtgctggatctgaagaactacatcgac aaacagctgctgcccatcttgaacaagcagagctgcagcatcagcaacat cgagacagtgatcgagttccagcagaagaacaaccggctgctggaaatca cccgcgagttcagcgtgaacgctggcgtgaccaccccccgtgtccacctac atgctgaccaacagcgagctgctgtccctgatcaacgacatgcccatcac caacgaccagaaaaagctgatgagcaacaacgtgcagatcgtgcggcagc agagctactccatcatgtgcatcatcaaagaagaggtgctggcctacgtg gtgcagctgcctctgtacggcgtgatcgacacccccctgctggaagctgca caccagccctctgtgcaccaccaacaccaaagagggctccaacatctgcc tgacccggaccgacagaggctggtactgcgataatgccggctccgtctca ttctttccacaagccgagacatgcaaggtgcagagcaaccgggtgttctg cgacaccatgaacagcctgaccctgccctccgaagtgaatctgtgcaacg tggacatcttcaaccctaagtacgactgcaagatcatgacctccaagacc gacgtgtccagctccgtgatcacaagcctgggcgccatcgtgtcctgcta cggcaagaccaagtgcaccgccagcaacaagaaccggggcatcatcaaga ccttcagcaacggctgcgactacgtgtccaacaagggggtggacaccgtg tctgtgggcaacaccctgtactacgtgaacaaacaggaaggcaagagcct gtacgtgaagggcgagcccatcatcaacttctacgacccccctggtgttcc ccagcgacgagttcgatgccagcatctcccaagtgaacgagaagatcaac cagagcctggccttcatcagaaagtccgatgagctgctgcacaatgtgaa cgccggcaagtccaccaccaatatcatgatcaccacaatcaccatcatca ttgtgatgattatcatcctcgtgatcatcaacatcacaatcatcgtcgtg attattaagttccaccggatccagggcaaggaccagaacgacaagaactc cgagccctacatcctgacaaaccggcagtga GenScript Optimized RSV F_A2_HEK_DS-Cav1_B3TMCT DNA Sequence:

(SEQ ID NO: 23)

atggaactgctgatcctgaaagccaacgctattactactatcctgaccgc cgtgacattttgcttcgcatctggacagaacattactgaggaattctacc agtcaacatgcagcgccgtgtccaaaggatacctgagcgccctgcggacc ggctggtatacatcagtgattactatcgagctgtccaacatcaaggaaaa caaatgtaatgggaccgacgcaaaggtgaaactgatcaagcaggagctgg ataagtacaaaaatgccgtgacagaactgcagctgctgatgcagtccaca ccagcaactaacaatcgcgcccggagagagctgccccggttcatgaacta taccctgaacaatgctaagaaaaccaatgtgacactgtccaagaaacgca agaggcgcttcctgggatttctgctgggcgtggggtctgccatcgctagt ggagtggccgtctgcaaagtcctgcacctggagggcgaagtgaacaagat caaaagcgccctgctgtccactaacaaggcagtggtcagtctgtcaaatg gcgtgtccgtcctgaccttcaaggtgctggacctgaaaaattatattgat aagcagctgctgcctatcctgaacaaacagagctgctccatttctaatat cgagacagtgatcgaattccagcagaagaacaatagactgctggagatta ccagagagttcagcgtgaacgccggcgtcaccacacccgtgtccacctac

```
atgctgacaaatagtgagctgctgtcactgattaacgacatgcctatcac

caatgatcagaagaaactgatgtccaacaatgtgcagatcgtcagacagc

agagttactcaatcatgtgcatcattaaggaggaagtcctggcctacgtg

gtccagctgccactgtatggcgtgatcgacaccccctgctggaaactgca

tacatctcctctgtgcactaccaacacaaaggaaggaagtaatatctgcc

tgactcgaaccgaccggggatggtactgtgataacgcaggcagcgtgtcc

ttctttccacaggccgagacctgcaaggtccagagcaacagggtgttctg

tgacactatgaatagcctgaccctgccttccgaagtcaacctgtgcaatg

tggacatctttaatccaaagtacgattgtaagatcatgactagcaagacc

gatgtcagctcctctgtgattacttctctgggggccatcgtgagttgcta

cggaaagacaaaatgtactgccagcaacaaaaatcgcggcatcattaaga

ccttctccaacgggtgcgactatgtctctaacaagggcgtggatacagtg

agtgtcgggaacactctgtactatgtcaataagcaggagggaaaaagcct

gtacgtgaagggcgaaccatcattaacttctatgaccccctggtgttcc

cttccgacgagtttgatgcatctattagtcaggtgaacgaaaaaatcaat

cagagtctggcctttattcggaagtcagatgagctgctgcacaacgtgaa

tgctggcaaatctacaactaacatcatgatcaccacaatcaccatcatta

tcgtgatgattatcattctggtcatcattaacatcacaatcattgtggtc

atcattaagttccaccggattcagggcaaggaccagaacgataaaaatag

cgagccctacatcctgaccaatagacagtga
```

In an embodiment, the recombinant paramyxovirus includes a recombinant Sendai virus genome including a heterologous gene encoding a recombinant hRSV F ectodomain. In such embodiments, the TM and CT linked to the RSV F ectodomain can be from a Sendai virus F protein, for example as set forth as residues 1-21 of SEQ ID NO: 103 (TM), residues 22-65 of SEQ ID NO: 103 (CT), or SEQ ID NO: 103 (TM+CT). For example, in some embodiments, the recombinant hRSV F ectodomain linked to the Sendai virus TM and/or CT can include the amino acid sequence set forth as one of SEQ ID NOs: 105-108:

hRSV F Protein from an A2 Strain Including HEK Substitutions, and Sendai Virus F CT Domain (RSV F_A2_HEK_SeVCT) Protein Sequence.

```
                                        (SEQ ID NO: 105)
MELLILKANAITTILTAVTFCFASGQNITEEFYQSTCSAVSKGYLSALRT

GWYTSVITIELSNIKENKCNGTDAKVKLIKQELDKYKNAVTELQLLMQST

PATNNRARRELPRFMNYTLNNAKKTNVTLSKKRKRRFLGFLLGVGSAIAS

GVAVSKVLHLEGEVNKIKSALLSTNKAVVSLSNGVSVLTSKVLDLKNYID

KQLLPIVNKQSCSISNIETVIEFQQKNNRLLEITREFSVNAGVTTPVSTY

MLTNSELLSLINDMPITNDQKKLMSNNVQIVRQQSYSIMSIIKEEVLAYV

VQLPLYGVIDTPCWKLHTSPLCTTNTKEGSNICLTRTDRGWYCDNAGSVS

FFPQAETCKVQSNRVFCDTMNSLTLPSEVNLCNVDIFNPKYDCKIMTSKT

DVSSSVITSLGAIVSCYGKTKCTASNKNRGIIKTFSNGCDYVSNKGVDTV

SVGNTLYYVNKQEGKSLYVKGEPIINFYDPLVFPSDEFDASISQVNEKIN

QSLAFIRKSDELLHNVNAGKSTTNIMITTIIIVIIVILLSLIAVGLLLYC

LYRLRRSMLMGNPDDRIPRDTYTLEPKIRHMYTNGGFDAMAEKR
```

hRSV F Protein from an A2 Strain Including HEK Substitutions, and Sendai Virus F TM and CT Domains (RSV F_A2_HEK_SeVTMCT) Protein Sequence.

```
                                        (SEQ ID NO: 106)
MELLILKANAITTILTAVTFCFASGQNITEEFYQSTCSAVSKGYLSALRT

GWYTSVITIELSNIKENKCNGTDAKVKLIKQELDKYKNAVTELQLLMQST

PATNNRARRELPRFMNYTLNNAKKTNVTLSKKRKRRFLGFLLGVGSAIAS

GVAVSKVLHLEGEVNKIKSALLSTNKAVVSLSNGVSVLTSKVLDLKNYID

KQLLPIVNKQSCSISNIETVIEFQQKNNRLLEITREFSVNAGVTTPVSTY

MLTNSELLSLINDMPITNDQKKLMSNNVQIVRQQSYSIMSIIKEEVLAYV

VQLPLYGVIDTPCWKLHTSPLCTTNTKEGSNICLTRTDRGWYCDNAGSVS

FFPQAETCKVQSNRVFCDTMNSLTLPSEVNLCNVDIFNPKYDCKIMTSKT

DVSSSVITSLGAIVSCYGKTKCTASNKNRGIIKTFSNGCDYVSNKGVDTV

SVGNTLYYVNKQEGKSLYVKGEPIINFYDPLVFPSDEFDASISQVNEKIN

QSLAFIRKSDELLHNVNAGKSTTNIMITTVITIIVVMVVILVVIIVIIIV

LYRLRRSMLMGNPDDRIPRDTYTLEPKIRHMYTNGGFDAMAEKR
```

hRSV F Protein from an A2 Strain Including HEK and DS-Cav1 Substitutions, and Sendai Virus F CT Domains (RSV F_A2_HEK_SeVCT) Protein Sequence

```
                                        (SEQ ID NO: 107)
MELLILKANAITTILTAVTFCFASGQNITEEFYQSTCSAVSKGYLSALRT

GWYTSVITIELSNIKENKCNGTDAKVKLIKQELDKYKNAVTELQLLMQST

PATNNRARRELPRFMNYTLNNAKKTNVTLSKKRKRRFLGFLLGVGSAIAS

GVAVCKVLHLEGEVNKIKSALLSTNKAVVSLSNGVSVLTFKVLDLKNYID

KQLLPILNKQSCSISNIETVIEFQQKNNRLLEITREFSVNAGVTTPVSTY

MLTNSELLSLINDMPITNDQKKLMSNNVQIVRQQSYSIMCIIKEEVLAYV

VQLPLYGVIDTPCWKLHTSPLCTTNTKEGSNICLTRTDRGWYCDNAGSVS

FFPQAETCKVQSNRVFCDTMNSLTLPSEVNLCNVDIFNPKYDCKIMTSKT

DVSSSVITSLGAIVSCYGKTKCTASNKNRGIIKTFSNGCDYVSNKGVDTV

SVGNTLYYVNKQEGKSLYVKGEPIINFYDPLVFPSDEFDASISQVNEKIN

QSLAFIRKSDELLHNVNAGKSTTNIMITTIIIVIIVILLSLIAVGLLLYC

LYRLRRSMLMGNPDDRIPRDTYTLEPKIRHMYTNGGFDAMAEKR
```

hRSV F Protein from an A2 Strain Including HEK and DS-Cav1 Substitutions, and Sendai Virus F TM and CT Domains (RSV F_A2_HEK_SeVTMCT) Protein Sequence

```
                                        (SEQ ID NO: 108)
MELLILKANAITTILTAVTFCFASGQNITEEFYQSTCSAVSKGYLSALRT

GWYTSVITIELSNIKENKCNGTDAKVKLIKQELDKYKNAVTELQLLMQST

PATNNRARRELPRFMNYTLNNAKKTNVTLSKKRKRRFLGFLLGVGSAIAS

GVAVCKVLHLEGEVNKIKSALLSTNKAVVSLSNGVSVLTFKVLDLKNYID
```

-continued

KQLLPILNKQSCSISNIETVIEFQQKNNRLLEITREFSVNAGVTTPVSTY

MLTNSELLSLINDMPITNDQKKLMSNNVQIVRQQSYSIMCIIKEEVLAYV

VQLPLYGVIDTPCWKLHTSPLCTTNTKEGSNICLTRTDRGWYCDNAGSVS

FFPQAETCKVQSNRVFCDTMNSLTLPSEVNLCNVDIFNPKYDCKIMTSKT

DVSSSVITSLGAIVSCYGKTKCTASNKNRGIIKTFSNGCDYVSNKGVDTV

SVGNTLYYVNKQEGKSLYVKGEPIINFYDPLVFPSDEFDASISQVNEKIN

QSLAFIRKSDELLHNVNAGKSTTNIMITTVITIIVVMVVILVVIIVIIIV

LYRLRRSMLMGNPDDRIPRDTYTLEPKIRHMYTNGGFDAMAEKR

In an embodiment, the recombinant paramyxovirus includes a recombinant NDV genome including a heterologous gene encoding a recombinant hRSV F ectodomain. In such embodiments, the TM and CT linked to the RSV F ectodomain can be from a NDV virus F protein, cytoplasmic tail, for example as set forth as residues 1-21 of SEQ ID NO: 104 (TM), residues 22-49 of SEQ ID NO: 104 (CT), or SEQ ID NO: 104 (TM+CT). For example, in some embodiments, the recombinant hRSV F ectodomain linked to the NDV TM and/or CT can include the amino acid sequence set forth as one of SEQ ID NOs: 109-113:

hRSV F Protein from an A2 Strain Including HEK Substitutions, and NDV F CT Domains (RSV F_A2_HEK_NDVCT) Protein Sequence (SEQ ID NO: 109)

MELLILKANAITTILTAVTFCFASGQNITEEFYQSTCSAVSKGYLSALRT

GWYTSVITIELSNIKENKCNGTDAKVKLIKQELDKYKNAVTELQLLMQST

PATNNRARRELPRFMNYTLNNAKKTNVTLSKKRKRRFLGFLLGVGSAIAS

GVAVSKVLHLEGEVNKIKSALLSTNKAVVSLSNGVSVLTSKVLDLKNYID

KQLLPIVNKQSCSISNIETVIEFQQKNNRLLEITREFSVNAGVTTPVSTY

MLTNSELLSLINDMPITNDQKKLMSNNVQIVRQQSYSIMSIIKEEVLAYV

VQLPLYGVIDTPCWKLHTSPLCTTNTKEGSNICLTRTDRGWYCDNAGSVS

FFPQAETCKVQSNRVFCDTMNSLTLPSEVNLCNVDIFNPKYDCKIMTSKT

DVSSSVITSLGAIVSCYGKTKCTASNKNRGIIKTFSNGCDYVSNKGVDTV

SVGNTLYYVNKQEGKSLYVKGEPIINFYDPLVFPSDEFDASISQVNEKIN

QSLAFIRKSDELLHNVNAGKSTTNIMITTIIIVIIVILLSLIAVGLLLYC

MYKQKAQQKTLLWLGNNTLDQMRATTKM hRSV F Protein from an A2 Strain Including HEK Substitutions, and NDV F TM and CT Domains (RSV F_A2_HEK_NDVTMCT) Protein Sequence (SEQ ID NO: 110)

MELLILKANAITTILTAVTFCFASGQNITEEFYQSTCSAVSKGYLSALRT

GWYTSVITIELSNIKENKCNGTDAKVKLIKQELDKYKNAVTELQLLMQST

PATNNRARRELPRFMNYTLNNAKKTNVTLSKKRKRRFLGFLLGVGSAIAS

GVAVSKVLHLEGEVNKIKSALLSTNKAVVSLSNGVSVLTSKVLDLKNYID

KQLLPIVNKQSCSISNIETVIEFQQKNNRLLEITREFSVNAGVTTPVSTY

MLTNSELLSLINDMPITNDQKKLMSNNVQIVRQQSYSIMSIIKEEVLAYV

-continued

VQLPLYGVIDTPCWKLHTSPLCTTNTKEGSNICLTRTDRGWYCDNAGSVS

FFPQAETCKVQSNRVFCDTMNSLTLPSEVNLCNVDIFNPKYDCKIMTSKT

DVSSSVITSLGAIVSCYGKTKCTASNKNRGIIKTFSNGCDYVSNKGVDTV

SVGNTLYYVNKQEGKSLYVKGEPIINFYDPLVFPSDEFDASISQVNEKIN

QSLAFIRKSDELLHNVNAGKSTTNIMITTIVLTIISLVFGILSLILACYL

MYKQKAQQKTLLWLGNNTLDQMRATTKM hRSV F Protein from an A2 Strain Including HEK and DS-Cav1 Substitutions, and NDV F CT Domains (RSV F_A2_HEK_NDVCT) Protein Sequence (SEQ ID NO: 112)

MELLILKANAITTILTAVTFCFASGQNITEEFYQSTCSAVSKGYLSALRT

GWYTSVITIELSNIKENKCNGTDAKVKLIKQELDKYKNAVTELQLLMQST

PATNNRARRELPRFMNYTLNNAKKTNVTLSKKRKRRFLGFLLGVGSAIAS

GVAVCKVLHLEGEVNKIKSALLSTNKAVVSLSNGVSVLTFKVLDLKNYID

KQLLPILNKQSCSISNIETVIEFQQKNNRLLEITREFSVNAGVTTPVSTY

MLTNSELLSLINDMPITNDQKKLMSNNVQIVRQQSYSIMCIIKEEVLAYV

VQLPLYGVIDTPCWKLHTSPLCTTNTKEGSNICLTRTDRGWYCDNAGSVS

FFPQAETCKVQSNRVFCDTMNSLTLPSEVNLCNVDIFNPKYDCKIMTSKT

DVSSSVITSLGAIVSCYGKTKCTASNKNRGIIKTFSNGCDYVSNKGVDTV

SVGNTLYYVNKQEGKSLYVKGEPIINFYDPLVFPSDEFDASISQVNEKIN

QSLAFIRKSDELLHNVNAGKSTTNIMITTIIIVIIVILLSLIAVGLLLYC

MYKQKAQQKTLLWLGNNTLDQMRATTKM hRSV F Protein from an A2 Strain Including HEK and DS-Cav1 Substitutions, and NDV F TM and CT Domains (RSV F_A2_HEK_NDVTMCT) Protein Sequence (SEQ ID NO: 113)

MELLILKANAITTILTAVTFCFASGQNITEEFYQSTCSAVSKGYLSALRT

GWYTSVITIELSNIKENKCNGTDAKVKLIKQELDKYKNAVTELQLLMQST

PATNNRARRELPRFMNYTLNNAKKTNVTLSKKRKRRFLGFLLGVGSAIAS

GVAVCKVLHLEGEVNKIKSALLSTNKAVVSLSNGVSVLTFKVLDLKNYID

KQLLPILNKQSCSISNIETVIEFQQKNNRLLEITREFSVNAGVTTPVSTY

MLTNSELLSLINDMPITNDQKKLMSNNVQIVRQQSYSIMCIIKEEVLAYV

VQLPLYGVIDTPCWKLHTSPLCTTNTKEGSNICLTRTDRGWYCDNAGSVS

FFPQAETCKVQSNRVFCDTMNSLTLPSEVNLCNVDIFNPKYDCKIMTSKT

DVSSSVITSLGAIVSCYGKTKCTASNKNRGIIKTFSNGCDYVSNKGVDTV

SVGNTLYYVNKQEGKSLYVKGEPIINFYDPLVFPSDEFDASISQVNEKIN

QSLAFIRKSDELLHNVNAGKSTTNIMITTVITIIVVMVVILVVIIVIIIV

LYRLRRSMLMGNPDDRIPRDTYTLEPKIRHMYTNGGFDAMAEKR

H. Additional Description of Recombinant Paramyxovirus Particular Embodiments

In some embodiments, a recombinant paramyxovirus is provided, comprising a recombinant parainfluenza virus (PIV) comprising a viral genome comprising, from upstream to downstream, a PIV genomic promoter followed by PIV N, P, M, F, HN, and L genes, and further comprising a heterologous gene encoding a type I membrane protein comprising a recombinant RSV F ectodomain, wherein the heterologous gene is located between the genomic promoter and the gene encoding the N protein, and wherein the RSV F ectodomain comprises 66E, 101P, 155C, 290C, 190F, and 207L substitutions and is linked to a TM and CT of the PIV F protein.

In some embodiments, a recombinant paramyxovirus is provided, comprising a recombinant HPIV1 comprising a viral genome comprising, from upstream to downstream, a HPIV1 genomic promoter followed by HPIV1 N, P, M, F, HN, and L genes, and further comprising a heterologous gene encoding a type I membrane protein comprising a recombinant RSV F ectodomain, wherein the heterologous gene is located between the genomic promoter and the gene encoding the N protein, and wherein the RSV F ectodomain comprises 66E, 101P, 155C, 290C, 190F, and 207L substitutions and is linked to a TM and CT of the HPIV1 F protein.

In some embodiments, a recombinant paramyxovirus is provided, comprising a recombinant HPIV1 comprising a viral genome comprising, from upstream to downstream, a HPIV1 genomic promoter followed by HPIV1N, P, M, F, HN, and L genes, and further comprising a heterologous gene encoding a type I membrane protein comprising a recombinant RSV F ectodomain, wherein the heterologous gene is located between the genes encoding the N and P proteins, and wherein the RSV F ectodomain comprises 66E, 101P, 155C, 290C, 190F, and 207L substitutions and is linked to a TM and CT of the HPIV1 F protein.

In some embodiments, a recombinant paramyxovirus is provided, comprising a recombinant HPIV3 comprising a viral genome comprising, from upstream to downstream, a HPIV3 genomic promoter followed by HPIV3N, P, M, F, HN, and L genes, and further comprising a heterologous gene encoding a type I membrane protein comprising a recombinant RSV F ectodomain, wherein the heterologous gene is located between the genomic promoter and the gene encoding the N protein, and wherein the RSV F ectodomain comprises 66E, 101P, 155C, 290C, 190F, and 207L substitutions and is linked to a TM and CT of the HPIV3 F protein.

In some embodiments, a recombinant paramyxovirus is provided, comprising a recombinant HPIV3 comprising a viral genome comprising, from upstream to downstream, a HPIV3 genomic promoter followed by HPIV3 N, P, M, F, HN, and L genes, and further comprising a heterologous gene encoding a type I membrane protein comprising a recombinant RSV F ectodomain, wherein the heterologous gene is located between the genes encoding the N and P proteins, and wherein the RSV F ectodomain comprises 66E, 101P, 155C, 290C, 190F, and 207L substitutions and is linked to a TM and CT of the HPIV3 F protein.

In some embodiments, a recombinant paramyxovirus is provided, comprising a recombinant HPIV3 comprising a viral genome comprising, from upstream to downstream, a HPIV3 genomic promoter followed by HPIV3 N, P, M, F, HN, and L genes, and further comprising a heterologous gene encoding a type I membrane protein comprising a recombinant RSV F ectodomain, wherein the heterologous gene is located between the genomic promoter and the gene encoding the N protein, and wherein the RSV F ectodomain comprises 66E, 101P, 155C, 290C, 190F, and 207L substitutions and is linked to a TM and CT of the BPIV3 F protein.

In some embodiments, a recombinant paramyxovirus is provided, comprising a recombinant HPIV3 comprising a viral genome comprising, from upstream to downstream, a HPIV3 genomic promoter followed by HPIV3 N, P, M, F, HN, and L genes, and further comprising a heterologous gene encoding a type I membrane protein comprising a recombinant RSV F ectodomain, wherein the heterologous gene is located between the genes encoding the N and P proteins, and wherein the RSV F ectodomain comprises 66E, 101P, 155C, 290C, 190F, and 207L substitutions and is linked to a TM and CT of the BPIV3 F protein.

In some embodiments, a recombinant paramyxovirus is provided, comprising a recombinant BPIV3 comprising a viral genome comprising, from upstream to downstream, a BPIV3 genomic promoter followed by BPIV3 N, P, M, F, HN, and L genes, and further comprising a heterologous gene encoding a type I membrane protein comprising a recombinant RSV F ectodomain, wherein the heterologous gene is located between the genomic promoter and the gene encoding the N protein, and wherein the RSV F ectodomain comprises 66E, 101P, 155C, 290C, 190F, and 207L substitutions and is linked to a TM and CT of the BPIV3 F protein.

In some embodiments, a recombinant paramyxovirus is provided, comprising a recombinant BPIV3 comprising a viral genome comprising, from upstream to downstream, a BPIV3 genomic promoter followed by BPIV3 N, P, M, F, HN, and L genes, and further comprising a heterologous gene encoding a type I membrane protein comprising a recombinant RSV F ectodomain, wherein the heterologous gene is located between the genes encoding the N and P proteins, and wherein the RSV F ectodomain comprises 66E, 101P, 155C, 290C, 190F, and 207L substitutions and is linked to a TM and CT of the BPIV3 F protein.

In some embodiments, a recombinant paramyxovirus is provided, comprising a recombinant B/HPIV3 comprising a viral genome comprising, from upstream to downstream, a BPIV3 genomic promoter followed by BPIV3 N, P, and M genes, HPIV3 F and HN genes, and a BPIV3 L gene, and further comprising a heterologous gene encoding a type I membrane protein comprising a recombinant RSV F ectodomain, wherein the heterologous gene is located between the genomic promoter and the gene encoding the N protein, and wherein the RSV F ectodomain comprises 66E, 101P, 155C, 290C, 190F, and 207L substitutions and is linked to a TM and CT of the BPIV3 F protein.

In some embodiments, a recombinant paramyxovirus is provided, comprising a recombinant B/HPIV3 comprising a viral genome comprising, from upstream to downstream, a BPIV3 genomic promoter followed by BPIV3 N, P, and M genes, HPIV3 F and HN genes, and a BPIV3 L gene, and further comprising a heterologous gene encoding a type I membrane protein comprising a recombinant RSV F ectodomain, wherein the heterologous gene is located between the genes encoding the N and P proteins, and wherein the RSV F ectodomain comprises 66E, 101P, 155C, 290C, 190F, and 207L substitutions and is linked to a TM and CT of the BPIV3 F protein.

In some embodiments, a recombinant paramyxovirus is provided, comprising a recombinant B/HPIV3 comprising a viral genome comprising, from upstream to downstream, a BPIV3 genomic promoter followed by BPIV3 N, P, and M genes, HPIV3 F and HN genes, and a BPIV3 L gene, and further comprising a heterologous gene encoding a type I membrane protein comprising a recombinant RSV F ectodomain, wherein the heterologous gene is located between the genomic promoter and the gene encoding the N protein, and wherein the RSV F ectodomain comprises 66E, 101P, 155C, 290C, 190F, and 207L substitutions and is linked to a TM and CT of the HPIV3 F protein.

In some embodiments, a recombinant paramyxovirus is provided, comprising a recombinant B/HPIV3 comprising a viral genome comprising, from upstream to downstream, a BPIV3 genomic promoter followed by BPIV3 N, P, and M genes, HPIV3 F and HN genes, and a BPIV3 L gene, and further comprising a heterologous gene encoding a type I membrane protein comprising a recombinant RSV F ectodomain, wherein the heterologous gene is located between the genes encoding the N and P proteins, and wherein the RSV F ectodomain comprises 66E, 101P, 155C, 290C, 190F, and 207L substitutions and is linked to a TM and CT of the HPIV3 F protein.

In some embodiments, a recombinant paramyxovirus is provided, comprising a recombinant sendai virus comprising a viral genome comprising, from upstream to downstream, a sendai virus genomic promoter followed by sendai virus N, P, M, F, HN, and L genes, and further comprising a heterologous gene encoding a type I membrane protein comprising a recombinant RSV F ectodomain, wherein the heterologous gene is located between the genomic promoter and the gene encoding the N protein, and wherein the RSV F ectodomain comprises 66E, 101P, 155C, 290C, 190F, and 207L substitutions and is linked to a TM and CT of the sendai virus F protein.

In some embodiments, a recombinant paramyxovirus is provided, comprising a recombinant sendai virus comprising a viral genome comprising, from upstream to downstream, a sendai virus genomic promoter followed by sendai virus N, P, M, F, HN, and L gene, and further comprising a heterologous gene encoding a type I membrane protein comprising a recombinant RSV F ectodomain, wherein the heterologous gene is located between the genes encoding the N and P proteins, and wherein the RSV F ectodomain comprises 66E, 101P, 155C, 290C, 190F, and 207L substitutions and is linked to a TM and CT of the sendai virus F protein.

In some embodiments, a recombinant paramyxovirus is provided, comprising a recombinant NDV comprising a viral genome comprising, from upstream to downstream, a NDV genomic promoter followed by NDV N, P, M, F, HN, and L genes, and further comprising a heterologous gene encoding a type I membrane protein comprising a recombinant RSV F ectodomain, wherein the heterologous gene is located between the genomic promoter and the gene encoding the N protein, and wherein the RSV F ectodomain comprises 66E, 101P, 155C, 290C, 190F, and 207L substitutions and is linked to a TM and CT of the NDV F protein.

In some embodiments, a recombinant paramyxovirus is provided, comprising a recombinant NDV comprising a viral genome comprising, from upstream to downstream, a NDV genomic promoter followed by NDV N, P, M, F, HN, and L gene, and further comprising a heterologous gene encoding a type I membrane protein comprising a recombinant RSV F ectodomain, wherein the heterologous gene is located between the genes encoding the N and P proteins, and wherein the RSV F ectodomain comprises 66E, 101P, 155C, 290C, 190F, and 207L substitutions and is linked to a TM and CT of the NDV F protein.

In some embodiments, a recombinant paramyxovirus is provided, comprising a recombinant PIV5 comprising a viral genome comprising, from upstream to downstream, a PIV5 genomic promoter followed by PIV5 N, P, M, F, HN, and L genes, and further comprising a heterologous gene encoding a type I membrane protein comprising a recombinant RSV F ectodomain, wherein the heterologous gene is located between the genomic promoter and the gene encoding the N protein, and wherein the RSV F ectodomain comprises 66E, 101P, 155C, 290C, 190F, and 207L substitutions and is linked to a TM and CT of the PIV5 F protein.

In some embodiments, a recombinant paramyxovirus is provided, comprising a recombinant PIV5 comprising a viral genome comprising, from upstream to downstream, a PIV5 genomic promoter followed by PIV5 N, P, M, F, HN, and L gene, and further comprising a heterologous gene encoding a type I membrane protein comprising a recombinant RSV F ectodomain, wherein the heterologous gene is located between the genes encoding the N and P proteins, and wherein the RSV F ectodomain comprises 66E, 101P, 155C, 290C, 190F, and 207L substitutions and is linked to a TM and CT of the PIV5 F protein.

In some embodiments, a recombinant paramyxovirus is provided, comprising a recombinant parainfluenza virus (PIV) comprising a viral genome comprising, from upstream to downstream, a PIV genomic promoter followed by PIV N, P, M, F, HN, and L genes, and further comprising a heterologous gene encoding a type I membrane protein comprising a recombinant RSV F ectodomain, wherein the heterologous gene is located between the genomic promoter and the gene encoding the N protein, and wherein the RSV F ectodomain comprises 66E, 101P, 155C, 290C, 190F, and 207L substitutions and is linked to a CT of the PIV F protein.

In some embodiments, a recombinant paramyxovirus is provided, comprising a recombinant HPIV1 comprising a viral genome comprising, from upstream to downstream, a HPIV1 genomic promoter followed by HPIV1 N, P, M, F, HN, and L genes, and further comprising a heterologous gene encoding a type I membrane protein comprising a recombinant RSV F ectodomain, wherein the heterologous gene is located between the genomic promoter and the gene encoding the N protein, and wherein the RSV F ectodomain comprises 66E, 101P, 155C, 290C, 190F, and 207L substitutions and is linked to a CT of the HPIV1 F protein.

In some embodiments, a recombinant paramyxovirus is provided, comprising a recombinant HPIV1 comprising a viral genome comprising, from upstream to downstream, a HPIV1 genomic promoter followed by HPIV1N, P, M, F, HN, and L genes, and further comprising a heterologous gene encoding a type I membrane protein comprising a recombinant RSV F ectodomain, wherein the heterologous gene is located between the genes encoding the N and P proteins, and wherein the RSV F ectodomain comprises 66E, 101P, 155C, 290C, 190F, and 207L substitutions and is linked to a CT of the HPIV1 F protein.

In some embodiments, a recombinant paramyxovirus is provided, comprising a recombinant HPIV3 comprising a viral genome comprising, from upstream to downstream, a HPIV3 genomic promoter followed by HPIV3N, P, M, F, HN, and L genes, and further comprising a heterologous gene encoding a type I membrane protein comprising a recombinant RSV F ectodomain, wherein the heterologous gene is located between the genomic promoter and the gene encoding the N protein, and wherein the RSV F ectodomain comprises 66E, 101P, 155C, 290C, 190F, and 207L substitutions and is linked to a CT of the HPIV3 F protein.

In some embodiments, a recombinant paramyxovirus is provided, comprising a recombinant HPIV3 comprising a viral genome comprising, from upstream to downstream, a HPIV3 genomic promoter followed by HPIV3 N, P, M, F, HN, and L genes, and further comprising a heterologous gene encoding a type I membrane protein comprising a recombinant RSV F ectodomain, wherein the heterologous gene is located between the genes encoding the N and P proteins, and wherein the RSV F ectodomain comprises 66E, 101P, 155C, 290C, 190F, and 207L substitutions and is linked to a CT of the HPIV3 F protein.

In some embodiments, a recombinant paramyxovirus is provided, comprising a recombinant HPIV3 comprising a viral genome comprising, from upstream to downstream, a HPIV3 genomic promoter followed by HPIV3 N, P, M, F, HN, and L genes, and further comprising a heterologous gene encoding a type I membrane protein comprising a recombinant RSV F ectodomain, wherein the heterologous gene is located between the genomic promoter and the gene encoding the N protein, and wherein the RSV F ectodomain comprises 66E, 101P, 155C, 290C, 190F, and 207L substitutions and is linked to a CT of the BPIV3 F protein.

In some embodiments, a recombinant paramyxovirus is provided, comprising a recombinant HPIV3 comprising a viral genome comprising, from upstream to downstream, a HPIV3 genomic promoter followed by HPIV3 N, P, M, F, HN, and L genes, and further comprising a heterologous gene encoding a type I membrane protein comprising a recombinant RSV F ectodomain, wherein the heterologous gene is located between the genes encoding the N and P proteins, and wherein the RSV F ectodomain comprises 66E, 101P, 155C, 290C, 190F, and 207L substitutions and is linked to a CT of the BPIV3 F protein.

In some embodiments, a recombinant paramyxovirus is provided, comprising a recombinant BPIV3 comprising a viral genome comprising, from upstream to downstream, a BPIV3 genomic promoter followed by BPIV3 N, P, M, F, HN, and L genes, and further comprising a heterologous gene encoding a type I membrane protein comprising a recombinant RSV F ectodomain, wherein the heterologous gene is located between the genomic promoter and the gene encoding the N protein, and wherein the RSV F ectodomain comprises 66E, 101P, 155C, 290C, 190F, and 207L substitutions and is linked to a CT of the BPIV3 F protein.

In some embodiments, a recombinant paramyxovirus is provided, comprising a recombinant BPIV3 comprising a viral genome comprising, from upstream to downstream, a BPIV3 genomic promoter followed by BPIV3 N, P, M, F, HN, and L genes, and further comprising a heterologous gene encoding a type I membrane protein comprising a recombinant RSV F ectodomain, wherein the heterologous gene is located between the genes encoding the N and P proteins, and wherein the RSV F ectodomain comprises 66E, 101P, 155C, 290C, 190F, and 207L substitutions and is linked to a CT of the BPIV3 F protein.

In some embodiments, a recombinant paramyxovirus is provided, comprising a recombinant B/HPIV3 comprising a viral genome comprising, from upstream to downstream, a BPIV3 genomic promoter followed by BPIV3 N, P, and M genes, HPIV3 F and HN genes, and a BPIV3 L gene, and further comprising a heterologous gene encoding a type I membrane protein comprising a recombinant RSV F ectodomain, wherein the heterologous gene is located between the genomic promoter and the gene encoding the N protein, and wherein the RSV F ectodomain comprises 66E, 101P, 155C, 290C, 190F, and 207L substitutions and is linked to a CT of the BPIV3 F protein.

In some embodiments, a recombinant paramyxovirus is provided, comprising a recombinant B/HPIV3 comprising a viral genome comprising, from upstream to downstream, a BPIV3 genomic promoter followed by BPIV3 N, P, and M genes, HPIV3 F and HN genes, and a BPIV3 L gene, and further comprising a heterologous gene encoding a type I membrane protein comprising a recombinant RSV F ectodomain, wherein the heterologous gene is located between the genes encoding the N and P proteins, and wherein the RSV F ectodomain comprises 66E, 101P, 155C, 290C, 190F, and 207L substitutions and is linked to a CT of the BPIV3 F protein.

In some embodiments, a recombinant paramyxovirus is provided, comprising a recombinant B/HPIV3 comprising a viral genome comprising, from upstream to downstream, a BPIV3 genomic promoter followed by BPIV3 N, P, and M genes, HPIV3 F and HN genes, and a BPIV3 L gene, and further comprising a heterologous gene encoding a type I membrane protein comprising a recombinant RSV F ectodomain, wherein the heterologous gene is located between the genomic promoter and the gene encoding the N protein, and wherein the RSV F ectodomain comprises 66E, 101P, 155C, 290C, 190F, and 207L substitutions and is linked to a CT of the HPIV3 F protein.

In some embodiments, a recombinant paramyxovirus is provided, comprising a recombinant B/HPIV3 comprising a viral genome comprising, from upstream to downstream, a BPIV3 genomic promoter followed by BPIV3 N, P, and M genes, HPIV3 F and HN genes, and a BPIV3 L gene, and further comprising a heterologous gene encoding a type I membrane protein comprising a recombinant RSV F ectodomain, wherein the heterologous gene is located between the genes encoding the N and P proteins, and wherein the RSV F ectodomain comprises 66E, 101P, 155C, 290C, 190F, and 207L substitutions and is linked to a CT of the HPIV3 F protein.

In some embodiments, a recombinant paramyxovirus is provided, comprising a recombinant sendai virus comprising a viral genome comprising, from upstream to downstream, a sendai virus genomic promoter followed by sendai virus N, P, M, F, HN, and L genes, and further comprising a heterologous gene encoding a type I membrane protein comprising a recombinant RSV F ectodomain, wherein the heterologous gene is located between the genomic promoter and the gene encoding the N protein, and wherein the RSV F ectodomain comprises 66E, 101P, 155C, 290C, 190F, and 207L substitutions and is linked to a CT of the sendai virus F protein.

In some embodiments, a recombinant paramyxovirus is provided, comprising a recombinant sendai virus comprising a viral genome comprising, from upstream to downstream, a sendai virus genomic promoter followed by sendai virus N, P, M, F, HN, and L gene, and further comprising a heterologous gene encoding a type I membrane protein comprising a recombinant RSV F ectodomain, wherein the heterologous gene is located between the genes encoding the N and P proteins, and wherein the RSV F ectodomain comprises 66E, 101P, 155C, 290C, 190F, and 207L substitutions and is linked to a CT of the sendai virus F protein.

In some embodiments, a recombinant paramyxovirus is provided, comprising a recombinant NDV comprising a viral genome comprising, from upstream to downstream, a NDV genomic promoter followed by NDV N, P, M, F, HN, and L genes, and further comprising a heterologous gene encoding a type I membrane protein comprising a recombinant RSV F ectodomain, wherein the heterologous gene is located between the genomic promoter and the gene encoding the N protein, and wherein the RSV F ectodomain comprises 66E, 101P, 155C, 290C, 190F, and 207L substitutions and is linked to a CT of the NDV F protein.

In some embodiments, a recombinant paramyxovirus is provided, comprising a recombinant NDV comprising a viral genome comprising, from upstream to downstream, a NDV genomic promoter followed by NDV N, P, M, F, HN, and L gene, and further comprising a heterologous gene encoding a type I membrane protein comprising a recombinant RSV F ectodomain, wherein the heterologous gene is located between the genes encoding the N and P proteins, and wherein the RSV F ectodomain comprises 66E, 101P, 155C, 290C, 190F, and 207L substitutions and is linked to a CT of the NDV F protein. In some embodiments, a recombinant paramyxovirus is provided, comprising a recombinant PIV5 comprising a viral genome comprising, from upstream to downstream, a PIV5 genomic promoter followed by PIV5 N, P, M, F, HN, and L genes, and further comprising a heterologous gene encoding a type I membrane protein comprising a recombinant RSV F ectodomain, wherein the heterologous gene is located between the genomic promoter and the gene encoding the N protein, and wherein the RSV F ectodomain comprises 66E, 101P, 155C, 290C, 190F, and 207L substitutions and is linked to a CT of the PIV5 F protein.

In some embodiments, a recombinant paramyxovirus is provided, comprising a recombinant PIV5 comprising a viral genome comprising, from upstream to downstream, a PIV5 genomic promoter followed by PIV5 N, P, M, F, HN, and L gene, and further comprising a heterologous gene encoding a type I membrane protein comprising a recombinant RSV F ectodomain, wherein the heterologous gene is located between the genes encoding the N and P proteins, and wherein the RSV F ectodomain comprises 66E, 101P, 155C, 290C, 190F, and 207L substitutions and is linked to a CT of the PIV5 F protein.

In some embodiments, a recombinant paramyxovirus is provided, comprising a recombinant parainfluenza virus (PIV) comprising a viral genome comprising, from upstream to downstream, a PIV genomic promoter followed by PIV N, P, M, F, HN, and L genes, and further comprising a heterologous gene encoding a type I membrane protein comprising a recombinant RSV F ectodomain, wherein the heterologous gene is located between the genomic promoter and the gene encoding the N protein, and wherein the RSV F ectodomain comprises 66E, 101P, 155C, 290C substitutions and is linked to a TM and CT of the PIV F protein.

In some embodiments, a recombinant paramyxovirus is provided, comprising a recombinant HPIV1 comprising a viral genome comprising, from upstream to downstream, a HPIV1 genomic promoter followed by HPIV1 N, P, M, F, HN, and L genes, and further comprising a heterologous gene encoding a type I membrane protein comprising a recombinant RSV F ectodomain, wherein the heterologous gene is located between the genomic promoter and the gene encoding the N protein, and wherein the RSV F ectodomain comprises 66E, 101P, 155C, 290C substitutions and is linked to a TM and CT of the HPIV1 F protein.

In some embodiments, a recombinant paramyxovirus is provided, comprising a recombinant HPIV1 comprising a viral genome comprising, from upstream to downstream, a HPIV1 genomic promoter followed by HPIV1N, P, M, F, HN, and L genes, and further comprising a heterologous gene encoding a type I membrane protein comprising a recombinant RSV F ectodomain, wherein the heterologous gene is located between the genes encoding the N and P proteins, and wherein the RSV F ectodomain comprises 66E, 101P, 155C, 290C substitutions and is linked to a TM and CT of the HPIV1 F protein.

In some embodiments, a recombinant paramyxovirus is provided, comprising a recombinant HPIV3 comprising a viral genome comprising, from upstream to downstream, a HPIV3 genomic promoter followed by HPIV3N, P, M, F, HN, and L genes, and further comprising a heterologous gene encoding a type I membrane protein comprising a recombinant RSV F ectodomain, wherein the heterologous gene is located between the genomic promoter and the gene encoding the N protein, and wherein the RSV F ectodomain comprises 66E, 101P, 155C, 290C substitutions and is linked to a TM and CT of the HPIV3 F protein.

In some embodiments, a recombinant paramyxovirus is provided, comprising a recombinant HPIV3 comprising a viral genome comprising, from upstream to downstream, a HPIV3 genomic promoter followed by HPIV3 N, P, M, F, HN, and L genes, and further comprising a heterologous gene encoding a type I membrane protein comprising a recombinant RSV F ectodomain, wherein the heterologous gene is located between the genes encoding the N and P proteins, and wherein the RSV F ectodomain comprises 66E, 101P, 155C, 290C substitutions and is linked to a TM and CT of the HPIV3 F protein.

In some embodiments, a recombinant paramyxovirus is provided, comprising a recombinant HPIV3 comprising a viral genome comprising, from upstream to downstream, a HPIV3 genomic promoter followed by HPIV3 N, P, M, F, HN, and L genes, and further comprising a heterologous gene encoding a type I membrane protein comprising a recombinant RSV F ectodomain, wherein the heterologous gene is located between the genomic promoter and the gene encoding the N protein, and wherein the RSV F ectodomain comprises 66E, 101P, 155C, 290C substitutions and is linked to a TM and CT of the BPIV3 F protein.

In some embodiments, a recombinant paramyxovirus is provided, comprising a recombinant HPIV3 comprising a viral genome comprising, from upstream to downstream, a HPIV3 genomic promoter followed by HPIV3 N, P, M, F, HN, and L genes, and further comprising a heterologous gene encoding a type I membrane protein comprising a recombinant RSV F ectodomain, wherein the heterologous gene is located between the genes encoding the N and P proteins, and wherein the RSV F ectodomain comprises 66E, 101P, 155C, 290C substitutions and is linked to a TM and CT of the BPIV3 F protein.

In some embodiments, a recombinant paramyxovirus is provided, comprising a recombinant BPIV3 comprising a viral genome comprising, from upstream to downstream, a BPIV3 genomic promoter followed by BPIV3 N, P, M, F, HN, and L genes, and further comprising a heterologous gene encoding a type I membrane protein comprising a recombinant RSV F ectodomain, wherein the heterologous gene is located between the genomic promoter and the gene encoding the N protein, and wherein the RSV F ectodomain comprises 66E, 101P, 155C, 290C substitutions and is linked to a TM and CT of the BPIV3 F protein.

In some embodiments, a recombinant paramyxovirus is provided, comprising a recombinant BPIV3 comprising a viral genome comprising, from upstream to downstream, a BPIV3 genomic promoter followed by BPIV3 N, P, M, F, HN, and L genes, and further comprising a heterologous gene encoding a type I membrane protein comprising a recombinant RSV F ectodomain, wherein the heterologous gene is located between the genes encoding the N and P proteins, and wherein the RSV F ectodomain comprises 66E, 101P, 155C, 290C substitutions and is linked to a TM and CT of the BPIV3 F protein.

In some embodiments, a recombinant paramyxovirus is provided, comprising a recombinant B/HPIV3 comprising a viral genome comprising, from upstream to downstream, a BPIV3 genomic promoter followed by BPIV3 N, P, and M genes, HPIV3 F and HN genes, and a BPIV3 L gene, and further comprising a heterologous gene encoding a type I membrane protein comprising a recombinant RSV F ectodomain, wherein the heterologous gene is located between the genomic promoter and the gene encoding the N protein, and wherein the RSV F ectodomain comprises 66E, 101P, 155C, 290C substitutions and is linked to a TM and CT of the BPIV3 F protein.

In some embodiments, a recombinant paramyxovirus is provided, comprising a recombinant B/HPIV3 comprising a viral genome comprising, from upstream to downstream, a BPIV3 genomic promoter followed by BPIV3 N, P, and M genes, HPIV3 F and HN genes, and a BPIV3 L gene, and further comprising a heterologous gene encoding a type I membrane protein comprising a recombinant RSV F ectodomain, wherein the heterologous gene is located between the genes encoding the N and P proteins, and wherein the RSV F ectodomain comprises 66E, 101P, 155C, 290C substitutions and is linked to a TM and CT of the BPIV3 F protein.

In some embodiments, a recombinant paramyxovirus is provided, comprising a recombinant B/HPIV3 comprising a viral genome comprising, from upstream to downstream, a BPIV3 genomic promoter followed by BPIV3 N, P, and M genes, HPIV3 F and HN genes, and a BPIV3 L gene, and further comprising a heterologous gene encoding a type I membrane protein comprising a recombinant RSV F ectodomain, wherein the heterologous gene is located between the genomic promoter and the gene encoding the N protein, and wherein the RSV F ectodomain comprises 66E, 101P, 155C, 290C substitutions and is linked to a TM and CT of the HPIV3 F protein.

In some embodiments, a recombinant paramyxovirus is provided, comprising a recombinant B/HPIV3 comprising a viral genome comprising, from upstream to downstream, a BPIV3 genomic promoter followed by BPIV3 N, P, and M genes, HPIV3 F and HN genes, and a BPIV3 L gene, and further comprising a heterologous gene encoding a type I membrane protein comprising a recombinant RSV F ectodomain, wherein the heterologous gene is located between the genes encoding the N and P proteins, and wherein the RSV F ectodomain comprises 66E, 101P, 155C, 290C substitutions and is linked to a TM and CT of the HPIV3 F protein.

In some embodiments, a recombinant paramyxovirus is provided, comprising a recombinant sendai virus comprising a viral genome comprising, from upstream to downstream, a sendai virus genomic promoter followed by sendai virus N, P, M, F, HN, and L genes, and further comprising a heterologous gene encoding a type I membrane protein comprising a recombinant RSV F ectodomain, wherein the heterologous gene is located between the genomic promoter and the gene encoding the N protein, and wherein the RSV F ectodomain comprises 66E, 101P, 155C, 290C substitutions and is linked to a TM and CT of the sendai virus F protein.

In some embodiments, a recombinant paramyxovirus is provided, comprising a recombinant sendai virus comprising a viral genome comprising, from upstream to downstream, a sendai virus genomic promoter followed by sendai virus N, P, M, F, HN, and L gene, and further comprising a heterologous gene encoding a type I membrane protein comprising a recombinant RSV F ectodomain, wherein the heterologous gene is located between the genes encoding the N and P proteins, and wherein the RSV F ectodomain comprises 66E, 101P, 155C, 290C substitutions and is linked to a TM and CT of the sendai virus F protein.

In some embodiments, a recombinant paramyxovirus is provided, comprising a recombinant NDV comprising a viral genome comprising, from upstream to downstream, a NDV genomic promoter followed by NDV N, P, M, F, HN, and L genes, and further comprising a heterologous gene encoding a type I membrane protein comprising a recombinant RSV F ectodomain, wherein the heterologous gene is located between the genomic promoter and the gene encoding the N protein, and wherein the RSV F ectodomain comprises 66E, 101P, 155C, 290C substitutions and is linked to a TM and CT of the NDV F protein.

In some embodiments, a recombinant paramyxovirus is provided, comprising a recombinant NDV comprising a viral genome comprising, from upstream to downstream, a NDV genomic promoter followed by NDV N, P, M, F, HN, and L gene, and further comprising a heterologous gene encoding a type I membrane protein comprising a recombinant RSV F ectodomain, wherein the heterologous gene is located between the genes encoding the N and P proteins, and wherein the RSV F ectodomain comprises 66E, 101P, 155C, 290C substitutions and is linked to a TM and CT of the NDV F protein.

In some embodiments, a recombinant paramyxovirus is provided, comprising a recombinant PIV5 comprising a viral genome comprising, from upstream to downstream, a PIV5 genomic promoter followed by PIV5 N, P, M, F, HN, and L genes, and further comprising a heterologous gene encoding a type I membrane protein comprising a recombinant RSV F ectodomain, wherein the heterologous gene is located between the genomic promoter and the gene encoding the N protein, and wherein the RSV F ectodomain comprises 66E, 101P, 155C, 290C substitutions and is linked to a TM and CT of the PIV5 F protein.

In some embodiments, a recombinant paramyxovirus is provided, comprising a recombinant PIV5 comprising a viral genome comprising, from upstream to downstream, a PIV5 genomic promoter followed by PIV5 N, P, M, F, HN, and L gene, and further comprising a heterologous gene encoding a type I membrane protein comprising a recombinant RSV F ectodomain, wherein the heterologous gene is located between the genes encoding the N and P proteins, and wherein the RSV F ectodomain comprises 66E, 101P, 155C, 290C substitutions and is linked to a TM and CT of the PIV5 F protein.

In some embodiments, a recombinant paramyxovirus is provided, comprising a recombinant parainfluenza virus (PIV) comprising a viral genome comprising, from upstream to downstream, a PIV genomic promoter followed by PIV N, P, M, F, HN, and L genes, and further comprising a heterologous gene encoding a type I membrane protein comprising a recombinant RSV F ectodomain, wherein the heterologous gene is located between the genomic promoter and the gene encoding the N protein, and wherein the RSV F ectodomain comprises 66E, 101P, 155C, 290C substitutions and is linked to a CT of the PIV F protein.

In some embodiments, a recombinant paramyxovirus is provided, comprising a recombinant HPIV1 comprising a viral genome comprising, from upstream to downstream, a HPIV1 genomic promoter followed by HPIV1 N, P, M, F, HN, and L genes, and further comprising a heterologous gene encoding a type I membrane protein comprising a recombinant RSV F ectodomain, wherein the heterologous gene is located between the genomic promoter and the gene encoding the N protein, and wherein the RSV F ectodomain comprises 66E, 101P, 155C, 290C substitutions and is linked to a CT of the HPIV1 F protein.

In some embodiments, a recombinant paramyxovirus is provided, comprising a recombinant HPIV1 comprising a viral genome comprising, from upstream to downstream, a HPIV1 genomic promoter followed by HPIV1N, P, M, F, HN, and L genes, and further comprising a heterologous gene encoding a type I membrane protein comprising a recombinant RSV F ectodomain, wherein the heterologous gene is located between the genes encoding the N and P proteins, and wherein the RSV F ectodomain comprises 66E, 101P, 155C, 290C substitutions and is linked to a CT of the HPIV1 F protein.

In some embodiments, a recombinant paramyxovirus is provided, comprising a recombinant HPIV3 comprising a viral genome comprising, from upstream to downstream, a HPIV3 genomic promoter followed by HPIV3N, P, M, F, HN, and L genes, and further comprising a heterologous gene encoding a type I membrane protein comprising a recombinant RSV F ectodomain, wherein the heterologous gene is located between the genomic promoter and the gene encoding the N protein, and wherein the RSV F ectodomain comprises 66E, 101P, 155C, 290C substitutions and is linked to a CT of the HPIV3 F protein.

In some embodiments, a recombinant paramyxovirus is provided, comprising a recombinant HPIV3 comprising a viral genome comprising, from upstream to downstream, a HPIV3 genomic promoter followed by HPIV3 N, P, M, F, HN, and L genes, and further comprising a heterologous gene encoding a type I membrane protein comprising a recombinant RSV F ectodomain, wherein the heterologous gene is located between the genes encoding the N and P proteins, and wherein the RSV F ectodomain comprises 66E, 101P, 155C, 290C substitutions and is linked to a CT of the HPIV3 F protein.

In some embodiments, a recombinant paramyxovirus is provided, comprising a recombinant HPIV3 comprising a viral genome comprising, from upstream to downstream, a HPIV3 genomic promoter followed by HPIV3 N, P, M, F, HN, and L genes, and further comprising a heterologous gene encoding a type I membrane protein comprising a recombinant RSV F ectodomain, wherein the heterologous gene is located between the genomic promoter and the gene encoding the N protein, and wherein the RSV F ectodomain comprises 66E, 101P, 155C, 290C substitutions and is linked to a CT of the BPIV3 F protein.

In some embodiments, a recombinant paramyxovirus is provided, comprising a recombinant HPIV3 comprising a viral genome comprising, from upstream to downstream, a HPIV3 genomic promoter followed by HPIV3 N, P, M, F, HN, and L genes, and further comprising a heterologous gene encoding a type I membrane protein comprising a recombinant RSV F ectodomain, wherein the heterologous gene is located between the genes encoding the N and P proteins, and wherein the RSV F ectodomain comprises 66E, 101P, 155C, 290C substitutions and is linked to a CT of the BPIV3 F protein.

In some embodiments, a recombinant paramyxovirus is provided, comprising a recombinant BPIV3 comprising a viral genome comprising, from upstream to downstream, a BPIV3 genomic promoter followed by BPIV3 N, P, M, F, HN, and L genes, and further comprising a heterologous gene encoding a type I membrane protein comprising a recombinant RSV F ectodomain, wherein the heterologous gene is located between the genomic promoter and the gene encoding the N protein, and wherein the RSV F ectodomain comprises 66E, 101P, 155C, 290C substitutions and is linked to a CT of the BPIV3 F protein.

In some embodiments, a recombinant paramyxovirus is provided, comprising a recombinant BPIV3 comprising a viral genome comprising, from upstream to downstream, a BPIV3 genomic promoter followed by BPIV3 N, P, M, F, HN, and L genes, and further comprising a heterologous gene encoding a type I membrane protein comprising a recombinant RSV F ectodomain, wherein the heterologous gene is located between the genes encoding the N and P proteins, and wherein the RSV F ectodomain comprises 66E, 101P, 155C, 290C substitutions and is linked to a CT of the BPIV3 F protein.

In some embodiments, a recombinant paramyxovirus is provided, comprising a recombinant B/HPIV3 comprising a viral genome comprising, from upstream to downstream, a BPIV3 genomic promoter followed by BPIV3 N, P, and M genes, HPIV3 F and HN genes, and a BPIV3 L gene, and further comprising a heterologous gene encoding a type I membrane protein comprising a recombinant RSV F ectodomain, wherein the heterologous gene is located between the genomic promoter and the gene encoding the N protein, and wherein the RSV F ectodomain comprises 66E, 101P, 155C, 290C substitutions and is linked to a CT of the BPIV3 F protein.

In some embodiments, a recombinant paramyxovirus is provided, comprising a recombinant B/HPIV3 comprising a viral genome comprising, from upstream to downstream, a BPIV3 genomic promoter followed by BPIV3 N, P, and M genes, HPIV3 F and HN genes, and a BPIV3 L gene, and further comprising a heterologous gene encoding a type I membrane protein comprising a recombinant RSV F ectodomain, wherein the heterologous gene is located between the genes encoding the N and P proteins, and wherein the RSV F ectodomain comprises 66E, 101P, 155C, 290C substitutions and is linked to a CT of the BPIV3 F protein.

In some embodiments, a recombinant paramyxovirus is provided, comprising a recombinant B/HPIV3 comprising a viral genome comprising, from upstream to downstream, a BPIV3 genomic promoter followed by BPIV3 N, P, and M genes, HPIV3 F and HN genes, and a BPIV3 L gene, and further comprising a heterologous gene encoding a type I membrane protein comprising a recombinant RSV F ectodomain, wherein the heterologous gene is located between the genomic promoter and the gene encoding the N protein, and wherein the RSV F ectodomain comprises 66E, 101P, 155C, 290C substitutions and is linked to a CT of the HPIV3 F protein.

In some embodiments, a recombinant paramyxovirus is provided, comprising a recombinant B/HPIV3 comprising a viral genome comprising, from upstream to downstream, a BPIV3 genomic promoter followed by BPIV3 N, P, and M genes, HPIV3 F and HN genes, and a BPIV3 L gene, and further comprising a heterologous gene encoding a type I membrane protein comprising a recombinant RSV F ectodomain, wherein the heterologous gene is located between the genes encoding the N and P proteins, and wherein the RSV F ectodomain comprises 66E, 101P, 155C, 290C substitutions and is linked to a CT of the HPIV3 F protein.

In some embodiments, a recombinant paramyxovirus is provided, comprising a recombinant sendai virus comprising a viral genome comprising, from upstream to downstream, a sendai virus genomic promoter followed by sendai virus N, P, M, F, HN, and L genes, and further comprising a heterologous gene encoding a type I membrane protein comprising a recombinant RSV F ectodomain, wherein the heterologous gene is located between the genomic promoter and the gene encoding the N protein, and wherein the RSV F ectodomain comprises 66E, 101P, 155C, 290C substitutions and is linked to a CT of the sendai virus F protein.

In some embodiments, a recombinant paramyxovirus is provided, comprising a recombinant sendai virus comprising a viral genome comprising, from upstream to downstream, a sendai virus genomic promoter followed by sendai virus N, P, M, F, HN, and L gene, and further comprising a heterologous gene encoding a type I membrane protein comprising a recombinant RSV F ectodomain, wherein the heterologous gene is located between the genes encoding the N and P proteins, and wherein the RSV F ectodomain comprises 66E, 101P, 155C, 290C substitutions and is linked to a CT of the sendai virus F protein.

In some embodiments, a recombinant paramyxovirus is provided, comprising a recombinant NDV comprising a viral genome comprising, from upstream to downstream, a NDV genomic promoter followed by NDV N, P, M, F, HN, and L genes, and further comprising a heterologous gene encoding a type I membrane protein comprising a recombinant RSV F ectodomain, wherein the heterologous gene is located between the genomic promoter and the gene encoding the N protein, and wherein the RSV F ectodomain comprises 66E, 101P, 155C, 290C substitutions and is linked to a CT of the NDV F protein.

In some embodiments, a recombinant paramyxovirus is provided, comprising a recombinant NDV comprising a viral genome comprising, from upstream to downstream, a NDV genomic promoter followed by NDV N, P, M, F, HN, and L gene, and further comprising a heterologous gene encoding a type I membrane protein comprising a recombinant RSV F ectodomain, wherein the heterologous gene is located between the genes encoding the N and P proteins, and wherein the RSV F ectodomain comprises 66E, 101P, 155C, 290C substitutions and is linked to a CT of the NDV F protein.

In some embodiments, a recombinant paramyxovirus is provided, comprising a recombinant PIV5 comprising a viral genome comprising, from upstream to downstream, a PIV5 genomic promoter followed by PIV5 N, P, M, F, HN, and L genes, and further comprising a heterologous gene encoding a type I membrane protein comprising a recombinant RSV F ectodomain, wherein the heterologous gene is located between the genomic promoter and the gene encoding the N protein, and wherein the RSV F ectodomain comprises 66E, 101P, 155C, 290C substitutions and is linked to a CT of the PIV5 F protein.

In some embodiments, a recombinant paramyxovirus is provided, comprising a recombinant PIV5 comprising a viral genome comprising, from upstream to downstream, a PIV5 genomic promoter followed by PIV5 N, P, M, F, HN, and L gene, and further comprising a heterologous gene encoding a type I membrane protein comprising a recombinant RSV F ectodomain, wherein the heterologous gene is located between the genes encoding the N and P proteins, and wherein the RSV F ectodomain comprises 66E, 101P, 155C, 290C substitutions and is linked to a CT of the PIV5 F protein.

In any of the embodiments of a recombinant paramyxovirus disclosed herein that includes a viral genome including a heterologous gene encoding an RSV F ectodomain (such as any of the recombinant paramyxoviruses discussed above, the heterologous gene encoding the recombinant RSV F ectodomain can encodes a polypeptide sequence comprising RSV F positions 1-529.

Additional Description

The disclosed recombinant paramyxoviruses are self-replicating, that is they are capable of replicating following infection of an appropriate host cell. In several embodiments, the recombinant paramyxoviruses have an attenuated phenotype, for example when administered to a human subject.

Attenuation of the recombinant paramyxoviruses can be achieved using various methods known in the art, for example, by introduction of one or more mutations that cause a change in the biological function of the recombinant paramyxoviruses result in the attenuated phenotype. Insertion of the heterologous gene can also result in an attenuated phenotype. Preferably, the paramyxovirus comprising a genome encoding a heterologous gene is attenuated about 100 to 5000 fold or more in a cell or mammal compared to wild type paramyxovirus.

The disclosed recombinant paramyxoviruses can be tested in well-known and in vitro and in vivo models to confirm adequate attenuation, resistance to phenotypic reversion, and immunogenicity. In in vitro assays, the modified paramyxovirus can be tested for one or more desired phenotypes, such as, for example, temperature sensitive replication. The disclosed recombinant paramyxoviruses can also be tested in animal models of infection with PIV and/or the viral pathogen of the heterologous gene included in the recombinant virus (e.g., RSV). A variety of animal models are known.

The recombinant attenuated paramyxoviruses are preferably attenuated about 100 to 5000 fold in a cell or mammal compared to wild type paramyxovirus. In some embodiments, it is preferred that the level of viral replication in vitro is sufficient to provide for production of viral vaccine for use on a wide spread scale. In some embodiments, it is preferred that the level of viral replication of attenuated paramyxovirus in vitro is at least $10^6$, more preferably at least $10^7$, and most preferably at least $10^8$ per ml. The attenuating mutation is preferably one that is stable. A recombinant paramyxovirus with at least two, three, four or ever more attenuating mutations is likely to be more stable.

Ongoing preclinical studies have identified a number of mutations or modifications that are attenuating for HPIV1, HPIV2, and HPIV3, and which can be introduced by reverse genetics to produce attenuated strains as potential vaccines and vector backbones. The inclusion of a foreign gene into an HPIV backbone also is attenuating on its own. This may due to a variety of effects including the increase in genome length and gene number as well as the effects of the foreign protein. Whatever the cause, the attenuating effect of the insert also has to be taken into account when attempting to achieve the appropriate level of attenuation.

Attenuated strains of HPIV1, 2, and 3 have been in or are presently in clinical studies in seronegative infants and children (Karron, et al. 2012. Vaccine 30:3975-3981; Schmidt, et al. 2011. Expert Rev. Respir. Med. 5:515-526). These attenuated HPIV1, HPIV2, and HPIV3 strains, or versions thereof, are potential vectors for expressing the heterologous RSV F protein.

Examples of modifications to the genome of a paramyxovirus that provide for an attenuated phenotype are known in the art and have been described, for example, in US Patent Publications 2012/0045471; 2010/0119547; 2009/0263883; 2009/0017517; 8084037; U.S. Pat. Nos. 6,410,023; 8,367,074; 7,951,383; 7,820,182; 7,704,509; 7,632,508; 7,622,123; 7,250,171; 7,208,161; 7,201,907; 7,192,593; 2012/0064112; 20140186397; and Newman et al. 2002. Virus genes 24:77-92, Tang et al., 2003. J Virol, 77(20):10819-10828; Basavarajappa et al. 2014 Vaccine, 32: 3555-3563; McGinnes et al., J. Virol., 85: 366-377, 2011; and Jones et al., *Vaccine,* 30:959-968, 2012, each of which is incorporated by reference herein in its entirety. For example, attenuation of PIV3 can be achieved by the presence of BPIV3-derived genes, which confers a host range restriction in primates including humans, such as the B/HPIV3 virus that contains BPIV3 genes except for the F and HN from HPIV3 (Skiadopoulos M H et al J Virol 77:1141-8, 2003). Sendai virus also is restricted in primates due to a host range restruction (Jones B G et al Vaccine 30:959-968 2012). Another means of attenuation is exemplified by missense mutations that can occur in multiple genes, such as in the cp45 HPIV3 virus (Skiadopoulos M H et al J Virol 73:1374-

81 1999). Other examples of attenuating point mutations are provided for HPIV1 in Example 2, below. Deletion of one or several codons also can confer an attenuation phenotype, as exemplified by HPIV1 in Example 2. As also exemplified in Example 1, the presence of vector TM plus CT, or CT domains linked to a heterologous ectodomain can strongly attenuate the vector. Other examples of attenuating mutations in HPIV1 are described by Bartlett E J et al Virol J 4:67 2007), and for HPIV2 by Nolan S M et al, Vaccine 23:4765-4774 2005). The deletion of all or part of one or more accessory genes also is a means of attenuation (Durbin A Virology 261:319-330 1999).

Immunogenicity of a recombinant attenuated paramyxovirus can be assessed in an animal model (such as a non-human primate, for example an African green monkey) by determining the number of animals that form antibodies to the paramyxovirus after one immunization and after a second immunization, and by measuring the magnitude of that response. In some embodiments, a recombinant paramyxovirus has sufficient immunogenicity if about 60 to 80% of the animals develop antibodies after the first immunization and about 80 to 100% of the animals develop antibodies after the second immunization. Preferably, the immune response protects against infection by both the originating paramyxovirus and the viral pathogen from which the heterologous gene included in the recombinant paramyxovirus is derived.

I. Additional Vectors

It will be appreciated that the recombinant RSV F proteins and nucleic acid molecules encoding same can be included (or expressed) on vectors other than a PIV vector. For example, plasmid vectors, as well as other viral vectors can be used, for example, for expression of the recombinant RSV F protein or fragment thereof in a host cell, or for immunization of a subject as disclosed herein. In some embodiments, the vectors can be administered to a subject as part of a prime-boost vaccination. In several embodiments, the vectors are included in a vaccine, such as a primer vaccine or a booster vaccine for use in a prime-boost vaccination.

In several examples, the vector can be a viral vector that is replication-competent and/or attenuated. The viral vector also can be conditionally replication-competent. In other examples, the viral vector is replication-deficient in host cells.

A number of viral vectors have been constructed, that can be used to express the recombinant RSV F protein or immunogenic fragment thereof, including polyoma, i.e., SV40 (Madzak et al., 1992, *J. Gen. Virol.,* 73:15331536), adenovirus (Berkner, 1992, *Cur. Top. Microbiol. Immunol.,* 158:39-6; Berliner et al., 1988, *Bio Techniques,* 6:616-629; Gorziglia et al., 1992, *J. Virol.,* 66:4407-4412; Quantin et al., 1992, *Proc. Natl. Acad. Sci. USA,* 89:2581-2584; Rosenfeld et al., 1992, *Cell,* 68:143-155; Wilkinson et al., 1992, *Nucl. Acids Res.,* 20:2233-2239; Stratford-Perricaudet et al., 1990, *Hum. Gene Ther.,* 1:241-256), vaccinia virus (Mackett et al., 1992, *Biotechnology,* 24:495-499), adeno-associated virus (Muzyczka, 1992, *Curr. Top. Microbiol. Immunol.,* 158:91-123; On et al., 1990, *Gene,* 89:279-282), herpes viruses including HSV and EBV (Margolskee, 1992, *Curr. Top. Microbiol. Immunol.,* 158:67-90; Johnson et al., 1992, *J. Virol.,* 66:29522965; Fink et al., 1992, *Hum. Gene Ther.* 3:11-19; Breakfield et al., 1987, *Mol. Neurobiol.,* 1:337-371; Fresse et al., 1990, *Biochem. Pharmacol.,* 40:2189-2199), Sindbis viruses (H. Herweijer et al., 1995, *Human Gene Therapy* 6:1161-1167; U.S. Pat. Nos. 5,091,309 and 5,2217, 879), alphaviruses (S. Schlesinger, 1993, *Trends Biotechnol.* 11:18-22; I. Frolov et al., 1996, *Proc. Natl. Acad. Sci. USA* 93:11371-11377) and retroviruses of avian (Brandyopadhyay et al., 1984, *Mol. Cell Biol.,* 4:749-754; Petropouplos et al., 1992, *J. Virol.,* 66:3391-3397), murine (Miller, 1992, *Curr. Top. Microbiol. Immunol.,* 158:1-24; Miller et al., 1985, *Mol. Cell Biol.,* 5:431-437; Sorge et al., 1984, *Mol. Cell Biol.,* 4:1730-1737; Mann et al., 1985, *J. Virol.,* 54:401-407), and human origin (Page et al., 1990, *J. Virol.,* 64:5370-5276; Buchschalcher et al., 1992, *J. Virol.,* 66:2731-2739). Baculovirus (*Autographa californica* multinuclear polyhedrosis virus; AcMNPV) vectors are also known in the art, and may be obtained from commercial sources (such as PharMingen, San Diego, Calif.; Protein Sciences Corp., Meriden, Conn.; Stratagene, La Jolla, Calif.).

In several embodiments, the viral vector can include an adenoviral vector that expresses a disclosed recombinant RSV F protein or immunogenic fragment thereof (such as the RSV F ectodomain) Adenovirus from various origins, subtypes, or mixture of subtypes can be used as the source of the viral genome for the adenoviral vector. Non-human adenovirus (e.g., simian, chimpanzee, gorilla, avian, canine, ovine, or bovine adenoviruses) can be used to generate the adenoviral vector. For example, a simian adenovirus can be used as the source of the viral genome of the adenoviral vector. A simian adenovirus can be of serotype 1, 3, 7, 11, 16, 18, 19, 20, 27, 33, 38, 39, 48, 49, 50, or any other simian adenoviral serotype. A simian adenovirus can be referred to by using any suitable abbreviation known in the art, such as, for example, SV, SAdV, SAV or sAV. In some examples, a simian adenoviral vector is a simian adenoviral vector of serotype 3, 7, 11, 16, 18, 19, 20, 27, 33, 38, or 39. In one example, a chimpanzee serotype C Ad3 vector is used (see, e.g., Peruzzi et al., Vaccine, 27:1293-1300, 2009). Human adenovirus can be used as the source of the viral genome for the adenoviral vector. Human adenovirus can be of various subgroups or serotypes. For instance, an adenovirus can be of subgroup A (e.g., serotypes 12, 18, and 31), subgroup B (e.g., serotypes 3, 7, 11, 14, 16, 21, 34, 35, and 50), subgroup C (e.g., serotypes 1, 2, 5, and 6), subgroup D (e.g., serotypes 8, 9, 10, 13, 15, 17, 19, 20, 22, 23, 24, 25, 26, 27, 28, 29, 30, 32, 33, 36-39, and 42-48), subgroup E (e.g., serotype 4), subgroup F (e.g., serotypes 40 and 41), an unclassified serogroup (e.g., serotypes 49 and 51), or any other adenoviral serotype. The person of ordinary skill in the art is familiar with replication competent and deficient adenoviral vectors (including singly and multiply replication deficient adenoviral vectors). Examples of replication-deficient adenoviral vectors, including multiply replication-deficient adenoviral vectors, are disclosed in U.S. Pat. Nos. 5,837,511; 5,851,806; 5,994,106; 6,127,175; 6,482,616; and 7,195,896, and International Patent Application Nos. WO 94/28152, WO 95/02697, WO 95/16772, WO 95/34671, WO 96/22378, WO 97/12986, WO 97/21826, and WO 03/022311.

III. Recombinant Methods, Vectors, and Host Cells

The recombinant paramyxoviruses and polynucleotides disclosed herein can be produced by synthetic and recombinant methods. Accordingly, polynucleotides encoding infectious paramyxovirus clones and host cells including the infectious clone, as well as methods of making such vectors and host cells by recombinant methods are also provided.

Isolated nucleic acid molecules encoding any of the recombinant RSV F proteins disclosed herein are also provided.

As discussed above, the disclosed paramyxovirus or polynucleotides may be synthesized or prepared by techniques well known in the art. See, for example, WO94/027037 and US20130052718. Nucleotide sequences for wild type paramyxovirus genomes are known and readily available, for example, on the Internet at GenBank (accessible at ncbi-nlm-nihgov/entrez). The nucleotide sequences encoding the disclosed recombinant paramyxovirus may be synthesized or amplified using methods known to those of ordinary skill in the art including utilizing DNA polymerases in a cell free environment. Further, one of skill in the art can readily use the genetic code to construct a variety of functionally equivalent nucleic acids, such as nucleic acids which differ in sequence but which encode the same protein sequence.

Exemplary nucleic acids can be prepared by cloning techniques. Examples of appropriate cloning and sequencing techniques, and instructions sufficient to direct persons of skill through many cloning exercises are known (see, e.g., Sambrook et al. (Molecular Cloning: A Laboratory Manual, $4^{th}$ ed, Cold Spring Harbor, N.Y., 2012, and Ausubel et al. (In Current Protocols in Molecular Biology, John Wiley & Sons, New York, through supplement 104, 2013). Product information from manufacturers of biological reagents and experimental equipment also provide useful information. Such manufacturers include the SIGMA Chemical Company (Saint Louis, Mo.), R&D Systems (Minneapolis, Minn.), Pharmacia Amersham (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersburg, Md.), Fluka Chemica-Biochemika Analytika (Fluka Chemie AG, Buchs, Switzerland), Invitrogen (Carlsbad, Calif.), and Applied Biosystems (Foster City, Calif.), as well as many other commercial sources known to one of skill.

The genome of the recombinant paramyxovirus can include one or more variations (for example, mutations that cause an amino acid deletion, substitution, or insertion) as long as the resulting recombinant paramyxovirus retains the desired biological function, such as a level of attenuation or immunogenicity. These variations in sequence can be naturally occurring variations or they can be engineered through the use of genetic engineering technique known to those skilled in the art. Examples of such techniques are found in see, e.g., Sambrook et al. (Molecular Cloning: A Laboratory Manual, $4^{th}$ ed., Cold Spring Harbor, N.Y., 2012) and Ausubel et al. (In Current Protocols in Molecular Biology, John Wiley & Sons, New York, through supplement 104, 2013, both of which are incorporated herein by reference in their entirety.

Modifications can be made to a nucleic acid encoding described herein without diminishing its biological activity Amino acid substitutions, insertions, and deletions can be made using known recombinant methods such as oligonucleotide-mediated (site-directed) mutagenesis, alanine scanning, PCR mutagenesis, site-directed mutagenesis, cassette mutagenesis, restriction selection mutagenesis, and the like (see, e.g., Sambrook et al. (Molecular Cloning: A Laboratory Manual, $4^{th}$ ed, Cold Spring Harbor, N.Y., 2012, and Ausubel et al. (In Current Protocols in Molecular Biology, John Wiley & Sons, New York, through supplement 104, 2013). Some modifications can be made to facilitate the cloning, expression, or incorporation of the targeting molecule into a fusion protein. Such modifications are well known to those of skill in the art and include, for example, termination codons, a methionine added at the amino terminus to provide an initiation, site, additional nucleotides placed on either terminus to create conveniently located restriction sites.

"Conservative" amino acid substitutions are those substitutions that do not substantially affect or decrease a function of a protein, such as the ability of the protein to induce an immune response when administered to a subject. The term conservative variation also includes the use of a substituted amino acid in place of an unsubstituted parent amino acid. Furthermore, one of ordinary skill will recognize that individual substitutions, deletions or additions which alter, add or delete a single amino acid or a small percentage of amino acids (for instance less than 5%, in some embodiments less than 1%) in an encoded sequence are conservative variations where the alterations result in the substitution of an amino acid with a chemically similar amino acid.

Conservative amino acid substitution tables providing functionally similar amino acids are well known to one of ordinary skill in the art. The following six groups are examples of amino acids that are considered to be conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

The disclosed recombinant paramyxovirus can be produced from virus isolated from biological samples. The polynucleotides and vectors may be produced by standard recombinant methods known in the art, such as polymerase chain reaction (Sambrook et al. (Molecular Cloning: A Laboratory Manual, $4^{th}$ ed, Cold Spring Harbor, N.Y., 2012, and Ausubel et al. (In Current Protocols in Molecular Biology, John Wiley & Sons, New York, through supplement 104, 2013). Methods of altering or modifying nucleic acid sequences are also known to those of skill in the art.

The paramyxovirus genome may be assembled from polymerase chain reaction cassettes sequentially cloned into a vector including a selectable marker for propagation in a host. Such markers include dihydrofolate reductase or neomycin resistance for eukaryotic cell culture and tetracycline or ampicillin resistance genes for culturing in *E. coli* and other bacteria.

The polynucleotide may be inserted into a replicable vector for cloning using standard recombinant methods. Various vectors are publicly available. The vector may, for example, be in the form of a plasmid, cosmid, viral particle, or phage. The appropriate nucleic acid sequence may be inserted into the vector by a variety of procedures. In general, a nucleic acid is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors including one or more of these components employs standard ligation techniques that are known to the skilled artisan.

Examples of suitable replicable vectors include, without limitation, pUC19 or pTM1. The polynucleotide can be operably linked to an appropriate promoter such as, for example, T7 polymerase promoter, cytomegalovirus promoter, cellular polymerase II promoter, or SP1 promoter. The replicable vectors may further include sites for transcription initiation, transcription termination, and a ribosome binding site for translation.

Introduction of a recombinant vector composed of a paramyxovirus genome or polynucleotide encoding a paramyxovirus protein into a host cell, such as for example a bacterial cell or eukaryotic cell, can be affected by calcium phosphate transfection, DEAE-dextran mediated transfection, cationic lipid-mediated transfection, electroporation, electrical nuclear transport, chemical transduction, electrotransduction, infection, or other methods. Such methods are described in standard laboratory manuals such as Sambrook et al. (Molecular Cloning: A Laboratory Manual, $4^{th}$ ed, Cold Spring Harbor, N.Y., 2012, and Ausubel et al. (In Current Protocols in Molecular Biology, John Wiley & Sons, New York, through supplement 104, 2013. Commercial transfection reagents, such as Lipofectamine (Invitrogen, Carlsbad, Calif.) and FuGENE 6™ (Roche Diagnostics, Indianapolis, Ind.), are also available. Suitable host cells include, but are not limited to, HEp-2 cells, FRhL-DBS2 cells, LLC-MK2 cells, MRC-5 cells, and Vero cells.

IV. Immunogenic Compositions

Immunogenic compositions comprising a recombinant paramyxoviruses as described herein (such as a recombinant PIV including a genome encoding a heterologous recombinant RSV F protein) and a pharmaceutically acceptable carrier are also provided. Such compositions can be administered to subjects by a variety of administration modes known to the person of ordinary skill in the art, for example, by an intranasal route. Actual methods for preparing administrable compositions will be known or apparent to those skilled in the art and are described in more detail in such publications as *Remingtons Pharmaceutical Sciences,* $19^{th}$ Ed., Mack Publishing Company, Easton, Pa., 1995.

Thus, a recombinant paramyxovirus described herein can be formulated with pharmaceutically acceptable carriers to help retain biological activity while also promoting increased stability during storage within an acceptable temperature range. Potential carriers include, but are not limited to, physiologically balanced culture medium, phosphate buffer saline solution, water, emulsions (e.g., oil/water or water/oil emulsions), various types of wetting agents, cryoprotective additives or stabilizers such as proteins, peptides or hydrolysates (e.g., albumin, gelatin), sugars (e.g., sucrose, lactose, sorbitol), amino acids (e.g., sodium glutamate), or other protective agents. The resulting aqueous solutions may be packaged for use as is or lyophilized. Lyophilized preparations are combined with a sterile solution prior to administration for either single or multiple dosing.

Formulated compositions, especially liquid formulations, may contain a bacteriostat to prevent or minimize degradation during storage, including but not limited to effective concentrations (usually 1% w/v) of benzyl alcohol, phenol, m-cresol, chlorobutanol, methylparaben, and/or propylparaben. A bacteriostat may be contraindicated for some patients; therefore, a lyophilized formulation may be reconstituted in a solution either containing or not containing such a component.

The pharmaceutical compositions of the disclosure can contain as pharmaceutically acceptable vehicles substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, and triethanolamine oleate.

The pharmaceutical composition may optionally include an adjuvant to enhance the immune response of the host. Suitable adjuvants are, for example, toll-like receptor agonists, alum, AlPO4, alhydrogel, Lipid-A and derivatives or variants thereof, oil-emulsions, saponins, neutral liposomes, liposomes containing the vaccine and cytokines, non-ionic block copolymers, and chemokines. Non-ionic block polymers containing polyoxyethylene (POE) and polyxylpropylene (POP), such as POE-POP-POE block copolymers, MPL™ (3-O-deacylated monophosphoryl lipid A; Corixa, Hamilton, Ind.) and IL-12 (Genetics Institute, Cambridge, Mass.), among many other suitable adjuvants well known in the art, may be used as an adjuvant (Newman et al., 1998, *Critical Reviews in Therapeutic Drug Carrier Systems* 15:89-142). These adjuvants have the advantage in that they help to stimulate the immune system in a non-specific way, thus enhancing the immune response to a pharmaceutical product.

In some embodiments, the composition can include a recombinant paramyxovirus encoding an RSV F ectodomain from one particular RSV subgroup or strain and also a recombinant paramyxovirus encoding an RSV F ectodomain from a different RSV subgroup or strain. For example, the composition can include recombinant paramyxovirus including recombinant RSV F proteins from subtype A and subtype B RSV. The different vectors can be in an admixture and administered simultaneously, or administered separately. Due to the phenomenon of cross-protection among certain strains of RSV, immunization with one paramyxovirus encoding a RSV F ectodomain from a first strain may protect against several different strains of the same or different subgroup.

In some instances it may be desirable to combine a recombinant viral vector, or a composition thereof, with other pharmaceutical products (e.g., vaccines) which induce protective responses to other agents, particularly those causing other childhood illnesses. For example, a composition including a recombinant paramyxovirus as described herein can be can be administered simultaneously (typically separately) or sequentially with other vaccines recommended by the Advisory Committee on Immunization Practices (ACIP; cdc.gov/vaccines/acip/index.html) for the targeted age group (e.g., infants from approximately one to six months of age). These additional vaccines include, but are not limited to, IN-administered vaccines. As such, a recombinant paramyxovirus including a recombinant RSV F protein described herein may be administered simultaneously or sequentially with vaccines against, for example, hepatitis B (HepB), diphtheria, tetanus and pertussis (DTaP), pneumococcal bacteria (PCV), *Haemophilus influenzae* type b (Hib), polio, influenza and rotavirus.

Recombinant paramyxoviruses for use in an immunogenic composition, such as for example a vaccine, are selected based on their attenuation and immunogenicity. These vaccine selection criteria are determined according to well-known methods. Preferably, candidate viruses have a stable attenuation phenotype, exhibit replication in an immunized host, and effectively elicit production of an immune response in a recipient, preferably a protective immune response. Preferably, the candidate viruses stimulate and expand the immune response, e.g., induce an immune response against different viral strains or subgroups and/or stimulate an immune response mediated by a different immunologic basis (e.g., secretory versus serum immunoglobulins, cellular immunity, and the like).

The pharmaceutical composition typically contains a effective amount of a disclosed paramyxovirus and can be prepared by conventional techniques. Typically, the amount of recombinant virus in each dose of the immunogenic composition is selected as an amount which induces an immune response without significant, adverse side effects. In some embodiments, the composition can be provided in unit dosage form for use to induce an immune response in a subject, for example, to prevent PIV and/or RSV infection in the subject. A unit dosage form contains a suitable single preselected dosage for administration to a subject, or suitable marked or measured multiples of two or more preselected unit dosages, and/or a metering mechanism for administering the unit dose or multiples thereof. In other embodiments, the composition further includes an adjuvant.

V. Methods of Eliciting an Immune Response

Provided herein are methods of eliciting an immune response in a subject by administering one or more of the disclosed recombinant paramyxoviruses to the subject. In a particular example, the subject is a human. The immune response can be a protective immune response, for example a response that prevents or reduces subsequent infection with the paramyxovirus or the virus of the heterologous gene included in the recombinant paramyxovirus. Elicitation of the immune response can also be used to treat or inhibit viral infection and illnesses associated therewith. In several embodiments, the method includes administration of an immunogenic composition including an attenuated recombinant parainfluenza virus including a viral genome including a heterologous gene encoding a recombinant RSV F ectodomain linked to a PIV F protein transmembrane (TM) domain and cytoplasmic tail.

A subject can be selected for treatment that has, or is at risk for developing a paramyxovirus infection, such as a RSV and/or a PIV infection, for example because of exposure or the possibility of exposure to RSV and/or PIV. Following administration of a disclosed immunogen, the subject can be monitored for paramyxovirus infection or symptoms associated therewith, or both.

Methods of intra-nasal administration of recombinant paramyxovirus to a subject are known to the person of ordinary skill in the art, as are methods of selecting subjects for administration, preparing immunogenic compositions including the recombinant paramyxovirus for intranasal administration, and evaluating the subject for an immune response to the recombinant paramyxovirus. Exemplary description of such methods can be found, for example, in Karron et al, 2012. Vaccine, 30(26), 3975-3981, which is incorporated by reference herein in its entirety.

Typical subjects intended for treatment with therapeutics and methods of the present disclosure include humans, as well as non-human primates and other animals Because nearly all humans are infected with RSV and PIV by the age of 5, the entire birth cohort is included as a relevant population for immunization. This could be done, for example, by beginning an immunization regimen anytime from birth to 6 months of age, from 6 months of age to 5 years of age, in pregnant women (or women of child-bearing age) to protect their infants by passive transfer of antibody, family members of newborn infants or those still in utero, and subjects greater than 50 years of age. The scope of this disclosure is meant to include maternal immunization. In several embodiments, the subject is a human subject that is seronegative for RSV or PIV3 specific antibodies. In additional embodiments, the subject is no more than one year old, such as no more than 6 months old, no more than 3 months, or no more than 1 month old.

Subjects at greatest risk of RSV and/or PIV infection with severe symptoms (e.g. requiring hospitalization) include children with prematurity, bronchopulmonary dysplasia, and congenital heart disease are most susceptible to severe disease. During childhood and adulthood, disease is milder but can be associated with lower airway disease and is commonly complicated by sinusitis. Disease severity increases in the institutionalized elderly (e.g., humans over 65 years old). Severe disease also occurs in persons with severe combined immunodeficiency disease or following bone marrow or lung transplantation. Thus, these subjects can be selected for administration of a disclosed recombinant paramyxovirus.

To identify subjects for prophylaxis or treatment according to the methods of the disclosure, accepted screening methods are employed to determine risk factors associated with a targeted or suspected disease or condition, or to determine the status of an existing disease or condition in a subject. These screening methods include, for example, conventional work-ups to determine environmental, familial, occupational, and other such risk factors that may be associated with the targeted or suspected disease or condition, as well as diagnostic methods, such as various ELISA and other immunoassay methods, which are available and well known in the art to detect and/or characterize paramyxovirus infection. These and other routine methods allow the clinician to select patients in need of therapy using the methods and pharmaceutical compositions of the disclosure. In accordance with these methods and principles, a composition can be administered according to the teachings herein, or other conventional methods known to the person of ordinary skill in the art, as an independent prophylaxis or treatment program, or as a follow-up, adjunct or coordinate treatment regimen to other treatments.

The administration of a disclosed recombinant paramyxovirus can be for prophylactic or therapeutic purpose. When provided prophylactically, the immunogen can be provided in advance of any symptom, for example in advance of infection. The prophylactic administration serves to elicit an immune response that can prevent or ameliorate any subsequent infection. In some embodiments, the methods can involve selecting a subject at risk for contracting a paramyxovirus infection, and administering an effective amount of a disclosed recombinant paramyxovirus to the subject. The recombinant paramyxovirus can be provided prior to the anticipated exposure to paramyxovirus so as to elicit an immune response that can attenuate the anticipated severity, duration or extent of an infection and/or associated disease symptoms, after exposure or suspected exposure to the virus, or after the actual initiation of an infection. In some examples, treatment using the methods disclosed herein prolongs the time of survival of the subject.

Administration of the disclosed recombinant paramyxoviruses including RSV and PIV antigens to a subject can elicit the production of an immune response that is protective against serious lower respiratory tract disease, such as pneumonia and bronchiolitis, or croup, when the subject is subsequently infected or re-infected with a wild-type RSV or PIV. While the naturally circulating virus is still capable of causing infection, particularly in the upper respiratory tract, there is a reduced possibility of rhinitis as a result of the vaccination and a possible boosting of resistance by subsequent infection by wild-type virus. Following vaccination, there are detectable levels of host engendered serum and secretory antibodies which are capable of neutralizing homologous (of the same subgroup) wild-type virus in vitro and in vivo. In many instances the host antibodies will also neutralize wild-type virus of a different, non-vaccine subgroup. To achieve higher levels of cross-protection, for example, against heterologous strains of another subgroup, subjects can be vaccinated with a composition including recombinant viral vectors including RSV F proteins from at least one predominant strain of both RSV subgroups A and B.

The recombinant viral vectors described herein, and immunogenic compositions thereof, are provided to a subject in an amount effective to induce or enhance an immune response against the antigens included in the virus in the subject, preferably a human. An effective amount will allow some growth and proliferation of the virus, in order to produce the desired immune response, but will not produce viral-associated symptoms or illnesses. Based on the guidance provided herein and knowledge in the art, persons skilled in the art will readily be able to determine the proper amount of virus to use in the live vaccine. The precise amounts will depend on several factors, for example, the subject's state of health and weight, the mode of administration, the degree of attenuation of the virus, the nature of the formulation, and whether the immune system of the subject is compromised.

An immunogenic composition including one or more of the disclosed recombinant paramyxoviruses can be used in coordinate (or prime-boost) vaccination protocols or combinatorial formulations. In certain embodiments, novel combinatorial immunogenic compositions and coordinate immunization protocols employ separate immunogens or formulations, each directed toward eliciting an anti-viral immune response, such as an immune response to RSV and PIV proteins. Separate immunogenic compositions that elicit the anti-viral immune response can be combined in a polyvalent immunogenic composition administered to a subject in a single immunization step, or they can be administered separately (in monovalent immunogenic compositions) in a coordinate (or prime-boost) immunization protocol.

It is contemplated that there can be several boosts, and that each boost can be a different disclosed immunogen. It is also contemplated in some examples that the boost may be the same immunogen as another boost, or the prime.

Upon administration of a disclosed recombinant paramyxovirus the immune system of the subject typically responds to the immunogenic composition by producing antibodies specific for viral protein. Such a response signifies that an immunologically effective dose was delivered to the subject.

For each particular subject, specific dosage regimens can be evaluated and adjusted over time according to the individual need and professional judgment of the person administering or supervising the administration of the immunogenic composition. In some embodiments, the antibody response of a subject will be determined in the context of evaluating effective dosages/immunization protocols. In most instances it will be sufficient to assess the antibody titer in serum or plasma obtained from the subject. Decisions as to whether to administer booster inoculations and/or to change the amount of therapeutic agent administered to the individual can be at least partially based on the antibody titer level. The antibody titer level can be based on, for example, an immunobinding assay which measures the concentration of antibodies in the serum which bind to an antigen including, for example, an RSV F protein. The actual dosage of disclosed immunogen will vary according to factors such as the disease indication and particular status of the subject (for example, the subject's age, size, fitness, extent of symptoms, susceptibility factors, and the like), time and route of administration, other drugs or treatments being administered concurrently, as well as the specific pharmacology of the composition for eliciting the desired activity or biological response in the subject. Dosage regimens can be adjusted to provide an optimum prophylactic or therapeutic response.

Determination of effective dosages is typically based on animal model studies followed up by human clinical trials and is guided by administration protocols that significantly reduce the occurrence or severity of targeted disease symptoms or conditions in the subject, or that induce a desired response in the subject (such as a neutralizing immune response). Suitable models in this regard include, for example, murine, rat, porcine, feline, ferret, non-human primate, and other accepted animal model subjects known in the art. Alternatively, effective dosages can be determined using in vitro models (for example, immunologic and histopathologic assays). Using such models, only ordinary calculations and adjustments are required to determine an appropriate concentration and dose to administer a therapeutically effective amount of the composition (for example, amounts that are effective to elicit a desired immune response or alleviate one or more symptoms of a targeted disease). In alternative embodiments, an effective amount or effective dose of the composition may simply inhibit or enhance one or more selected biological activities correlated with a disease or condition, as set forth herein, for either therapeutic or diagnostic purposes. In one embodiment, a general range of virus administration is about $10^3$ to about $10^7$ plaque forming units (PFU) or more of virus per human subject, including about $10^4$ to about $10^5$ PFU virus per human subject.

Administration of an immunogenic composition that induces an immune response to reduce or prevent an infection, can, but does not necessarily completely, eliminate such an infection, so long as the infection is measurably diminished, for example, by at least about 50%, such as by at least about 70%, or about 80%, or even by about 90% the infection in the absence of the agent, or in comparison to a reference agent. Those in need of treatment include the general population and/or patients infected with or at risk of infection with a paramyxovirus, such as RSV and/or PIV In one example, a desired response is to inhibit or reduce or prevent RSV and/or PIV infection or reinfection. The RSV and/or PIV infection does not need to be completely eliminated or reduced or prevented for the method to be effective. For example, administration of an effective amount of a disclosed recombinant paramyxovirus can decrease subsequence RSV and/or PIV infection (for example, as measured by infection of cells, or by number or percentage of subjects infected by RSV and/or PIV) by a desired amount, for example by at least 10%, at least 20%, at least 50%, at least 60%, at least 70%, at least 80%, at least 90%, at least 95%, at least 98%, or even at least 100% (elimination or prevention of detectable RSV and/or PIV infection, as compared to a suitable control.

The dosage and number of doses will depend on the setting, for example, in an adult or any one primed by prior paramyxovirus infection or immunization, a single dose may be a sufficient booster. In naïve subjects, in some examples, at least two doses can be given, for example, at least three doses. In some embodiments, an annual boost is given, for example, along with an annual influenza vaccination.

Following immunization of a subject, serum can be collected from the subject at appropriate time points, frozen, and stored for assay of antibody titer and/or neutralization testing. Quantification of antibody levels can be performed by subtype-specific Neutralization assay or ELISA. Methods to assay for neutralization activity are known to the person of ordinary skill in the art and are further described herein, and include, but are not limited to, plaque reduction neutralization (PRNT) assays, microneutralization assays, flow cytometry based assays, single-cycle infection assays. In some embodiments, the serum neutralization activity can be assayed using a panel of RSV or PIV pseudoviruses. Virus-neutralizing antibody titres were determined in serum samples by a PRVN assay as described previously (de Graaf et al., *J. Virol Methods,* 143: 169-174, 2007). In brief, serum samples can be diluted and incubated for 60 min at 37° C. with approximately 50 p.f.u. of NL/1/00 or NL/1/99, expressing an enhanced green fluorescent protein. Subsequently, the virus-serum mixtures are added to Vero-118 cells in 24-well plates and incubated at 37° C. After 2 h, the supernatants are replaced by a mixture of equal amounts of infection medium and 2% methyl cellulose. Six days later, fluorescent plaques are counted using a Typhoon 9410 Variable Mode Imager (GE Healthcare). Antibody titres are expressed as the dilution resulting in 50% reduction of the number of plaques, calculated according to the method of Reed & Muench, *Am. J. Hyg.,* 27, 493-497, 1938.

Additional Embodiments:

Clause 1. A recombinant paramyxovirus, comprising (a) a viral genome comprising a heterologous gene encoding the ectodomain of a type I transmembrane protein of a heterologous virus linked to the transmembrane domain (TM) and cytoplasmic tail (CT) of the F protein of the paramyxovirus; or (b) a viral genome comprising a heterologous gene encoding the ectodomain of a type II transmembrane protein of a heterologous virus linked to the TM and CT of the HN protein of the paramyxovirus.

Clause 2. The recombinant paramyxovirus of clause 1, wherein the recombinant paramyxovirus is a recombinant human/bovine parainfluenza virus 3 (B/HPIV3), a recombinant human parainfluenza virus 1 (HPIV1), a recombinant human parainfluenza virus 1 (HPIV2), a recombinant human parainfluenza virus 1 (HPIV3), a recombinant parainfluenza virus 5 (PIV5) a recombinant Sendai virus, or a recombinant Newcastle disease virus (NDV).

Clause 3. The recombinant paramyxovirus of clause 2, comprising: a recombinant parainfluenza virus (PIV) comprising a viral genome comprising a heterologous gene encoding a recombinant respiratory syncytial virus (RSV) F ectodomain linked to a PIV F protein TM and CT; a recombinant NDV comprising a viral genome comprising a heterologous gene encoding a recombinant RSV F ectodomain linked to a NDV F protein TM and CT; or a recombinant Sendai virus comprising a viral genome comprising a heterologous gene encoding a recombinant RSV F ectodomain linked to a Sendai virus F protein TM and CT.

Clause 4. The recombinant paramyxovirus of any of clauses 1-3, comprising: a recombinant PIV comprising a viral genome comprising a heterologous gene encoding a recombinant RSV F ectodomain linked to a PIV F protein TM and CT.

Clause 5. The recombinant paramyxovirus of clause 4, wherein the RSV F ectodomain is from a human RSV (hRSV) F protein.

Clause 6. The recombinant paramyxovirus of clause 4 or claim 5, wherein the hRSV F protein is from a subtype A hRSV or subtype B hRSV.

Clause 7. The recombinant paramyxovirus of any one of clauses 4-6, wherein the RSV F ectodomain is stabilized in a RSV F prefusion-conformation by one or more amino acid substitutions compared to a native RSV F protein sequence.

Clause 8. The recombinant paramyxovirus of any one of clauses 4-7, wherein the RSV F ectodomain comprises amino acids set forth as: (a) 66E; (b) 101P; (c) 155C and 290C; (d) 190F; (e) 207L; or (f) a combination of (a) and (b); (a) and (c); (a) and (d); (a) and (e); (a), (d), and (e); (a), (c), (d), and (e); (a), (b), and (c); (a), (b), and (d); (a), (b), and (e); (a), (b), (e), and (d); (a), (b), (c), (d), and (e); (c) and (d); or (c) and (e); or (c), (d), and (e), wherein the amino acid numbering corresponds to the RSV F protein sequence set forth as SEQ ID NO: 1.

Clause 9. The recombinant paramyxovirus of clause 8, wherein the RSV F ectodomain comprises amino acid substitutions are set forth as: (a) K66E; (b) Q101P; (c) S155C and S290C; (d) S190F; (e) V207L; or (f) a combination of (a) and (b); (a) and (c); (a) and (d); (a) and (e); (a), (d), and (e); (a), (c), (d), and (e); (a), (b), and (c); (a), (b), and (d); (a), (b), and (e); (a), (b), (e), and (d); (a), (b), (c), (d), and (e); (c) and (d); or (c) and (e); or (c), (d), and (e).

Clause 10. The recombinant paramyxovirus of clause 8 or clause 9, wherein the RSV F ectodomain comprises 66E, 101P, 115C, 290C, 190F, and 207L.

Clause 11. The recombinant paramyxovirus of any one of clauses 4-10, wherein the RSV F ectodomain comprises an amino acid sequence at least 85% identical to the RSV ectodomain of one of SEQ ID NOs: 1 (WT RSV F A), 2 (WT RSV F B), 12 (A2 HEK), 14 (A2 HEK+DS), or 21 (A2 HEK+DS-Cav1), or comprises the amino acid sequence of the RSV ectodomain of SEQ ID NO: 12, 14, or 21.

Clause 12. The recombinant paramyxovirus of any one of clauses 4-11, wherein the PIV is a recombinant PIV1, a recombinant PIV2, or a recombinant PIV3.

Clause 13. The recombinant paramyxovirus of clause 12, wherein the recombinant PIV is: a recombinant PIV1, and the TM and CT linked to the RSV F ectodomain are from a PIV1 F protein; a recombinant PIV2, and the TM and CT linked to the RSV F ectodomain are from a PIV2 F protein; or a recombinant PIV3, and the TM and CT linked to the RSV F ectodomain are from a PIV3 F protein.

Clause 14. The recombinant paramyxovirus of clause 12 or clause 13, wherein the recombinant PIV is: a recombinant HPIV1 and the PIV F TM and CT linked to the RSV F ectodomain are from a HPIV1 F protein; a recombinant HPIV2 and the PIV F TM and CT linked to the RSV F ectodomain are from a HPIV2 F protein; a recombinant HPIV3 and the PIV F TM and CT linked to the RSV F ectodomain are from a HPIV3 F protein; or a recombinant B/HPIV3 and the PIV F TM and CT linked to the RSV F ectodomain are from a BPIV3 F protein.

Clause 15. The recombinant paramyxovirus of any one of clauses 4-14, wherein the RSV F ectodomain is from a hRSV F protein, and the TM and CT are from a BPIV3 F protein.

Clause 16. The recombinant paramyxovirus of any one of clauses 4-15, wherein the recombinant PIV is: a recombinant HPIV1 and the PIV F TM and CT linked to the RSV F ectodomain comprise the amino acid sequence set forth as SEQ ID NO: 31, or an amino acid sequence at least 90% identical to SEQ ID NO: 31; a recombinant HPIV2 and the PIV F TM and CT linked to the RSV F ectodomain comprise the amino acid sequence set forth as SEQ ID NO: 39, or an amino acid sequence at least 90% identical to SEQ ID NO: 39; a recombinant HPIV3 and the PIV F TM and CT linked to the RSV F ectodomain comprise the amino acid sequence set forth as SEQ ID NO: 46, or an amino acid sequence at least 90% identical to SEQ ID NO: 46; or a recombinant B/HPIV3 and the PIV F TM and CT linked to the RSV F ectodomain comprise the amino acid sequence set forth as SEQ ID NO: 53, or an amino acid sequence at least 90% identical to SEQ ID NO: 53.

Clause 17. The recombinant paramyxovirus of any one of clauses 4-16, wherein the recombinant PIV is: a recombinant HPIV3 and the heterologous gene encodes a hRSV F ectodomain linked to a HPIV3 F TM and CT comprising the amino acid sequence set forth as SEQ ID NO: 10, or an amino acid sequence at least 90% identical thereto; or a recombinant B/HPIV3 and the heterologous gene encodes a hRSV F ectodomain linked to a BPIV3 F TM and CT comprising the amino acid sequence set forth as SEQ ID NO: 21, or an amino acid sequence at least 90% identical thereto.

Clause 18. The recombinant paramyxovirus of any one of clauses 4-17, wherein the RSV F ectodomain is from a hRSV F protein and the recombinant PIV comprises a viral genome encoding: HPIV3 F and HN proteins and BPIV3 N, P, C, V, M, and L proteins, and wherein the TM and CT linked to the RSV F ectodomain are from a BPIV3 F protein; HPIV1 N, P, C, M, F, HN and L proteins, and wherein the TM and CT linked to the RSV F ectodomain are from a HPIV1 F protein; HPIV2 N, P, V, M, F, HN and L proteins, and wherein the TM and CT linked to the RSV F ectodomain are from a HPIV2 F protein; or HPIV3 N, P, C, M, F, HN and L proteins, and wherein the TM and CT linked to the RSV F ectodomain are from a HPIV3 F protein.

Clause 19. The recombinant paramyxovirus of any one of clauses 4-18, wherein the recombinant RSV F ectodomain linked to the PIV TM and CT is encoded by the first or second gene downstream of a genomic promoter of the PIV genome.

Clause 20. The recombinant paramyxovirus of clause 18 or clause 19, wherein the viral genome comprises, from upstream to downstream: a PIV genomic promoter followed by the N, P, C/V, M, F, HN, and L genes; and wherein the gene encoding the recombinant RSV F ectodomain linked to the PIV TM and CT is located between the genomic promoter and the gene encoding the N protein, or between the genes encoding the N and the P protein.

Clause 21. The recombinant paramyxovirus of any one of clauses 18-19, comprising a viral genome encoding: HPIV3 F and HN genes and BPIV3 N, P, C, V, M, and L genes comprising the amino acid sequences set forth as SEQ ID NOs: 21, 101, 47, 48, 49, 52, respectively, or sequences at least 90% identical thereto.

Clause 22. The recombinant paramyxovirus of any one of the prior clauses, wherein the heterologous gene is codon-optimized for expression in human cells.

Clause 23. The recombinant paramyxovirus of clause 22, wherein the recombinant paramyxovirus is: a recombinant HPIV3 and the heterologous gene encodes an RSV F ectodomain linked to a HPIV3 F TM and CT, and comprises the nucleotide sequence set forth as SEQ ID NO: 11 (GenScript RSV F_HEK_DS-Cav1_H3TMCT); or a recombinant B/HPIV3 and the heterologous gene encodes an RSV F ectodomain linked to a BPIV3 F TM and CT, and comprises the nucleotide sequence set forth as SEQ ID NO: 22 (GenArt RSV F_HEK_DS-Cav1_B3TMCT) or SEQ ID NO: 23 (GenScript RSV F_HEK_DS-Cav1_B3TMCT).

Clause 24. A recombinant viral vector, comprising: a viral genome comprising a heterologous gene encoding a RSV F ectodomain linked to the TM and CT of a type I membrane protein of the viral genome.

Clause 25. The viral vector of clause 24, wherein the RSV F ectodomain comprises K66E and Q101P amino acid substitutions.

Clause 26. A recombinant viral vector, comprising a viral genome comprising a heterologous gene encoding a RSV F ectodomain comprising K66E and Q101P amino acid substitutions.

Clause 27. The viral vector of any one of clauses 24-26, wherein the RSV F protein is stabilized in a prefusion or a postfusion conformation by one or more amino acid substitutions.

Clause 28. The viral vector of any one of clauses 24-27, wherein the RSV F ectodomain is stabilized in the prefusion conformation by S155C, S290C, S190F, and V207L amino acid substitutions Clause 29. The viral vector of any one of clauses 26-28, wherein the RSV F ectodomain is soluble and can be secreted from a host cell comprising the viral vector.

Clause 30. The viral vector of any one of clauses 24-29, wherein the viral vector is a recombinant human/bovine parainfluenza virus 3 (B/HPIV3), a recombinant human parainfluenza virus 1 (HPIV1), a recombinant human parainfluenza virus 1 (HPIV2), a recombinant human parainfluenza virus 1 (HPIV3), a recombinant parainfluenza virus 5 (PIV5) a recombinant Sendai virus, or a recombinant Newcastle disease virus (NDV).

Clause 31. The viral vector of any one of clauses 24-30, wherein the RSV F ectodomain is from a human RSV (hRSV) F protein.

Clause 32. The viral vector of any one of clauses 24-31, wherein the heterologous gene encoding the RSV F protein comprises the nucleic acid sequence set forth as nucleotides 1-1587 of SEQ ID NO: 18. (ectodomain encoded by GenScript optimized RSV F_A2_HEK_DS-Cav1_B3CT DNA sequence)

Clause 33. The recombinant paramyxovirus or viral vector of any one of the prior clauses, wherein at least 90% of viral particles produced by a host cell infected with the recombinant paramyxovirus or viral vector comprise a viral envelope comprising the ectodomain encoded by the heterologous gene.

Clause 34. The recombinant paramyxovirus or viral vector of any one of the previous clauses, wherein the recombinant paramyxovirus or viral vector is attenuated.

Clause 35. An immunogenic composition comprising the recombinant paramyxovirus or viral vector of any one of the prior clauses and a pharmaceutically acceptable carrier.

Clause 36. The immunogenic composition of clause 35, further comprising an adjuvant.

Clause 37. A method of eliciting an immune response to a virus and a heterologous antigen encoded thereby in a subject comprising administering a therapeutically effective amount of the immunogenic composition of clause 35 or clause 36 to the subject.

Clause 38. A method of eliciting an immune response to a paramyxovirus and a heterologous antigen encoded thereby in a subject comprising administering a therapeutically effective amount of the immunogenic composition of clause 35 or clause 36 to the subject, wherein the immunogenic composition comprises a recombinant paramyxovirus comprising a heterologous gene encoding the heterologous antigen.

Clause 39. A method of eliciting an immune response to RSV and PIV in a subject, comprising administering an immunogenic composition comprising a therapeutically effective amount of the immunogenic composition of clause 35 or clause 36 to the subject, wherein the immunogenic composition comprises a recombinant paramyxovirus comprising a heterologous gene encoding an RSV antigen.

Clause 40. The method of any one of clauses 37-39, wherein the immune response is a protective immune response.

Clause 41. The method of any one of clauses 37-40, comprising a prime-boost administration of the immunogenic composition.

Clause 42. The method of any one of clauses 37-41, comprising intranasal or parenteral administration of the immunogenic composition.

Clause 43. The method of any one of clauses 37-42, wherein the subject is a human or a veterinary subject.

Clause 44. The method of any one of clauses 37-43, wherein the subject is at risk of or has a RSV or a PIV infection.

Clause 45. The method of any one of clauses 37-44, wherein the subject is less than one year old.

Clause 46. A nucleic acid molecule comprising the genome of the recombinant paramyxovirus of any one of clauses 1-25.

Clause 47. A recombinant RSV F protein or immunogenic fragment thereof comprising K66E and Q101P amino acid substitutions.

Clause 48. The recombinant RSV F protein or immunogenic fragment thereof of clause 47, further comprising: (a) S155C and S290C; (b) S190F; (c) V207L; or (f) a combination of (a) and (b); (a) and (c); (b) and (c); or (a), (b), and (c).

Clause 49. The immunogenic fragment of the recombinant RSV F protein of clause 47 or clause 48, comprising the RSV F ectodomain.

Clause 50. A nucleic acid molecule encoding the recombinant RSV F protein of any one of clauses 47-49.

EXAMPLES

The following examples are provided to illustrate particular features of certain embodiments, but the scope of the claims should not be limited to those features exemplified.

Example 1

Improved Expression and Immunogenicity of the Respiratory Syncytial Virus (RSV) Fusion (F) Glycoprotein Expressed by an Attenuated Parainfluenza Virus Vector This example describes approaches to enhance the immunogenicity and stability of RSV F expressed by a recombinant B/HPIV3 by using RSV F sequence from an early passage virus, by codon-optimization, by using stable and highly immunogenic pre-fusion and post-fusion forms of RSV F, and by engineering the RSV F protein TM and CT so that it was more efficiently incorporated into vector particles.

Introduction.

Live attenuated RSV strains administered represent one strategy for an RSV vaccine, and these are currently under development (Hurwitz. 2011. Expert. Rev. Vaccines. 10:1415-1433; Collins and Melero. 2011. Virus Res. 162: 80-99; Karron, et al. 2013. Current Topics Microbiology and Immunology 372:259-284). A live attenuated RSV strain typically would be administered by the intranasal (IN) route. However attenuation generally results in reduced antigen synthesis, resulting in reduced immunogenicity. Obtaining a suitable balance between attenuation and immunogenicity has been challenging for RSV.

Complete, infectious HPIVs can be generated entirely from cloned cDNAs in transfected cell culture (using reverse genetics). A foreign gene designed for expression would be modified so that it is flanked by HPIV transcription signals (called the gene-start and gene-end signals, located at the beginning and end of each gene, respectively) and would be inserted as an additional gene into the HPIV genome by reverse genetics. The foreign gene would then be transcribed into a separate mRNA, like the other HPIV genes. HPIVs can accommodate and express several added foreign genes (Skiadopoulos, et al. 2002. Virology 297:136-152). However, multiple genes can be overly attenuating and can collect point mutations (Skiadopoulos, et al. 2002. Virology 297:136-152).

HPIV transcription initiates at a single promoter at the 3' end of the genome and proceeds sequentially. A fraction of the polymerase disengages from the template at each gene junction, resulting in a negative gradient of gene transcription. Therefore, promoter-proximal genes are expressed more frequently than downstream genes. Placement of a foreign gene close to the promoter would increase expression, but has the potential to affect expression of downstream vector genes. Other features, such as differences in the efficiency of gene-start or gene-end transcription signals or effects of other structural features in the RNA template that sometimes are present but are poorly understood, also can unpredictably affect expression of an inserted gene or open reading frame (ORF) (Whelan, et al. 2004. Current Topics Microbiology and Immunology 283:61-119). In addition, in some cases the properties of viral constructs can be greatly affected by factors that remain unidentified; for example, the insertion of the RSV F gene into the P-M gene junction of a PIV3 vector resulted in a virus that was substantially temperature-sensitive and attenuated (Liang B, et al. 2014. J Virol 88:4237-4250). Thus, while the broad details of expression from HPIV genomes is generally known, specific constructions can give unpredictable results.

In previous studies, the B/HPIV3 vector was used as a vector to express the RSV G gene and F proteins from added genes in the first and second genome positions after the promoter or to express the RSV F gene from an added gene in the second genome position between the N and P genes. The latter virus, called MEDI-534, has been evaluated in clinical studies in seronegative children and was attenuated, well tolerated, and infectious but was less immunogenic against RSV than hoped (Bernstein, et al. 2012. Pediatric Infectious Disease Journal 31:109-114). Analysis of shed vaccine virus from vaccine recipients showed that ~50% of specimens contained vaccine virus with mutations that would be predicted to perturb RSV F expression. This likely reduced immunogenicity. Retrospective analysis of the clinical trial material (CTM) showed that 2.5% of this virus did not express RSV F (Yang, et al. 2013. Vaccine 31:2822-2827). In addition, the observation that the RSV F insert accumulated mutations that inactivated its expression at the protein level, and that these mutations were amplified during growth, suggests that there was a selective advantage to silencing expression of the RSV F protein. This likely could be due to the highly fusogenic nature of the RSV F protein, which efficiently mediates syncytium formation. In vitro, this results in destruction of the cell substrate, which could reduce vector replication. In addition, the synthesis of high levels of a foreign glycoprotein could interfere with the synthesis, processing and transport of the vector glycoproteins through the endoplasmic reticulum and exocytic pathway, and could interfere sterically with virion morphogenesis, among other things. These effects might occur both in vitro and in vivo.

Expression of an Early-Passage (HEK) Version of the RSV F Protein and Codon-Optimized Versions of the RSV F Open Reading Frame (ORF).

Increased expression of viral antigen typically provides enhanced immunogenicity. Codon-optimization of the ORF encoding a vectored antigen can increase its expression and in turn enhance its immunogenicity, for example as has been shown with human immunodeficiency virus antigens expressed from viral or DNA vectors (Gao, et al. 2003.

AIDS research and human retroviruses 19:817-823; Carnero, et al. 2009. J Virol 83:584-597). However, these sequence changes can have effects beyond improving translation, such as effects on mRNA stability and transport, and so the effects of altering the nucleotide sequence of an mRNA can be complex and unpredictable. Therefore, a codon-optimized version of the RSV F sequence was designed using GeneArt (GA) algorithms and was evaluated to determine whether it conferred protein expression.

When designing this codon-optimized ORF, the amino acid sequence of an early-passage version of RSV strain A2 from the 1960s was mistakenly used (Connors, et al. 1995. Virology 208:478-484; Whitehead, et al. 1998. J Virol 72:4467-4471). This early-passage (or low-passage) strain from the 1960s is called HEK after the human embryonic kidney (HEK) cell culture used in its propagation. The HEK virus differed from current, highly passaged laboratory version of RSV strain A2 by two amino acid assignments (Connors, et al. 1995. Virology 208:478-484; Whitehead, et al. 1998. J Virol 72:4467-4471). The HEK version had assignments 66E and 101P whereas the highly passaged laboratory A2 strain had assignments 66K and 101Q (hereafter called "non-HEK" assignments) (FIG. 1). However, the occurrence of sequence differences between virus strains or between stocks of a given strain is common for RNA viruses given their high mutation rate, and the HEK differences previously had no known importance. Further, the presence of the HEK assignments in an attenuated RSV vaccine candidate called RSV NIH ΔM2-2 was associated with a small reduction in the efficiency of replication in cell culture. Additionally, the HEK assignment at position 66 was identified to affect syncytium formation during RSV infection. Thus, it was intended to avoid the HEK assignments given their association with reduced replication. However, because the version of RSV F containing the HEK assignments was accidentally used for the initial codon optimization, a parallel GA-optimized non-HEK version was constructed and the two versions were compared (FIG. 1). The two versions of RSV F were placed under the control of BPIV3 gene-start and gene-end transcription signals and inserted into the 2' position of the rB/HPIV3 vector (FIG. 1). The transcription signals and insert position were used in all subsequent rB/HPIV3 constructs expressing RSV F so as to provide direct comparisons throughout.

Figures 2A, 2B:
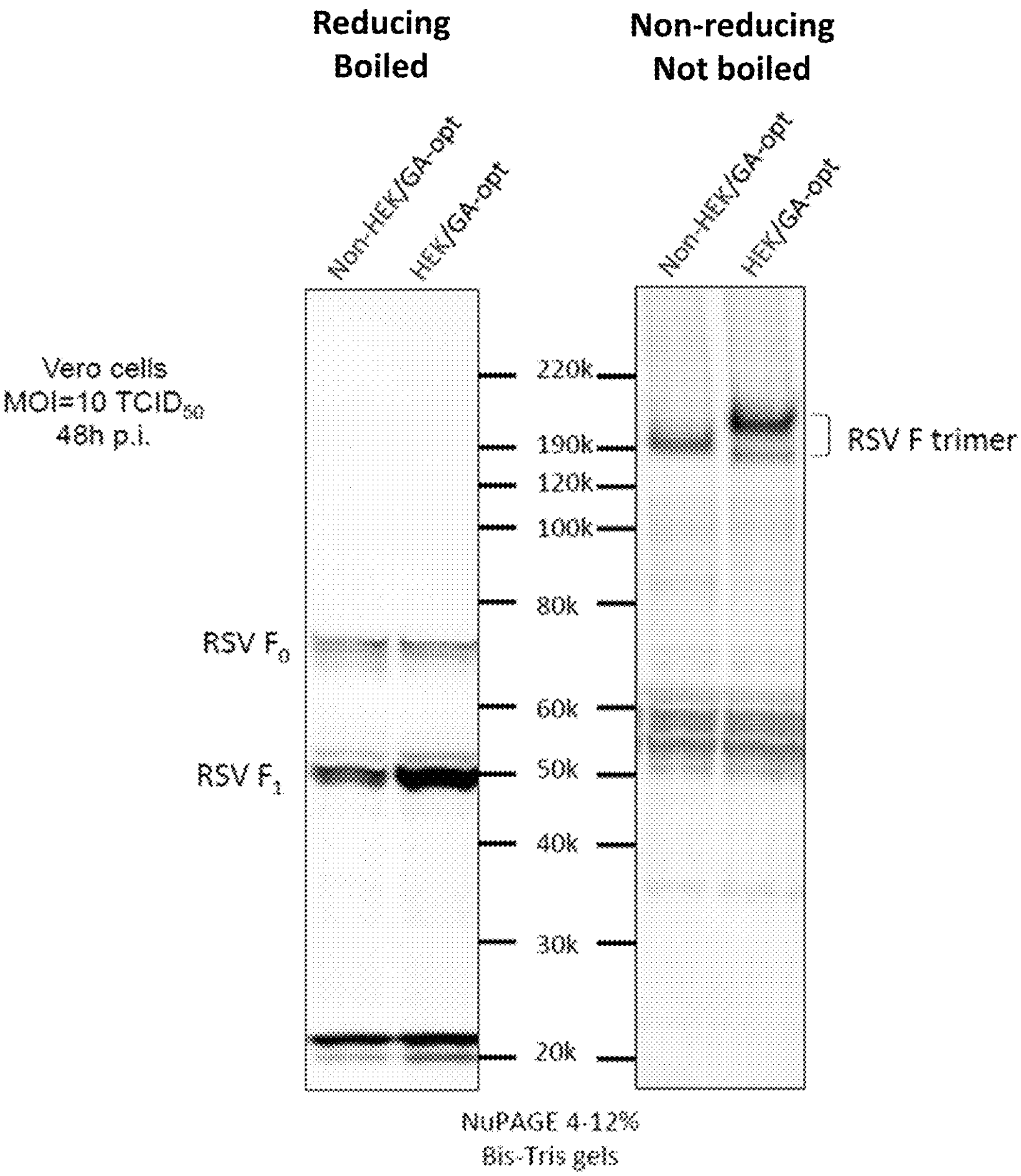
FIGS. 2A and 2B. The presence of the HEK assignments in the RSV F protein resulted in increased protein expression and a reduction in protein trimer mobility in polyacrylamide gel electrophoresis compared to that of non-HEK F protein. Vero cells were infected with vectors expressing HEK or non-HEK RSV F (from GA-optimized ORFs, shown in FIG. 1) at an MOI of 10 $TCID_{50}$ at 32° C. Cell lysates were prepared at 48 hours post-infection. Equal amounts of cell lysates were analyzed by electrophoresis after being boiled and reduced (A) or without being boiled and reduced (B). Denatured and reduced RSV F monomer was detected with a commercially-obtained RSV F-specific mouse monoclonal antibody (A). Native RSV F trimer was detected with polyclonal antibodies raised in rabbits by repeated immunizations with sucrose purified RSV particles (B).

Vero cells were infected with the two different vectors (called "HEK/GA-opt" and "non-HEK/GA-opt"), cell lysates were prepared 48 h post-infection, and the proteins were subjected to gel electrophoresis in the presence of denaturing detergent and under reducing or non-reducing conditions. The separated proteins were transferred to membranes by Western blotting and were analyzed using antibodies specific to RSV F (FIG. 2). This showed that the presence of the HEK assignments was associated with a small (~2-fold) but consistent increase in the expression of RSV F protein (FIG. 2). One non-limiting explanation for this finding is that the HEK assignments increased F protein stability although an effect on protein synthesis is possible but seems less likely given that the HEK and non-HEK versions of the F ORF were identical except for two codons. In addition, when analyzed under non-reducing conditions, the presence of the HEK assignments was associated with a reduction in the gel mobility of the RSV F trimer (FIG. 2). This suggested that these assignments altered the F protein trimer structure. More strikingly, expression of the HEK version of RSV F was associated with a drastic reduction in syncytium formation compared to the non-HEK version (FIG. 3) even though the HEK version was expressed at a slightly increased level, as already noted. This assay takes advantage of the general lack of evident syncytia induced in cells infected by the rB/HPIV3 empty vector, whereas the expression of the RSV F protein from the vector results in syncytium formation that is generally proportional to the amount of expression of RSV F protein. This provides an assay for the quantity and functionality of RSV F protein expressed from a PIV vector. These observations concerning HEK indicated that the HEK assignments were associated with differences in synthesis/stability, structure, and fusogenic activity of RSV F, and that these effects occurred in the absence of any other RSV proteins and thus were directly relevant to expression from a heterologous vector.

Because the HEK assignments are from a low-passage stock of RSV strain A2 from the 1960s, they are likely to be representative of the original clinical isolate, whereas the non-HEK assignments had appeared during extensive passage in vitro over subsequent decades. This suggests that the hypo-fusogenic phenotype of the HEK version of F is more representative of the original biological virus. The non-HEK version may represent a hyper-fusogenic variant that was selected for during passage in cell culture. A hyper-fusogenic version of RSV F might be less favored in nature because it might destabilize the virus, but might be selected for in a laboratory setting of rapid growth in a cell monolayer. 226 sequences of RSV F from clinical isolates in the GenBank database were examined and it was found that clinical isolates usually contained the HEK assignments. This is consistent with these assignments being representative of circulating RSV. In any event, the HEK assignments provided a modest increase in F protein expression and provided a form of RSV F that was hypo-fusogenic. The reduction in syncytium formation is advantageous because it reduces cytopathogenicity that might otherwise interfere with HPIV vector replication and favor selection of vector in which the RSV F insert was silenced. Therefore, the HEK assignments have the triple advantage of representing a more native and clinically relevant form of the F protein, providing a modest increase in protein expression, and reducing selective pressure to silence the RSV F insert.

Figure 4:
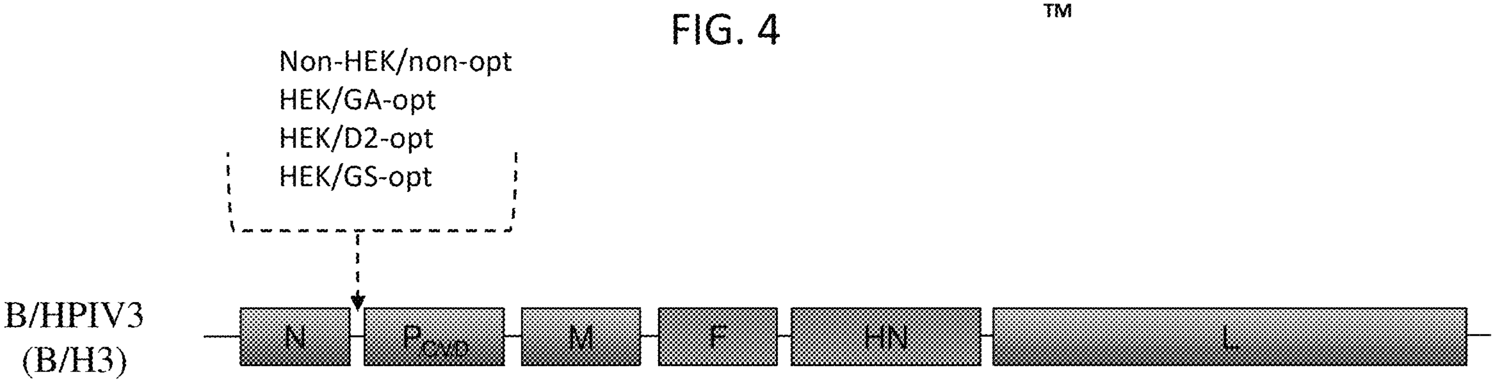
FIG. 4. Construction of rB/HPIV3 vectors expressing RSV F ORFs that were codon-optimized (for human expression) by different algorithms and contained the HEK assignments. The ORF encoding the RSV F protein with HEK assignments was optimized for human codon usage with the GA algorithm (HEK/GA-opt, shown in FIG. 1), the DNA2.0 algorithm (HEK/D2-opt), or the GenScript (GS) algorithm (HEK/GS-opt). These codon-optimized ORFs were compared with the non-HEK, non-optimized version of the RSV F ORF (Non-HEK/non-opt). These RSV F ORFs were inserted into the rB/HPIV3 vector in exactly the same position and with the same vector signals as in FIG. 1.
Figure 5B:
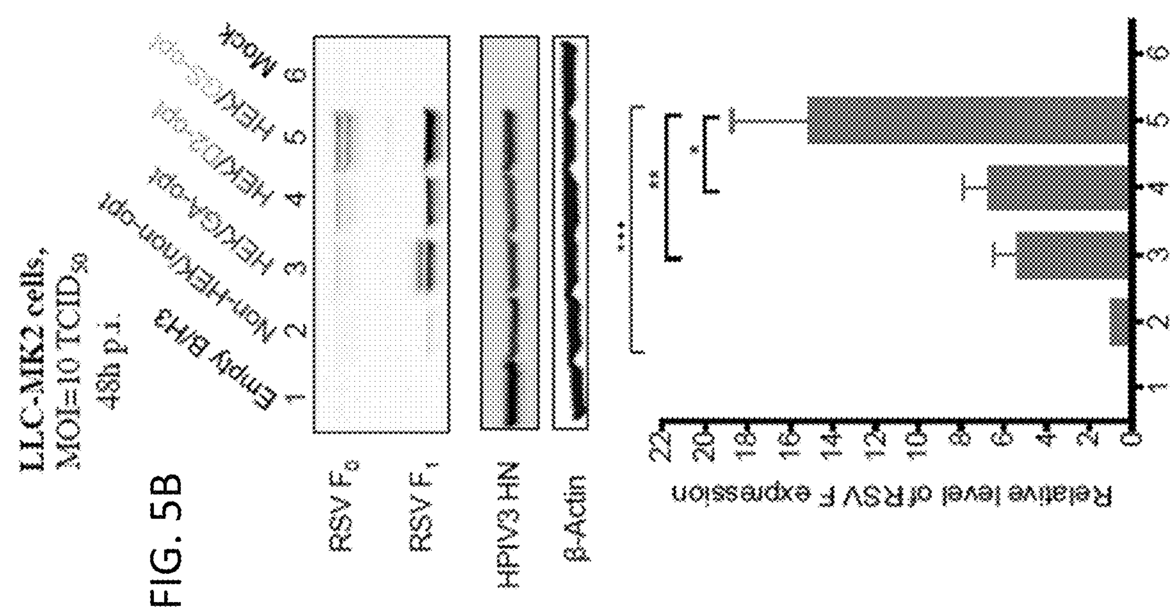
FIGS. 5A and 5B. Increased in vitro expression of RSV F protein from rB/HPIV3 vectors due to the HEK assignments and codon optimization. Expression of RSV F in (A) Vero and (B) LLC-MK2 cells was evaluated by Western blot analysis. Cells were infected at an MOI of 10 $TCID_{50}$ at 32° C. with the indicated rB/HPIV3 vectors, and cell lysates were harvested at 48 hours post-infection. Lysates were subjected to gel electrophoresis under reducing and denaturing conditions and analyzed by Western blotting. Proteins were visualized by reaction with fluorescent antibodies and detected by infrared imaging. The experiment was performed with a total of three wells per virus. A monoclonal antibody specific to RSV F detected the uncleaved $F_0$ precursor and cleaved $F_1$ subunit. RSV $F_1$ band densities were quantified and normalized to the band density of the Non-HEK/non-opt samples indicated as "1". Expression of the HPIV3 HN protein also was determined as an internal control for vector protein expression and to ensure equivalence of MOI and replication; β-actin was used as the loading control.
Figure 5A:
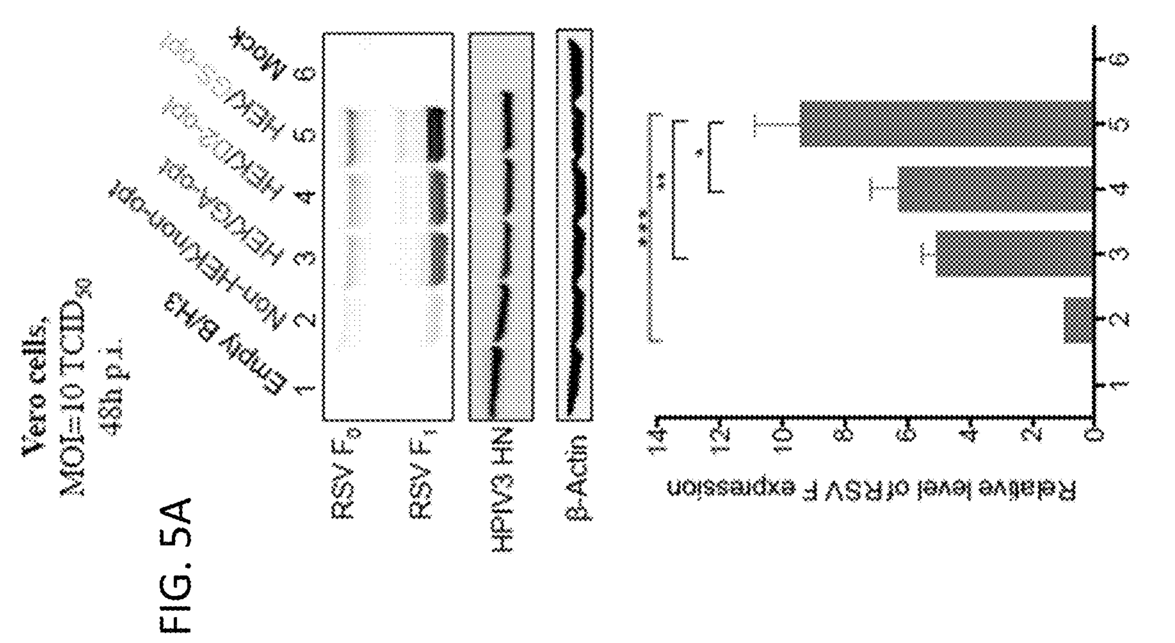

The effect of codon-optimization on RSV F expression and immunogenicity was also evaluated. The HEK-containing and GA-optimized version (HEK/GA-opt) described above was used along with two other codon-optimized RSV HEK F sequences made by two other different algorithms. Evaluation of multiple optimized versions is not a typical practice, since it increases the expense and inconvenience and had not been shown to be useful. The two other sources were DNA2.0 (D2) and GenScript (GS) algorithms; also included for comparison was the non-HEK, non-codon-optimized version (FIG. 4). Codon optimization resulted in significantly enhanced RSV F protein synthesis that, surprisingly, differed in magnitude for the different versions. The highest expression was observed for the HEK-containing GenScript-optimized F protein (HEK/GS-opt), which was 10-fold (Vero cells) and 16-fold (LLC-MK2 cells) higher than the unmodified RSV F (non-HEK/non-opt) (FIG. 5). The levels of expression with the more efficient ORFs were so high that progressively increasing levels of syncytium formation were evident in association with increasing levels of F expression despite the presence of the HEK assignments (FIG. 6), although it can be presumed that syncytium formation would have been even faster and more extensive in the absence of the HEK assignments.

Codon-pair optimization was also evaluated as a means to increase F protein expression, using an algorithm that was previously described (Coleman, et al. 2008. Science 320:

1784-1787). Codon-pair optimization increases the frequency of codon pairs associated with high expression. However, this did not confer any increase in expression in the case of RSV F.

Figure 7A:
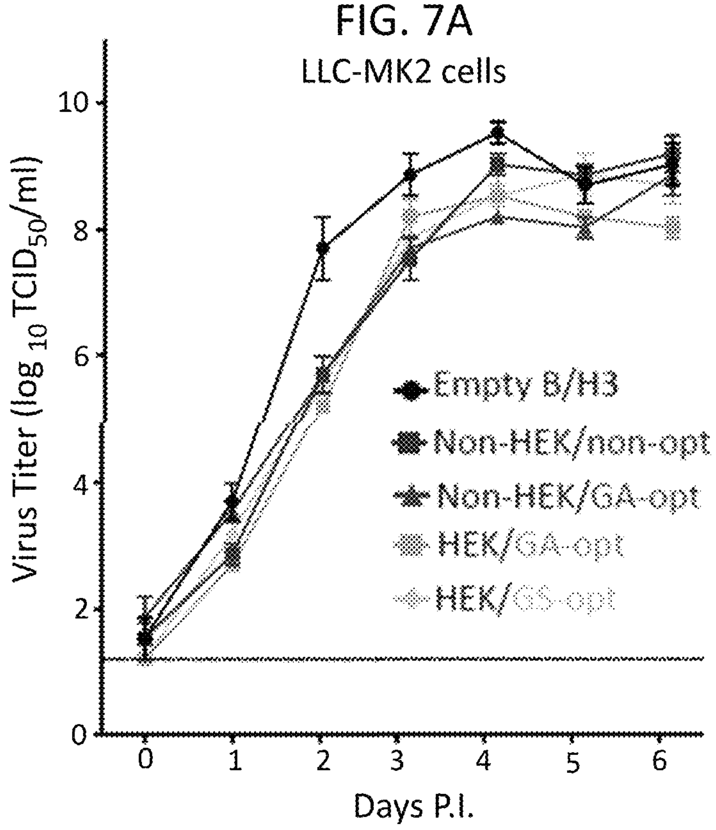
FIGS. 7A and 7B. Multi-cycle in vitro replication of rB/HPIV3 vectors expressing HEK or non-HEK RSV F protein from non-optimized or codon-optimized ORFs. (A) LLC-MK2 and (B) Vero cells were infected in triplicate at 32° C. at an MOI of 0.01 $TCID_{50}$ with empty rB/HPIV3 vector (empty B/H3) or vector expressing the RSV F ORF that was non-HEK-containing and non-optimized (Non-HEK/non-opt) or was non-HEK-containing and GA-optimized (Non-HEK/GA-opt) or was HEK-containing and GA-optimized (HEK/GA-opt) or was HEK-containing and GS-optimized (HEK/GS-opt). Aliquots of medium supernatant were collected at 24 h intervals for 6 days and viral titers were determined by limiting dilution assay on LLC-MK2 cells at 32° C. and reported as $TCID_{50}$/ml. Mean titers±SEM from three independent experiments are shown.
Figure 7B:
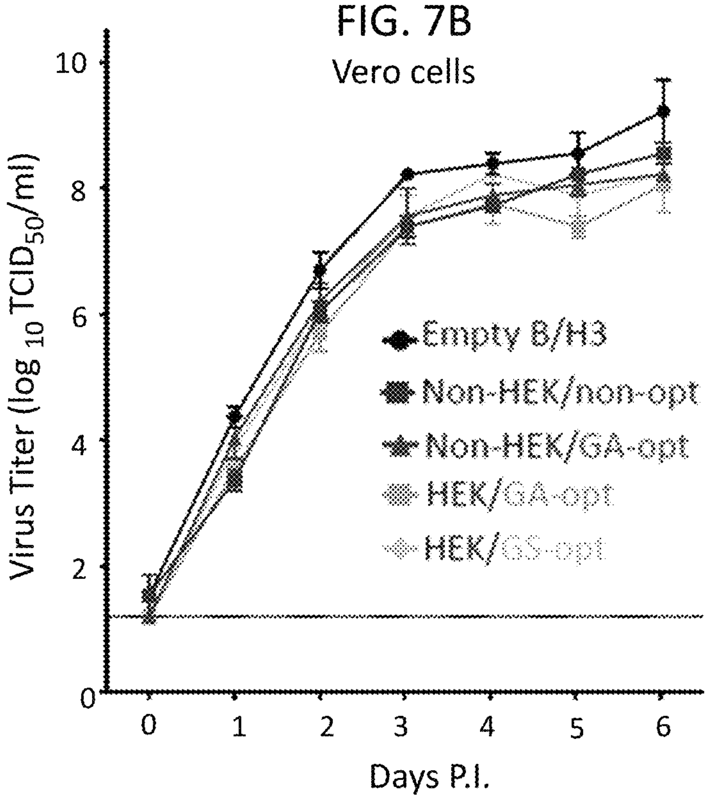

Contrary to expectations, the 10- to 16-fold increase in RSV F expression and concomitant increase in syncytium formation did not have a significant negative impact on vector replication in cell culture (FIG. 7). It might have been anticipated that high levels of RSV F expression and syncytium formation would have interfered with the vector at any of a number of steps, as already noted, including vector glycoprotein synthesis, processing, exocytosis, vector particle formation, and cell viability, but this was not the case. This was particularly surprising because, as already noted, the accumulation and amplification of mutations that silenced expression of the RSV F gene in MEDI-534 suggested that there was a substantial selective pressure against expression of RSV F protein. Compared with the empty vector, all vectors with RSV F insert were moderately attenuated (FIG. 7)—perhaps involving a common attenuating effect such as the increase in genome length and gene number—but replicated with similar kinetics to each other and grew to high peak titers that were slightly lower than the peak titer of empty vector (FIG. 7). Modest variance of peak titers likely represents experimental variability.

Figure 8A:
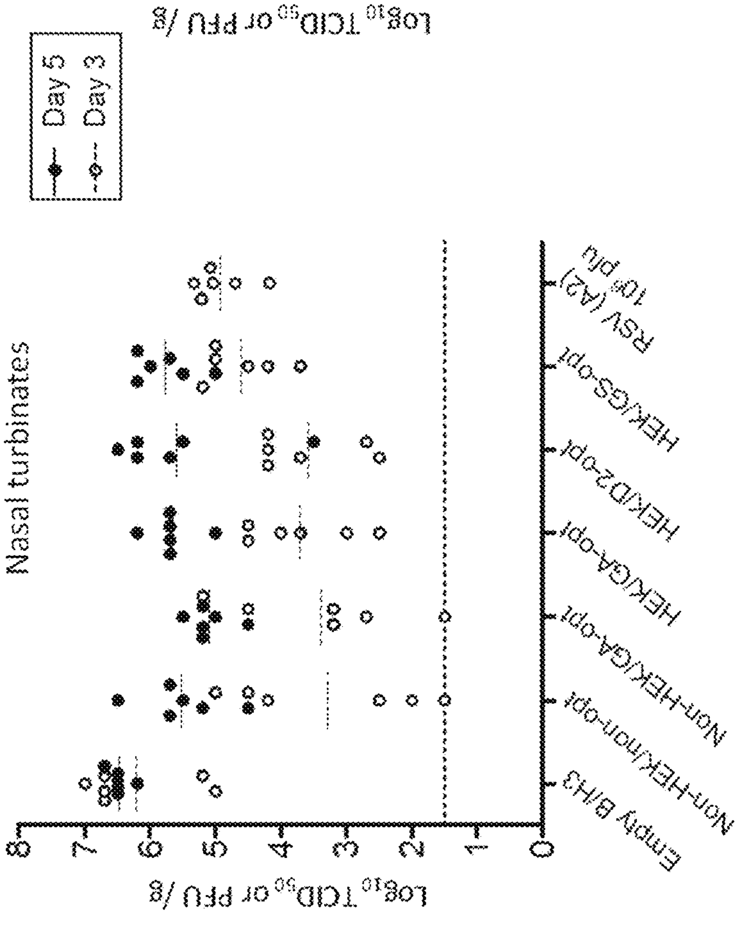
FIGS. 8A and 8B. Replication in hamsters of rB/HPIV3 vectors expressing HEK or non-HEK RSV F protein from non-optimized or codon-optimized ORFs. Golden Syrian hamsters were infected intranasally (IN) with $10^5$ $TCID_{50}$ of the indicated rB/HPIV3 vectors or $10^6$ PFU of wt RSV (strain A2) in a 0.1 ml inoculum. Hamsters were euthanized (n=6 per virus per day) on day 3 and 5 post-infection and the (A) nasal turbinates and (B) lungs were removed and homogenized and viral titers were determined by limiting dilution on LLC-MK2 (rB/HPIV3 vectors) or Vero (RSV) cells at 32° C.: open and closed circles indicate titers for animals sacrificed on day 3 and 5, respectively. Each symbol represents an individual animal, and the mean titer of each group is indicated by a dashed and a solid horizontal line for day 3 and 5, respectively. The limit of detection (LOD) was 1.5 login $TCID_{50}$/g of tissue, indicated with a dotted line. The rB/HPIV3 vectors were titrated by limiting dilution assays on LLC-MK2 cells and reported as $TCID_{50}$/g; RSV was titrated by plaque assays on Vero cells and reported as PFU/g.
Figure 8B:
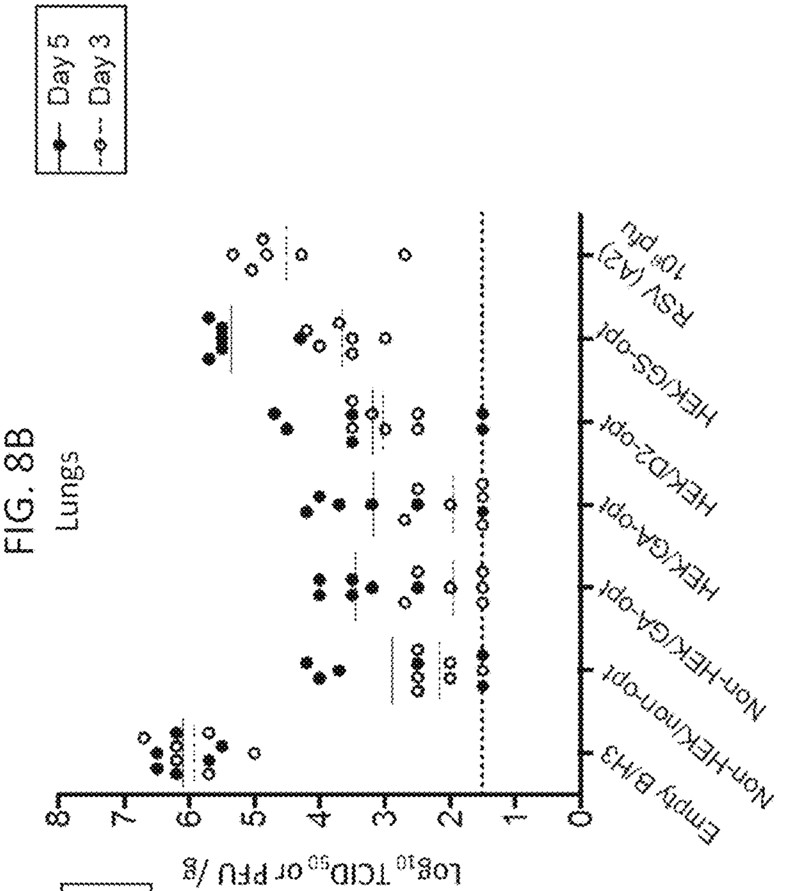

In vivo replication, immunogenicity, and protective efficacy of the rB/HPIV3 vectors was evaluated in a hamster model. Groups of hamsters were immunized intranasally with the rB/HPIV3 vectors at a dose of $10^5$ tissue-culture-infection-dose-50 units ($TCID_{50}$) per animal. In addition, wildtype (wt) RSV given at a dose of $10^6$ plaque forming units (pfu) was included as positive control for the induction of RSV-specific immunity. The wt RSV control was included with the caveat that wt RSV was a non-attenuated virus whereas the vectors were attenuated and might be relatively less immunogenic for that reason. Six animals per virus per day were euthanized on days 3 and 5 post-infection, and nasal turbinates and lungs were collected for virus titration to measure replication in vivo. This showed that vectors bearing the RSV F insert were moderately attenuated in the nasal turbinates (upper respiratory tract), and substantially attenuated in the lungs (lower respiratory tract) as compared with the empty vector (FIG. 8). Increased attenuation compared to the empty vector was evident by the lower values for virus shedding. It also was evident by comparison of the day 3 and day 5 titers: for the empty vector, the titers on days 3 and 5 were comparable, whereas for the vectors bearing RSV F, the day 3 titers were lower than the day 5 titers, indicating that these constructs took longer to achieve their maximum titers. Surprisingly, among the vectors with RSV F insert, those with enhanced RSV F expression were not more attenuated than the one with less RSV F expression, i.e., non-HEK/non-opt. Thus, the addition of the RSV F insert to the rB/HPIV3 vector was attenuating in vivo—perhaps due to some common feature such as the increase in genome length or gene number—but this did not appear to be substantially influenced by the level of synthesis of the RSV F protein.

Figure 9:
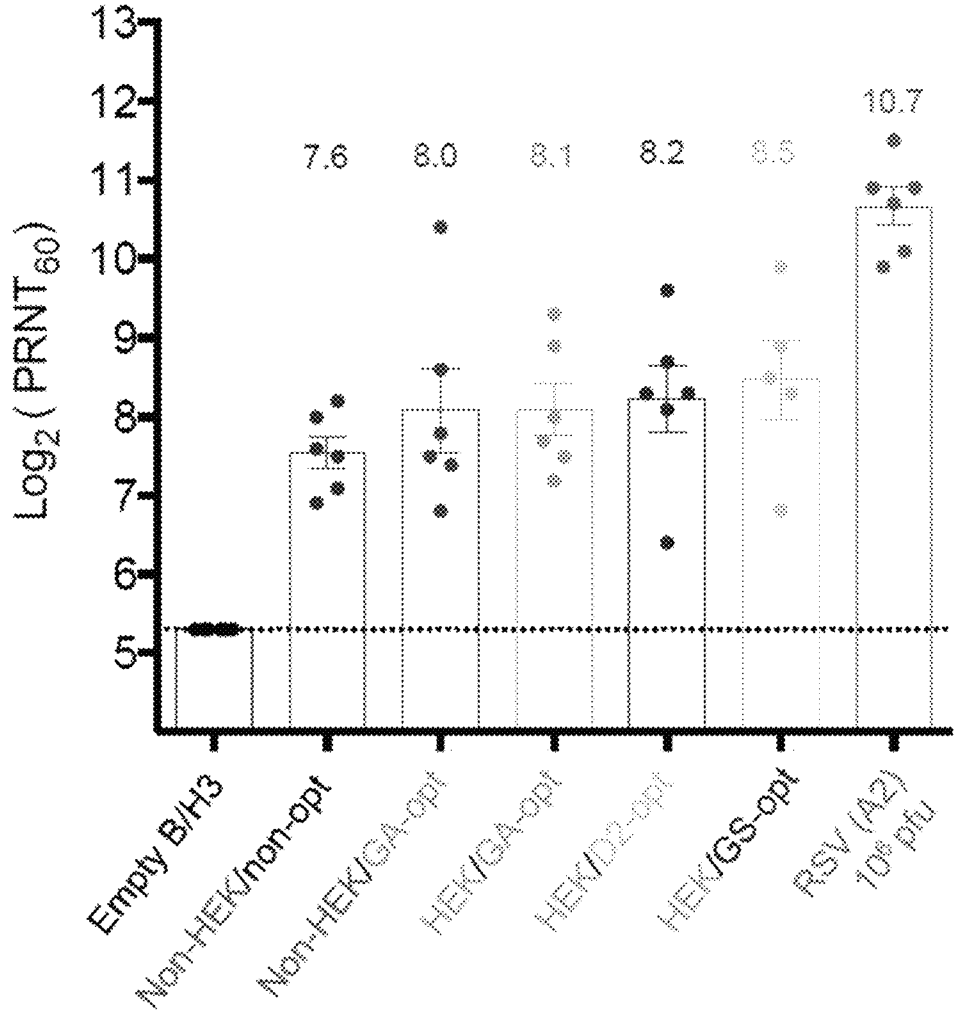
FIG. 9. Serum RSV-neutralizing antibody titers from hamsters infected with rB/HPIV3 vectors expressing HEK or non-HEK RSV F protein from non-optimized or codon-optimized ORFs. Hamsters (n=6 animals per virus) were inoculated IN with $10^5$ $TCID_{50}$ of the indicated rB/HPIV3 vectors or $10^6$ PFU of wt RSV in a 0.1 ml inoculum. Serum samples were collected at 28 days post-immunization, and RSV-neutralizing antibody titers were determined by using a 60% plaque reduction neutralization test ($PRNT_{60}$) performed on Vero cells at 32° C. in the presence of guinea pig complement. Each symbol represents an individual animal. The height of each bar represents the mean titer of each group. The values of mean titers are shown above the bars. The standard error of the mean is shown by the horizontal lines. The detection limit for the neutralization assay was 5.3 reciprocal $log_2$ $PRNT_{60}$, indicated with a dotted line.

The immunogenicity of the vectors was assessed by measuring the serum titers of RSV-neutralizing antibodies by a 60% plaque reduction assay supplemented with guinea pig complement, which is a standard assay. All vectors expressing RSV F induced similarly high titers of RSV-neutralizing serum antibodies, irrespective of HEK assignments or codon-optimization (FIG. 9). There was a modest progressive increase in neutralizing titers associated with increasing RSV F expression, but the differences were not statistically significant. WT RSV that had been infected in parallel as a control induced significantly higher titers of RSV-neutralizing antibodies than the vectors. However, it is important to note that the neutralizing antibodies induced by RSV infection included contributions from both the F and G neutralization antigens, whereas the vectors only had F-specific antibodies contributing to the neutralizing titers. In addition, the non-attenuated wt RSV control replicated more efficiently than the attenuated vectors, especially in the lungs (FIG. 8), which would have increased its immunogenicity compared to that of the vectors.

Figure 10B:
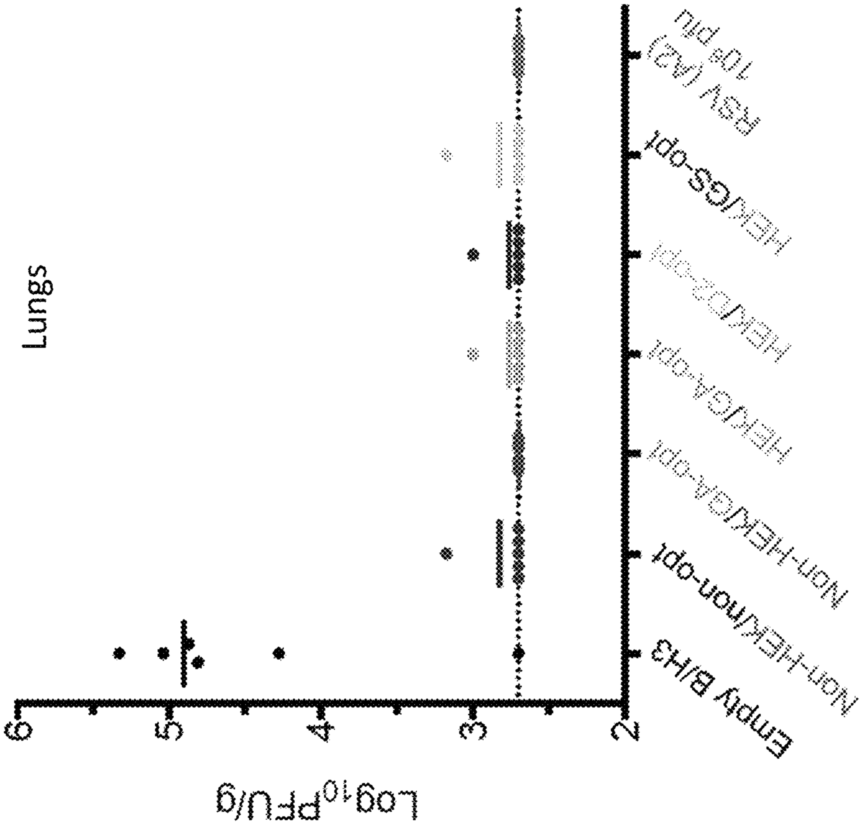
FIGS. 10A and 10B. Protection of immunized hamsters against RSV challenge. The hamsters (n=6 animals per virus) that had been immunized as shown in FIG. 9 with the indicated rB/HPIV3 vectors or with wt RSV, were challenged IN on day 31 post-immunization with $10^6$ PFU of wt RSV in a 0.1 ml inoculum. On day 3 post-challenge, hamsters were euthanized and (A) nasal turbinates and (B) lungs were collected. RSV titers in tissue homogenates were determined by plaque assay in Vero cells. Each symbol represents an individual animal and mean viral titers of the groups are shown as horizontal lines. The detection limit of the assay was login 2.7 PFU/g of tissue, indicated as a dashed line.
Figure 10A:
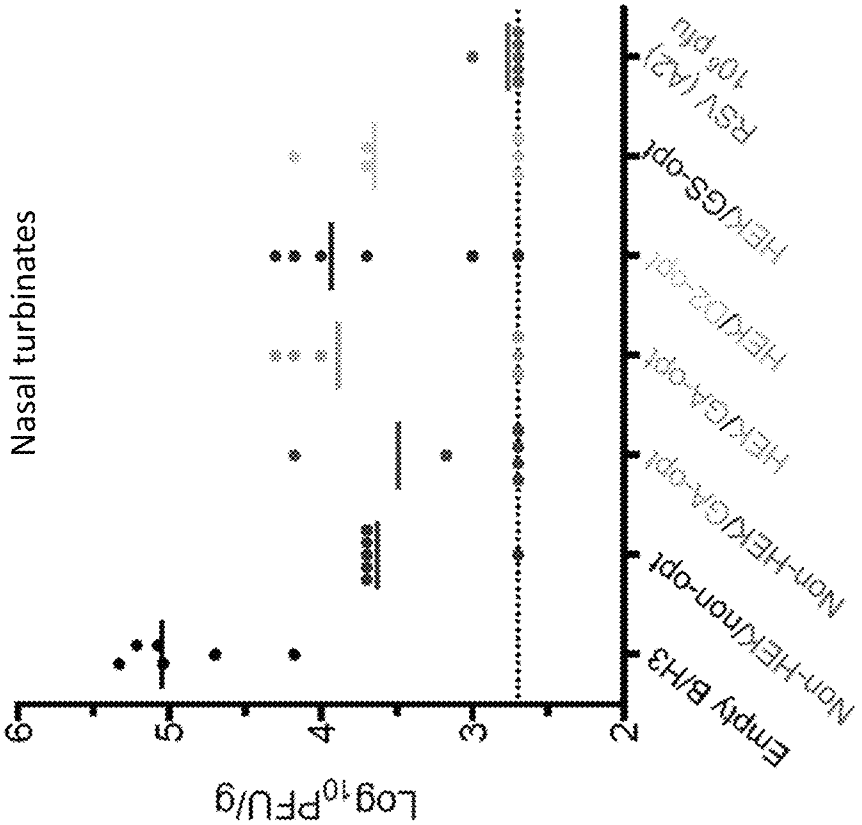

In order to assess the protective efficacy of these vectors, immunized hamsters in groups of 6 animals, from the experiment in FIG. 9, were challenged 30 days post-immunization by intranasal infection with $10^6$ pfu of wt RSV per animal Nasal turbinates and lungs were collected from euthanized animals at 3 days post-challenge, and tissue homogenates were prepared and evaluated by plaque assay to measure the levels of challenge RSV replication. Vectors expressing RSV F conferred almost complete protection in the lungs and intermediate levels of protection in the nasal turbinates, while wt RSV conferred almost complete protection in both anatomical sites (FIG. 10). There was no significant difference among the vectors expressing RSV F in the protective efficacy against RSV challenge. It should be noted that the protection conferred by RSV would include contributions from neutralizing antibodies against both the F and G proteins as well as cellular immunity against potentially all of the RSV proteins, whereas protection conferred by the vectors would include humoral and cellular immunity against solely the F protein. In addition, as noted, the RSV control was a non-attenuated wt virus that replicated to higher titers than the vectors during immunization (FIG. 8), especially in the lungs, which would increase its immunogenicity and protective efficacy.

These results showed that the 10- to 16-fold increase in expression of the RSV F protein expression resulting from the use of the HEK assignments and codon-optimized sequence did not result in a significant increase in the induction of RSV-neutralizing serum antibodies (although a trend towards an increase was observed) or a significant increase in protection against wt RSV challenge. In contrast, a similar level of increase in expression for human immunodeficiency virus antigens had resulted in enhanced protection with other viral vectors and DNA vaccines in different animal models (Gao, et al. 2003. AIDS research and human retroviruses 19:817-823; Carnero, et al. 2009. J Virol 83:584-597). Previously, it had also been observed that a 30- to 69-fold difference in the expression of RSV F due to insertion at positions 1 or 2 versus 6 in the rB/HPIV3 vector induced significant differences in the protective efficacy in hamsters (Liang B, et al. 2014. J Virol 88:4237-4250). Thus, it is generally thought that an increase in antigen synthesis would confer an increase in immunogenicity. However in some cases this effect might not be of sufficient magnitude to be detected unambiguously, or it may be that a given in vivo model might not be sufficiently sensitive. Thus, the 10- to 16-fold difference in the present study might not be sufficient to induce an effect of sufficient magnitude to be statistically significant in the semi-permissive hamster model. The beneficial effect of higher RSV F expression might be more prominent in combination with other features, or in a permissive host, i.e. primates and humans, with a larger sample size in a pre-clinical and clinical evaluation. In particular, the 10- to 16-fold increase in F protein expression observed in this study was in Vero (African green monkey) or LLC-MK2 (rhesus monkey) cells, in which codon-optimization for human use would likely be effective given the relatively close phylogenetic relatedness of these primates to humans. In contrast, the in vivo immunogenicity assay employed hamsters, in which codon optimization for human use might not be effective in increasing expression and, thereby, immunogenicity.

Evaluation of the Immunogenicity of the Pre-Fusion and Post-Fusion Forms of RSV F Expressed by the rB/HPIV3 Vector.

Like all paramyxovirus F proteins, the RSV F protein initially assembles into a pre-fusion conformation that is the version that initially accumulates on the surface of infected cells and is incorporated into virions. Pre-fusion F can be triggered, such as by contact with an adjacent target cell membrane, to undergo massive conformational changes that mediate membrane fusion, with the F protein ending in a post-fusion conformation (Calder, et al. 2000. Virology 271:122-131; McLellan, et al. 2013. Science 340:1113-1117; McLellan, et al. 2011. J Virol 85:7788-7796; Swanson, et al. 2011. Proc. Nat'l Acad. Sci. U.S.A. 108:9619-9624). The RSV F protein is notable among the paramyxoviruses for being highly susceptible to triggering and can readily be triggered prematurely, which may contribute to the marked instability of RSV infectivity. There also is evidence that much of the RSV F protein that accumulates in infected cells is conformationally heterogeneous, which may act as a decoy to reduce the induction of virus-neutralizing antibodies (Sakurai, et al. 1999. J Virol 73:2956-2962). Therefore, it would be advantageous for more than one reason to express RSV F in a stabilized conformation.

Recently, a stable post-fusion form of RSV F was described (McLellan, et al. 2011. J Virol 85:7788-7796; Swanson, et al. 2011. Proc. Nat'l Acad. Sci. U.S.A. 108: 9619-9624). This stable post-fusion form was generated recombinantly by truncation of the hydrophobic fusion peptide and removal of the C-terminal transmembrane domain (TM) and cytoplasmic tail (CT) (Ruiz-Arguello, et al. 2004. J General Virology 85:3677-3687). With the lack of the TM and CT, this post-fusion form would not be membrane-anchored and would be secreted. The post-fusion form of RSV F has been shown to be immunogenic and protective in mice (Swanson, et al. 2011. Proc. Nat'l Acad. Sci. U.S.A. 108:9619-9624).

However, it is thought that the pre-fusion form of RSV F is much more immunogenic than the post-fusion form (McLellan, et al. 2013. Science 340:1113-1117). This is based on the observation that the vast majority of the neutralizing activity in convalescent animal and human sera was conferred by antibodies that do not bind to the post-fusion F protein and presumably are specific to the pre-fusion form (McLellan, et al. 2013. Science 340:1113-1117; Magro, et al. 2012. Proc Nat'l Acad. Sci. U.S.A. 109:3089-3094). Recently, the structure of the pre-fusion form of RSV F was determined, and it became possible to stabilize this pre-fusion conformation through structure-based mutations: one of these involves the introduction of a disulfide bond (DS), and another involves amino acid substitutions in a predicted cavity in the timer structure (Cav1), and the combination of these is called DS-Cav1 (McLellan, et al. 2013. Science 342:592-598). The recombinant DS and DS-Cav1 forms of the RSV F protein were evaluated as subunit vaccines in mice and macaques and were shown to induce significantly higher levels of RSV neutralizing serum antibodies than the post-fusion form, with the DS-Cav1 form being more immunogenic than the DS form (McLellan, et al. 2013. Science 342:592-598).

Figure 11:
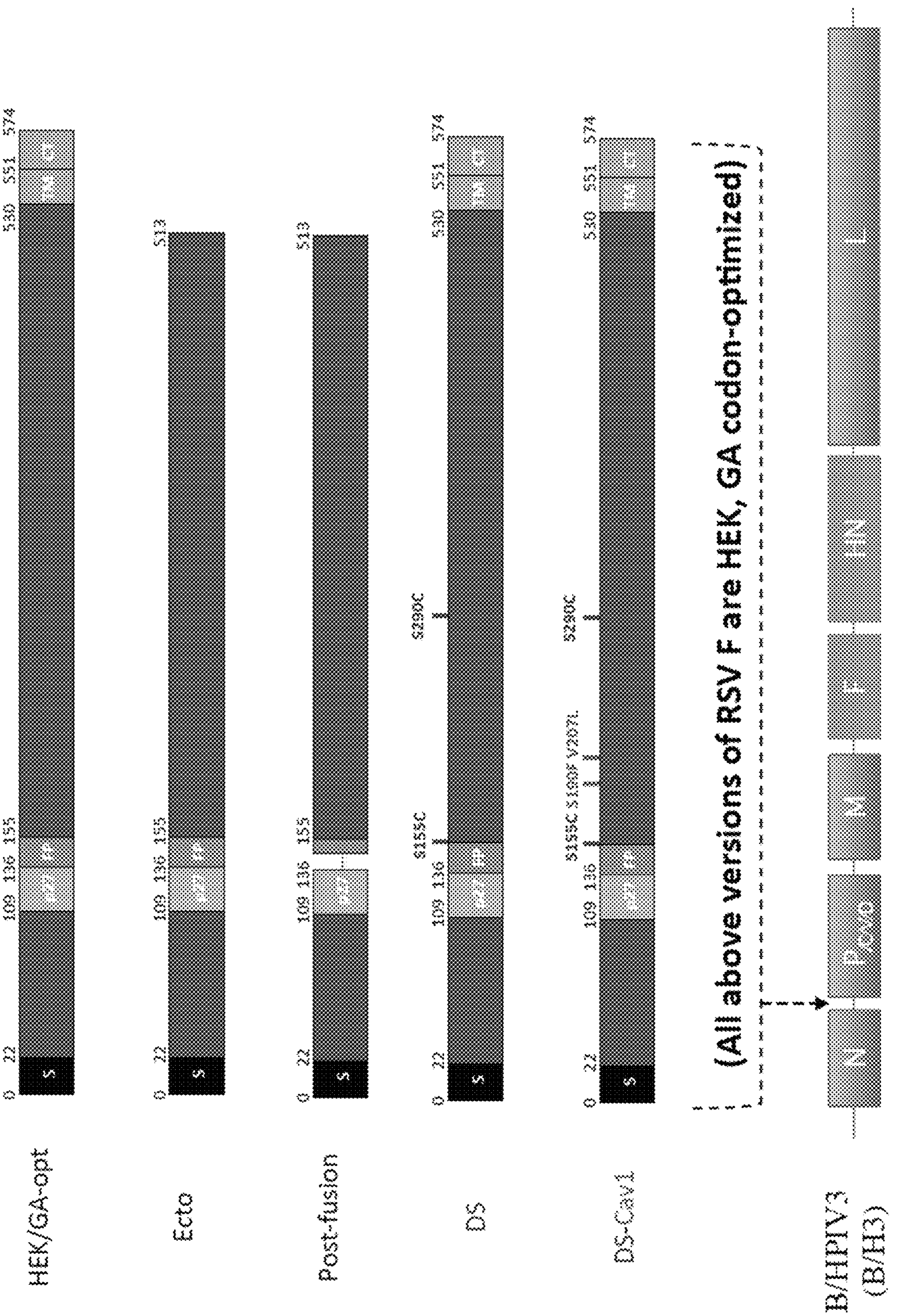
FIG. 11. Construction of rB/HPIV3 vectors expressing secreted (Ecto), post-fusion, and stabilized pre-fusion forms of the RSV F protein. Each of these modified proteins contained the HEK assignments and was expressed from a GA-optimized (for human expression) ORF. Annotations: S, signal sequence; p27, 27k protein fragment liberated by cleavage-activation; FP, fusion peptide; TM, transmembrane; CT, cytoplasmic tail. The HEK/GA-opt construct expresses full-length RSV F. The ectodomain or "ecto" form consisted of amino acids 1-513 of the RSV F protein; it lacks the CT and TM anchor and would be available for secretion. The "post-fusion" form was derived from the ectodomain (1-513aa) by the further deletion of the first 10 aa from the N-terminal end of the fusion peptide (FP; 137-146aa) (McLellan et al, 2011, J Virol 85:7788-96). "DS" and "DS-Cav1" are two versions of full-length RSV F protein stabilized in the pre-fusion form by the S155C/S290C mutations (DS) or by the DS and S190F/V207L (Cav1) mutations (McLellan et al, 2013, Science 342:931). The ORFs encoding these various forms of RSV F were inserted into the rB/HPIV3 vector at the same position and with the same vector signals as described in FIGS. 1 and 4.

The immunogenicity of post-fusion and pre-fusion forms of RSV F when expressed from the live attenuated rB/HPIV3 vector was evaluated. The post-fusion and stabilized pre-fusion forms (DS and DS-Cav1) of RSV F with HEK assignments were GA codon-optimized and inserted into the $2^1$ genome position of the rB/HPIV3 vector (FIG. 11). These were compared with HEK/GA-opt as well as with a version of HEK-containing, GA-optimized F protein from which the CT and TM had been deleted, leaving the ectodomain (Ecto)(FIG. 11). These constructs were also compared to the non-HEK/non-opt construct.

GA-optimized F ORF was used in the data presented in FIG. 11 and subsequent experiments. Parallel constructs with the GS-optimized ORF have been constructed in some instances (see FIG. 35) but remain to be evaluated. Given the superior expression of the GS-optimized ORF (FIG. 5), GS-optimized versions may be more immunogenic and protective. Also, the identifiers "HEK" and "GA-opt" are sometimes omitted from construct names in in FIG. 11 and subsequent Figures and in the subsequent text for the sake of simplicity, but the presence of these features is indicated in the Figures (i.e. "All above versions of RSV F are HEK, GA-optimized", FIG. 11).

Figures 12A, 12B:
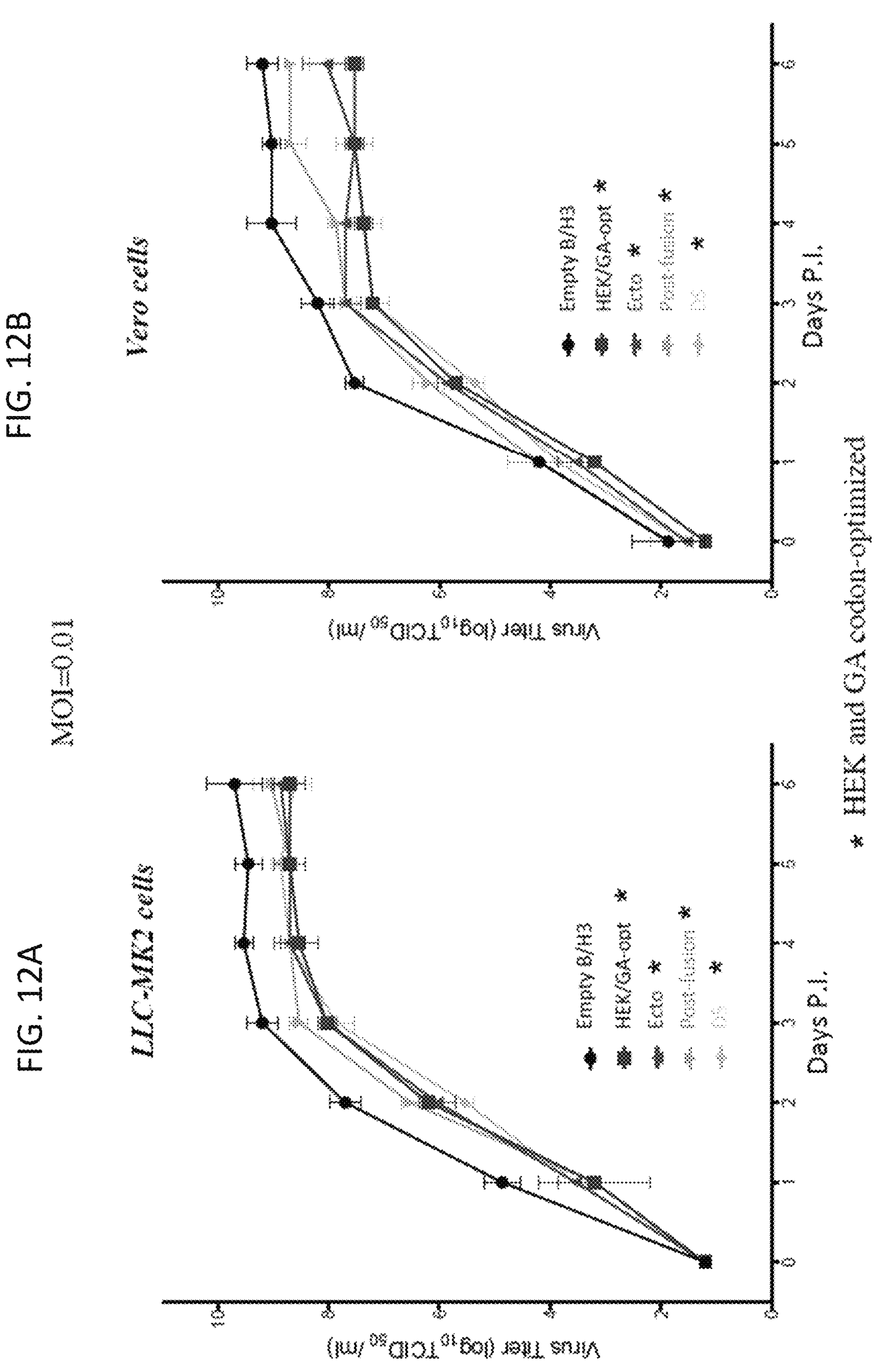
FIGS. 12A and 12B. Multi-cycle in vitro replication of rB/HPIV3 vectors expressing secreted, post-fusion, and stabilized pre-fusion forms of the RSV F protein. (A) LLC-MK2 and (B) Vero cells were infected at an MOI of 0.01 $TCID_{50}$ with empty rB/HPIV3 vector (empty B/H3) or with the indicated constructs: HEK/GA-opt; Ecto; Post-fusion; and DS (see FIG. 11 for descriptions). Viral replication during a period of 6 days at 32° C. was determined by collecting medium supernatant samples at 24-h intervals and performing virus titration by limiting dilution on LLC-MK2 cells. See FIG. 11 for diagrams of the mutant proteins. The asterisk * indicates that all of these RSV F constructs were HEK and GA-optimized.

Vectors with these various forms of RSV F were rescued, and each grew to high, similar titers in vitro (FIG. 12). These were generally slightly attenuated in terms of growth kinetics and final yield compared to the empty rB/HPIV3 vector, as was noted previously for other vector constructs (see FIG. 7).

Figures 13A, 13B:
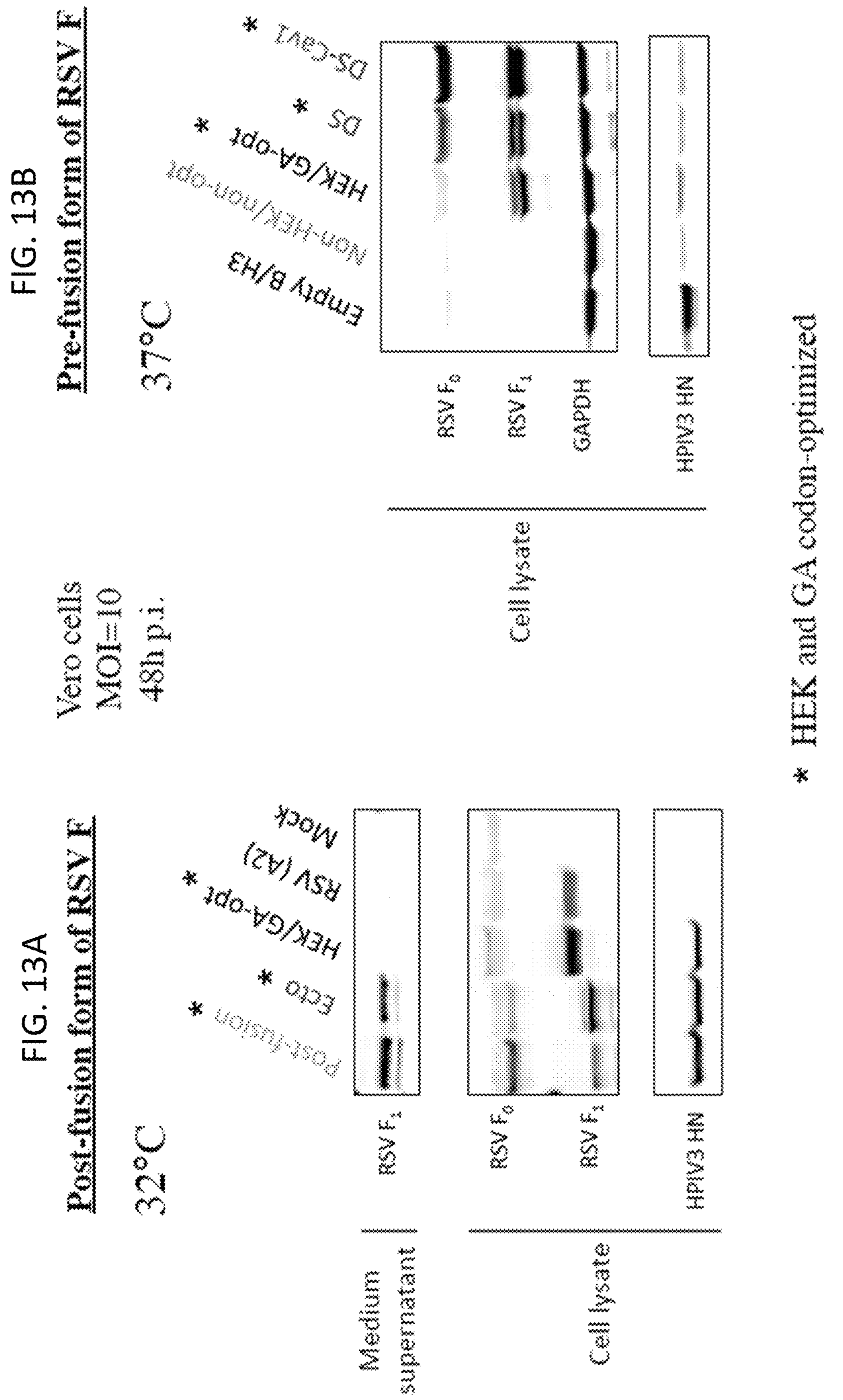
FIGS. 13A and 13B. In vitro expression of secreted (Ecto), post-fusion, and stabilized pre-fusion forms of the RSV F protein from rB/HPIV3 vectors. Vero cells were infected with the indicated rB/HPIV3 vectors at an MOI of 10 $TCID_{50}$ or with wt RSV at an MOI of 10 PFU. Infected cells were incubated at (A) 32° C. or (B) 37° C. for 48 h. (A) Medium supernatants and lysates of cells infected with the rB/HPIV3 vectors expressing post-fusion, Ecto, or HEK/GA-opt, or with wt RSV, and (B) lysates of cells infected with rB/HPIV3 vectors with non-HEK/non-opt, HEK/GA-opt, DS, or DS-Cav1 forms of RSV F were harvested and analyzed for RSV F expression by Western blot. The constructs indicated by asterisk * contained the HEK assignments and were GA-optimized.

The efficiency of expression of the various forms of RSV F protein was evaluated in Vero and LLC-MK2 cells infected with the various constructs (FIGS. 13A and B). Infected cell cultures were harvested 48 h post-infection and analyzed by Western blotting. The native form of RSV F (i.e., HEK/GA-opt) was cell-associated, as expected. The post-fusion and Ecto forms were found to be secreted as well as to be cell-associated. The secretion of post-fusion F was consistently more efficient than that of the Ecto form: the latter might remain more cell-associated because it contained a higher content of hydrophobic sequence. Unexpectedly, the DS and DS-Cav1 forms of F were expressed more efficiently (FIG. 13B). Since these viruses replicated at similar kinetics and since the ORFs were similarly GA-optimzed, this increase in expression likely reflected increased protein stability of the DS and DS-Cav1 forms. Protein engineering can substantially affect the expression, processing, and stability of a glycoprotein, and often in a negative way, and so the efficient expression of DS and DS-Cav1 by this live vector was an essential property that could not have been reliably predicted.

Figure 14B:
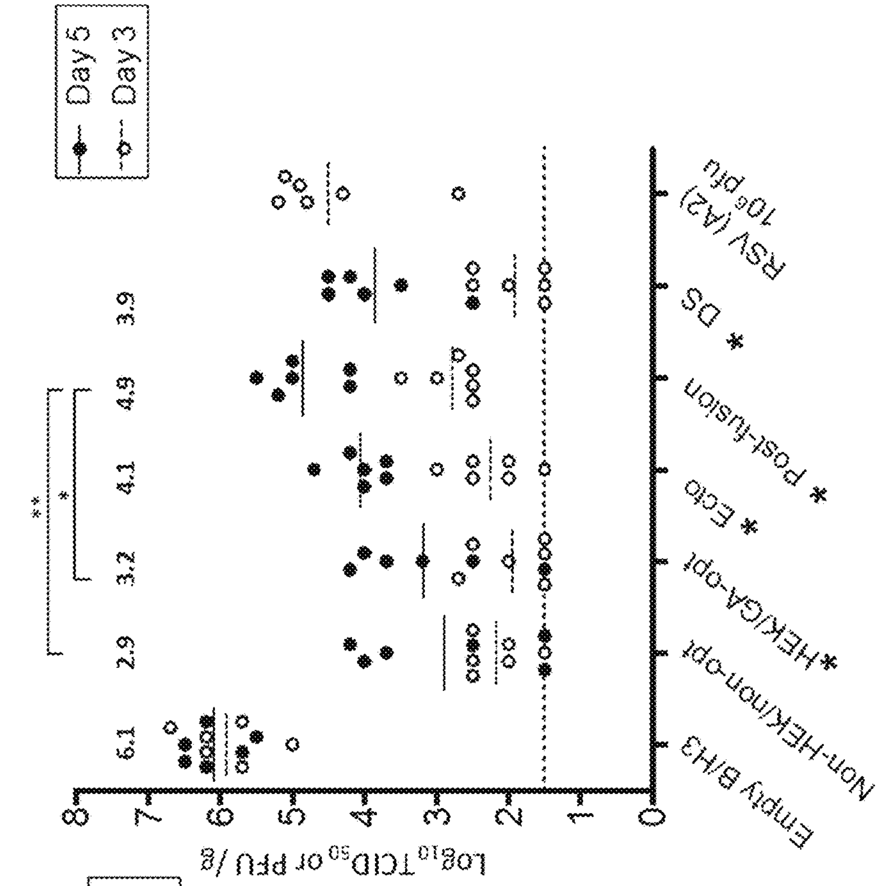
FIGS. 14A and 14B. Replication in hamsters of rB/HPIV3 vectors expressing secreted (Ecto), post-fusion, and stabilized pre-fusion forms of the RSV F protein. Hamsters were infected IN with $10^5$ $TCID_{50}$ of the indicated rB/HPIV3 vectors or $10^6$ PFU of wt RSV in a 0.1 ml inoculum Hamsters were euthanized (n=6 per virus per day) on days 3 and 5 post-infection and the (A) nasal turbinates and (B) lungs were removed and homogenized and viral titers were determined by limiting dilution on LLC-MK2 cells (rB/HPIV3 vectors) or Vero (RSV) cells at 32° C.: open and closed circles indicate titers for animals sacrificed on day 3 and 5, respectively. Each symbol represents an individual animal, and the mean titer of each group is indicated by a dashed or solid horizontal line for day 3 and 5, respectively. Mean values of day 5 titers are shown at the top. The rB/HPIV3 vectors were titrated by limiting dilution assays on LLC-MK2 cells and reported as $TCID_{50}$/g; RSV was titrated by plaque assays on Vero cells and reported as PFU/g. The limit of detection (LOD) is 1.5 login $TCID_{50}$/g of tissue, indicated with a dotted line. The statistical significance of difference among peak titers was determined by Tukey-Kramer test and indicated by asterisks; *, $P \leq 0.05$; , $P \leq 0.01$; or *, $P \leq 0.001$. The constructs indicated by asterisk * contained the HEK assignments and were GA-optimized for human expression.
Figure 14A:
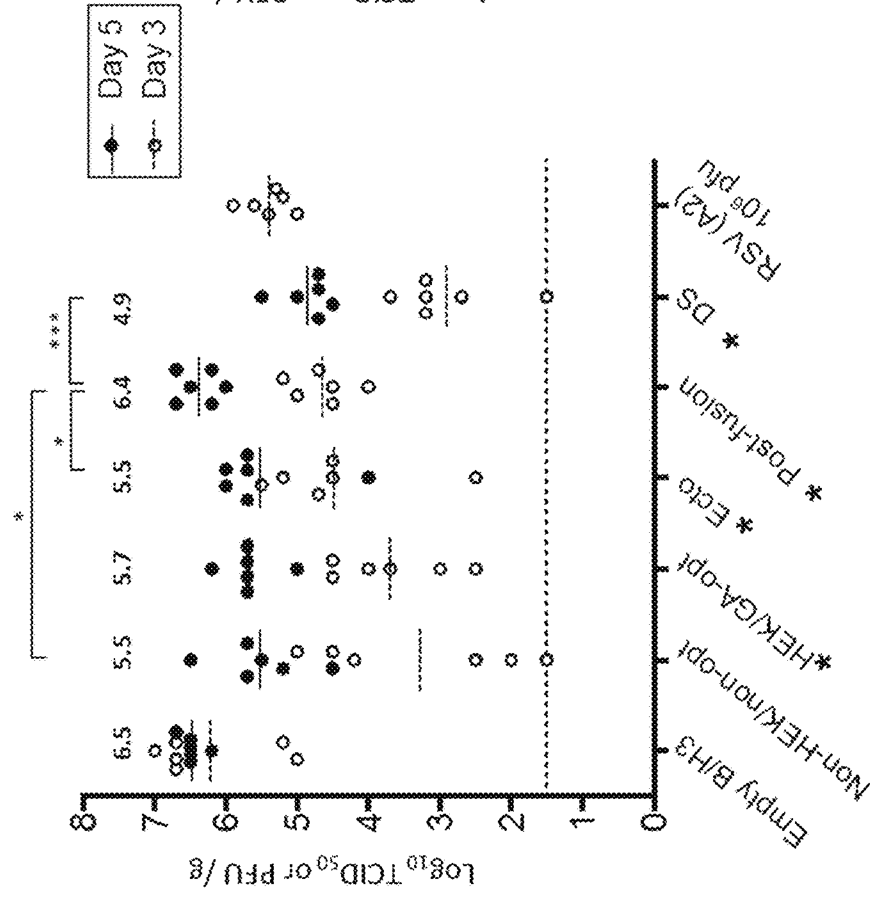

Replication of these vectors in vivo was evaluated in hamsters (FIG. 14). In the nasal turbinates, all vectors with RSV F inserts were moderately more attenuated than the empty vector (FIG. 14A). Increased attenuation compared to the empty vector was evident by the lower values for virus shedding. It also was evident by comparison of the day 3 and day 5 titers: for the empty vector, these values were comparable, whereas for the vectors bearing RSV F, the day 5 titers were higher than the day 3 titers, indicating that these constructs took longer to achieve their maximum titers. The vector with post-fusion F replicated to a higher titer than those with other forms of F whereas the vector with pre-fusion F (DS) replicated to a lower titer, which might represent experimental variability or might represent authentic disparate effects on vector replication. In the lungs, all vectors with RSV F insert were substantially more attenuated than the empty vector (FIG. 14B). Consistent with the nasal turbinates, the vector with post-fusion F also replicated to somewhat higher titer than other vectors in the lungs whereas the vector expressing the pre-fusion (DS) version appeared to be somewhat more attenuated. The RSV control, which is a fully wt virus, replicated more efficiently than the attenuated rB/HPIV3 vectors expressing RSV F; for example, wt RSV replicated to 100- and 1000-fold higher titers in the nasal turbinates and lungs, respectively, than the vector expressing pre-fusion (DS) F. RSV-neutralizing serum antibody titers were determined by a 60% plaque reduction assay. This was performed in two ways: (i) in the presence of added complement (which is the usual practice, as already shown in FIG. 9), and (ii) in the absence of added complement (FIGS. 15 A and B, respectively). The presence of added complement provides for the most sensitive detection of virus-specific antibodies, since complement potentially confers viral-lysis capability to all antibodies that bound to the virion, and also can exert steric effects (Yoder et al 2004 J Med Virol 72:688-694). In contrast, the complement-independent neutralization assay would detect only high quality neutralizing antibodies that are able to neutralize RSV without involving the viral-lysis function or steric effects of the complement proteins. It has been suggested that "neutralization assays performed without complement may be most reflective of physiologic conditions in the respiratory tract" (Yoder et al 2004 J Med Virol 72:688-694). In the complement-containing assay (FIG. 15A), vector with post-fusion F was poorly immunogenic among the vectors even though it replicated to the highest titers in hamsters; while the vector with pre-fusion (DS) F was the most immunogenic among the tested vectors even though it was the most attenuated. In the complement-independent assay (FIG. 15B), among the vectors, only the one expressing pre-fusion (DS) F induced high titers of neutralizing antibodies. None of the other vectors with unmodified, post-fusion, or Ecto F were effective at inducing high quality neutralizing antibodies. The wt RSV control was efficient at inducing antibodies that were neutralizing in both the complement-containing and complement-independent assays. Remarkably, the vector with pre-fusion (DS) F was statistically similar to wt RSV in inducing high-quality RSV neutralizing antibodies (FIG. 15B). This is noteworthy because this attenuated vector replicated 100 to 1000 times less efficiently than non-attenuated wt RSV and the neutralizing activity conferred by wt RSV had the additional contribution from the RSV G protein. This suggested that the vector expressing pre-fusion (DS) form of RSV F was very potent and highly immunogenic in inducing very effective neutralizing antibodies.

Figure 16A:
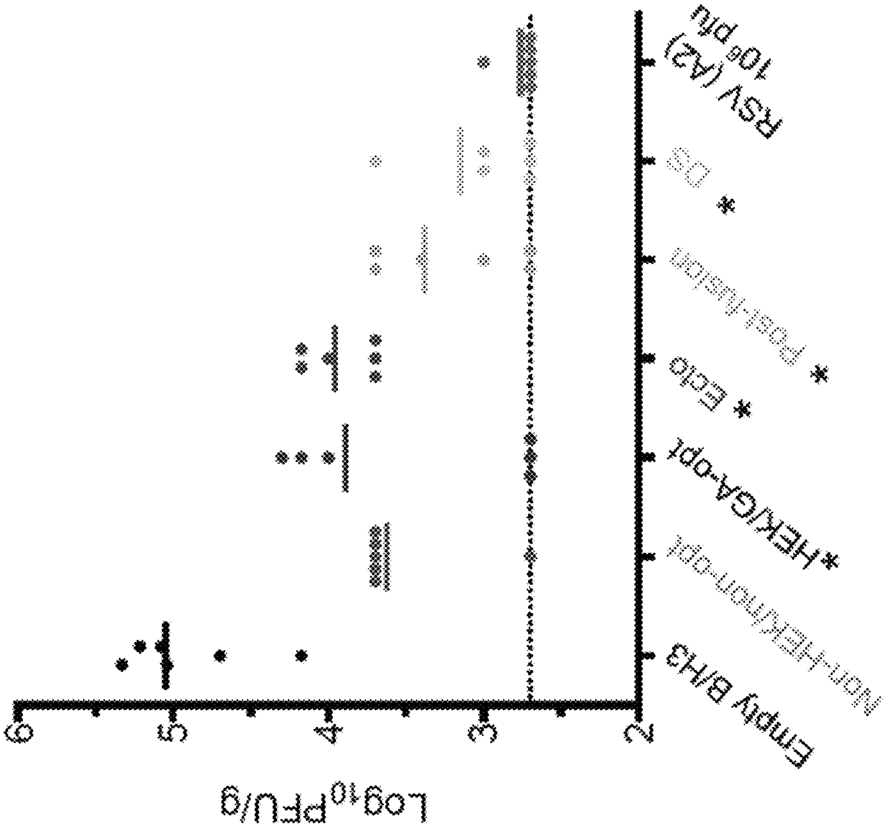
FIGS. 16A and 16B. Protection of immunized hamsters against RSV challenge. The hamsters (n=6 animals per virus) that had been immunized as shown in FIG. 15 were challenged IN on day 31 post-immunization with $10^6$ PFU of wt RSV in a 0.1 ml inoculum. On day 3 post-challenge, hamsters were euthanized and (A) nasal turbinates and (B) lungs were collected. RSV titers in tissue homogenates were determined by plaque assay in Vero cells at 32° C. Each symbol represents an individual animal and mean viral titers of the groups are shown as horizontal lines. The detection limit of the assay was $\log_{10}$ 2.7 PFU/g of tissue, indicated as a dotted line.
Figure 16B:
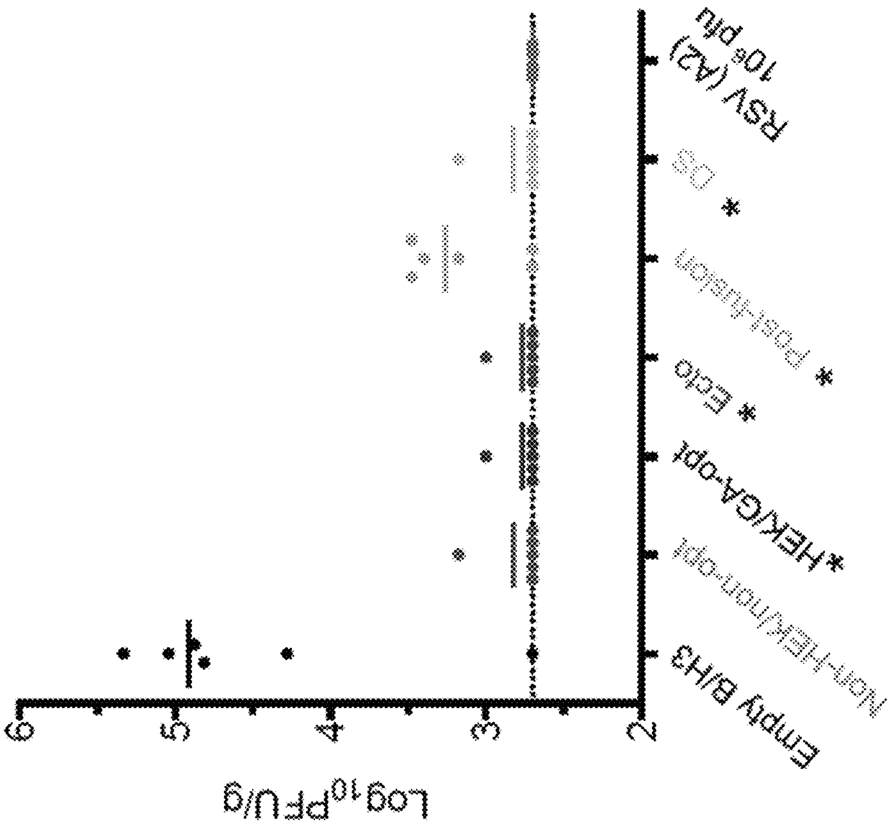

In order to assess the protective efficacy of these vectors, immunized hamsters from the experiment in FIG. 15 were challenged 30 days post-immunization by intranasal infection with $10^6$ pfu of wt RSV per animal. The animals were sacrificed 3 days post infection and nasal turbinates and lungs were harvested and processed into tissue homogenates that were assayed by plaque titration (FIG. 16). In the nasal turbinates (FIG. 16A), constructs expressing non-HEK/non-opt F, or HEK/GA-opt, or Ecto F, conferred a moderate level of protection, whereas post-fusion F and especially pre-fusion (DS) F were somewhat more protective. In the lungs (FIG. 16B), all of the vector constructs provided substantial protection against RSV challenge, except the post-fusion form, which conferred the least protection (FIG. 16B). The wt RSV control provided nearly-complete protection in the nasal turbinates and complete protection in the lungs; however, as already noted, wt RSV had the advantage of expressing both the F and G neutralization antigens, in addition to expressing all of the RSV proteins as potential antigens for cellular immunity, as well as replicating up to 1000-fold more efficiently (FIG. 14).

Figure 6:
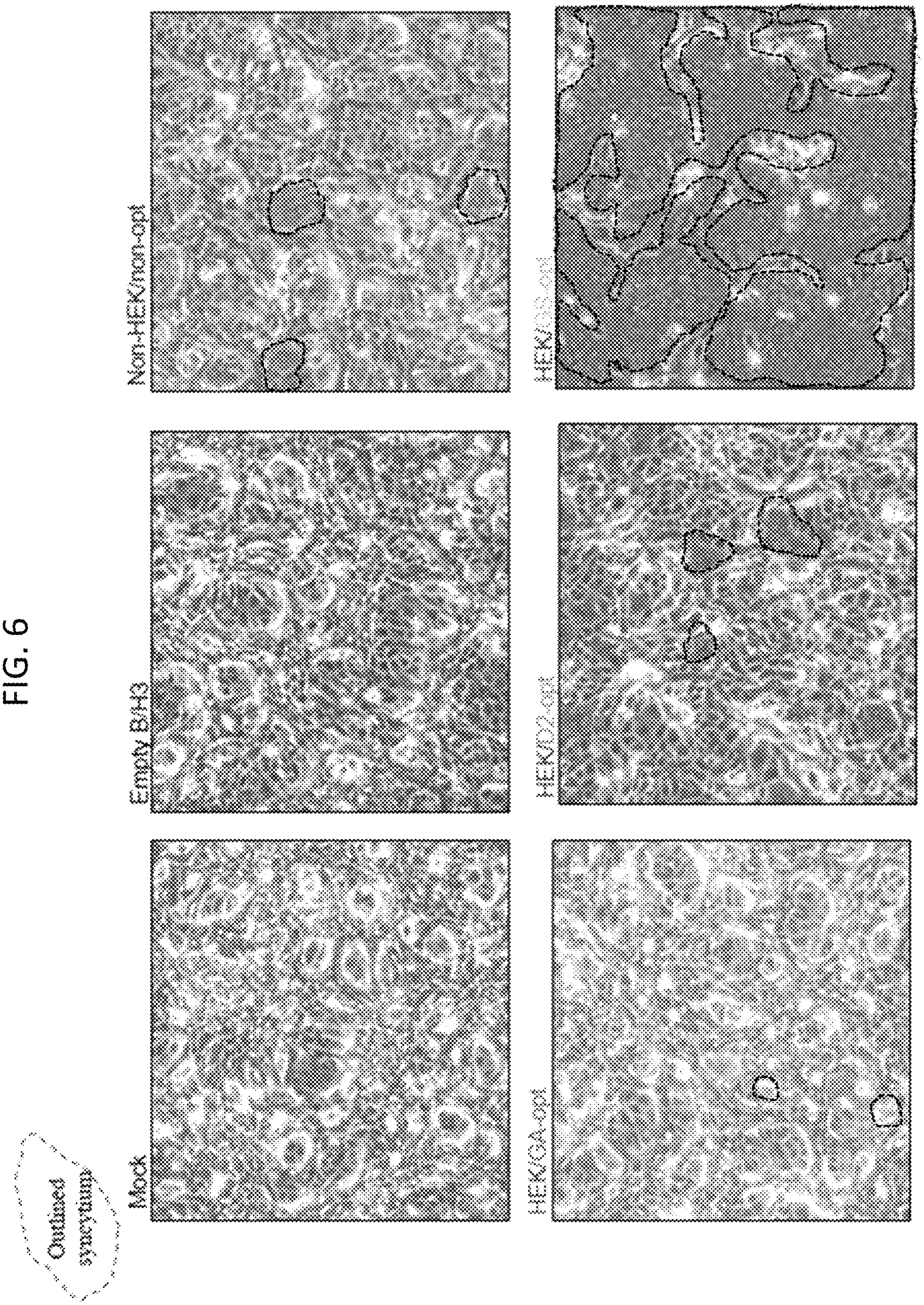
FIG. 6. Effects of HEK and codon-optimization of the F ORF on the formation of syncytia in vector-infected Vero cell monolayers. Cells were mock-infected (mock) or infected with empty rB/HPIV3 vector (empty B/H3) or with rB/HPIV3 vector expressing the RSV F ORF that was non-HEK and non-optimized (Non-HEK/non-opt) or was HEK and GA-optimized (HEK/GA-opt) or HEK and DNA2.0-optimized (HEK/D2-opt) or HEK and GS-optimized (HEK/GS-opt). Infections were performed at an MOI of 10 $TCID_{50}$ at 32° C. and images were acquired at 48 hours post-infection. Representative syncytia are indicated with dashed outline in some of the panels.

The addition of the Cav-1 mutations to the DS construct provided increased immunogenicity as a subunit vaccine (McLellan, et al. 2013. Science 342:592-598) and is anticipated to further enhance the immunogenicity of the pre-fusion RSV F expressed from a viral vector. Also, the DS and DS-Cav1 forms of RSV F remain to be evaluated for immunogenicity and protective efficacy in the context of the GS-optimization, which provided the greatest increase in expression (FIGS. 5 and 6). These further constructs have been constructed and recovered and prepared as working pools (FIG. 35).

Enhancing the Immunogenicity of RSV F Protein by Facilitating its Incorporation into the Virion Particle of the rB/HPIV3 Vector.

The incorporation of antigens into virus like particles (VLP) or adeno-associated virus particles has been shown to increase their immunogenicity (Rybniker, et al. 2012. J Virol 86:13800-13804; McGinnes, et al. 2011. J Virol 85:366-377). But whether the incorporation of a heterologous antigen into the viral envelope of an infectious virus could enhance its immunogenicity was unclear. When expressed by rB/HPIV3, the native RSV F protein (i.e., HEK/GA-opt) is incorporated into the vector particle only in trace amounts (see below).

A previous study by Zimmer et al (Zimmer et al J Virol 2005 79:10467-77) evaluated the expression of RSV F protein from an added gene in Sendai virus, which is a murine relative of HPIV1 and also is closely related to HPIV3. That study showed that, as with rB/HPIV3, very little RSV F protein was incorporated into the Sendai virus vector particle. The investigators replaced the CT or CT plus TM of the RSV F protein with the corresponding sequences from the Sendai F protein on the premise that this would improve the efficiency of interaction of the foreign RSV F protein with the vector particle. These modifications indeed increased incorporation of the engineered RSV F into the Sendai particle, but only if the Sendai F protein gene was deleted. That requirement to delete the vector F protein would be undesirable in the present study because deleting the vector F protein from rB/HPIV3 would have the potential of substantially altering its replicative properties, especially in vivo, and also would remove one of the HPIV3 protective antigens.

Figure 17A:
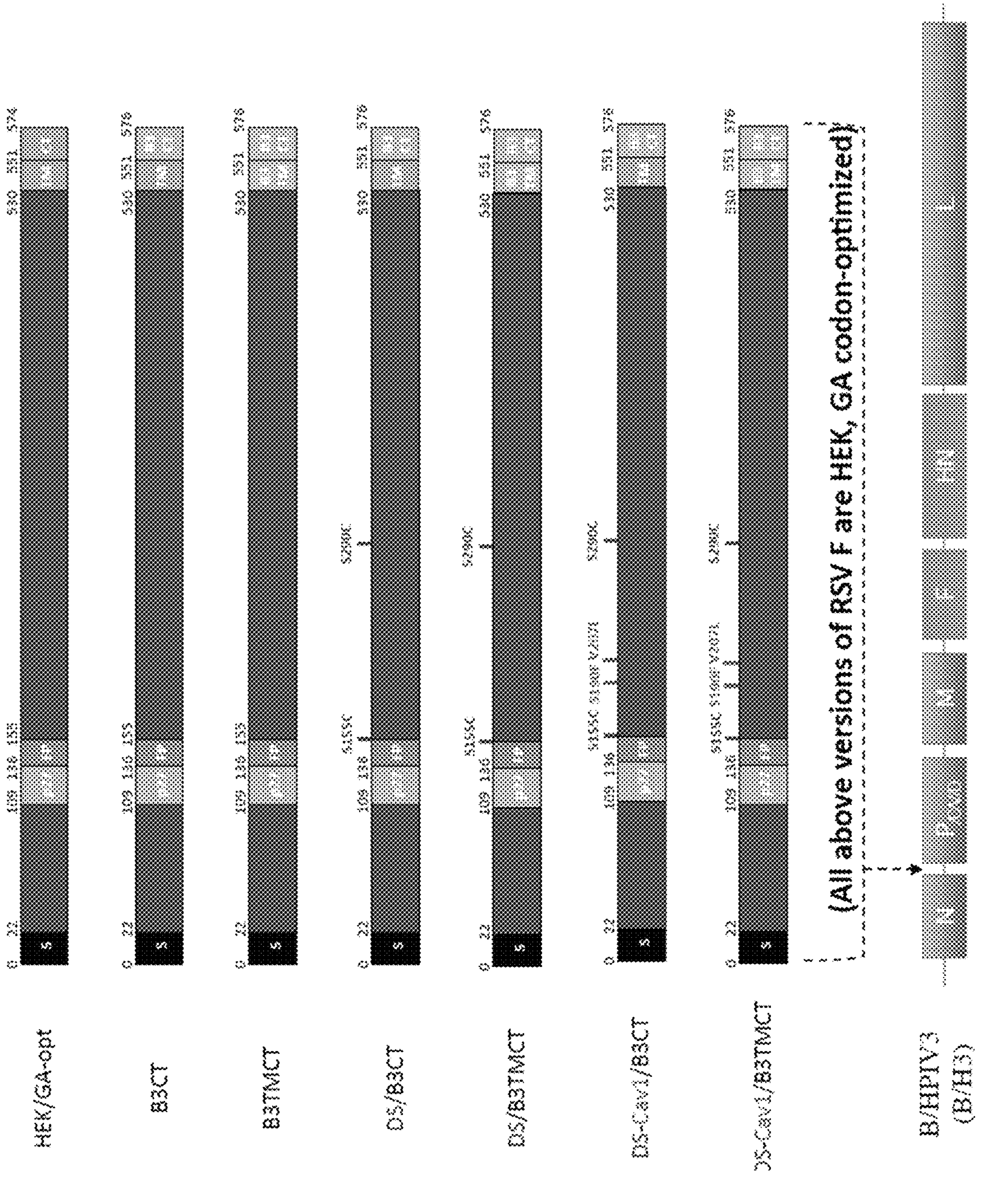

Despite this clear precedent indicating that this strategy would be not be suitable, rB/HPIV3 constructs were made in which the RSV F protein had CT or CT plus TM replaced with that of the vector(PIV) F protein (resulting in constructs called B3CT and B3TMCT, respectively, FIG. 17). The TM and CT regions from rB/HPIV3 were 21 and 26 amino acids in length respectively. The constructions in the present study were done with the version of the F protein that contained the HEK assignment and GA optimization in native F protein (HEK/GA-opt), and also with the pre-fusion DS and DS-Cav1 forms (FIG. 17). (The GA-optimized F ORF was used). All chimeric F genes were inserted into the 2' position of rB/HPIV3 for direct comparison with the constructs described above.

All of the viruses were readily recovered by reverse genetics. To quantify the packaging efficiency of RSV F and its modified derivatives, sucrose-purified viruses were prepared for Western blot analysis to determine the amount of RSV F in the particle (FIG. 18). Equal amounts of each sucrose-purified stock (0.5 ug protein per sample) were subjected to denaturing, reducing gel electrophoresis and analyzed by Western blotting. This showed that non-chimeric F protein (from HEK/GA-opt) had relatively poor incorporation into the rB/HPIV3 virions (FIG. 18, lane 2). However, the B3CT and B3TMCT modifications dramatically enhanced the incorporation efficiency by 19- to 20-fold (FIG. 18, lanes 3 and 4). Indeed, when compared to an equal protein mass of wt RSV virions (FIG. 18, lane 5), the amount of incorporated B3CT and B3TMCT F protein in the vector particles appeared to be equal to the amount of native F in the RSV particles. Similarly enhanced efficiency of packaging also was observed for the chimeric pre-fusion (DS) form of RSV F with B3CT or B3TMCT (FIG. 18, lanes 6 and 7). Thus, efficient packaging of RSV F B3CT and B3TMCT into the rB/HPIV3 vector did not require deletion of the vector F protein, and thus differed dramatically from the Sendai precedent.

Packaging of RSV F also was examined with transmission electron microscopy (TEM) using RSV-specific antibody and immune-gold labeling (FIG. 19 A-F). RSV F spikes on the surface of RSV particles were labeled (FIG. 19A), while no labeling could be observed on the surface of the empty rB/HPIV3 vector (FIG. 19B). Very limited labeling of native RSV F was detected in the vector envelope (FIG. 19C), consistent with the results in FIG. 18 showing that very little native F was detected in purified rB/HPIV3 virions by Western blot analysis. In contrast, vectors expressing chimeric F with B3CT or B3TMCT showed enhanced labeling (FIGS. 19D and E), indicating efficient packaging of these chimeric forms into the vector envelope. Likewise, the pre-fusion (DS) RSV F with B3TMCT also was efficiently packaged into the vector particles (FIG. 19F). This confirmed that the B3CT and B3TMCT modifications resulted in dramatically increased incorporation of RSV F into the rB/HPIV3 particles. In addition, this showed that the incorporated RSV F protein was present in immunologically active surface spikes similar in appearance to those of authentic RSV particles. Furthermore, stabilized pre-fusion DS F protein also efficiently appeared at the virion surface.

The high efficiency of packaging of RSV F B3CT and B3TMCT into the vector particles raised the possibility that this would be attenuating to vector replication, since it is generally assumed that a virion surface is organized for efficiency and is limited in its capacity for surface proteins, so that changes in the composition of surface proteins could be attenuating, especially since the modified B3CT and B3TMCT RSV F proteins contained the CT or the TMCT regions of vector F protein that are thought to interact with internal viral proteins. For example, efficient incorporation of RSV F into the vector envelope might displace vector HN and F glycoproteins, or might interfere with interactions between vector components (such as between the vector F and HN glycoproteins and the internal M protein during virion assembly, or between the vector F and HN proteins that must interact to efficiently initiate virus entry). Surprisingly, it was found that all of the vectors bearing RSV F B3CT and B3TMCT replicated efficiently in vitro to high titers that were indistinguishable from those of vector with RSV F protein that was unmodified with respect to TM and CT (HEK/GA-opt, FIG. 20). Thus, there was no evidence of any reduction in replication in vitro due to the increased incorporation of RSV F into the vector particle. This is important because efficient vector replication in vitro would be essential for efficient vaccine manufacturing and clinical evaluation. It also suggests that the high efficiency of incorporation will not place a strong selective pressure for mutations that silence expression of RSV F.

Figures 21A, 21B:
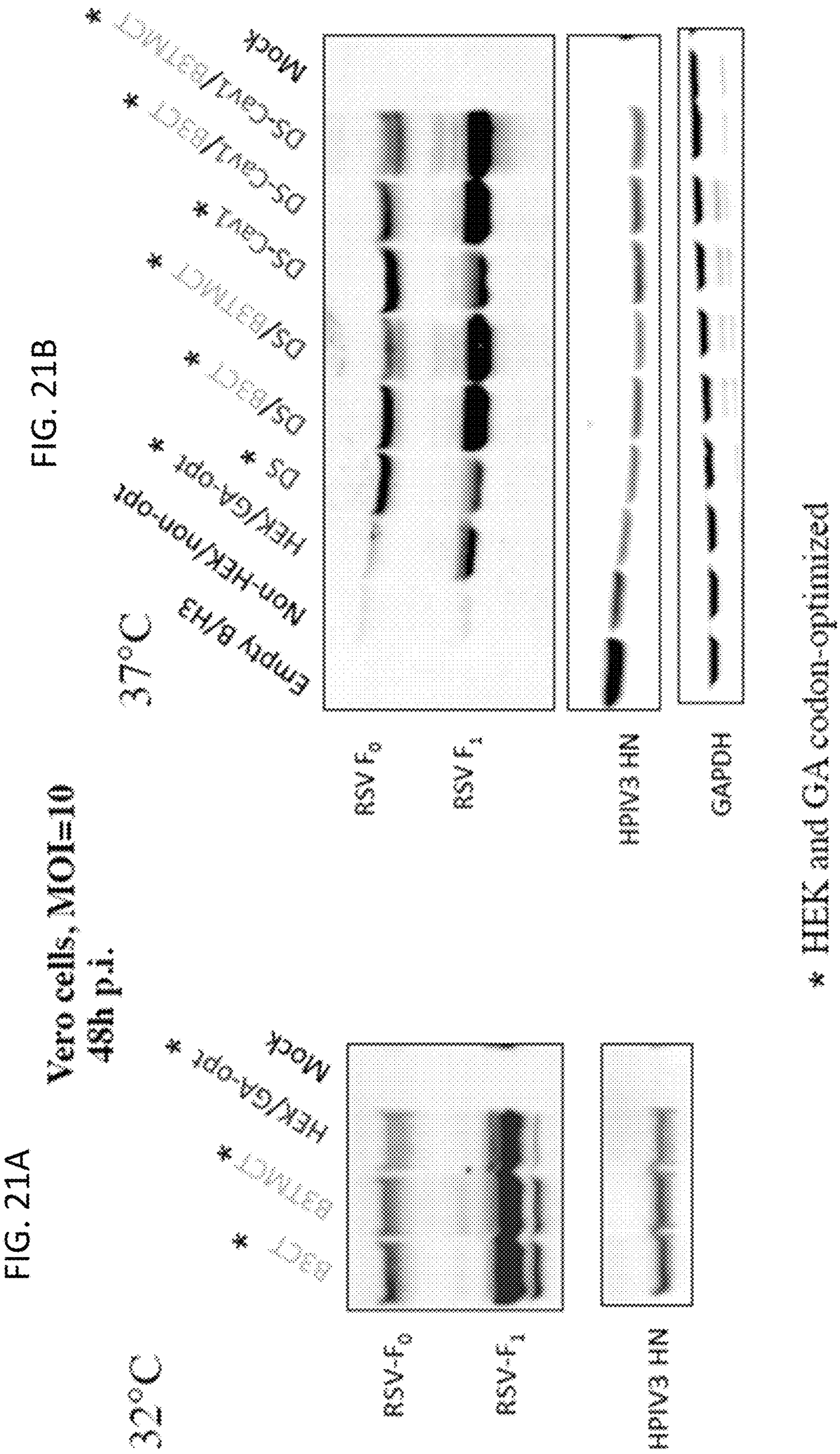
FIGS. 21A and 21B. In vitro expression of B3CT and B3TMCT versions of the RSV F protein with or without the DS or DS-Cav1 mutations that stabilize the pre-fusion form of RSV F protein. Expression of (A) B3CT and B3TMCT; and (B) DS and DS-Cav1 in combination with B3CT and B3TMCT. Vero cells were infected with the indicated rB/HPIV3 vectors at an MOI of 10 $TCID_{50}$, or with RSV at an MOI of 10 PFU. Infected cells were incubated at (A) 32° C. or (B) 37° C. for 48 h. Cell lysates were analyzed for RSV F expression by Western blot. HPIV3 HN protein was used as a control to show equivalence of vector replication; GAPDH was used as loading control. The constructs indicated by asterisk * contained the HEK assignments and were GA-codon-optimized for human expression.

The intracellular expression of the chimeric forms of RSV F by the rB/HPIV3 vectors was examined by Western blotting. This was evaluated in Vero cells that were harvested 48 h post-infection (FIG. 21). Interestingly, the B3CT and B3TMCT versions of F were both expressed efficiently, and indeed appeared to be expressed slightly more efficiently than the native F (i.e., HEK/GA-opt) (FIG. 21A). In addition, the DS or DS-Cav1 modifications appeared to further increase expression (FIG. 21B), as noted previously (FIG. 13B). These effects appeared to be additive, since the DS or DS-Cav1 constructs with B3CT or B3TMCT were expressed even more efficiently than those with DS or DS-Cav1 alone. This increased expression would be advantageous for vaccine purposes since it provides a higher level of antigen. As noted, protein engineering and domain swapping have the potential to negatively affect the expression, processing, and stability of a glycoprotein, and so the efficient expression of these glycoproteins with DS, DS-Cav1, B3CT, and B3TMCT modifications by this live vector was a property that could not have been reliably predicted.

Figure 3A:
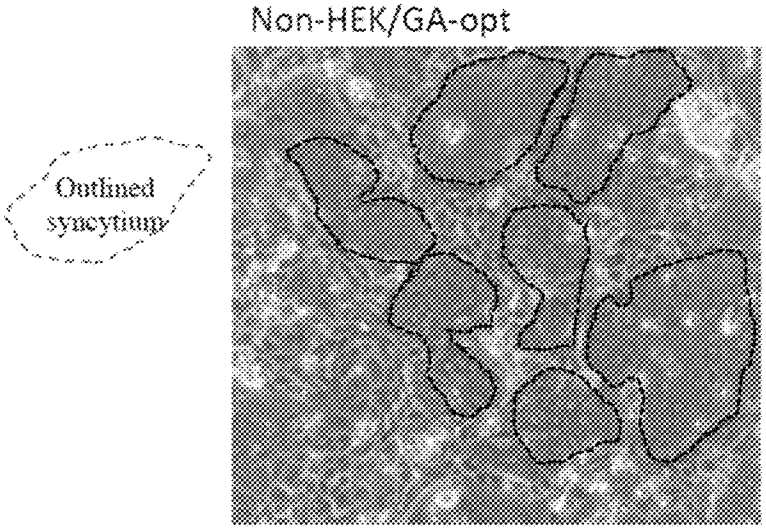
FIGS. 3A and 3B. Formation of syncytia in Vero cell monolayers infected with rB/HPIV3 vectors expressing non-HEK or HEK RSV F protein. Cells were infected with rB/HPIV3 expressing GA-codon-optimized RSV F (see FIG. 1) with (A) non-HEK or (B) HEK assignments at an MOI of 10 $TCID_{50}$ at 32° C. Images of the infected cells were acquired at 48 hours post-infection. Representative syncytia are marked with dashed outline.
Figure 3B:
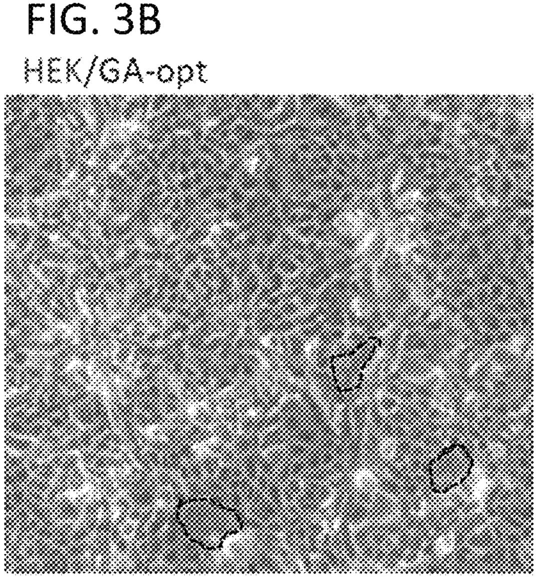
Figure 22:
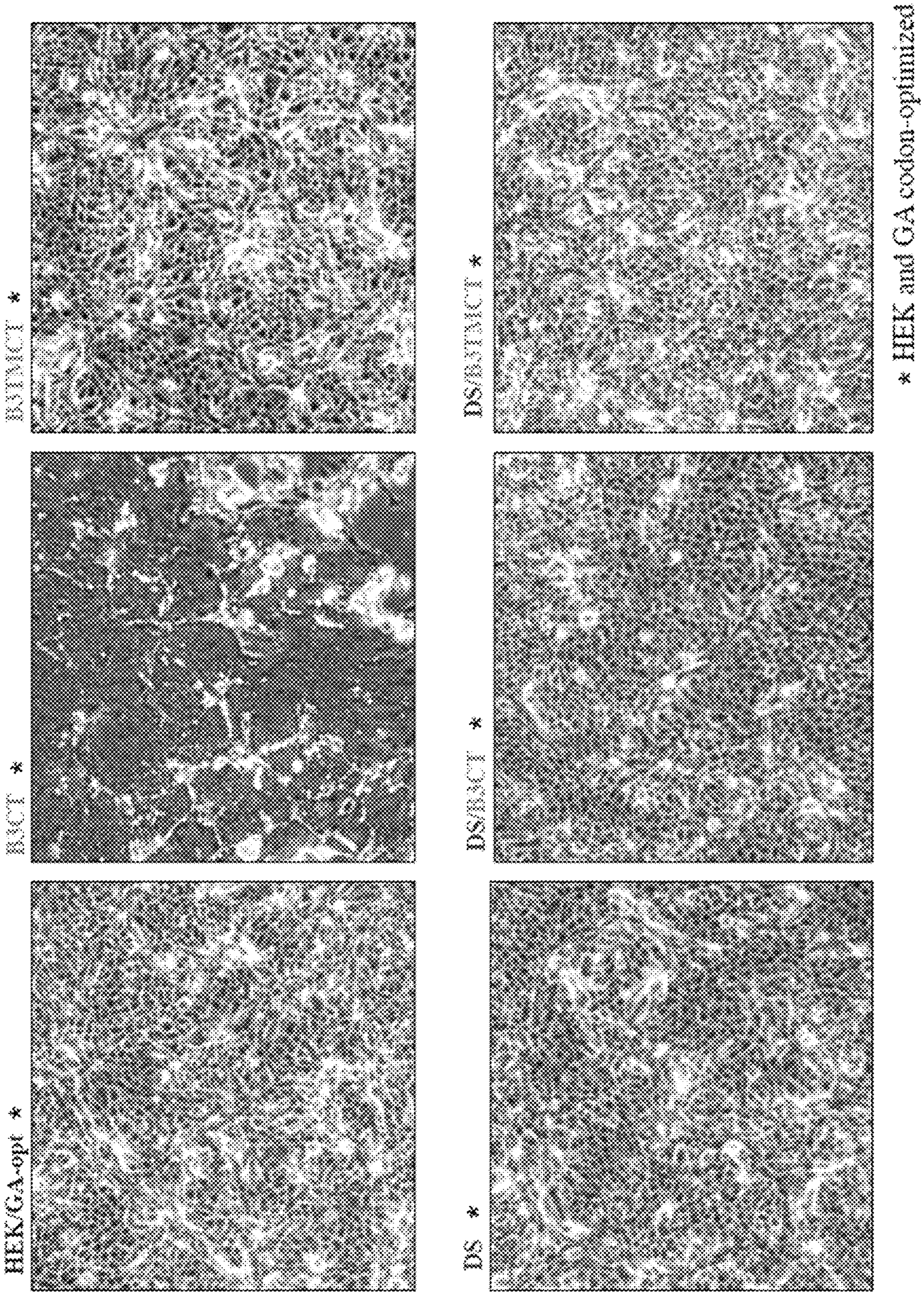
FIG. 22. Formation of syncytia in Vero cell monolayers infected with rB/HPIV3 vectors expressing the B3CT or B3TMCT version of the RSV F protein with or without the DS mutations that stabilize the pre-fusion form of RSV F protein. Vero cells were infected at an MOI of 10 $TCID_{50}$ with rB/HPIV3 vectors expressing the indicated versions of RSV F protein and incubated at 32° C. Images were acquired at 48 h post-infection. The constructs indicated by asterisk * contained the HEK assignments and were GA-codon-optimized for human expression.

The ability of these constructs to induce syncytium formation in Vero cells was assayed. Unexpectedly, RSV F bearing the B3CT substitution exhibited a hyper-fusogenic phenotype, while that bearing the B3TMCT substitution resembled native F (e.g., HEK/GA-opt) in being hypo-fusogenic (FIG. 22; also see FIG. 3). Upon extended incubation, B3TMCT did induce syncytium formation in the cell monolayer, indicating it was still functional and thus was conformationally intact. These findings suggested that, between the B3CT and B3TMCT constructs, the latter would be preferred since extensive syncytium formation and resulting cytopathology might reduce vector production in vitro and in vivo by prematurely destroying the cell substrate, and also might interfere with the stability of infectivity due to premature triggering. None of the pre-fusion DS forms induced syncytia in the cell monolayers. This was not completely unexpected, since a stabilized version of the pre-fusion F protein should be less able to undergo the massive conformation changes needed to mediate fusion. These findings suggest that the pre-fusion DS form of RSV F indeed was substantially stabilized in the context of vector-infected cells.

Figure 20A:
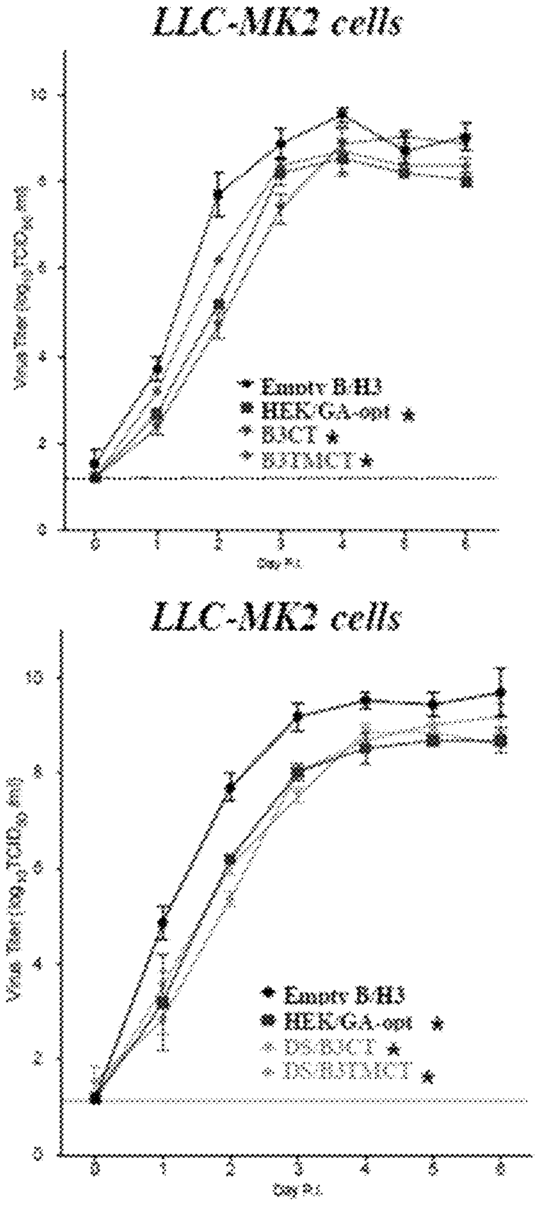
FIGS. 20A and 20B. Multi-cycle in vitro replication of rB/HPIV3 vectors expressing B3CT and B3TMCT versions of the RSV F protein. (A) LLC-MK2 and (B) Vero cells were infected at 32° C. with an MOI of 0.01 $TCID_{50}$ with empty rB/HPIV3 vector (empty B/H3) or vector expressing HEK/GA-opt, or B3CT (upper panels), or B3TMCT (upper panels), or DS/B3CT (lower panels) or DS/B3TMCT (lower panels). Aliquots of medium supernatant were collected at 24 h intervals for 6 days and viral titers were determined by limiting dilution assay on LLC-MK2 cells at 32° C. and reported as $TCID_{50}$/ml. The constructs indicated by asterisk * contained the HEK assignments and were GA-codon-optimized for human expression. Multiplicity of infection in the assays was 0.01.
Figure 20B:
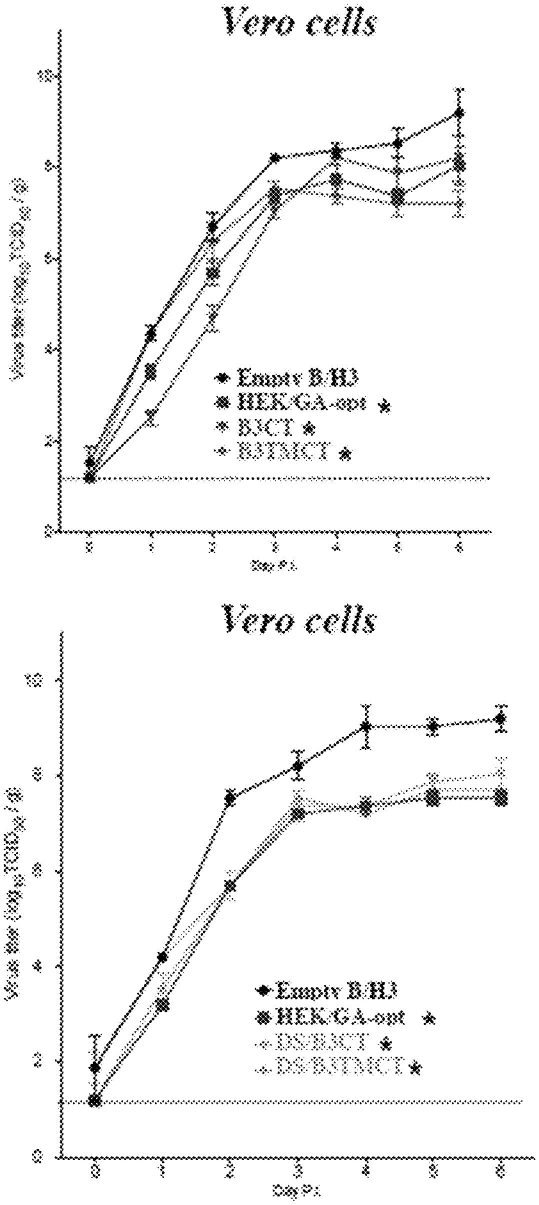
Figures 23A, 23B:
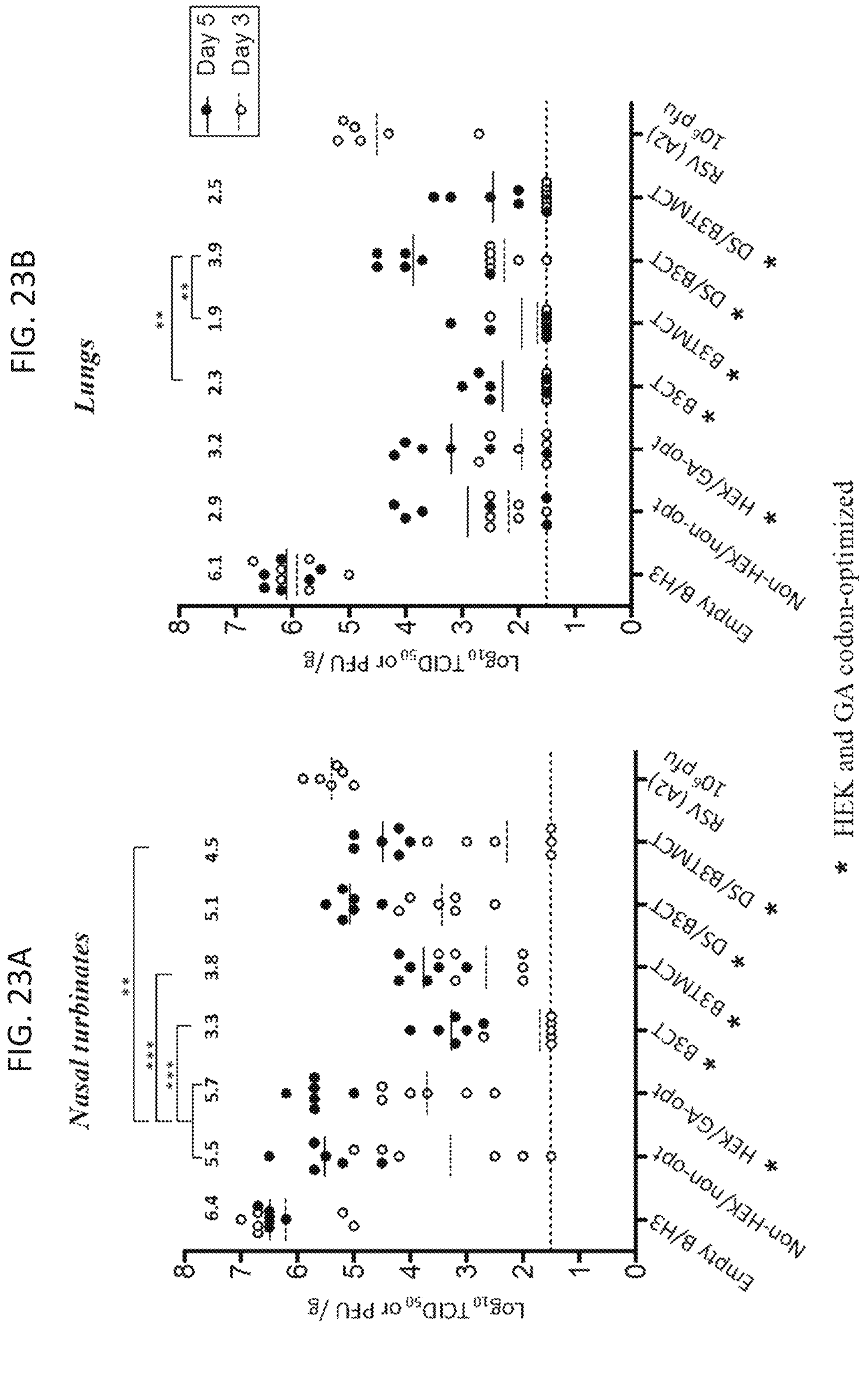
FIGS. 23A and 23B. Replication in hamsters of rB/HPIV3 vectors expressing the B3CT or B3TMCT version of the RSV F protein with or without the DS mutations that stabilize the pre-fusion form of RSV F protein. Hamsters were infected IN with $10^5$ $TCID_{50}$ of rB/HPIV3 vectors or $10^6$ PFU of wt RSV in a 0.1 ml inoculum. Hamsters were euthanized (6 per virus per day) on day 3 and 5 post-infection and the (A) nasal turbinates and (B) lungs were removed and homogenized and viral titers were determined by limiting dilution on LLC-MK2 (rB/HPIV3 vectors) or Vero (RSV) cells at 32° C.: open and closed circles indicate titers for animals sacrificed on day 3 and 5, respectively. Each symbol represents an individual animal, and the mean titer of each group is indicated by a dashed or solid horizontal line for day 3 and 5, respectively. Mean values of day 5 titers are shown at the top. The rB/HPIV3 vectors were titrated by limiting dilution assays on LLC-MK2 cells and reported as $TCID_{50}$/g; RSV was titrated by plaque assays on Vero cells and reported as PFU/g. The limit of detection (LOD) is 1.5 login $TCID_{50}$/g of tissue, indicated with a dotted line. The statistical significance of difference among peak titers was determined by Tukey-Kramer test and indicated by asterisks (*, P≤0.05; , P≤0.01; or *, P≤0.001). The constructs indicated by asterisk * along the x-axis contained the HEK assignments and were GA-codon-optimized for human expression. Constructs containing the DS-Cav1 modification were not examined because they were not available at the time of this experiment.

Replication of vectors expressing the B3CT and B3TMCT RSV F constructs was examined in hamsters by intranasal infection (FIG. 23). Vectors with F that was non-HEK non-optimized (non-HEK/non-opt) or F that was HEK and GA-optimized (HEK/GA-opt) were somewhat more attenuated in the nasal turbinates compared to empty rB/HPIV3 vector, illustrating the attenuating effect of the insert. Increased attenuation compared to the empty vector was evident by the lower values for virus shedding. It also was evident by comparison of the day 3 and day 5 titers: for the empty vector, these values were comparable, whereas for the vectors bearing RSV F, the day 3 titers were lower than the day 5 titers, indicating that these constructs took longer to achieve their maximum titers.) The vectors expressing B3CT, or B3TMCT, or pre-fusion F (DS) with B3CT (DS/B3CT) or B3TMCT (DS/B3TMCT) were substantially (and in most cases significantly) more attenuated in the nasal turbinates (FIG. 23A). This likely reflects an attenuating effect of the incorporation of the RSV F protein into the vector particle: this attenuating effect was not observed in vitro (FIG. 20). In the lungs, all of the vectors expressing RSV F were substantially more attenuated compared to empty vector (FIG. 23B). It is noteworthy that the hyper-fusogenic B3CT construct was significantly more attenuated in both the nasal turbinates and the lungs than the parallel stabilized DS/B3CT construct, suggesting that increased fusion indeed was attenuating (i.e., interfered with replication) in vivo under these conditions. If this was evident in a semi-permissive host such as the hamster, it might be substantially more pronounced in the human host. The non-attenuated wt RSV (A2) control replicated to 100- to 1000-fold higher titer in nasal turbinates, and 1000 to 10,000-fold higher titer in lungs, compared to the attenuated vectors.

Figure 24A:
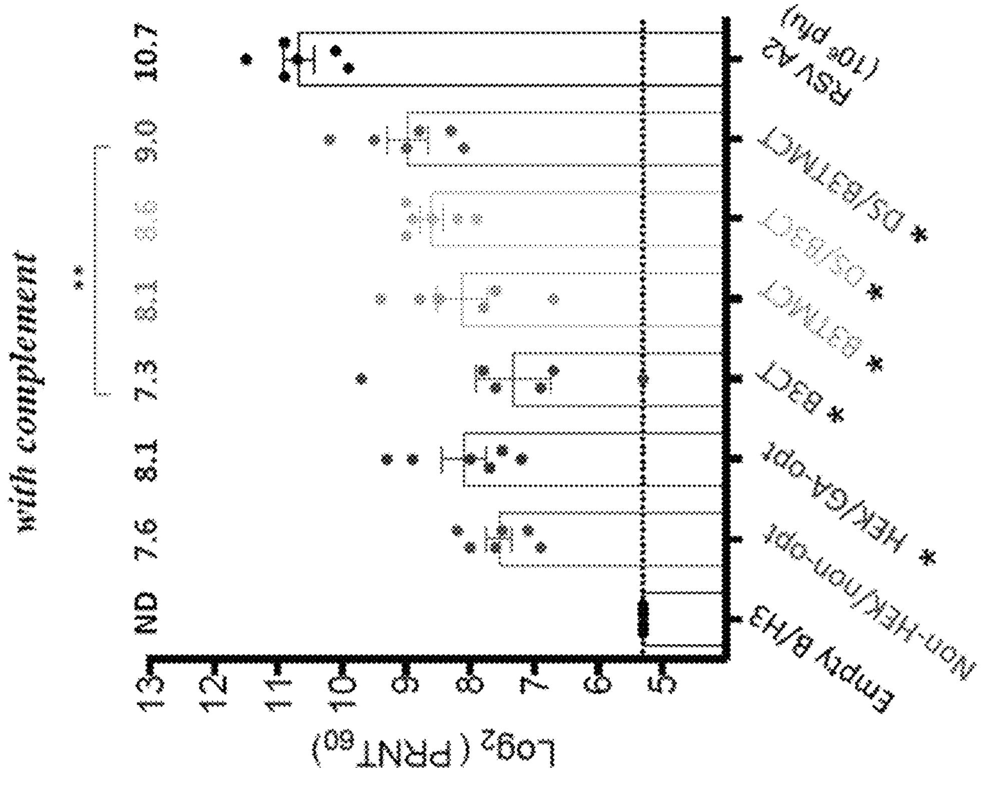
FIGS. 24A and 24B. Serum RSV-neutralizing antibody titers from hamsters infected with rB/HPIV3 vectors expressing the B3CT or B3TMCT version of the RSV F protein with or without the DS mutations that stabilize the pre-fusion form of RSV F protein. Hamsters (n=6 animals per virus) were inoculated IN with $10^5$ $TCID_{50}$ of the indicated rB/HPIV3 vectors or $10^6$ PFU of wt RSV in a 0.1 ml inoculum. Serum samples were collected at 28 days post-immunization, and antibody titers were determined by a 60% plaque reduction neutralization test ($PRNT_{60}$) with (A) or without (B) added guinea pig complement. The height of each bar represents the mean titer shown along with the SEM. The values of mean titers are shown above the bars. The detection limit for the neutralization assay is indicated with a dotted line. The statistical significance of difference in the mean titers was determined by Tukey-Kramer test and indicated by asterisks (*, P≤0.05; **, P≤0.01; ns, P≥0.05). ND, neutralization titer was below the detection limit. The constructs indicated by asterisk * along the x-axis contained the HEK assignments and were GA-codon-optimized for human expression.

The immunogenicity of the vectors was determined by analyzing hamster sera for RSV-neutralizing antibodies by a 60% plaque reduction assay in the presence or absence of added complement (FIGS. 24 A and B, respectively). All of the constructs expressing F protein with B3CT or B3TMCT modifications induced substantial titers of RSV-neutralizing serum antibodies detected in the presence of complement (FIG. 24A). The constructs that combined B3CT or B3TMCT with the prefusion DS mutations gave somewhat higher levels of neutralizing antibodies compared to the parallel constructs without the DS mutations. When assayed in the presence of complement (FIG. 24A), all of the attenuated vector constructs induced lower titers of RSV-neutralizing antibodies compared to non-attenuated wt RSV, although as noted wt RSV has the advantage of the further contribution of the G neutralization antigen and replicated 100- to 10,000-fold more efficiently than the attenuated vectors.

Figure 24B:
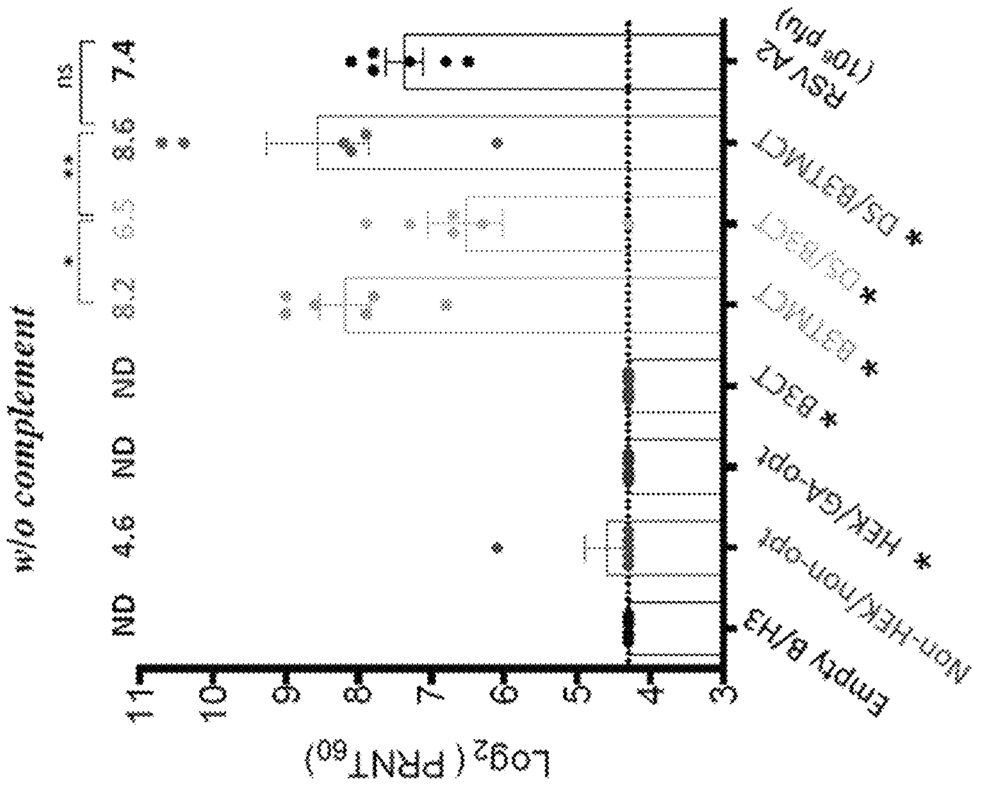

In the version of the assay performed without complement (FIG. 24B) three vectors efficiently induced RSV-neutralizing antibodies detected under these conditions, namely the one expressing B3TMCT F and the ones expressing prefusion DS F containing the B3CT and B3TMCT modifications. The B3TMCT and DS/B3TMCT constructs induced somewhat more high-quality RSV-neutralizing serum antibodies than wt RSV, although this difference was not significant. Nonetheless, this finding was remarkable given that the vectors expressed only one of the two RSV neutralizing antigens and replicated 10- to 10,000-fold less efficiently compared to wt RSV (FIG. 22). In contrast to the B3TMCT vectors, B3CT did not induce a significant antibody response when assayed in the absence of complement (FIG. 24B), even though it was incorporated in the virions at a similar efficiency as the B3TMCT (FIG. 18). Similarly, DS/B3CT also was less immunogenic than B3TMCT, DS (FIG. 24B). This indicated that B3TMCT may be a structurally or antigenically superior form of RSV F compared to B3CT, or it may be that the hyperfusogenic phenotype of B3CT reduced its expression and immunogenicity in vivo. These studies clearly showed that B3TMCT greatly enhanced the immunogenicity of RSV F.

Figure 25B:
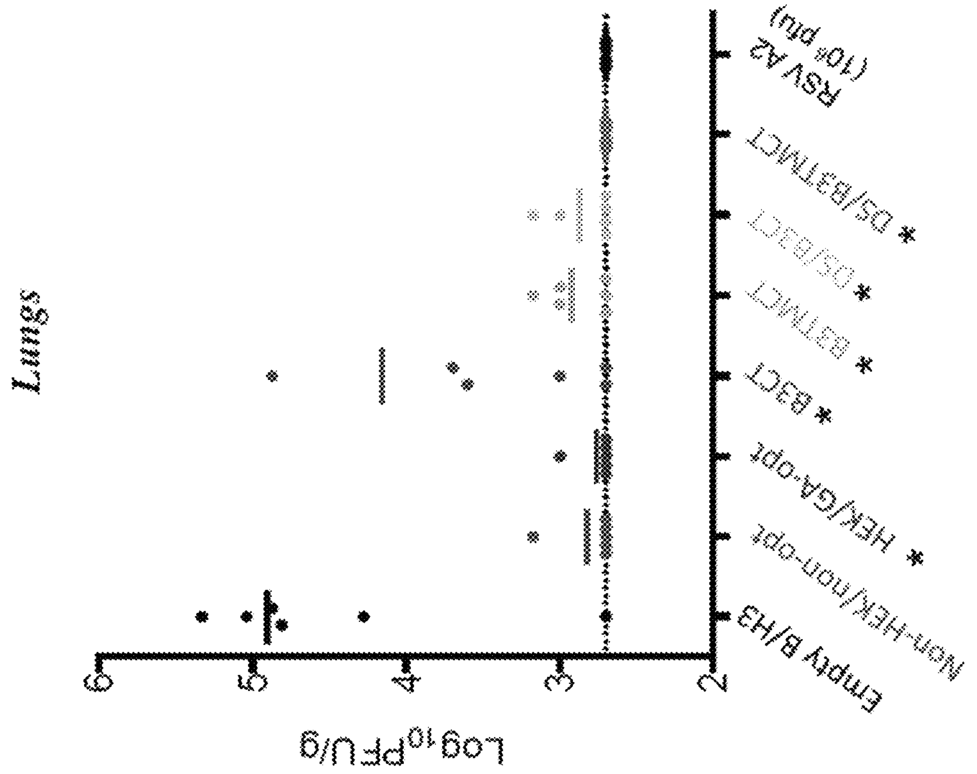
FIGS. 25A and 25B. Protection of immunized hamsters against RSV challenge. The hamsters (n=6 animals per virus) that had been immunized as shown in FIG. 24 were challenged IN on day 31 post-immunization with $10^6$ PFU of wt RSV in a 0.1 ml inoculum. On day 3 post-challenge, hamsters were euthanized and (A) nasal turbinates and (B) lungs were collected. RSV titers in tissue homogenates were determined by plaque assay in Vero cells at 32° C. Each symbol represents an individual animal and mean viral titers of the groups are shown as horizontal lines. The detection limit of the assay was $\log_{10}$ 2.7 PFU/g of tissue, indicated as a dotted line.
Figure 25A:
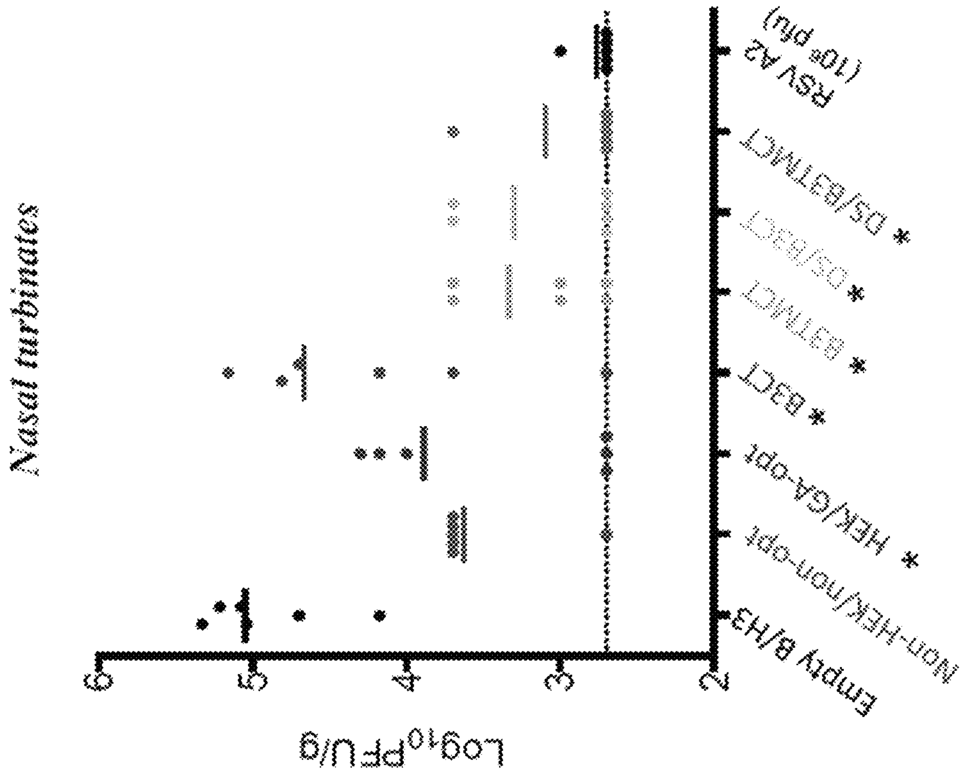

To evaluate the protective efficacy of the vectors, immunized hamsters were challenged intranasally with $10^6$ pfu of wt RSV at 30 days post-immunization (FIG. 25). In agreement with the immunogenicity data, B3CT was less protective in both the nasal turbinates and the lungs. B3TMCT was more protective against RSV challenge, and DS/B3TMCT was the most protective of the vector constructs (although the difference was small), with only one immunized hamster showing detectable RSV replication in the nasal turbinates and all being completely protected in the lungs, providing protection similar to that conferred by the non-attenuated wt RSV control (FIG. 24). The comparable level of protective efficacy between the DS/B3TMCT construct and wt RSV was particularly noteworthy because the latter replicated to 2-4 log titers higher than DS/B3TMCT, expressed both the F and G RSV neutralization antigens, and expressed all of the RSV proteins as potential antigens for cellular immunity. This indicates that rB/HPIV3 vector with packaged prefusion form of RSV F (DS/B3TMCT) is very highly immunogenic and protective.

Stability of the rB/HPIV3-RSV-F Constructs in Hamsters.

Give the experience with the genetic instability of MEDI-534 in clinical studies (Yang et al 2013 Vaccine 31:2822-2827), a key issue was whether expression of the RSV F insert remained stable during replication in vivo. The genetic stability of all of the 12 different rB/HPIV3-RSV-F constructs that had been analyzed in hamsters in FIGS. 8, 14, and 23 was assayed. Tissue homogenates of the lungs and nasal turbinates that were collected on days 3 and 5 following infection were analyzed by a fluorescence double-staining plaque assay that can simultaneously detect the expression of the RSV F protein and the vector proteins in the viral plaques (FIG. 26). In this assay, RSV F expression was detected with an F-specific antibody visualized by red fluorescence, and expression of PIV3 antigen was detected with an HPIV3-specific antiserum (from rabbits that were hyperimmunized with purified HPIV3 virions) visualized by green fluorescence. When merged, rB/HPIV3 plaques that maintained expression of RSV F appeared yellow while those that have lost expression of the RSV F insert remained green (FIG. 26). This analysis showed that the RSV F insert generally was stable during replication in hamsters (FIG. 26). For majority of the samples, all of recovered viruses in higher dilution wells (in which individual plaques could be discerned) appeared as yellow plaques and thus expressed RSV F protein. In a subset of other specimens there was sporadic loss of expression of RSV F in a subset of plaques, resulting in a small percentage of green plaques (usually <12%). In addition, there was no evidence that loss of expression of RSV F increased progressively with time; in other words, there was not a higher frequency of loss of expression on specimens from day 5 compared to day 3. In a single case, there was a high level of loss of expression in a single nasal turbinate specimen from day 3 (14% remaining expression, hamster #511 in group #9), whereas the lung specimen from the same animal had 100% expression. In general, this indicated that expression of the RSV F insert was substantially stable for all of the tested constructs. It also showed that none of the constructs appeared to be disproportionately unstable. Thus, high levels of expression of RSV F and syncytium formation, or expression of stabilized forms of RSV, or high levels of incorporation of modified F into the vector particles that was attenuating for the rB/HPIV3 vector, did not appear to favor the emergence of mutants in which expression of RSV F was silenced.

Figures 27, 28:
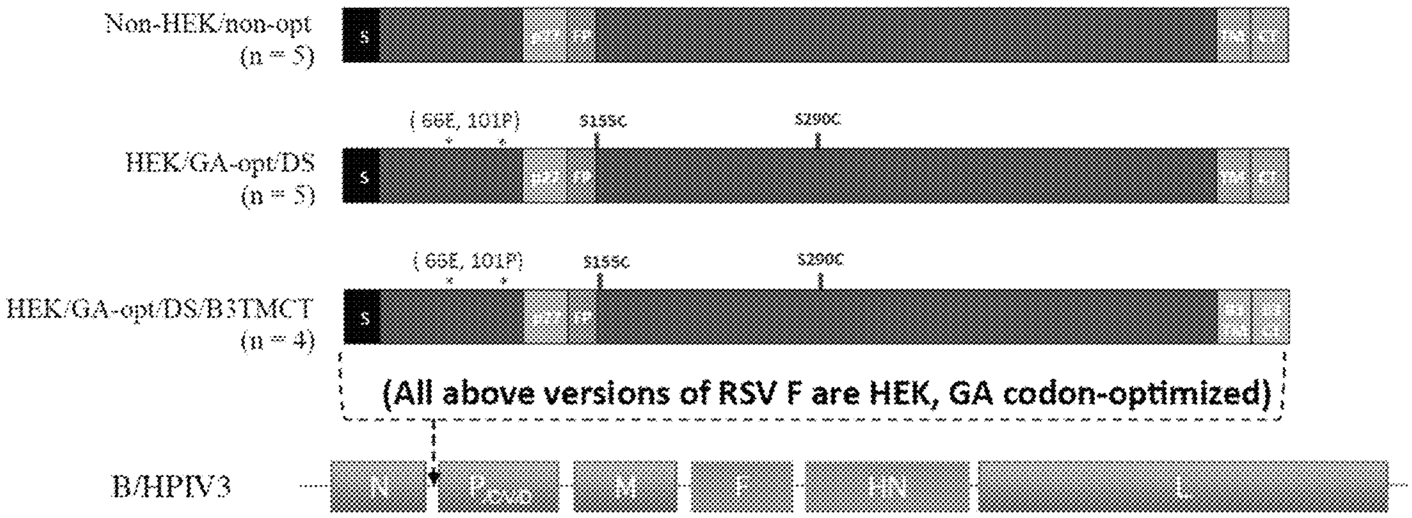
FIG. 27. Temperature sensitivity phenotypes of B/HPIV3 vectors. The indicated vectors were evaluated for the ability to form plaques on LLC-MK2 cells at the indicated temperatures. Reduction in plaque formation of ≥100-fold is indicative of temperature sensitivity. The lowest such restrictive temperature for each virus is indicated in bold, underlining, and is called the shut-off temperature.
FIG. 28. rB/HPIV3 constructs that were evaluated for attenuation and immunogenicity in non-human primates (Rhesus macaques). Rhesus macaques were infected by the combined IN and intratracheal routes with $10^6$ $TCID_{50}$ per site of the following constructs: Non-HEK/non-opt; HEK/GA-opt/DS; and HEK/GA-opt/DS/B3TMCT in groups of five, five and four animals, respectively.

The 12 rB/HPIV3 constructs described and evaluated in FIGS. 1-26 were further evaluated for possible temperature sensitivity phenotype. For each vector, equal aliquots were plagued under methylcellulose at 32, 35, 36, 37, 38, 39, and 40° C. (FIG. 27). A reduction in plaque formation of ≥100-fold was indicative of temperature sensitivity at that temperature. The empty rB/HPIV3 vector was temperature sensitive (ts) at 40° C. (FIG. 27), whereas neither HPIV3 nor BPIV3 is ts at this temperature. This indicates that chimerization (i.e., the replacement of the HPIV3 F and HN genes into the BPIV3 backbone) conferred a slight ts phenotype. Every vector that in addition contained the RSV F insert was ts at 37-38° C., indicating that the presence of the additional gene augmented the ts phenotype. The constructs that were the most ts were B3CT, B3TMCT, and DS/B3CT (#7, 8, 12 in FIG. 27). This implied that packaging of RSV F into the virus particle augmented this phenotype. One possible explanation would be that the presence of RSV F in the vector made the particle somewhat unstable and susceptible to elevated temperature. The remaining construct with efficient packaging of RSV F, namely DS/B3TMCT (construct 13 in FIG. 27), was slightly less ts, suggesting that the hypo-fusogenic phenotypes associated with DS and B3TMCT ameliorated the instability to some extent. Taken together, these findings provide a means to confer attenuation or to mitigate attenuation, depending on the construct design, and in any event provide information important in designing vaccine viruses.

Evaluation of Selected rB/HPIV3-RSV-F Constructs in Rhesus Macaques.

To further investigate the effects of the "DS" and "B3TMCT" mutations on vector replication, immunogenicity, and protective efficacy, two candidates (HEK/GA-opt/DS and HEK/GA-opt/DS/B3TMCT) were evaluated for replication and immunogenicity in rhesus macaques (FIG. 28). The B/HPIV3 vector with unmodified RSV F (non-HEK/non-opt) was included as a baseline control for comparison. A limited number of constructs were evaluated given the expense and ethical consideration of studies in primates. Monkeys were immunized with a total of $2\times10^6$ $TCID_{50}$ of each rBHPIV3 vector by the combined IN and intratracheal (IT) routes. Nasopharyngeal swabs and tracheal lavage samples were collected on indicated days (FIG. 29) to monitor virus shedding as a measure of replication. Sera were collected on day 0, 14, 21, and 28 days. All animals were challenged on day 28 with wt RSV IN and IT, with $10^6$ pfu per site, and serum samples were collected on days 35 and 56.

Figure 29A:
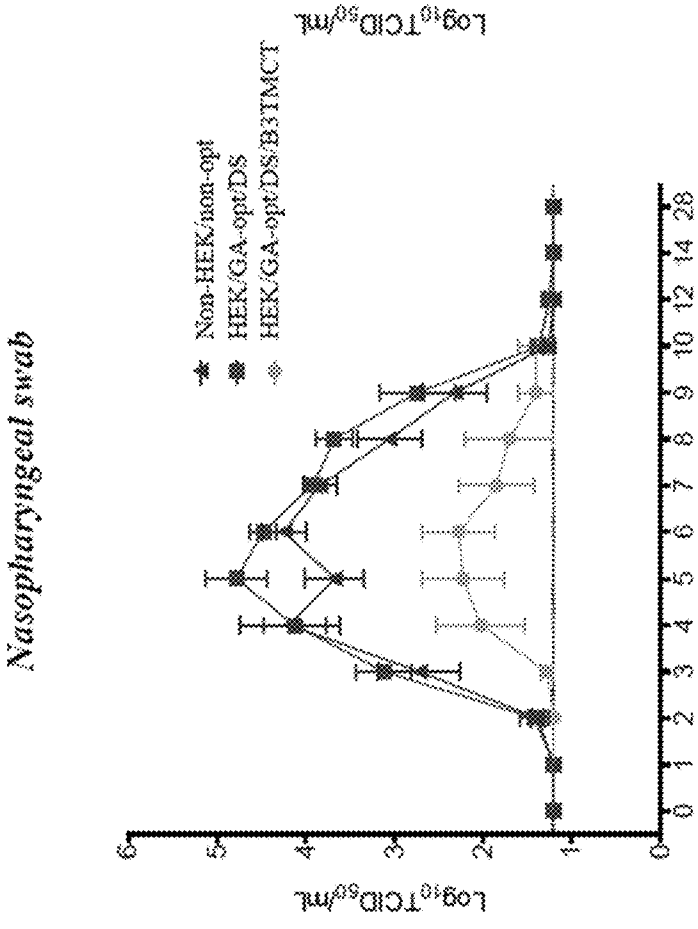
FIGS. 29A and 29B. Replication of rB/HPIV3 vectors in rhesus macaques. Rhesus macaques were infected with the indicated rB/HPIV3 vectors as described in FIG. 28. Vector replication in the respiratory tract was assessed by collecting (A) nasopharyngeal swabs and (B) tracheal lavages on the indicated days and determining the viral titers by limiting dilution assay. Limit of detection is 1.2 $\log_{10}$ $TCID_{50}$/mL shown as dotted line.
Figure 29B:
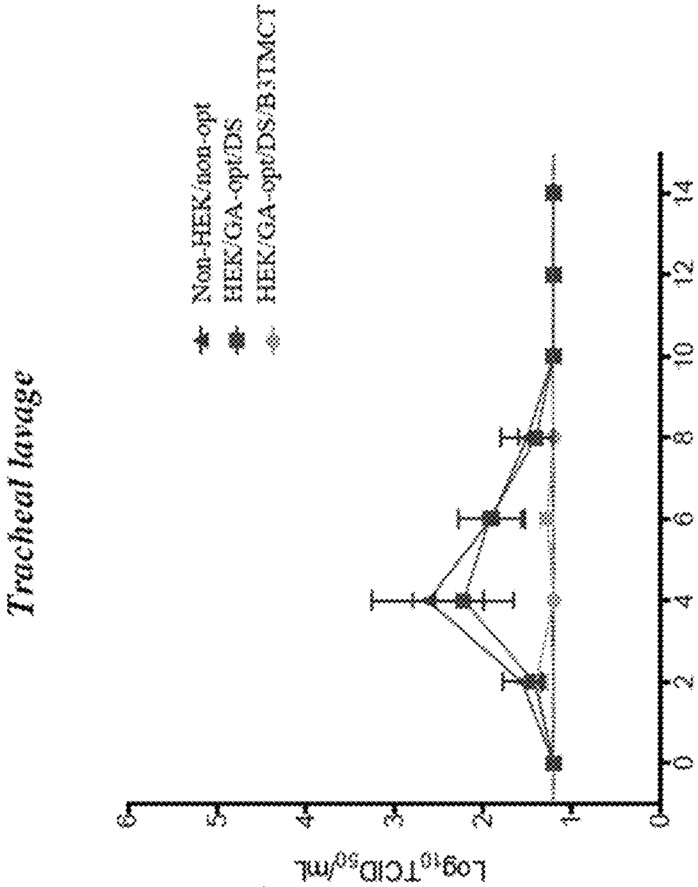

The non-HEK/non-opt and HEK/GA-opt/DS viruses replicated to peak titers of approximately $10^5$ and $10^3$ $TCID_{50}$ units per ml in the upper and lower respiratory tracts (FIGS. 29A and B, respectively). In contrast, the HEK/GA-opt/DS/B3TMCT construct was dramatically more attenuated in both the upper and lower respiratory tracts of rhesus monkeys (FIGS. 29 A and B). This indicated that B3TMCT conferred substantial attenuation to the rB/HPIV3 construct, whereas the DS mutations did not appear to confer significant attenuation. Thus, the mild tendency of the B3TMCT modification to confer attenuation in hamsters (FIG. 23) was substantially greater in non-human primates.

Figure 30:
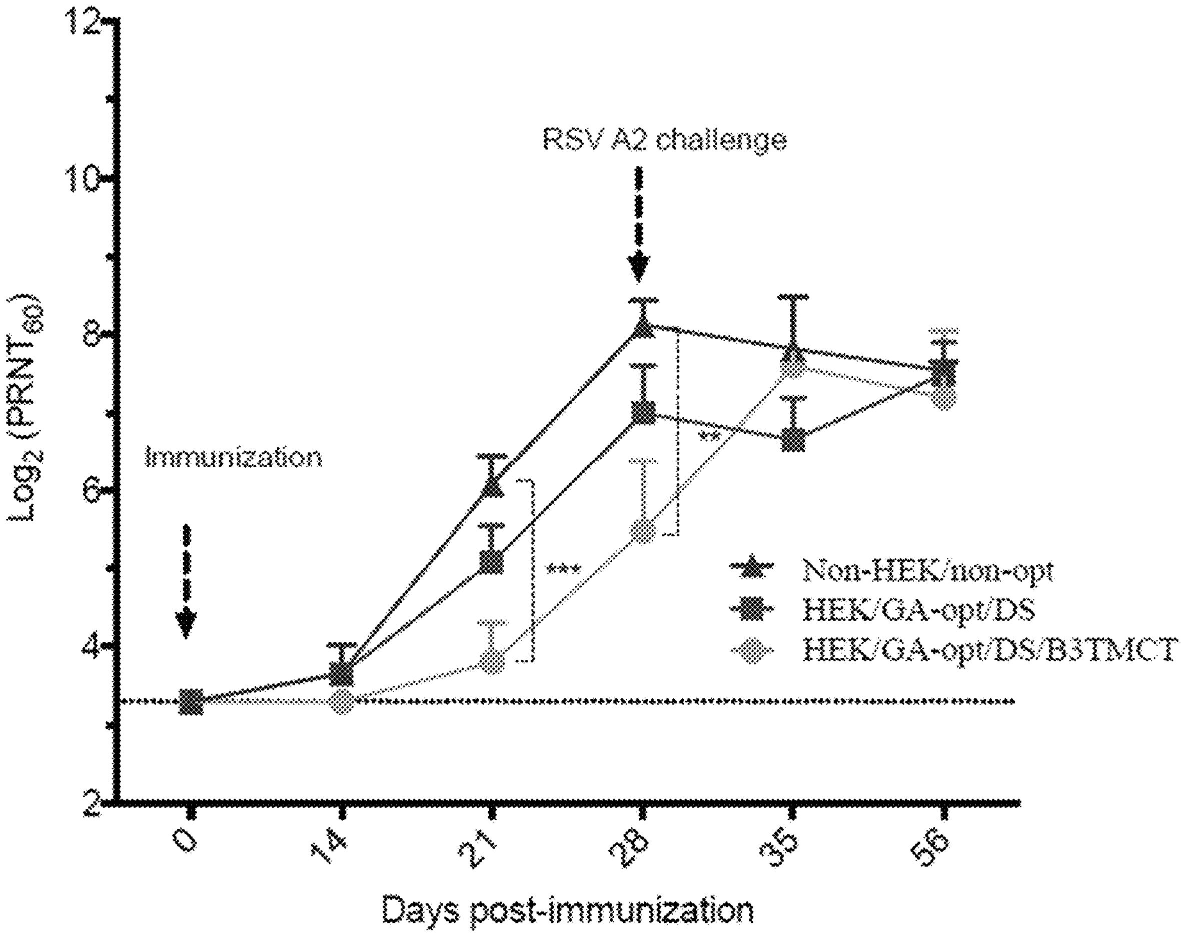
FIG. 30. Serum HPIV3-neutralizing antibody titers induced by rB/HPIV3 vectors. Monkey sera were collected at 0, 14, 21, 28, 35 and 56 days post-immunization and HPIV3-neutralizing antibody titers were determined by a 60% plaque reduction neutralization test ($PRNT_{60}$) in the presence of added guinea pig complement. The detection limit for the neutralization assay is indicated with a dotted line. The day of RSV challenge is indicated.

As noted, sera were collected on days 0, 14, 21, 28, 35, and 56. Serum antibodies specific to the rB/HPIV3 vector were analyzed by a 60% plaque reduction assay against HPIV3 (FIG. 30). This showed that the vector-specific neutralizing serum antibody response to the highly attenuated HEK/GA-opt/DS/B3TMCT construct was slower and somewhat reduced compared to the non-HEK/non-opt and HEK/GA-opt/DS constructs. This is consistent with the expectation that reduced antigenic load would reduce immunogenicity. After 28 days the titers became more similar and, as expected, there was no boost in vector-specific immunity from the RSV challenge on day 28 (since RSV did not contain any vector antigens).

Figure 31:
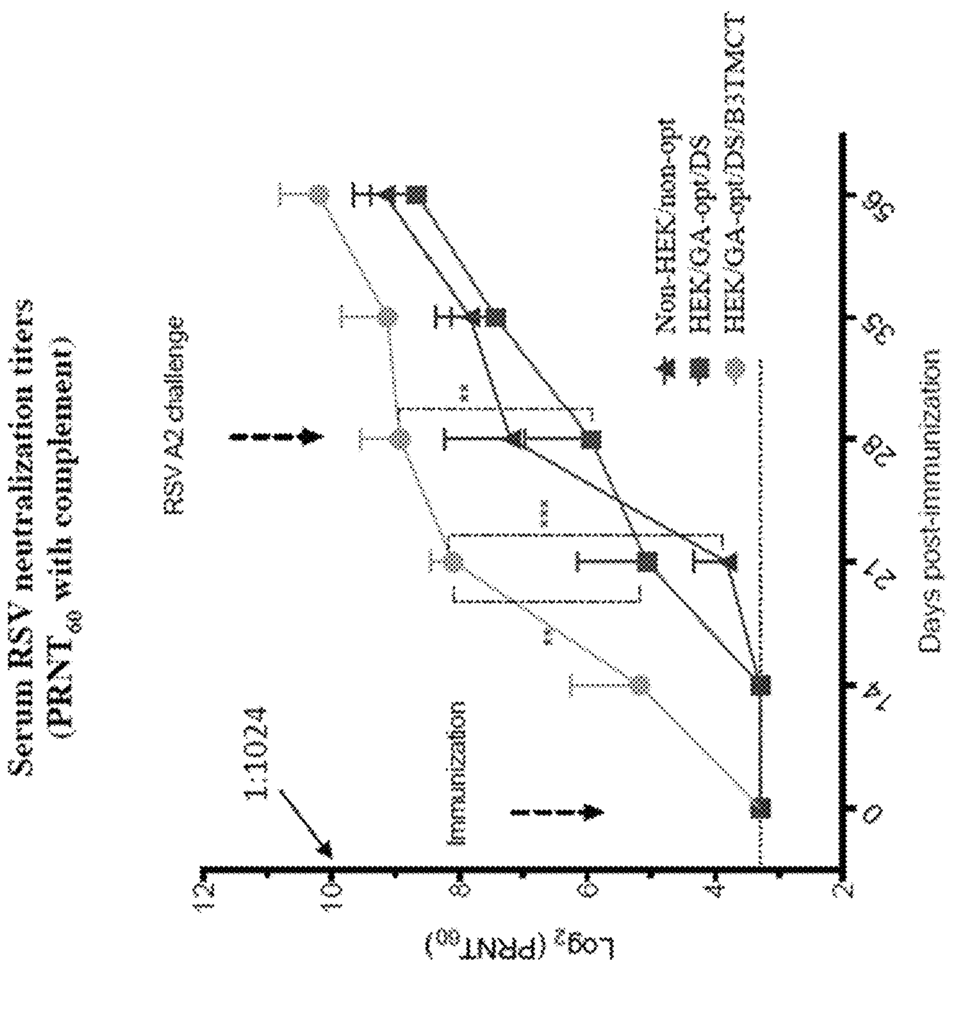
FIGS. 31 and 32. Serum RSV-neutralizing antibody titers induced by rB/HPIV3 vectors. Monkey sera were collected at 0, 14, 21, 28, 35 and 56 days post-immunization.
Figure 32:
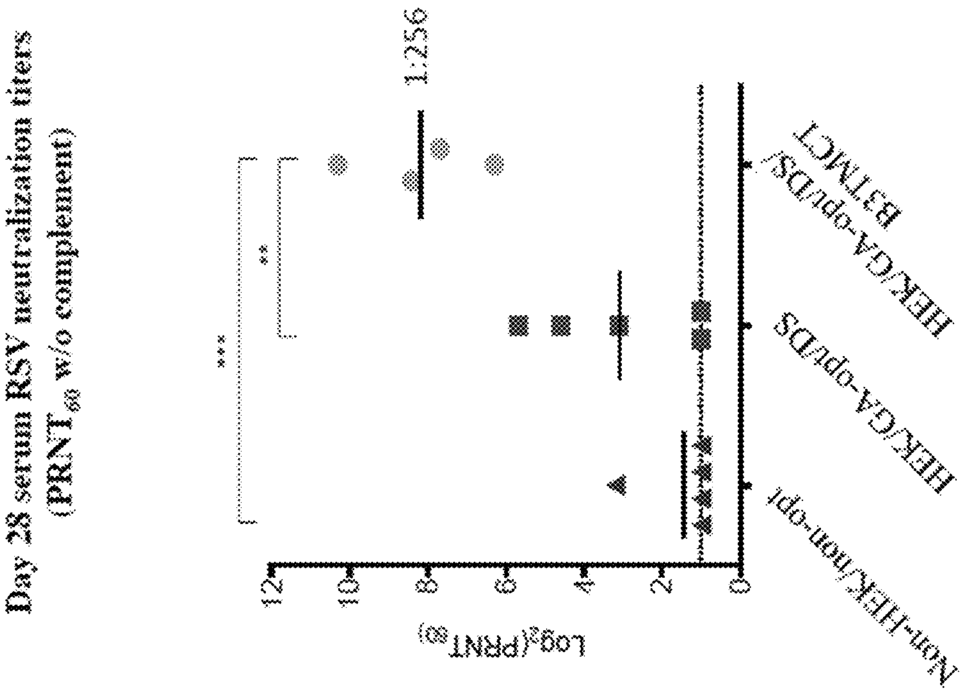
Figure 34:
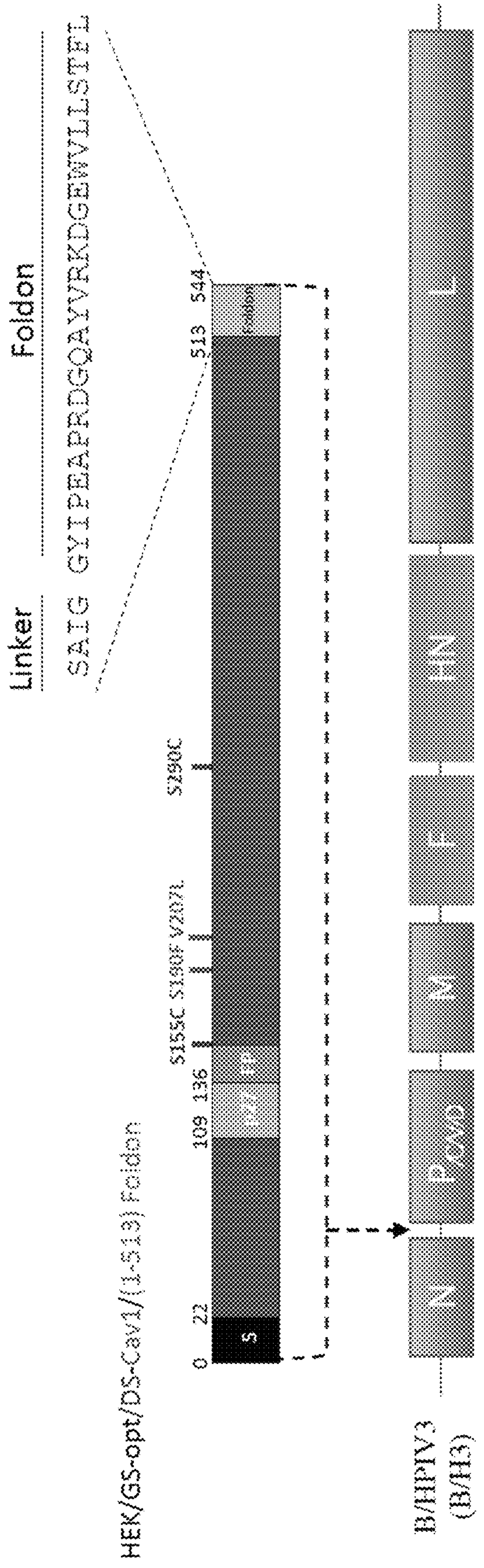
FIG. 34. Construction of an rB/HPIV3 vector expressing a secreted version of HEK/GS-opt/DS-Cav1 RSV F protein that contains a C-terminal "foldon" sequence. RSV F protein containing the HEK assignments and expressed from a GS-codon-optimized (for human expression) ORF with DS-Cav1 mutations was engineered to contain the N-terminal 513 amino acids of the F protein (i.e., lacking the TM and CT domains), fused to the indicated 4-amino acid linker and the indicated 27-amino acid foldon sequence from T4 phage (SEQ ID NO: 132, see Efimov et al. 1994, J Mol Biol 242:470-486; Miroshnikov et al 1998 Protein Eng. 11:329-332). The ORF was inserted into the rB/HPIV3 vector at the same position and with the same vector signals as described in FIGS. 1, 4, 11, and 17.

The RSV-specific neutralizing serum antibody responses were quantified by a plaque reduction assay performed in the presence and absence of complement (FIGS. 31 and 32, respectively). The assay in the presence of complement showed that RSV-neutralizing serum antibodies were induced more rapidly and to significantly higher titer in response to the HEK/GA-opt/DS/B3TMCT construct than for the other two constructs (FIG. 31). This greater induction of RSV-specific neutralizing serum antibodies was noteworthy and surprising since this construct was much more highly restricted in replication (FIG. 29). When assayed previously in hamsters (FIG. 24), this construct had given an apparent increase compared to HEK/GA-opt/DS that was not statistically significant: the greater increase observed in non-human primates is consistent with the idea that the hamster model is a less sensitive model for these human and bovine/human viruses. For example, The greater induction of RSV-neutralizing serum antibodies in the rhesus macaques in response to the HEK/GA-opt/DS/B3TMCT construct also was observed when the assay was performed in the absence of complement to measure high-quality antibodies on day 28: indeed, the difference in titer for this construct versus the other two constructs was substantially greater than what was observed in the presence of complement (FIG. 32). Taken together, these results indicated that the DS mutation did not substantially increase the quantity of RSV-neutralizing serum antibodies (FIG. 31) but did increase the quality (FIG. 32), while the further addition of the B3TMCT modification dramatically increased both the quantity (FIG. 31) and quality (FIG. 32) of the RSV-neutralizing serum antibodies.

The RSV challenge virus administered on day 28 was completely restricted by all vectors and no infectious challenge RSV could be recovered from the nasopharyngeal swabs and tracheal lavage samples from any animal, and therefore this experiment did not provide further information on the comparative properties of these viruses. Complete protection against short-term RSV challenge in experimental animals is sometimes observed because the semi-permissive nature of RSV replication in these models facilitates restriction of replication. The RSV-specific antibody responses continued to increase following day 28, but it is not clear whether this response was due to the primary infection or the challenge.

The fluorescence double-staining plaque assay was used to analyze virus recovered from the rhesus macaques on days 4, 5, and 6, which was the time of peak shedding, for the expression of RSV F protein. A summary of the data is shown in FIG. 33. This analysis showed that the RSV F inserts generally were stable during replication in monkeys. The results were very similar to those shown in FIG. 26 for the hamster study. For majority of the samples from the rhesus monkeys, nearly all of recovered viruses appeared as yellow plaques and thus expressed RSV F protein. There was sporadic loss of RSV F expression in some specimens, typically <10% of recovered plaques in a given specimen. There was no evidence that loss of expression increased significantly with time, and sometimes evidence of loss of expression was observed at an early time point but not at a later time point from the same animal There also was no evidence that a particular construct was associated with disproportionately greater loss of RSV F expression versus another construct. For example, even though the expression of HEK/GA-opt/B3TMCT was highly attenuating for the rB/HPIV3 vector, there was no evidence of increased selection of virus in which expression of RSV F was lost.

A rB/HPIV3 vector expressing the ectodomain of RSV F (amino acids 1-513, lacking the TM and CT domains) with GenScript (GS) optimization, and containing the HEK assignments and the DS-Cav1 modifications was also generated. The ectodomain was fused to a 4-amino acid linked followed by a trimer-stabilizing foldon sequence at its C-terminus, i.e. construct #19 (HEK/GS-opt/DS-Cav1/[1-513] Foldon). This form of pre-fusion RSV F was previously evaluated as subunit vaccine in mice and rhesus monkeys (McLellan, et al. 2013. Science 342:592-598). This RSV F protein should be expressed as a partially secreted form, resembling construct #8 (HEK/GA-opt/Ecto), but with the improvements of more efficient translation due to the GS optimization, better immunogenicity due to the DS-Cav1 modifications, and greater trimer stability due to the foldon stabilization domain. This construct can be used to compare how immunogenic the secreted DS-Cav1 form is compared with the membrane anchored form, i.e. #16 (HEK/GS-opt/DS-Cav1) and the virion-incorporated form, i.e. #18 (HEK/GS-opt/DS-Cav1/B3TMCT).

Points from this study: (1) The hamster model, while convenient, may be somewhat insensitive to changes in replication, expression, and immunogenicity with the various constructs, and it may be that the effects associated with these constructs, such as attenuation and immunogenicity, would be substantially greater in the human host for which these vaccine constructs are intended. For example, while the presence of the B3TMCT modification in the HEK/GA-opt/DS/B3TMCT construct conferred only a modest increase in attenuation in the hamster model (FIG. 23), it was substantially more attenuating in rhesus macaque (FIG. 29), which is more closely related to the authentic human host. Furthermore, the difference in immunogenicity for RSV-neutralizing antibodies between HEK/GA-opt/DS/B3TMCT and the other constructs was substantially greater in rhesus macaques (FIG. 31) than in hamsters (FIG. 24), even though that construct was substantially more attenuated in rhesus macaques (FIG. 29). Thus, the inherent immunogenicity per pfu of HEK/GA-opt/DS/B3TMCT appeared to be much greater in rhesus macaques than in hamsters, and thus might similarly be greater in humans. This apparent insensitivity in the hamster may explain, for example, why the hamster model did not reliably provide a difference in immunogenicity associated with a 16-fold increase in RSV F expression (FIG. 9). It also should be noted that codon-optimization for human use might not provide comparable increases in expression in hamsters as compared to primate cells (and the human vaccinee), which might contribute to reduced immunogenicity in the hamster model compared to primates. (2) Another theme was the desirability to reduce the amount of syncytium formation induced by RSV F. In vitro, syncytium formation did not appear to restrict replication in monolayer cultures, although it is possible that it might become a factor in microcarrier cell culture systems used for manufacture, and so it seems prudent to control syncytium formation. With most of the constructs, the HEK assignments were present, which strongly suppressed syncytium formation. The DS and DS-Cav1 constructs, like the HEK assignments, also strongly suppressed syncytium formation and thus provided an unexpected benefit. One construct that was associated with up-regulated syncytium formation, namely HEK/GA-opt/B3CT, did exhibit reduced replication (FIG. 23) and immunogenicity (FIG. 24) in hamsters, giving an indication that increased syncytium formation can be deleterious in vivo. This might be more pronounced in a primate host. Therefore, the combination of GS-opt, HEK, DS or DS-Cav1, and B3TMCT was identified as a combination that would give the highest level of expression of RSV F (due to HEK plus GS-opt, plus stabilization of the pre-fusion F protein that appeared to provide increased F protein accumulation) in the context of two suppressors of syncytium formation (HEK and DS-Cav1), and in the presence of packaging signals that were not hyper-fusogenic (B3TMCT). (3) Two features (namely B3TMCT and the DS mutations) independently were associated with substantial induction of high quality RSV-neutralizing serum antibodies. The rhesus macaque study suggested that the B3TMCT was the more important of these two factors in a primate host, relevant to anticipated vaccine performance in humans (FIG. 32). Importantly, the B3TMCT modification also dramatically increased the quantity (FIG. 31) of the RSV-neutralizing serum antibody response. (4) Unexpectedly and fortuitously, the features that improved the expression and packaging of RSV F did not appear to confer a significant selective pressure for loss of expression of RSV F, when evaluated by a dual immunofluorescence assay. As already noted, loss of expression of the RSV F insert was a problem with MEDI-534, but a number of features were employed in the present study to down-regulate fusion that were not employed in MEDI-534, and this may have played a major role in stabilizing the RSV F insert. In addition, by evaluating two overlapping sets of packaging signals, it was possible to identify and avoid one that was hyperfusogenic, and to identify and choose one that had substantially reduced fusion. (5) The B3TMCT modification in particular emerged as an important factor in increasing immunogenicity. The HEK, GA-opt or GS-opt, and DS or DS-Cav1 modifications emerged as secondary improvements. B3TMCT had the effect of strongly attenuating the vector in rhesus macaques, as noted. The use of this modification in the context of the highly attenuated rB/HPIV3 vector resulted in a vector that appeared to be substantially over-attenuated. However, using reverse genetics, the B3TMCT F protein (with HEK, plus GA- or GS-opt, plus DS or DS-Cav1 modifications, as desired) can be combined with a less-attenuated vector backbone, such as wild type HPIV1, 2, or 3 or versions bearing one or more known, stabilized attenuating mutations, to create a construct that is less attenuated. Since the B3TMCT construct in rB/HPIV3 was very highly immunogenic despite being very over-attenuated, a construct expressing this protein that replicates 10- to 100-fold better should be suitably attenuated and substantially more immunogenic.

Additional Assays with Recombinant rB/HPIV3 Vectors Expressing Modified Versions of the RSV F ORF and Protein.

Additional assays were preformed to evaluate: (i) GS-opt versions of constructs including the DS prefusion stabilization mutations and the B3TMCT packaging signal, and (ii) the DS-Cav1 prefusion stabilization mutations, which include the two cavity-filling mutations S190F and V270L combined with the DS mutations. The F proteins assayed also contain the two HEK amino acid assignments that result in an amino acid sequence identical to that of an early passage (called HEK-7) of the A2 strain, as described above. These assays show that:

1. DS-Cav1 and B3TMCT independently confer the ability to induce significant levels of complement-independent RSV-neutralizing antibodies, which are considered to be the most relevant for in vivo protection.

2. The combination of DS-Cav1 plus B3TMCT gives a further increase in immunogenicity.

3. The two most immunogenic constructs were HEK/GA-opt/DS-Cav1/B3TMCT (FIG. 53, group #7) and HEK/GS-opt/DS-Cav1/B3TMCT (group #10), which differ only in the source of codon optimization, with GS-opt appearing to be the most immunogenic.

4. Although HEK/GA-opt/DS-Cav1/B3TMCT (group #7) and HEK/GS-opt/DS-Cav1/B3TMCT (FIG. 53, group #10) were not statistically distinguishable in a pair-wise comparison, the latter was significantly more immunogenic than wt RSV. These findings show that HEK/GS-opt/DS-Cav1/B3TMCT (group #10) was the most immunogenic construct in the hamster model, particularly for highly-efficient neutralizing antibodies detected without the need to add complement (FIG. 53), and thus the further modification with GS-opt and DS-Cav1 appeared to increase immunogenicity. This also was the most protective construct in the hamster challenge study.

5. The propensity for the rB/HPIV3 vector to acquire mutations conferring a large-plaque phenotype and attenuation was essentially eliminated by three nucleotide and two amino acid mutations in the vector HN protein.

6. The HEK/GS-opt/DS-Cav1/B3TMCT insert was expressed from the first gene position (pre-N), resulting in a construct that replicated efficiently in Vero cells, could be obtained in a preparation with a high percentage of RSV F expression, and efficiently expressed the RSV F protein.

Summary of Animal Studies.

Figure 54B:
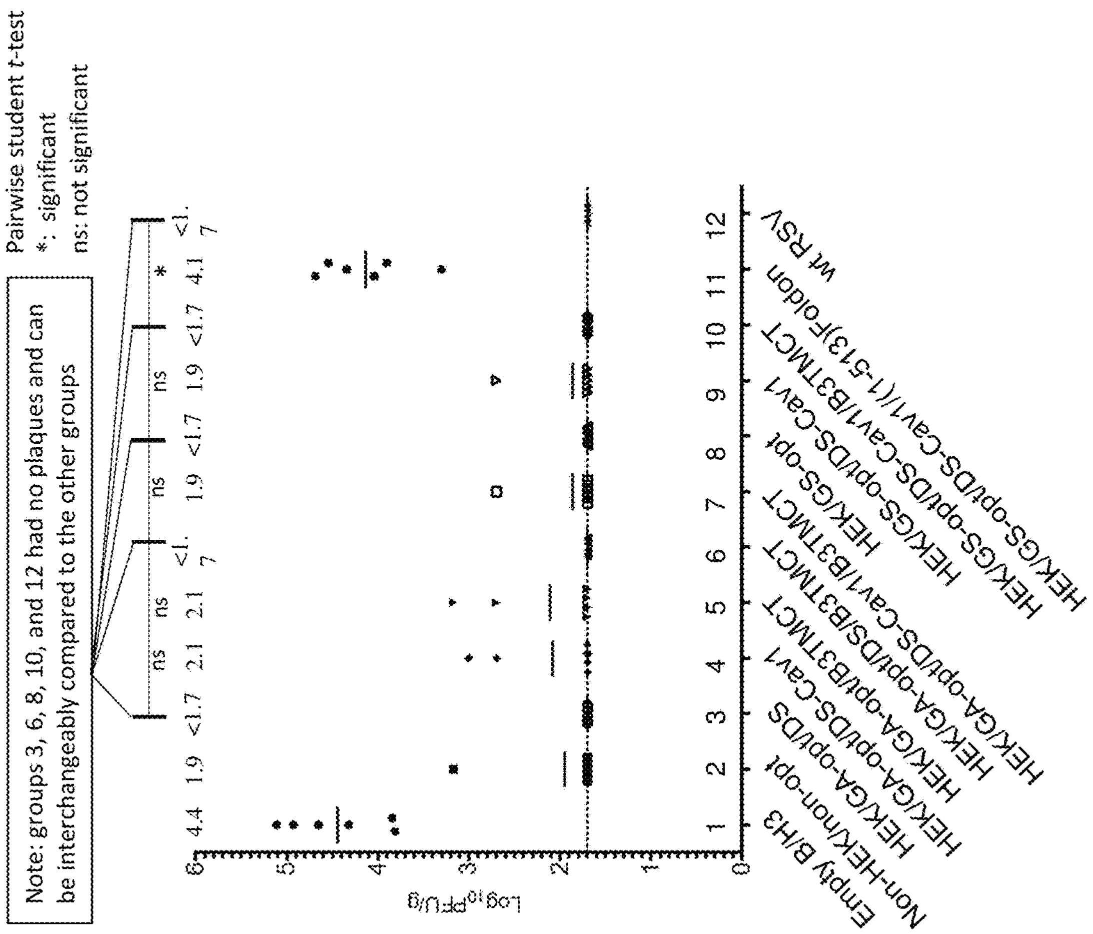
FIGS. 54A and 54B. Protection against RSV challenge of hamsters immunized with the indicated rB/HPIV3 vectors. The hamsters (n=6 animals per immunization group) that had been immunized as shown in FIG. 53 were challenged IN on day 30 post-immunization with $10^6$ PFU of wt RSV in a 0.1 ml inoculum. On day 3 post-challenge, hamsters were euthanized and (A) nasal turbinates and (B) lungs were collected. RSV titers in tissue homogenates were determined by plaque assay in Vero cells at 37° C. Each symbol represents an individual animal and mean values of viral titers of the groups are shown above the symbols and indicated as short horizontal lines. The pairwise student t-test was used to evaluate the statistical significance of differences between values: in each of the horizontal lines over the mean titers, the value(s) indicated with a vertical bar(s) was compared pair-wise to each of the others and recorded as being significantly (*, $p<0.05$) or not significantly (ns) different. The detection limit of the assay was $\log_{10}$ 1.7 PFU/g of tissue, indicated as a dotted line.
Figure 54A:
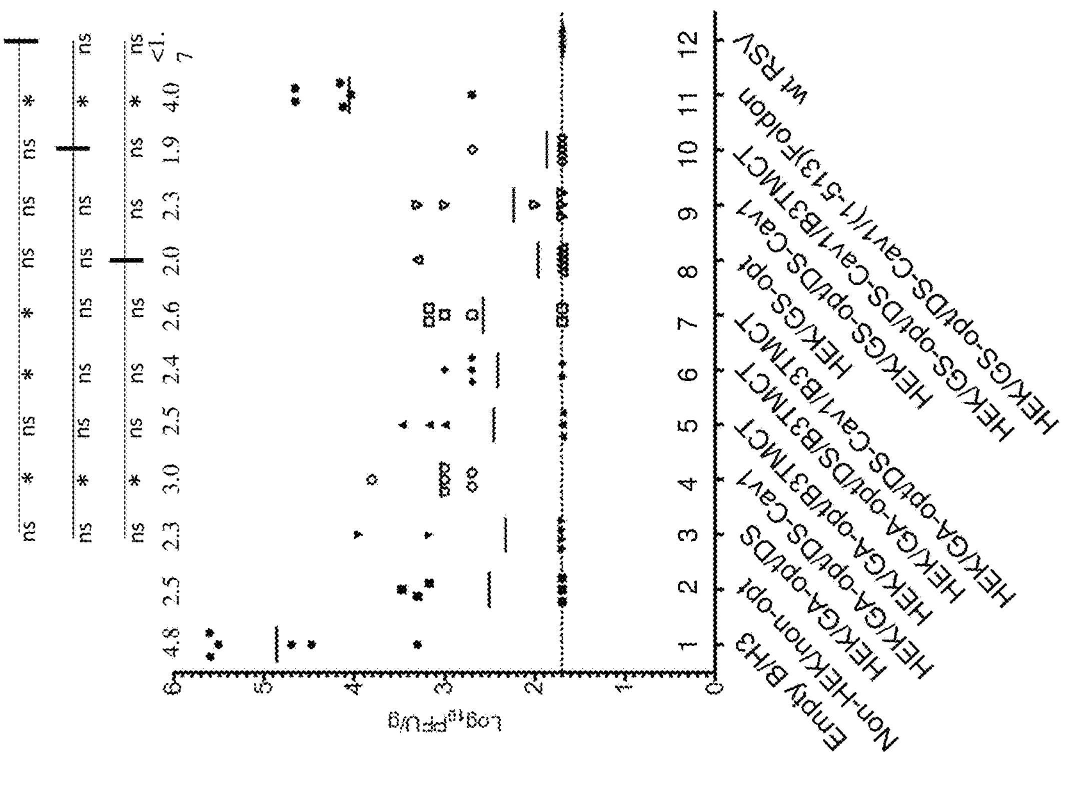
Figure 55:
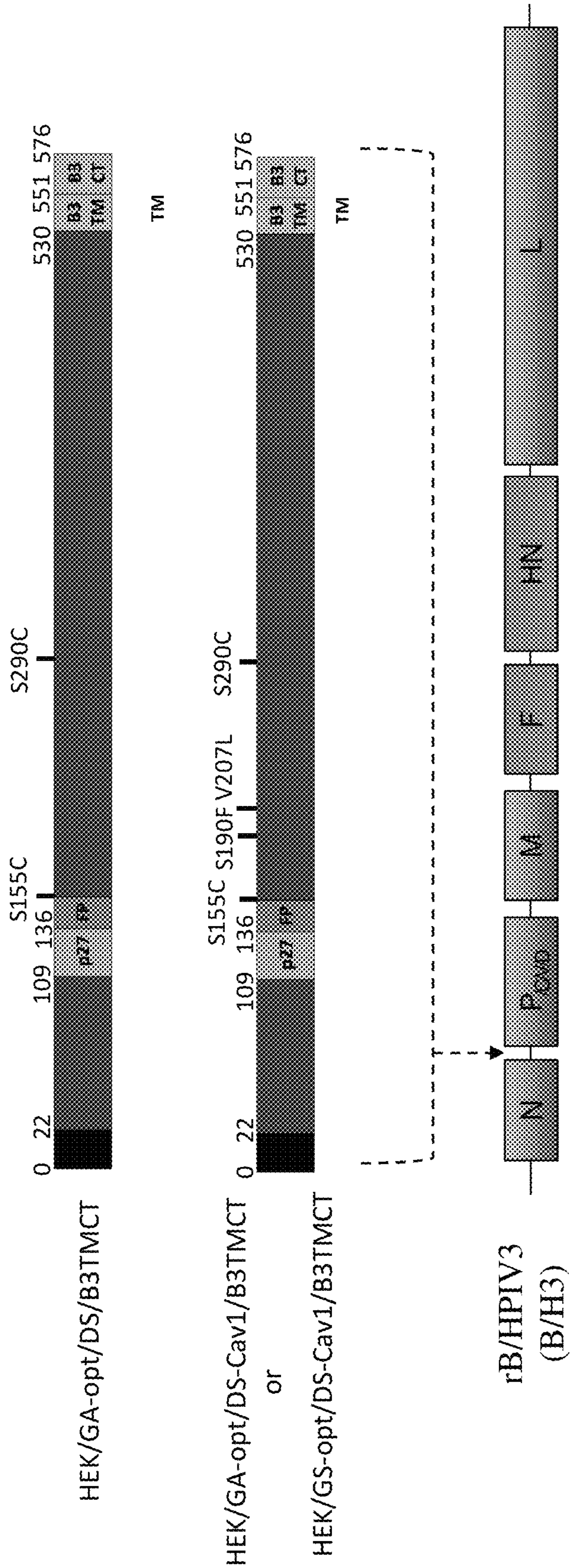
FIG. 55. rB/HPIV3 constructs that were evaluated for attenuation and immunogenicity in non-human primates (Rhesus macaques). Rhesus macaques were infected by the combined IN and intratracheal routes with $10^6$ $TCID_{50}$ per site of the following constructs: HEK/GA-opt/DS/B3TMCT; HEK/GA-opt/DS-Cav1/B3TMCT; and HEK/GS-opt/DS-Cav1/B3TMCT in groups of four, six and six animals, respectively.
Figure 57A:
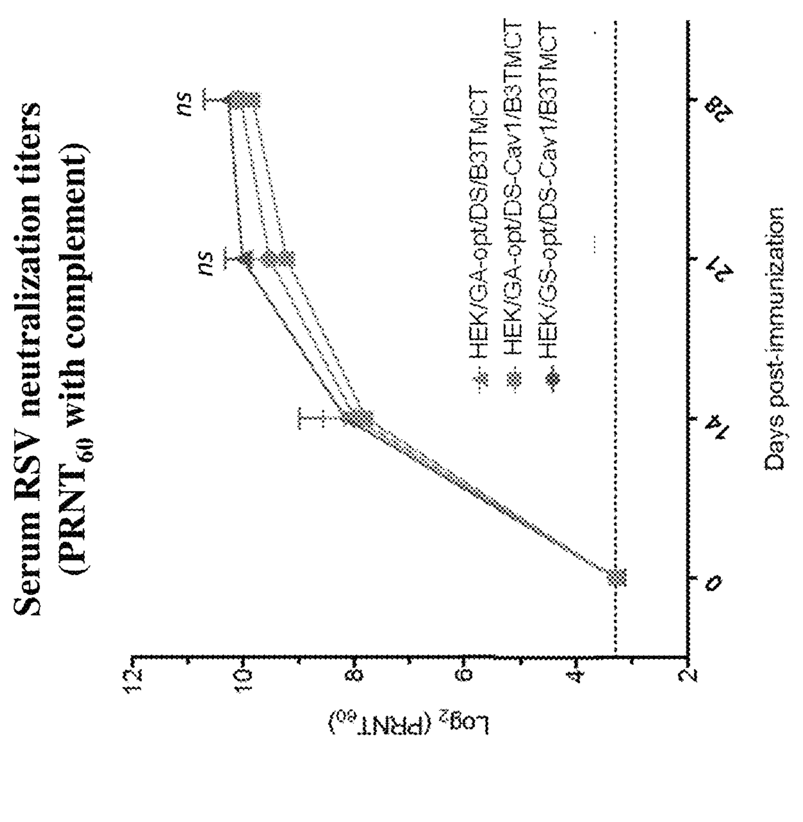
FIGS. 57A and 57B. Serum RSV-neutralizing antibody titers induced by rB/HPIV3 vectors. From the experiment shown in FIGS. 55 and 56, sera were collected at 0, 14, 21, and 28 days post-immunization.
Figure 57B:
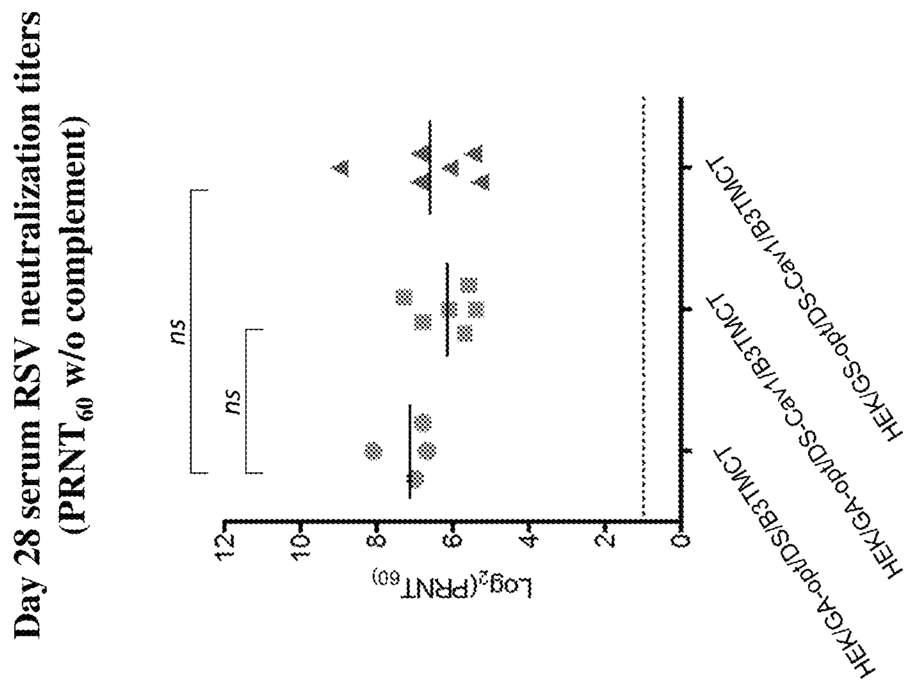

FIG. 35 indicates the constructs that have been evaluated in two different studies in hamsters and two different studies in rhesus monkeys, as indicated: the "1$^{st}$ hamster study" encompasses FIGS. 8-9, 14-16, and 23-26; the "1$^{st}$ NHP study" encompasses FIGS. 29-33; the "2$^{nd}$ hamster study" encompasses FIGS. 51-54; the "2$^{nd}$ NHP study" encompasses FIGS. 55 and 57.

Multi-Cycle Replication In Vitro of GA-Opt Viruses.

Figure 46:
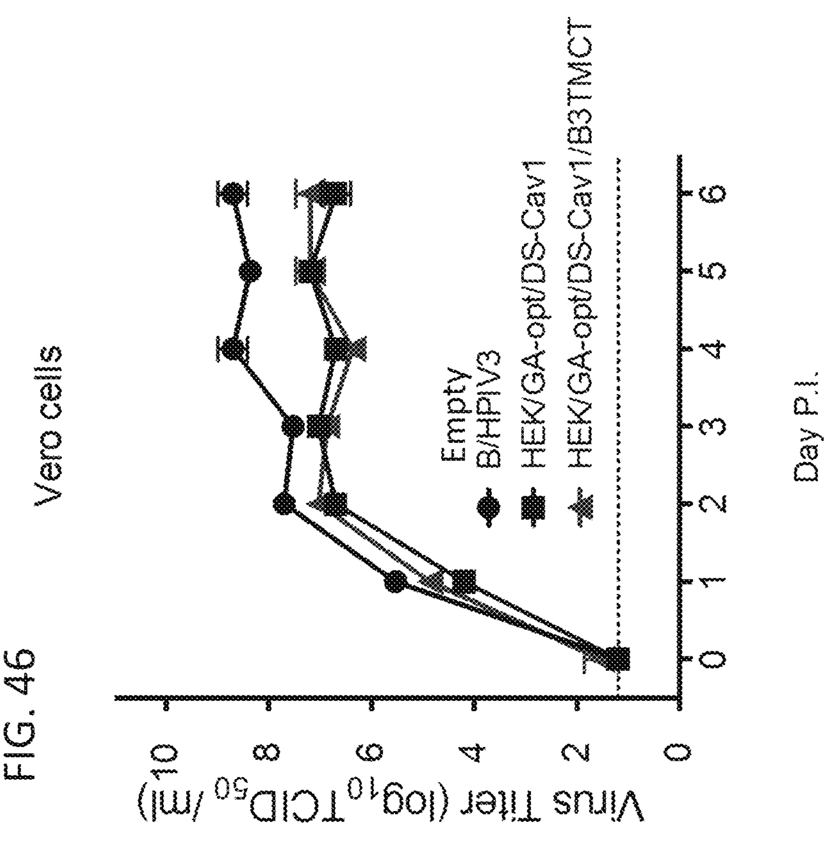
FIGS. 46 and 47. Multi-cycle in vitro replication of rB/HPIV3 vectors expressing GA-optimized (GA-opt) prefusion form of RSV F with DS-Cav1 mutations.
Figure 47:
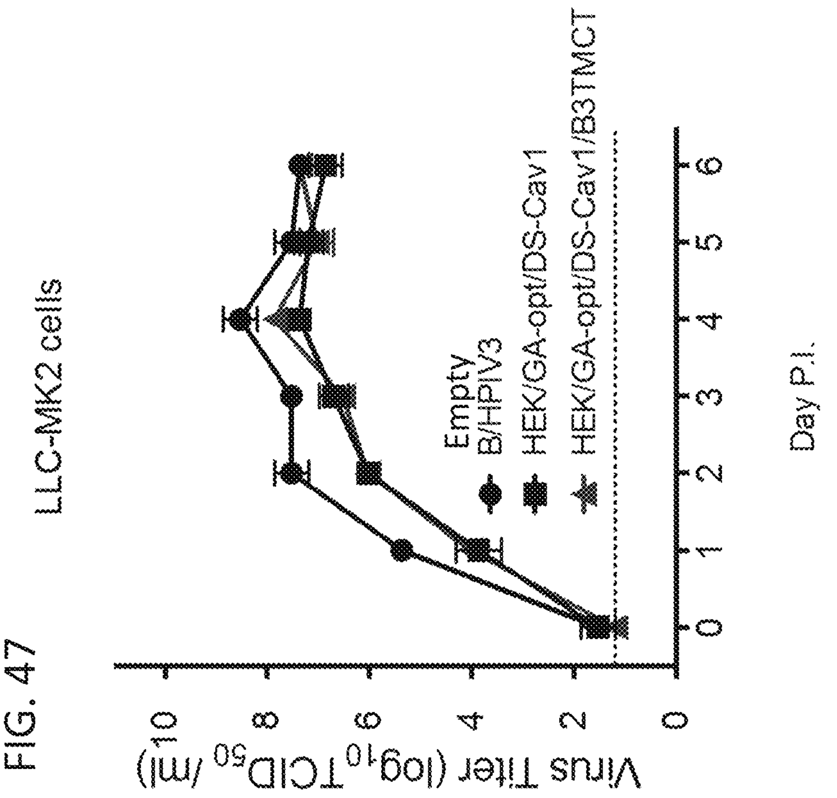

FIGS. 46 and 47 illustrate multi-cycle replication of the HEK/GA-opt/DS-Cav1 construct on its own or with the further addition of the B3TMCT packaging signal (constructs #13 and 15 in FIG. 35), compared to the empty vector. This was done in African Green monkey kidney Vero cells (FIG. 46), which is the cell substrate used for vaccine manufacture, and in rhesus monkey kidney LLC-MK2 cells (B), which is a common laboratory cell line that, unlike Vero cells, typically is induced by virus infection to express type I interferons. This experiment showed that the two DS-Cav1-containing constructs (with or without B3TMCT) replicated efficiently and similarly to each other, and were modestly attenuated compared to the empty vector. Despite this modest attenuation, both DS-Cav1-containing constructs replicated to titers higher than $10^7$ $TCID_{50}$/ml. This pattern of modest attenuation is very similar to results obtained with other rB/HPIV3 vectors expressing different versions of RSV F (e.g. FIGS. 7, 12, and 20). Thus, these results showed that rB/HPIV3 bearing these modified inserts replicated in an efficient manner that is fully satisfactory for vaccine manufacture.

Multi-Cycle Replication In Vitro of GS-Opt Viruses.

Figure 48B:
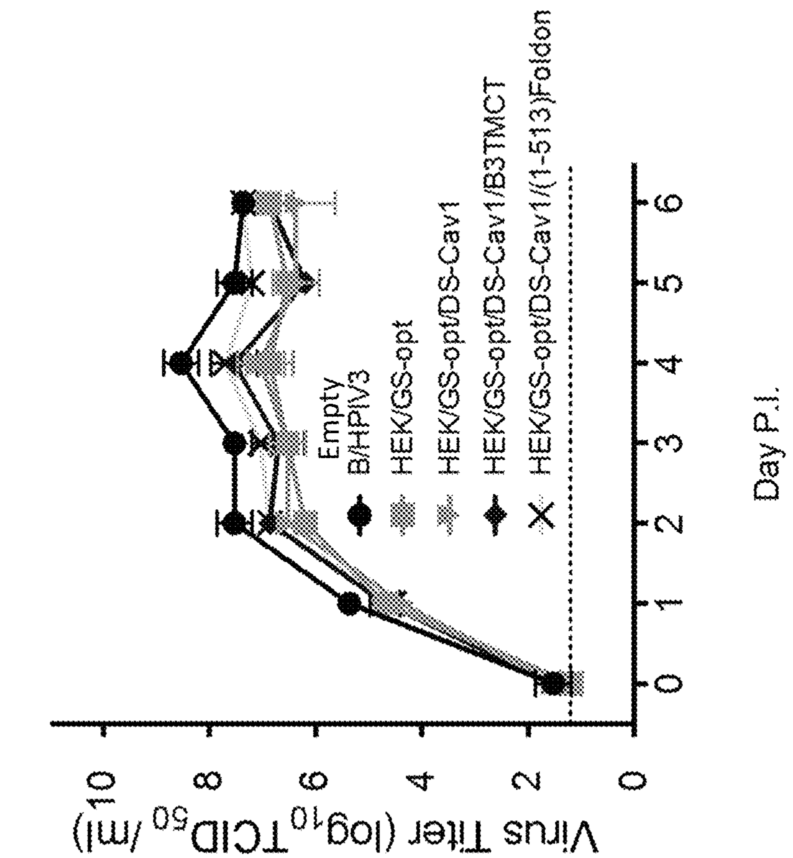
FIGS. 48A and 48B. Multi-cycle in vitro replication of rB/HPIV3 vectors expressing GS-optimized (GS-opt) RSV F with different modifications. (A) Vero and (B) LLC-MK2 cells were infected in triplicate at 32° C. at an MOI of 0.01 $TCID_{50}$ with empty rB/HPIV3 vector (empty B/H3) or vector expressing the RSV F ORF that was HEK-containing and GS-opt RSV F (HEK/GS-opt), or was HEK-containing, GS-opt and bearing DS-Cav1 prefusion stabilizing mutations (HEK/GS-opt/DS-Cav1), or was HEK-containing, GS-opt, and bearing the DS-Cav1 mutations and BPIV3-specific TM and CT domains (HEK/GS-opt/DS-Cav1/B3TMCT), or was a truncated RSV F with amino acids from 1 to 513 that was fused to a four-amino acid linker and 27-amino acid oligomerization sequence from T4 phage, which was HEK-containing, GS-opt and bearing DS-Cav1 mutations (HEK/GS-opt/DS-Cav1/(1-513)Foldon). Aliquots of medium supernatants were collected at 24 h intervals for 6 days and viral titers were determined by limiting dilution assay on LLC-MK2 cells at 32° C. and reported as $TCID_{50}$/ml. Mean titers±SEM from three independent experiments are shown.
Figure 48A:
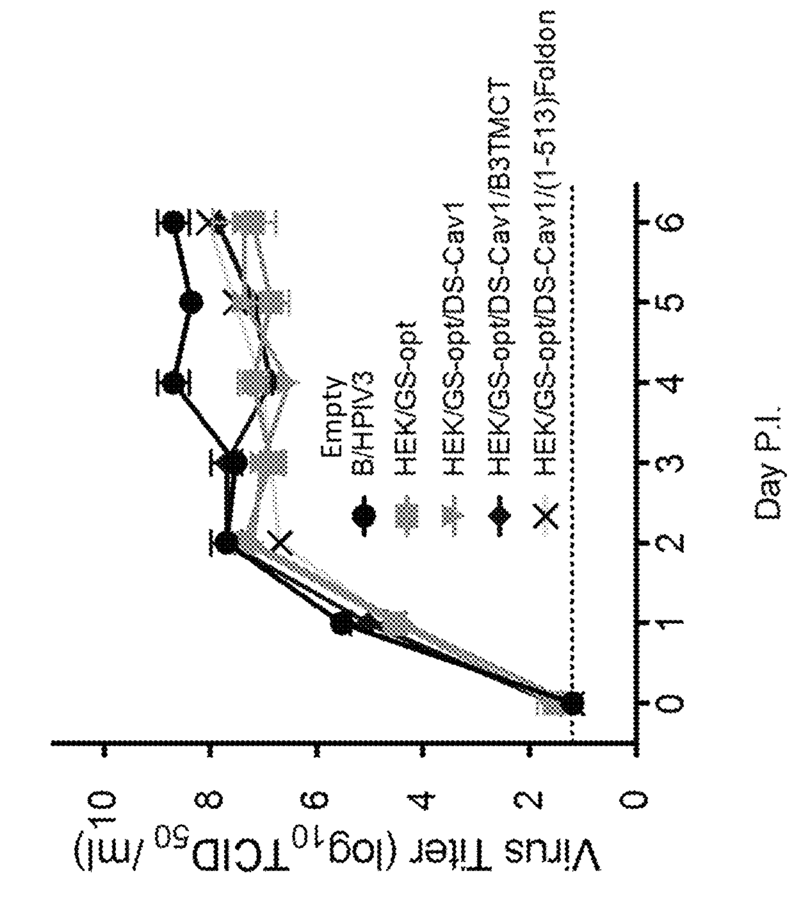
Figure 49A:
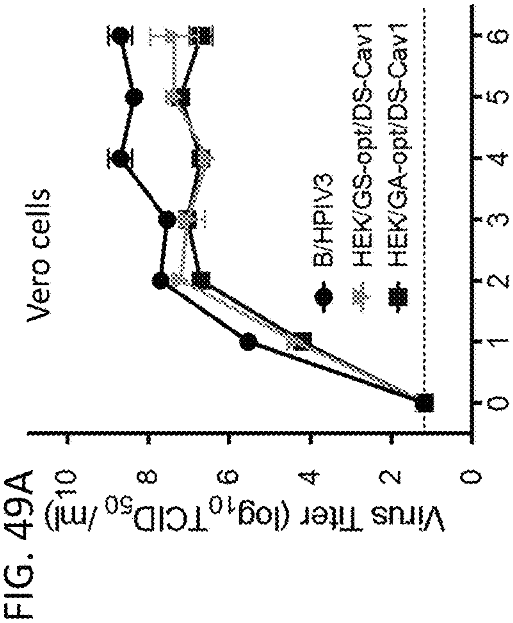
FIGS. 49A-49D. Comparison of multi-cycle in vitro replication of rB/HPIV3 vectors expressing GS-opt and GA-opt RSV F.
Figure 49B:
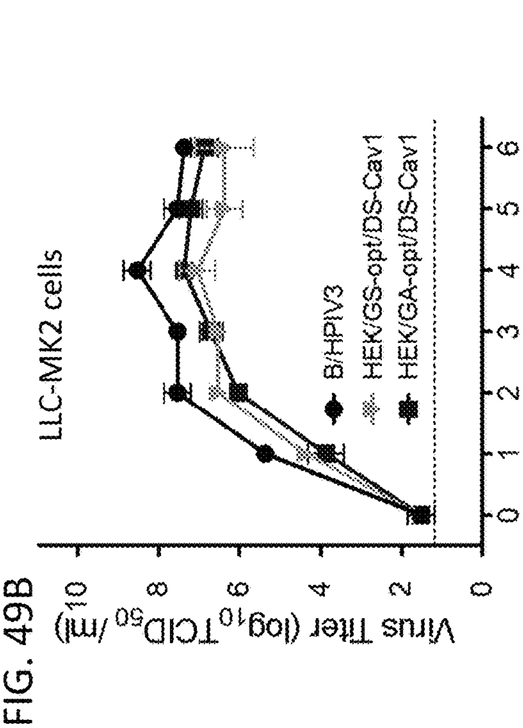
Figure 49C:
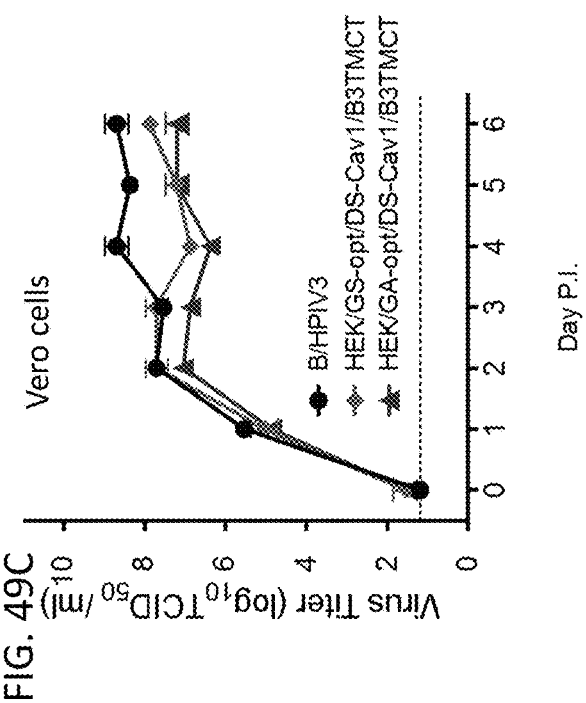
Figure 49D:
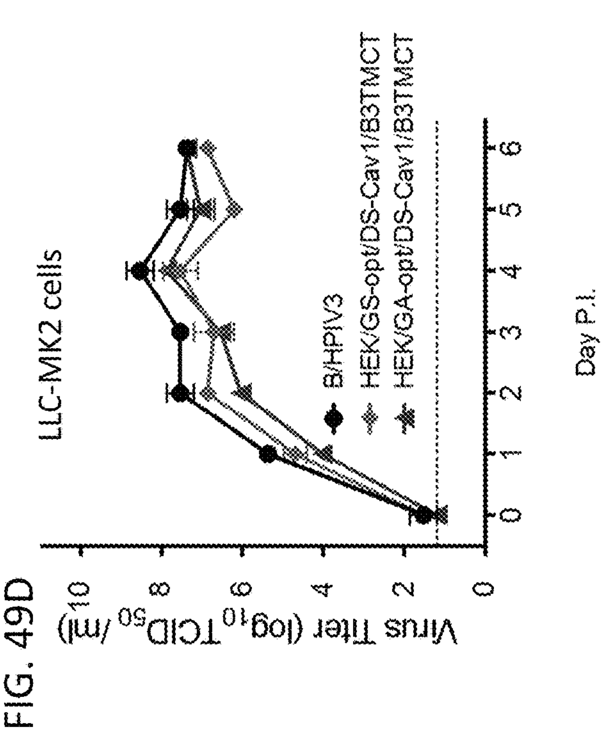

FIG. 48 illustrates multi-cycle replication of the HEK/GS-opt backbone (construct #5 in FIG. 35) compared with versions with the further additions of DS-Cav1 (#16), the combination of DS-Cav1/B3TMCT (#18), and the combination of DS-Cav1, ectodomain 1-513, and a C-terminal "foldon" domain to promote ectodomain oligomerization (#19), with empty vector for comparison. Evaluation in Vero (FIG. 48A) and LLC-MK2 (B) cells showed that the vectors expressing the various forms of RSV F replicated with very similar kinetics and yield, and were modestly attenuated compared to the empty vector. They all replicated to titer higher than $10^7$ $TCID_{50}$/mL in cell culture. These results showed that rB/HPIV3 bearing these modified inserts replicated in an efficient manner that is fully satisfactory for vaccine manufacture.

Multi-Cycle Replication In Vitro of GA- and GS-Opt Viruses.

FIG. 49 illustrates multi-cycle replication of pairs of constructs that differ in being GA-optimized or GS-optimized: specifically: HEK/GS-opt/DS-Cav1 versus HEK/GA-opt/DS-Cav1 (top panels, constructs #16 and 13 respectively from FIG. 35), and HEK/GS-opt/DS-Cav1/B3TMCT versus HEK/GA-opt/DS-Cav1/B3TMCT (bottom panels, constructs #18 and 15 respectively from FIG. 35). The two pairs of constructs were each evaluated in Vero (FIG. 49A, C) and LLC-MK2 (B, D) cells. The GS-opt constructs sometimes replicated marginally more efficiently than the GA-opt constructs (e.g. FIGS. 49C and 49D), especially during the first 3-4 days of incubation.

Expression of RSV F In Vitro.

Figure 50A:
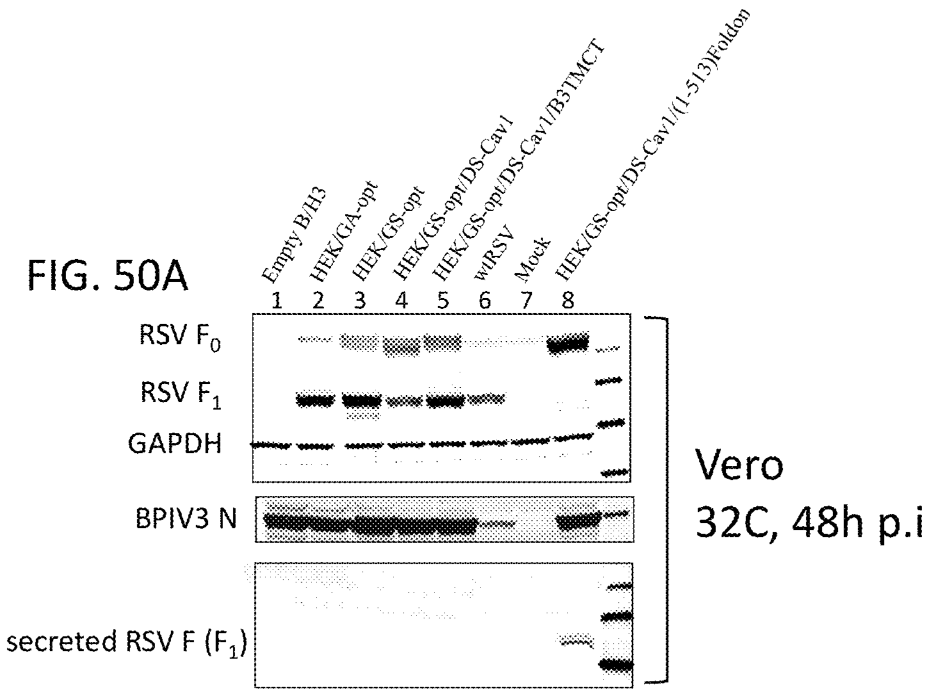
FIGS. 50A-50C. Expression of various modified forms of RSV F by rB/HPIV3 vectors in cell culture. (A) Vero and (B, C) LLC-MK2 cells were infected with empty rB/HPIV3 vector (lane 1), or rB/HPIV3 vector expressing the indicated modified forms of RSV F (lanes 2-5 and 8), or wt RSV (wt RSV, lane 6) at MOI of 3 PFU/cell, or uninfected (mock, lane 7). Infected Vero (A) and LLC-MK2 (B) cells were incubated at 32° C., and LLC-MK2 (C) cells were incubated at 37° C. Cell lysates and medium supernatant of Vero cells were collected at 48 hpi and were subjected to Western blot analysis for the expression of RSV F, which was detected as cleaved $F_1$ and/or un-cleaved $F_0$ forms. BPIV3 N was used as an internal control for the expression of vector protein; GAPDH was used as a loading control.
Figure 50B:
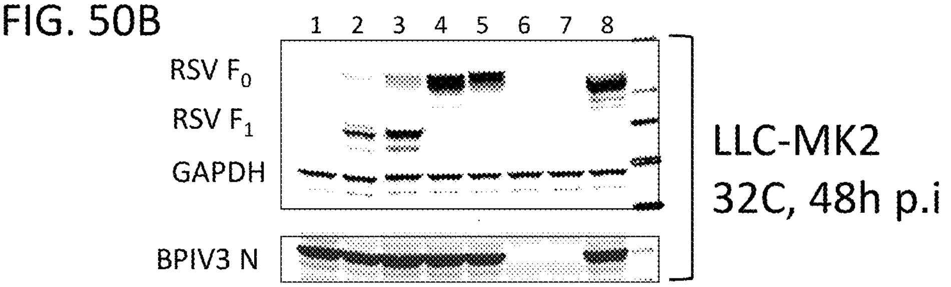
Figure 50C:
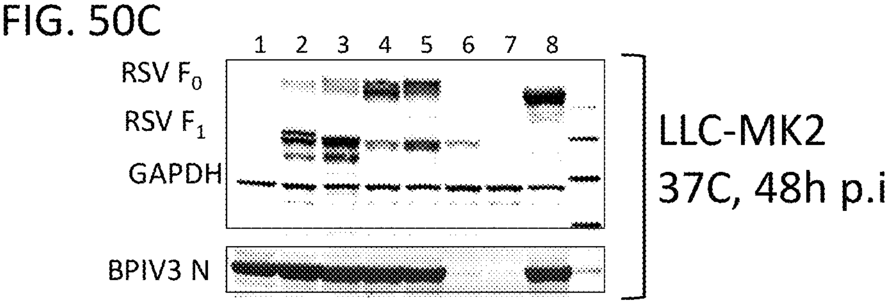

FIG. 50 illustrates expression of RSV F and vector proteins by rB/HPIV3 constructs in Vero and LLC-MK2 cells. This compares expression by HEK/GA-opt (FIG. 50, lane 2; FIG. 35, construct #3) versus HEK/GS-opt (FIG. 50, lane 3; FIG. 35, construct 5): consistent with results described in Example 1 (FIG. 5), the GS-optimization resulted in somewhat greater expression of RSV F protein. The HEK/GS-opt construct also was compared to versions that, in addition, contained DS-Cav1 (FIG. 50, lane 3; FIG. 35, construct #16), or DS-Cav1/B3TMCT (FIG. 50, lane 5; FIG. 35, construct #18), or DS-Cav1/(1-513)Foldon (FIG. 50, lane 8; FIG. 35, construct #19). Also included for comparison were cells infected with wt RSV (FIG. 50, lane 6) or mock-infected (lane 7). The results showed that each of the GS-opt constructs directed efficient expression of RSV F, and indeed expressed much more RSV F than did wt RSV (FIG. 50, lane 6). Cells infected with the three GS-opt constructs encoding full-length DS-Cav1 F protein (FIG. 50, lanes 4, 5, and 8) had a somewhat greater accumulation of the F0 precursor of RSV F protein, suggesting that its prefusion stabilization may have marginally reduced the efficiency of cleavage. In general, however, each of the constructs was very efficient in expressing the RSV F protein. The prefusion Foldon construct, HEK/GS-opt/DS-Cav1/(1-513)Foldon (FIG. 50, lane 8), was only partly secreted into the medium (FIG. 50A, lower panel), and the secreted form was entirely the cleaved $F_1$ chain (FIG. 4A, lower panel, lane 8), whereas all of the cell-associated form was uncleaved $F_0$ (FIG. 4A, upper panel, B and C, lane 8). None of other tested forms of RSV F was detected in the medium supernatant, indicating they were not secreted. The inefficient cleavage and secretion of the DS-Cav1/(1-513) Foldon construct was unexpected, since this trimerization domain had been successfully used previously to prepare purified F protein (McLellan et al Science 2013 Nov. 1; 342(6158):592-8. doi: 10.1126/science.1243283). This illustrates that expression of foreign proteins by vectored constructs can be unpredictable, whereas the detailed evaluation of multiple constructs herein provides comprehensive evaluation leading to the identification of a number of suitable, successful constructs.

Hamster Studies.

A number of GA-opt and GS-opt constructs that contained the further additions of B3TMCT, DS, and DS-Cav1 (the constructs are identified in FIG. 35 as the "2$^{nd}$ hamster study") were evaluated in hamsters for efficiency of replication (FIG. 51), stability of expression of RSV F protein, stimulation of RSV-neutralizing serum antibodies (FIGS. 52 and 53), and protective efficacy against RSV challenge (FIG. 54).

Replication in Hamsters.

Figure 51B:
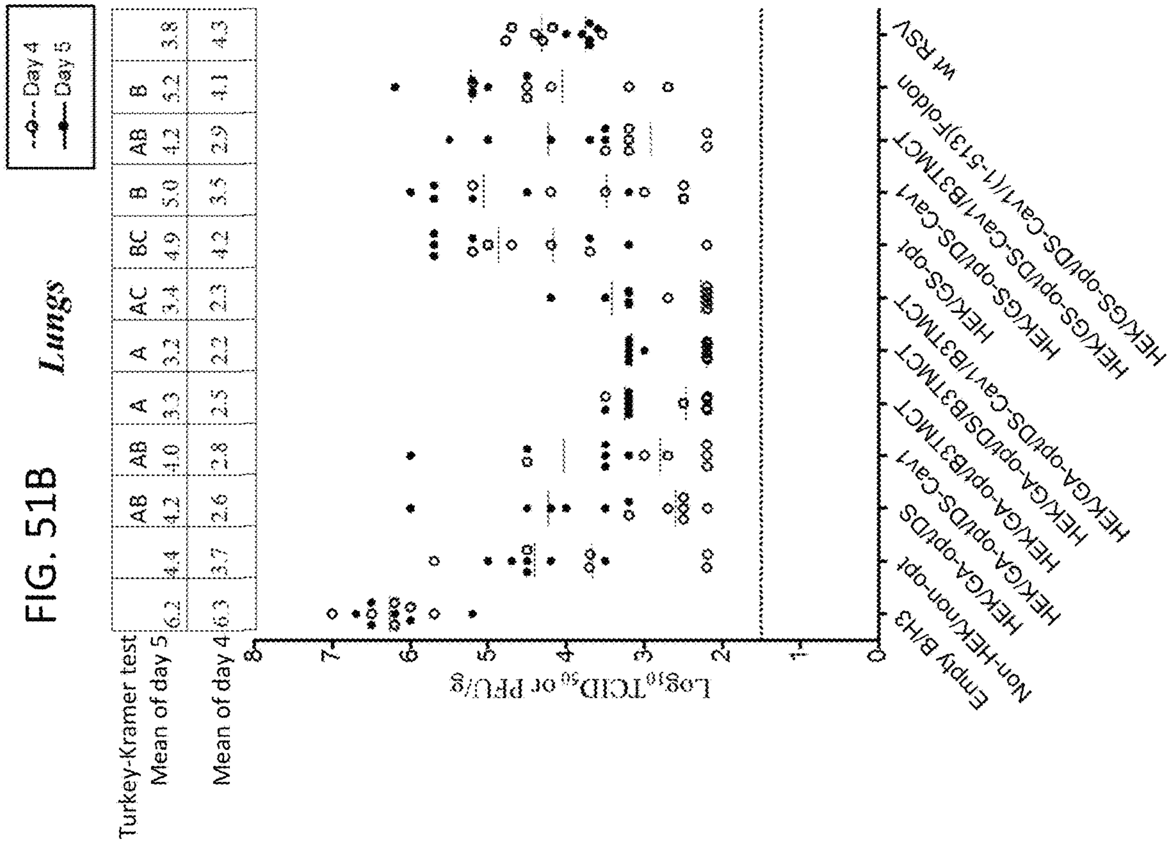
FIGS. 51A and 51B. Replication of rB/HPIV3 vectors in the upper and lower respiratory tract of hamsters. Hamsters were infected IN with $10^5$ $TCID_{50}$ of the indicated rB/HPIV3 vectors or $10^6$ PFU of wt RSV in a 0.1 ml inoculum Hamsters were euthanized (n=6 per virus per day) on days 4 and 5 post-infection and the (A) nasal turbinates and (B) lungs were removed and homogenized, and viral titers were determined by limiting dilution on LLC-MK2 cells at 32° C. and reported as $TCID_{50}$/g (rB/HPIV3 vectors) or were determined by plaque assays on Vero cells at 32° C. and reported as PFU/g (wt RSV). The limit of detection (LOD) is 1.5 login $TCID_{50}$/g of tissue, indicated with a dotted line. Open and closed circles indicate titers for individual animals sacrificed on day 4 and 5, respectively. The mean titers of each group are indicated by a dashed and solid horizontal line for day 4 and 5, respectively. The values of the mean titers on day 4 and 5 are shown at the top. The mean viral titers on day 5 were assigned to different groups using the Tukey-Kramer test: mean titers with different letters are statistically different ($p<0.05$), whereas titers indicated with two letters are not significantly different than those indicated with either letter.
Figure 51A:
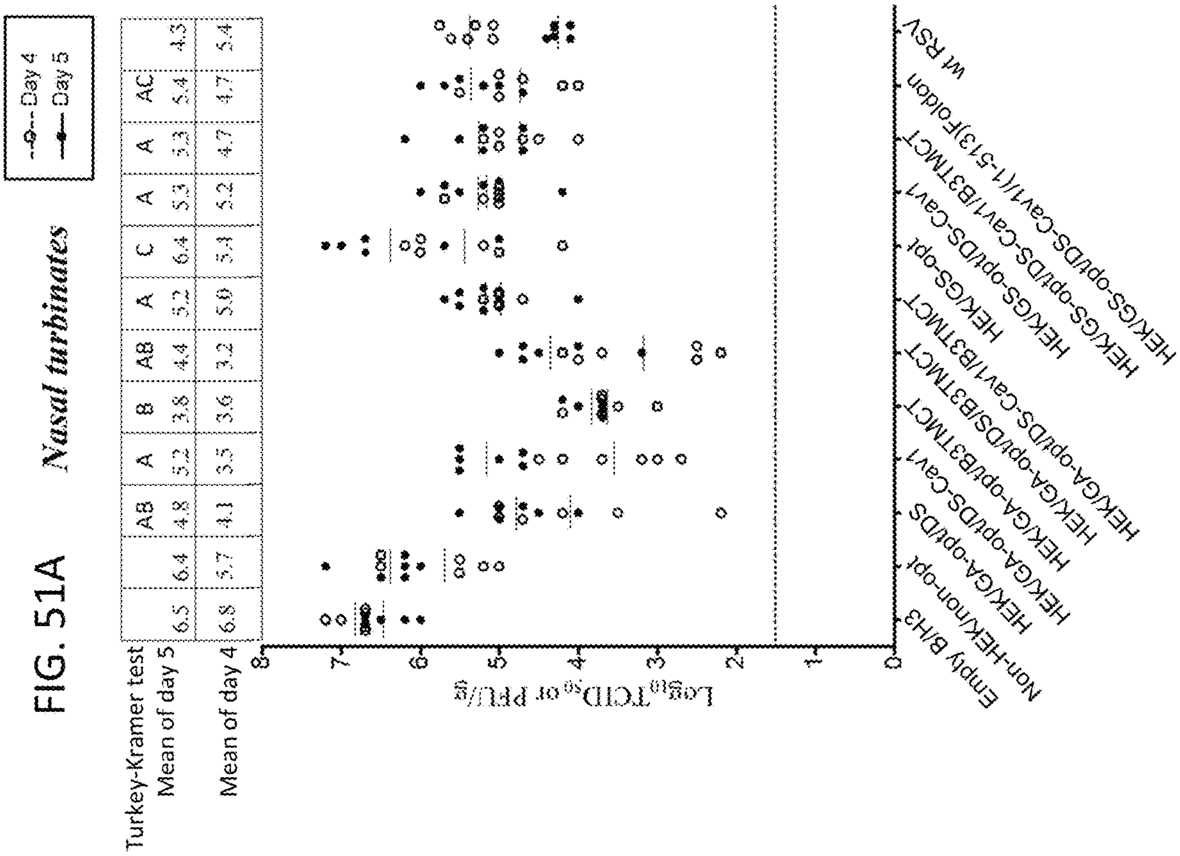

GA-opt and GS-opt constructs were evaluated for replication in the upper (nasal turbinates) and lower (lungs) respiratory tract of hamsters (FIG. 51). In the nasal turbinates, HEK/GA-opt/B3TMCT (group #5) and HEK/GA-opt/DS/B3TMCT (group #6) were more restricted than others. In the lungs, GA-opt constructs with B3TMCT (HEK/GA-opt/B3TMCT, group #5, HEK/GA-opt/DS/B3TMCT, group #6, and HEK/GA-opt/DS-Cav1/B3TMCT, group #7) were more restricted. Similarly, GS-opt constructs with B3TMCT, i.e., HEK/GS-opt/DS-Cav1/B3TMCT (group #10) was also more attenuated than HEK/GS-opt/DS-Cav1 (group #9). These observations suggested that B3TMCT increases the level of attenuation. In addition, GA-opt constructs appeared to be more attenuated than GS-opt constructs. For example, GS-opt constructs of DS-Cav1 and DS-Cav1/B3TMCT, i.e., HEK/GS-opt/DS-Cav1 (group #9) and HEK/GS-opt/DS-Cav1/B3TMCT (group #10) replicated to mean peak titers of 5.0 and 4.2 $Log_{10}$ $TCID_{50}$/g in the LRT, which was higher than the mean titers of equivalent GA-opt constructs, i.e. 4.0 and 3.4 $Log_{10}$ $TCID_{50}$/g (groups #4 and 7). This suggested that GS-opt RSV F inserts were less attenuating than GA-opt RSV F.

Stability of Expression of RSV F Protein.

The stability of RSV F expression by rB/HPIV3 vectors during their replication in vivo was evaluated with double-staining plaque assay by analyzing nasal turbinate and lung samples of immunized hamsters harvested on day 5 post-immunization. Most of samples (92 out of 107) had more than 90% of replicated vectors still expressing RSV F; 6 out of 107 had 89-80% vectors expressing RSV F; 9 out of 107 had less than 79% of replicated vectors expressing RSV F; only 7 samples had >50% of vectors losing RSV F expression. Among these seven samples with >50% vectors losing RSV F expression, four were GA-opt constructs, three were GS-opt constructs. There was no evidence that GA-opt, or GS-opt, or DS, or DS-Cav1, or TMCT were associated with any particular increase in instability. It is likely that the varying levels of instability among individual preparations reflect sporadic mutations that are largely independent of the specific construct, and thus evaluation of several independent preparations of each construct likely would identify one or more with a very high percentage of expression of RSV F protein.

Titers of RSV-Neutralizing Serum Antibodies.

Figure 52:
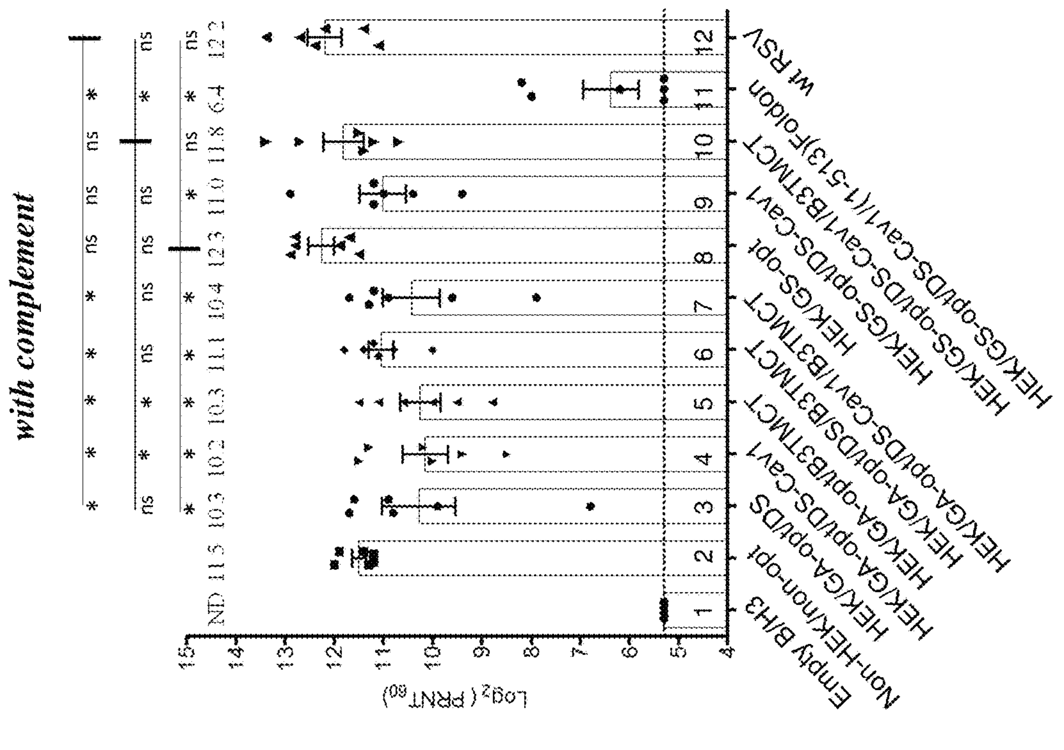
FIGS. 52 and 53. Serum RSV-neutralizing antibody titers from hamsters infected with the indicated rB/HPIV3 vectors expressing the GA-opt or GS-opt RSV F protein with or without the DS or DS-Cav1 or B3TMCT modifications. Hamsters (n=6 animals per virus) were inoculated IN with $10^5$ $TCID_{50}$ of the indicated rB/HPIV3 vectors or $10^6$ PFU of wt RSV in a 0.1 ml inoculum. Serum samples were collected at 28 days post-immunization, and antibody titers were determined by a 60% plaque reduction neutralization test ($PRNT_{60}$) with (FIG. 52) or without (FIG. 53) added guinea pig complement. The height of each bar represents the mean titer shown along with the SEM. The values of mean titers are shown above the bars. The pairwise student t-test was used to evaluate the statistical significance of differences between values: in each of the three horizontal lines over the mean titers, the value indicated with a vertical bar was compared pair-wise to each of the others and recorded as being significantly (*, $p<0.05$) or not significantly (ns) different. The detection limit for the neutralization assay is indicated with a dotted line. ND, neutralization titer was below the detection limit.
Figure 53:
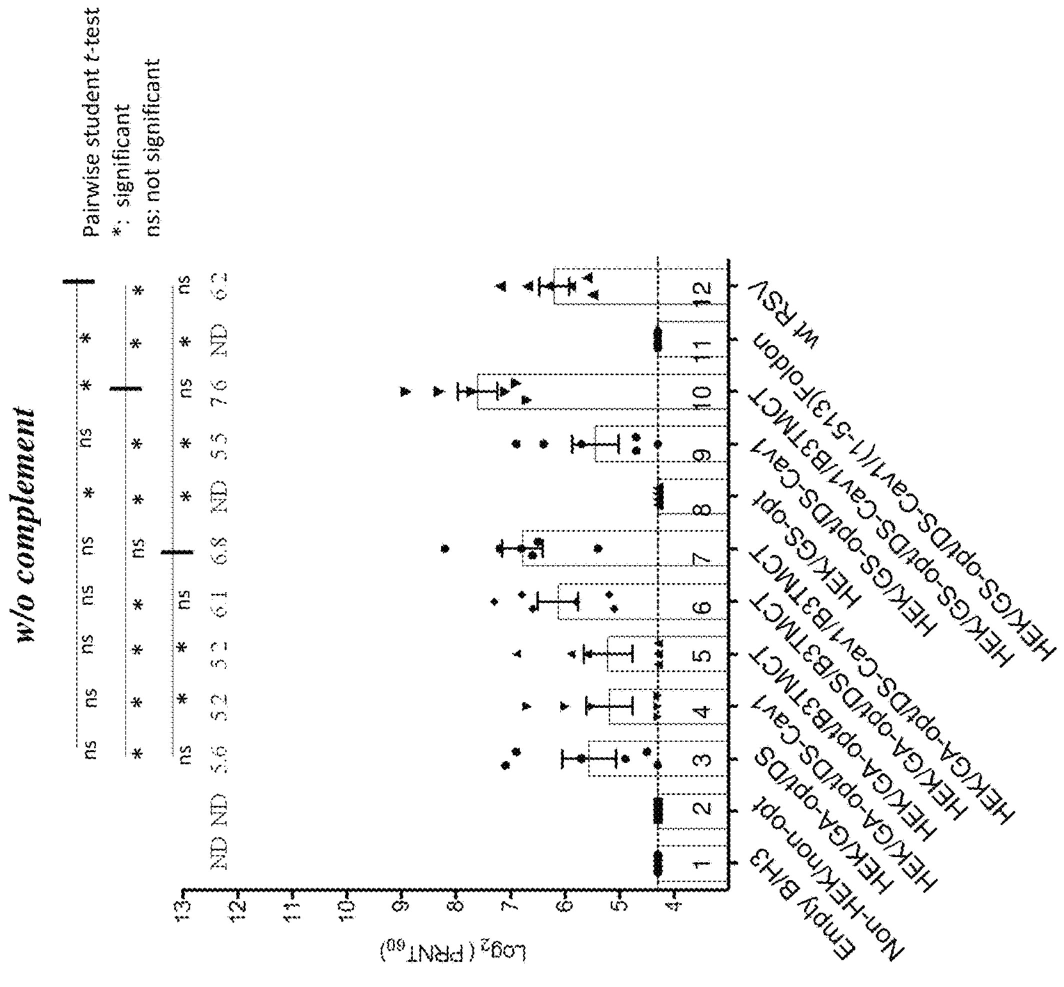

RSV neutralizing serum antibody titers were determined by RSV neutralization assays with added guinea pig complement (FIG. 52) or in the absence of complement (FIG. 53). The assay performed with added complement is commonly used for RSV and HPIV3 neutralization assays because it allows sensitive detection of virus-specific antibodies, since complement can confer viral-lysis and steric-hindrance capabilities to antibodies that otherwise might not be neutralizing in vitro (Yoder et al J Med Virol 72:688-694, 2004). In contrast, antibodies that neutralize RSV in vitro in the absence of complement have been suggested to be the most relevant for protection (Yoder et al J Med Virol 72:688-694, 2004), and in prior studies have associated with a higher level of protection against RSV challenge (Liang et al J Virol 89:9499-9510, 2015). Antibodies that neutralize in vitro independent of added complement are considered to be “high quality” and to be indicative of qualitatively superior immunogenicity.

In the complement-dependent assay (FIG. 52), all rB/HPIV3 vectors expressing RSV F induced high titers of RSV neutralizing antibodies except for the poorly immunogenic HEK/GS-opt/DS-Cav/(1-513)Foldon construct. GS-opt constructs induced higher titers of RSV serum neutralizing antibodies than their counterparts of GA-opt constructs (11.0 $Log_2$ $PRNT_{60}$ for HEK/GS-opt/DS-Cav1, group #9 versus 10.2 $Log_2$ $PRNT_{60}$ for HEK/GA-opt/DS-Cav1 group #4; 11.8 $Log_2$ $PRNT_{60}$ for HEK/GS-opt/DS-Cav1/B3TMCT, group #10 versus 10.4 $Log_2$ $PRNT_{60}$ for HEK/GA-opt/DS-Cav1/B3TMCT, group #7). In the complement-dependent assay (FIG. 52), it was noteworthy that the three constructs that were statistically as immunogenic as wt RSV (the gold standard) were the GS-opt constructs HEK/GS-opt (group #8), HEK/GS-opt/DS-Cav1 (group #9), and HEK/GS-opt/DS-Cav1/B3TMCT (group #10).

In the complement-independent assay (FIG. 53), vectors expressing native forms of RSV F (Non-HEK/non-opt and HEK/GS-opt) did not induce detectable RSV neutralizing antibodies, confirming and extending results from Example 1. Prefusion stabilizing mutations (DS, DS-Cav1) and the packaging signal B3TMCT independently increased immunogenicity for high quality RSV-neutralizing antibodies (e.g., constructs with DS and/or Cav1 in the absence of B3TMCT are exemplified by groups #3, 4, and 9, whereas a construct with B3TMCT in the absence of DS/Cav-1 is exemplified by group #5). The combination of prefusion stabilizing mutations plus B3TMCT had additive improvement in immunogenicity, which was observed with GA-opt as well as GS-opt constructs (e.g., groups 6, 7, and 10). In the complement-independent assay, the HEK/GS-opt/DS-Cav1/B3TMCT construct (group #10) induced significantly higher titers of RSV-neutralizing serum antibodies (7.6 $Log_2$ $PRNT_{60}$) than that induced by any of the other vectors except for its GA-opt counterpart HEK/GA-opt/DS-Cav1/B3TMCT (group #7) which induced a lower titer (6.8 $Log_2$ $PRNT_{60}$) but was not significantly lower. However, the antibody titer induced by HEK/GS-opt/DS-Cav1/B3TMCT construct (group #10), but not HEK/GA-opt/DS-Cav1/B3TMCT (group #7) was significantly higher than that of wt RSV (group 12), and therefore the HEK/GS-opt/DS-Cav1/B3TMCT construct (group #10) was the most immunogenic among the vectors and wt RSV for high quality RSV-neutralizing antibodies.

Rsv Challenge.

The immunized hamsters were challenged IN with wt RSV to evaluate protective efficacy (FIG. 54). As shown in FIG. 54, all of the RSV F-expressing vectors, except for the DS-Cav1/(1-513)Foldon construct, induced significant protection in the URT (FIG. 54A) and LRT (FIG. 54B). The lack of protection by DS-Cav1/(1-513)Foldon was in line with its poor immunogenicity shown in the RSV serum neutralization assays (FIGS. 52 and 53). Compared with the sterile immunity conferred by wt RSV, the HEK/GS-opt/DS-Cav1/B3TMCT conferred the greatest protection among all tested vectors and was nearly equivalent to wt RSV: only one hamster immunized by this vector had detectable wt RSV, and only at very low level in the nasal turbinates. The protective efficacy of HEK/GS-opt/DS-Cav1/B3TMCT (group #10) was statistically indistinguishable from that of wt RSV (group #12) in the nasal turbinates, whereas HEK/GA-opt/DS-Cav1/B3TMCT (group #7) was significantly less protective, supporting the idea that the former construct is the most immunogenic construct. This equivalence in protection to wt RSV is remarkable because wt RSV expresses two neutralization antigens, G and F, and also expresses all of the viral proteins as potential antigens for cellular immunity, whereas the vectors express only the RSV F protein. Cellular immunity has been shown to confer potent protection in RSV challenge studies in rodents (e.g., Connors et al J Virol 66:1277-1281 1992).

Evaluation in Rhesus Monkeys.

Three vectors with greatest immunogenicity in hamsters were selected to evaluate their replication and immunogenicity in rhesus monkeys (FIG. 55). These constructs included HEK/GA-opt/DS/B3TMCT (the construct at the top of FIG. 55), which was identified as particularly effective in the $1^{st}$ NHP study (FIGS. 28-32, in Example 1). The second construct was HEK/GA-opt/DS-Cav1/B3TMCT, which is the same as the first construct except that it has DS-Cav1 instead of DS. The third construct was HEK/GS-opt/DS-Cav1/B3TMCT, which differs from the previous construct in having GS-opt instead of GA-opt. These latter two constructs induced the highest titers of "high quality" RSV-neutralizing serum antibodies in FIG. 53.

Replication in Rhesus Monkeys.

Figure 56A:
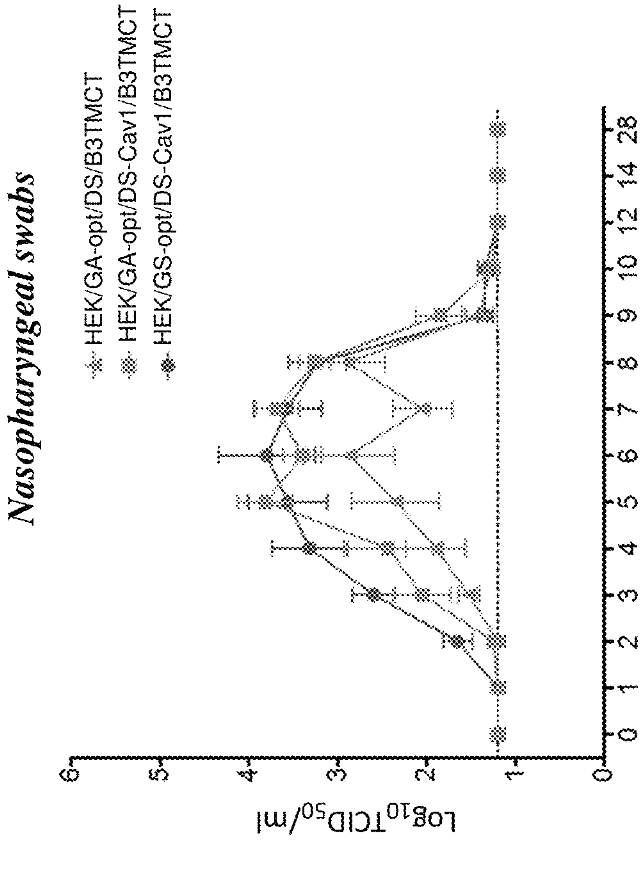
FIGS. 56A and 56B. Replication of rB/HPIV3 vectors in rhesus macaques. Rhesus macaques were infected with the rB/HPIV3 vectors indicated in FIG. 55. Vector replication in the respiratory tract was assessed by collecting (A) nasopharyngeal swabs and (B) tracheal lavages on the indicated days and determining the viral titers by limiting dilution assay. Limit of detection is 1.2 $\log_{10}$ $TCID_{50}$/mL shown as dotted line.
Figure 56B:
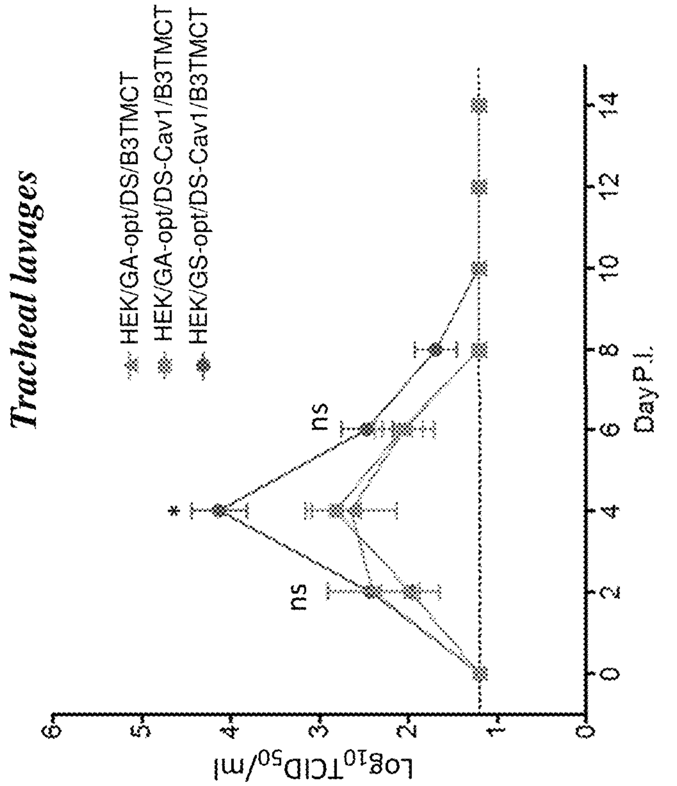

The parallel constructs with GA-opt and GS-opt versions of HEK/DS-Cav1/B3TMCT replicated in similar kinetics in the URT, as sampled by nasopharyngeal swabs (FIG. 56A). However, this equivalency was not observed in the LRT, as sampled by tracheal lavage: the GS-opt version was less attenuated than GA-opt version (FIG. 56B). These results are consistent with what was observed in hamsters in FIG. 51. With regard to the comparison of parallel constructs with DS versus DS-Cav1 (HEK/GA-opt/DS/B3TMCT versus HEK/GA-opt/DS-Cav1/B3TMCT), the former virus was more attenuated in the URT (FIG. 56A); but they replicated at similar efficiency in the LRT (FIG. 56B). These results also are consistent with what was observed in hamsters in FIG. 51. It is noticeable that the HEK/GA-opt/DS/B3TMCT replicated to significantly higher titers (~10-fold higher) in both URT and LRT in this study, compared to the same construct tested in the 1$^{st}$ NHP study (FIG. 29, Example 1). The monkeys in the previous study (FIG. 29) were 6 years older and 2-3 times bigger in weight than monkeys used in FIG. 56. It may be that replication of these viruses is more efficient in younger monkeys, or the difference might reflect variability between these two experiments.

RSV-Neutralizing Serum Antibodies.

Although the three vectors in FIG. 56 replicated at slightly different efficiencies in rhesus monkeys, they induced comparably high levels of RSV-neutralizing serum antibodies determined by complement-dependent (FIG. 57A) and complement-independent (FIG. 57B) assays.

Insertion of RSV F at the First Gene Position.

Figure 58A:
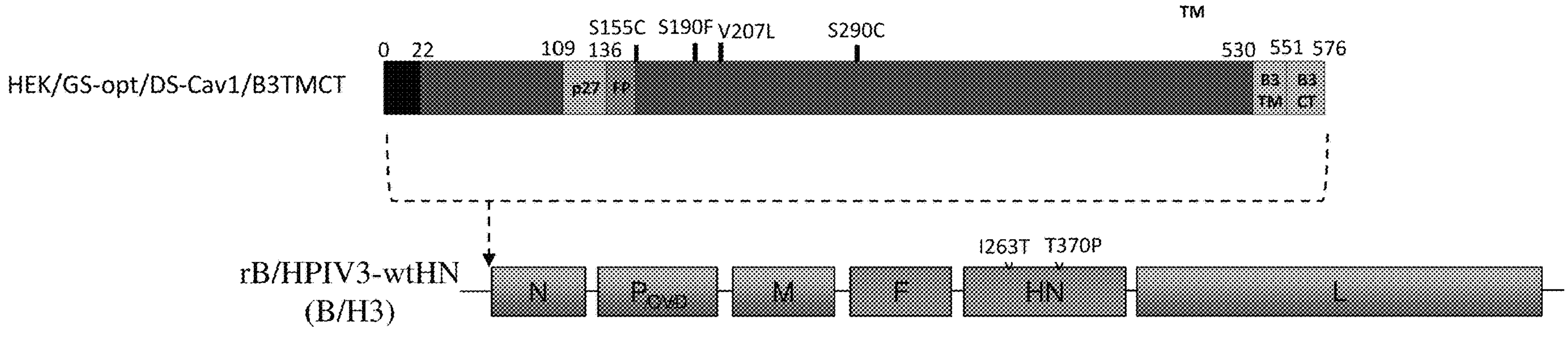
FIGS. 58A and 58B. Construction of a rB/HPIV3 vector expressing HEK/GS-opt/DS-Cav1/B3TMCT from the pre-N position, and modification of the amino acid sequence of the HPIV3 HN protein to achieve increased phenotypic stability of the vector.

All of the previous B/HPIV3-RSV-F constructs in Examples 1 and the present Example involved an RSV gene inserted in the second gene position, between the vector N and P genes. Insertion of unmodified RSV F at the first position was not associated with any evident problems of impaired growth or reduced stability of expression of RSV F protein. Whether an optimized, engineered form of RSV F could be efficiently and stably expressed from the first gene position was investigated. Specifically, the HEK/GS-opt/DS-Cav1/B3TMCT version of RSV F was inserted into the pre-N position (FIG. 58A).

Identification and Modification of Two Amino Acid Assignments in HN that Conferred Phenotypic Instability of the Vector.

Figure 58B:
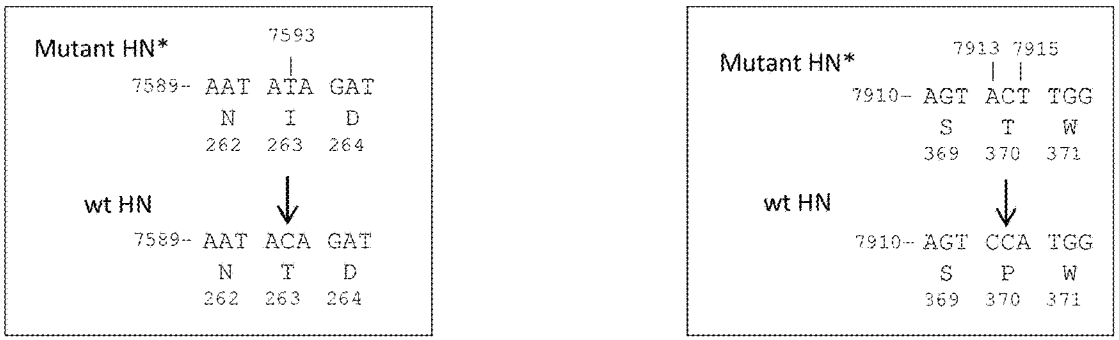

The rB/HPIV3 vector was previously noted to exhibit phenotypic instability upon passage in vitro (Liang et al J Virol 88:4237-4250). Specifically, a substantial proportion of vector acquired a large-plaque phenotype during passage. This occurred with different inserts as well as with empty vector, indicating that it was a property of the vector alone and not specific to the foreign gene. Whole-genome sequence analysis of six cloned large-plaque viruses showed that each had acquired an H552Q missense mutation in HN, as well as one of three different missense mutations in F, and in some cases one or two missense mutations in L (Liang et al J Virol 88:4237-4250). Partial sequencing of 11 additional large-plaque clones showed that seven of these contained the H552Q mutation in HN, while the other four each contained one of four other missense mutation in HN (N240K, P241L, R242K, or F558L). Comparison with the crystal structure of the HPIV3 HN protein (Lawrence et al J Mol Biol 335: 1343-1357 2004) indicated that all of these HN mutations are located in the dimer interface of the HN globular head. In addition, the H552Q mutation had previously been described in an HPIV3 variant that had been selected by growth on neuraminidase-treated cells, and which had a large-plaque phenotype, had higher avidity to sialic acid-containing receptor, had enhanced triggering of F protein, and was attenuating in rodents (Moscona et al J Virol 67:6463-6468; Porotto et al J Virol 81:3216-3228; Palermo et al J Virol 83:6900-6908). This suggested that the adventitious mutations in the HPIV3 HN gene in the rB/HIPIV3 vector were similar and probably were selected for because they increased the binding affinity of the rB/HPIV3 vector for Vero cells. However, the observation by others (Moscona et al J Virol 67:6463-6468; Porotto et al J Virol 81:3216-3228; Palermo et al J Virol 83:6900-6908) that the large-plaque phenotype was associated with substantial attenuation in vivo would be disadvantageous for the present vectors because this likely would lead to over-attenuation. The HPIV3 reverse genetic system contained two mutations in the HN gene: there was an adventitious C7589T nucleotide mutation (relative to the complete antigenome sequence) in the cDNA clone leading to a T2631 missense mutation, and C7913A and A7915T mutations leading to a P370T mutation that had been purposefully introduced as a marker (Durbin et al Virology 235:323-332, 1997). This latter missense mutation had been designed to ablate an epitope recognized by two available HPIV3-neutralizing monoclonal antibodies (MAbs 423/6 and 170/7). These mutations were restored to their wild-type assignments, namely 7593C (263T) and 7913C+7915A (370P) (FIG. 58B). Remarkably, these changes prevented acquisition of the large-plaque phenotype during passage in Vero cells (not shown). Therefore, further vector constructs bearing the HPIV3 HN gene (including but not limited to rB/HPIV3- and HPIV3-based vectors) preferably should contain these assignments. For example, the I263T and T370P mutations were incorporated into the HEK/GS-opt/DS-Cav1/B3TMCT/pre-N construct shown in FIG. 58A. All vectors of interest that bear the HPIV3 HN gene will be modified to contain the 263T and 370P assignments.

Virus Recovery.

The rB/HPIV3 vector with HEK/GS-opt/DS-Cav1/B3TMCT inserted in the pre-N position (FIG. 58A) was recovered and grew to titers up to 8.2 $log_{10}$ $TCID_{50}$/mL, and thus had little or no growth restriction with regard to viral yield, which is important for vaccine manufacture. The plaque size of this virus was generally smaller than the same version of RSV F inserted in the second position (not shown), indicating that there was a modest restriction on growth that was not evident in the virus yield.

Stability of Expression of RSV F Protein.

Two preparations of viruses were analyzed by a double-staining plaque assay, to evaluate stability of expression of the RSV F protein. Double-staining plaque phenotype of two independent rescued virus pools, designated CL20a and CL24a, were performed. Plaque assay was carried out on Vero monolayer in 24-well plates infected with 10-fold serially diluted virus. Infected monolayers were overlaid with medium containing 0.8% methylcellulose and incubated at 32° C. for 6 days. After fixing in ice-cold 80% methanol, the monolayers were incubated with a mixture of three mouse monoclonal antibodies against RSV F (1129, 1109, 1243) and a rabbit anti-HPIV3 hyperimmune serum, followed by incubation with IRDye 680 (red, detecting RSV F) conjugated goat anti-mouse and IRDye 800 (green, detecting HPIV3) conjugated goat anti-rabbit antibodies.

One preparation was stable after passaging in cell culture, whereas a second preparation had green staining in ~40% of viruses and thus had evidence of loss of RSV F expression. These results indicated that loss of RSV F expression can occur and can be amplified in the virus preparation, but it appeared to be sporadic and careful monitoring can identify preparations with a high proportion of expression.

Intracellular protein expression. Expression of RSV F from the pre-N position was analyzed in Vero (FIG. 59A) and LLC-MK2 (FIG. 59B) cells. In Vero cells, HEK/GS-opt/DS-Cav1/B3TMCT version of RSV F was expressed as $F_1$ and $F_0$ chains (FIG. 59A), and the total expression from the pre-N position was comparable to that expressed from the N-P position. But in LLC-MK2 cells (FIG. 59B), this version of RSV F was predominantly expressed as $F_0$ chain, and expression from pre-N was substantially more efficient than that from N-P position (FIG. 59B, lane 3, 4, 5). In both types of cells, this version of RSV F was expressed at a much higher level than unmodified RSV F (Non-HEK/non-opt, FIG. 59A, 59B, lanes 3 and 4 versus lane 6).

Example 2

Attenuated Human Parainfluenza Virus Type 1 (HPIV1) Expressing the Fusion F Glycoprotein of Human Respiratory Syncytial Virus (RSV) as a Bivalent HPIV1/RSV Vaccine This example illustrates the development and pre-clinical evaluation of a live attenuated rHPIV1 vectored RSV vaccine expressing RSV F antigen from three genome positions of the two attenuated rHPIV1 backbones. Pre-clinical evaluation in hamsters indicated that the rHPIV1 $C^{\Delta170}$-F1 vector, bearing attenuating deletion mutation ($C^{\Delta170}$) in the P/C gene and expressing RSV F from the pre-N position was sufficiently attenuated, stable and immunogenic against RSV and HPIV1 and provided significant protection against RSV challenge infection. This study demonstrated that rHPIV1 could be used as an RSV vaccine vector to achieve bivalent protection against two major childhood diseases.

Introduction.

Compared to an RSV vaccine comprising an attenuated strain of RSV, an RSV vaccine comprising a live attenuated HPIV vector (such as one developed from HPIV1) expressing the RSV F protein offers several advantages. One advantage is that it provides a bivalent vaccine against RSV and the HPIV serotype used as a vector. This is important because, as noted, the HPIVs also are important, uncontrolled agents of pediatric respiratory tract disease, with characteristics of epidemiology and pathogenesis that overlap those of RSV. Thus, a combined HPIV/RSV vaccine is a logical combination that would broaden the coverage against pediatric respiratory tract disease. In addition, RSV infectivity is notorious for being prone to instability during handling, which complicates vaccine development, manufacture, and delivery. The HPIVs are substantially more stable, which may be critical for extending RSV vaccines to developing countries where their need is the greatest. RSV grown in vitro often forms long filaments that complicate manufacture, whereas the HPIVs form smaller spherical particles. It also may be that RSV is inherently more pathogenic and even possibly immunosuppressive compared to the HPIVs, which would be another advantage of an HPIV-vectored RSV vaccine. It has also been have found that, in rodents, the use of an HPIV-vectored vaccine as a boost administered subsequent to a live attenuated RSV strain was more immunogenic than a second dose of the same attenuated RSV strain. Thus, RSV-specific immunity resulting from a primary immunization might be expected to restrict replication of a second dose of an attenuated RSV strain more efficiently than that of an HPIV-vectored virus, and indicates another potential advantage of HPIV-vectored RSV vaccines.

The HPIV1 genome is a single strand of negative sense RNA. It consists of a short 3' leader region followed by 6 genes encoding the N, P, C, M, F, HN, and L proteins, and a short trailer region. Each gene encodes a major viral protein: N, nucleoprotein; P, phosphoprotein; M, internal matrix protein; F, fusion glycoprotein; HN, hemagglutinin-neuraminidase glycoprotein; and L, major polymerase subunit. In addition, the P gene carries an overlapping ORF expressing a set of carboxy-co-terminal C accessory proteins that inhibit the host interferon (IFN) response and block apoptosis (Bartlett, et al. 2008. J virology 82:8965-8977). Like other nonsegmented negative strand RNA viruses, HPIV1 transcription initiates at the 3' end promoter and proceeds down the genome in a start-stop process regulated by the gene end (GE)-intergenic (IG)-gene start (GS) signals to generate a series of monocistronic mRNAs. There is a 3' to 5' gradient of decreasing transcription, with the promoter-proximal genes expressed at higher levels (Nagai. 1999. Reviews in medical virology 9:83-99). Like other paramyxoviruses, complete infectious, replication-competent HPIV1 can be recovered in cell culture from transfected cDNAs (reverse genetics).

Previous studies have described the development of a chimera of bovine and human PIV3 as a vector for RSV F protein (Schmidt et al 2000 J Virol 74:8922-8929; Schmidt et al 2001 J Virol 75:4594-4603; Schmidt et al 2002 J Virol 76:1088-1089; Tang et al 2002 J Virol 78:11198-11207; Bernstein et al 2012 Pediatr Infect Dis 31:109-114; see also Example 1). This virus, called rB/HPIV3, consists of BPIV3 in which the F and HN genes were replaced using reverse genetics with those of HPIV3, combining the attenuation phenotype of BPIV3 in primates with the major neutralization antigens of HPIV3 (Schmidt et al 2001 J Virol 75:4594-4603; Schmidt et al 2002 J Virol 76:1088-1089; Tang et al 2002 J Virol 78:11198-11207; Bernstein et al 2012 Pediatr Infect Dis 31:109-114) rB/HPIV3 was shown to efficiently express the RSV F and G genes. Clinical evaluation of a lead rB/HPIV3/RSV-F construct as a bivalent vaccine for RSV and HPIV3 in seronegative children showed that it was infectious, well tolerated, and attenuated, but was less immunogenic against RSV F than hoped (Bernstein et al 2012 Pediatr Infect Dis 31:109-114). This appeared to be due at least in part to genetic instability in the clinical trial material that silenced expression of the RSV F insert (Yang, et al. 2013. Vaccine 31:2822-2827). However, further studies are underway to stabilize the RSV F insert and to obtain increased immunogenicity by characterizing and optimizing various parameters of vector construction (Liang, et al. 2014. J virology 88:4237-4250). HPIV1 is another attractive vector for expressing RSV F antigen. In particular, HPIV1 infects somewhat later in childhood than RSV or HPIV3 (Counihan, et al. 2001. Pediatric infectious disease journal 20:646-653; Reed, et al. 1997. J Infect Dis 175:807-813), and so an HPIV1-vectored RSV vaccine might be used subsequent to a live attenuated RSV or rB/HPIV3-vectored vaccine to boost immune responses to RSV.

In the present study, two parameters for developing an HPIV1-vectored vaccine expressing RSV F protein were evaluated (FIGS. 36 and 42): (i) two different attenuated HPIV1 backbones were compared, and (ii) insertion of the RSV F gene at the first, second, and third genome positions of the HPIV1 vector was compared. The first parameter, the level of attenuation, is important because it is linked to safety and, inversely, to immunogenicity. Specifically, the HPIV1 vector must be sufficiently attenuated so as to be non-pathogenic and well tolerated, but must replicate and express antigens sufficiently well to be satisfactorily immunogenic. The addition of a foreign gene, such as RSV F, to an HPIV vector also typically confers attenuation and also can confer the temperature-sensitivity (ts) phenotype (Liang, et al. 2014. J virology 88:4237-4250), and so the combined effect of the insert and specific attenuating mutation(s) had to be determined. The two different HPIV1 backbones used in the present study each contained a single attenuating mutation ($C^{\Delta170}$ or $L^{Y942A}$) developed in previous studies (1, 3, 25). Each of these mutations has been shown to be moderately attenuating in vivo (Bartlett, et al. 2006. Vaccine 24:2674-2684; Bartlett, et al. 2007. Virology J 4:67; Newman, et al. 2004. J Virol 78:2017-2028). The $C^{\Delta170}$ mutation is non-temperature sensitive. It reduces the ability of C proteins to inhibit the host type I interferon response and apoptosis (Bartlett, et al. 2006. Vaccine 24:2674-2684; Bartlett, et al. 2008. J virology 82:8965-8977; Newman, et al. 2004. J Virol 78:2017-2028) resulting in virus attenuation. The mechanism of attenuation has the potential to increase the inherent immunogenicity of the construct because this mutation in C increases the host interferon response and apoptosis response, both of which have the potential to increase immunogenicity. The $C^{\Delta170}$ mutation consists of a 6-nucleotide deletion in the overlapping P and C ORFs. In the C ORF, this results in the deletion of two amino acids and the substitution of a third amino acid (specifically, the triplet 168-RDF-170 was changed to the single amino acid S), whereas in the overlapping P ORF it results in deletion of two amino acids (172-GF-173). Deletion mutations are thought to have increased stability because they offer greater genotypic and phenotypic stability due to low risk of same site reversion. The $L^{Y942A}$ mutation is temperature-sensitive. It is a missense mutation (942-Y to A) in the L ORF that was designed to involve 3 nt substitutions so as to be highly resistant to de-attenuation (FIG. 42), as has been directly documented (McAuliffe et al 2004. J Virol 78:2029-2036). (ii) The second parameter investigated in the present study, the position of insertion of the foreign gene in the HPIV genome, is important because it affects the level of expression of the foreign gene as well as its attenuating impact on the vector. In an HPIV genome, insertion of the RSV F gene closer to the promoter would be expected to provide a higher level of expression, due to the transcription gradient. However, the closer the foreign gene is to the promoter, the greater the number of downstream vector genes it can impact, because each of these vector genes is now one position further removed from the promoter and consequently is expressed less efficiently. In addition, placement of the foreign gene in the first position has the potential to affect the functioning of the promoter. The insertion of the foreign gene also can have unpredictable effects. It also can be attenuating through effects such as the increase in genome length and gene number.

Six viruses, representing three different insertion sites for RSV F in two different attenuated HPIV1 backbones, were constructed, rescued by reverse genetics, and analyzed for in vitro replication and expression of RSV F and vector proteins. The hamster model was used to assess in vivo replication (upper and lower respiratory tract), vaccine virus stability, immunogenicity, and protection against wt RSV challenge.

Materials and Methods

Cells and Viruses.

LLC-MK2 (ATCC CCL-7) rhesus monkey kidney and Vero (ATCC CCL-81) African green monkey kidney cell lines were maintained in Opti-MEMI medium with GlutaMAX (Life Technologies, Grand Island, N.Y.) supplemented with 5% fetal bovine serum (FBS; HyClone/Logan, Utah) and 1 mM L-glutamine (Life Technologies). BSR T7/5 cells are baby hamster kidney 21 (BHK-21) cells that constitutively express T7 RNA polymerase (Buchholz, et al. 1999. J Virol 73:251-259). These cells were maintained in Glasgow minimal essential medium (GMEM; Life Technologies) supplemented with 10% FBS, 2 mM L-glutamine and 2% MEM amino acids (Life Technologies). Medium was also supplemented with 2% Geneticin (Life Technologies) at every other passage to select for cells that posses the T7 polymerase construct.

HPIV1 was propagated in LLC-MK2 cells. Before virus inoculation, LLC-MK2 cells, grown in media containing 5% FBS, were washed twice with 1× phosphate buffered saline (PBS) to remove FBS. Infection with HPIV1 was always performed in serum-free Opti-MEMI media containing 1.2% trypsin (TrypLE Select; Life Technologies), 100 U/ml Penicillin, 100 μg/ml Streptomycin (Life Technologies) and 1 mM L-glutamine. Infected cells were incubated at 32° C. till the appearance of cytopathic effects. For virus stock harvest, culture supernatant was harvested and clarified by centrifugation at 1500 rpm for 10 min at 4° C. Aliquots of virus stocks were snap-frozen on dry ice and stored at −80° C. HPIV1 titers were determined by 10-fold serial dilutions in 96-well plates on LLC-MK2 cells with serum-free Opti-MEMI media containing 1.2% trypsin as described above followed by incubation at 32° C. for 7 days. Infected cells were detected by hemadsorption (HAD) using guinea pig erythrocytes and titers were calculated as login tissue culture infective dose 50% ($TCID_{50}$/ml) as previously described (Bartlett, et al. 2006. Vaccine 24:2674-2684). The temperature sensitivity (ts) phenotype of each of the virus was studied by evaluating their efficiency of replication at 32, 35, 36, 37, 38, 39, and 40° C. as previously described Skiadopoulos, et al. 1999. Vaccine 18:503-510). Titration of each virus was performed in 96-well replicate plates of LLC-MK2 cells, as described above, and incubated in sealed containers in temperature-controlled water baths at various temperatures for 7 days. Titers were determined by HAD and reported as $TCID_{50}$/ml.

Design of rHPIV1-$C^{\Delta170}$ and rHPIV1-$L^{Y942A}$ Viruses Expressing the RSV F Antigen.

The rHPIV1 viruses were constructed using the reverse genetic system derived from the wild type (wt) HPIV1 strain Washington/20993/1964 (GenBank accession AF457102) (Newman, et al. 2002. Virus Genes 24:77-92). The recombinant full-length antigenomic cDNA clone (pFLC) of HPIV1 was modified by site-directed mutagenesis to contain 3 additional unique restriction sites: MluI (ACGCGT, pre-N position, nucleotide numbers 113-118), AscI (GGCGCGCC, N-P position, nucleotide numbers 1776-1783) and NotI (GCGGCCGC, P-M position, nucleotide numbers 3609-3616). Two attenuated cDNA backbones were generated by introducing either the $C^{\Delta170}$ (Bartlett, et al. 2007. Virology J 4:67) or the $L^{Y942A}$ (Bartlett, et al. 2007. Virology J 4:67; McAuliffe, et al. 2004. J virology 78:2029-2036) mutation into the P/C or L ORF, respectively, using the QuikChange Lightning Mutagensis Kit (Agilent, Santa Clara, Calif.) as per manufacturer's instructions. The following mutagenesis primers were used to generate the attenuated HPIV1 backbones. For HPIV1 $C^{\Delta170}$ mutation, the forward primer was AAGAAGACCAAGTTGAGCCAGAAGAGGTACGAAG (SEQ ID NO: 121) and the reverse primer was CTTCGTACCTCTTCTGGCTCAACTTGGTCTTCTT (SEQ ID NO: 122). These primers introduced a 6-nucleotide deletion (GGATTT) between positions 17 and 18 compared to the P/C ORF (FIG. 42) keeping with the rule of six (Calain, et al. 1993. J Virol 67:4822-4830; Kolakofsky, et al. 1998. J Virol 72:891-899). As previously described (Bartlett, et al. 2007. Virology J 4:67), the C$^{\Delta 170}$ deletion in the P/C ORF includes an R168S substitution and a deletion of D and F from position 169-170 resulting in a change in the amino acid sequence of C protein from RDF to S. This mutation also affects the P ORF involving a deletion of two residues G and F from position 172-173. For the L$^{Y942A}$ mutation, the forward primer was CCAGCTAACATAGGAGGGTT-CAACGCGATGTCTACAGCTAGATGTTTTGTC (SEQ ID NO: 123) and the reverse primer was GACAAAA-CATCTAGCTGTAGACAT CGCGTTGAACCCTCCTATGTTAGCTGG (SEQ ID NO: 124). In these primer sequences the mutation site TAT (Y) to GCG (A) at aa 942 in the L ORF is underlined. Mutagenesis primer pairs were PAGE 2-Step purified (Operon, Huntsville, Ala.). Clones with the desired mutation, as determined by sequencing, were then purified by plasmid maxiprep (EndoFree Plasmid Maxi Kit; Qiagen) and sequenced in entirety. The rHPIV1 pFLCs with either the C$^{\Delta 170}$ or the L$^{Y942A}$ mutation were digested with MluI, AscI, or NotI enzymes (New England Biolabs, Ipswich Mass.), treated with Calf Intestinal Phosphatase (New England Biolabs), and purified by gel extraction (QIAEX II Gel Extraction Kit; Qiagen, Valencia Calif.).

Figure 36:
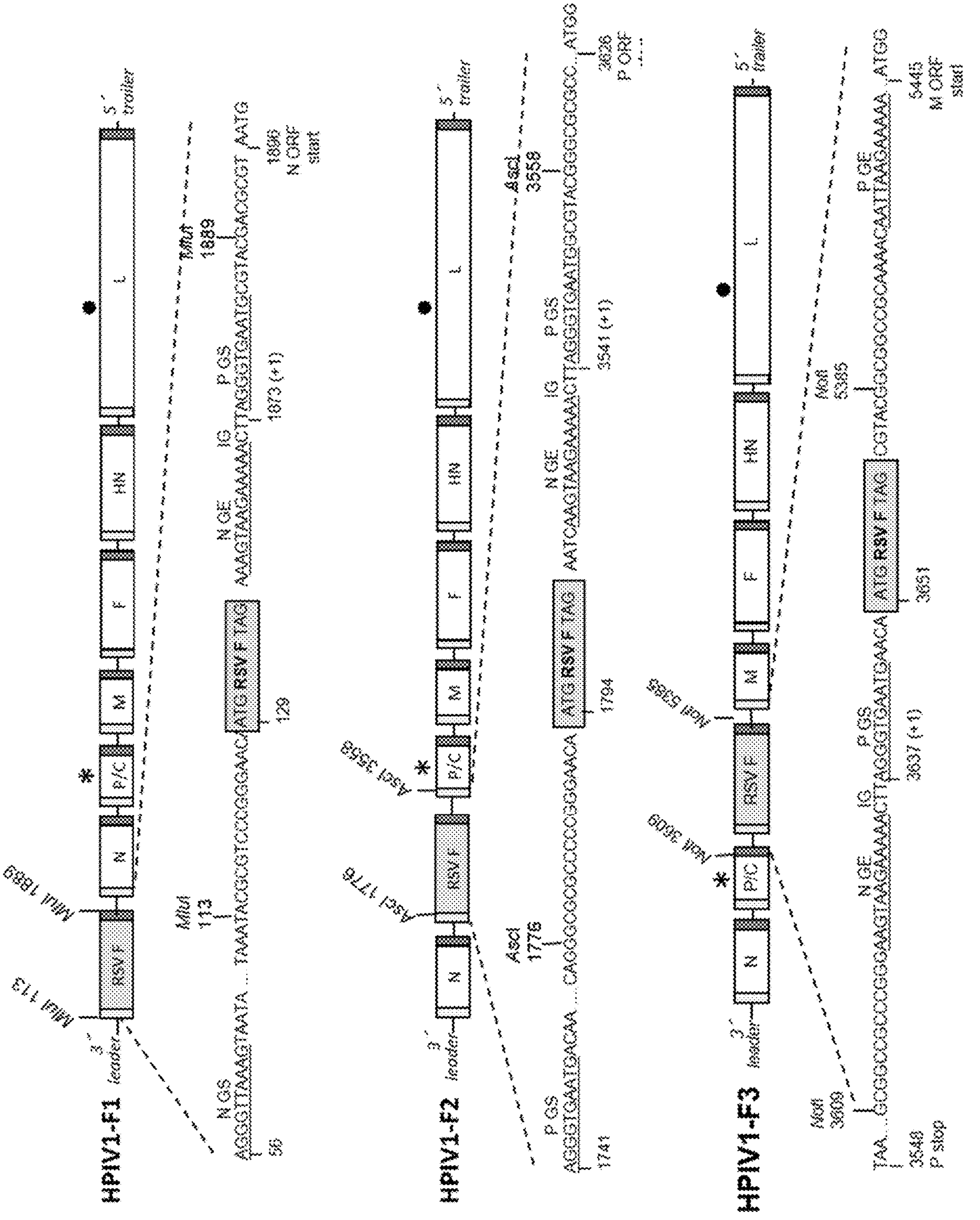
FIG. 36. Construction of antigenomic cDNAs of the HPIV1 $C^{D170}$ and $L^{Y942A}$ mutants containing the RSV F gene insert at the first (F1), second (F2), or third (F3) genome positions. The rHPIV1 backbones used for RSV F expression contained either of the two attenuating mutations: namely the $C^{D170}$ mutation (indicated by *) in the P/C gene or the $L^{Y942A}$ mutation (indicated by •) in L gene. For the HPIV1-F1 constructs, the RSV F gene was inserted at the first genome position before the HPIV1 N gene at the MluI site located in the upstream non-translated region of the N gene. In case of HPIV1-F2, the RSV F gene was inserted between the HPIV1 N and P genes at the AscI site located in the upstream non-translated region of the P gene. For the HPIV1-F3, the RSV F gene was cloned between the HPIV1 P and M genes at the NotI site situated in the downstream non-translated region of the P gene. For all constructs, the RSV F ORF was codon optimized for human expression and contained HEK amino acid assignments. A copy of the N gene-end (GE), intergenic (IG) CTT triplet, and P gene-start (GS) sequence was added following (F1, F2) or before (F3) the RSV F insert so that it was under the control of a set of HPIV1 transcription signals. The sequences of SEQ ID NOs: 138-140 are shown flanking the RSV F insert under HPIV1-F1; the sequences of SEQ ID NOs: 141-143 are shown flanking the RSV F insert under HPIV1-F2, and the sequences of SEQ ID NOs: 144-145 are shown flanking the RSV F insert under HPIV1-F3.

The RSV F gene from strain A2 with HEK amino acid assignments: Glu and Pro at aa position 66 and 101, respectively (Whitehead, et al. 1998. J virology 72:4467-4471) was optimized for human codon usage (GeneArt, Life Technologies, Grand Island, N.Y.). RSV F gene insert was designed (FIG. 36) to include the HPIV1 transcriptional regulatory sequences: gene end (GE)-intergenic (IG)-gene start (GS) signals to allow for RSV F expression as an independent transcript. For all constructs, the RSV F gene insert was designed to include HPIV1 N GE (AAGTAAGAAAAA, SEQ ID NO: 125) and P GS (AGGGTGAATG, SEQ ID NO: 126) sequences along with the conserved IG sequence (CTT), while keeping the +1 phasing for the P GS. RSV F inserts were generated by PCR with the corresponding flanking MluI, AscI, or NotI restriction sites complimentary to those in the HPIV1 FLCs for insertion in the first Pre-N(F1), second N-P (F2), or third P-M (F3) positions, respectively (FIG. 36). The following PCR primers were used to generate the RSV F inserts. For RSV F fragments containing MluI restriction sites for insertion into the first F1 gene position the forward primer was ACGCGTCCCGGGAACAATGG AACTGCTGATCCT-GAAGGCCAACGCC (SEQ ID NO: 127) and the reverse primer was ACGCGTCGTACGCATTCACCCTAAGTTT-TTCTTACTTTCTATCAGTTGGAGAAGGCGATATT GTTGATGCCGG (SEQ ID NO: 128). For RSV F fragments containing the AscI restriction sites for insertion into the second F2 gene position the forward primer was (SEQ ID NO: 129)
GGCGCGCCCCCGGGAACAATGGAACTGCTGATCCTGAAGGCCAACGCC and the reverse primer was (SEQ ID NO: 130)
GGCGCGCCCGTACGCCATTCACCCTAAGTTTTTCTTACTTGATTCTATCA
GTTGGAGAAGGCGATATTGTTGATGCCGG.

For RSV F fragments containing the NotI restriction sites for insertion into the third F3 gene position the forward primer was (SEQ ID NO: 131)
GCGGCCGCCCGGGAAGTAAGAAAAACTTAGGGTGAATGAACAATGGAAC
TGCTGATCCTGAAGGCCAACGCC and the reverse primer was (SEQ ID NO: 111)
GCGGCCGCCGTACGCTATCAGTTGGAGAAGGCGATATTGTTGATGCCGG.

Recovery of rHPIV1 C$^{\Delta 170}$ and rHPIV1 L$^{Y942A}$ Viruses Expressing the RSV F Antigen.

The rHPIV1 C$^{\Delta 170}$ backbones expressing RSV F from the first (HPIV1 C$^{\Delta 170}$-F1), second (HPIV1 C$^{\Delta 170}$-F2), and third (HPIV1 C$^{\Delta 170}$-F3) positions and the rHPIV1 L$^{Y942A}$ viruses expressing RSV F from the first (HPIV1 L$^{Y942A}$-F1), second (HPIV1 L$^{Y942A}$-F2), and third (HPIV1 L$^{Y942A}$-F3) positions were rescued from cDNA by using the HPIV1 reverse genetics system (Newman, et al. 2002. Virus Genes 24:77-92) in BSR T7/5 cells constitutively expressing T7 RNA polymerase (Buchholz et al. 1999. J. Virology 73:251-259). This rHPIV1 cDNA is derived from the Washington/20993/1964 (HPIV1 WASH/64) clinical isolate. The BSR T7/5 cells were grown to 90% confluency in 6-well plates and co-transfected with the antigenome pFLC plasmid (5 ug) to be rescued along with pTM-N (0.8 ug), pTM-P (0.8 ug) and pTM-L (0.1 ug) support plasmids expressing HPIV1 N, P and L proteins, respectively, using Lipofectamine 2000 (20 ul) (Life Technologies) as previously described (Bartlett, et al. 2005. Vaccine 23:4631-4646; Newman, et al. 2002. Virus Genes 24:77-92). Transfected cells were incubated overnight at 37° C., washed twice with OptiMEM media (Life Technologies, Grand Island, N.Y.) and fresh OptiMEM containing 1 mM L-glutamine and 1.2% trypsin was added to the cells followed by incubation at 32° C. At 48 h post-transfection, cells were harvested by scraping into the medium and the cell suspension was added to 50% confluent monolayers of LLC-MK2 cells in OptiMEM, 1 mM L-glutamine, 1.2% trypsin (Life Technologies) and incubated at 32° C. Virus was harvested after 7 days and was further amplified by one (HPIV1-C$^{\Delta 170}$) or two (HPIV1-L$^{Y942A}$) passages in LLC-MK2 cells at 32° C. Virus titers were determined by 10-fold serial dilutions on LLC-MK2 cells in 96-well plates as described above. All recombinant viruses were sequenced to confirm the lack of adventitious mutations. For this, viral RNA was extracted (QiaAmp Viral RNA Mini Kit; Qiagen, Valencia, Calif.) from virus stocks and treated with RNase free DNase I (Qiagen) to remove the plasmid DNA used for virus rescue. RNA was reverse transcribed (SuperScript First-Strand Synthesis System for RT-PCR; Invitrogen/Life Technologies) and overlapping genome regions were amplified by RT-PCR (Advantage-HF 2 PCR Kit; Clontech Laboratories). RT-PCR controls lacking the reverse transcriptase were included for all viruses, which showed that the amplified products were derived from viral RNA and not from the pFLC cDNA used for virus recovery. The genome sequence of each virus construct was determined by direct Sanger sequencing of the overlapping amplified RT-PCR products. Sequence reads were aligned and the genome sequence was assembled using Sequencher program-version 5.1 (Gene Codes Corporation, Ann Arbor, Mich.).

Replication of Chimeric rHPIV1 Viruses in Vero and LLC-MK2 Cells.

Triplicate wells of Vero or LLC-MK2 cell monolayers in 6-well plates were infected at a multiplicity of infection (MOI) of 0.01 $TCID_{50}$ with HPIV1 ($C^{\Delta170}$ or $L^{Y942A}$) viruses expressing RSV F (F1, F2, or F3), or the empty HPIV1 $C^{\Delta170}$ or HPIV1 $L^{Y942A}$ vector, or wt HPIV1. Cultures were incubated at 32° C. Aliquots of 0.5 ml from a total 2 ml cell culture supernatant medium were collected at 24 h intervals from each well and replaced by fresh media. The samples were flash frozen and stored at −80° C. Virus titers (login $TCID_{50}$/ml) were determined by serial dilution on LLC-MK2 cells followed by detection of infected cells by HAD as described above.

Analysis of RSV F and HPIV1 Vector Protein Expression by Western Blotting.

Vero cells ($1\times10^6$) were infected with HPIV1 $C^{\Delta170}$ or HPIV1 $L^{Y942A}$ constructs expressing RSV F from either of the three genome positions (F1, F2, or F3) Empty HPIV1 $C^{\Delta170}$ and HPIV1 $L^{Y942A}$ vector, wt HPIV1, and mock treated cells were used as controls. Infections were performed at an MOI of 5 $TCID_{50}$ per cell and incubated at 32° C. At 48 h post-infection (post-infection), monolayers were washed twice with PBS and lysed with 400 ul of 1×LDS sample buffer (Life Technologies). For electrophoresis, lysates were reduced and denatured by mixing with 1× reducing reagent (Life Technologies) and incubation at 37° C. for 30 min. Reduced denatured lysate (40 μl) was loaded onto 4 to 12% Bis-Tris NuPAGE gels (Novex-Life Technologies) and electrophoresis performed in 1×MOPS buffer. Proteins were transferred onto PVDF membranes using the iBlot protein transfer system (Life Technologies). Membranes were blocked for 1 h in Licor blocking buffer (Licor Inc. Lincoln, Nebr.) and probed with a murine monoclonal RSV F specific antibody (ab43812; Abcam, Cambridge, Mass.) and a rabbit polyclonal HPIV1 N specific antibody (HPIV1-N-485) at 1:1000 dilution in blocking buffer. HPIV1-N-485 was generated by immunization of rabbits with the KLH-conjugated N peptide spanning the amino acid (aa) residues 485-499 of N as previously described (Bartlett, et al. 2010. Vaccine 28:767-779). Replicate blots performed with the same set of lysates were probed with the rabbit polyclonal antisera for HPIV1 P (SKIA-1), F (SKIA-15), or HN (SKIA-13) which were also raised by repeated immunization of rabbits with the KLH-conjugated peptide, and were used at 1:200 dilution. After overnight incubation with the above antibodies, the membranes were washed 4×, 5 min each, followed by incubation with the secondary antibodies, diluted in the Licor blocking buffer, for 1 h. The corresponding infra-red dye-conjugated secondary antibodies were goat anti-mouse IRDye 680LT and goat anti-rabbit IRDye 800CW (LiCor). Membranes were scanned and the blot images were acquired using an Odyssey infrared imaging system (LiCor). Fluorescence intensities of the protein bands, derived from three independent experiments, were quantified by using the Licor image analysis suite (Image Studio) and reported as expression of RSV F or HPIV1 vector proteins (N, P, F, and HN) relative to F3 viruses.

Percentage of Virions Expressing RSV F Determined by Fluorescent Double-Staining Plaque Assay.

An infrared fluorescence based two-color plaque assay was developed to simultaneously detect the expression of RSV F and HPIV1 proteins in the plaques formed by the HPIV1 vectors expressing RSV F on Vero cell monolayers. Each virus was 10-fold serially diluted in OptiMEM media containing 1 mM L-glutamine and 1.2% trypsin and 100 μl of each dilution was added in duplicate to Vero cell monolayers grown in 24-well plates. Inoculated cells were incubated for 2 h at 32 C on a rocker after which an overlay OptiMEMI media containing 0.8% methylcellulose (Sigma Aldrich, St. Louis, Mo.), 1 mM L-glutamine, 4% trypsin, 100 U/ml Penicillin, and 100 μg/ml Streptomycin was added to each well. For animal tissue derived virus samples, Timentin (200 mg/ml), Ampicillin (100 mg/ml), Cleocin (150 mg/ml), and Amphotericin B (250 μg/ml) were included in the methylcellulose overlay instead of Penicillin and Streptomycin. After incubation for 6 days at 32 C, cells were fixed twice with 80% cold methanol. The rHPIV1-RSV F plaques were detected on infected Vero cell monolayers by co-immunostaining with a mixture of three RSV F-specific monoclonal antibodies at a 1:2000 dilution each, as previously described (Murphy, et al. 1990. Vaccine 8:497-502) and an HPIV1 specific goat polyclonal antibody (ab20791; Abcam) at a 1:1600 dilution in Licor blocking buffer. After 1 h incubation, cells were washed once with 1 ml blocking buffer and incubated with the secondary antibody mixture containing infrared dye-conjugated goat anti-mouse 680LT and the donkey anti-goat 800CW (LiCor) each at a 1:800 dilution in the blocking buffer. Cells were washed twice with 1×PBS and images of the co-stained plaques were acquired by scanning the plates on an Odyssey infrared imaging system (LiCor). Wells containing fewer than 50 plaques were chosen for analysis and the percentage of rHPIV1 plaques positive for RSV F expression was determined. This assay was employed to assess the stability of RSV F expression by determining the percent population expressing RSV F in the vaccine inoculum as well as in the virus isolated from hamsters after in vivo replication.

Hamster Studies

Virus Replication in Hamsters.

All animal studies were approved by the National Institutes of Health (NIH) Institutional Animal Care and Use Committee (IACUC). In vivo replication of each virus at 3 and 5 days post-infection as well as the immunogenicity was assessed in hamsters. Six-week old Golden Syrian hamsters were confirmed to be seronegative for HPIV1 and RSV by analyzing pre-immune sera by hemagglutination inhibition (HAI) assay and an RSV neutralization assay, respectively (Coates, et al. 1966. Am J Epidemiol 83:299-313; Coates, et al. 1966. J Bacteriol 91:1263-1269; van Wyke Coelingh, et al. 1988. J Infect Dis 157:655-662). Groups of 6 hamsters per virus were anesthetized and inoculated intranasally with 0.1 ml L15 medium (Life Technologies) containing $10^5$ $TCID_{50}$ of the virus per animal. To evaluate replication, hamsters were euthanized on days 3 and 5 post-infection and nasal turbinates and lungs were collected for virus titration. Tissue homogenates in L15 medium containing Timentin (200 mg/ml), Ampicillin (100 mg/ml), Cleocin (150 mg/ml), and Amphotericin B (250 ug/ml) were titrated by serial dilution on LLC-MK2 cells followed by detection of virus infection by HAD. Virus titers were reported as $TCID_{50}$/gram of hamster tissue. Tissue homogenates were also titrated by plaque assay on Vero cells and stained for the expression of RSV F and HPIV1 proteins by using the fluorescent double staining plaque assay as described above. Results were reported as percent HPIV1 plaques expressing RSV F.

Immunogenicity

Induction of Virus Neutralizing Antibodies (NAbs) in Serum Against RSV and HPIV1 [60% Plaque Reduction Neutralization Test ($PRNT_{60}$)].

To assess immunogenicity of the vaccine candidates, hamsters were immunized as described above and sera were collected from hamsters at day 28 after immunization. Titers of RSV specific neutralizing antibodies (NAbs) were determined by $PRNT_{60}$ on Vero cells as previously described (Coates, et al. 1966. Am J Epidemiol 83:299-313) using the eGFP-expressing RSV (Munir, et al. 2008. J Virol 82:8780-8796). Hamster sera were incubated at 56° C. for 30 min to inactivate the complement proteins followed by serial dilution in Opti-MEMI, 2% FBS, 1× Gentamicin media in 96-well plates. RSV-eGFP diluted in Opti-MEM, 2% FBS, 1× Gentamicin, 10% guinea pig complement (Yoder, et al. 2004. J medical virology 72:688-694) (Lonza, Walkersville, Md.) was further diluted 1:1 by mixing with an equal volume of serially diluted serum samples followed by 30 min incubation at 37° C. A volume of 100 μl of serum-virus mix was added to Vero cells grown in 24-well plates and virus was allowed to adsorb for 2 h on the rocker at 32° C. An overlay of Opti-MEMI, 8% methylcellulose, 2% FBS, 1× Gentamicin was added and incubated for 5-6 days to allow plaque formation. RSV plaques on monolayers were visualized by scanning and acquiring images using Typhoon Imager (GE Healthcare, Piscataway, N.J.). Plaque counts for each sample were determined and the NAb titer was determined as described (Coates, et al. 1966. Am J Epidemiol 83:299-313). Titers of HPIV1-specific NAbs were also determined by 60% plaque reduction assay on Vero cells, using the methods as described for RSV, using GFP-expressing rHPIV1 with the following modifications: First, in case of HPIV1 neutralization assay, guinea pig complement was not used as it was found to neutralize the virus, second, the inoculated Vero cells were washed twice with 1×PBS after virus adsorption to remove serum, and third a methylcellulose overlay medium containing 4% trypsin and lacking FBS was used.

The ability of vaccine candidates to protect against RSV infection was tested by challenge infection of hamsters at 30 days post-immunization by intranasal inoculation with 0.1 ml L15 medium containing $10^6$ PFU of wt RSV strain A2. Hamsters were euthanized and nasal turbinates and lungs were harvested 3 days post-challenge and viral loads of challenge RSV in these tissues were determined by plaque assay on Vero cells (Durbin, et al. 2003. Clinical infectious diseases 37:1668-1677; Luongo, et al. 2013. J virology 87:1985-1996).

Results

Creation of two attenuated HPIV1 backbones (rHPIV1 $C^{\Delta170}$ and rHPIV1 $L^{Y942A}$) expressing the RSV F protein from three different genome locations. Two attenuated HPIV1 backbones were prepared that each contained a different, previously identified attenuating mutation (namely, $C^{\Delta170}$ and $L^{Y942A}$) that had been designed for stability against de-attenuation (Introduction, FIGS. 36 and 42). The $C^{\Delta170}$ mutation did not confer temperature-sensitivity while the $L^{Y942A}$ mutation was a temperature sensitivity mutation. Next, the RSV F ORF of strain A2 was codon-optimized for human expression and engineered to be under the control of HPIV1 gene-start and gene-end signals, and was inserted into the rHPIV1 $C^{\Delta170}$ and rHPIV1 $L^{Y942A}$ backbones at three different, parallel genome locations: namely at the first gene position (Pre-N, yielding rHPIV1 $C^{\Delta170}$-F1 and rHPIV1 $L^{Y942A}$-F1); at the second gene position (N-P, yielding rHPIV1 $C^{\Delta170}$-F2 and rHPIV1 $L^{Y942A}$-F2): and at the third gene position (P-M, yielding rHPIV1 $C^{\Delta170}$-F3 and rHPIV1 $L^{Y942A}$-F3) (FIG. 36). Each construct conformed to the "rule of six" (Calain, et al. 1993. J Virol 67:4822-4830). Each vector gene maintained its original hexamer spacing, while the F1, F2, and F3 inserts assumed the original hexamer spacing of the N, P, and P genes, respectively. The RSV F protein also carried the HEK amino acid assignments, Glu and Pro at residues 66 and 101, respectively (Whitehead, et al. 1998. J virology 72:4467-4471) which matches with the sequence of RSV F from early passages of strain A2 and also is consistent with most other clinical isolates.

The rHPIV1/RSV F viruses were recovered by reverse genetics. All viruses were rescued readily except for the rHPIV1 $L^{Y942A}$-F2 construct, which appeared to be recovered with low efficiency and required multiple passages to make a working pool. The complete sequence of each virus was determined to verify the absence of adventitious mutations. All of the rHPIV1/RSV-F virus working pools were free of apparent adventitious mutations except for the rHPIV1 $L^{Y42A}$-F2 virus: for this virus, nine clones were rescued of which only one had the correct genome sequence lacking adventitious mutations. The other eight clones contained adventitious mutations, which were predominantly in the HPIV1 transcriptional signals downstream of the HPIV1 N gene (N gene end-intergenic-P gene start) and preceding the RSV F ORF. Since the insertion sites of the RSV F gene in the second positions of the parallel rHPIV1 $L^{Y942A}$-F2 and rHPIV1 $C^{\Delta170}$-F2 constructs were identical, this suggests that the problem with the former virus was specific to the $L^{Y942A}$ mutation (e.g., altered polymerase function) rather than the insertion site by itself.

Replication of HPIV1/RSV F Viruses in Vero and LLC-MK2 Cells.

Replication of HPIV1/RSV viruses was evaluated in vitro by determining their multistep growth kinetics in Vero (FIGS. 37A and 37C) and LLC-MK2 (FIGS. 37B and 37D) cells. Cells were infected at an MOI of 0.01 $TCID_{50}$ and incubated at 32° C. Supernatant was harvested at 24 h intervals over 7 days and virus titers were determined by HAD and reported as $TCID_{50}$/ml (FIG. 37). The Student t test was used to determine the statistical significance of difference between the titer of each virus versus wt HPIV1 for day 2 and 7 p.i. On day 7, all viruses replicated to final titers greater than 7.2 $\log_{10}$ $TCID_{50}$/ml in Vero cells and 7.4 $\log_{10}$ $TCID_{50}$/ml in LLC-MK2 cells, with slight differences among the viruses that were statistically insignificant compared to wt HPIV1 in both cell lines (FIG. 37). However, differences were observed at earlier time points, especially day 2 p.i. In the case of the rHPIV1 $C^{\Delta170}$ viruses (FIGS. 37A and B), the rHPIV1 $C^{\Delta170}$ empty vector and rHPIV1 $C^{\Delta170}$-F3 replicated similar to wt HPIV1 in both cell lines on day 2 post-infection. However, the replication of rHPIV1 $C^{\Delta170}$-F1 was significantly reduced in Vero ($p<0.001$) and LLC-MK2 ($p<0.05$) cells and that of the rHPIV1$C^{\Delta170}$-F2 was significantly reduced ($p<0.01$) in Vero cells. For the rHPIV1 $L^{Y942A}$ viruses (FIGS. 37C and 37D), replication of the rHPIV1 $L^{Y942A}$ empty vector was significantly lower than that of the wt rHPIV1 in Vero cells, but both grew to similar titers in LLC-MK2 cells on day 2 post-infection. Highly significant reductions ($p<0.0001$) in replication as compared to wt rHPIV1 were observed for rHPIV1 $L^{Y942A}$-F1, -F2 and -F3 viruses in Vero cells. Likewise, the rHPIV1 $L^{Y942A}$-F1, -F2, and -F3 viruses showed significantly reduced ($p<0.01$, $p<0.0001$, and $p<0.01$, respectively) replication in LLC-MK2 cells. In Vero cells, rHPIV1 $L^{Y942A}$-F1 grew at the same rate as its parent rHPIV1 $L^{Y942A}$ empty vector while the growth of rHPIV1 $L^{Y942A}$-F2 and -F3 viruses (FIG. 37C) was relatively reduced, but these differences among the chimeric viruses were statistically insignificant.

Expression of RSV F and HPIV Vector Proteins by the Chimeric rHPIV1/RSV-F Viruses.

Expression of the RSV F protein and the HPIV1 vector N, P, F and HN proteins was evaluated for all viruses by Western blot analyses. Vero cells were infected at an MOI of 5 $TCID_{50}$ and incubated for 48 h at 32° C. Denatured and reduced lysates were subjected to SDS-PAGE and Western blot, and were analyzed using antibodies specific to each individual protein. RSV F is initially translated as the F0 precursor that is post-translationally cleaved by furin-like protease into disulfide-linked F1 and F2 subunits Immunostaining with a monoclonal antibody specific to RSV F detected both F0 (70 kD) and F1 (48 kD). The HPIV1 N, P, F, and HN proteins were detected with corresponding anti-peptide polyclonal antibodies. Representative blots from one of three independent experiments are shown in FIG. 38A, and results from all three experiments are quantified for the rHPIV1 $C^{\Delta170}$ and rHPIV1 $L^{Y942A}$ constructs in FIGS. 38B and C, respectively, with the values normalized relative to those of the F3 construct in each series as 1.0.

The HPIV1 $C^{\Delta170}$-F1, -F2, and F3 viruses expressed substantial amounts of RSV F (FIG. 38A, lanes 1-3, and FIG. 38B) that were only slightly higher for F1 and F2 as compared to F3 as indicated by the protein band quantification (FIG. 38B) with the differences being statistically insignificant. Thus, unexpectedly, a 3'-5' polar gradient of expression from F1 to F3 was not observed. In contrast, however, a strong polar gradient of RSV F expression was observed in case of HPIV1 $L^{Y942A}$ viruses, with a significantly higher expression of RSV F by the F1 virus as compared to the F2 ($p<0.01$) and F3 ($p<0.05$) viruses (FIG. 38A, lanes 5-6, and FIG. 38C).

The expression of the vector N, P, F, and HN proteins was evaluated for wt HPIV1, the empty vectors, and the F1, F2, and F3 constructs in the $C^{\Delta170}$ and $L^{Y942A}$ series. In general, the $C^{\Delta170}$ mutation did not affect vector protein expression, with the result that the rHPIV1 $C^{\Delta170}$ empty vector had a vector protein expression profile similar to that of wt rHPIV1 (FIG. 38B). In the case of the three versions of rHPIV1$C^{\Delta170}$ vector expressing RSV F, the F3 virus expressed N, P, F, and HN at levels similar to that of empty rHPIV1$C^{\Delta170}$ vector. The F2 virus expressed N protein similar to the empty rHPIV1$C^{\Delta170}$ vector but showed reduced expression of P, F, and HN proteins of which only the HN reduction was statistically significant compared to the empty vector. The F1 virus demonstrated significant reduction in all vector proteins including N ($p<0.05$), P ($p<0.01$), F ($p<0.05$), and HN ($p<0.05$) compared to the empty vector. Thus, insertion of the RSV F gene into the rHPIV1 $C^{\Delta170}$ vector reduced the expression of downstream vector genes except in the F3 virus. Both the F1 and F2 viruses exhibited significantly reduced replication early during infection of Vero cells (FIG. 37A), and the reduced synthesis of vector proteins provides a plausible explanation.

Figure 38A:
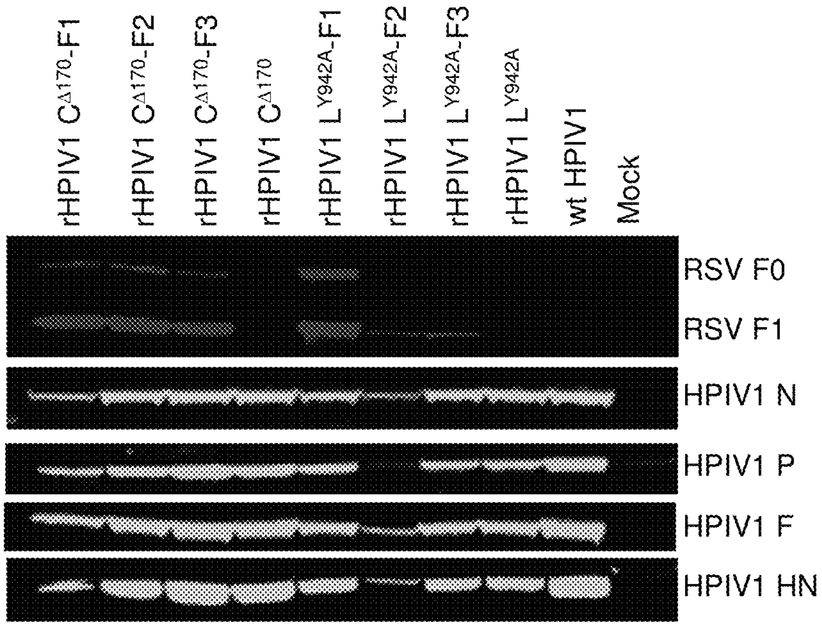
FIGS. 38A-38C. Analysis of the RSV F and HPIV1 vector protein expression by Western blot. Vero cells were infected with the indicated viruses at an MOI of 5. At 48 h post-infection cells were lysed with SDS sample buffer. All samples were denatured, reduced and subjected to SDS-PAGE and Western blot. Proteins were transferred onto PVDF membranes and probed with either RSV F-specific mouse monoclonal antibody or HPIV1 N-, P-, HN-, or F-specific polyclonal antibodies that had been raised by immunizing rabbits separately with synthetic peptides representing the respective proteins. (A) Bound antibodies were visualized using corresponding anti-mouse (IRDye 680LT) and anti-rabbit (IRDye 800CW) antibodies conjugated with infra-red dye. Images were acquired by scanning the blots using the Odyssey infrared imaging system. The images shown are from a single experiment that is representative of three independent experiments. (B and C) The intensity of protein bands for the rHPIV1 $C^{\Delta170}$ (B) and the rHPIV1 $L^{Y942A}$ (C) constructs was quantified for three independent experiments and expression is shown relative to the F3 virus set at 1.0. Plots show data as mean±SEM from three independent experiments that were analyzed by one-way ANOVA with Dunnett multiple comparisons test using 95% confidence interval. Expression of the HPIV1 proteins by the F1, F2 and F3 viruses was statistically compared with that of their corresponding empty vector backbone. *, $p<0.05$; , $p<0.01$; *, $p<0.001$.
Figure 38B:
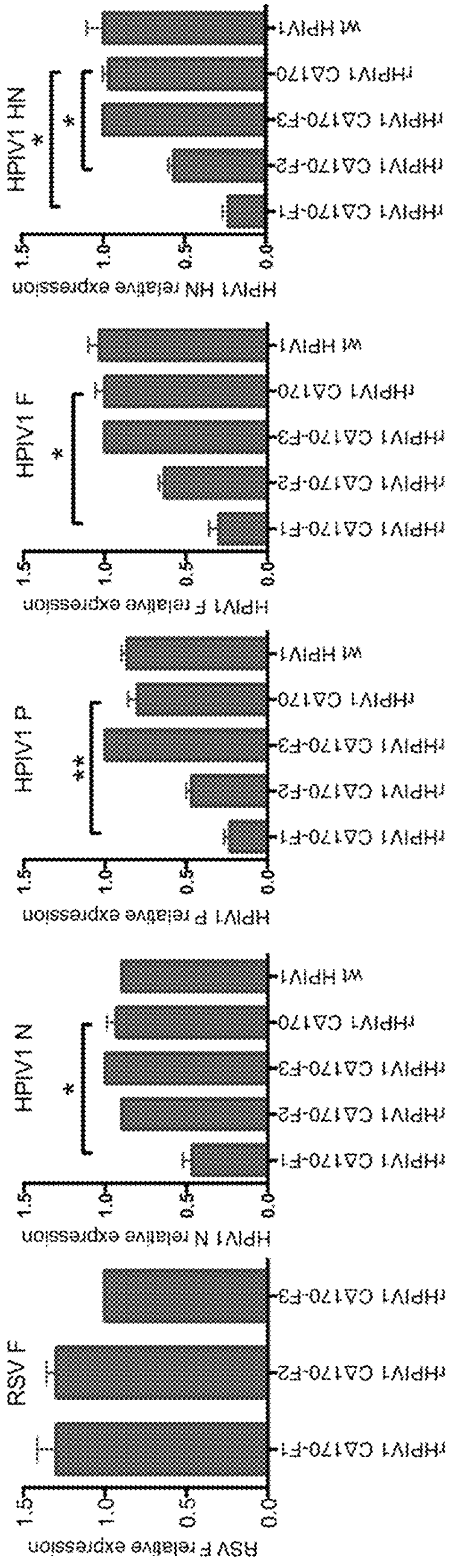
Figure 38C:
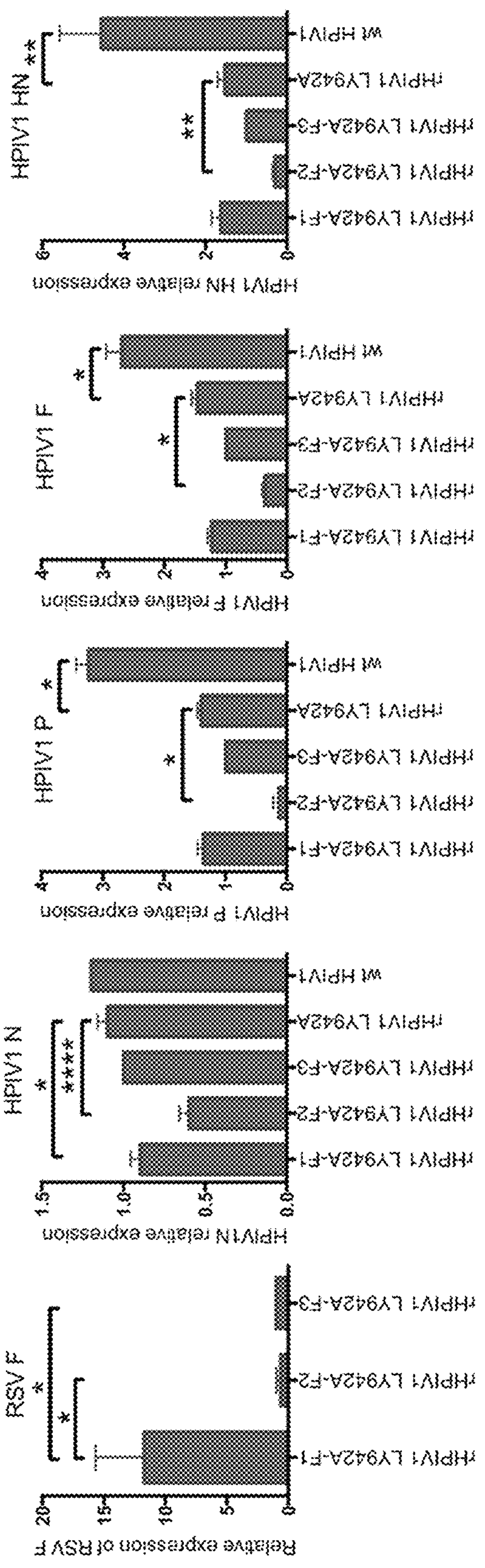
Figure 39A:
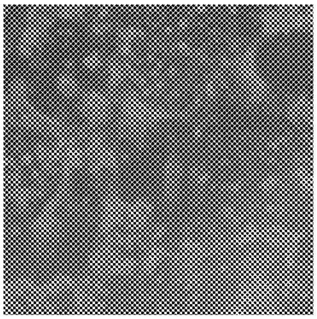
FIGS. 39A-39I. Formation of cytopathic effects and syncytia on LLC-MK2 cell monolayers infected with the rHPIV1 vectors expressing RSV F. MK2 cells were infected at an MOI of 0.01 $TCID_{50}$, incubated for 5 days and images were acquired at 40× magnification using phase contrast with a light microscope. Photomicrographs of (A) rHPIV1 $C^{\Delta170}$-F1; (B) rHPIV1 $C^{\Delta170}$-F2; (C) rHPIV1 $C^{\Delta170}$-F3; (D) rHPIV1 $C^{\Delta170}$; (E) rHPIV1 $L^{Y942A}$-F1; (F) rHPIV1 $L^{Y942A}$-F2; (G) rHPIV1 $L^{Y942A}$-F3; (H) rHPIV1 $L^{Y942A}$; and (I) wt HPIV1 are shown.
Figure 39B:
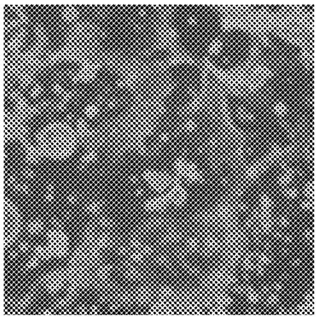
Figure 39C:
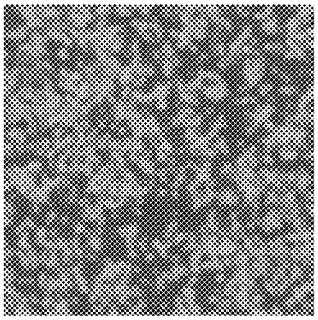
Figure 39D:
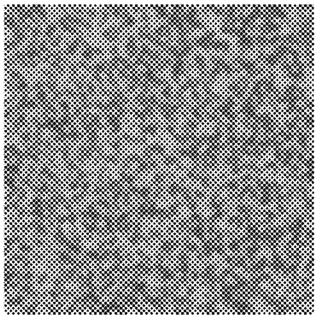
Figure 39E:
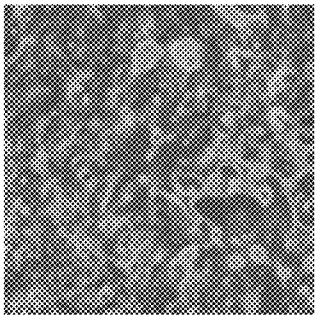
Figure 39F:
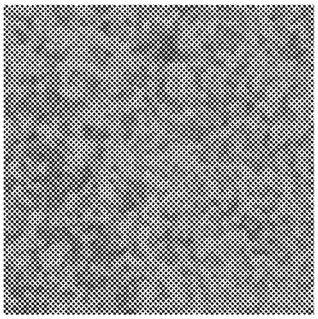
Figure 39G:
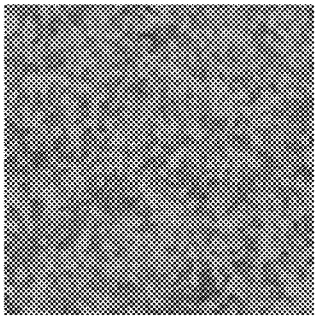
Figure 39H:
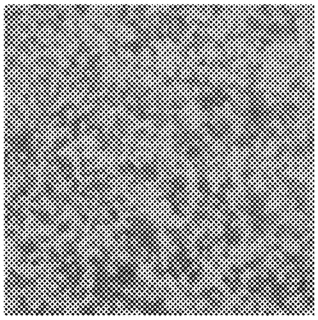
Figure 39I:
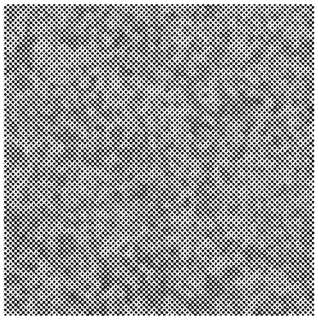

In contrast to the $C^{\Delta170}$ mutation, the $L^{Y942A}$ mutation did affect the expression of vector proteins: specifically, compared with wt HPIV1, the rHPIV1 $L^{Y942A}$ empty vector had significantly reduced expression of the P ($p<0.05$), F ($p<0.05$), and HN ($P<0.01$) proteins, with no significant difference for the N protein (FIGS. 38A, C). In case of the three versions of rHPIV1 $L^{Y942A}$ expressing RSV F, the F3 virus had modest reductions in the abundance of vector proteins as compared with the empty backbone, but none of the reductions was significant. Interestingly, this lack of significant vector protein reduction was consistent with the rHPIV1 $C^{\Delta170}$-F3 virus, suggesting that the F3 insert position does not interfere with vector protein expression and provides a site for which interference with the vector is minimal. The F2 virus on the other hand exhibited highly pronounced and significant reduction in N, P, F, and HN proteins as compared to the rHPIV1 $L^{Y942A}$ empty vector. In comparison, the rHPIV1 $C^{\Delta170}$-F2 virus, also showed reduced expression of the P, F, and HN proteins but not the N protein. This was to be expected because insertion after N at the second F2 position might be expected to reduce the expression of downstream genes due to the 3'-5' polar transcriptional gradient, whereas the upstream N gene might be expected to be unaffected, as was observed. Unexpectedly, however, in case of the rHPIV1 $L^{Y942A}$-F2, although RSV F was inserted downstream of the N gene, the expression of N protein was also negatively affected. The rHPIV1 $L^{Y942A}$-F1 had significantly reduced expression only in the case of the N protein, while expression of the P, F, and HN proteins was comparable to that of the rHPIV1 $L^{Y942A}$ empty vector.

Comparison of Syncytium Formation by rHPIV1/RSV-F Vectors.

A hallmark of RSV infection in vitro is the characteristic syncytium formation mediated by the RSV F protein. Infection of LLC-MK2 cell monolayers by wt HPIV3 or the rHPIV1 $C^{\Delta170}$ or $L^{Y942A}$ empty vectors did not induce evident syncytium formation (FIG. 39, panels I, D, or H, respectively). In sharp contrast, HPIV1 vectors expressing high levels of RSV F protein, namely the rHPIV1 $C^{\Delta170}$-F1 and -F2 viruses (FIGS. 39A and 39B) and the rHPIV1-$L^{Y942A}$-F1 virus (FIG. 39E), induced high levels of syncytia. Syncytium formation was not evident with the rHPIV1 $C^{\Delta170}$-F3 virus (FIG. 39C) even though the level of expression of RSV F protein was only modestly less than with the F1 and F2 viruses (FIG. 38). Syncytium formation also was not evident with the rHPIV1-$L^{Y942A}$-F2 and -F3 viruses (FIGS. 39F and 39G), which expressed very low levels of RSV F protein (FIG. 38). This functional assay (syncytium formation) suggested that the RSV F protein expressed from the HPIV1 vectors was folded and processed correctly and accumulated at the cell surface in active form.

In addition, the $C^{\Delta170}$ mutation was associated with a second cytopathic effect, namely increased apoptosis. This was most evident with the rHPIV1-$C^{\Delta170}$ empty vector (FIG. 39D), because the enhanced apoptosis was more readily observed in the absence of syncytium formation. Enhanced induction of apoptosis due to the $C^{\Delta170}$ mutation may explain why the rHPIV1-$L^{Y942A}$-F3 virus was inefficient in inducing syncytium formation (FIG. 39C) despite the expression of a high level of RSV-F (FIG. 38B): it is reasonable to suggest that the cell rounding associated with the $C^{\Delta170}$-mediated enhanced apoptosis (e.g., FIG. 39D) might reduce the cell-to-cell contact necessary for syncytium formation, but very efficient expression of RSV F with other constructs might allow syncytium formation to begin sufficiently early to overcome the apoptosis effect (e.g., FIG. 39B versus FIG. 39C).

The observations made with LLC-MK2 cells in FIG. 39 also were obtained with Vero cells.

Temperature Sensitivity of the rHPIV1/RSV-F Viruses.

As noted, the $C^{\Delta170}$ mutation did not confer the ts phenotype in previous studies, whereas the $L^{Y942A}$ mutation did so (McAuliffe, et al. 2004. J virology 78:2029-2036; Newman, et al. 2004. J Virol 78:2017-2028). Insertion of RSV F into an HPIV vector also has been shown to confer the ts phenotype (Liang, et al. 2014. J virology 88:4237-4250). The HPIV1/RSV-F constructs were therefore evaluated for the presence and magnitude of the ts phenotype. Specifically, 10-fold serial dilutions were prepared and used to infect LLC-MK2 cells and incubated at 32, 35, 36, 37, 38, 39, and 40° C., in 7 replicates. Virus titers were determined by HAD using guinea pig erythrocytes, and titers were reported as $\log_{10}$ $TCID_{50}$/ml (FIG. 43). The reduction in titer ($\log_{10}$) at each restrictive temperature compared to the titer at the permissive temperature of 32° C. was calculated. The shut-off temperature for a given virus was defined as the lowest restrictive temperature at which the mean $\log_{10}$ reduction in virus titer at that temperature versus 32° C. was ≥2.0 $\log_{10}$ compared to that of wt rHPIV1 at the same two temperatures (Bartlett, et al. 2005. Vaccine 23:4631-4646). The ts phenotype was defined as having a shut-off temperature of ≤40° C.

While the $C^{\Delta170}$ mutation did not confer the ts phenotype in previous studies, in the present study the rHPIV1 $C^{\Delta170}$ empty vector had a shut-off temperature of 40° C. (FIG. 39) and thus was ts compared to wt HPIV1, but the effect was small. The rHPIV1 $C^{\Delta170}$-F2 and -F3 constructs also had shut-off temperatures of 40° C. and thus did not differ significantly from the empty vector. However, the rHPIV1 $C^{\Delta170}$-F1 virus had a lower shut-off temperature of 39° C. (FIG. 43). In the present study the rHPIV1 $L^{Y942A}$ empty vector had a shut-off temperature of 36° C., similar to the values of 35-37° C. associated with this mutation in previous studies (McAuliffe et al JVI 78:2029-2036, 2004; Bartlett et al Virol J 4:67, 2007). The rHPIV1 $L^{Y942A}$-F1 and -F2 constructs were more ts than the empty vector, with shut-off temperatures of 35° C., while the rHPIV1 $L^{Y942A}$-F3 vector had the same 36° C. shut-off temperature as the empty vector (FIG. 43). Thus, insertion of the RSV F gene into the F1 position of either attenuated backbone increased the ts phenotype, insertion into the F3 position of either backbone did not increase the ts phenotype, and insertion into the F2 position increased the phenotype only for the $L^{Y942A}$ backbone.

Percentage of Virions in the Vaccine Inoculum that Express RSV-F (Vaccine Stability In Vitro).

The working pools of the rHPIV1/RSV-F constructs were evaluated for the frequency of RSV F expression in individual viral plaques using a fluorescent double-staining plaque assay. Vero cells were inoculated with 10-fold serially diluted viruses and allowed to form plaques for 6 days under a methycellulose overlay at the permissive temperature of 32° C. Viral plaques were co-immunstained for RSV F and HPIV1 proteins by using a mix of three RSV F-specific murine monoclonal antibodies and a goat HPIV1-specific polyclonal antiserum (see Materials and Methods). The primary antibodies were detected using anti-mouse-IgG and anti-goat-IgG second antibodies conjugated with red and green infrared dyes, and the percentage of HPIV1 plaques expressing RSV F was determined. A total number of 140, 77, and 59 plaques were counted for rHPIV1 $C^{\Delta170}$-F1, -F2, and -F3, respectively, and all were found to have 100% of the HPIV1 plaques expressing RSV F protein. F1 made plaques of smaller size than F2 and F3 while F2 and F3 plaque size was similar to each other. A total of 214, 70, and 192 plaques were counted for rHPIV1 $L^{Y942A}$-F1, -F2, and -F3, respectively, that showed 100%, 100%, and 97% of the HPIV1 plaques expressing RSV F antigen. Overall, the rHPIV1 $L^{Y942A}$ viruses formed plaques of much smaller size as compared to the rHPIV1 $C^{\Delta170}$ viruses. Since the assay was performed at the permissive temperature (32° C.), the smaller plaque phenotype, suggesting a relatively more attenuated phenotype and slower spread, may not be a ts effect. This was also consistent with their relatively slower replication profile (FIG. 37).

Replication of the rHPIV1/RSV-F Viruses in the Respiratory Tract of Hamsters.

Figure 40B:
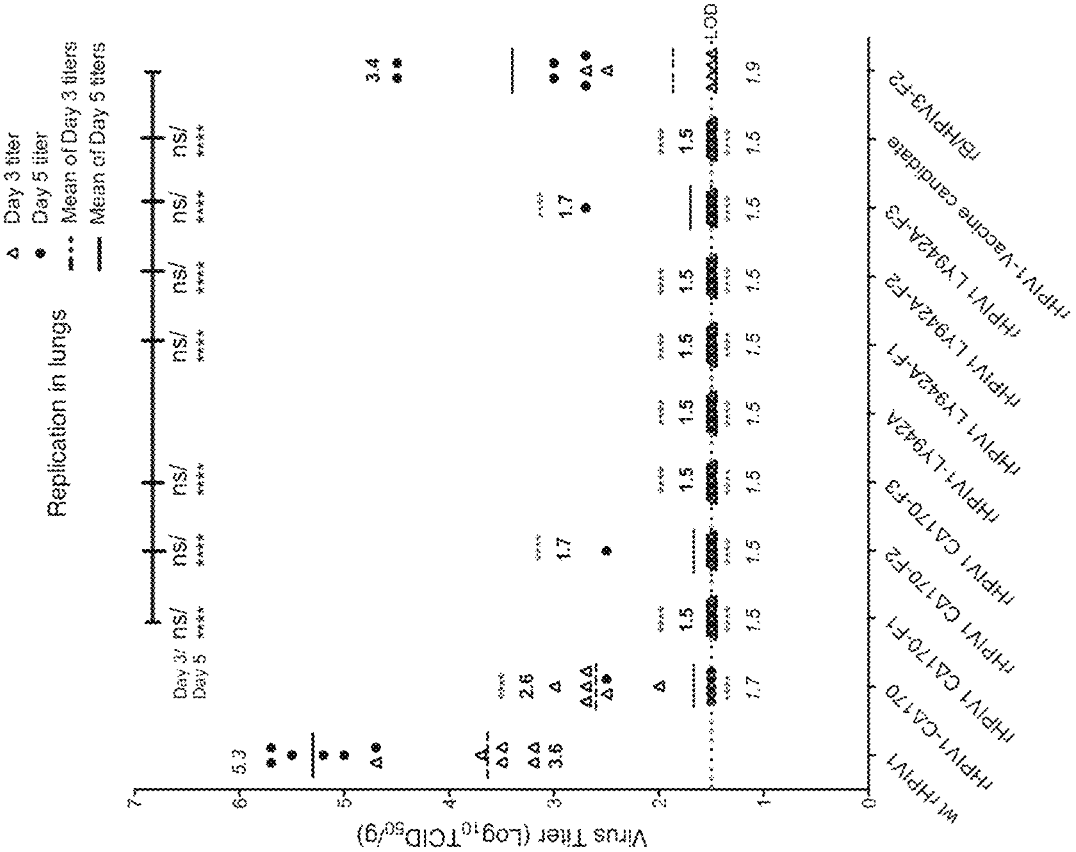
FIGS. 40A and 40B. Replication of RSV F expressing HPIV1 vectors in the nasal turbinates (40A) and lungs (40B) of hamsters. Hamsters were inoculated intra-nasally with $10^5$ $TCID_{50}$ of the wt HPIV1, rHPIV1 $C^{D170}$ or rHPIV1 $L^{Y942A}$ empty vectors, rHPIV1 $C^{D170}$ or rHPIV1 $L^{Y942A}$ expressing RSV F from three genome positions (F1, F2, or F3), rHPIV1-$C^{R84G}C^{D170}HN^{553A}L^{Y942A}$ (a previously-described HPIV1 vaccine candidate (Bartlett et al 2007 Virol J 4:6)), or the rB/HPIV3-F2, a chimeric bovine/human PIV3 expressing RSV F from the $2^{nd}$ position (also known as HEK/GA-opt, see FIG. 1). Virus titers were determined in LLC-MK2 cells by hemadsorption assay and reported as $Log_{10}$ $TCID_{50}$/g of tissue. Titers for individual animals (6 per group) are shown for day 3 (Δ) and day 5 (•), each symbol representing an individual animal. The mean values are shown for each group in boldface for day 3 and in italicized type for day 5. The limit of detection (LOD) was 1.5 $log_{10}$ $TCID_{50}$/ml, indicated with a dotted line across the bottom of each graph. The statistical significance of the difference between each virus versus wt HPIV1 (red asterisks) or versus rB/HPIV3-F2 (bar at the top) was determined by One-way ANOVA at 95% confidence interval using Tukey's multiple comparisons test for day 3 and day 5 p.i. *, $p \le 0.05$; *, $p \le 0.001$; **, $p \le 0.0001$; or ns, not significant.

Viruses were evaluated for their ability to replicate in the upper and lower respiratory tract (URT and LRT, respectively) of hamsters. Hamsters were inoculated intranasally with a dose of $10^5$ $TCID_{50}$/0.1 ml per animal. To assess virus replication, hamsters were euthanized on days 3 and 5 post-infection (6 animals per virus per day) and the nasal turbinates (URT) and lungs (LRT) were collected. Homogenates of individual nasal turbinates and lungs were analyzed for virus replication by titration on LLC-MK2 cells using HAD assay, and the titers were reported as $\log_{10}$ $TCID_{50}$/ml. Virus titers are shown for days 3 and 5 as open triangles and filled circles, respectively, in the URT (FIG. 40A) and the LRT (FIG. 40B). Each symbol represents an individual animal.

Overall, the peak virus titers for all rHPIV1 vectors expressing RSV F were lower than that of the wt HPIV1 suggesting the attenuating effects of the backbone mutations ($C^{\Delta170}$ or the $L^{Y942A}$) as well as that of the inserted RSV F gene. In the URT, the rHPIV1 $C^{\Delta170}$ empty vector was significantly attenuated on day 5 and not on day 3 but was significantly restricted on both days in the lungs as compared to the wt HPIV1. In the URT, significantly reduced replication was observed for rHPIV1 $C^{\Delta170}$-F1 on day 3 ($p<0.05$) only and for -F2 on both days ($p<0.0001$); -F3 replicated at levels similar to those of wt rHPIV1 on both days. rHPIV1 $C^{\Delta170}$-F1, -F2, and -F3 were all significantly ($p<0.0001$) attenuated in the lungs on day 3 and 5; F1 and F3 were undetectable in all and F2 was undetectable in 5 of 6 animals. The rHPIV1 $L^{Y942A}$ empty vector replication was significantly reduced on day 3 and no virus was detected on day 5 in the URT whereas no virus was detected on both days in the lungs suggesting significant attenuation consistent with the is phenotype of the $L^{Y942A}$ mutation (McAuliffe, et al. 2004. J virology 78:2029-2036) (FIG. 43). The rHPIV1 $L^{Y942A}$-F1, -F2, and -F3 viruses were also significantly ($p<0.0001$) attenuated both in the URT and lungs on day 3 and 5 with virus replication undetectable for majority of the animals.

The HPIV1 vaccine candidate (rHPIV1-$C^{R84G/\Delta170}$ $HN^{553A}LY^{942A}$), previously demonstrated to be strongly attenuated in AGMs (Bartlett, et al. 2007. Virology J 4:67) and over attenuated in sero-negative children, was included as a control for replication comparison and to assess the level of attenuation of the vaccine candidates being developed. As expected, this virus was significantly attenuated in hamsters with no replication observed in the URT and lungs on day 3 and 5. The observation that most of the constructs developed in the present study had attenuated but detectable replication suggests that they are somewhat less attenuated than the previous vaccine candidate, which was over-attenuated in children, suggesting that the constructs developed in the present study may have suitable attenuation phenotypes. The chimeric bovine/human PIV3 expressing RSV F from the second genome position (rB/HPIV3-F2) is being developed as a live RSV vaccine (Introduction, and Example 1). In clinical trials, this vaccine candidate was found to be safe in 6-24 month old RSV seronegative children with a safe and well-tolerated level of replication (Bernstein, et al. 2012. Pediatric infectious disease journal 31:109-114). The rB/HPIV3-F2 virus was included as a reference virus for the comparative assessment of attenuation and immunogenicity of the rHPIV1 vaccine candidates being tested. The replication level of the rHPIV1 $C^{\Delta170}$-F1, -F2, or -F3 on both days was either statistically similar to or significantly lower than that of the rB/HPIV3-F2 in both the URT and lungs. Likewise, the rHPIV1 $L^{Y942A}$-F1, -F2, and -F3 viruses also showed significantly reduced replication in both the URT and lungs on day 3 and 5 as compared to rB/HPIV3-F2. These data suggest that the HPIV1 vectors with either the $C^{\Delta170}$ or the $L^{Y942A}$ backbone mutations are sufficiently attenuated in vivo and show replication phenotype that is similar to or even more attenuated than the rB/HPIV3-F2 virus.

In the URT, the titers for all viruses (except rHPIV1 $L^{Y942A}$-F1 and -F3, which did not replicate) were higher on day 3 (FIG. 40A) than on day 5. In contrast, rB/HPIV3-F2 attained peak titer on day 5. Overall, in the lungs, all vectors expressing RSV F were significantly ($p \leq 0.0001$) restricted as compared to wt HPIV1 on days 3 and 5 post-infection (FIG. 40B) and were also significantly restricted as compared to rB/HPIV3-F2 on day 5.

Stability of RSV F Protein Expression by the Chimeric rHPIV1 Viruses after In Vivo Replication.

Positive selection of viruses that silence the expression of RSV F may happen during replication in vivo that may compromise RSV F immunogenicity (Yang, et al. 2013. Vaccine 31:2822-2827). Mutations may occur in the RSV F ORF or the regulatory transcriptional signals controlling its expression such that the RSV F protein expression is either reduced or ablated. To evaluate the rHPIV1 vectors for in vivo stability, Vero cells were infected with serially diluted homogenates of the nasal turbinates and lungs of the infected hamsters. A fluorescent double immunostaining plaque assay was performed to determine the percentage of virus particles expressing RSV F. Consistent with the lack of replication in the lungs (FIG. 40B), no plaques could be detected for all vectors expressing RSV F in the lung homogenates. Similarly, no plaques were detectable for the rHPIV1 $L^{Y942A}$ viruses expressing RSV F in the URT due to poor replication. The stability results for rHPIV1 $C^{\Delta170}$ viruses, which replicated efficiently in the URT are shown (FIG. 44). These viruses were stable after in vivo replication with an overall >98% plaques expressing RSV F on days 3 and 5 post-infection Of the 30 samples analyzed, 29 had 100% and only one sample had 98% (2% loss) PFUs expressing RSV F. These data suggest that the rHPIV1 $C^{\Delta170}$ vectors expressing RSV F are quite stable in hamster model and did not show evidence of the selection of mutants with silenced RSV F expression after in vivo replication for at least 5 days.

Immunogenicity

Immunization with the Chimeric rHPIV1 Viruses Expressing RSV F Induces Serum Virus Neutralizing Antibodies (NAbs) Against RSV and HPIV1.

Figure 40A:
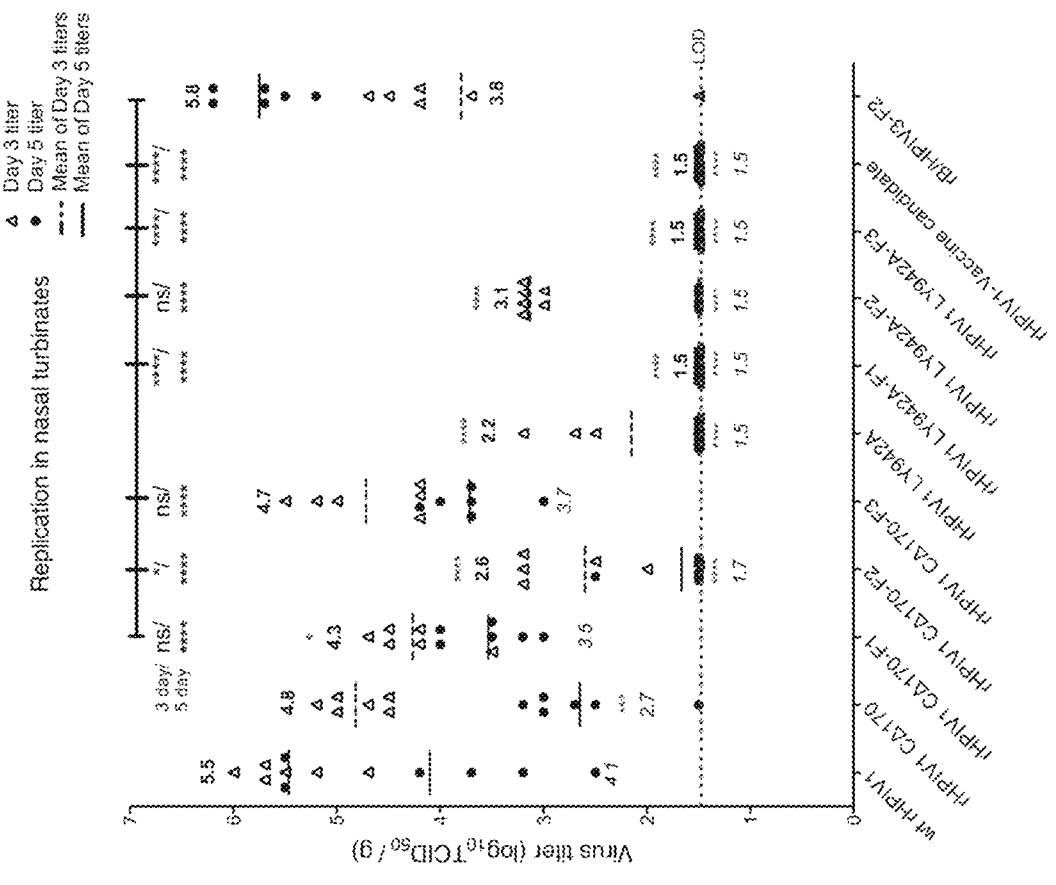

To determine the immunogenicity of the rHPIV1 viruses expressing RSV F, groups of six hamsters per virus were inoculated intranasally with $10^5$ $TCID_{50}$ per animal. wt RSV, rHPIV1 $C^{\Delta170}$, rHPIV1 $L^{Y942A}$, and rB/HPIV3-F2 were included as controls. Sera from immunized hamsters were collected at 28 days post-infection and the NAb titers against RSV and HPIV1 were determined by $PRNT_{60}$ assay (FIG. 45). The rHPIV1 $C^{\Delta170}$-F1, -F2, and -F3 induced RSV-specific NAbs at titers that were not statistically different from each other. This was not surprising because all three viruses showed similar level of RSV F protein expression (FIGS. 38A and 38B). The rHPIV1 $C^{\Delta170}$-F1 and -F2 had a slightly higher RSV F expression than the -F3 virus but this difference was not statistically significant (FIG. 38B). Likewise, the -F1 and -F2 viruses also showed relatively higher fusion activity and syncytia formation than the -F3 virus that is presumably correlated with the amount of RSV F synthesized during infection (FIG. 39A-39C) Although statistically insignificant, the NAb titer seems to be slightly higher for F1 and F3 viruses as compared to F2 which is more consistent with their in vivo replication profile (FIG. 40A) rather than the amount of RSV F expressed. The RSV NAb titer induced by rHPIV1 $C^{\Delta170}$-F1, -F2, and -F3 were significantly lower than that induced by rB/HPIV3-F2, a difference that likely stems from the significantly reduced replication of these viruses as compared to rB/HPIV3-F2 (FIGS. 40A and 40B).

The rHPIV1 $L^{Y942A}$-F1, -F2, and -F3 viruses failed to induce NAb response to RSV. This was unexpected because the rHPIV1 $L^{Y942A}$-F1 showed RSV F expression similar to that of rHPIV1 $C^{\Delta170}$-F1, -F2, and -F3 on in vitro infection of Vero cells (FIG. 38A). However, it is important to note that the $L^{Y942A}$ mutation is highly attenuating and confers a ts phenotype with a shut-off temperature of 36° C. (FIG. 43). The $L^{Y942A}$ mutant viruses were expected to show minimal or no detectable replication in hamsters (body temperature: 36.7 to 38.3° C.; The Merck Manual). Consistent with the backbone phenotype, the rHPIV1 $L^{Y942A}$-F1, -F2, and -F3 were also ts with a shut off temperature of 35° C., 35° C., and 36° C., respectively, indicating that the insertion of RSV F at the F1 and F2 positions reduced the shut off temperature by 1° C. making them even more ts. Therefore, although the rHPIV1 $L^{Y942A}$-F1 was able to express RSV F at levels comparable to those of the rHPIV1 $C^{\Delta170}$-F1, -F2, and -F3 viruses at permissive temperature (FIG. 38A), it failed to induce RSV NAbs likely due to its strong ts phenotype and inability to replicate in vivo. The rHPIV1 $L^{Y942A}$-F2 and -F3 viruses seemingly had two confounding factors: they showed relatively poor RSV F expression (FIGS. 38A and 38C) and in addition were ts and did not replicate in vivo (FIGS. 40A and 40B), resulting in lack of an RSV NAb response. Thus, the rHPIV1 $L^{Y942A}$-F1, -F2, and -F3 viruses were not immunogenic and did not generate vaccine candidates because of their over attenuated ts phenotype and lack of replication and immunogenicity in vivo.

The HPIV1 specific NAb response in hamsters was also evaluated by $PRNT_{60}$ assay (FIG. 45). Overall, the levels of HPIV1 NAb titers were lower as compared to the RSV NAb titers. As indicated in the methods, guinea pig complement was included in the neutralization assay for RSV but was excluded from the HPIV1 neutralization assay as it neutralizes HPIV1. The lack of complement may be the reason for generally reduced HPIV1 NAb titers. The rHPIV1 $C^{\Delta170}$-F2 and -F3 viruses did not induce detectable levels of HPIV1 NAbs. Only the rHPIV1 $C^{\Delta170}$ empty vector and the rHPIV1 $C^{\Delta170}$-F1 induced detectable HPIV1-specific NAb responses, which were at titers that were not statistically different from each other. This was contrary to the expectation because the expression of all vector proteins was significantly reduced for rHPIV1 $C^{\Delta170}$-F1 (FIGS. 38A and 38B). It also had a lower shut off temperature by 1 C as compared to the F2 or F3 viruses and it replicated in vivo at levels similar to those of F3 virus. Thus, the rHPIV1 $C^{\Delta170}$-F1 was expected to induce similar or weaker HPIV1 specific NAb response as compared to the -F3 virus. However, the poor HPIV1 immunogenicity of the $C^{\Delta170}$-F2 was consistent with its reduced expression of F and HN proteins (FIG. 38B) and poor replication in the URT and LRT (FIG. 40). The lack of HPIV1 NAb response was unexpected for the $C^{\Delta170}$-F3 virus. It expressed all HPIV1 proteins at levels similar to those of the empty vector (FIGS. 38A and 38B), replicated similarly, and had the shut off temperature similar to that of the empty vector but showed no detectable NAb response.

All of the rHPIV1 $L^{Y942A}$ viruses, including the empty vector, did not induce detectable levels of HPIV1 specific NAbs. All rHPIV1 $L^{Y942A}$ viruses expressed reduced levels of HPIV1 proteins in vitro (FIGS. 38A and 38C) and showed poor or no replication in vivo. Consistent with this, these viruses also showed lack of immunogenicity against RSV. Their poor immunogenicity is likely a result of their strong ts phenotype (FIG. 43) and lack of in vivo replication (FIG. 40).

Immunization with rHPIV1 Vectors Expressing RSV F Provides Protection Against Wt RSV Challenge.

Figure 41A:
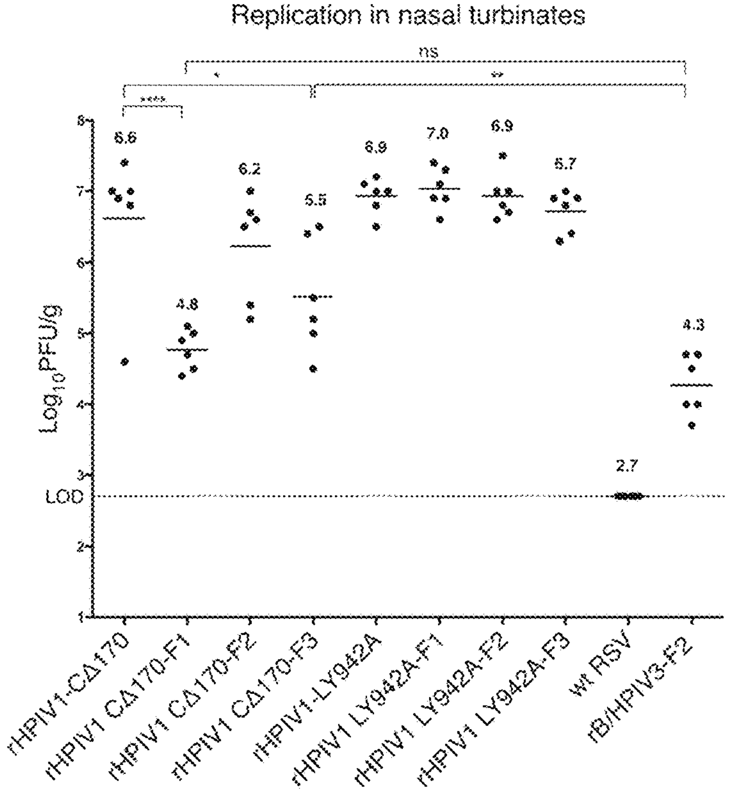
FIGS. 41A and 41B. Protection against wt RSV challenge virus replication in the nasal turbinates (41A) and lungs (41B) of the immunized hamsters Hamsters (n=6) in each group were challenged intranasally with $10^6$ PFU of wt RSV A2 at 30 days post-immunization. Nasal turbinates and lungs were collected from euthanized animals on day 3 post-challenge, virus titers were determined for each sample by RSV specific plaque assay on Vero cells and reported as $Log_{10}$ PFU/g of tissue. Mean value for each group is shown in bold face number and by a horizontal bar. Statistical significance of difference among viruses was determined by one-way ANOVA at 95% confidence interval using Tukey's multiple comparisons test and is indicated by *, $p<0.05$; , $p<0.01$; **$p<0.0001$; or ns, not significant.
Figure 41B:
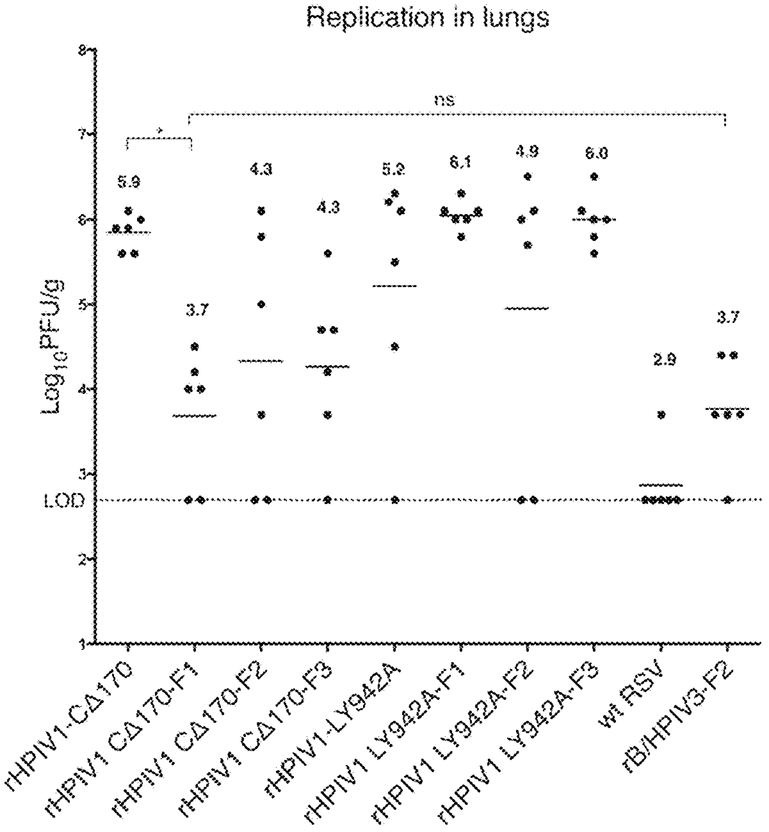

Hamsters were immunized with rHPIV1 expressing RSV F as described above and were challenged on day 30 post-immunization with $10^6$ PFU of wt RSV. Hamsters were euthanized on day 3 post-challenge and RSV titers in the nasal turbinates and lungs were determined by plaque assay on Vero cells to assess the protection against challenge RSV replication (FIGS. 41A and 41B). The protection provided by vaccine candidates against RSV infection and replication correlated with their ability to induce RSV specific serum NAb. The rHPIV1 $C^{\Delta170}$-F1 and -F3 provided significant protection against RSV replication and showed significantly reduced ($p<0.0001$ and $p<0.05$, respectively) RSV titers in the URT as compared with the rHPIV1 $C^{\Delta170}$ empty vector, with the -F2 virus having no effect. In the lungs, although all three rHPIV1 $C^{\Delta170}$-F1, -F2, and -F3 viruses reduced the mean RSV titers as compared to the rHPIV1 $C^{\Delta170}$ empty vector, only the RSV reduction by -F1 virus was statistically significant ($p<0.05$). As expected, the rB/HPIV3-F2 provided significant protection against RSV challenge in the URT ($P<0.0001$) and lungs ($p<0.05$), which was consistent with a previous report (Liang, et al. 2014. J virology 88:4237-4250, and Example 1).

Statistical comparison of the rHPIV1 vaccine candidates with the rB/HPIV3-F2 virus showed that the protection provided by rHPIV1 $C^{\Delta170}$-F1 was statistically similar to that of rB/HPIV3-F2 both in the URT and lungs. The rHPIV1 $C^{\Delta170}$-F1 replicated in hamsters to titers similar to those of rB/HPIV3-F2 on day 3 post-infection but demonstrated significantly reduced replication on day 5 post-infection suggesting that the rHPIV1 $C^{\Delta170}$-F1 may be sufficiently attenuated in vivo. This along with its ability to protect against RSV challenge similar to that of rB/HPIV3-F2 also indicated that rHPIV1 $C^{\Delta170}$-F1 has desirable features of attenuation and immunogenicity and should be further developed as a live attenuated RSV vaccine candidate.

The rHPIV1 $L^{Y942A}$-F1, -F2, and -F3 viruses did not provide protection against RSV challenge in the URT and lungs and showed challenge RSV loads similar to that of the rHPIV1 $L^{Y942A}$ empty vector. This was consistent with their lack of in vivo replication and immunogenicity against RSV.

Discussion

Figure 37B:
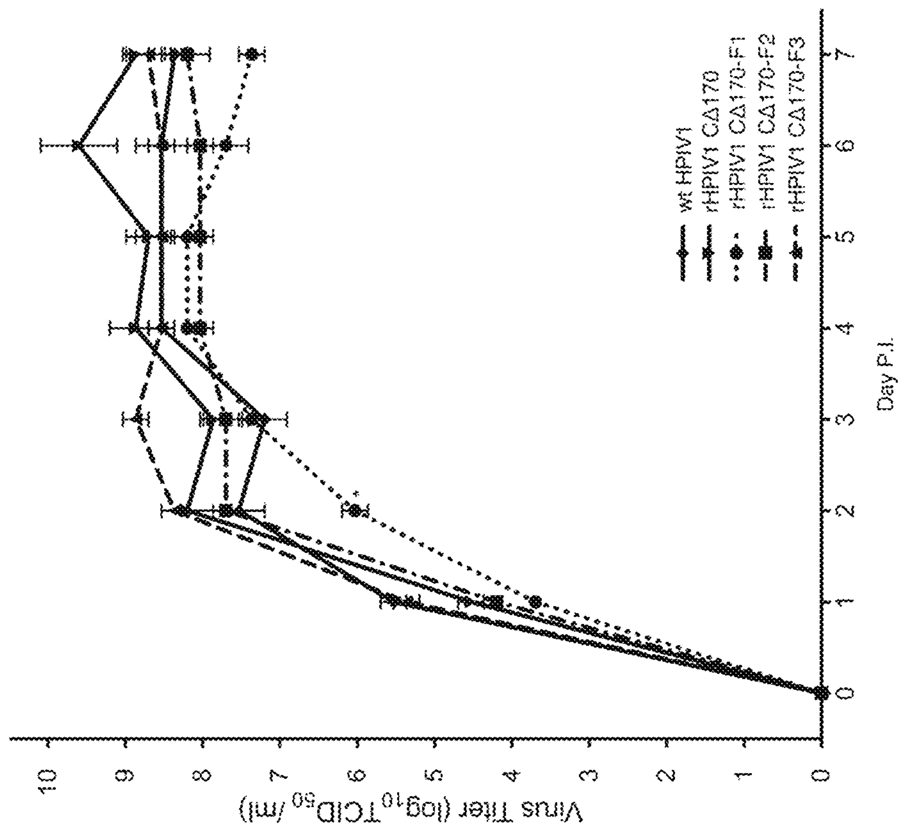
FIGS. 37A-37D. Multistep replication of HPIV1/RSV-F viruses in Vero (37A and 37C) and LLC-MK2 (37B and 37D) cells. Triplicate wells of cell monolayers in 6-well plates were infected at an MOI of 0.01 $TCID_{50}$ with HPIV1 $C^{\Delta170}$ (A and B) or $L^{Y942A}$ (C and D) viruses expressing RSV F (F1, F2, or F3), in parallel with wt HPIV1, HPIV1 $L^{Y942A}$, and HPIV1 $C^{\Delta170}$. Cultures were incubated at 32° C. Aliquots of cell culture medium were collected at 24 h intervals and virus titers (login $TCID_{50}$/ml) were determined by serial dilution on LLC-MK2 cells and hemadsorption assay at 32° C. Mean titers with standard errors of the mean (SEM) are shown. The statistical significance of difference between the titer of each virus versus wt HPIV1 for day 2 post-infection was determined using the one-way ANOVA with Tukey's multiple comparisons test and is indicated by asterisks as follows: *, $p \le 0.05$; , $p \le 0.01$; *, $p \le 0.001$; ****, $p \le 0.0001$.
Figure 37A:
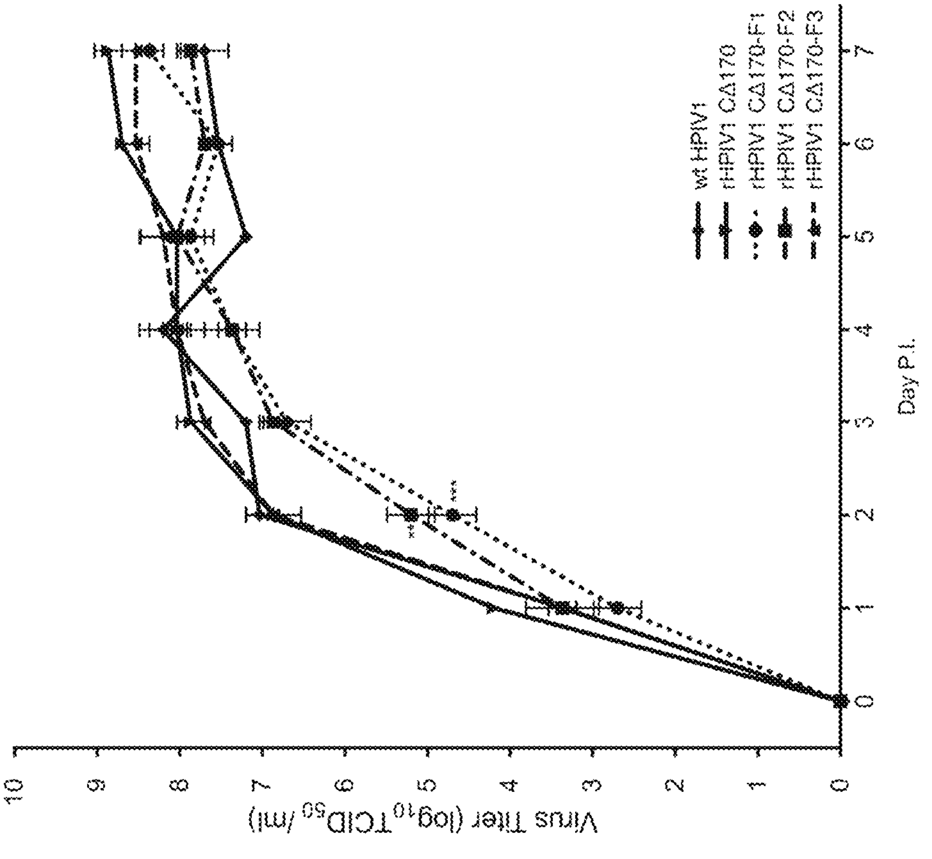
Figure 37C:
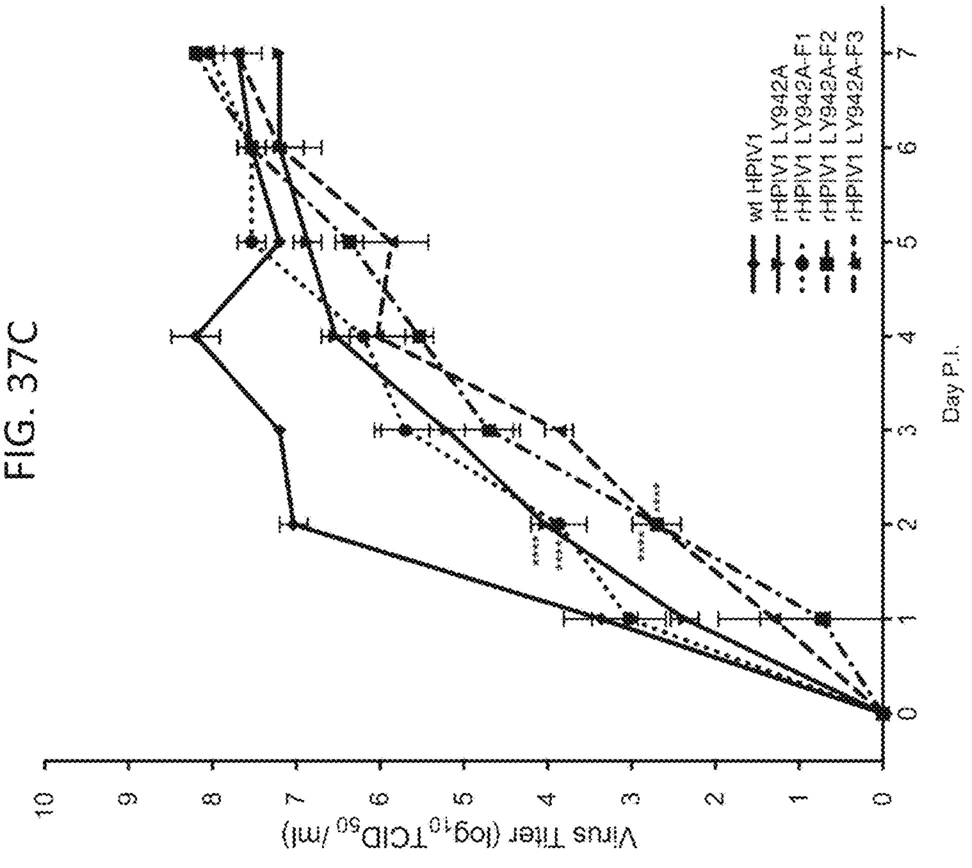
Figure 37D:
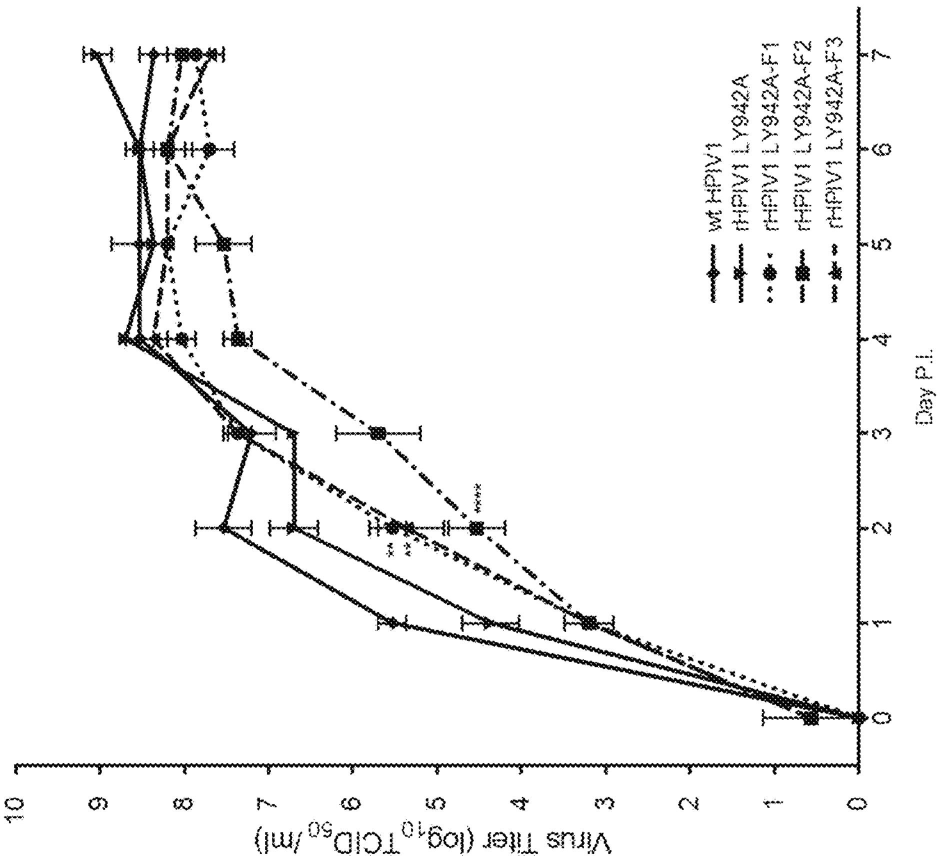

Various attenuated versions of rHPIV1 bearing attenuating and/or is mutations have been previously developed that were immunogenic in rodents and/or non-human primates. Two attenuated rHPIV1 backbones containing either the $C^{\Delta170}$ or the $L^{Y942A}$ mutation involving a deletion of 6 and substitution of 3 nucleotides, respectively, were assayed. RSV F was inserted at the first, second, or third genome position of each backbone with the aim to identify a construct that is appropriately attenuated and yet sufficiently immunogenic and protects against wt RSV challenge. All rHPIV1 viruses expressing RSV F were successfully rescued by reverse genetics. Growth kinetics in Vero and LLC-MK2 cells indicated that all viruses grew to very similar and statistically indistinguishable final titers determined at 7 days post-infection (FIG. 37). However significant differences in replication were observed on day 2 in both cell lines. The $L^{Y942A}$ mutation seemed to have a stronger attenuating effect than the $C^{\Delta170}$ mutation at least in Vero cells. Contrary to the expectation, the rHPIV1$C^{\Delta170}$ viruses were not attenuated in type I interferon (IFN-I) competent LLC-MK2 as compared to IFN-I deficient Vero cells. Among the rHPIV1$C^{\Delta170}$ viruses expressing RSV F, significant attenuation as compared to the wt HPIV1 was observed for the -F1 and -F2 viruses in Vero (FIG. 37A) and for -F1 in LLC-MK2 cells (FIG. 37B), whereas the -F3 replication was similar to the empty vector and wt HPIV1. These data suggest that insertion of RSV F closer to the 3' proximal positions in -F1 or -F2 viruses may be attenuating but this effect was transient and all viruses grew to similar final titers (FIGS. 37A and 37B). All rHPIV1 $L^{Y942A}$ backbone vectors including -F1, -F2 and -F3 grew to similar final titers on day 7. However, they also demonstrated reduced replication in both Vero and LLC-MK2 cells on days 2, 3, and 4 but were similar to wt HPIV1 between 5-7 days. The RSV F insert induced attenuation was much greater in magnitude for the rHPIV1$L^{Y942A}$ as compared to the rHPIV1$C^{\Delta170}$ vectors (FIG. 37D) indicating that RSV F insertion has a stronger attenuating effect on a backbone that is already significantly attenuated.

All viruses were examined for their ability to express RSV F protein by Western blot analysis of infected Vero cells incubated at a permissive temperature of 32° C. The expression of the HPIV1 N, P, F, and HN proteins was also evaluated to determine the effect of RSV F insertion at various positions on the vector protein expression. Unexpectedly, a polar gradient of RSV F expression was not observed for the rHPIV1$C^{\Delta170}$ vectors. The rHPIV1$C^{\Delta170}$-F1 demonstrated significantly decreased expression of all vector proteins tested. Similarly, with the exception of N protein, the rHPIV1$C^{\Delta170}$-F2 also showed reduced expression of P, F, and HN proteins (FIGS. 38A and 38B). Consistent with this both the -F1 and -F2 viruses showed reduced replication in Vero cells early during infection (FIG. 37A). These data suggest that for F1 and F2 viruses, the combined effect of reduced vector protein synthesis and the consequent attenuated replication might be responsible for reduced RSV F expression and a lack of its polar gradient. rHPIV1 $C^{\Delta170}$-F3 showed a modest reduction in RSV F expression as compared to F1 and F2, likely due to its distal genome location. The RSV F expression profile was very different for the rHPIV1 $L^{Y942A}$ vectors that demonstrated a strong polar gradient of expression (FIGS. 38A and 38C) with the F1 virus showing significantly higher RSV F expression as compared to F2 and F3. As anticipated, insertion of RSV F in the first position significantly reduced the N protein expression for the F1 vector while the P, F and HN proteins were unaffected and had expression similar to that of their empty vector counterpart (FIGS. 38A and 38C). The rHPIV1 $L^{Y942A}$-F2 showed very poor expression of RSV F as well as all vector proteins (FIGS. 38A and 38C). As stated above, this virus was the most difficult to rescue due to its highly attenuated phenotype and the accumulation of mutations during rescue. However, the virus finally used in the experiments had no adventitious mutations confirmed by genome sequencing. Therefore, it appears that insertion of RSV F at the F2 location in rHPIV1 $L^{Y942A}$ backbone seems to be quite detrimental with the virus showing drastically significant reduction of all vector proteins tested including RSV F. One non-limiting explanation for this result is that this is a combined effect of insert position and the highly attenuated backbone because such effects were not observed for rHPIV1 $C^{\Delta170}$-F2. Referring to its growth kinetics (FIGS. 37C-37D), the rHPIV1$L^{Y942A}$-F2 was the most attenuated of all the rHPIV1 $L^{Y942A}$ vectors. Thus, it seems that an overall reduction of vector protein synthesis significantly reduced its replication resulting in reduced RSV F expression. The rHPIV1 $L^{Y942A}$-F3 virus expressed vector proteins at levels similar to the empty vector but showed a >10-fold reduction in RSV F expression as compared to F1 (FIGS. 38A and 38C). This indicates that RSV F insertion at the third genome position did not negatively affect vector protein expression (FIGS. 38A and 38C) but demonstrated poor RSV F expression likely due to its distal location in the polar transcriptional gradient.

Native RSV F causes plasma membrane fusion of the neighboring infected cells resulting in syncytia formation. The HPIV1 vector F protein does not cause syncytium formation, which therefore could be used as an indicator of RSV F functionality and native form as well as quantity of expression. Formation of syncytia by RSV F expressed from rHPIV1 $C^{\Delta170}$ or $L^{Y942A}$ vectors was evaluated in Vero and LLC-MK2 cells. Extensive syncytia formation showing fusion of the majority of cells in the monolayer was observed with the rHPIV1 $C^{\Delta170}$-F1 and -F2 as well as with the rHPIV1 $L^{Y942A}$-F1 (FIG. 39) suggesting that the recombinant RSV F protein is functional and presumably in a native conformation. The rHPIV1 $C^{\Delta170}$ F3 and $L^{Y942A}$-F2 and -F3 did not show apparently obvious syncytia formation. The extent of syncytia formation was consistent with the level of RSV F expression detected by Western blot (FIGS. 38A-38C).

Since the ts phenotype plays an important role in virus replication in vivo and may determine immunogenicity, the ts phenotype of the vectors expressing RSV F was evaluated. In contrast to the wt HPIV1 that is not ts even at 40° C., the rHPIV1 $C^{\Delta170}$ and $L^{Y942A}$ backbones were ts at 40° C. and 36° C., respectively (FIG. 43). Important to note is that the insertion of RSV F in the rHPIV1 $C^{\Delta170}$ at F1 and the rHPIV1 $L^{Y942A}$ at F1 or F2 positions lowered the shut off temperature by 1° C. thus making them slightly more ts. This effect may not be unique to HPIV1 because similar effect was observed on RSV F insertion into the rB/HPIV3 vector in a previous study Liang, et al. 2014. J virology 88:4237-4250). The enhancement of ts phenotype was observed for rHPIV1 $L^{Y942A}$-F2 but not for rHPIV1 $C^{\Delta170}$-F2 indicating that the insertion of foreign gene may enhance the ts phenotype of a virus that is already significantly ts.

The rHPIV1 vectors were evaluated in hamsters to assess their replication and immunogenicity. All of the rHPIV1 $L^{Y942A}$ viruses were over-attenuated and virus replication was undetectable in the URT and lungs of the majority of animals. This is consistent with their highly ts phenotype with a shut off temperature of 35-36 C. Failure to replicate seems not to be due to RSV F insertion but is likely an effect of their ts phenotype because even the empty vector did not replicate in the lungs and had poor replication in the URT. The rHPIV1 $C^{\Delta170}$-F1, -F2, and -F3 were overall highly restricted and undetectable in the lungs while the empty rHPIV1 $C^{\Delta170}$ vector did show low level replication, which was significantly lower than that of the wt HPIV1, suggesting that the presence of RSV F insert had an additional attenuating effect on the already attenuated rHPIV1 $C^{\Delta170}$ backbone in the lungs. In contrast to the lungs, all rHPIV1 $C^{\Delta170}$ vectors replicated well in the URT of all animals. The F1 and F2 viruses, but not F3, were significantly attenuated as compared to wt HPIV1, with F2 being more attenuated than F1. This was unexpected because in general insertion closer to the 3' end of the genome results in higher attenuation. This was also consistent with the relatively slower early growth of F1 and F2, but not F3, in vitro (FIG. 37) indicating that insertion of RSV F, in the F1 and particularly at F2 position, has an additive attenuating effect. The F1 virus appears to have the desired degree of attenuation, whereas the F2 and F3 viruses are over- and under-attenuated, respectively.

Attaining an optimal balance between attenuation and immunogenicity is a challenge with live attenuated vaccines. To assess if the attenuated rHPIV1 vectors were sufficiently attenuated, their replication was compared with that of the rB/HPIV3-F2, a leading RSV vaccine vector expressing RSV F from the second genome position (Liang, et al. 2014. J virology 88:4237-4250). The replication of rHPIV1 $C^{\Delta170}$-F1, -F2, or -F3 on day 3 and 5 was either statistically similar to or significantly lower than that of the rB/HPIV3-F2 in both the URT and lungs. This suggests that the $C^{\Delta170}$ mutation together with the insertion of RSV F appear to have achieved the desired level of attenuation, at least in this animal model, such that all three vectors are highly restricted in the lungs but do demonstrate attenuated replication similar to rB/HPIV3-F2 in the URT that will be needed for immunogenicity.

A difficulty encountered by RNA virus vectored vaccines is the instability of the foreign antigen gene in vivo (Yang, et al. 2013. Vaccine 31:2822-2827). Mutations are generated due to the error prone polymerase, and the lack of a need to maintain the expression of the insert. Any mutations in the foreign antigen acquired due to infidelity of the RNA dependent RNA polymerase could be positively selected as they provide a selective advantage. To determine the stability of RSV F expression in vivo after immunization, viruses recovered from respiratory tissues of hamsters were analyzed by fluorescent double staining plaque assay. This could only be performed for HPIV1 $C^{\Delta170}$-F1, -F2, and F3 viruses that showed detectable replication in the URT (FIG. 44). For majority of the samples, stable RSV F expression was observed for all three viruses, except one HPIV1 $C^{\Delta170}$-F1 sample for which RSV F expression was detected for 98% plaques. These data indicated that the rHPIV1 $C^{\Delta170}$ vectors maintain a stable expression of RSV F during in vivo replication.

Immunogenicity of the rHPIV1 vectors was evaluated by performing the $PRNT_{60}$ assay. The assay for RSV was performed in the presence of guinea pig complement, which was excluded from the HPIV1 neutralization assay because of the direct neutralization of HPIV1 by the complement alone. The rHPIV1 $C^{\Delta170}$-F1, -F2, and -F3 induced RSV neutralizing antibodies at a $PRNT_{60}$ ($log_2$) titer of 7.3, 4.7, and 6.7, respectively (FIG. 45). Although F1 demonstrated the highest antibody titer, it was statistically similar to that induced by F2 and F3. These titers were significantly lower than those induced by rB/HPIV3-F2 or wt RSV controls which could be a result of their overall relatively reduced replication both in the URT and lungs. The rHPIV1 $L^{Y942A}$-F1, F2, and F3 viruses did not induce a detectable RSV or HPIV1 neutralizing antibody response, which was consistent with their lack of replication in vivo. Only the rHPIV1 $C^{\Delta170}$-F1, and not the F2 or F3, induced detectable HPIV1 neutralizing antibodies. This was unexpected because the F2 and F3 did show replication in hamsters (FIG. 40) and induced RSV NAbs. As indicated above guinea pig complement, known to enhance the $PRNT_{60}$ read out, could not be included in the HPIV1 neutralization assay. The overall low HPIV1 antibody titers and lack of a detectable response, even for viruses that replicated in hamsters, could be due to weaker sensitivity of the assay lacking complement.

To determine the protective efficacy of the vectors against RSV infection, all immunized hamsters were intranasally challenged at 30 days post-immunization with a high dose ($10^6$ pfu) of wt RSV per animal Protection against challenge was assessed by determining RSV replication in the nasal turbinates and lungs (FIGS. 41A and 41B). Protection directly correlated with the immunogenicity (FIG. 45). Highly consistent with the RSV NAb titers, rHPIV1 $C^{\Delta170}$-F1 was more protective than F3 and no protection was afforded by F2. The protection was statistically significant for F1 in both the URT and lungs and for F3 in the URT only. Importantly, rHPIV1 $C^{\Delta170}$-F1 afforded protection in the URT and lungs that was statistically indistinguishable from rB/HPIV3-F2. This was somewhat unexpected because the rHPIV1 $C^{\Delta170}$-F1 induced significantly lower RSV NAb titer than that of the rB/HPIV3-F2 suggesting that the relatively lower NAb titer was sufficient to achieve similar protection. This interpretation is supported by the evidence that RSV replication in the respiratory tract of cotton rats could be reduced if the serum NAb titer was 1:100 or greater (Prince, et al. 1985. J Virol 55:517-520). Again, consistent with their lack of sero-conversion, rHPIV1 $L^{Y942A}$-F1, F2, and F3 did not provide any protection against challenge and had RSV loads similar to that of the empty vector. These data clearly show that the rHPIV1 $L^{Y942A}$ vectors were over-attenuated due to their is phenotype and did not replicate in the hamsters resulting in a lack of immunogenicity both for RSV and HPIV1. In contrast, the rHPIV1 $C^{\Delta170}$ vectors, although highly restricted in the lungs, did replicate in the URT. Among the vectors tested in this study, the rHPIV1 $C^{\Delta107}$-F1 appears to be adequately attenuated and yet sufficiently immunogenic against RSV. It is recognized that constructs that appear to be over-attenuated in hamsters may perform more suitably when evaluated in a more permissive primate host.

In summary, this example identifies the rHPIV1 $C^{\Delta170}$ as a promising attenuated backbone suitable for expressing RSV F antigen from an inserted gene. It was also systematically determined that the F1 (pre-N) genome position of the rHPIV1 $C^{\Delta170}$ vector was preferred among the positions tested for inserting RSV F. This study also demonstrated that the rHPIV1 $C^{\Delta170}$-F1 is a promising vaccine candidate and possesses several desirable features: (i) it is based on a backbone well characterized for attenuation in non-human primates (3), (ii) it replicated in Vero cells to final titers similar to that of wt HPIV1, an essential feature for vaccine manufacture, (iii) insertion of RSV F attenuated it slightly more than the empty $C^{\Delta170}$ backbone to a level similar to rB/HPIV3-F2, (iv) the construct was stable after in vivo replication and maintained RSV F expression, and (v) it was the most immunogenic HPIV1 vector inducing the highest RSV and HPIV1 neutralizing antibody titer and was also the most protective against a wt RSV challenge.

The findings indicate that it is possible to use an HPIV1 vector expressing RSV F as a bivalent vaccine for mucosal immunization against RSV and HPIV1. An HPIV1 vectored RSV vaccine could be used either as a primary RSV vaccine or to boost immunity primarily induced by a live attenuated RSV. The HPIV1 vectored RSV vaccine approach would obviate the inherent problems associated with developing attenuated RSV strains and may facilitate RSV immunization programs even in resource-limited settings.

Example 3

Development of rHPIV1-$C^{\Delta170}$ Vectors Expressing Optimized Versions of RSV F Protein This example presents assays showing that a gene encoding a modified RSV F ectodomain can be inserted into a HPIV1 vector backbone to produce a recombinant virus that expresses RSV F ectodomain on its envelope, is attenuated, infective, and can induce a protective antibody response. The F2 position also was identified as an effective insertion site. These findings indicate that:

1. The operational boundaries of the HPIV1 F TMCT domains have been identified (FIG. 60).

2. The HPIV1 F TMCT domain can be added to a recombinant RSV F ectodomain, e.g., HEK/GS-opt/DS-Cav1 to achieve a protein that is efficiently expressed at the cell surface and reactive with anti-RSV-F antibodies.

3. RSV F containing the HPIV1 F TMCT (HEK/GS-opt/DS-Cav1/H1TMCT) was efficiently packaged into the HPIV1 vector particle (i.e., at a higher level per μg virion protein than RSV, FIG. 64). This was completely contrary to expectations based on previous studies with Sendai virus (the murine relative of HPIV1, and hence presumably a close predictive model), in which RSV F containing the Sendai virus CT or TMCT was packaged efficiently into the particle only if the endogenous Sendai virus F protein was deleted (Zimmer et al 2005 J Virol 79:10467-10477).

3. HEK/GS-opt/DS-Cav1 and HEK/GS-opt/DS-Cav1/H1TMCT forms of the RSV F protein can be inserted into the first or second gene positions to yield vector constructs that stably express RSV F, replicate efficiently in vitro (FIG. 63), and are efficiently incorporated into the vector particle (when HPIV1 F TMCT is present, FIG. 64).

4. Unexpectedly, while either the F1 or F2 positions are efficient in expressing RSV F protein that is fusogenic (e.g., HEK/GA-opt, Example 2), the F2 position was particularly efficient for intracellular expression of RSV F that was non-fusogenic (e.g., HEK/GS-opt/DS-Cav1).

5. The rHPIV1-$C^{\Delta170}$-F2/HEK/GS-opt/DS-Cav1 and rHPIV1-$C^{\Delta170}$-F2/HEK/GS-opt/DS-Cav1/H1TMCT constructs were identified as ones that efficiently expressed RSV F protein and, particularly in the latter case, efficiently incorporated RSV F into the vector particle.

HEK/GS-opt/DS-Cav1.

In the present Example, the rHPIV1-$C^{\Delta170}$ vector was used to express further-modified versions of the RSV F protein. All inserts contain RSV F that was codon optimized by Genescript (GS-opt) for human expression and had two HEK amino acid assignments, i.e., Glu and Pro at residues 66 and 101. In addition, the HEK/GS-opt RSV F protein contained the stabilized pre-fusion mutations DS (S155C and S290C) and Cav1 (S190F, and V207L) to stabilize the RSV F prefusion head and antigenic site Ø that have been shown to be responsible for the preponderance of RSV-neutralizing antibodies (McLellan et al 2013 Science 342: 592-598).

HPIV1 TMCT.

In addition, a version of the HEK/GS-opt/DS-Cav1 RSV F protein was made in which its TMCT domain was replaced by that of HPIV1 F protein. The composition of the HPIV1 TM and CT domains had not been previously determined. FIG. 60 indicates the TM and CT domains of RSV F protein (top line) and HPIV1 F protein (second line), and shows a chimera in which the predicted ectodomain of RSV F protein was attached to the predicted TMCT domains of HPIV1 F protein. This was done with the goal of increasing the incorporation of the RSV F protein into the HPIV1 vector, on the premise that the HPIV1 F-specific TMCT domain would interact more efficiently with the other vector proteins during viral assembly, and would facilitate incorporation of the chimeric RSV F protein.

rHPIV1-$C^{\Delta 170}$ Vector Constructs.

Figure 61:
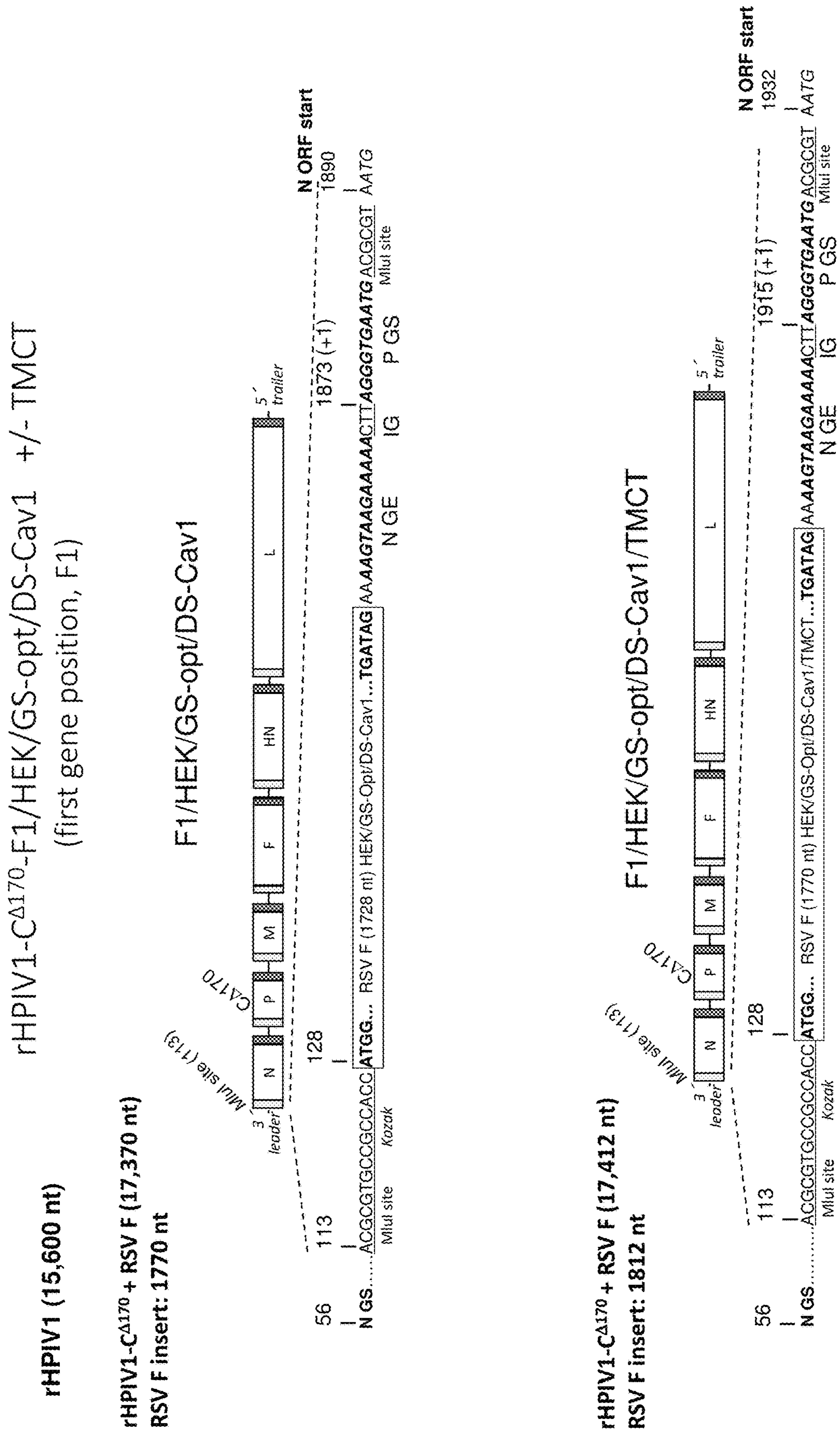
FIGS. 61 and 62. Construction of HPIV1-$C^{\Delta170}$ vectors expressing versions of RSV F protein designed to be stabilized in the prefusion conformation (DS-Cav1) and to have increased incorporation into the HPIV1 vector particle. Each of these modified RSV F inserts contained the HEK assignments (HEK) and was codon-optimized by GS for human expression (GS-opt). The RSV F insert was engineered to be stabilized in the prefusion conformation by the DS and Cav1 mutations (DS-Cav1) alone (upper construct in FIGS. 61 and 62) or with further modification by the replacement of its TMCT domain with those from HPIV1 F (TMCT, lower construct in FIGS. 61 and 62). The resulting HEK/GS-opt/DS-Cav1 and HEK/GS-opt/DS-Cav1/TMCT versions of RSV F were modified by flanking sequence and inserted into the HPIV1-$C^{\Delta170}$ vector (see Example 2 for an explanation of the HPIV1 vector and $C^{\Delta170}$ mutation) at the (FIG. 61) first gene position (MluI site), or (FIG. 62) second gene position (AscI site). In each case, the RSV F was under the control of HPIV1 transcription signals for expression as a separate mRNA. Nucleotide numbering is relative to the complete antigenome RNA sequence of the final construct. The sequences of SEQ ID NOs: 146 and 147 are shown flanking the RSV F insert under the diagrams for F1/HEK/GS-opt/DS-Cav1, F1/HEK/GS-opt/DS-Cav1/TMCT, F2/HEK/GS-opt/DS-Cav1, and F2/HEK/GS-opt/DS-Cav1/TMCT.
Figure 62:
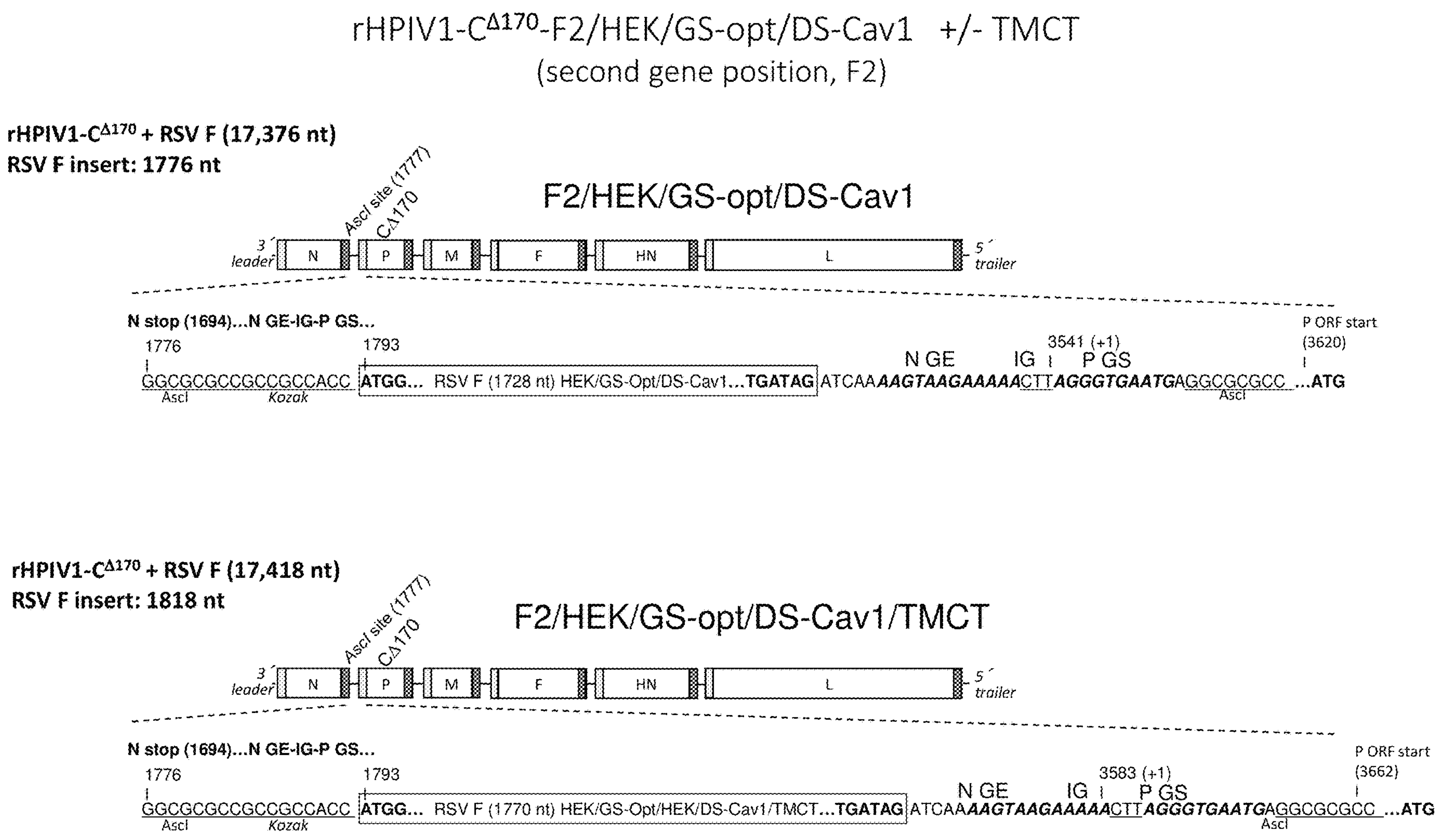

FIGS. 61 and 62 show constructs in which the rHPIV1-$C'^{70}$ vector from Example 2 was used to accept either of two inserts, placed in the first gene position (F1): expressed RSV F HEK/GS-opt/DS-Cav1, yielding rHPIV1-$C^{\Delta 170}$-F1/HEK/GS-opt/DS-Cav1 (FIGS. 61 and 62, top construct); or RSV F HEK/GS-opt/DS-Cav1/H1TMCT, yielding rHPIV1-$C^{\Delta 170}$-F1/HEK/GS-opt/DS-Cav1/H1TMCT (bottom construct). Note that these two constructs differ only in that the RSV F in the second construct has TMCT from HPIV1 F protein. FIG. 62 shows two parallel constructs in which either insert was placed in the second gene position (F2) of the rHPIV1-$C^{\Delta 170}$ vector. All viruses were designed to keep the hexameric genome nucleotide length (rule of six) (Kolakofsky et al 1998 J Virol 72:891-899). Each vector gene maintained its wild type hexamer phasing; the F1 and F2 inserts had the hexamer phasing of the N and P genes, respectively Recovery of Viruses.

The four constructs were rescued by co-transfecting BHK BSR T7/5 cells (baby hamster kidney cells that constitutively express T7 RNA polymerase (Buchholz et al 1999 J Virol 73:251-259)) with each of the full-length anti-genome plasmids and three expression plasmids expressing the HPIV1 N, P, and L proteins. Double staining plaque assays detecting co-expression of HPIV1 and RSV F proteins were performed to determine the stability of RSV F expression. The vast majority of plaques efficiently expressed RSV F protein. These same four preparations were subjected to consensus sequence analysis by automated sequencing (which analyzed each genome in its entirety except for 22 and 26 nucleotides at the 3' and 5' end, respectively, which were obscured by primers). The viruses were found to be free of adventitious mutations detectable by this method.

Multi-Cycle Replication In Vitro.

Figure 63:
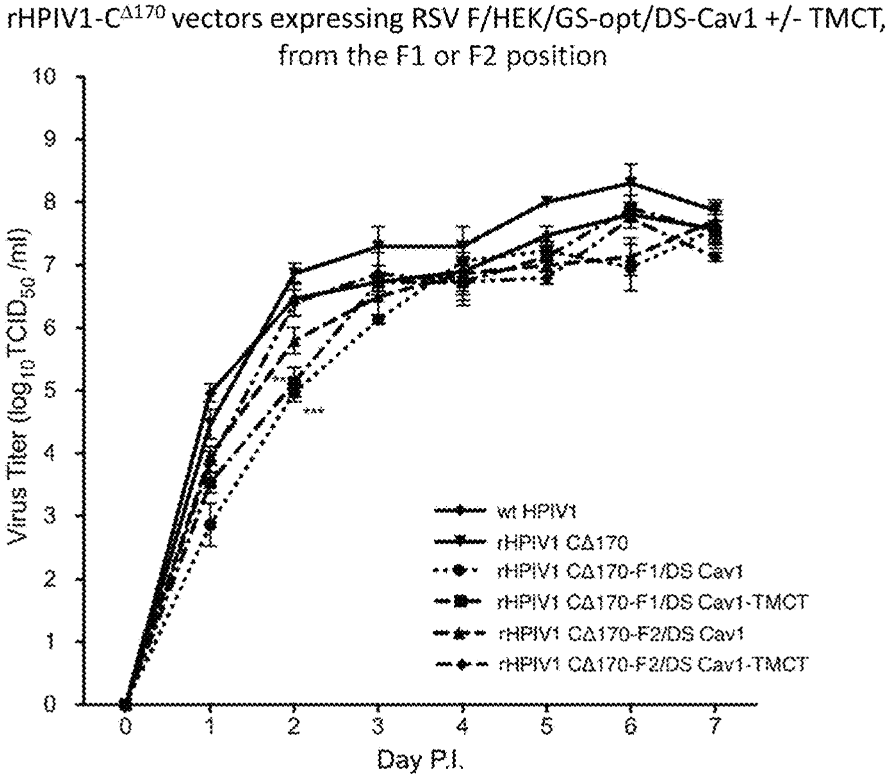
FIG. 63. Kinetics of multi-cycle growth in Vero cells of rHPIV1-$C^{\Delta170}$ vectors expressing RSV F stabilized in the prefusion conformation (DS-Cav1), without or with TMCT from HPIV1 F protein. Vero cells were infected with the constructs in triplicate at an MOI of 0.01 and incubated for 7 days at 32 C. At 24 h intervals, 0.5 mL of the total 3 mL culture supernatant was collected over 7 days. After sample collection, 0.5 mL fresh media was added to each culture to restore the original volume. Virus titration of the collected samples was performed on LLC-MK2 cells by hemadsorption assay and values are plotted as means±SEM.

The four recovered viruses (i.e., HEK/GS-opt/DS-Cav1, with or without H1TMCT, in the F1 or F2 position) were evaluated for multi-cycle replication in vitro by infecting Vero cells at an MOI of 0.01 $TCID_{50}$ per cell with each virus in triplicate and collecting culture supernatant every 24 h for 7 days. Virus titers in the collected samples were determined by serial dilution on LLC-MK2 cells and hemadsorption assay. All vectors with RSV F insert were relatively attenuated as compared to wt HPIV1 and rHPIV1-$C^{\Delta 170}$ and grew to final titers around 7.0 $TCID_{50}$/mL (FIG. 63). The F1/DS-Cav1 and F1/DS-Cav1/H1TMCT (note, the "HEK/GS-opt" part of the name may be omitted in the text and figures for the sake of brevity) replicated slower than the F2/DS-Cav1 and F2/DS-Cav1/H1TMCT on day 1 and 2 post-infection (p.i.) (during the exponential phase of replication) but reached high titers by day 7 (harvest day) that were similar to F2/DS-Cav1 and F2/DS-Cav1/H1TMCT. Thus, all constructs grew to high final titers that are amenable to vaccine manufacture in Vero cells.

Incorporation of Proteins into Vector Virions.

Figure 64:
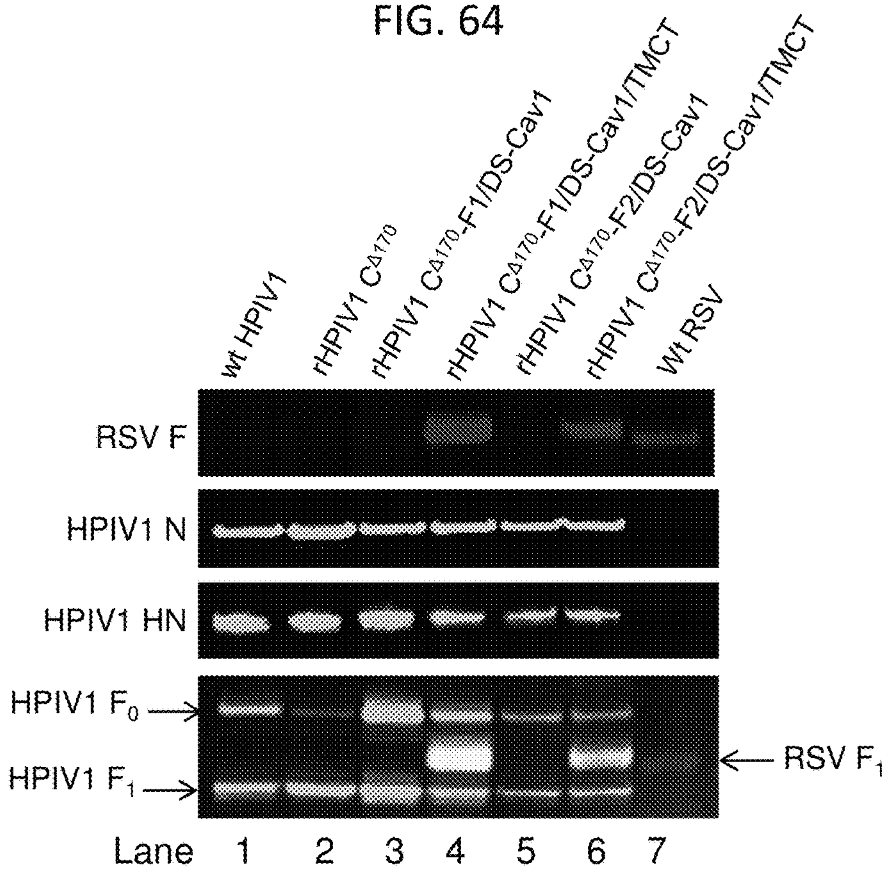
FIG. 64. Incorporation into HPIV1-$C^{\Delta170}$ virion particles of RSV F protein stabilized in the prefusion conformation (DS-Cav1) without or with TMCT from HPIV1 F protein. The indicated virus constructs (the designations HEK/GS-opt were omitted for the sake of brevity) were grown in LLC-MK2 cells and virions were purified by sucrose gradient centrifugation. Protein concentration of the purified viruses was determined by BCA assay. 1 µg total protein from each purified virus was lysed in RIPA lysis buffer, reduced, denatured, and subjected to SDS-PAGE and Western blot analysis. RSV F (top panel) and HPIV1 proteins (second, third, and fourth panels) were detected with mouse monoclonal and rabbit polyclonal HPIV1-peptide-specific (N, F, and HN) antibodies, respectively. Infrared-labeled secondary antibodies were used to detect bound primary antibodies. The chimeric RSV-F-DS-Cav1/TMCT protein in lanes 2 and 4 (fourth panel) are visible because the antipeptide serum specific to HPIV1 F protein was raised using a synthetic peptide containing the C-terminal 18 amino acids of the CT domain, and thus reacts with RSV F protein bearing the HPIV1 F protein TMCT domains.

The set of four constructs along with wt HPIV1, and rHPIV1-$C^{\Delta 170}$ empty vector were grown in LLC-MK2 cells and purified by sucrose gradient centrifugation. wt RSV was propagated in Vero cells followed by sucrose gradient purification and was included as a control. Approximately 1 μg of each sucrose-purified virus was lysed in RIPA buffer, reduced, denatured and subjected to SDS-PAGE and Western blot analysis. RSV F protein and HPIV1 proteins (N, F, and HN) were detected with mouse monoclonal (Abcam) and rabbit polyclonal peptide-specific antibodies (see Example 2), respectively, along with their corresponding infrared dye-conjugated secondary antibodies as previously described (Example 2; Mackow et al 2015 J Virol 89:10319-10332) (FIG. 64). Analysis of the F1/DS-Cav1 and F2/DS-Cav1 purified virions, which expressed full length RSV F from the 1" and 2' position, respectively, demonstrated no detectable packaging of RSV F in the HPIV1 vector virions (FIG. 64, top panel, lanes 3 and 5. In contrast, both the F1/DS Cav1-H1TMCT and F2/DS Cav1-H1TMCT virions (FIG. 64, lanes 4 and 6) showed considerable incorporation, which was higher for the F1/DS Cav1-H1TMCT than F2/DS Cav1-H1TMCT. Interestingly, both H1TMCT versions show higher amounts of RSV F packaged in the virions as compared to wt RSV (FIG. 64, lane 7), per μg of virion protein.

In the same experiment, the incorporation of the HPIV1 N, HN, and F proteins into the HPIV1 vector virions was also evaluated (FIG. 64). The virion incorporation of HPIV1 N protein was little affected by expression of any of the inserts (FIG. 64, second panel from the top). HN protein was reduced for F1/DS-Cav1/H1TMCT, F2/DS-Cav1, and F2/DS-Cav1/H1TMCT constructs (FIG. 64, third panel from the top, lanes 4, 5, and 6). Virion incorporation of HPIV1 F protein was reduced for F2/DS-Cav1 and F2/DS-Cav1/H1TMCT (FIG. 64, fourth panel from the top, lanes 5 and 6). Note that the antiserum for the HPIV1 F protein had been raised against a peptide containing the last 18 amino acids of the CT domain of the HPIV1 F protein, and thus this antiserum detected, in addition to the HPIV1 $F_0$ and $F_1$ proteins, the forms of RSV F protein containing the HPIV1 F protein TMCT, namely F1/DS-Cav1/H1TMCT and F2/DS-Cav1/TMCT. The identity of the RSV F band was confirmed by co-staining with the anti-RSV F monoclonal antibody; this confirms that RSV F is indeed expressed with HPIV1 F TMCT domain Intracellular Protein Expression.

Figure 65:
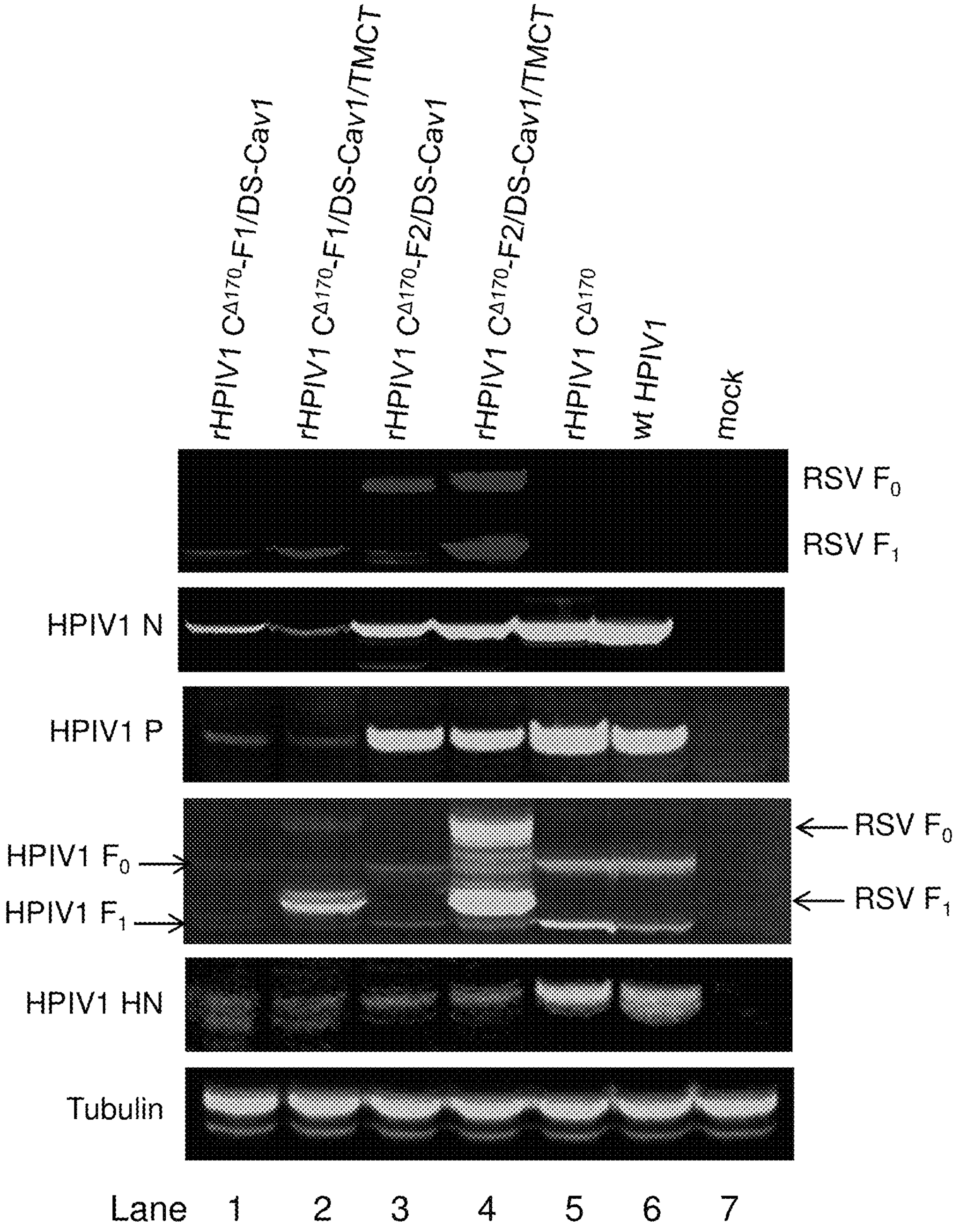
FIG. 65. Expression in infected Vero cells of RSV F protein stabilized in the prefusion conformation (DS-Cav1) without and with TMCT from HPIV1 F protein. Vero cell monolayers in 6-well plates were inoculated with the indicated viruses (the designations HEK/GS-opt were omitted for the sake of brevity) including the wt HPIV1 and rHPIV1-$C^{\Delta170}$ empty vector controls at an MOI of 5 and incubated for 48 h at 32° C. Cell lysates were prepared by lysing the monolayers in 200 µL LDS sample buffer. Protein samples were reduced and denatured, and 45 µL of each sample were electrophoresed followed by protein transfer to PVDF membranes. RSV F and HPIV1 proteins were detected using the same primary and secondary antibodies as described for FIG. 64.

Next, the intracellular expression of RSV F protein and HPIV1 vector proteins in vector-infected cells was evaluated. Vero cells were infected at an MOI of 10 $TCID_{50}$ per cell with each construct and incubated at 32° C. for 48 h. Cellular proteins were harvested by direct lysis of the monolayer with 1×LDS buffer, reduced, denatured, and subjected to SDS-PAGE and Western blot analysis (FIG. 65). RSV F and HPIV1 proteins were detected by using the same antibodies as described in FIG. 64. All constructs were able to express RSV F protein in infected cells; F2/DS-Cav1/H1TMCT had the highest expression followed by F2/DS-Cav1, F1/DS-Cav1/H1TMCT, and F1/DS-Cav1 (FIG. 65, lanes 4, 3, 2, and 1). Contrary to the expectation that insertion of the RSV F insert into the first gene position would result in the highest levels of expression (due to the transcriptional gradient), the F1/DS-Cav1 and F1/DS-Cav1/H1TMCT viruses (FIG. 64, lanes 1 and 2) had reduced RSV F expression as compared to the F2 viruses (lanes 3 and 4). As already noted, the F1 viruses replicated somewhat more slowly during exponential growth than the F2 viruses (FIG. 63), which likely contributed to the reduced RSV F expression. The low level of intracellular expression of RSV F in cells infected with the F1 viruses is in contrast to the virion incorporation profile (FIG. 64) that shows higher incorporation of RSV F for F1/DS-Cav1/H1TMCT as compared to F2/DS-Cav1/H1TMCT (lane 4 versus 6). In both F1 and F2 positions, DS-Cav1 with TMCT was expressed at somewhat higher level than DS-Cav1 alone, suggesting TMCT may enhance the RSV F expression by making the protein or mRNA transcript more stable. Similar effect was also observed with RSV F with BPIV3 F TMCT in Vero cells infected by B/HPIV3 vectors (FIG. 50A). It also is noteworthy that the intracellular expression of the HPIV1 N, P, F, and HN proteins also was very low for the F1 viruses compared to the F2 viruses (FIG. 65, second, third, and fourth panels, lanes 1 and 2 versus 3 and 4). This reveals very low gene expression for the F1 viruses (FIG. 65, lanes 1 and 2), although the RSV F protein that is made apparently was very efficiently incorporated into the HPIV1 virion in the case of RSV F bearing the HPIV1 TMCT (FIG. 64, lane 4).

Reduced RSV F expression by the F1 viruses in this present experiment is in contrast to the results reported in Example 2 involving expression of an HEK/GA-opt form of the RSV F protein from the first gene position of this same vector. In that case, intracellular expression of the RSV F protein was efficient and was very similar for the F1 versus the F2 construct, whereas the expression of the HPIV1 vector proteins was somewhat reduced for F1 versus F2, but not drastically so (FIG. 38A, first two lanes at the left, and FIG. 38B). The difference may be that the version of RSV F expressed in FIG. 38 was fusogenic, and this may have helped the virus spread more efficiently through the cell monolayer and promote a more efficient infection resulting in greater protein synthesis, whereas the F protein expressed in FIG. 64 was the DS-Cav1 version that was frozen in the prefusion conformation and thus would be non-fusogenic. While the constructs expressing DS-Cav1 may not have spread efficiently, each infected cell might have made more RSV F protein, and this could account for the higher level of virion incorporation. However, since a relatively high MOI of infection was used in each experiment (MOI of 5), and thus the great majority of cells should have been infected and spread may not have been a major factor. Therefore, the reduced intracellular expression of the DS-Cav1 form of the F protein from the F1 position was unexpected and points to the F2 position as likely being the more suitable for vector use.

Example 4

Development of Wt rHPIV3 Strain JS Vectors Expressing Optimized Versions of RSV F Protein As discussed above, the addition of the TMCT of the BPIV3 F protein (B3TMCT) to the RSV F HEK/GA-opt/DS construct resulted in substantial attenuation of the rB/HPIV3 vector in rhesus monkeys (FIG. 29). There also was evidence of attenuation in hamsters due to the B3TMCT (FIG. 51). This raised the possibility that this would render the rB/HPIV3 vector over-attenuated. One solution would be to use a less attenuated virus, such as wt HPIV3, as vector. In addition, if an HPIV3 vector was used (i.e, all of the backbone genes were derived from HPIV3), this would provide a complete complement of HPIV3 proteins as antigens for cellular immunity against HPIV3, and thus an HPIV3-based vector might be more protective against HPIV3 than an rB/HPIV3-based vector. The findings discussed in this example indicate that, unexpectedly, the stability of expression of the RSV F insert F1-HEK/GS-opt/DS-Cav1/H3TMCT appeared to be more stable than its version lacking TMCT, namely F1-HEK/GS-opt/DS-Cav 1. This is contrary to expectations, since incorporation into the vector particle might have been expected to place an added selective pressure against maintenance of RSV F expression, but this was not observed.

Wt rHPIV3 JS Strain Vector.

The wild type (wt) recombinant (r)HPIV3 JS strain (which also was the source of the F and HN genes in rB/HPIV3) was selected as vector. The biological version of this virus was previously shown to be naturally attenuated in adults (Clements et al. J Clin Microbiol 29:1175-1182, 1991) compared to a previously-evaluated strain (Kapikian et al 1961 JAMA 178:123-127), presumably due to one or more adventitious attenuating mutations that remain to be identified. The recombinant version of this virus (rHPIV3) has two mutations in HN (A263T and T370P) that were introduced when the HPIV3 reverse-genetic system was established. In the present study, the rHPIV3 vector was modified to contain the 263T and 370P amino acid assignments in the HN protein that had been found to prevent large plaque formation by the rB/HPIV3 vector (the mutations were shown in detail in FIG. 58B). In addition, the rHPIV3 vector was modified by the creation of a unique BlpI site at positions 103-109 (FIG. 67A, top construct), for insertion of RSV F (or potentially any other insert) in the first gene position, or the creation of a unique AscI site at positions 1675-1682 (FIG. 67B, top construct), for insertion of RSV F in the second gene position.

HEK/GS-opt/DS-Cav1+/−H3TMCT. The wt rHPIV3 JS vector was used to express the RSV F HEK/GS-opt/DS-Cav1 protein as is or with the further modification in which the TMCT domains of the RSV F protein was replaced by that of the HPIV3 F protein (called H3TMCT, FIG. 66). The activity of the TM and CT domains of HPIV3 F protein (H3TMCT) in the context of the RSV F protein was not known. FIG. 66 also shows a chimera in which the H3TMCT was introduced into the RSV F protein.

Figure 67A:
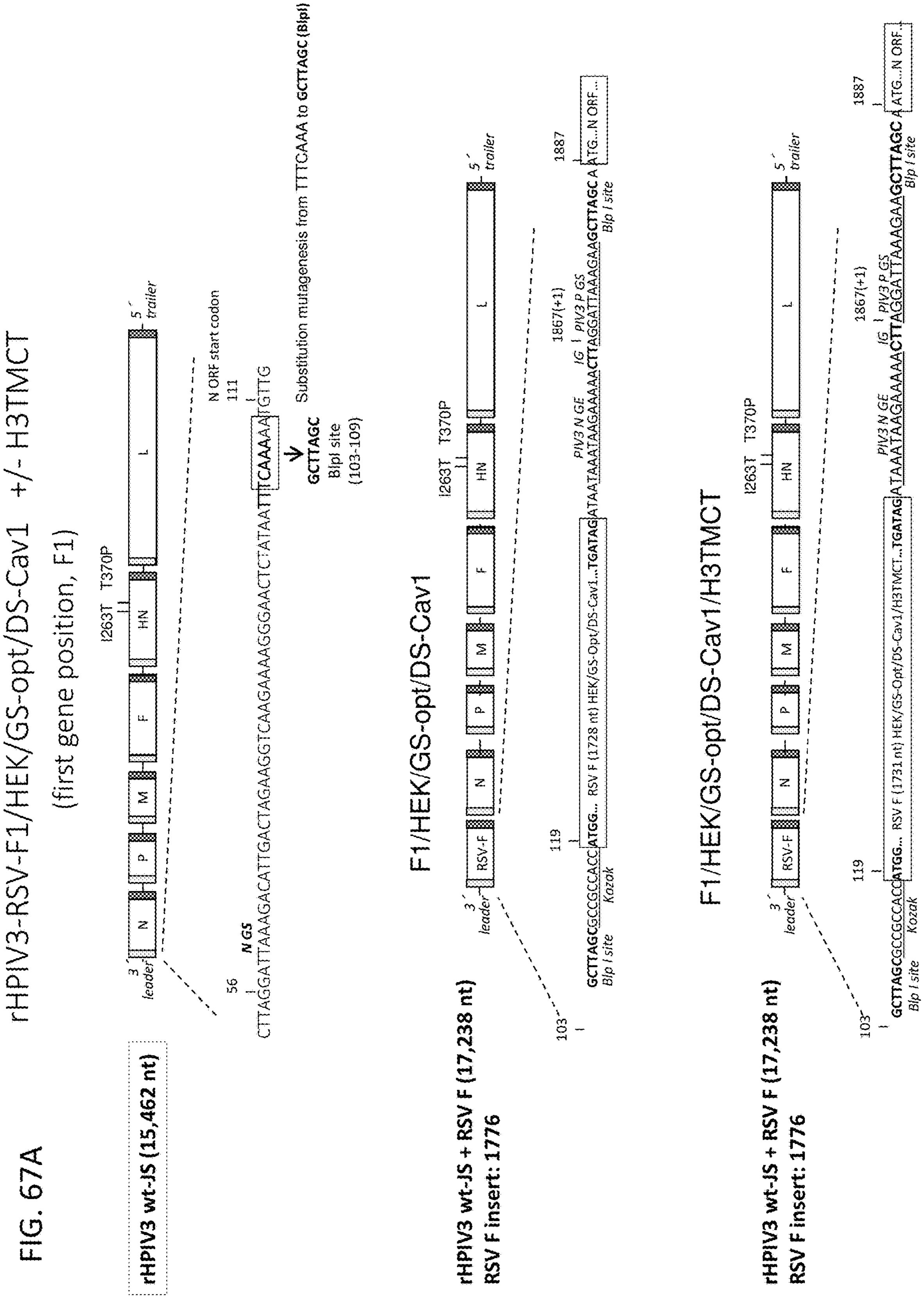
FIGS. 67A and 67B. Construction of rHPIV3 vectors expressing versions of RSV F protein designed to be stabilized in the prefusion conformation (DS-Cav1) and to have increased incorporation into the rHPIV3 vector particle. The vector is wild type rHPIV3 strain JS which was modified to contain the 263T and 370P amino acid assignments in the HN protein (see FIG. 58B), which were found to confer phenotypic stability to the vector. In addition, the rHPIV3 vector was modified by the creation of a BlpI site at positions 103-109 (A, top construct), for insertion of RSV F (or potentially any other insert) in gene position 1, or the creation of an AscI site at positions 1675-1682 (B, top construct), for insertion of RSV F in gene position 2. Each of the modified RSV F inserts contained the HEK assignments (HEK) and was codon-optimized by GS for human expression (GS-opt). In addition, the RSV F insert was engineered to be stabilized in the prefusion conformation by the DS and Cav1 mutations (DS Cav1) alone (A and B, second construct) or with further modification by the replacement of its TMCT domains with those from rHPIV3 F (H3TMCT, A and B, third construct). The resulting HEK/GS-opt/DS-Cav1 and HEK/GS-opt/DS-Cav1/H3TMCT versions of RSV F were modified by flanking sequence and inserted into the (A) first gene position (BlpI site), or (B) second gene position (AscI site) of wt rHPIV3 JS. In each case, the RSV F was under the control of HPIV3 transcription signals for expression as a separate mRNA. Nucleotide numbering is relative to the complete antigenome RNA sequence of the final construct. The sequence of SEQ ID NOs: 148 is shown under the diagram for rHPIV3 wt-JS. The sequences of SEQ ID NOs: 149 and 150 are shown flanking the RSV F insert under the diagrams for F1/HEK/GS-opt/DS-Cav1, F1/HEK/GS-opt/DS-Cav1/H3TMCT, F2/HEK/GS-opt/DS-Cav1, and F2/HEK/GS-opt/DS-Cav1/H3TMCT.
Figure 67B:
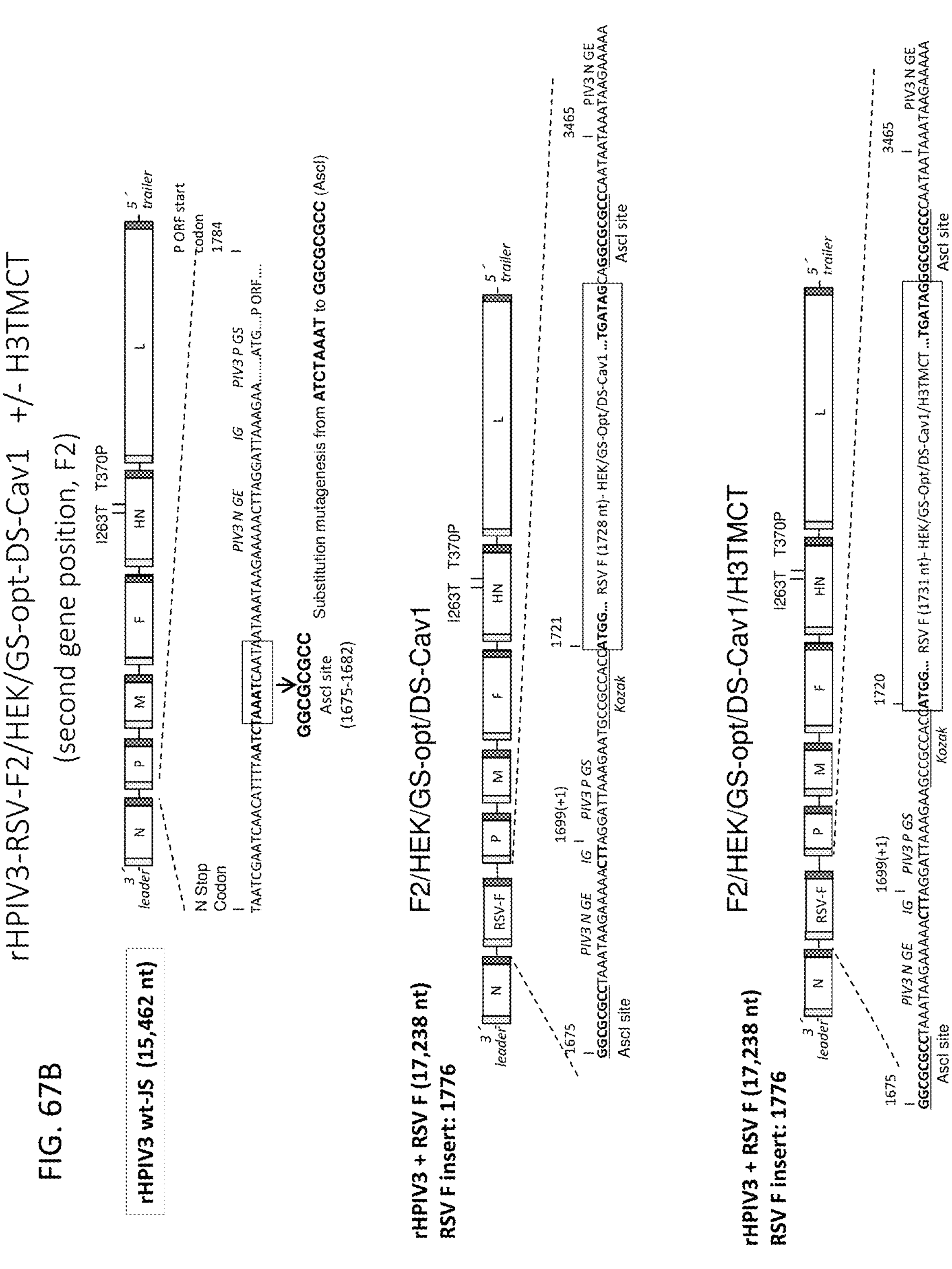

Examples of four rHPIV3-based constructs expressing RSV F are shown in FIG. 67. Specifically, the examples are:

HEK/GS-opt/DS-Cav1 inserted into the first gene position (F1) (FIG. 67A);

HEK/GS-opt/DS-Cav1/H3TMCT inserted into the first gene position (F1) (FIG. 67A);

HEK/GS-opt/DS-Cav1 inserted into the second gene position (F2) (FIG. 67B);

HEK/GS-opt/DS-Cav1/H3TMCT inserted into the second gene position (F2) (FIG. 67B).

Note that these RSV F ORFs are the same as were inserted into the rHPIV1-C$^{\Delta 170}$ vector in FIGS. 61 and 62, except that the TMCT in FIG. 67 is H3TMCT derived from HPIV3 F protein. In addition, each RSV F insert in FIG. 67 was under the control of HPIV3 transcription signals for expression as a separate mRNA. Nucleotide numbering (FIG. 67) is relative to the complete antigenome RNA sequence of each final construct. All viruses were designed to maintain the hexameric genome length and wild type hexamer phasing; the F1 and F2 inserts had the hexamer phasing of the original N and P genes (normally in the first and second gene positions), respectively. All inserts were synthetically derived (Genscript).

Recovery of Viruses and Double Staining Analysis.

The viruses were rescued by co-transfecting BHK BSR T7/5 cells with each of the full-length anti-genome plasmid and three expression plasmids expressing the HPIV3 N, P, and L proteins. All viruses were successfully rescued, and two P2 (i.e., second passage) viral stocks were prepared for each of the four constructs.

Comments on the Results Shown in Examples 1-4

The following examples show that several different PIV vector systems (including rB/HPIV3, rHPIV1, and rHPIV3 JS) can be used to efficiently express the RSV F protein as an added gene. Panels of mutants were constructed to systematically evaluate a variety of variables with the vectors (e.g., insert position, level of attenuation, etc.) and the RSV F insert (e.g. prefusion stabilization, packaging into the vector particle, etc.), The panels of mutants were subjected to detailed analysis in cell culture, in hamsters, and in non-human primates to identify effective mutants with regard to expression level, stability in vitro and in vivo, attenuation in vivo, immunogenicity, and protective efficacy.

Previous studies had shown that highly fusogenic proteins like RSV F can be unstable in nonsegmented negative strand viral vectors because their high level of syncytium formation interferes with vector replication: for example, the fusion F protein of measles virus was shown to exhibit "extreme instability" when expressed by the prototype virus vesicular stomatitis virus (VSV) (Quinones-Kochs et al 2001 Virology 287; 427-435). Since respiratory syncytial virus is notorious for its high level of syncytium formation, and since high levels of syncytium formation indeed were observed when functional RSV F protein was expressed from PIV vectors (e.g., Example 1), it was very surprising that this did not interfere with vector replication in vitro. Thus, efficiencies of replication of the disclosed constructs allows for efficient vaccine manufacture in Vero cells. Furthermore, modifications that reduced (HEK assignments) or essentially eliminated (DS, DS-Cav1) gross syncytium formation were introduced, which thus would obviate any problems due to high levels of syncytium formation.

Multiple specific strategies were demonstrated to increase the expression of the foreign RSV F gene, including inclusion of HEK assignments, codon optimization, and placement in promoter-proximal positions. However, the results were not necessarily predictable, illustrating the importance of the extensive experimentation provided in this disclosure. In addition, while expression from the first gene position would be expected to yield the highest levels of expression, this was not the case with the HPIV1 vector when it expressed RSV F protein that was non-fusogenic due to the DS-Cav1 mutations (FIG. 65). Thus, the nature of the vector and the nature of the insert contributed to yield novel characteristics.

Multiple means of attenuation were investigated, including the use of the bovine/human chimera rB/HPIV3, the use of the naturally-attenuated HPIV3 JS strain, and the use of stabilized point and deletion mutations exemplified with HPIV1 ($C^{\Delta 170}$ and LY'). In addition, presence of the foreign insert provided attenuation in some circumstances, and the B3TMCT modification was substantially attenuating. Thus, the reagents and biological characterization provide vectors exhibiting a range of useful attenuation phenotypes. Importantly, the vectors of interest were shown to have retained efficient replication and stability in Vero cells, necessary for vaccine manufacture.

The stability of expression of the RSV F insert was a major problem with a prior construct (Bernstein et al 2012, Pediatr Infect Dis 31:109-114). However, the modified constructs described in the present disclosure were substantially stable. Factors such as reducing or inhibiting syncytium formation likely contributed to stability. In some case, unpredictable factors were identified. For example, the HN gene in the rB/HPIV3 vector was found to exhibit substantial instability that resulted in a large plaque phenotype. However, this problem was eliminated by I263T and T370P substitutions in the HN gene (FIG. 58). Another example of an unexpected finding regarding stability was the increased stability of RSV F expression with the combination of the HEK/GS-opt/DS-Cav1/H3TMCT construct expressed from the F1 position of rHPIV3 JS (FIG. 67A). It might have been expected that expression from the F1 position would be the most unstable, because of the high level of expression, but this was not observed. It also might have been expected that packaging of the RSV F protein into the vector also would place a selective pressure for loss of expression, but this was not observed.

Two modifications were shown to be of primary importance for increasing immunogenicity: namely, mutations DS and Cav1 that stabilize the prefusion conformation of the RSV F protein, and the TMCT modification that serves as a packaging signal to direct efficient incorporation of the foreign glycoprotein into the vector particle. It was not known if RSV F that was stabilized in the prefusion conformation would be expressed efficiently and would be compatible with a virus infection, but this was the case. It also was surprising that the TMCT packaging signals worked with such a high degree of efficiency of packaging, which equaled or exceeded that of RSV particles examined in parallel. It also was surprising that this highly efficient packaging did not disrupt the production of vector particles, such as by displacing the endogenous F and HN surface glycoproteins.

Particularly unexpected was the finding that the DS and DS-Cav1 modifications on the one hand, and the TMCT modification on the other hand, each provided a very substantial increase in the production of high quality RSV-neutralizing antibodies, which are thought to be the most relevant for protection in vivo. These two types of modifications likely achieved this effect through different mechanisms: specifically, the DS and Cav1 modifications presumably have their effect by stabilizing the antigenic site 0, whereas packaging mediated by TMCT likely provides a tightly-packed highly-repetitive array of RSV F antigen produced in a particle form, providing for increased antigen presentation. Importantly, these effects were very evident in non-human primates (FIG. 31), yielding reciprocal titers of >250 from a single primary dose for complement-independent antibodies. In addition, the two effects (DS-Cav1 and TMCT) were additive to some extent.

It will be apparent that the precise details of the methods or compositions described may be varied or modified without departing from the spirit of the described embodiments. We claim all such modifications and variations that fall within the scope and spirit of the claims below.

We claim:

1. A recombinant paramyxovirus, comprising:

a viral genome comprising genes encoding parainfluenza virus (PIV) N, P, M, F, HN, and L proteins, and further comprising a heterologous gene encoding a type I membrane protein comprising a recombinant respiratory syncytial virus (RSV) F ectodomain linked to a transmembrane domain (TM) and cytoplasmic tail (CT) of a PIV F protein; and wherein the recombinant paramyxovirus is a recombinant human parainfluenza virus 1 (HPIV1); and wherein the heterologous gene comprises the nucleotide sequence set forth as SEQ ID NO: 136.

2. The recombinant paramyxovirus of claim 1, wherein the heterologous gene encoding the recombinant RSV F ectodomain is the first, second, or third gene downstream of a genomic promoter of the viral genome.

3. The recombinant paramyxovirus of claim 1, wherein recombinant paramyxovirus is:

the recombinant HPIV1, and wherein the viral genome comprises, from upstream to downstream, a HPIV1 genomic promoter followed by the genes encoding the HPIV1 N, P, M, F, HN, and L proteins, and wherein the heterologous gene encoding the recombinant RSV F ectodomain is located between the genomic promoter and the gene encoding the N protein or between the genes encoding the N and the P proteins.

4. The recombinant paramyxovirus of claim 1, wherein: the HPIV1 comprises a $C^{\Delta170}$ or a $LY^{942A}$ attenuating mutation.

5. The recombinant paramyxovirus of claim 1, wherein at least 90% of viral particles produced by a host cell infected with the recombinant paramyxovirus or viral vector comprise a viral envelope comprising the ectodomain encoded by the heterologous gene.

6. The recombinant paramyxovirus of claim 1, wherein the recombinant paramyxovirus is an infectious, attenuated, and self-replicating virus.

7. The recombinant paramyxovirus of claim 1, wherein the RSV F ectodomain is present on the viral envelope of the paramyxovirus.

8. An immunogenic composition comprising the recombinant paramyxovirus of claim 1 and a pharmaceutically acceptable carrier.

9. A method of eliciting an immune response to RSV and/or PIV in a subject comprising administering a therapeutically effective amount of the immunogenic composition of claim 8 to the subject.

10. The method of claim 9, comprising intranasal administration of the immunogenic composition.

11. The method of claim 9, wherein the subject is at risk of or has a RSV or a PIV infection.

12. The method of claim 9, wherein the subject is less than one year old.

13. The method of claim 9, wherein the subject is immunocompromised or is elderly.

14. A nucleic acid molecule comprising the genome of the recombinant paramyxovirus of claim 1.

15. The recombinant paramyxovirus of claim 1, wherein the recombinant paramyxovirus is the recombinant HPIV1, and wherein the HPIV1 N, P, M, F, HN, and L proteins comprise amino acid sequences at least 90% identical to SEQ ID NOs: 24, 25, 26, 27, 28, 29, and 30, respectively.

* * * * *

SEQUENCE LISTING

```
<160> NUMBER OF SEQ ID NOS: 153

<210> SEQ ID NO 1
<211> LENGTH: 574
<212> TYPE: PRT
```

<213> ORGANISM: Artificial sequence
<220> FEATURE:
<223> OTHER INFORMATION: Recombinant RSV F

<400> SEQUENCE: 1

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
    370                 375                 380
```

-continued

```
Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu His Asn Val Asn Ala Gly Lys Ser Thr Thr Asn Ile Met Ile Thr
        515                 520                 525

Thr Ile Ile Ile Val Ile Ile Val Ile Leu Leu Ser Leu Ile Ala Val
    530                 535                 540

Gly Leu Leu Leu Tyr Cys Lys Ala Arg Ser Thr Pro Val Thr Leu Ser
545                 550                 555                 560

Lys Asp Gln Leu Ser Gly Ile Asn Asn Ile Ala Phe Ser Asn
                565                 570


<210> SEQ ID NO 2
<211> LENGTH: 574
<212> TYPE: PRT
<213> ORGANISM: Respiratory syncytial virus

<400> SEQUENCE: 2

Met Glu Leu Leu Ile His Arg Leu Ser Ala Ile Phe Leu Thr Leu Ala
1               5                   10                  15

Ile Asn Ala Leu Tyr Leu Thr Ser Ser Gln Asn Ile Thr Glu Glu Phe
            20                  25                  30

Tyr Gln Ser Thr Cys Ser Ala Val Ser Arg Gly Tyr Phe Ser Ala Leu
        35                  40                  45

Arg Thr Gly Trp Tyr Thr Ser Val Ile Thr Ile Glu Leu Ser Asn Ile
    50                  55                  60

Lys Glu Thr Lys Cys Asn Gly Thr Asp Thr Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Asn Thr Pro Ala Ala Asn Asn Arg Ala Arg Arg Glu Ala Pro
            100                 105                 110

Gln Tyr Met Asn Tyr Thr Ile Asn Thr Thr Lys Asn Leu Asn Val Ser
        115                 120                 125

Ile Ser Lys Lys Arg Lys Arg Arg Phe Leu Gly Phe Leu Leu Gly Val
    130                 135                 140

Gly Ser Ala Ile Ala Ser Gly Ile Ala Val Ser Lys Val Leu His Leu
145                 150                 155                 160

Glu Gly Glu Val Asn Lys Ile Lys Asn Ala Leu Leu Ser Thr Asn Lys
                165                 170                 175
```

```
Ala Val Val Ser Leu Ser Asn Gly Val Ser Val Leu Thr Ser Lys Val
            180                 185                 190

Leu Asp Leu Lys Asn Tyr Ile Asn Asn Gln Leu Leu Pro Ile Val Asn
        195                 200                 205

Gln Gln Ser Cys Arg Ile Ser Asn Ile Glu Thr Val Ile Glu Phe Gln
    210                 215                 220

Gln Lys Asn Ser Arg Leu Leu Glu Ile Asn Arg Glu Phe Ser Val Asn
225                 230                 235                 240

Ala Gly Val Thr Thr Pro Leu Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Ser Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Ile Tyr Gly Val Ile Asp Thr Pro Cys Trp Lys Leu His Thr Ser Pro
305                 310                 315                 320

Leu Cys Thr Thr Asn Ile Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Asp Thr Cys Lys Val Gln Ser Asn Arg Val Phe Cys Asp
        355                 360                 365

Thr Met Asn Ser Leu Thr Leu Pro Ser Glu Val Ser Leu Cys Asn Thr
    370                 375                 380

Asp Ile Phe Asn Ser Lys Tyr Asp Cys Lys Ile Met Thr Ser Lys Thr
385                 390                 395                 400

Asp Ile Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Leu Glu Gly
    450                 455                 460

Lys Asn Leu Tyr Val Lys Gly Glu Pro Ile Ile Asn Tyr Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Arg Ser Asp Glu Leu
            500                 505                 510

Leu His Asn Val Asn Thr Gly Lys Ser Thr Thr Asn Ile Met Ile Thr
        515                 520                 525

Thr Ile Ile Ile Val Ile Ile Val Val Leu Leu Ser Leu Ile Ala Ile
    530                 535                 540

Gly Leu Leu Leu Tyr Cys Lys Ala Lys Asn Thr Pro Val Thr Leu Ser
545                 550                 555                 560

Lys Asp Gln Leu Ser Gly Ile Asn Asn Ile Ala Phe Ser Lys
                565                 570
```

<210> SEQ ID NO 3
<211> LENGTH: 1725

<212> TYPE: RNA
<213> ORGANISM: Respiratory syncytial virus

<400> SEQUENCE: 3
auggagcugc ugauccacag guuaagugca aucuuccuaa cucuugcuau uaaugcauug 60
uaccucaccu caagucagaa cauaacugag gaguuuuacc aaucgacaug uagugcaguu 120
agcagagguu auuuuagugc uuuaagaaca gguugguaua ccagugucau aacaauagaa 180
uuaaguaaua uaaaagaaac caaaugcaau ggaacugaca cuaaaguaaa acuuauaaaa 240
caagaauuag auaaguauaa gaaugcagug acagaauuac agcuacuuau gcaaaacaca 300
ccagcugcca acaaccgggc cagaagagaa gcaccacagu auaugaacua uacaaucaau 360
accacuaaaa accuaaaugu aucaauaagc aagaagagga aacgaagauu ucugggcuuc 420
uuguuaggug uaggaucugc aauagcaagu gguauagcug uauccaaagu ucuacaccuu 480
gaaggagaag ugaacaagau caaaaaugcu uuguuaucua caaacaaagc uguagucagu 540
cuaucaaaug ggucagugu uuuaaccagc aaaguguuag aucucaagaa uuacauaaau 600
aaccaauuau uacccauagu aaaucaacag agcugucgca ucuccaacau ugaaacaguu 660
auagaauucc agcagaagaa cagcagauug uuggaaauca acagagaauu caguguc aau 720 gcagguguaa caacaccuuu aagcacuuac auguuaacaa acagugaguu acuaucauug 780
aucaaugaua ugccuauaac aaaugaucag aaaaaauuaa ugucaagcaa uguucagaua 840
guaaggcaac aaaguuauuc uaucaugucu auaauaaagg aagaaguccu ugcauauguu 900
guacagcuac cuaucuaugg uguaauagau acaccuugcu ggaaauuaca cacaucaccu 960
cuaugcacca ccaacaucaa agaaggauca aauauuuguu uaacaaggac ugauagagga 1020
ugguauugug auaaugcagg aucaguaucc uucuuuccac aggcugacac uuguaaagua 1080
caguccaauc gaguauuuug ugacacuaug aacaguuuga cauuaccaag ugaagucagc 1140
cuuuguaaca cugacauauu caauuccaag uaugacugca aaauuaugac aucaaaaaca 1200
gacauaagca gcucaguaau uacuucucuu ggagcuauag ugucaugcua ugguaaaacu 1260
aaaugcacug cauccaacaa aaaucguggg auuauaaaga cauuuucuaa ugguugugac 1320
uaugugucaa acaaaggagu agauacugug ucagugggca acacuuuaua cuauguaaac 1380
aagcuggaag gcaagaaccu uuauguaaaa ggggaaccua uaauaaauua cuaugacccu 1440
cuaguguuuc cuucugauga guuugaugca ucaauaucuc aagucaauga aaaaaucaau 1500
caaaguuuag cuuuuauucg uagaucugau gaauuacuac auaauguaaa uacuggcaaa 1560
ucuacuacaa auauuaugau aacuacaauu auuauaguaa ucauuguagu auuguuauca 1620
uuaauagcua uugguuugcu guuguauugc aaagccaaaa acacaccagu uacacuaagc 1680
aaagaccaac uaaguggaau caauaauauu gcauucagca aauag 1725

<210> SEQ ID NO 4
<211> LENGTH: 1725
<212> TYPE: DNA
<213> ORGANISM: Artificial sequence
<220> FEATURE:
<223> OTHER INFORMATION: Recombinant RSV F

<400> SEQUENCE: 4
atggaactgc tgatcctgaa ggccaacgcc atcacaacaa tcctgaccgc cgtgaccttc 60
tgcttcgcca gcggccagaa catcaccgag gaattctacc agagcacctg tagcgccgtg 120
tccaagggct acctgagcgc cctgagaacc ggctggtaca ccagcgtgat caccatcgag 180

```
ctgtccaaca tcaaagaaaa caagtgcaac ggcaccgacg ccaaagtgaa gctgatcaag    240
caggaactgg acaagtacaa gaacgccgtg accgagctgc agctgctgat gcagtccacc    300
cccgccacca acaaccgggc cagaagagaa ctgccccggt tcatgaacta caccctcaac    360
aacgccaaaa agaccaacgt gaccctgagc aagaagcgga agcggcggtt cctgggcttc    420
ctgctgggcg tgggcagcgc cattgcctct ggcgtggccg tgtctaaggt gctgcacctg    480
gaaggcgaag tgaacaagat caagagcgcc ctgctgtcca caaacaaggc cgtggtgtcc    540
ctgagcaacg gcgtgtccgt gctgacctcc aaggtgctgg atctgaagaa ctacatcgac    600
aagcagctgc tgcccatcgt gaacaagcag agctgcagca tcagcaacat cgagacagtg    660
atcgagttcc agcagaagaa caaccggctg ctggaaatca cccgcgagtt cagcgtgaac    720
gccggcgtga ccacccccgt gtccacctac atgctgacca acagcgagct gctgtccctg    780
atcaatgaca tgcccatcac caacgaccag aaaaagctga tgagcaacaa cgtgcagatc    840
gtgcggcagc agagctactc catcatgagc atcatcaaag aagaggtgct ggcctacgtg    900
gtgcagctgc ccctgtacgg cgtgatcgac accccctgct ggaagctgca caccagcccc    960
ctgtgcacca ccaacacaaa agagggcagc aacatctgcc tgacccggac cgaccggggc   1020
tggtactgcg ataatgccgg cagcgtgtca ttctttccac aggccgagac atgcaaggtg   1080
cagagcaacc gggtgttctg cgacaccatg aacagcctga ccctgccctc cgaagtgaac   1140
ctgtgcaacg tggacatctt caaccctaag tacgactgca agatcatgac cagcaagacc   1200
gacgtgtcca gctccgtgat cacctccctg ggcgccatcg tgtcctgcta cggcaagacc   1260
aagtgcaccg ccagcaacaa gaaccggggc atcatcaaga ccttcagcaa cggctgcgac   1320
tacgtgtcca acaagggggt ggacaccgtg tccgtgggca acaccctgta ctacgtgaac   1380
aaacaggaag gcaagagcct gtacgtgaag ggcgagccca tcatcaactt ctacgacccc   1440
ctggtgttcc ccagcgacga gttcgacgcc agcatcagcc aggtcaacga gaagatcaac   1500
cagagcctgg ccttcatcag aaagagcgac gagctgctgc acaatgtgaa tgccggcaag   1560
agcaccacaa acatcatgat caccactatc atcatcgtga tcatcgtcat cctgctgagt   1620
ctgatcgccg tgggcctgct gctgtactgc aaggccagat ccacccctgt gaccctgtcc   1680
aaggatcagc tgtccggcat caacaatatc gccttctcca actga                   1725
```

```
<210> SEQ ID NO 5
<211> LENGTH: 1725
<212> TYPE: DNA
<213> ORGANISM: Artificial sequence
<220> FEATURE:
<223> OTHER INFORMATION: Recombinant RSV F

<400> SEQUENCE: 5

atggaactgc tgatcctgaa agccaacgct attactacta tcctgaccgc cgtgacattt     60
tgcttcgcat ctggacagaa cattactgag gaattctacc agtcaacatg cagcgccgtg    120
tccaaaggat acctgagcgc cctgcggacc ggctggtata catcagtgat tactatcgag    180
ctgtccaaca tcaaggaaaa caaatgtaat gggaccgacg caaaggtgaa actgatcaag    240
caggagctgg ataagtacaa aaatgccgtg acagaactgc agctgctgat gcagtccaca    300
ccagcaacta acaatcgcgc ccggagagag ctgccccggt tcatgaacta taccctgaac    360
aatgctaaga aaaccaatgt gacactgtcc aagaaacgca agaggcgctt cctgggattt    420
ctgctgggcg tggggtctgc catcgctagt ggagtggccg tctctaaagt cctgcacctg    480
gagggcgaag tgaacaagat caaaagcgcc ctgctgtcca ctaacaaggc agtggtcagt    540
```

ctgtcaaatg gcgtgtccgt cctgacctct aaggtgctgg acctgaaaaa ttatattgat 600
aagcagctgc tgcctatcgt caacaaacag agctgctcca tttctaatat cgagacagtg 660
atcgaattcc agcagaagaa caatagactg ctggagatta ccagagagtt cagcgtgaac 720
gccggcgtca ccacacccgt gtccacctac atgctgacaa atagtgagct gctgtcactg 780
attaacgaca tgcctatcac caatgatcag aagaaactga tgtccaacaa tgtgcagatc 840
gtcagacagc agagttactc aatcatgtct atcattaagg aggaagtcct ggcctacgtg 900
gtccagctgc cactgtatgg cgtgatcgac accccctgct ggaaactgca tacatctcct 960
ctgtgcacta ccaacacaaa ggaaggaagt aatatctgcc tgactcgaac cgaccgggga 1020
tggtactgtg ataacgcagg cagcgtgtcc ttctttccac aggccgagac ctgcaaggtc 1080
cagagcaaca gggtgttctg tgacactatg aatagcctga ccctgccttc cgaagtcaac 1140
ctgtgcaatg tggacatctt taatccaaag tacgattgta agatcatgac tagcaagacc 1200
gatgtcagct cctctgtgat tacttctctg gggggccatcg tgagttgcta cggaaagaca 1260
aaatgtactg ccagcaacaa aaatcgcggc atcattaaga ccttctccaa cgggtgcgac 1320
tatgtctcta acaagggcgt ggatacagtg agtgtcggga acactctgta ctatgtcaat 1380
aagcaggagg gaaaaagcct gtacgtgaag ggcgaaccca tcattaactt ctatgacccc 1440
ctggtgttcc cttccgacga gtttgatgca tctattagtc aggtgaacga aaaaatcaat 1500
cagagtctgg cctttattcg gaagtcagat gagctgctgc acaacgtgaa tgctggcaaa 1560
tctacaacta acatcatgat caccacaatc atcatcgtga ttatcgtcat tctgctgtca 1620
ctgatcgctg tggggctgct gctgtactgt aaggcaagaa gcaccccagt cactctgtca 1680
aaagaccagc tgtcagggat taacaacatt gccttcagta actga 1725

<210> SEQ ID NO 6
<211> LENGTH: 1725
<212> TYPE: DNA
<213> ORGANISM: Artificial sequence
<220> FEATURE:
<223> OTHER INFORMATION: Recombinant RSV F

<400> SEQUENCE: 6
atggaactgc tgatcctgaa ggccaacgcc atcacaacaa tcctgaccgc cgtgaccttc 60
tgcttcgcca gcggccagaa catcaccgag gaattctacc agagcacctg tagcgccgtg 120
tccaagggct acctgagcgc cctgagaacc ggctggtaca ccagcgtgat caccatcgag 180
ctgtccaaca tcaaagaaaa caagtgcaac ggcaccgacg ccaaagtgaa gctgatcaag 240
caggaactgg acaagtacaa gaacgccgtg accgagctgc agctgctgat gcagtccacc 300
cccgccacca acaaccgggc cagaagagaa ctgccccggt tcatgaacta caccctcaac 360
aacgccaaaa agaccaacgt gaccctgagc aagaagcgga agcggcggtt cctgggcttc 420
ctgctgggcg tgggcagcgc cattgcctct ggcgtggccg tgtctaaggt gctgcacctg 480
gaaggcgaag tgaacaagat caagagcgcc ctgctgtcca caaacaaggc cgtggtgtcc 540
ctgagcaacg gcgtgtccgt gctgacctcc aaggtgctgg atctgaagaa ctacatcgac 600
aagcagctgc tgcccatcgt gaacaagcag agctgcagca tcagcaacat cgagacagtg 660
atcgagttcc agcagaagaa caaccggctg ctggaaatca cccgcgagtt cagcgtgaac 720
gccggcgtga ccaccccccgt gtccacctac atgctgacca acagcgagct gctgtccctg 780
atcaatgaca tgcccatcac caacgaccag aaaaagctga tgagcaacaa cgtgcagatc 840

-continued

```
gtgcggcagc agagctactc catcatgagc atcatcaaag aagaggtgct ggcctacgtg    900

gtgcagctgc ccctgtacgg cgtgatcgac accccctgct ggaagctgca caccagcccc    960

ctgtgcacca ccaacacaaa agagggcagc aacatctgcc tgacccggac cgaccggggc   1020

tggtactgcg ataatgccgg cagcgtgtca ttctttccac aggccgagac atgcaaggtg   1080

cagagcaacc gggtgttctg cgacaccatg aacagcctga ccctgccctc cgaagtgaac   1140

ctgtgcaacg tggacatctt caaccctaag tacgactgca agatcatgac cagcaagacc   1200

gacgtgtcca gctccgtgat cacctccctg ggcgccatcg tgtcctgcta cggcaagacc   1260

aagtgcaccg ccagcaacaa gaaccggggc atcatcaaga ccttcagcaa cggctgcgac   1320

tacgtgtcca acaagggggt ggacaccgtg tccgtgggca acaccctgta ctacgtgaac   1380

aaacaggaag gcaagagcct gtacgtgaag ggcgagccca tcatcaactt ctacgacccc   1440

ctggtgttcc ccagcgacga gttcgacgcc agcatcagcc aggtcaacga gaagatcaac   1500

cagagcctgg ccttcatcag aaagagcgac gagctgctgc acaatgtgaa tgccggcaag   1560

agcaccacaa acatcatgat caccactatc atcatcgtga tcatcgtcat cctgctgagt   1620

ctgatcgccg tgggcctgct gctgtactgc aaggccagat ccacccctgt gaccctgtcc   1680

aaggatcagc tgtccggcat caacaatatc gccttctcca actga                   1725
```

<210> SEQ ID NO 7
<211> LENGTH: 1725
<212> TYPE: DNA
<213> ORGANISM: Artificial sequence
<220> FEATURE:
<223> OTHER INFORMATION: Recombinant RSV F

<400> SEQUENCE: 7

```
atggaactgc tgatcctgaa agccaacgct attactacta tcctgaccgc cgtgacattt     60

tgcttcgcat ctggacagaa cattactgag gaattctacc agtcaacatg cagcgccgtg    120

tccaaaggat acctgagcgc cctgcggacc ggctggtata catcagtgat tactatcgag    180

ctgtccaaca tcaaggaaaa caaatgtaat gggaccgacg caaaggtgaa actgatcaag    240

caggagctgg ataagtacaa aaatgccgtg acagaactgc agctgctgat gcagtccaca    300

ccagcaacta acaatcgcgc ccggagagag ctgccccggt tcatgaacta taccctgaac    360

aatgctaaga aaaccaatgt gacactgtcc aagaaacgca agaggcgctt cctgggattt    420

ctgctgggcg tggggtctgc catcgctagt ggagtggccg tctctaaagt cctgcacctg    480

gagggcgaag tgaacaagat caaaagcgcc ctgctgtcca ctaacaaggc agtggtcagt    540

ctgtcaaatg gcgtgtccgt cctgacctct aaggtgctgg acctgaaaaa ttatattgat    600

aagcagctgc tgcctatcgt caacaaacag agctgctcca tttctaatat cgagacagtg    660

atcgaattcc agcagaagaa caatagactg ctggagatta ccagagagtt cagcgtgaac    720

gccggcgtca ccacacccgt gtccacctac atgctgacaa atagtgagct gctgtcactg    780

attaacgaca tgcctatcac caatgatcag aagaaactga tgtccaacaa tgtgcagatc    840

gtcagacagc agagttactc aatcatgtct atcattaagg aggaagtcct ggcctacgtg    900

gtccagctgc cactgtatgg cgtgatcgac accccctgct ggaaactgca tacatctcct    960

ctgtgcacta ccaacacaaa ggaaggaagt aatatctgcc tgactcgaac cgaccgggga   1020

tggtactgtg ataacgcagg cagcgtgtcc ttctttccac aggccgagac ctgcaaggtc   1080

cagagcaaca gggtgttctg tgacactatg aatagcctga ccctgccttc cgaagtcaac   1140

ctgtgcaatg tggacatctt taatccaaag tacgattgta agatcatgac tagcaagacc   1200
```

```
gatgtcagct cctctgtgat tacttctctg ggggccatcg tgagttgcta cggaaagaca   1260

aaatgtactg ccagcaacaa aaatcgcggc atcattaaga ccttctccaa cgggtgcgac   1320

tatgtctcta acaagggcgt ggatacagtg agtgtcggga acactctgta ctatgtcaat   1380

aagcaggagg gaaaaagcct gtacgtgaag ggcgaaccca tcattaactt ctatgacccc   1440

ctggtgttcc cttccgacga gtttgatgca tctattagtc aggtgaacga aaaaatcaat   1500

cagagtctgg cctttattcg gaagtcagat gagctgctgc acaacgtgaa tgctggcaaa   1560

tctacaacta acatcatgat caccacaatc atcatcgtga ttatcgtcat tctgctgtca   1620

ctgatcgctg tggggctgct gctgtactgt aaggcaagaa gcaccccagt cactctgtca   1680

aaagaccagc tgtcagggat taacaacatt gccttcagta actga                   1725


<210> SEQ ID NO 8
<211> LENGTH: 573
<212> TYPE: PRT
<213> ORGANISM: Artificial sequence
<220> FEATURE:
<223> OTHER INFORMATION: Recombinant RSV F

<400> SEQUENCE: 8

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Cys Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Phe Lys Val
            180                 185                 190

Leu Asp Leu Lys Asn Tyr Ile Asp Lys Gln Leu Leu Pro Ile Leu Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270
```

```
Leu Met Ser Asn Asn Val Gln Ile Val Arg Gln Gln Ser Tyr Ser Ile
        275                 280                 285

Met Cys Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu His Asn Val Asn Ala Gly Lys Ser Thr Thr Asn Ile Met Ile Thr
        515                 520                 525

Thr Ile Ile Ile Val Ile Ile Val Ile Leu Leu Ser Leu Ile Ala Val
    530                 535                 540

Gly Leu Leu Leu Tyr Cys Lys Tyr Tyr Arg Ile Gln Lys Arg Asn Arg
545                 550                 555                 560

Val Asp Gln Asn Asp Lys Pro Tyr Val Leu Thr Asn Lys
                565                 570
```

<210> SEQ ID NO 9
<211> LENGTH: 1722
<212> TYPE: DNA
<213> ORGANISM: Artificial sequence
<220> FEATURE:
<223> OTHER INFORMATION: Recombinant RSV F

<400> SEQUENCE: 9

```
atggaactgc tgatcctgaa agccaacgct attactacta tcctgaccgc cgtgacattt     60

tgcttcgcat ctggacagaa cattactgag gaattctacc agtcaacatg cagcgccgtg    120

tccaaaggat acctgagcgc cctgcggacc ggctggtata catcagtgat tactatcgag    180

ctgtccaaca tcaaggaaaa caaatgtaat gggaccgacg caaaggtgaa actgatcaag    240

caggagctgg ataagtacaa aaatgccgtg acagaactgc agctgctgat gcagtccaca    300

ccagcaacta acaatcgcgc ccggagagag ctgccccggt tcatgaacta taccctgaac    360
```

```
aatgctaaga aaaccaatgt gacactgtcc aagaaacgca agaggcgctt cctgggattt    420

ctgctgggcg tggggtctgc catcgctagt ggagtggccg tctgcaaagt cctgcacctg    480

gagggcgaag tgaacaagat caaaagcgcc ctgctgtcca ctaacaaggc agtggtcagt    540

ctgtcaaatg gcgtgtccgt cctgaccttc aaggtgctgg acctgaaaaa ttatattgat    600

aagcagctgc tgcctatcct gaacaaacag agctgctcca tttctaatat cgagacagtg    660

atcgaattcc agcagaagaa caatagactg ctggagatta ccagagagtt cagcgtgaac    720

gccggcgtca ccacacccgt gtccacctac atgctgacaa atagtgagct gctgtcactg    780

attaacgaca tgcctatcac caatgatcag aagaaactga tgtccaacaa tgtgcagatc    840

gtcagacagc agagttactc aatcatgtgc atcattaagg aggaagtcct ggcctacgtg    900

gtccagctgc cactgtatgg cgtgatcgac accccctgct ggaaactgca tacatctcct    960

ctgtgcacta ccaacacaaa ggaaggaagt aatatctgcc tgactcgaac cgaccgggga   1020

tggtactgtg ataacgcagg cagcgtgtcc ttctttccac aggccgagac ctgcaaggtc   1080

cagagcaaca gggtgttctg tgacactatg aatagcctga ccctgccttc cgaagtcaac   1140

ctgtgcaatg tggacatctt taatccaaag tacgattgta agatcatgac tagcaagacc   1200

gatgtcagct cctctgtgat tacttctctg gggggccatcg tgagttgcta cggaaagaca   1260

aaatgtactg ccagcaacaa aaatcgcggc atcattaaga ccttctccaa cgggtgcgac   1320

tatgtctcta acaagggcgt ggatacagtg agtgtcggga acactctgta ctatgtcaat   1380

aagcaggagg gaaaaagcct gtacgtgaag ggcgaaccca tcattaactt ctatgacccc   1440

ctggtgttcc cttccgacga gtttgatgca tctattagtc aggtgaacga aaaaatcaat   1500

cagagtctgg cctttattcg gaagtcagat gagctgctgc acaacgtgaa tgctggcaaa   1560

tctacaacta acatcatgat caccacaatc atcatcgtga ttatcgtcat tctgctgtca   1620

ctgatcgctg tggggctgct gctgtactgt aagtactacc gtatccagaa gaggaacaga   1680

gttgaccaga acgataagcc atacgtgctc actaacaagt ga                      1722
```

<210> SEQ ID NO 10
<211> LENGTH: 575
<212> TYPE: PRT
<213> ORGANISM: Artificial sequence
<220> FEATURE:
<223> OTHER INFORMATION: Recombinant RSV F

<400> SEQUENCE: 10

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110
```

-continued

```
Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Cys Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Phe Lys Val
            180                 185                 190

Leu Asp Leu Lys Asn Tyr Ile Asp Lys Gln Leu Leu Pro Ile Leu Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Cys Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu His Asn Val Asn Ala Gly Lys Ser Thr Thr Asn Ile Met Ile Thr
        515                 520                 525
```

-continued

Thr Ile Ile Ile Ile Leu Ile Met Ile Ile Ile Leu Phe Ile Ile Asn
    530                 535                 540

Ile Thr Ile Ile Thr Ile Ala Ile Lys Tyr Tyr Arg Ile Gln Lys Arg
545                 550                 555                 560

Asn Arg Val Asp Gln Asn Asp Lys Pro Tyr Val Leu Thr Asn Lys
                565                 570                 575

<210> SEQ ID NO 11
<211> LENGTH: 1728
<212> TYPE: DNA
<213> ORGANISM: Artificial sequence
<220> FEATURE:
<223> OTHER INFORMATION: Recombinant RSV F

<400> SEQUENCE: 11
atggaactgc tgatcctgaa agccaacgct attactacta tcctgaccgc cgtgacattt 60
tgcttcgcat ctggacagaa cattactgag gaattctacc agtcaacatg cagcgccgtg 120
tccaaaggat acctgagcgc cctgcggacc ggctggtata catcagtgat tactatcgag 180
ctgtccaaca tcaaggaaaa caaatgtaat gggaccgacg caaaggtgaa actgatcaag 240
caggagctgg ataagtacaa aaatgccgtg acagaactgc agctgctgat gcagtccaca 300
ccagcaacta acaatcgcgc ccggagagag ctgccccggt tcatgaacta taccctgaac 360
aatgctaaga aaaccaatgt gacactgtcc aagaaacgca agaggcgctt cctgggattt 420
ctgctgggcg tggggtctgc catcgctagt ggagtggccg tctgcaaagt cctgcacctg 480
gagggcgaag tgaacaagat caaaagcgcc ctgctgtcca ctaacaaggc agtggtcagt 540
ctgtcaaatg gcgtgtccgt cctgaccttc aaggtgctgg acctgaaaaa ttatattgat 600
aagcagctgc tgcctatcct gaacaaacag agctgctcca tttctaatat cgagacagtg 660
atcgaattcc agcagaagaa caatagactg ctggagatta ccagagagtt cagcgtgaac 720
gccggcgtca ccacacccgt gtccacctac atgctgacaa atagtgagct gctgtcactg 780
attaacgaca tgcctatcac caatgatcag aagaaactga tgtccaacaa tgtgcagatc 840
gtcagacagc agagttactc aatcatgtgc atcattaagg aggaagtcct ggcctacgtg 900
gtccagctgc cactgtatgg cgtgatcgac accccctgct ggaaactgca tacatctcct 960
ctgtgcacta ccaacacaaa ggaaggaagt aatatctgcc tgactcgaac cgaccgggga 1020
tggtactgtg ataacgcagg cagcgtgtcc ttctttccac aggccgagac ctgcaaggtc 1080
cagagcaaca gggtgttctg tgacactatg aatagcctga ccctgccttc cgaagtcaac 1140
ctgtgcaatg tggacatctt taatccaaag tacgattgta agatcatgac tagcaagacc 1200
gatgtcagct cctctgtgat tacttctctg gggggccatcg tgagttgcta cggaaagaca 1260
aaatgtactg ccagcaacaa aaatcgcggc atcattaaga ccttctccaa cgggtgcgac 1320
tatgtctcta acaagggcgt ggatacagtg agtgtcggga acactctgta ctatgtcaat 1380
aagcaggagg gaaaaagcct gtacgtgaag ggcgaaccca tcattaactt ctatgacccc 1440
ctggtgttcc cttccgacga gtttgatgca tctattagtc aggtgaacga aaaaatcaat 1500
cagagtctgg cctttattcg gaagtcagat gagctgctgc acaacgtgaa tgctggcaaa 1560
tctacaacta acatcatgat caccacaatc atcatcatct tgatcatgat catcatcctg 1620
ttcatcatca acatcacaat catcaccatc gctatcaagt actaccgtat ccagaagagg 1680
aacagagttg accagaacga taagccatac gtgctcacta acaagtga 1728

<210> SEQ ID NO 12

-continued

<211> LENGTH: 576
<212> TYPE: PRT
<213> ORGANISM: Artificial sequence
<220> FEATURE:
<223> OTHER INFORMATION: Recombinant RSV F

<400> SEQUENCE: 12

Met Glu Leu Leu Ile Leu Lys Ala Asn Ala Ile Thr Thr Ile Leu Thr
1 5 10 15

Ala Val Thr Phe Cys Phe Ala Ser Gly Gln Asn Ile Thr Glu Glu Phe
20 25 30

Tyr Gln Ser Thr Cys Ser Ala Val Ser Lys Gly Tyr Leu Ser Ala Leu
35 40 45

Arg Thr Gly Trp Tyr Thr Ser Val Ile Thr Ile Glu Leu Ser Asn Ile
50 55 60

Lys Glu Asn Lys Cys Asn Gly Thr Asp Ala Lys Val Lys Leu Ile Lys
65 70 75 80

Gln Glu Leu Asp Lys Tyr Lys Asn Ala Val Thr Glu Leu Gln Leu Leu
85 90 95

Met Gln Ser Thr Pro Ala Thr Asn Asn Arg Ala Arg Arg Glu Leu Pro
100 105 110

Arg Phe Met Asn Tyr Thr Leu Asn Asn Ala Lys Lys Thr Asn Val Thr
115 120 125

Leu Ser Lys Lys Arg Lys Arg Arg Phe Leu Gly Phe Leu Leu Gly Val
130 135 140

Gly Ser Ala Ile Ala Ser Gly Val Ala Val Ser Lys Val Leu His Leu
145 150 155 160

Glu Gly Glu Val Asn Lys Ile Lys Ser Ala Leu Leu Ser Thr Asn Lys
165 170 175

Ala Val Val Ser Leu Ser Asn Gly Val Ser Val Leu Thr Ser Lys Val
180 185 190

Leu Asp Leu Lys Asn Tyr Ile Asp Lys Gln Leu Leu Pro Ile Val Asn
195 200 205

Lys Gln Ser Cys Ser Ile Ser Asn Ile Glu Thr Val Ile Glu Phe Gln
210 215 220

Gln Lys Asn Asn Arg Leu Leu Glu Ile Thr Arg Glu Phe Ser Val Asn
225 230 235 240

Ala Gly Val Thr Thr Pro Val Ser Thr Tyr Met Leu Thr Asn Ser Glu
245 250 255

Leu Leu Ser Leu Ile Asn Asp Met Pro Ile Thr Asn Asp Gln Lys Lys
260 265 270

Leu Met Ser Asn Asn Val Gln Ile Val Arg Gln Gln Ser Tyr Ser Ile
275 280 285

Met Ser Ile Ile Lys Glu Glu Val Leu Ala Tyr Val Val Gln Leu Pro
290 295 300

Leu Tyr Gly Val Ile Asp Thr Pro Cys Trp Lys Leu His Thr Ser Pro
305 310 315 320

Leu Cys Thr Thr Asn Thr Lys Glu Gly Ser Asn Ile Cys Leu Thr Arg
325 330 335

Thr Asp Arg Gly Trp Tyr Cys Asp Asn Ala Gly Ser Val Ser Phe Phe
340 345 350

Pro Gln Ala Glu Thr Cys Lys Val Gln Ser Asn Arg Val Phe Cys Asp
355 360 365

Thr Met Asn Ser Leu Thr Leu Pro Ser Glu Val Asn Leu Cys Asn Val
370 375 380

```
Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu His Asn Val Asn Ala Gly Lys Ser Thr Thr Asn Ile Met Ile Thr
        515                 520                 525

Thr Ile Thr Ile Ile Ile Val Met Ile Ile Ile Leu Val Ile Ile Asn
    530                 535                 540

Ile Thr Ile Ile Val Val Ile Ile Lys Phe His Arg Ile Gln Gly Lys
545                 550                 555                 560

Asp Gln Asn Asp Lys Asn Ser Glu Pro Tyr Ile Leu Thr Asn Arg Gln
                565                 570                 575


<210> SEQ ID NO 13
<211> LENGTH: 1731
<212> TYPE: DNA
<213> ORGANISM: Artificial sequence
<220> FEATURE:
<223> OTHER INFORMATION: Recombinant RSV F

<400> SEQUENCE: 13

atggaactgc tgatcctgaa ggccaacgcc atcaccacca tcctgaccgc cgtgaccttc      60

tgctttgcca gcggccagaa catcaccgag gaattctacc agagcacctg tagcgccgtg     120

tccaagggct acctgagcgc cctgagaacc ggctggtaca ccagcgtgat caccatcgag     180

ctgagcaaca tcaaagaaaa caagtgcaac ggcaccgacg ccaaagtgaa gctgatcaag     240

caggaactgg acaagtacaa gaatgccgtg accgaactgc agctgctgat gcagagcacc     300

cccgccacca acaaccgggc cagaagagaa ctgcccagat tcatgaacta caccctgaac     360

aacgccaaaa agaccaacgt gaccctgagc aagaagcgga agcggcggtt cctgggcttt     420

ctgctgggag tgggaagcgc cattgctagc ggagtggccg tgtctaaggt gctgcacctg     480

gaaggcgaag tgaacaagat caagtccgcc ctgctgagca ccaacaaggc cgtggtgtct     540

ctgagcaacg gcgtgtccgt gctgaccagc aaggtgctgg atctgaagaa ctacatcgac     600

aaacagctgc tgcccatcgt gaacaagcag agctgcagca tcagcaacat cgagacagtg     660

atcgagttcc agcagaagaa caaccggctg ctggaaatca cccgcgagtt cagcgtgaac     720

gctggcgtga ccacccccgt gtccacctac atgctgacca acagcgagct gctgtccctg     780

atcaacgaca tgcccatcac caacgaccag aaaaagctga tgagcaacaa cgtgcagatc     840

gtgcggcagc agagctactc catcatgagc attatcaaag aagaggtgct ggcctacgtg     900

gtgcagctgc ctctgtacgg cgtgatcgac accccctgct ggaagctgca caccagccct     960
```

-continued

```
ctgtgcacca ccaacaccaa agagggctcc aacatctgcc tgacccggac cgacagaggc   1020

tggtactgcg ataatgccgg ctccgtctca ttctttccac aagccgagac atgcaaggtg   1080

cagagcaacc gggtgttctg cgacaccatg aacagcctga ccctgccctc cgaagtgaat   1140

ctgtgcaacg tggacatctt caaccctaag tacgactgca agatcatgac ctccaagacc   1200

gacgtgtcca gctccgtgat cacaagcctg ggcgccatcg tgtcctgcta cggcaagacc   1260

aagtgcaccg ccagcaacaa gaaccggggc atcatcaaga ccttcagcaa cggctgcgac   1320

tacgtgtcca acaagggggt ggacaccgtg tctgtgggca acaccctgta ctacgtgaac   1380

aaacaggaag gcaagagcct gtacgtgaag ggcgagccca tcatcaactt ctacgacccc   1440

ctggtgttcc ccagcgacga gttcgatgcc agcatctccc aagtgaacga gaagatcaac   1500

cagagcctgg ccttcatcag aaagtccgat gagctgctgc acaatgtgaa cgccggcaag   1560

tccaccacca atatcatgat caccacaatc accatcatca ttgtgatgat tatcatcctc   1620

gtgatcatca acatcacaat catcgtcgtg attattaagt tccaccggat ccagggcaag   1680

gaccagaacg acaagaactc cgagccctac atcctgacaa accggcagtg a            1731
```

```
<210> SEQ ID NO 14
<211> LENGTH: 576
<212> TYPE: PRT
<213> ORGANISM: Artificial sequence
<220> FEATURE:
<223> OTHER INFORMATION: Recombinant RSV F

<400> SEQUENCE: 14

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Cys Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Glu Phe Gln
    210                 215                 220
```

-continued

```
Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Cys Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu His Asn Val Asn Ala Gly Lys Ser Thr Thr Asn Ile Met Ile Thr
        515                 520                 525

Thr Ile Ile Ile Val Ile Ile Val Ile Leu Leu Ser Leu Ile Ala Val
    530                 535                 540

Gly Leu Leu Leu Tyr Cys Ile Ile Lys Phe His Arg Ile Gln Gly Lys
545                 550                 555                 560

Asp Gln Asn Asp Lys Asn Ser Glu Pro Tyr Ile Leu Thr Asn Arg Gln
                565                 570                 575
```

<210> SEQ ID NO 15
<211> LENGTH: 1731
<212> TYPE: DNA
<213> ORGANISM: Artificial sequence
<220> FEATURE:
<223> OTHER INFORMATION: Recombinant RSV F

<400> SEQUENCE: 15

```
atggaactgc tgatcctgaa ggccaacgcc atcaccacca tcctgaccgc cgtgaccttc      60
tgctttgcca gcggccagaa catcaccgag gaattctacc agagcacctg tagcgccgtg     120
tccaagggct acctgagcgc cctgagaacc ggctggtaca ccagcgtgat caccatcgag     180
ctgagcaaca tcaaagaaaa caagtgcaac ggcaccgacg ccaaagtgaa gctgatcaag     240
caggaactgg acaagtacaa gaatgccgtg accgaactgc agctgctgat gcagagcacc     300
cccgccacca acaaccgggc cagaagagaa ctgcccagat tcatgaacta caccctgaac     360
aacgccaaaa agaccaacgt gaccctgagc aagaagcgga agcggcggtt cctgggcttt     420
ctgctgggag tgggaagcgc cattgctagc ggagtggccg tgtgcaaggt gctgcacctg     480
gaaggcgaag tgaacaagat caagtccgcc ctgctgagca ccaacaaggc cgtggtgtct     540
ctgagcaacg gcgtgtccgt gctgaccagc aaggtgctgg atctgaagaa ctacatcgac     600
aaacagctgc tgcccatcgt gaacaagcag agctgcagca tcagcaacat cgagacagtg     660
atcgagttcc agcagaagaa caaccggctg ctggaaatca cccgcgagtt cagcgtgaac     720
gctggcgtga ccacccccgt gtccacctac atgctgacca acagcgagct gctgtccctg     780
atcaacgaca tgcccatcac caacgaccag aaaaagctga tgagcaacaa cgtgcagatc     840
gtgcggcagc agagctactc catcatgtgc atcatcaaag aagaggtgct ggcctacgtg     900
gtgcagctgc ctctgtacgg cgtgatcgac accccctgct ggaagctgca caccagccct     960
ctgtgcacca ccaacaccaa agagggctcc aacatctgcc tgacccggac cgacagaggc    1020
tggtactgcg ataatgccgg ctccgtctca ttctttccac aagccgagac atgcaaggtg    1080
cagagcaacc gggtgttctg cgacaccatg aacagcctga ccctgccctc cgaagtgaat    1140
ctgtgcaacg tggacatctt caaccctaag tacgactgca agatcatgac ctccaagacc    1200
gacgtgtcca gctccgtgat cacaagcctg ggcgccatcg tgtcctgcta cggcaagacc    1260
aagtgcaccg ccagcaacaa gaaccggggc atcatcaaga ccttcagcaa cggctgcgac    1320
tacgtgtcca acaagggggt ggacaccgtg tctgtgggca acaccctgta ctacgtgaac    1380
aaacaggaag gcaagagcct gtacgtgaag ggcgagccca tcatcaactt ctacgacccc    1440
ctggtgttcc ccagcgacga gttcgatgcc agcatctccc aagtgaacga gaagatcaac    1500
cagagcctgg ccttcatcag aaagtccgat gagctgctgc acaatgtgaa cgccggcaag    1560
tccaccacca atatcatgat caccacaatc atcatcgtga ttatcgtgat cctgctgagc    1620
ctgatcgccg tgggcctgct gctgtactgt atcatcaagt tccaccggat ccagggcaag    1680
gaccagaacg acaagaactc cgagccctac atcctgacaa accggcagtg a             1731
```

<210> SEQ ID NO 16
<211> LENGTH: 576
<212> TYPE: PRT
<213> ORGANISM: Artificial sequence
<220> FEATURE:
<223> OTHER INFORMATION: Recombinant RSV F

<400> SEQUENCE: 16

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45
```

-continued

```
Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Cys Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Phe Lys Val
            180                 185                 190

Leu Asp Leu Lys Asn Tyr Ile Asp Lys Gln Leu Leu Pro Ile Leu Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Cys Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
    450                 455                 460
```

-continued

```
Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu His Asn Val Asn Ala Gly Lys Ser Thr Thr Asn Ile Met Ile Thr
        515                 520                 525

Thr Ile Ile Ile Val Ile Ile Val Ile Leu Leu Ser Leu Ile Ala Val
    530                 535                 540

Gly Leu Leu Leu Tyr Cys Ile Ile Lys Phe His Arg Ile Gln Gly Lys
545                 550                 555                 560

Asp Gln Asn Asp Lys Asn Ser Glu Pro Tyr Ile Leu Thr Asn Arg Gln
                565                 570                 575
```

<210> SEQ ID NO 17
<211> LENGTH: 1731
<212> TYPE: DNA
<213> ORGANISM: Artificial sequence
<220> FEATURE:
<223> OTHER INFORMATION: Recombinant RSV F

<400> SEQUENCE: 17

```
atggaactgc tgatcctgaa ggccaacgcc atcaccacca tcctgaccgc cgtgaccttc     60

tgctttgcca gcggccagaa catcaccgag gaattctacc agagcacctg tagcgccgtg    120

tccaagggct acctgagcgc cctgagaacc ggctggtaca ccagcgtgat caccatcgag    180

ctgagcaaca tcaaagaaaa caagtgcaac ggcaccgacg ccaaagtgaa gctgatcaag    240

caggaactgg acaagtacaa gaatgccgtg accgaactgc agctgctgat gcagagcacc    300

cccgccacca acaaccgggc cagaagagaa ctgcccagat tcatgaacta caccctgaac    360

aacgccaaaa agaccaacgt gaccctgagc aagaagcgga agcggcggtt cctgggcttt    420

ctgctgggag tgggaagcgc cattgctagc ggagtggccg tgtgcaaggt gctgcacctg    480

gaaggcgaag tgaacaagat caagtccgcc ctgctgagca ccaacaaggc cgtggtgtct    540

ctgagcaacg gcgtgtccgt gctgaccttc aaggtgctgg atctgaagaa ctacatcgac    600

aaacagctgc tgcccatctt gaacaagcag agctgcagca tcagcaacat cgagacagtg    660

atcgagttcc agcagaagaa caaccggctg ctggaaatca cccgcgagtt cagcgtgaac    720

gctggcgtga ccacccccgt gtccacctac atgctgacca acagcgagct gctgtccctg    780

atcaacgaca tgcccatcac caacgaccag aaaaagctga tgagcaacaa cgtgcagatc    840

gtgcggcagc agagctactc catcatgtgc atcatcaaag aagaggtgct ggcctacgtg    900

gtgcagctgc ctctgtacgg cgtgatcgac accccctgct ggaagctgca caccagccct    960

ctgtgcacca ccaacaccaa agagggctcc aacatctgcc tgacccggac cgacagaggc   1020

tggtactgcg ataatgccgg ctccgtctca ttctttccac aagccgagac atgcaaggtg   1080

cagagcaacc gggtgttctg cgacaccatg aacagcctga ccctgccctc cgaagtgaat   1140

ctgtgcaacg tggacatctt caaccctaag tacgactgca agatcatgac ctccaagacc   1200

gacgtgtcca gctccgtgat cacaagcctg ggcgccatcg tgtcctgcta cggcaagacc   1260

aagtgcaccg ccagcaacaa gaaccggggc atcatcaaga ccttcagcaa cggctgcgac   1320

tacgtgtcca acaagggggt ggacaccgtg tctgtgggca acaccctgta ctacgtgaac   1380

aaacaggaag gcaagagcct gtacgtgaag ggcgagccca tcatcaactt ctacgacccc   1440
```

-continued

```
ctggtgttcc ccagcgacga gttcgatgcc agcatctccc aagtgaacga gaagatcaac   1500

cagagcctgg ccttcatcag aaagtccgat gagctgctgc acaatgtgaa cgccggcaag   1560

tccaccacca atatcatgat caccacaatc atcatcgtga ttatcgtgat cctgctgagc   1620

ctgatcgccg tgggcctgct gctgtactgt atcatcaagt tccaccggat ccagggcaag   1680

gaccagaacg acaagaactc cgagccctac atcctgacaa accggcagtg a            1731
```

<210> SEQ ID NO 18
<211> LENGTH: 1728
<212> TYPE: DNA
<213> ORGANISM: Artificial sequence
<220> FEATURE:
<223> OTHER INFORMATION: Recombinant RSV F

<400> SEQUENCE: 18

```
atggaactgc tgatcctgaa agccaacgct attactacta tcctgaccgc cgtgacattt     60

tgcttcgcat ctggacagaa cattactgag gaattctacc agtcaacatg cagcgccgtg    120

tccaaaggat acctgagcgc cctgcggacc ggctggtata catcagtgat tactatcgag    180

ctgtccaaca tcaaggaaaa caaatgtaat gggaccgacg caaaggtgaa actgatcaag    240

caggagctgg ataagtacaa aaatgccgtg acagaactgc agctgctgat gcagtccaca    300

ccagcaacta acaatcgcgc ccggagagag ctgccccggt tcatgaacta taccctgaac    360

aatgctaaga aaaccaatgt gacactgtcc aagaaacgca agaggcgctt cctgggattt    420

ctgctgggcg tggggtctgc catcgctagt ggagtggccg tctgcaaagt cctgcacctg    480

gagggcgaag tgaacaagat caaaagcgcc ctgctgtcca ctaacaaggc agtggtcagt    540

ctgtcaaatg gcgtgtccgt cctgaccttc aaggtgctgg acctgaaaaa ttatattgat    600

aagcagctgc tgcctatcct gaacaaacag agctgctcca tttctaatat cgagacagtg    660

atcgaattcc agcagaagaa caatagactg ctggagatta ccagagagtt cagcgtgaac    720

gccggcgtca ccacacccgt gtccacctac atgctgacaa atagtgagct gctgtcactg    780

attaacgaca tgcctatcac caatgatcag aagaaactga tgtccaacaa tgtgcagatc    840

gtcagacagc agagttactc aatcatgtgc atcattaagg aggaagtcct ggcctacgtg    900

gtccagctgc cactgtatgg cgtgatcgac accccctgct ggaaactgca tacatctcct    960

ctgtgcacta ccaacacaaa ggaaggaagt aatatctgcc tgactcgaac cgaccgggga   1020

tggtactgtg ataacgcagg cagcgtgtcc ttctttccac aggccgagac ctgcaaggtc   1080

cagagcaaca gggtgttctg tgacactatg aatagcctga ccctgccttc cgaagtcaac   1140

ctgtgcaatg tggacatctt taatccaaag tacgattgta agatcatgac tagcaagacc   1200

gatgtcagct cctctgtgat tacttctctg gggccatcg tgagttgcta cggaaagaca   1260

aaatgtactg ccagcaacaa aaatcgcggc atcattaaga ccttctccaa cgggtgcgac   1320

tatgtctcta acaagggcgt ggatacagtg agtgtcggga acactctgta ctatgtcaat   1380

aagcaggagg gaaaaagcct gtacgtgaag ggcgaaccca tcattaactt ctatgacccc   1440

ctggtgttcc cttccgacga gtttgatgca tctattagtc aggtgaacga aaaaatcaat   1500

cagagtctgg cctttattcg gaagtcagat gagctgctgc acaacgtgaa tgctggcaaa   1560

tctacaacta acatcatgat caccacaatc atcatcgtga ttatcgtcat tctgctgtca   1620

ctgatcgctg tggggctgct gctgtactgt atcattaagt tccaccggat ccagggcaag   1680

gaccagaacg ataaaaatag cgagccctac attctgacca acagacag                1728
```

<210> SEQ ID NO 19
<211> LENGTH: 576
<212> TYPE: PRT
<213> ORGANISM: Artificial sequence
<220> FEATURE:
<223> OTHER INFORMATION: Recombinant RSV F

<400> SEQUENCE: 19

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Cys Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Cys Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365
```

-continued

```
Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu His Asn Val Asn Ala Gly Lys Ser Thr Thr Asn Ile Met Ile Thr
        515                 520                 525

Thr Ile Thr Ile Ile Ile Val Met Ile Ile Ile Leu Val Ile Ile Asn
    530                 535                 540

Ile Thr Ile Ile Val Val Ile Ile Lys Phe His Arg Ile Gln Gly Lys
545                 550                 555                 560

Asp Gln Asn Asp Lys Asn Ser Glu Pro Tyr Ile Leu Thr Asn Arg Gln
                565                 570                 575
```

<210> SEQ ID NO 20
<211> LENGTH: 1731
<212> TYPE: DNA
<213> ORGANISM: Artificial sequence
<220> FEATURE:
<223> OTHER INFORMATION: Recombinant RSV F

<400> SEQUENCE: 20

```
atggaactgc tgatcctgaa ggccaacgcc atcaccacca tcctgaccgc cgtgaccttc     60

tgctttgcca gcggccagaa catcaccgag gaattctacc agagcacctg tagcgccgtg    120

tccaagggct acctgagcgc cctgagaacc ggctggtaca ccagcgtgat caccatcgag    180

ctgagcaaca tcaaagaaaa caagtgcaac ggcaccgacg ccaaagtgaa gctgatcaag    240

caggaactgg acaagtacaa gaatgccgtg accgaactgc agctgctgat gcagagcacc    300

cccgccacca acaaccgggc cagaagagaa ctgcccagat tcatgaacta caccctgaac    360

aacgccaaaa agaccaacgt gaccctgagc aagaagcgga agcggcggtt cctgggcttt    420

ctgctgggag tgggaagcgc cattgctagc ggagtggccg tgtgcaaggt gctgcacctg    480

gaaggcgaag tgaacaagat caagtccgcc ctgctgagca ccaacaaggc cgtggtgtct    540

ctgagcaacg gcgtgtccgt gctgaccagc aaggtgctgg atctgaagaa ctacatcgac    600

aaacagctgc tgcccatcgt gaacaagcag agctgcagca tcagcaacat cgagacagtg    660

atcgagttcc agcagaagaa caaccggctg ctggaaatca cccgcgagtt cagcgtgaac    720

gctggcgtga ccacccccgt gtccacctac atgctgacca acagcgagct gctgtccctg    780

atcaacgaca tgcccatcac caacgaccag aaaaagctga tgagcaacaa cgtgcagatc    840

gtgcggcagc agagctactc catcatgtgc atcatcaaag aagaggtgct ggcctacgtg    900
```

```
gtgcagctgc ctctgtacgg cgtgatcgac accccctgct ggaagctgca caccagccct    960

ctgtgcacca ccaacaccaa agagggctcc aacatctgcc tgacccggac cgacagaggc   1020

tggtactgcg ataatgccgg ctccgtctca ttctttccac aagccgagac atgcaaggtg   1080

cagagcaacc gggtgttctg cgacaccatg aacagcctga ccctgccctc cgaagtgaat   1140

ctgtgcaacg tggacatctt caaccctaag tacgactgca agatcatgac ctccaagacc   1200

gacgtgtcca gctccgtgat cacaagcctg ggcgccatcg tgtcctgcta cggcaagacc   1260

aagtgcaccg ccagcaacaa gaaccggggc atcatcaaga ccttcagcaa cggctgcgac   1320

tacgtgtcca acaaggggggt ggacaccgtg tctgtgggca acaccctgta ctacgtgaac   1380

aaacaggaag gcaagagcct gtacgtgaag ggcgagccca tcatcaactt ctacgacccc   1440

ctggtgttcc ccagcgacga gttcgatgcc agcatctccc aagtgaacga gaagatcaac   1500

cagagcctgg ccttcatcag aaagtccgat gagctgctgc acaatgtgaa cgccggcaag   1560

tccaccacca atatcatgat caccacaatc accatcatca ttgtgatgat tatcatcctc   1620

gtgatcatca acatcacaat catcgtcgtg attattaagt tccaccggat ccagggcaag   1680

gaccagaacg acaagaactc cgagccctac atcctgacaa accggcagtg a            1731
```

<210> SEQ ID NO 21
<211> LENGTH: 576
<212> TYPE: PRT
<213> ORGANISM: Artificial sequence
<220> FEATURE:
<223> OTHER INFORMATION: Recombinant RSV F

<400> SEQUENCE: 21

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Cys Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Phe Lys Val
            180                 185                 190

Leu Asp Leu Lys Asn Tyr Ile Asp Lys Gln Leu Leu Pro Ile Leu Asn
        195                 200                 205
```

-continued

```
Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Cys Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu His Asn Val Asn Ala Gly Lys Ser Thr Thr Asn Ile Met Ile Thr
        515                 520                 525

Thr Ile Thr Ile Ile Ile Val Met Ile Ile Ile Leu Val Ile Ile Asn
    530                 535                 540

Ile Thr Ile Ile Val Val Ile Ile Lys Phe His Arg Ile Gln Gly Lys
545                 550                 555                 560

Asp Gln Asn Asp Lys Asn Ser Glu Pro Tyr Ile Leu Thr Asn Arg Gln
                565                 570                 575
```

<210> SEQ ID NO 22
<211> LENGTH: 1731
<212> TYPE: DNA
<213> ORGANISM: Artificial sequence
<220> FEATURE:
<223> OTHER INFORMATION: Recombinant RSV F

<400> SEQUENCE: 22

```
atggaactgc tgatcctgaa ggccaacgcc atcaccacca tcctgaccgc cgtgaccttc     60
tgctttgcca gcggccagaa catcaccgag gaattctacc agagcacctg tagcgccgtg    120
tccaagggct acctgagcgc cctgagaacc ggctggtaca ccagcgtgat caccatcgag    180
ctgagcaaca tcaaagaaaa caagtgcaac ggcaccgacg ccaaagtgaa gctgatcaag    240
caggaactgg acaagtacaa gaatgccgtg accgaactgc agctgctgat gcagagcacc    300
cccgccacca acaaccgggc cagaagagaa ctgcccagat tcatgaacta caccctgaac    360
aacgccaaaa agaccaacgt gaccctgagc aagaagcgga agcggcggtt cctgggcttt    420
ctgctgggag tgggaagcgc cattgctagc ggagtggccg tgtgcaaggt gctgcacctg    480
gaaggcgaag tgaacaagat caagtccgcc ctgctgagca ccaacaaggc cgtggtgtct    540
ctgagcaacg gcgtgtccgt gctgaccttc aaggtgctgg atctgaagaa ctacatcgac    600
aaacagctgc tgcccatctt gaacaagcag agctgcagca tcagcaacat cgagacagtg    660
atcgagttcc agcagaagaa caaccggctg ctggaaatca cccgcgagtt cagcgtgaac    720
gctggcgtga ccaccccgt gtccacctac atgctgacca acagcgagct gctgtccctg    780
atcaacgaca tgcccatcac caacgaccag aaaaagctga tgagcaacaa cgtgcagatc    840
gtgcggcagc agagctactc catcatgtgc atcatcaaag aagaggtgct ggcctacgtg    900
gtgcagctgc ctctgtacgg cgtgatcgac accccctgct ggaagctgca caccagccct    960
ctgtgcacca ccaacaccaa agagggctcc aacatctgcc tgacccggac cgacagaggc   1020
tggtactgcg ataatgccgg ctccgtctca ttctttccac aagccgagac atgcaaggtg   1080
cagagcaacc gggtgttctg cgacaccatg aacagcctga ccctgccctc cgaagtgaat   1140
ctgtgcaacg tggacatctt caaccctaag tacgactgca agatcatgac ctccaagacc   1200
gacgtgtcca gctccgtgat cacaagcctg ggcgccatcg tgtcctgcta cggcaagacc   1260
aagtgcaccg ccagcaacaa gaaccggggc atcatcaaga ccttcagcaa cggctgcgac   1320
tacgtgtcca acaaggggt ggacaccgtg tctgtgggca acaccctgta ctacgtgaac    1380
aaacaggaag gcaagagcct gtacgtgaag ggcgagccca tcatcaactt ctacgacccc   1440
ctggtgttcc ccagcgacga gttcgatgcc agcatctccc aagtgaacga gaagatcaac   1500
cagagcctgg ccttcatcag aaagtccgat gagctgctgc acaatgtgaa cgccggcaag   1560
tccaccacca atatcatgat caccacaatc accatcatca ttgtgatgat tatcatcctc   1620
gtgatcatca acatcacaat catcgtcgtg attattaagt tccaccggat ccagggcaag   1680
gaccagaacg acaagaactc cgagccctac atcctgacaa accggcagtg a            1731
```

<210> SEQ ID NO 23
<211> LENGTH: 1731
<212> TYPE: DNA
<213> ORGANISM: Artificial sequence
<220> FEATURE:
<223> OTHER INFORMATION: Recombinant RSV F

<400> SEQUENCE: 23

```
atggaactgc tgatcctgaa agccaacgct attactacta tcctgaccgc cgtgacattt     60
tgcttcgcat ctggacagaa cattactgag gaattctacc agtcaacatg cagcgccgtg    120
tccaaaggat acctgagcgc cctgcggacc ggctggtata catcagtgat tactatcgag    180
ctgtccaaca tcaaggaaaa caaatgtaat gggaccgacg caaaggtgaa actgatcaag    240
```

```
caggagctgg ataagtacaa aaatgccgtg acagaactgc agctgctgat gcagtccaca    300

ccagcaacta acaatcgcgc ccggagagag ctgccccggt tcatgaacta taccctgaac    360

aatgctaaga aaaccaatgt gacactgtcc aagaaacgca agaggcgctt cctgggattt    420

ctgctgggcg tggggtctgc catcgctagt ggagtggccg tctgcaaagt cctgcacctg    480

gagggcgaag tgaacaagat caaaagcgcc ctgctgtcca ctaacaaggc agtggtcagt    540

ctgtcaaatg gcgtgtccgt cctgaccttc aaggtgctgg acctgaaaaa ttatattgat    600

aagcagctgc tgcctatcct gaacaaacag agctgctcca tttctaatat cgagacagtg    660

atcgaattcc agcagaagaa caatagactg ctggagatta ccagagagtt cagcgtgaac    720

gccggcgtca ccacacccgt gtccacctac atgctgacaa atagtgagct gctgtcactg    780

attaacgaca tgcctatcac caatgatcag aagaaactga tgtccaacaa tgtgcagatc    840

gtcagacagc agagttactc aatcatgtgc atcattaagg aggaagtcct ggcctacgtg    900

gtccagctgc cactgtatgg cgtgatcgac accccctgct ggaaactgca tacatctcct    960

ctgtgcacta ccaacacaaa ggaaggaagt aatatctgcc tgactcgaac cgaccgggga   1020

tggtactgtg ataacgcagg cagcgtgtcc ttctttccac aggccgagac ctgcaaggtc   1080

cagagcaaca gggtgttctg tgacactatg aatagcctga ccctgccttc cgaagtcaac   1140

ctgtgcaatg tggacatctt taatccaaag tacgattgta agatcatgac tagcaagacc   1200

gatgtcagct cctctgtgat tacttctctg ggggccatcg tgagttgcta cggaaagaca   1260

aaatgtactg ccagcaacaa aaatcgcggc atcattaaga ccttctccaa cgggtgcgac   1320

tatgtctcta acaagggcgt ggatacagtg agtgtcggga acactctgta ctatgtcaat   1380

aagcaggagg gaaaaagcct gtacgtgaag ggcgaaccca tcattaactt ctatgacccc   1440

ctggtgttcc cttccgacga gtttgatgca tctattagtc aggtgaacga aaaaatcaat   1500

cagagtctgg cctttattcg gaagtcagat gagctgctgc acaacgtgaa tgctggcaaa   1560

tctacaacta acatcatgat caccacaatc accatcatta tcgtgatgat tatcattctg   1620

gtcatcatta acatcacaat cattgtggtc atcattaagt tccaccggat tcagggcaag   1680

gaccagaacg ataaaaatag cgagccctac atcctgacca atagacagtg a            1731
```

<210> SEQ ID NO 24
<211> LENGTH: 524
<212> TYPE: PRT
<213> ORGANISM: Human parainfluenza virus 1

<400> SEQUENCE: 24

```
Met Ala Gly Leu Leu Ser Thr Phe Asp Thr Phe Ser Ser Arg Arg Ser
1               5                   10                  15

Glu Ser Ile Asn Lys Ser Gly Gly Gly Ala Ile Ile Pro Gly Gln Arg
            20                  25                  30

Ser Thr Val Ser Val Phe Thr Leu Gly Pro Ser Val Thr Asp Asp Ala
        35                  40                  45

Asp Lys Leu Leu Ile Ala Thr Thr Phe Leu Ala His Ser Leu Asp Thr
    50                  55                  60

Asp Lys Gln His Ser Gln Arg Gly Gly Phe Leu Val Ser Leu Leu Ala
65                  70                  75                  80

Met Ala Tyr Ser Ser Pro Glu Leu Tyr Leu Thr Thr Asn Gly Val Asn
                85                  90                  95

Ala Asp Val Lys Tyr Val Ile Tyr Asn Ile Glu Arg Asp Pro Lys Arg
            100                 105                 110
```

```
Thr Lys Thr Asp Gly Phe Ile Val Lys Thr Arg Asp Met Glu Tyr Glu
        115                 120                 125

Arg Thr Thr Glu Trp Leu Phe Gly Pro Met Ile Asn Lys Asn Pro Leu
    130                 135                 140

Phe Gln Gly Gln Arg Glu Asn Ala Asp Leu Glu Ala Leu Leu Gln Thr
145                 150                 155                 160

Tyr Gly Tyr Pro Ala Cys Leu Gly Ala Ile Ile Val Gln Val Trp Ile
                165                 170                 175

Val Leu Val Lys Ala Ile Thr Ser Ser Ala Gly Leu Arg Lys Gly Phe
            180                 185                 190

Phe Asn Arg Leu Glu Ala Phe Arg Gln Asp Gly Thr Val Lys Ser Ala
        195                 200                 205

Leu Val Phe Thr Gly Asp Thr Val Glu Gly Ile Gly Ala Val Met Arg
    210                 215                 220

Ser Gln Gln Ser Leu Val Ser Leu Met Val Glu Thr Leu Val Thr Met
225                 230                 235                 240

Asn Thr Ser Arg Ser Asp Leu Thr Thr Leu Glu Lys Asn Ile Gln Ile
                245                 250                 255

Val Gly Asn Tyr Ile Arg Asp Ala Gly Leu Ala Ser Phe Met Asn Thr
            260                 265                 270

Ile Lys Tyr Gly Val Glu Thr Lys Met Ala Ala Leu Thr Leu Ser Asn
        275                 280                 285

Leu Arg Pro Asp Ile Asn Lys Leu Arg Ser Leu Val Asp Ile Tyr Leu
    290                 295                 300

Ser Lys Gly Ala Arg Ala Pro Phe Ile Cys Ile Leu Arg Asp Pro Val
305                 310                 315                 320

His Gly Asp Phe Ala Pro Gly Asn Tyr Pro Ala Leu Trp Ser Tyr Ala
                325                 330                 335

Met Gly Val Ala Val Val Gln Asn Lys Ala Met Gln Gln Tyr Val Thr
            340                 345                 350

Gly Arg Thr Tyr Leu Asp Met Glu Met Phe Leu Leu Gly Gln Ala Val
        355                 360                 365

Ala Lys Asp Ala Asp Ser Lys Ile Ser Ser Ala Leu Glu Glu Glu Leu
    370                 375                 380

Gly Val Thr Asp Thr Ala Lys Glu Arg Leu Arg His His Leu Thr Asn
385                 390                 395                 400

Leu Ser Gly Gly Asp Gly Ala Tyr His Lys Pro Thr Gly Gly Gly Ala
                405                 410                 415

Ile Glu Val Ala Ile Asp His Thr Asp Ile Thr Phe Gly Val Glu Asp
            420                 425                 430

Thr Ala Asp Arg Asp Asn Lys Asn Trp Thr Asn Asp Ser Asn Glu Arg
        435                 440                 445

Trp Met Asn His Ser Ile Ser Asn His Thr Ile Thr Ile Arg Gly Ala
    450                 455                 460

Glu Glu Leu Glu Glu Glu Thr Asn Asp Glu Asp Ile Thr Asp Ile Glu
465                 470                 475                 480

Asn Lys Ile Ala Arg Arg Leu Ala Asp Arg Lys Gln Arg Leu Ser Gln
                485                 490                 495

Ala Asn Asn Lys Arg Asp Thr Ser Ser Asp Ala Asp Tyr Glu Asn Asp
            500                 505                 510

Asp Asp Ala Thr Ala Ala Ala Gly Ile Gly Gly Ile
        515                 520
```

<210> SEQ ID NO 25
<211> LENGTH: 568
<212> TYPE: PRT
<213> ORGANISM: Human parainfluenza virus 1

<400> SEQUENCE: 25

```
Met Asp Gln Asp Ala Phe Phe Phe Glu Arg Asp Pro Glu Ala Glu Gly
1               5                   10                  15

Glu Ala Pro Arg Lys Gln Glu Ser Leu Ser Asp Val Ile Gly Leu Leu
            20                  25                  30

Asp Val Val Leu Ser Tyr Lys Pro Thr Glu Ile Gly Glu Asp Arg Ser
        35                  40                  45

Trp Leu His Gly Ile Ile Asp Asn Pro Lys Glu Asn Lys Pro Ser Cys
    50                  55                  60

Lys Ala Asp Asp Asn Asn Lys Asp Arg Ala Ile Ser Thr Ser Thr Gln
65                  70                  75                  80

Asp His Arg Ser Ser Glu Glu Ser Gly Ile Ser Arg Arg Thr Ser Glu
                85                  90                  95

Ser Lys Thr Glu Thr His Ala Arg Ile Leu Asp Gln Gln Gly Ile His
            100                 105                 110

Arg Ala Ser Arg Arg Gly Thr Ser Pro Asn Pro Leu Pro Glu Asn Met
        115                 120                 125

Gly Asn Glu Arg Asn Thr Arg Ile Asp Glu Asp Ser Pro Asn Glu Arg
    130                 135                 140

Arg His Gln Arg Ser Val Leu Thr Asp Glu Asp Arg Lys Met Ala Glu
145                 150                 155                 160

Asn Ser Asn Lys Arg Glu Glu Asp Gln Val Glu Gly Phe Pro Glu Glu
                165                 170                 175

Val Arg Arg Ser Thr Pro Leu Ser Asp Asp Gly Glu Gly Arg Thr Asn
            180                 185                 190

Asn Asn Gly Arg Ser Met Glu Thr Ser Ser Thr His Ser Thr Arg Ile
        195                 200                 205

Thr Asp Val Ile Thr Asn Pro Ser Pro Glu Leu Glu Asp Ala Val Leu
    210                 215                 220

Gln Arg Asn Lys Arg Arg Pro Thr Thr Ile Lys Arg Asn Gln Thr Arg
225                 230                 235                 240

Ser Glu Arg Thr Gln Ser Ser Glu Leu His Lys Ser Thr Ser Glu Asn
                245                 250                 255

Ser Ser Asn Leu Glu Asp His Asn Thr Lys Thr Ser Pro Lys Val Pro
            260                 265                 270

Pro Ser Lys Asn Glu Glu Ser Ala Ala Thr Pro Lys Asn Asn His Asn
        275                 280                 285

His Arg Lys Thr Arg Tyr Thr Thr Asn Asn Ala Asn Asn Asn Thr Lys
    290                 295                 300

Ser Pro Pro Thr Pro Glu His Asp Ala Thr Ala Asn Glu Glu Glu Thr
305                 310                 315                 320

Ser Asn Thr Ser Val Asp Glu Met Ala Lys Leu Leu Val Ser Leu Gly
                325                 330                 335

Val Met Lys Ser Gln His Glu Phe Glu Leu Ser Arg Ser Ala Ser His
            340                 345                 350

Val Phe Ala Lys Arg Met Leu Lys Ser Ala Asn Tyr Lys Glu Met Thr
        355                 360                 365

Phe Asn Leu Cys Gly Met Leu Ile Ser Val Glu Lys Ser Leu Glu Asn
    370                 375                 380
```

```
Lys Val Glu Glu Asn Arg Thr Leu Leu Lys Gln Ile Gln Glu Glu Ile
385                 390                 395                 400

Asn Ser Ser Arg Asp Leu His Lys Arg Phe Ser Glu Tyr Gln Lys Glu
                405                 410                 415

Gln Asn Ser Leu Met Met Ala Asn Leu Ser Thr Leu His Ile Ile Thr
            420                 425                 430

Asp Arg Gly Gly Lys Thr Gly Asn Pro Ser Asp Thr Thr Arg Ser Pro
        435                 440                 445

Ser Val Phe Thr Lys Gly Lys Asp Asn Lys Val Lys Lys Thr Arg Phe
    450                 455                 460

Asp Pro Ser Met Glu Ala Leu Gly Gly Gln Glu Phe Lys Pro Asp Leu
465                 470                 475                 480

Ile Arg Glu Asp Glu Leu Arg Asp Asp Ile Lys Asn Pro Val Leu Glu
                485                 490                 495

Glu Asn Asn Asn Glu Pro Gln Ala Ser Asn Ala Ser Arg Leu Ile Pro
            500                 505                 510

Ser Thr Glu Lys His Thr Leu His Ser Leu Lys Leu Val Ile Glu Asn
        515                 520                 525

Ser Pro Leu Ser Arg Val Glu Lys Lys Ala Tyr Ile Lys Ser Leu Tyr
    530                 535                 540

Lys Cys Arg Thr Asn Gln Glu Val Lys Asn Val Met Glu Leu Phe Glu
545                 550                 555                 560

Glu Asp Ile Asp Ser Leu Thr Asn
                565


<210> SEQ ID NO 26
<211> LENGTH: 204
<212> TYPE: PRT
<213> ORGANISM: Human parainfluenza virus 1

<400> SEQUENCE: 26

Met Pro Ser Phe Leu Arg Gly Ile Leu Lys Pro Lys Glu Arg His His
1               5                   10                  15

Glu Asn Lys Asn His Ser Gln Met Ser Ser Asp Ser Leu Thr Ser Ser
            20                  25                  30

Tyr Pro Thr Ser Pro Gln Lys Leu Glu Lys Thr Glu Ala Gly Ser Met
        35                  40                  45

Val Ser Ser Thr Thr Gln Lys Lys Thr Ser His His Ala Lys Pro Thr
    50                  55                  60

Ile Thr Thr Lys Thr Glu Gln Ser Gln Arg Arg Pro Lys Ile Ile Asp
65                  70                  75                  80

Gln Val Arg Arg Val Glu Ser Leu Gly Glu Gln Val Ser Gln Lys Gln
                85                  90                  95

Arg His Met Leu Glu Ser Leu Ile Asn Lys Val Tyr Thr Gly Pro Leu
            100                 105                 110

Gly Glu Glu Leu Val Gln Thr Leu Tyr Leu Arg Ile Trp Ala Met Lys
        115                 120                 125

Glu Thr Pro Glu Ser Thr Lys Ile Leu Gln Met Arg Glu Asp Ile Arg
    130                 135                 140

Asp Gln Tyr Leu Arg Met Lys Thr Glu Arg Trp Leu Arg Thr Leu Ile
145                 150                 155                 160

Arg Gly Lys Lys Thr Lys Leu Arg Asp Phe Gln Lys Arg Tyr Glu Glu
                165                 170                 175

Val His Pro Tyr Leu Met Met Glu Arg Val Glu Gln Ile Ile Met Glu
            180                 185                 190
```

```
Glu Ala Trp Lys Leu Ala Ala His Ile Val Gln Glu
        195                 200


<210> SEQ ID NO 27
<211> LENGTH: 348
<212> TYPE: PRT
<213> ORGANISM: Human parainfluenza virus 1

<400> SEQUENCE: 27

Met Ala Glu Thr Tyr Arg Phe Pro Arg Phe Ser His Glu Glu Asn Gly
1               5                   10                  15

Thr Val Glu Pro Leu Pro Leu Lys Thr Gly Pro Asp Lys Lys Ala Ile
            20                  25                  30

Pro His Ile Arg Ile Val Lys Val Gly Asp Pro Pro Lys His Gly Val
        35                  40                  45

Arg Tyr Leu Asp Val Leu Leu Leu Gly Phe Phe Glu Thr Pro Lys Gln
    50                  55                  60

Gly Pro Leu Ser Gly Ser Ile Ser Asp Leu Thr Glu Ser Thr Ser Tyr
65                  70                  75                  80

Ser Ile Cys Gly Ser Gly Ser Leu Pro Ile Gly Ile Ala Lys Tyr Tyr
                85                  90                  95

Gly Thr Asp Gln Glu Leu Leu Lys Ala Cys Ile Asp Leu Lys Ile Thr
            100                 105                 110

Val Arg Arg Thr Val Arg Ser Gly Glu Met Ile Val Tyr Met Val Asp
        115                 120                 125

Ser Ile His Ala Pro Leu Leu Pro Trp Ser Ser Arg Leu Arg Gln Gly
    130                 135                 140

Met Ile Tyr Asn Ala Asn Lys Val Ala Leu Ala Pro Gln Cys Leu Pro
145                 150                 155                 160

Val Asp Lys Asp Ile Arg Phe Arg Val Val Phe Val Asn Gly Thr Ser
                165                 170                 175

Leu Gly Thr Ile Thr Ile Ala Lys Val Pro Lys Thr Leu Ala Asp Leu
            180                 185                 190

Ala Leu Pro Asn Ser Ile Ser Val Asn Leu Leu Val Thr Leu Arg Ala
        195                 200                 205

Gly Val Ser Thr Glu Gln Lys Gly Ile Leu Pro Val Leu Asp Asp Asp
    210                 215                 220

Gly Glu Lys Lys Leu Asn Phe Met Val His Leu Gly Ile Ile Arg Arg
225                 230                 235                 240

Lys Val Gly Lys Ile Tyr Ser Val Glu Tyr Cys Lys Asn Lys Ile Glu
                245                 250                 255

Lys Met Lys Leu Ile Phe Ser Leu Gly Leu Val Gly Gly Ile Ser Phe
            260                 265                 270

His Val His Ala Thr Gly Thr Leu Ser Lys Thr Leu Met Ser Gln Leu
        275                 280                 285

Ala Trp Lys Lys Ala Val Cys Tyr Pro Leu Met Asp Val Asn Pro His
    290                 295                 300

Met Asn Leu Val Ile Trp Ala Ala Ser Val Glu Ile Thr Ser Val Asp
305                 310                 315                 320

Ala Val Phe Gln Pro Ala Ile Pro Lys Glu Phe Arg Tyr Tyr Pro Asn
                325                 330                 335

Val Val Ala Lys Ser Ile Gly Lys Ile Arg Arg Ile
            340                 345
```

<210> SEQ ID NO 28
<211> LENGTH: 555
<212> TYPE: PRT
<213> ORGANISM: Human parainfluenza virus 1

<400> SEQUENCE: 28

Met Gln Lys Ser Glu Ile Leu Phe Leu Val Tyr Ser Ser Leu Leu Leu
1               5                   10                  15

Ser Ser Ser Leu Cys Gln Ile Pro Val Glu Lys Leu Ser Asn Val Gly
            20                  25                  30

Val Ile Ile Asn Glu Gly Lys Leu Leu Lys Ile Ala Gly Ser Tyr Glu
        35                  40                  45

Ser Arg Tyr Ile Val Leu Ser Leu Val Pro Ser Ile Asp Leu Gln Asp
    50                  55                  60

Gly Cys Gly Thr Thr Gln Ile Ile Gln Tyr Lys Asn Leu Leu Asn Arg
65                  70                  75                  80

Leu Leu Ile Pro Leu Lys Asp Ala Leu Asp Leu Gln Glu Ser Leu Ile
                85                  90                  95

Thr Ile Thr Asn Asp Thr Thr Val Thr Asn Asp Asn Pro Gln Thr Arg
            100                 105                 110

Phe Phe Gly Ala Val Ile Gly Thr Ile Ala Leu Gly Val Ala Thr Ala
        115                 120                 125

Ala Gln Ile Thr Ala Gly Ile Ala Leu Ala Glu Ala Arg Glu Ala Arg
    130                 135                 140

Lys Asp Ile Ala Leu Ile Lys Asp Ser Ile Val Lys Thr His Asn Ser
145                 150                 155                 160

Val Glu Leu Ile Gln Arg Gly Ile Gly Glu Gln Ile Ile Ala Leu Lys
                165                 170                 175

Thr Leu Gln Asp Phe Val Asn Asp Glu Ile Arg Pro Ala Ile Gly Glu
            180                 185                 190

Leu Arg Cys Glu Thr Thr Ala Leu Lys Leu Gly Ile Lys Leu Thr Gln
        195                 200                 205

His Tyr Ser Glu Leu Ala Thr Ala Phe Ser Ser Asn Leu Gly Thr Ile
    210                 215                 220

Gly Glu Lys Ser Leu Thr Leu Gln Ala Leu Ser Ser Leu Tyr Ser Ala
225                 230                 235                 240

Asn Ile Thr Glu Ile Leu Ser Thr Thr Lys Lys Asp Lys Ser Asp Ile
                245                 250                 255

Tyr Asp Ile Ile Tyr Thr Glu Gln Val Lys Gly Thr Val Ile Asp Val
            260                 265                 270

Asp Leu Glu Lys Tyr Met Val Thr Leu Leu Val Lys Ile Pro Ile Leu
        275                 280                 285

Ser Glu Ile Pro Gly Val Leu Ile Tyr Arg Ala Ser Ser Ile Ser Tyr
    290                 295                 300

Asn Ile Glu Gly Glu Glu Trp His Val Ala Ile Pro Asn Tyr Ile Ile
305                 310                 315                 320

Asn Lys Ala Ser Ser Leu Gly Gly Ala Asp Val Thr Asn Cys Ile Glu
                325                 330                 335

Ser Lys Leu Ala Tyr Ile Cys Pro Arg Asp Pro Thr Gln Leu Ile Pro
            340                 345                 350

Asp Asn Gln Gln Lys Cys Ile Leu Gly Asp Val Ser Lys Cys Pro Val
        355                 360                 365

Thr Lys Val Ile Asn Asn Leu Val Pro Lys Phe Ala Phe Ile Asn Gly
    370                 375                 380

-continued

```
Gly Val Val Ala Asn Cys Ile Ala Ser Thr Cys Thr Cys Gly Thr Asn
385                 390                 395                 400

Arg Ile Pro Val Asn Gln Asp Arg Ser Arg Gly Val Thr Phe Leu Thr
                405                 410                 415

Tyr Thr Asn Cys Gly Leu Ile Gly Ile Asn Gly Ile Glu Leu Tyr Ala
            420                 425                 430

Asn Lys Arg Gly Arg Asp Thr Thr Trp Gly Asn Gln Ile Ile Lys Val
        435                 440                 445

Gly Pro Ala Val Ser Ile Arg Pro Val Asp Ile Ser Leu Asn Leu Ala
    450                 455                 460

Ser Ala Thr Asn Phe Leu Glu Glu Ser Lys Thr Glu Leu Met Lys Ala
465                 470                 475                 480

Arg Ala Ile Ile Ser Ala Val Gly Gly Trp His Asn Thr Glu Ser Thr
                485                 490                 495

Gln Ile Ile Met Ile Ile Ile Val Cys Ile Leu Ile Ile Ile Ile Cys
            500                 505                 510

Gly Ile Leu Tyr Tyr Leu Tyr Arg Val Arg Arg Leu Leu Val Met Ile
        515                 520                 525

Asn Ser Thr His Asn Ser Pro Val Asn Ala Tyr Thr Leu Glu Ser Arg
    530                 535                 540

Met Arg Asn Pro Tyr Met Gly Asn Asn Ser Asn
545                 550                 555
```

<210> SEQ ID NO 29
<211> LENGTH: 575
<212> TYPE: PRT
<213> ORGANISM: Human parainfluenza virus 1

<400> SEQUENCE: 29

```
Met Ala Glu Lys Gly Lys Thr Asn Ser Ser Tyr Trp Ser Thr Thr Arg
1               5                   10                  15

Asn Asp Asn Ser Thr Val Asn Thr His Ile Asn Thr Pro Ala Gly Arg
            20                  25                  30

Thr His Ile Trp Leu Leu Ile Ala Thr Thr Met His Thr Val Leu Ser
        35                  40                  45

Phe Ile Ile Met Ile Leu Cys Ile Asp Leu Ile Ile Lys Gln Asp Thr
    50                  55                  60

Cys Met Lys Thr Asn Ile Met Thr Val Ser Ser Met Asn Glu Ser Ala
65                  70                  75                  80

Lys Ile Ile Lys Glu Thr Ile Thr Glu Leu Ile Arg Gln Glu Val Ile
                85                  90                  95

Ser Arg Thr Ile Asn Ile Gln Ser Ser Val Gln Ser Gly Ile Pro Ile
            100                 105                 110

Leu Leu Asn Lys Gln Ser Arg Asp Leu Thr Gln Leu Ile Glu Lys Ser
        115                 120                 125

Cys Asn Arg Gln Glu Leu Ala Gln Ile Cys Glu Asn Thr Ile Ala Ile
    130                 135                 140

His His Ala Asp Gly Ile Ser Pro Leu Asp Pro His Asp Phe Trp Arg
145                 150                 155                 160

Cys Pro Val Gly Glu Pro Leu Leu Ser Asn Asn Pro Asn Ile Ser Leu
                165                 170                 175

Leu Pro Gly Pro Ser Leu Leu Ser Gly Ser Thr Thr Ile Ser Gly Cys
            180                 185                 190

Val Arg Leu Pro Ser Leu Ser Ile Gly Asp Ala Ile Tyr Ala Tyr Ser
        195                 200                 205
```

-continued

```
Ser Asn Leu Ile Thr Gln Gly Cys Ala Asp Ile Gly Lys Ser Tyr Gln
    210                 215                 220

Val Leu Gln Leu Gly Tyr Ile Ser Leu Asn Ser Asp Met Tyr Pro Asp
225                 230                 235                 240

Leu Asn Pro Val Ile Ser His Thr Tyr Asp Ile Asn Asp Asn Arg Lys
                245                 250                 255

Ser Cys Ser Val Ile Ala Ala Gly Thr Arg Gly Tyr Gln Leu Cys Ser
            260                 265                 270

Leu Pro Thr Val Asn Glu Thr Thr Asp Tyr Ser Ser Glu Gly Ile Glu
        275                 280                 285

Asp Leu Val Phe Asp Ile Leu Asp Leu Lys Gly Lys Thr Lys Ser His
    290                 295                 300

Arg Tyr Lys Asn Glu Asp Ile Thr Phe Asp His Pro Phe Ser Ala Met
305                 310                 315                 320

Tyr Pro Ser Val Gly Ser Gly Ile Lys Ile Glu Asn Thr Leu Ile Phe
                325                 330                 335

Leu Gly Tyr Gly Gly Leu Thr Thr Pro Leu Gln Gly Asp Thr Lys Cys
            340                 345                 350

Val Ile Asn Arg Cys Thr Asn Val Asn Gln Ser Val Cys Asn Asp Ala
        355                 360                 365

Leu Lys Ile Thr Trp Leu Lys Lys Arg Gln Val Val Asn Val Leu Ile
    370                 375                 380

Arg Ile Asn Asn Tyr Leu Ser Asp Arg Pro Lys Ile Val Val Glu Thr
385                 390                 395                 400

Ile Pro Ile Thr Gln Asn Tyr Leu Gly Ala Glu Gly Arg Leu Leu Lys
                405                 410                 415

Leu Gly Lys Lys Ile Tyr Ile Tyr Thr Arg Ser Ser Gly Trp His Ser
            420                 425                 430

Asn Leu Gln Ile Gly Ser Leu Asp Ile Asn Asn Pro Met Thr Ile Lys
        435                 440                 445

Trp Ala Pro His Glu Val Leu Ser Arg Pro Gly Asn Gln Asp Cys Asn
    450                 455                 460

Trp Tyr Asn Arg Cys Pro Arg Glu Cys Ile Ser Gly Val Tyr Thr Asp
465                 470                 475                 480

Ala Tyr Pro Leu Ser Pro Asp Ala Val Asn Val Ala Thr Thr Thr Leu
                485                 490                 495

Tyr Ala Asn Thr Ser Arg Val Asn Pro Thr Ile Met Tyr Ser Asn Thr
            500                 505                 510

Ser Glu Ile Ile Asn Met Leu Arg Leu Lys Asn Val Gln Leu Glu Ala
        515                 520                 525

Ala Tyr Thr Thr Thr Ser Cys Ile Thr His Phe Gly Lys Gly Tyr Cys
    530                 535                 540

Phe His Ile Val Glu Ile Asn Gln Thr Ser Leu Asn Thr Leu Gln Pro
545                 550                 555                 560

Met Leu Phe Lys Thr Ser Ile Pro Lys Ile Cys Lys Ile Thr Ser
                565                 570                 575
```

<210> SEQ ID NO 30
<211> LENGTH: 2223
<212> TYPE: PRT
<213> ORGANISM: Human parainfluenza virus 1

<400> SEQUENCE: 30

Met Asp Lys Gln Glu Ser Thr Gln Asn Ser Ser Asp Ile Leu Tyr Pro
1               5                   10                  15

Glu Cys His Leu Asn Ser Pro Ile Val Lys Ser Lys Ile Ala Gln Leu
            20                  25                  30

His Val Leu Leu Asp Ile Asn Gln Pro Tyr Asp Leu Lys Asp Asn Ser
        35                  40                  45

Ile Ile Asn Ile Thr Lys Tyr Lys Ile Arg Asn Gly Gly Leu Ser Pro
    50                  55                  60

Arg Gln Ile Lys Ile Arg Ser Leu Gly Lys Ile Leu Lys Gln Glu Ile
65                  70                  75                  80

Lys Asp Ile Asp Arg Tyr Thr Phe Glu Pro Tyr Pro Ile Phe Ser Leu
                85                  90                  95

Glu Leu Leu Arg Leu Asp Ile Pro Glu Ile Cys Asp Lys Ile Arg Ser
            100                 105                 110

Ile Phe Ser Val Ser Asp Arg Leu Ile Arg Glu Leu Ser Ser Gly Phe
        115                 120                 125

Gln Glu Leu Trp Leu Asn Ile Leu Arg Gln Leu Gly Cys Val Glu Gly
    130                 135                 140

Lys Glu Gly Phe Asp Ser Leu Lys Asp Val Asp Ile Ile Pro Asp Ile
145                 150                 155                 160

Thr Asp Lys Tyr Asn Lys Asn Thr Trp Tyr Arg Pro Phe Leu Thr Trp
                165                 170                 175

Phe Ser Ile Lys Tyr Asp Met Arg Trp Met Gln Lys Asn Lys Ser Gly
            180                 185                 190

Asn His Leu Asp Val Ser Asn Ser His Asn Phe Leu Asp Cys Lys Ser
        195                 200                 205

Tyr Ile Leu Ile Ile Tyr Arg Asp Leu Val Ile Ile Ile Asn Lys Leu
    210                 215                 220

Lys Leu Thr Gly Tyr Val Leu Thr Pro Glu Leu Val Leu Met Tyr Cys
225                 230                 235                 240

Asp Val Val Glu Gly Arg Trp Asn Met Ser Ser Ala Gly Arg Leu Asp
                245                 250                 255

Lys Arg Ser Ser Lys Ile Thr Cys Lys Gly Glu Glu Leu Trp Glu Leu
            260                 265                 270

Ile Asp Ser Leu Phe Pro Asn Leu Gly Glu Asp Val Tyr Asn Ile Ile
        275                 280                 285

Ser Leu Leu Glu Pro Leu Ser Leu Ala Leu Ile Gln Leu Asp Asp Pro
    290                 295                 300

Val Thr Asn Leu Lys Gly Ala Phe Met Arg His Val Leu Thr Glu Leu
305                 310                 315                 320

His Thr Ile Leu Ile Lys Asp Asn Ile Tyr Thr Asp Ser Glu Ala Asp
                325                 330                 335

Ser Ile Met Glu Ser Leu Ile Lys Ile Phe Arg Glu Thr Ser Ile Asp
            340                 345                 350

Glu Lys Ala Glu Ile Phe Ser Phe Phe Arg Thr Phe Gly His Pro Ser
        355                 360                 365

Leu Glu Ala Ile Thr Ala Ala Asp Lys Val Arg Thr His Met Tyr Ser
    370                 375                 380

Ser Lys Lys Ile Ile Leu Lys Thr Leu Tyr Glu Cys His Ala Ile Phe
385                 390                 395                 400

```
Cys Ala Ile Ile Ile Asn Gly Tyr Arg Glu Arg His Gly Gly Gln Trp
                405                 410                 415

Pro Pro Cys Glu Phe Pro Asn His Val Cys Leu Glu Leu Lys Asn Ala
            420                 425                 430

Gln Gly Ser Asn Ser Ala Ile Ser Tyr Glu Cys Ala Val Asp Asn Tyr
        435                 440                 445

Ser Ser Phe Ile Gly Phe Lys Phe Leu Lys Phe Ile Glu Pro Gln Leu
    450                 455                 460

Asp Glu Asp Leu Thr Ile Tyr Met Lys Asp Lys Ala Leu Ser Pro Arg
465                 470                 475                 480

Lys Ala Ala Trp Asp Ser Val Tyr Pro Asp Ser Asn Leu Tyr Tyr Lys
                485                 490                 495

Val Pro Glu Ser Glu Glu Thr Arg Arg Leu Ile Glu Val Phe Ile Asn
            500                 505                 510

Asp Asn Asn Phe Asn Pro Ala Asp Ile Ile Asn Tyr Val Glu Ser Gly
        515                 520                 525

Glu Trp Leu Asn Asp Asp Ser Phe Asn Ile Ser Tyr Ser Leu Lys Glu
    530                 535                 540

Lys Glu Ile Lys Gln Glu Gly Arg Leu Phe Ala Lys Met Thr Tyr Lys
545                 550                 555                 560

Met Arg Ala Val Gln Val Leu Ala Glu Thr Leu Leu Ala Lys Gly Val
                565                 570                 575

Gly Glu Leu Phe Ser Glu Asn Gly Met Val Lys Gly Glu Ile Asp Leu
            580                 585                 590

Leu Lys Arg Leu Thr Thr Leu Ser Val Ser Gly Val Pro Arg Ser Asn
        595                 600                 605

Ser Val Tyr Asn Asn Pro Ile Leu His Glu Lys Leu Ile Lys Asn Met
    610                 615                 620

Asn Lys Cys Asn Ser Asn Gly Tyr Trp Asp Glu Arg Lys Lys Ser Lys
625                 630                 635                 640

Asn Glu Phe Lys Ala Ala Asp Ser Ser Thr Glu Gly Tyr Glu Thr Leu
                645                 650                 655

Ser Cys Phe Leu Thr Thr Asp Leu Lys Lys Tyr Cys Leu Asn Trp Arg
            660                 665                 670

Phe Glu Ser Thr Ala Leu Phe Gly Gln Arg Cys Asn Glu Ile Phe Gly
        675                 680                 685

Phe Lys Thr Phe Phe Asn Trp Met His Pro Ile Leu Glu Lys Ser Thr
    690                 695                 700

Ile Tyr Val Gly Asp Pro Tyr Cys Pro Val Pro Asp Arg Met His Lys
705                 710                 715                 720

Glu Leu Gln Asp His Asp Asp Thr Gly Ile Phe Ile His Asn Pro Arg
                725                 730                 735

Gly Gly Ile Glu Gly Tyr Cys Gln Lys Leu Trp Thr Leu Ile Ser Ile
            740                 745                 750

Ser Ala Ile His Leu Ala Ala Val Lys Val Gly Val Arg Val Ser Ala
        755                 760                 765

Met Val Gln Gly Asp Asn Gln Ala Ile Ala Val Thr Ser Arg Val Pro
    770                 775                 780

Val Thr Gln Thr Tyr Lys Gln Lys Lys Thr His Val Tyr Glu Glu Ile
785                 790                 795                 800

Thr Arg Tyr Phe Gly Ala Leu Arg Glu Val Met Phe Asp Ile Gly His
                805                 810                 815
```

-continued

```
Glu Leu Lys Leu Asn Glu Thr Ile Ile Ser Ser Lys Met Phe Val Tyr
            820                 825                 830

Ser Lys Arg Ile Tyr Tyr Asp Gly Lys Ile Leu Pro Gln Cys Leu Lys
        835                 840                 845

Ala Leu Thr Arg Cys Val Phe Trp Ser Glu Thr Leu Val Asp Glu Asn
    850                 855                 860

Arg Ser Ala Cys Ser Asn Ile Ala Thr Ser Ile Ala Lys Ala Ile Glu
865                 870                 875                 880

Asn Gly Tyr Ser Pro Ile Leu Gly Tyr Cys Ile Ala Leu Phe Lys Thr
                885                 890                 895

Cys Gln Gln Val Cys Ile Ser Leu Gly Met Thr Ile Asn Pro Thr Ile
            900                 905                 910

Thr Ser Thr Ile Lys Asp Gln Tyr Phe Lys Gly Lys Asn Trp Leu Arg
        915                 920                 925

Cys Ala Ile Leu Ile Pro Ala Asn Ile Gly Gly Phe Asn Tyr Met Ser
    930                 935                 940

Thr Ala Arg Cys Phe Val Arg Asn Ile Gly Asp Pro Ala Val Ala Ala
945                 950                 955                 960

Leu Ala Asp Leu Lys Arg Phe Ile Lys Ala Gly Leu Leu Asp Lys Gln
                965                 970                 975

Val Leu Tyr Arg Val Met Asn Gln Glu Pro Gly Asp Ser Ser Phe Leu
            980                 985                 990

Asp Trp Ala Ser Asp Pro Tyr Ser  Cys Asn Leu Pro His  Ser Gln Ser
        995                 1000                1005

Ile Thr  Thr Ile Ile Lys Asn  Val Thr Ala Arg Ser  Val Leu Gln
    1010                1015                1020

Glu Ser  Pro Asn Pro Leu Leu  Ser Gly Leu Phe Ser  Glu Ser Ser
    1025                1030                1035

Ser Glu  Glu Asp Leu Asn Leu  Ala Ser Phe Leu Met  Asp Arg Lys
    1040                1045                1050

Ala Ile  Leu Pro Arg Val Ala  His Glu Ile Leu Asp  Asn Ser Leu
    1055                1060                1065

Thr Gly  Val Arg Glu Ala Ile  Ala Gly Met Leu Asp  Thr Thr Lys
    1070                1075                1080

Ser Leu  Val Arg Ala Ser Val  Arg Arg Gly Gly Leu  Ser Tyr Ser
    1085                1090                1095

Ile Leu  Arg Arg Leu Ile Asn  Tyr Asp Leu Leu Gln  Tyr Glu Thr
    1100                1105                1110

Leu Thr  Arg Thr Leu Arg Lys  Pro Val Lys Asp Asn  Ile Glu Tyr
    1115                1120                1125

Glu Tyr  Met Cys Ser Val Glu  Leu Ala Ile Gly Leu  Arg Gln Lys
    1130                1135                1140

Met Trp  Phe His Leu Thr Tyr  Gly Arg Pro Ile His  Gly Leu Glu
    1145                1150                1155

Thr Pro  Asp Pro Leu Glu Leu  Leu Arg Gly Ser Phe  Ile Glu Gly
    1160                1165                1170

Ser Glu  Ile Cys Lys Phe Cys  Arg Ser Glu Gly Asn  Asn Pro Met
    1175                1180                1185

Tyr Thr  Trp Phe Tyr Leu Pro  Asp Asn Ile Asp Leu  Asp Thr Leu
    1190                1195                1200

Ser Asn  Gly Ser Pro Ala Ile  Arg Ile Pro Tyr Phe  Gly Ser Ala
    1205                1210                1215
```

```
Thr Asp  Glu Arg Ser Glu Ala  Gln Leu Gly Tyr Val  Lys Asn Leu
    1220                 1225                 1230

Ser Lys  Pro Ala Lys Ala Ala  Ile Arg Ile Ala Met  Val Tyr Thr
    1235                 1240                 1245

Trp Ala  Tyr Gly Thr Asp Glu  Ile Ser Trp Met Glu  Ala Ala Leu
    1250                 1255                 1260

Ile Ala  Gln Thr Arg Ala Asn  Leu Ser Leu Glu Asn  Leu Lys Leu
    1265                 1270                 1275

Leu Thr  Pro Val Ser Thr Ser  Thr Asn Leu Ser His  Arg Leu Arg
    1280                 1285                 1290

Asp Thr  Ala Thr Gln Met Lys  Phe Ser Ser Ala Thr  Leu Val Arg
    1295                 1300                 1305

Ala Ser  Arg Phe Ile Thr Ile  Ser Asn Asp Asn Met  Ala Leu Lys
    1310                 1315                 1320

Glu Ala  Gly Glu Ser Lys Asp  Thr Asn Leu Val Tyr  Gln Gln Ile
    1325                 1330                 1335

Met Leu  Thr Gly Leu Ser Leu  Phe Glu Phe Asn Met  Arg Tyr Lys
    1340                 1345                 1350

Gln Gly  Ser Leu Ser Lys Pro  Met Ile Leu His Leu  His Leu Asn
    1355                 1360                 1365

Asn Lys  Cys Cys Ile Ile Glu  Ser Pro Gln Glu Leu  Asn Ile Pro
    1370                 1375                 1380

Pro Arg  Ser Thr Leu Asp Leu  Glu Ile Thr Gln Glu  Asn Asn Lys
    1385                 1390                 1395

Leu Ile  Tyr Asp Pro Asp Pro  Leu Lys Asp Ile Asp  Leu Glu Leu
    1400                 1405                 1410

Phe Ser  Lys Val Arg Asp Val  Val His Thr Ile Asp  Met Asn Tyr
    1415                 1420                 1425

Trp Ser  Asp Asp Glu Ile Ile  Arg Ala Thr Ser Ile  Cys Thr Ala
    1430                 1435                 1440

Met Thr  Ile Ala Asp Thr Met  Ser Gln Leu Asp Arg  Asp Asn Leu
    1445                 1450                 1455

Lys Glu  Met Ile Ala Leu Ile  Asn Asp Asp Asp Ile  Asn Ser Leu
    1460                 1465                 1470

Ile Thr  Glu Phe Met Val Ile  Asp Ile Pro Leu Phe  Cys Ser Thr
    1475                 1480                 1485

Phe Gly  Gly Ile Leu Ile Asn  Gln Phe Ala Tyr Ser  Leu Tyr Gly
    1490                 1495                 1500

Leu Asn  Val Arg Gly Arg Asp  Glu Ile Trp Gly Tyr  Val Ile Arg
    1505                 1510                 1515

Ile Ile  Lys Asp Thr Ser His  Ala Val Leu Lys Val  Leu Ser Asn
    1520                 1525                 1530

Ala Leu  Ser His Pro Lys Ile  Phe Lys Arg Phe Trp  Asp Ala Gly
    1535                 1540                 1545

Val Val  Glu Pro Val Tyr Gly  Pro Asn Leu Ser Asn  Gln Asp Lys
    1550                 1555                 1560

Ile Leu  Leu Ala Ile Ser Val  Cys Glu Tyr Ser Val  Asp Leu Phe
    1565                 1570                 1575

Met Arg  Asp Trp Gln Glu Gly  Ile Pro Leu Glu Ile  Phe Ile Cys
    1580                 1585                 1590

Asp Asn  Asp Pro Asn Ile Ala  Glu Met Arg Lys Leu  Ser Phe Leu
    1595                 1600                 1605
```

-continued

```
Ala Arg  His Leu Ala Tyr Leu  Cys Ser Leu Ala Glu  Ile Ala Lys
    1610                 1615                 1620

Glu Gly  Pro Lys Leu Glu Ser  Met Thr Ser Leu Glu  Arg Leu Glu
    1625                 1630                 1635

Ser Leu  Lys Glu Tyr Leu Glu  Leu Thr Phe Leu Asp  Asp Pro Ile
    1640                 1645                 1650

Leu Arg  Tyr Ser Gln Leu Thr  Gly Leu Val Ile Lys  Ile Phe Pro
    1655                 1660                 1665

Ser Thr  Leu Thr Tyr Ile Arg  Lys Ser Ser Ile Lys  Val Leu Arg
    1670                 1675                 1680

Val Arg  Gly Ile Gly Ile Pro  Glu Val Leu Glu Asp  Trp Asp Pro
    1685                 1690                 1695

Asp Ala  Asp Ser Met Leu Leu  Asp Asn Ile Thr Ala  Glu Val Gln
    1700                 1705                 1710

His Asn  Ile Pro Leu Lys Lys  Asn Glu Arg Thr Pro  Phe Trp Gly
    1715                 1720                 1725

Leu Arg  Val Ser Lys Ser Gln  Val Leu Arg Leu Arg  Gly Tyr Glu
    1730                 1735                 1740

Glu Ile  Lys Arg Glu Glu Arg  Gly Arg Ser Gly Val  Gly Leu Thr
    1745                 1750                 1755

Leu Pro  Phe Asp Gly Arg Tyr  Leu Ser His Gln Leu  Arg Leu Phe
    1760                 1765                 1770

Gly Ile  Asn Ser Thr Ser Cys  Leu Lys Ala Leu Glu  Leu Thr Tyr
    1775                 1780                 1785

Leu Leu  Asn Pro Leu Val Asn  Lys Asp Lys Asp Arg  Leu Tyr Leu
    1790                 1795                 1800

Gly Glu  Gly Ala Gly Ala Met  Leu Ser Cys Tyr Asp  Ala Thr Leu
    1805                 1810                 1815

Gly Pro  Cys Met Asn Tyr Tyr  Asn Ser Gly Val Asn  Ser Cys Asp
    1820                 1825                 1830

Leu Asn  Gly Gln Arg Glu Leu  Asn Ile Tyr Pro Ser  Glu Val Ala
    1835                 1840                 1845

Leu Val  Gly Lys Lys Leu Asn  Asn Val Thr Ser Leu  Cys Gln Arg
    1850                 1855                 1860

Val Lys  Val Leu Phe Asn Gly  Asn Pro Gly Ser Thr  Trp Ile Gly
    1865                 1870                 1875

Asn Asp  Glu Cys Glu Thr Leu  Ile Trp Asn Glu Leu  Gln Asn Asn
    1880                 1885                 1890

Ser Ile  Gly Phe Ile His Cys  Asp Met Glu Gly Gly  Glu His Lys
    1895                 1900                 1905

Cys Asp  Gln Val Val Leu His  Glu His Tyr Ser Val  Ile Arg Ile
    1910                 1915                 1920

Ala Tyr  Leu Val Gly Asp Lys  Asp Val Ile Leu Val  Ser Lys Ile
    1925                 1930                 1935

Ala Pro  Arg Leu Gly Thr Asp  Trp Thr Lys Gln Leu  Ser Leu Tyr
    1940                 1945                 1950

Leu Arg  Tyr Trp Arg Asp Val  Ser Leu Ile Val Leu  Lys Thr Ser
    1955                 1960                 1965

Asn Pro  Ala Ser Thr Glu Met  Tyr Leu Ile Ser Lys  Asp Pro Lys
    1970                 1975                 1980

Ser Asp  Ile Ile Glu Asp Ser  Asn Thr Val Leu Ala  Asn Leu Leu
    1985                 1990                 1995
```

Pro Leu Ser Lys Glu Asp Ser Ile Lys Ile Glu Lys Trp Ile Leu
    2000                2005                2010

Val Glu Lys Ala Lys Val His Asp Trp Ile Val Arg Glu Leu Lys
    2015                2020                2025

Glu Gly Ser Ala Ser Ser Gly Met Leu Arg Pro Tyr His Gln Ala
    2030                2035                2040

Leu Gln Ile Phe Gly Phe Glu Pro Asn Leu Asn Lys Leu Cys Arg
    2045                2050                2055

Asp Phe Leu Ser Thr Leu Asn Ile Val Asp Thr Lys Asn Cys Ile
    2060                2065                2070

Ile Thr Phe Asp Arg Val Leu Arg Asp Thr Ile Phe Glu Trp Thr
    2075                2080                2085

Arg Ile Lys Asp Ala Asp Lys Lys Leu Arg Leu Thr Gly Lys Tyr
    2090                2095                2100

Asp Leu Tyr Pro Leu Arg Asp Ser Gly Lys Leu Lys Val Ile Ser
    2105                2110                2115

Arg Arg Leu Val Ile Ser Trp Ile Ala Leu Ser Met Ser Thr Arg
    2120                2125                2130

Leu Val Thr Gly Ser Phe Pro Asp Ile Lys Phe Glu Ser Arg Leu
    2135                2140                2145

Gln Leu Gly Ile Val Ser Ile Ser Ser Arg Glu Ile Lys Asn Leu
    2150                2155                2160

Arg Val Ile Ser Lys Ile Val Ile Asp Lys Phe Glu Asp Ile Ile
    2165                2170                2175

His Ser Val Thr Tyr Arg Phe Leu Thr Lys Glu Ile Lys Ile Leu
    2180                2185                2190

Met Lys Ile Leu Gly Ala Val Lys Leu Phe Gly Ala Arg Gln Ser
    2195                2200                2205

Thr Ser Ala Asp Ile Thr Asn Ile Asp Thr Ser Asp Ser Ile Gln
    2210                2215                2220

<210> SEQ ID NO 31
<211> LENGTH: 59
<212> TYPE: PRT
<213> ORGANISM: Human parainfluenza virus 1

<400> SEQUENCE: 31

Gln Ile Ile Met Ile Ile Ile Val Cys Ile Leu Ile Ile Ile Ile Cys
1               5                   10                  15

Gly Ile Leu Tyr Tyr Leu Tyr Arg Val Arg Arg Leu Leu Val Met Ile
            20                  25                  30

Asn Ser Thr His Asn Ser Pro Val Asn Ala Tyr Thr Leu Glu Ser Arg
        35                  40                  45

Met Arg Asn Pro Tyr Met Gly Asn Asn Ser Asn
    50                  55

<210> SEQ ID NO 32
<211> LENGTH: 543
<212> TYPE: PRT
<213> ORGANISM: Human parainfluenza virus 2

<400> SEQUENCE: 32

Met Ser Ser Val Leu Lys Thr Phe Glu Arg Phe Thr Ile Gln Gln Glu
1               5                   10                  15

Leu Gln Glu Gln Ser Glu Asp Thr Pro Ile Pro Leu Glu Thr Ile Arg
            20                  25                  30

```
Pro Thr Ile Arg Val Phe Val Ile Asn Asn Asn Asp Pro Ile Val Arg
        35                  40                  45

Ser Arg Leu Leu Phe Phe Asn Leu Arg Ile Ile Met Ser Asn Thr Ala
    50                  55                  60

Arg Glu Gly His Arg Ala Gly Ala Leu Leu Ser Leu Leu Ser Leu Pro
65                  70                  75                  80

Ser Ala Ala Met Ser Asn His Ile Lys Leu Ala Met His Ser Pro Glu
                85                  90                  95

Ala Ser Ile Asp Arg Val Glu Ile Thr Gly Phe Glu Asn Asn Ser Phe
            100                 105                 110

Arg Val Ile Pro Asp Ala Arg Ser Thr Met Ser Arg Gly Glu Val Leu
        115                 120                 125

Ala Phe Glu Ala Leu Ala Glu Asp Ile Pro Asp Thr Leu Asn His Gln
    130                 135                 140

Thr Pro Phe Val Asn Asn Asp Val Glu Asp Asp Ile Phe Asp Glu Thr
145                 150                 155                 160

Glu Lys Phe Leu Asp Val Cys Tyr Ser Val Leu Met Gln Ala Trp Ile
                165                 170                 175

Val Thr Cys Lys Cys Met Thr Ala Pro Asp Gln Pro Pro Val Ser Val
            180                 185                 190

Ala Lys Arg Met Ala Lys Tyr Gln Gln Gln Gly Arg Ile Asn Ala Arg
        195                 200                 205

Tyr Val Leu Gln Pro Glu Ala Gln Arg Leu Ile Gln Asn Ala Ile Arg
    210                 215                 220

Lys Ser Met Val Val Arg His Phe Met Thr Tyr Glu Leu Gln Leu Ser
225                 230                 235                 240

Gln Ser Arg Ser Leu Leu Ala Asn Arg Tyr Tyr Ala Met Val Gly Asp
                245                 250                 255

Ile Gly Lys Tyr Ile Glu His Ser Gly Met Gly Gly Phe Phe Leu Thr
            260                 265                 270

Leu Lys Tyr Gly Leu Gly Thr Arg Trp Pro Thr Leu Ala Leu Ala Ala
        275                 280                 285

Phe Ser Gly Glu Leu Gln Lys Leu Lys Ala Leu Met Leu His Tyr Gln
    290                 295                 300

Ser Leu Gly Pro Met Ala Lys Tyr Met Ala Leu Leu Glu Ser Pro Lys
305                 310                 315                 320

Leu Met Asp Phe Val Pro Ser Glu Tyr Pro Leu Val Tyr Ser Tyr Ala
                325                 330                 335

Met Gly Ile Gly Thr Val Leu Asp Thr Asn Met Arg Asn Tyr Ala Tyr
            340                 345                 350

Gly Arg Ser Tyr Leu Asn Pro Gln Tyr Phe Gln Leu Gly Val Glu Thr
        355                 360                 365

Ala Arg Lys Gln Gln Gly Ala Val Asp Asn Arg Thr Ala Glu Asp Leu
    370                 375                 380

Gly Met Thr Ala Ala Asp Lys Ala Asp Leu Thr Ala Thr Ile Ser Lys
385                 390                 395                 400

Leu Ser Leu Ser Gln Leu Pro Arg Gly Arg Gln Pro Ile Ser Asp Pro
                405                 410                 415

Phe Ala Gly Ala Asn Asp Arg Glu Thr Gly Gly Gln Ala Thr Asp Thr
            420                 425                 430

Pro Val Tyr Asn Phe Asn Pro Ile Asn Asn Arg Arg Tyr Asp Asn Tyr
        435                 440                 445
```

```
Asp Ser Asp Ser Glu Asp Arg Ile Asp Asn Asp Gln Asp Gln Ala Ile
    450                 455                 460

Arg Glu Asn Arg Gly Glu Pro Gly Gln Pro Asn Asn Gln Thr Ser Glu
465                 470                 475                 480

Asn Gln Gln Arg Leu Asn Leu Pro Val Pro Gln Arg Thr Ser Gly Met
                485                 490                 495

Ser Ser Glu Glu Phe Gln His Ser Met Asn Gln Tyr Ile Arg Ala Met
            500                 505                 510

His Glu Gln Tyr Arg Gly Ser Gln Asp Asp Asp Ala Asn Asp Ala Thr
        515                 520                 525

Asp Gly Asn Asp Ile Ser Leu Glu Leu Val Gly Asp Phe Asp Ser
    530                 535                 540


<210> SEQ ID NO 33
<211> LENGTH: 395
<212> TYPE: PRT
<213> ORGANISM: Human parainfluenza virus 2

<400> SEQUENCE: 33

Met Ala Glu Glu Pro Thr Tyr Thr Thr Glu Gln Val Asp Glu Leu Ile
1               5                   10                  15

His Ala Gly Leu Gly Thr Val Asp Phe Phe Leu Ser Arg Pro Ile Asp
            20                  25                  30

Ala Gln Ser Ser Leu Gly Lys Gly Ser Ile Pro Pro Gly Val Thr Ala
        35                  40                  45

Val Leu Thr Asn Ala Ala Glu Ala Lys Ser Lys Pro Val Ala Ala Gly
    50                  55                  60

Pro Val Lys Pro Arg Arg Lys Lys Val Ile Ser Asn Thr Thr Pro Tyr
65                  70                  75                  80

Thr Ile Ala Asp Asn Ile Pro Pro Glu Lys Leu Pro Ile Asn Thr Pro
                85                  90                  95

Ile Pro Asn Pro Leu Leu Pro Leu Ala Arg Pro His Gly Lys Met Thr
            100                 105                 110

Asp Ile Asp Ile Val Thr Gly Asn Ile Thr Glu Gly Ser Tyr Lys Gly
        115                 120                 125

Val Glu Leu Ala Lys Leu Gly Lys Gln Thr Leu Leu Thr Arg Phe Thr
    130                 135                 140

Ser Asn Glu Pro Val Ser Ser Ala Gly Ser Ala Gln Asp Pro Asn Phe
145                 150                 155                 160

Lys Arg Gly Gly Glu Leu Ile Glu Lys Glu Gln Glu Ala Thr Ile Gly
                165                 170                 175

Glu Asn Gly Val Leu His Gly Ser Glu Ile Arg Ser Lys Ser Ser Ser
            180                 185                 190

Gly Val Ile Pro Gly Val Pro Gln Ser Arg Leu Gln Leu Ala Ser Ser
        195                 200                 205

Pro Ala His Val Asp Pro Ala Pro Ala Ser Ala Glu Asn Val Lys Glu
    210                 215                 220

Ile Ile Glu Leu Leu Lys Gly Leu Asp Leu Arg Leu Gln Thr Val Glu
225                 230                 235                 240

Gly Lys Val Asp Lys Ile Leu Ala Thr Ser Ala Thr Ile Ile Asn Leu
                245                 250                 255

Lys Asn Glu Met Thr Ser Leu Lys Ala Ser Val Ala Thr Val Glu Gly
            260                 265                 270

Met Ile Thr Thr Ile Lys Ile Met Asp Pro Ser Thr Pro Thr Asn Val
        275                 280                 285
```

-continued

```
Pro Val Glu Glu Ile Arg Lys Ser Leu His Asn Val Pro Val Val Ile
    290                 295                 300

Ala Gly Pro Thr Ser Gly Gly Phe Thr Ala Glu Gly Ser Asp Met Ile
305                 310                 315                 320

Ser Met Asp Glu Leu Ala Arg Pro Thr Leu Ser Ser Thr Lys Lys Ile
                325                 330                 335

Thr Arg Lys Pro Glu Ser Lys Lys Asp Leu Thr Gly Ile Lys Leu Thr
            340                 345                 350

Leu Met Gln Leu Ala Asn Asp Cys Ile Ser Arg Pro Asp Thr Lys Thr
        355                 360                 365

Glu Phe Val Thr Lys Ile Gln Ala Ala Thr Thr Glu Ser Gln Leu Asn
    370                 375                 380

Glu Ile Lys Arg Ser Ile Ile Arg Ser Ala Ile
385                 390                 395
```

<210> SEQ ID NO 34
<211> LENGTH: 225
<212> TYPE: PRT
<213> ORGANISM: Human parainfluenza virus 2

<400> SEQUENCE: 34

```
Met Ala Glu Glu Pro Thr Tyr Thr Thr Glu Gln Val Asp Glu Leu Ile
1               5                   10                  15

His Ala Gly Leu Gly Thr Val Asp Phe Phe Leu Ser Arg Pro Ile Asp
            20                  25                  30

Ala Gln Ser Ser Leu Gly Lys Gly Ser Ile Pro Pro Gly Val Thr Ala
        35                  40                  45

Val Leu Thr Asn Ala Ala Glu Ala Lys Ser Lys Pro Val Ala Ala Gly
    50                  55                  60

Pro Val Lys Pro Arg Arg Lys Lys Val Ile Ser Asn Thr Thr Pro Tyr
65                  70                  75                  80

Thr Ile Ala Asp Asn Ile Pro Pro Glu Lys Leu Pro Ile Asn Thr Pro
                85                  90                  95

Ile Pro Asn Pro Leu Leu Pro Leu Ala Arg Pro His Gly Lys Met Thr
            100                 105                 110

Asp Ile Asp Ile Val Thr Gly Asn Ile Thr Glu Gly Ser Tyr Lys Gly
        115                 120                 125

Val Glu Leu Ala Lys Leu Gly Lys Gln Thr Leu Leu Thr Arg Phe Thr
    130                 135                 140

Ser Asn Glu Pro Val Ser Ser Ala Gly Ser Ala Gln Asp Pro Asn Phe
145                 150                 155                 160

Lys Arg Gly Gly Ala Asn Arg Glu Arg Ala Arg Gly Asn His Arg Arg
                165                 170                 175

Glu Trp Ser Ile Ala Trp Val Gly Asp Gln Val Lys Val Phe Glu Trp
            180                 185                 190

Cys Asn Pro Arg Cys Ala Pro Val Thr Ala Ser Ala Arg Lys Phe Thr
        195                 200                 205

Cys Thr Cys Gly Ser Cys Pro Ser Ile Cys Gly Glu Cys Glu Gly Asp
    210                 215                 220

His
225
```

<210> SEQ ID NO 35
<211> LENGTH: 377
<212> TYPE: PRT

<213> ORGANISM: Human parainfluenza virus 2

<400> SEQUENCE: 35

```
Met Pro Ile Ile Ser Leu Pro Ala Asp Pro Thr Ser Pro Ser Gln Ser
1               5                   10                  15

Leu Thr Pro Phe Pro Ile Gln Leu Asp Thr Lys Asp Gly Lys Ala Gly
            20                  25                  30

Lys Leu Leu Lys Gln Ile Arg Ile Arg Tyr Leu Asn Glu Pro Asn Ser
        35                  40                  45

Arg His Thr Pro Ile Thr Phe Ile Asn Thr Tyr Gly Phe Val Tyr Ala
    50                  55                  60

Arg Asp Thr Ser Gly Gly Ile His Ser Glu Ile Ser Ser Asp Leu Ala
65                  70                  75                  80

Ala Gly Ser Ile Thr Ala Cys Met Met Thr Leu Gly Pro Gly Pro Asn
                85                  90                  95

Ile Gln Asn Ala Asn Leu Val Leu Arg Ser Leu Asn Glu Phe Tyr Val
            100                 105                 110

Lys Val Lys Lys Thr Ser Ser Gln Arg Glu Glu Ala Val Phe Glu Leu
        115                 120                 125

Val Asn Ile Pro Thr Leu Leu Arg Glu His Ala Leu Cys Lys Arg Lys
    130                 135                 140

Thr Leu Val Cys Ser Ala Glu Lys Phe Leu Lys Asn Pro Ser Lys Leu
145                 150                 155                 160

Gln Ala Gly Phe Glu Tyr Val Tyr Ile Pro Thr Phe Val Ser Ile Thr
                165                 170                 175

Tyr Ser Pro Arg Asn Leu Asn Tyr Gln Val Ala Arg Pro Ile Leu Lys
            180                 185                 190

Phe Arg Ser Arg Phe Val Tyr Ser Ile His Leu Glu Leu Ile Leu Arg
        195                 200                 205

Leu Leu Cys Lys Ser Asp Ser Pro Leu Met Lys Ser Tyr Asn Ala Asp
    210                 215                 220

Arg Thr Gly Arg Gly Cys Leu Ala Ser Val Trp Ile His Val Cys Asn
225                 230                 235                 240

Ile Leu Lys Asn Lys Ser Ile Lys Gln Gln Gly Arg Glu Ser Tyr Phe
                245                 250                 255

Ile Ala Lys Cys Met Ser Met Gln Leu Gln Val Ser Ile Ala Asp Leu
            260                 265                 270

Trp Gly Pro Thr Ile Ile Ile Lys Ser Leu Gly His Ile Pro Lys Thr
        275                 280                 285

Ala Leu Pro Phe Phe Ser Lys Asp Gly Ile Ala Cys His Pro Leu Gln
    290                 295                 300

Asp Val Ser Pro Thr Leu Thr Lys Ser Leu Trp Ser Val Gly Cys Glu
305                 310                 315                 320

Ile Glu Ser Ala Lys Leu Ile Leu Gln Glu Ser Asp Ile Asn Glu Leu
                325                 330                 335

Met Gly His Gln Asp Leu Ile Thr Asp Lys Ile Ala Ile Arg Ser Gly
            340                 345                 350

Gln Arg Thr Phe Glu Arg Ser Lys Phe Ser Pro Phe Lys Lys Tyr Ala
        355                 360                 365

Ser Ile Pro Asn Leu Glu Ala Ile Asn
    370                 375
```

<210> SEQ ID NO 36
<211> LENGTH: 551

<212> TYPE: PRT
<213> ORGANISM: Human parainfluenza virus 2

<400> SEQUENCE: 36

```
Met His His Leu His Pro Met Ile Val Cys Ile Phe Val Met Tyr Thr
1               5                   10                  15

Gly Ile Val Gly Ser Asp Ala Ile Ala Gly Asp Gln Leu Leu Asn Val
            20                  25                  30

Gly Val Ile Gln Ser Lys Ile Arg Ser Leu Met Tyr Tyr Thr Asp Gly
        35                  40                  45

Gly Ala Ser Phe Ile Val Val Lys Leu Leu Pro Asn Leu Pro Pro Ser
    50                  55                  60

Asn Gly Thr Cys Asn Ile Thr Ser Leu Asp Ala Tyr Asn Val Thr Leu
65                  70                  75                  80

Phe Lys Leu Leu Thr Pro Leu Ile Glu Asn Leu Ser Lys Ile Ser Ala
                85                  90                  95

Val Thr Asp Thr Lys Pro Arg Arg Glu Arg Phe Ala Gly Val Val Ile
            100                 105                 110

Gly Leu Ala Ala Leu Gly Val Ala Thr Ala Ala Gln Ile Thr Ala Ala
        115                 120                 125

Val Ala Ile Val Lys Ala Asn Ala Asn Ala Ala Ala Ile Asn Asn Leu
    130                 135                 140

Ala Ser Ser Ile Gln Ser Thr Asn Lys Ala Val Ser Asp Val Ile Thr
145                 150                 155                 160

Ala Ser Arg Thr Ile Ala Thr Ala Val Gln Ala Ile Gln Asp His Ile
                165                 170                 175

Asn Gly Ala Ile Val Asn Gly Ile Thr Ser Ala Ser Cys Arg Ala His
            180                 185                 190

Asp Ala Leu Ile Gly Ser Ile Leu Asn Leu Tyr Leu Thr Glu Leu Thr
        195                 200                 205

Thr Ile Phe His Asn Gln Ile Thr Asn Pro Ala Leu Thr Pro Leu Ser
    210                 215                 220

Ile Gln Ala Leu Arg Ile Leu Leu Gly Ser Thr Leu Pro Ile Val Ile
225                 230                 235                 240

Glu Ser Lys Leu Asn Thr Lys Leu Asn Thr Ala Glu Leu Leu Ser Ser
                245                 250                 255

Gly Leu Leu Thr Gly Gln Ile Ile Ser Ile Ser Pro Met Tyr Met Gln
            260                 265                 270

Met Leu Ile Gln Ile Asn Val Pro Thr Phe Ile Met Gln Pro Gly Ala
        275                 280                 285

Lys Val Ile Asp Leu Ile Ala Ile Ser Ala Asn His Lys Leu Gln Glu
    290                 295                 300

Val Val Val Gln Val Pro Asn Arg Ile Leu Glu Tyr Ala Asn Glu Leu
305                 310                 315                 320

Gln Asn Tyr Pro Ala Asn Asp Cys Val Val Thr Pro Asn Ser Val Phe
                325                 330                 335

Cys Arg Tyr Asn Glu Gly Ser Pro Ile Pro Glu Ser Gln Tyr Gln Cys
            340                 345                 350

Leu Arg Gly Asn Leu Asn Ser Cys Thr Phe Thr Pro Ile Ile Gly Asn
        355                 360                 365

Phe Leu Lys Arg Phe Ala Phe Ala Asn Gly Val Leu Tyr Ala Asn Cys
    370                 375                 380

Lys Ser Leu Leu Cys Lys Cys Ala Asp Pro Pro His Val Val Ser Gln
385                 390                 395                 400
```

```
Asp Asp Asn Gln Gly Ile Ser Ile Ile Asp Ile Lys Arg Cys Ser Glu
                405                 410                 415

Met Met Leu Asp Thr Phe Ser Phe Arg Ile Thr Ser Thr Phe Asn Ala
            420                 425                 430

Thr Tyr Val Thr Asp Phe Ser Met Ile Asn Ala Asn Ile Val His Leu
        435                 440                 445

Ser Pro Leu Asp Leu Ser Asn Gln Ile Asn Ser Ile Asn Lys Ser Leu
    450                 455                 460

Lys Ser Ala Glu Asp Trp Ile Ala Asp Ser Asn Phe Phe Ala Asn Gln
465                 470                 475                 480

Ala Arg Thr Ala Lys Thr Leu Tyr Ser Leu Ser Ala Ile Ala Leu Ile
                485                 490                 495

Leu Ser Val Ile Thr Leu Val Val Val Gly Leu Leu Ile Ala Tyr Ile
            500                 505                 510

Ile Lys Leu Val Ser Gln Ile His Gln Phe Arg Ala Leu Ala Ala Thr
        515                 520                 525

Thr Met Phe His Arg Glu Asn Pro Ala Val Phe Ser Lys Asn Asn His
    530                 535                 540

Gly Asn Ile Tyr Gly Ile Ser
545                 550


<210> SEQ ID NO 37
<211> LENGTH: 571
<212> TYPE: PRT
<213> ORGANISM: Human parainfluenza virus 2

<400> SEQUENCE: 37

Met Glu Asp Tyr Ser Asn Leu Ser Leu Lys Ser Ile Pro Lys Arg Thr
1               5                   10                  15

Cys Arg Ile Ile Phe Arg Thr Ala Thr Ile Leu Gly Ile Cys Thr Leu
            20                  25                  30

Ile Val Leu Cys Ser Ser Ile Leu His Glu Ile Ile His Leu Asp Val
        35                  40                  45

Ser Ser Gly Leu Met Asn Ser Asp Glu Ser Gln Gln Gly Ile Ile Gln
    50                  55                  60

Pro Ile Ile Glu Ser Leu Lys Ser Leu Ile Ala Leu Ala Asn Gln Ile
65                  70                  75                  80

Leu Tyr Asn Val Ala Ile Val Ile Pro Leu Lys Ile Asp Ser Ile Glu
                85                  90                  95

Thr Val Ile Leu Ser Ala Leu Lys Asp Met His Thr Gly Ser Met Ser
            100                 105                 110

Asn Ala Asn Cys Thr Pro Gly Asn Leu Leu Leu His Asp Ala Ala Tyr
        115                 120                 125

Ile Asn Gly Ile Asn Lys Phe Leu Val Leu Glu Ser Tyr Asn Gly Thr
    130                 135                 140

Pro Lys Tyr Gly Pro Leu Leu Asn Ile Pro Ser Phe Ile Pro Ser Ala
145                 150                 155                 160

Thr Ser Pro His Gly Cys Thr Arg Ile Pro Ser Phe Ser Leu Ile Lys
                165                 170                 175

Thr His Trp Cys Tyr Thr His Asn Val Met Leu Gly Asp Cys Leu Asp
            180                 185                 190

Phe Thr Ala Ser Asn Gln Tyr Leu Ser Met Gly Ile Ile Gln Gln Ser
        195                 200                 205
```

-continued

```
Ala Ala Gly Phe Pro Ile Phe Arg Thr Met Lys Thr Ile Tyr Leu Ser
    210                 215                 220

Asp Gly Ile Asn Arg Lys Ser Cys Ser Val Thr Ala Ile Pro Gly Gly
225                 230                 235                 240

Cys Val Leu Tyr Cys Tyr Val Ala Thr Arg Ser Glu Lys Glu Asp Tyr
                245                 250                 255

Ala Thr Thr Asp Leu Ala Glu Leu Arg Leu Ala Phe Tyr Tyr Tyr Asn
            260                 265                 270

Asp Thr Phe Ile Glu Arg Val Ile Ser Leu Pro Asn Thr Thr Gly Gln
        275                 280                 285

Trp Ala Thr Ile Asn Pro Ala Val Gly Ser Gly Ile Tyr His Leu Gly
    290                 295                 300

Phe Ile Leu Phe Pro Val Tyr Gly Gly Leu Ile Asn Gly Thr Thr Ser
305                 310                 315                 320

Tyr Asn Glu Gln Ser Ser Arg Tyr Phe Ile Pro Lys His Pro Asn Ile
                325                 330                 335

Thr Cys Ala Gly Asn Ser Ser Lys Gln Ala Ala Ile Ala Arg Ser Ser
            340                 345                 350

Tyr Val Ile Arg Tyr His Ser Asn Arg Leu Ile Gln Ser Ala Val Leu
        355                 360                 365

Ile Cys Pro Leu Ser Asp Met His Thr Glu Glu Cys Asn Leu Val Met
    370                 375                 380

Phe Asn Asn Ser Gln Val Met Met Gly Ala Glu Gly Arg Leu Tyr Val
385                 390                 395                 400

Ile Gly Asn Asn Leu Tyr Tyr Tyr Gln Arg Ser Ser Ser Trp Trp Ser
                405                 410                 415

Ala Ser Leu Phe Tyr Arg Ile Asn Thr Asp Phe Ser Lys Gly Ile Pro
            420                 425                 430

Pro Ile Ile Glu Ala Gln Trp Val Pro Ser Tyr Gln Val Pro Arg Pro
        435                 440                 445

Gly Val Met Pro Cys Asn Ala Thr Ser Phe Cys Pro Ala Asn Cys Ile
    450                 455                 460

Thr Gly Val Tyr Ala Asp Val Trp Pro Leu Asn Asp Pro Glu Leu Met
465                 470                 475                 480

Ser Arg Asn Ala Leu Asn Pro Asn Tyr Arg Phe Ala Gly Ala Phe Leu
                485                 490                 495

Lys Asn Glu Ser Asn Arg Thr Asn Pro Thr Phe Tyr Thr Ala Ser Ala
            500                 505                 510

Asn Ser Leu Leu Asn Thr Thr Gly Phe Asn Asn Thr Asn His Lys Ala
        515                 520                 525

Ala Tyr Thr Ser Ser Thr Cys Phe Lys Asn Thr Gly Thr Gln Lys Ile
    530                 535                 540

Tyr Cys Leu Ile Ile Ile Glu Met Gly Ser Ser Leu Leu Gly Glu Phe
545                 550                 555                 560

Gln Ile Ile Pro Phe Leu Arg Glu Leu Met Leu
                565                 570
```

<210> SEQ ID NO 38
<211> LENGTH: 2263
<212> TYPE: PRT
<213> ORGANISM: Human parainfluenza virus 2

<400> SEQUENCE: 38

Met Ala Ala Ser Ser Glu Ile Leu Leu Pro Glu Val His Leu Asn Ser
1               5                   10                  15

Pro Ile Val Lys His Lys Leu Ile Tyr Tyr Leu Leu Leu Gly His Phe
            20                  25                  30

Pro His Asp Leu Asp Ile Ser Glu Ile Ser Pro Leu His Asn Asn Asp
        35                  40                  45

Trp Asp Gln Ile Ala Arg Glu Glu Ser Asn Leu Ala Glu Arg Leu Gly
    50                  55                  60

Val Ala Lys Ser Glu Leu Ile Lys Arg Val Pro Ala Phe Arg Ala Thr
65                  70                  75                  80

Arg Trp Arg Ser His Ala Ala Val Leu Ile Trp Pro Ser Cys Ile Pro
                85                  90                  95

Phe Leu Val Lys Phe Leu Pro His Ser Lys Leu Gln Pro Ile Glu Gln
            100                 105                 110

Trp Tyr Lys Leu Ile Asn Ala Ser Cys Asn Thr Ile Ser Asp Ser Ile
        115                 120                 125

Asp Arg Cys Met Glu Asn Ile Ser Ile Lys Leu Thr Gly Lys Asn Asn
    130                 135                 140

Leu Phe Ser Arg Ser Arg Gly Thr Ala Gly Ala Gly Lys Asn Ser Lys
145                 150                 155                 160

Ile Thr Leu Asn Asp Ile Gln Ser Ile Trp Glu Ser Asn Lys Trp Gln
                165                 170                 175

Pro Asn Val Ser Leu Trp Leu Thr Ile Lys Tyr Gln Met Arg Gln Leu
            180                 185                 190

Ile Met His Gln Ser Ser Arg Gln Pro Thr Asp Leu Val His Ile Val
        195                 200                 205

Asp Thr Arg Ser Gly Leu Ile Val Ile Thr Pro Glu Leu Val Ile Cys
    210                 215                 220

Phe Asp Arg Leu Asn Asn Val Leu Met Tyr Phe Thr Phe Glu Met Thr
225                 230                 235                 240

Leu Met Val Ser Asp Met Phe Glu Gly Arg Met Asn Val Ala Ala Leu
                245                 250                 255

Cys Thr Ile Ser His Tyr Leu Ser Pro Leu Gly Pro Arg Ile Asp Arg
            260                 265                 270

Leu Phe Ser Ile Val Asp Glu Leu Ala Gln Leu Leu Gly Asp Thr Val
        275                 280                 285

Tyr Lys Ile Ile Ala Ser Leu Glu Ser Leu Val Tyr Gly Cys Leu Gln
    290                 295                 300

Leu Lys Asp Pro Val Val Glu Leu Thr Gly Ser Phe His Ser Phe Ile
305                 310                 315                 320

Thr Gln Glu Ile Ile Asp Ile Leu Ile Gly Ser Lys Ala Leu Asp Lys
                325                 330                 335

Asp Glu Ser Ile Thr Val Thr Thr Gln Leu Leu Asp Ile Phe Ser Asn
            340                 345                 350

Leu Ser Pro Asp Leu Ile Ala Glu Met Leu Cys Leu Met Arg Leu Trp
        355                 360                 365

Gly His Pro Thr Leu Thr Ala Ala Gln Ala Ala Gly Lys Val Arg Glu
    370                 375                 380

Ser Met Cys Ala Gly Lys Leu Leu Asp Phe Pro Thr Ile Met Lys Thr
385                 390                 395                 400

-continued

```
Leu Ala Phe Phe His Thr Ile Leu Ile Asn Gly Tyr Arg Arg Lys Lys
                405                 410                 415

Asn Gly Met Trp Pro Pro Leu Ile Leu Pro Lys Asn Ala Ser Lys Ser
            420                 425                 430

Leu Ile Glu Phe Gln His Asp Asn Ala Glu Ile Ser Tyr Glu Tyr Thr
        435                 440                 445

Leu Lys His Trp Lys Glu Ile Ser Leu Ile Glu Phe Arg Lys Cys Phe
    450                 455                 460

Asp Phe Asp Pro Gly Glu Glu Leu Ser Ile Phe Met Lys Asp Lys Ala
465                 470                 475                 480

Ile Ser Ala Pro Lys Ser Asp Trp Met Ser Val Phe Arg Arg Ser Leu
                485                 490                 495

Ile Lys Gln Arg His Gln Arg His His Ile Pro Met Pro Asn Pro Phe
            500                 505                 510

Asn Arg Arg Leu Leu Leu Asn Phe Leu Glu Asp Asp Ser Phe Asp Pro
        515                 520                 525

Val Ala Glu Leu Gln Tyr Val Thr Ser Gly Glu Tyr Leu Arg Asp Asp
    530                 535                 540

Thr Phe Cys Ala Ser Tyr Ser Leu Lys Glu Lys Glu Ile Lys Pro Asp
545                 550                 555                 560

Gly Arg Ile Phe Ala Lys Leu Thr Asn Arg Met Arg Ser Cys Gln Val
                565                 570                 575

Ile Ala Glu Ala Ile Leu Ala Asn His Ala Gly Thr Leu Met Lys Glu
            580                 585                 590

Asn Gly Val Val Leu Asn Gln Leu Ser Leu Thr Lys Ser Leu Leu Thr
        595                 600                 605

Met Ser Gln Ile Gly Ile Ile Ser Glu Lys Ala Lys Arg Tyr Thr Arg
    610                 615                 620

Asp Asn Ile Ser Ser Gln Gly Phe His Thr Ile Lys Thr Asp Ser Lys
625                 630                 635                 640

Asn Lys Lys Lys Ser Lys Ile Ala Ser Ser Tyr Leu Thr Asp Pro Asp
                645                 650                 655

Asp Thr Phe Glu Leu Ser Ala Cys Phe Ile Thr Thr Asp Leu Ala Lys
            660                 665                 670

Tyr Cys Leu Gln Trp Arg Tyr Gln Thr Ile Ile His Phe Ala Arg Thr
        675                 680                 685

Leu Asn Arg Met Tyr Gly Val Pro His Leu Phe Glu Trp Ile His Leu
    690                 695                 700

Arg Leu Ile Arg Ser Thr Leu Tyr Val Gly Asp Pro Phe Asn Pro Pro
705                 710                 715                 720

Ala Thr Thr Asp Ala Phe Asp Leu Asp Lys Val Leu Asn Gly Asp Ile
                725                 730                 735

Phe Ile Val Ser Pro Lys Gly Gly Ile Glu Gly Leu Cys Gln Lys Met
            740                 745                 750

Trp Thr Met Ile Ser Ile Ser Val Ile Ile Leu Ser Ser Ala Glu Ser
        755                 760                 765

Lys Thr Arg Val Met Ser Met Val Gln Gly Asp Asn Gln Ala Ile Ala
    770                 775                 780

Val Thr Thr Arg Val Pro Arg Ser Leu Pro Ser Val Gln Lys Lys Glu
785                 790                 795                 800

Leu Ala Tyr Ala Ala Ser Lys Leu Phe Phe Glu Arg Leu Arg Ala Asn
                805                 810                 815
```

```
Asn Tyr Gly Leu Gly His Gln Leu Lys Ala Gln Glu Thr Ile Ile Ser
            820                 825                 830

Ser Thr Phe Phe Ile Tyr Ser Lys Arg Val Phe Tyr Gln Gly Arg Ile
        835                 840                 845

Leu Thr Gln Ala Leu Lys Asn Ala Ser Lys Leu Cys Leu Thr Ala Asp
    850                 855                 860

Val Leu Gly Glu Cys Thr Gln Ala Ser Cys Ser Asn Ser Ala Thr Thr
865                 870                 875                 880

Ile Met Arg Leu Thr Glu Asn Gly Val Glu Lys Asp Thr Cys Tyr Lys
                885                 890                 895

Leu Asn Ile Tyr Gln Ser Ile Arg Gln Leu Thr Tyr Asp Leu Ile Phe
            900                 905                 910

Pro Gln Tyr Ser Ile Pro Gly Glu Thr Ile Ser Glu Ile Phe Leu Gln
        915                 920                 925

His Pro Arg Leu Ile Ser Arg Ile Val Leu Leu Pro Ser Gln Leu Gly
    930                 935                 940

Gly Leu Asn Tyr Leu Ala Cys Ser Arg Leu Phe Asn Arg Asn Ile Gly
945                 950                 955                 960

Asp Pro Leu Gly Thr Ala Val Ala Asp Leu Lys Arg Leu Ile Lys Cys
                965                 970                 975

Gly Ala Leu Glu Ser Trp Ile Leu Tyr Asn Leu Leu Ala Arg Lys Pro
            980                 985                 990

Gly Lys Gly Ser Trp Ala Thr Leu  Ala Ala Asp Pro Tyr  Ser Leu Asn
        995                 1000                 1005

Gln Glu  Tyr Leu Tyr Pro Pro  Thr Thr Ile Leu Lys  Arg His Thr
    1010                 1015                 1020

Gln Asn  Thr Leu Met Glu Ile  Cys Arg Asn Pro Met  Leu Lys Gly
    1025                 1030                 1035

Val Phe  Thr Asp Asn Ala Lys  Glu Glu Glu Asn Leu  Leu Ala Lys
    1040                 1045                 1050

Phe Leu  Leu Asp Arg Asp Ile  Val Leu Pro Arg Val  Ala His Ile
    1055                 1060                 1065

Ile Ile  Asp Gln Ser Ser Ile  Gly Arg Lys Lys Gln  Ile Gln Gly
    1070                 1075                 1080

Phe Phe  Asp Thr Thr Arg Thr  Ile Met Arg Arg Ser  Phe Glu Ile
    1085                 1090                 1095

Lys Pro  Leu Ser Thr Lys Lys  Thr Leu Ser Val Ile  Glu Tyr Asn
    1100                 1105                 1110

Thr Asn  Tyr Leu Ser Tyr Asn  Tyr Pro Val Ile Leu  Asn Pro Leu
    1115                 1120                 1125

Pro Ile  Pro Gly Tyr Leu Asn  Tyr Ile Thr Asp Gln  Thr Cys Ser
    1130                 1135                 1140

Ile Asp  Ile Ser Arg Ser Leu  Arg Lys Leu Ser Trp  Ser Ser Leu
    1145                 1150                 1155

Leu Asn  Gly Arg Thr Leu Glu  Gly Leu Glu Thr Pro  Asp Pro Ile
    1160                 1165                 1170

Glu Val  Val Asn Gly Ser Leu  Ile Val Gly Thr Gly  Asp Cys Asp
    1175                 1180                 1185

Phe Cys  Met Gln Gly Asp Asp  Lys Phe Thr Trp Phe  Phe Leu Pro
    1190                 1195                 1200

Met Gly  Ile Ile Ile Asp Gly  Asn Pro Glu Thr Asn  Pro Pro Ile
    1205                 1210                 1215
```

-continued

```
Arg Val  Pro Tyr Ile Gly Ser  Arg Thr Glu Glu Arg  Arg Val Ala
    1220                1225                1230

Ser Met  Ala Tyr Ile Lys Gly  Ala Thr His Ser Leu  Lys Ala Ala
    1235                1240                1245

Leu Arg  Gly Ala Gly Val Tyr  Ile Trp Ala Phe Gly  Asp Thr Val
    1250                1255                1260

Val Asn  Trp Asn Asp Ala Leu  Asp Ile Ala Asn Thr  Arg Val Lys
    1265                1270                1275

Ile Ser  Leu Glu Gln Leu Gln  Thr Leu Thr Pro Leu  Pro Thr Ser
    1280                1285                1290

Ala Asn  Ile Thr His Arg Leu  Asp Asp Gly Ala Thr  Thr Leu Lys
    1295                1300                1305

Phe Thr  Pro Ala Ser Ser Tyr  Ala Phe Ser Ser Tyr  Thr His Ile
    1310                1315                1320

Ser Asn  Asp Gln Gln Tyr Leu  Glu Ile Asp Gln Arg  Val Val Asp
    1325                1330                1335

Ser Asn  Ile Ile Tyr Gln Gln  Leu Met Ile Thr Gly  Leu Gly Ile
    1340                1345                1350

Ile Glu  Thr Tyr His Asn Pro  Pro Ile Arg Thr Ser  Thr Gln Glu
    1355                1360                1365

Ile Thr  Leu His Leu His Thr  Ser Ser Ser Cys Cys  Val Arg Ser
    1370                1375                1380

Val Asp  Gly Cys Leu Ile Cys  Glu Ser Asn Gly Glu  Val Pro Gln
    1385                1390                1395

Ile Thr  Val Pro Tyr Thr Asn  Ser Phe Val Tyr Asp  Pro Asp Pro
    1400                1405                1410

Leu Ala  Asp Tyr Glu Ile Ala  His Leu Asp Tyr Leu  Ser Tyr Gln
    1415                1420                1425

Ala Lys  Ile Gly Ser Thr Asp  Tyr Tyr Ser Leu Thr  Asp Lys Ile
    1430                1435                1440

Asp Leu  Leu Ala His Leu Thr  Ala Lys Gln Met Ile  Asn Ser Ile
    1445                1450                1455

Ile Gly  Leu Asp Glu Thr Val  Ser Ile Val Asn Asp  Ala Val Ile
    1460                1465                1470

Leu Ser  Asp Tyr Thr Asn Asn  Trp Ile Ser Glu Cys  Ser Tyr Thr
    1475                1480                1485

Lys Ile  Asp Leu Val Phe Lys  Leu Met Ala Trp Asn  Phe Leu Leu
    1490                1495                1500

Glu Leu  Ala Phe Gln Met Tyr  Tyr Leu Arg Ile Ser  Ser Trp Thr
    1505                1510                1515

Asn Ile  Phe Asp Tyr Thr Tyr  Met Thr Leu Arg Arg  Ile Pro Gly
    1520                1525                1530

Thr Ala  Leu Asn Asn Ile Ala  Ala Thr Ile Ser His  Pro Lys Leu
    1535                1540                1545

Leu Arg  Arg Ala Met Asn Leu  Asp Ile Ile Thr Pro  Ile His Ala
    1550                1555                1560

Pro Tyr  Leu Ala Ser Leu Asp  Tyr Val Lys Leu Ser  Ile Asp Ala
    1565                1570                1575

Ile Gln  Trp Gly Val Lys Gln  Val Leu Ala Asp Leu  Ser Asn Gly
    1580                1585                1590

Ile Asp  Leu Glu Ile Leu Ile  Leu Ser Glu Asp Ser  Met Glu Ile
    1595                1600                1605
```

-continued

```
Ser Asp  Arg Ala Met Asn Leu  Ile Ala Arg Lys Leu  Thr Leu Leu
    1610                 1615                 1620

Ala Leu  Val Lys Gly Glu Asn  Tyr Thr Phe Pro Lys  Ile Lys Gly
    1625                 1630                 1635

Met Pro  Pro Glu Glu Lys Cys  Leu Val Leu Thr Glu  Tyr Leu Ala
    1640                 1645                 1650

Met Cys  Tyr Gln Asn Thr His  His Leu Asp Pro Asp  Leu Gln Lys
    1655                 1660                 1665

Tyr Leu  Tyr Asn Leu Thr Asn  Pro Lys Leu Thr Ala  Phe Pro Ser
    1670                 1675                 1680

Asn Asn  Phe Tyr Leu Thr Arg  Lys Ile Leu Asn Gln  Ile Arg Glu
    1685                 1690                 1695

Ser Asp  Glu Gly Gln Tyr Ile  Ile Thr Ser Tyr Tyr  Glu Ser Phe
    1700                 1705                 1710

Glu Gln  Leu Glu Thr Asp Ile  Ile Leu His Ser Thr  Leu Thr Ala
    1715                 1720                 1725

Pro Tyr  Asp Asn Ser Glu Thr  Leu Thr Lys Phe Asp  Leu Ser Leu
    1730                 1735                 1740

Asp Ile  Phe Pro His Pro Glu  Ser Leu Glu Lys Tyr  Pro Leu Pro
    1745                 1750                 1755

Val Asp  His Asp Ser Gln Ser  Ala Ile Ser Thr Leu  Ile Pro Gly
    1760                 1765                 1770

Pro Pro  Ser His His Val Leu  Arg Pro Leu Gly Val  Ser Ser Thr
    1775                 1780                 1785

Ala Trp  Tyr Lys Gly Ile Ser  Tyr Cys Arg Tyr Leu  Glu Thr Gln
    1790                 1795                 1800

Lys Ile  Gln Thr Gly Asp His  Leu Tyr Leu Ala Glu  Gly Ser Gly
    1805                 1810                 1815

Ala Ser  Met Ser Leu Leu Glu  Leu Leu Phe Pro Gly  Asp Thr Val
    1820                 1825                 1830

Tyr Tyr  Asn Ser Leu Phe Ser  Ser Gly Glu Asn Pro  Pro Gln Arg
    1835                 1840                 1845

Asn Tyr  Ala Pro Leu Pro Thr  Gln Phe Val Gln Ser  Val Pro Tyr
    1850                 1855                 1860

Lys Leu  Trp Gln Ala Asp Leu  Ala Asp Asp Ser Asn  Leu Ile Lys
    1865                 1870                 1875

Asp Phe  Val Pro Leu Trp Asn  Gly Asn Gly Ala Val  Thr Asp Leu
    1880                 1885                 1890

Ser Thr  Lys Asp Ala Val Ala  Phe Ile Ile His Lys  Val Gly Ala
    1895                 1900                 1905

Glu Lys  Ala Ser Leu Val His  Ile Asp Leu Glu Ser  Thr Ala Asn
    1910                 1915                 1920

Ile Asn  Gln Gln Thr Leu Ser  Arg Ser Gln Ile His  Ser Leu Ile
    1925                 1930                 1935

Ile Ala  Thr Thr Val Leu Lys  Arg Gly Gly Ile Leu  Val Tyr Lys
    1940                 1945                 1950

Thr Ser  Trp Leu Pro Phe Ser  Arg Phe Ser Gln Leu  Ala Ser Leu
    1955                 1960                 1965

Leu Trp  Cys Phe Phe Asp Arg  Ile His Leu Ile Arg  Ser Ser Tyr
    1970                 1975                 1980

Ser Asp  Pro His Ser His Glu  Val Tyr Leu Val Cys  Arg Leu Ala
    1985                 1990                 1995
```

```
Ala Asp  Phe Arg Thr Ile Gly  Phe Ser Ala Ala Leu  Val Thr Ala
    2000                 2005                 2010

Thr Thr  Leu His Asn Asp Gly  Phe Thr Thr Ile His  Pro Asp Val
    2015                 2020                 2025

Val Cys  Ser Tyr Trp Gln His  His Leu Glu Asn Val  Gly Arg Val
    2030                 2035                 2040

Glu Lys  Val Ile Asp Glu Ile  Leu Asp Gly Leu Ala  Thr Asn Phe
    2045                 2050                 2055

Phe Ala  Gly Asp Asn Gly Leu  Ile Leu Arg Cys Gly  Gly Thr Pro
    2060                 2065                 2070

Ser Ser  Arg Lys Trp Leu Glu  Ile Asp Gln Leu Ala  Ser Phe Asp
    2075                 2080                 2085

Ser Val  Gln Asp Ala Leu Val  Thr Leu Ile Thr Ile  His Leu Lys
    2090                 2095                 2100

Glu Ile  Ile Glu Val Gln Ser  Ser His Thr Glu Asp  Tyr Thr Ser
    2105                 2110                 2115

Leu Leu  Phe Thr Pro Tyr Asn  Ile Gly Ala Ala Gly  Lys Val Arg
    2120                 2125                 2130

Thr Ile  Ile Lys Leu Ile Leu  Glu Arg Ser Leu Met  Tyr Thr Val
    2135                 2140                 2145

Arg Asn  Trp Leu Val Leu Pro  Ser Ser Ile Arg Asp  Ser Val Arg
    2150                 2155                 2160

Gln Asp  Leu Glu Leu Gly Ser  Phe Arg Leu Met Ser  Ile Leu Ser
    2165                 2170                 2175

Glu Gln  Thr Phe Leu Lys Lys  Thr Pro Thr Lys Lys  Tyr Leu Leu
    2180                 2185                 2190

Asp Gln  Leu Thr Arg Thr Tyr  Ile Ser Thr Phe Phe  Asn Ser His
    2195                 2200                 2205

Ser Val  Leu Pro Leu His Arg  Pro Tyr Gln Lys Gln  Ile Trp Lys
    2210                 2215                 2220

Ala Leu  Gly Ser Val Ile Tyr  Cys Ser Glu Thr Val  Asp Ile Pro
    2225                 2230                 2235

Leu Ile  Arg Asp Ile Gln Ile  Glu Asp Ile Asn Asp  Phe Glu Asp
    2240                 2245                 2250

Ile Glu  Arg Gly Ile Asp Gly  Glu Glu Leu
    2255                 2260
```

```
<210> SEQ ID NO 39
<211> LENGTH: 66
<212> TYPE: PRT
<213> ORGANISM: Human parainfluenza virus 2

<400> SEQUENCE: 39

Thr Leu Tyr Ser Leu Ser Ala Ile Ala Leu Ile Leu Ser Val Ile Thr
1               5                   10                  15

Leu Val Val Val Gly Leu Leu Ile Ala Tyr Ile Ile Lys Leu Val Ser
            20                  25                  30

Gln Ile His Gln Phe Arg Ala Leu Ala Ala Thr Thr Met Phe His Arg
        35                  40                  45

Glu Asn Pro Ala Val Phe Ser Lys Asn Asn His Gly Asn Ile Tyr Gly
    50                  55                  60

Ile Ser
65
```

-continued

<210> SEQ ID NO 40
<211> LENGTH: 515
<212> TYPE: PRT
<213> ORGANISM: Human parainfluenza virus 3

<400> SEQUENCE: 40

```
Met Leu Ser Leu Phe Asp Thr Phe Asn Ala Arg Arg Gln Glu Asn Ile
1               5                   10                  15

Thr Lys Ser Ala Gly Gly Ala Ile Ile Pro Gly Gln Lys Asn Thr Val
            20                  25                  30

Ser Ile Phe Ala Leu Gly Pro Thr Ile Thr Asp Asp Asn Glu Lys Met
        35                  40                  45

Thr Leu Ala Leu Leu Phe Leu Ser His Ser Leu Asp Asn Glu Lys Gln
    50                  55                  60

His Ala Gln Arg Ala Gly Phe Leu Val Ser Leu Leu Ser Met Ala Tyr
65                  70                  75                  80

Ala Asn Pro Glu Leu Tyr Leu Thr Thr Asn Gly Ser Asn Ala Asp Val
                85                  90                  95

Lys Tyr Val Ile Tyr Met Ile Glu Lys Asp Leu Lys Arg Gln Lys Tyr
            100                 105                 110

Gly Gly Phe Val Val Lys Thr Arg Glu Met Ile Tyr Glu Lys Thr Thr
        115                 120                 125

Asp Trp Ile Phe Gly Ser Asp Leu Asp Tyr Asp Gln Glu Thr Met Leu
    130                 135                 140

Gln Asn Gly Arg Asn Asn Ser Thr Ile Glu Asp Leu Val His Thr Phe
145                 150                 155                 160

Gly Tyr Pro Ser Cys Leu Gly Ala Leu Ile Ile Gln Ile Trp Ile Val
                165                 170                 175

Leu Val Lys Ala Ile Thr Ser Ile Ser Gly Leu Arg Lys Gly Phe Phe
            180                 185                 190

Thr Arg Leu Glu Ala Phe Arg Gln Asp Gly Thr Val Gln Ala Gly Leu
        195                 200                 205

Val Leu Ser Gly Asp Thr Val Asp Gln Ile Gly Ser Ile Met Arg Ser
    210                 215                 220

Gln Gln Ser Leu Val Thr Leu Met Val Glu Thr Leu Ile Thr Met Asn
225                 230                 235                 240

Thr Ser Arg Asn Asp Leu Thr Thr Ile Glu Lys Asn Ile Gln Ile Val
                245                 250                 255

Gly Asn Tyr Ile Arg Asp Ala Gly Leu Ala Ser Phe Phe Asn Thr Ile
            260                 265                 270

Arg Tyr Gly Ile Glu Thr Arg Met Ala Ala Leu Thr Leu Ser Thr Leu
        275                 280                 285

Arg Pro Asp Ile Asn Arg Leu Lys Ala Leu Met Glu Leu Tyr Leu Ser
    290                 295                 300

Lys Gly Pro Arg Ala Pro Phe Ile Cys Ile Leu Arg Asp Pro Ile His
305                 310                 315                 320

Gly Glu Phe Ala Pro Gly Asn Tyr Pro Ala Ile Trp Ser Tyr Ala Met
                325                 330                 335

Gly Val Ala Val Val Gln Asn Arg Ala Met Gln Gln Tyr Val Thr Gly
            340                 345                 350

Arg Ser Tyr Leu Asp Ile Asp Met Phe Gln Leu Gly Gln Ala Val Ala
        355                 360                 365

Arg Asp Ala Glu Ala Gln Met Ser Ser Thr Leu Glu Asp Glu Leu Gly
    370                 375                 380
```

```
Val Thr His Glu Ser Lys Glu Ser Leu Lys Arg His Ile Arg Asn Ile
385                 390                 395                 400

Asn Ser Ser Glu Thr Ser Phe His Lys Pro Thr Gly Gly Ser Ala Ile
                405                 410                 415

Glu Met Ala Ile Asp Glu Glu Pro Glu Gln Phe Glu His Arg Ala Asp
            420                 425                 430

Gln Glu Gln Asn Gly Glu Pro Gln Ser Ser Ile Ile Gln Tyr Ala Trp
        435                 440                 445

Ala Glu Gly Asn Arg Ser Asp Asp Gln Thr Glu Gln Ala Thr Glu Ser
    450                 455                 460

Asp Asn Ile Lys Thr Glu Gln Gln Asn Ile Arg Asp Arg Leu Asn Lys
465                 470                 475                 480

Arg Leu Asn Asp Lys Lys Lys Gln Ser Ser Gln Pro Pro Thr Asn Pro
                485                 490                 495

Thr Asn Arg Thr Asn Gln Asp Glu Ile Asp Asp Leu Phe Asn Ala Phe
            500                 505                 510

Gly Ser Asn
        515


<210> SEQ ID NO 41
<211> LENGTH: 603
<212> TYPE: PRT
<213> ORGANISM: Human parainfluenza virus 3

<400> SEQUENCE: 41

Met Glu Ser Asp Ala Lys Asn Tyr Gln Ile Met Asp Ser Trp Glu Glu
1               5                   10                  15

Glu Ser Arg Asp Lys Ser Thr Asn Ile Ser Ser Ala Leu Asn Ile Ile
            20                  25                  30

Glu Phe Ile Leu Ser Thr Asp Pro Gln Glu Asp Leu Ser Glu Asn Asp
        35                  40                  45

Thr Ile Asn Thr Arg Thr Gln Gln Leu Ser Ala Thr Ile Cys Gln Pro
    50                  55                  60

Glu Ile Lys Pro Thr Glu Thr Ser Glu Lys Asp Ser Gly Ser Thr Asp
65                  70                  75                  80

Lys Asn Arg Gln Ser Gly Ser Ser His Glu Cys Thr Thr Glu Ala Lys
                85                  90                  95

Asp Arg Asn Ile Asp Gln Glu Thr Val Gln Arg Gly Pro Gly Arg Arg
            100                 105                 110

Ser Ser Ser Asp Ser Arg Ala Glu Thr Val Val Ser Gly Gly Ile Pro
        115                 120                 125

Arg Ser Ile Thr Asp Ser Lys Asn Gly Thr Gln Asn Thr Glu Asp Ile
    130                 135                 140

Asp Leu Asn Glu Ile Arg Lys Met Asp Lys Asp Ser Ile Glu Gly Lys
145                 150                 155                 160

Met Arg Gln Ser Ala Asn Val Pro Ser Glu Ile Ser Gly Ser Asp Asp
                165                 170                 175

Ile Phe Thr Thr Glu Gln Ser Arg Asn Ser Asp His Gly Arg Ser Leu
            180                 185                 190

Glu Ser Ile Ser Thr Pro Asp Thr Arg Ser Ile Ser Val Val Thr Ala
        195                 200                 205

Ala Thr Pro Asp Asp Glu Glu Ile Leu Met Lys Asn Ser Arg Thr
    210                 215                 220

Lys Lys Ser Ser Ser Thr His Gln Glu Asp Asp Lys Arg Ile Lys Lys
225                 230                 235                 240
```

```
Gly Gly Lys Gly Lys Asp Trp Phe Lys Lys Ser Lys Asp Thr Asp Asn
                245                 250                 255

Gln Ile Pro Thr Ser Asp Tyr Arg Ser Thr Ser Lys Gly Gln Lys Lys
            260                 265                 270

Ile Ser Lys Thr Thr Thr Thr Asn Thr Asp Thr Lys Gly Gln Thr Glu
        275                 280                 285

Ile Gln Thr Glu Ser Ser Glu Thr Gln Ser Ser Ser Trp Asn Leu Ile
    290                 295                 300

Ile Asp Asn Asn Thr Asp Arg Asn Glu Gln Thr Ser Thr Thr Pro Pro
305                 310                 315                 320

Thr Thr Thr Ser Arg Ser Thr Tyr Thr Lys Glu Ser Ile Arg Thr Asn
                325                 330                 335

Ser Glu Ser Lys Pro Lys Thr Gln Lys Thr Asn Gly Lys Glu Arg Lys
            340                 345                 350

Asp Thr Glu Glu Ser Asn Arg Phe Thr Glu Arg Ala Ile Thr Leu Leu
        355                 360                 365

Gln Asn Leu Gly Val Ile Gln Ser Thr Ser Lys Leu Asp Leu Tyr Gln
    370                 375                 380

Asp Lys Arg Val Val Cys Val Ala Asn Val Leu Asn Asn Val Asp Thr
385                 390                 395                 400

Ala Ser Lys Ile Asp Phe Leu Ala Gly Leu Val Ile Gly Val Ser Met
                405                 410                 415

Asp Asn Asp Thr Lys Leu Thr Gln Ile Gln Asn Glu Met Leu Asn Leu
            420                 425                 430

Lys Ala Asp Leu Lys Lys Met Asp Glu Ser His Arg Arg Leu Ile Glu
        435                 440                 445

Asn Gln Arg Glu Gln Leu Ser Leu Ile Thr Ser Leu Ile Ser Asn Leu
    450                 455                 460

Lys Ile Met Thr Glu Arg Gly Gly Lys Lys Asp Gln Asn Glu Ser Asn
465                 470                 475                 480

Glu Arg Val Ser Met Ile Lys Thr Lys Leu Lys Glu Glu Lys Ile Lys
                485                 490                 495

Lys Thr Arg Phe Asp Pro Leu Met Glu Ala Gln Gly Ile Asp Lys Asn
            500                 505                 510

Ile Pro Asp Leu Tyr Arg His Ala Gly Asp Thr Leu Glu Asn Asp Val
        515                 520                 525

Gln Val Lys Ser Glu Ile Leu Ser Ser Tyr Asn Glu Ser Asn Ala Thr
    530                 535                 540

Arg Leu Ile Pro Lys Lys Val Ser Ser Thr Met Arg Ser Leu Val Ala
545                 550                 555                 560

Val Ile Asn Asn Ser Asn Leu Ser Gln Ser Thr Lys Gln Ser Tyr Ile
                565                 570                 575

Asn Glu Leu Lys Arg Cys Lys Asn Asp Glu Glu Val Ser Glu Leu Met
            580                 585                 590

Asp Met Phe Asn Glu Asp Val Asn Asn Cys Gln
        595                 600
```

<210> SEQ ID NO 42
<211> LENGTH: 353
<212> TYPE: PRT
<213> ORGANISM: Human parainfluenza virus 3

<400> SEQUENCE: 42

Met Ser Ile Thr Asn Ser Ala Ile Tyr Thr Phe Pro Glu Ser Ser Phe
1               5                   10                  15

Ser Glu Asn Gly His Ile Glu Pro Leu Pro Leu Lys Val Asn Glu Gln
            20                  25                  30

Arg Lys Ala Val Pro His Ile Arg Val Ala Lys Ile Gly Asn Pro Pro
        35                  40                  45

Lys His Gly Ser Arg Tyr Leu Asp Val Phe Leu Leu Gly Phe Phe Glu
    50                  55                  60

Met Glu Arg Ile Lys Asp Lys Tyr Gly Ser Val Asn Asp Leu Asp Ser
65                  70                  75                  80

Asp Pro Ser Tyr Lys Val Cys Gly Ser Gly Ser Leu Pro Ile Gly Leu
                85                  90                  95

Ala Lys Tyr Thr Gly Asn Asp Gln Glu Leu Leu Gln Ala Ala Thr Lys
            100                 105                 110

Leu Asp Ile Glu Val Arg Arg Thr Val Lys Ala Lys Glu Met Val Val
        115                 120                 125

Tyr Thr Val Gln Asn Ile Lys Pro Glu Leu Tyr Pro Trp Ser Asn Arg
    130                 135                 140

Leu Arg Lys Gly Met Leu Phe Asp Ala Asn Lys Val Ala Leu Ala Pro
145                 150                 155                 160

Gln Cys Leu Pro Leu Asp Arg Ser Ile Lys Phe Arg Val Ile Phe Val
                165                 170                 175

Asn Cys Thr Ala Ile Gly Ser Ile Thr Leu Phe Lys Ile Pro Lys Ser
            180                 185                 190

Met Ala Ser Leu Ser Leu Pro Asn Thr Ile Ser Ile Asn Leu Gln Val
        195                 200                 205

His Ile Lys Thr Gly Val Gln Thr Asp Ser Lys Gly Ile Val Gln Ile
    210                 215                 220

Leu Asp Glu Lys Gly Glu Lys Ser Leu Asn Phe Met Val His Leu Gly
225                 230                 235                 240

Leu Ile Lys Arg Lys Val Gly Arg Met Tyr Ser Val Glu Tyr Cys Lys
                245                 250                 255

Gln Lys Ile Glu Lys Met Arg Leu Ile Phe Ser Leu Gly Leu Val Gly
            260                 265                 270

Gly Ile Ser Leu His Val Asn Ala Thr Gly Ser Ile Ser Lys Thr Leu
        275                 280                 285

Ala Ser Gln Leu Val Phe Lys Arg Glu Ile Cys Tyr Pro Leu Met Asp
    290                 295                 300

Leu Asn Pro His Leu Asn Leu Val Ile Trp Ala Ser Ser Val Glu Ile
305                 310                 315                 320

Thr Arg Val Asp Ala Ile Phe Gln Pro Ser Leu Pro Gly Glu Phe Arg
                325                 330                 335

Tyr Tyr Pro Asn Ile Ile Ala Lys Gly Val Gly Lys Ile Lys Gln Trp
            340                 345                 350

Asn

<210> SEQ ID NO 43
<211> LENGTH: 539
<212> TYPE: PRT
<213> ORGANISM: Human parainfluenza virus 3

<400> SEQUENCE: 43

Met Pro Thr Ser Ile Leu Leu Ile Ile Thr Thr Met Ile Met Ala Ser
1 5 10 15

Phe Cys Gln Ile Asp Ile Thr Lys Leu Gln His Val Gly Val Leu Val
20 25 30

Asn Ser Pro Lys Gly Met Lys Ile Ser Gln Asn Phe Glu Thr Arg Tyr
35 40 45

Leu Ile Leu Ser Leu Ile Pro Lys Ile Glu Asp Ser Asn Ser Cys Gly
50 55 60

Asp Gln Gln Ile Lys Gln Tyr Lys Lys Leu Leu Asp Arg Leu Ile Ile
65 70 75 80

Pro Leu Tyr Asp Gly Leu Arg Leu Gln Lys Asp Val Ile Val Thr Asn
85 90 95

Gln Glu Ser Asn Glu Asn Thr Asp Pro Arg Thr Lys Arg Phe Phe Gly
100 105 110

Gly Val Ile Gly Thr Ile Ala Leu Gly Val Ala Thr Ser Ala Gln Ile
115 120 125

Thr Ala Ala Val Ala Leu Val Glu Ala Lys Gln Ala Arg Ser Asp Ile
130 135 140

Glu Lys Leu Lys Glu Ala Ile Arg Asp Thr Asn Lys Ala Val Gln Ser
145 150 155 160

Val Gln Ser Ser Ile Gly Asn Leu Ile Val Ala Ile Lys Ser Val Gln
165 170 175

Asp Tyr Val Asn Lys Glu Ile Val Pro Ser Ile Ala Arg Leu Gly Cys
180 185 190

Glu Ala Ala Gly Leu Gln Leu Gly Ile Ala Leu Thr Gln His Tyr Ser
195 200 205

Glu Leu Thr Asn Ile Phe Gly Asp Asn Ile Gly Ser Leu Gln Glu Lys
210 215 220

Gly Ile Lys Leu Gln Gly Ile Ala Ser Leu Tyr Arg Thr Asn Ile Thr
225 230 235 240

Glu Ile Phe Thr Thr Ser Thr Val Asp Lys Tyr Asp Ile Tyr Asp Leu
245 250 255

Leu Phe Thr Glu Ser Ile Lys Val Arg Val Ile Asp Val Asp Leu Asn
260 265 270

Asp Tyr Ser Ile Thr Leu Gln Val Arg Leu Pro Leu Leu Thr Arg Leu
275 280 285

Leu Asn Thr Gln Ile Tyr Lys Val Asp Ser Ile Ser Tyr Asn Ile Gln
290 295 300

Asn Arg Glu Trp Tyr Ile Pro Leu Pro Ser His Ile Met Thr Lys Gly
305 310 315 320

Ala Phe Leu Gly Gly Ala Asp Val Lys Glu Cys Ile Glu Ala Phe Ser
325 330 335

Ser Tyr Ile Cys Pro Ser Asp Pro Gly Phe Val Leu Asn His Glu Ile
340 345 350

Glu Ser Cys Leu Ser Gly Asn Ile Ser Gln Cys Pro Arg Thr Thr Val
355 360 365

Thr Ser Asp Ile Val Pro Arg Tyr Ala Phe Val Asn Gly Gly Val Val
370 375 380

Ala Asn Cys Ile Thr Thr Thr Cys Thr Cys Asn Gly Ile Gly Asn Arg
385 390 395 400

```
Ile Asn Gln Pro Pro Asp Gln Gly Val Lys Ile Ile Thr His Lys Glu
                405                 410                 415

Cys Ser Thr Ile Gly Ile Asn Gly Met Leu Phe Asn Thr Asn Lys Glu
            420                 425                 430

Gly Thr Leu Ala Phe Tyr Thr Pro Asn Asp Ile Thr Leu Asn Asn Ser
        435                 440                 445

Val Ala Leu Asp Pro Ile Asp Ile Ser Ile Glu Leu Asn Lys Ala Lys
    450                 455                 460

Ser Asp Leu Glu Glu Ser Lys Glu Trp Ile Arg Arg Ser Asn Gln Lys
465                 470                 475                 480

Leu Asp Ser Ile Gly Asn Trp His Gln Ser Ser Thr Thr Ile Ile Ile
                485                 490                 495

Ile Leu Ile Met Ile Ile Ile Leu Phe Ile Ile Asn Ile Thr Ile Ile
            500                 505                 510

Thr Ile Ala Ile Lys Tyr Tyr Arg Ile Gln Lys Arg Asn Arg Val Asp
        515                 520                 525

Gln Asn Asp Lys Pro Tyr Val Leu Thr Asn Lys
    530                 535


<210> SEQ ID NO 44
<211> LENGTH: 572
<212> TYPE: PRT
<213> ORGANISM: Human parainfluenza virus 3

<400> SEQUENCE: 44

Met Glu Tyr Trp Lys His Thr Asn His Gly Lys Asp Ala Gly Asn Glu
1               5                   10                  15

Leu Glu Thr Ser Met Ala Thr His Gly Asn Lys Leu Thr Asn Lys Ile
            20                  25                  30

Ile Tyr Ile Leu Trp Thr Ile Ile Leu Val Leu Leu Ser Ile Val Phe
        35                  40                  45

Ile Ile Val Leu Ile Asn Ser Ile Lys Ser Glu Lys Ala His Glu Ser
    50                  55                  60

Leu Leu Gln Asp Ile Asn Asn Glu Phe Met Glu Ile Thr Glu Lys Ile
65                  70                  75                  80

Gln Met Ala Ser Asp Asn Thr Asn Asp Leu Ile Gln Ser Gly Val Asn
                85                  90                  95

Thr Arg Leu Leu Thr Ile Gln Ser His Val Gln Asn Tyr Ile Pro Ile
            100                 105                 110

Ser Leu Thr Gln Gln Met Ser Asp Leu Arg Lys Phe Ile Ser Glu Ile
        115                 120                 125

Thr Ile Arg Asn Asp Asn Gln Glu Val Leu Pro Gln Arg Ile Thr His
    130                 135                 140

Asp Val Gly Ile Lys Pro Leu Asn Pro Asp Asp Phe Trp Arg Cys Thr
145                 150                 155                 160

Ser Gly Leu Pro Ser Leu Met Lys Thr Pro Lys Ile Arg Leu Met Pro
                165                 170                 175

Gly Pro Gly Leu Leu Ala Met Pro Thr Thr Val Asp Gly Cys Val Arg
            180                 185                 190

Thr Pro Ser Leu Val Ile Asn Asp Leu Ile Tyr Ala Tyr Thr Ser Asn
        195                 200                 205

Leu Ile Thr Arg Gly Cys Gln Asp Ile Gly Lys Ser Tyr Gln Val Leu
    210                 215                 220
```

Gln Ile Gly Ile Ile Thr Val Asn Ser Asp Leu Val Pro Asp Leu Asn
225 230 235 240

Pro Arg Ile Ser His Thr Phe Asn Ile Asn Asp Asn Arg Lys Ser Cys
245 250 255

Ser Leu Ala Leu Leu Asn Thr Asp Val Tyr Gln Leu Cys Ser Thr Pro
260 265 270

Lys Val Asp Glu Arg Ser Asp Tyr Ala Ser Ser Gly Ile Glu Asp Ile
275 280 285

Val Leu Asp Ile Val Asn Tyr Asp Gly Ser Ile Ser Thr Thr Arg Phe
290 295 300

Lys Asn Asn Asn Ile Ser Phe Asp Gln Pro Tyr Ala Ala Leu Tyr Pro
305 310 315 320

Ser Val Gly Pro Gly Ile Tyr Tyr Lys Gly Lys Ile Ile Phe Leu Gly
325 330 335

Tyr Gly Gly Leu Glu His Pro Ile Asn Glu Asn Val Ile Cys Asn Thr
340 345 350

Thr Gly Cys Pro Gly Lys Thr Gln Arg Asp Cys Asn Gln Ala Ser His
355 360 365

Ser Pro Trp Phe Ser Asp Arg Arg Met Val Asn Ser Ile Ile Val Val
370 375 380

Asp Lys Gly Leu Asn Ser Ile Pro Lys Leu Lys Val Trp Thr Ile Ser
385 390 395 400

Met Arg Gln Asn Tyr Trp Gly Ser Glu Gly Arg Leu Leu Leu Leu Gly
405 410 415

Asn Lys Ile Tyr Ile Tyr Thr Arg Ser Thr Ser Trp His Ser Lys Leu
420 425 430

Gln Leu Gly Ile Ile Asp Ile Thr Asp Tyr Ser Asp Ile Arg Ile Lys
435 440 445

Trp Thr Trp His Asn Val Leu Ser Arg Pro Gly Asn Asn Glu Cys Pro
450 455 460

Trp Gly His Ser Cys Pro Asp Gly Cys Ile Thr Gly Val Tyr Thr Asp
465 470 475 480

Ala Tyr Pro Leu Asn Pro Thr Gly Ser Ile Val Ser Ser Val Ile Leu
485 490 495

Asp Ser Gln Lys Ser Arg Val Asn Pro Val Ile Thr Tyr Ser Thr Ala
500 505 510

Thr Glu Arg Val Asn Glu Leu Ala Ile Leu Asn Arg Thr Leu Ser Ala
515 520 525

Gly Tyr Thr Thr Thr Ser Cys Ile Thr His Tyr Asn Lys Gly Tyr Cys
530 535 540

Phe His Ile Val Glu Ile Asn His Lys Ser Leu Asn Thr Phe Gln Pro
545 550 555 560

Met Leu Phe Lys Thr Glu Ile Pro Lys Ser Cys Ser
565 570

<210> SEQ ID NO 45
<211> LENGTH: 2233
<212> TYPE: PRT
<213> ORGANISM: Human parainfluenza virus 3

<400> SEQUENCE: 45

Met Asp Thr Glu Ser Asn Asn Gly Thr Val Ser Asp Ile Leu Tyr Pro
1 5 10 15

-continued

```
Glu Cys His Leu Asn Ser Pro Ile Val Lys Gly Lys Ile Ala Gln Leu
            20                  25                  30

His Thr Ile Met Ser Leu Pro Gln Pro Tyr Asp Met Asp Asp Asp Ser
        35                  40                  45

Ile Leu Val Ile Thr Arg Gln Lys Ile Lys Leu Asn Lys Leu Asp Lys
    50                  55                  60

Arg Gln Arg Ser Ile Arg Arg Leu Lys Leu Ile Leu Thr Glu Lys Val
65                  70                  75                  80

Asn Asp Leu Gly Lys Tyr Thr Phe Ile Arg Tyr Pro Glu Met Ser Lys
                85                  90                  95

Glu Met Phe Lys Leu Tyr Ile Pro Gly Ile Asn Ser Lys Val Thr Glu
            100                 105                 110

Leu Leu Leu Lys Ala Asp Arg Thr Tyr Ser Gln Met Thr Asp Gly Leu
        115                 120                 125

Arg Asp Leu Trp Ile Asn Val Leu Ser Lys Leu Ala Ser Lys Asn Asp
    130                 135                 140

Gly Ser Asn Tyr Asp Leu Asn Glu Glu Ile Asn Asn Ile Ser Lys Val
145                 150                 155                 160

His Thr Thr Tyr Lys Ser Asp Lys Trp Tyr Asn Pro Phe Lys Thr Trp
                165                 170                 175

Phe Thr Ile Lys Tyr Asp Met Arg Arg Leu Gln Lys Ala Arg Asn Glu
            180                 185                 190

Ile Thr Phe Asn Val Gly Lys Asp Tyr Asn Leu Leu Glu Asp Gln Lys
        195                 200                 205

Asn Phe Leu Leu Ile His Pro Glu Leu Val Leu Ile Leu Asp Lys Gln
    210                 215                 220

Asn Tyr Asn Gly Tyr Leu Ile Thr Pro Glu Leu Val Leu Met Tyr Cys
225                 230                 235                 240

Asp Val Val Glu Gly Arg Trp Asn Ile Ser Ala Cys Ala Lys Leu Asp
                245                 250                 255

Pro Lys Leu Gln Ser Met Tyr Gln Lys Gly Asn Asn Leu Trp Glu Val
            260                 265                 270

Ile Asp Lys Leu Phe Pro Ile Met Gly Glu Lys Thr Phe Asp Val Ile
        275                 280                 285

Ser Leu Leu Glu Pro Leu Ala Leu Ser Leu Ile Gln Thr His Asp Pro
    290                 295                 300

Val Lys Gln Leu Arg Gly Ala Phe Leu Asn His Val Leu Ser Glu Met
305                 310                 315                 320

Glu Leu Ile Phe Glu Ser Arg Glu Ser Ile Lys Glu Phe Leu Ser Val
                325                 330                 335

Asp Tyr Ile Asp Lys Ile Leu Asp Ile Phe Asn Lys Ser Thr Ile Asp
            340                 345                 350

Glu Ile Ala Glu Ile Phe Ser Phe Phe Arg Thr Phe Gly His Pro Pro
        355                 360                 365

Leu Glu Ala Ser Ile Ala Ala Glu Lys Val Arg Lys Tyr Met Tyr Ile
    370                 375                 380

Gly Lys Gln Leu Lys Phe Asp Thr Ile Asn Lys Cys His Ala Ile Phe
385                 390                 395                 400

Cys Thr Ile Ile Ile Asn Gly Tyr Arg Glu Arg His Gly Gly Gln Trp
                405                 410                 415

Pro Pro Val Thr Leu Pro Asp His Ala His Glu Phe Ile Ile Asn Ala
            420                 425                 430
```

-continued

```
Tyr Gly Ser Asn Ser Ala Ile Ser Tyr Glu Asn Ala Val Asp Tyr Tyr
        435                 440                 445

Gln Ser Phe Ile Gly Ile Lys Phe Asn Lys Phe Ile Glu Pro Gln Leu
    450                 455                 460

Asp Glu Asp Leu Thr Ile Tyr Met Lys Asp Lys Ala Leu Ser Pro Lys
465                 470                 475                 480

Lys Ser Asn Trp Asp Thr Val Tyr Pro Ala Ser Asn Leu Leu Tyr Arg
                485                 490                 495

Thr Asn Ala Ser Asn Glu Ser Arg Arg Leu Val Glu Val Phe Ile Ala
            500                 505                 510

Asp Ser Lys Phe Asp Pro His Gln Ile Leu Asp Tyr Val Glu Ser Gly
        515                 520                 525

Asp Trp Leu Asp Asp Pro Glu Phe Asn Ile Ser Tyr Ser Leu Lys Glu
    530                 535                 540

Lys Glu Ile Lys Gln Glu Gly Arg Leu Phe Ala Lys Met Thr Tyr Lys
545                 550                 555                 560

Met Arg Ala Thr Gln Val Leu Ser Glu Thr Leu Leu Ala Asn Asn Ile
                565                 570                 575

Gly Lys Phe Phe Gln Glu Asn Gly Met Val Lys Gly Glu Ile Glu Leu
            580                 585                 590

Leu Lys Arg Leu Thr Thr Ile Ser Ile Ser Gly Val Pro Arg Tyr Asn
        595                 600                 605

Glu Val Tyr Asn Asn Ser Lys Ser His Thr Asp Asp Leu Lys Thr Tyr
    610                 615                 620

Asn Lys Ile Ser Asn Leu Asn Leu Ser Ser Asn Gln Lys Ser Lys Lys
625                 630                 635                 640

Phe Glu Phe Lys Ser Thr Asp Ile Tyr Asn Asp Gly Tyr Glu Thr Val
                645                 650                 655

Ser Cys Phe Leu Thr Thr Asp Leu Lys Lys Tyr Cys Leu Asn Trp Arg
            660                 665                 670

Tyr Glu Ser Thr Ala Leu Phe Gly Glu Thr Cys Asn Gln Ile Phe Gly
        675                 680                 685

Leu Asn Lys Leu Phe Asn Trp Leu His Pro Arg Leu Glu Gly Ser Thr
    690                 695                 700

Ile Tyr Val Gly Asp Pro Tyr Cys Pro Pro Ser Asp Lys Glu His Ile
705                 710                 715                 720

Ser Leu Glu Asp His Pro Asp Ser Gly Phe Tyr Val His Asn Pro Arg
                725                 730                 735

Gly Gly Ile Glu Gly Phe Cys Gln Lys Leu Trp Thr Leu Ile Ser Ile
            740                 745                 750

Ser Ala Ile His Leu Ala Ala Val Arg Ile Gly Val Arg Val Thr Ala
        755                 760                 765

Met Val Gln Gly Asp Asn Gln Ala Ile Ala Val Thr Thr Arg Val Pro
    770                 775                 780

Asn Asn Tyr Asp Tyr Arg Val Lys Lys Glu Ile Val Tyr Lys Asp Val
785                 790                 795                 800

Val Arg Phe Phe Asp Ser Leu Arg Glu Val Met Asp Asp Leu Gly His
                805                 810                 815

Glu Leu Lys Leu Asn Glu Thr Ile Ile Ser Ser Lys Met Phe Ile Tyr
            820                 825                 830

Ser Lys Arg Ile Tyr Tyr Asp Gly Arg Ile Leu Pro Gln Ala Leu Lys
        835                 840                 845
```

-continued

```
Ala Leu Ser Arg Cys Val Phe Trp Ser Glu Thr Val Ile Asp Glu Thr
    850                 855                 860

Arg Ser Ala Ser Ser Asn Leu Ala Thr Ser Phe Ala Lys Ala Ile Glu
865                 870                 875                 880

Asn Gly Tyr Ser Pro Val Leu Gly Tyr Ala Cys Ser Ile Phe Lys Asn
                885                 890                 895

Ile Gln Gln Leu Tyr Ile Ala Leu Gly Met Asn Ile Asn Pro Thr Ile
            900                 905                 910

Thr Gln Asn Ile Arg Asp Gln Tyr Phe Arg Asn Pro Asn Trp Met Gln
        915                 920                 925

Tyr Ala Ser Leu Ile Pro Ala Ser Val Gly Gly Phe Asn Tyr Met Ala
    930                 935                 940

Met Ser Arg Cys Phe Val Arg Asn Ile Gly Asp Pro Ser Val Ala Ala
945                 950                 955                 960

Leu Ala Asp Ile Lys Arg Phe Ile Lys Ala Asn Leu Leu Asp Arg Ser
                965                 970                 975

Val Leu Tyr Arg Ile Met Asn Gln Glu Pro Gly Glu Ser Ser Phe Leu
            980                 985                 990

Asp Trp Ala Ser Asp Pro Tyr Ser  Cys Asn Leu Pro Gln  Ser Gln Asn
        995                 1000                1005

Ile Thr  Thr Met Ile Lys Asn  Ile Thr Ala Arg Asn  Val Leu Gln
    1010                1015                1020

Asp Ser  Pro Asn Pro Leu Leu  Ser Gly Leu Phe Thr  Asn Thr Met
    1025                1030                1035

Ile Glu  Glu Asp Glu Glu Leu  Ala Glu Phe Leu Met  Asp Arg Lys
    1040                1045                1050

Val Ile  Leu Pro Arg Val Ala  His Asp Ile Leu Asp  Asn Ser Leu
    1055                1060                1065

Thr Gly  Ile Arg Asn Ala Ile  Ala Gly Met Leu Asp  Thr Thr Lys
    1070                1075                1080

Ser Leu  Ile Arg Val Gly Ile  Asn Arg Gly Gly Leu  Thr Tyr Ser
    1085                1090                1095

Leu Leu  Arg Lys Ile Ser Asn  Tyr Asp Leu Val Gln  Tyr Glu Thr
    1100                1105                1110

Leu Ser  Arg Thr Leu Arg Leu  Ile Val Ser Asp Lys  Ile Lys Tyr
    1115                1120                1125

Glu Asp  Met Cys Ser Val Asp  Leu Ala Ile Ala Leu  Arg Gln Lys
    1130                1135                1140

Met Trp  Ile His Leu Ser Gly  Gly Arg Met Ile Ser  Gly Leu Glu
    1145                1150                1155

Thr Pro  Asp Pro Leu Glu Leu  Leu Ser Gly Val Val  Ile Thr Gly
    1160                1165                1170

Ser Glu  His Cys Lys Ile Cys  Tyr Ser Ser Asp Gly  Thr Asn Pro
    1175                1180                1185

Tyr Thr  Trp Met Tyr Leu Pro  Gly Asn Ile Lys Ile  Gly Ser Ala
    1190                1195                1200

Glu Thr  Gly Ile Ser Ser Leu  Arg Val Pro Tyr Phe  Gly Ser Val
    1205                1210                1215

Thr Asp  Glu Arg Ser Glu Ala  Gln Leu Gly Tyr Ile  Lys Asn Leu
    1220                1225                1230

Ser Lys  Pro Ala Lys Ala Ala  Ile Arg Ile Ala Met  Ile Tyr Thr
    1235                1240                1245
```

-continued

```
Trp Ala  Phe Gly Asn Asp Glu  Ile Ser Trp Met Glu  Ala Ser Gln
    1250                 1255                 1260

Ile Ala  Gln Thr Arg Ala Asn  Phe Thr Leu Asp Ser  Leu Lys Ile
    1265                 1270                 1275

Leu Thr  Pro Val Ala Thr Ser  Thr Asn Leu Ser His  Arg Leu Lys
    1280                 1285                 1290

Asp Thr  Ala Thr Gln Met Lys  Phe Ser Ser Thr Ser  Leu Ile Arg
    1295                 1300                 1305

Val Ser  Arg Phe Ile Thr Met  Ser Asn Asp Asn Met  Ser Ile Lys
    1310                 1315                 1320

Glu Ala  Asn Glu Thr Lys Asp  Thr Asn Leu Ile Tyr  Gln Gln Ile
    1325                 1330                 1335

Met Leu  Thr Gly Leu Ser Val  Phe Glu Tyr Leu Phe  Arg Leu Lys
    1340                 1345                 1350

Glu Thr  Thr Gly His Asn Pro  Ile Val Met His Leu  His Ile Glu
    1355                 1360                 1365

Asp Glu  Cys Cys Ile Lys Glu  Ser Phe Asn Asp Glu  His Ile Asn
    1370                 1375                 1380

Pro Glu  Ser Thr Leu Glu Leu  Ile Arg Tyr Pro Glu  Ser Asn Glu
    1385                 1390                 1395

Phe Ile  Tyr Asp Lys Asp Pro  Leu Lys Asp Val Asp  Leu Ser Lys
    1400                 1405                 1410

Leu Met  Val Ile Lys Asp His  Ser Tyr Thr Ile Asp  Met Asn Tyr
    1415                 1420                 1425

Trp Asp  Asp Thr Asp Ile Ile  His Ala Ile Ser Ile  Cys Thr Ala
    1430                 1435                 1440

Ile Thr  Ile Ala Asp Thr Met  Ser Gln Leu Asp Arg  Asp Asn Leu
    1445                 1450                 1455

Lys Glu  Ile Ile Val Ile Ala  Asn Asp Asp Asp Ile  Asn Ser Leu
    1460                 1465                 1470

Ile Thr  Glu Phe Leu Thr Leu  Asp Ile Leu Val Phe  Leu Lys Thr
    1475                 1480                 1485

Phe Gly  Gly Leu Leu Val Asn  Gln Phe Ala Tyr Thr  Leu Tyr Ser
    1490                 1495                 1500

Leu Lys  Ile Glu Gly Arg Asp  Leu Ile Trp Asp Tyr  Ile Met Arg
    1505                 1510                 1515

Thr Leu  Arg Asp Thr Ser His  Ser Ile Leu Lys Val  Leu Ser Asn
    1520                 1525                 1530

Ala Leu  Ser His Pro Lys Val  Phe Lys Arg Phe Trp  Asp Cys Gly
    1535                 1540                 1545

Val Leu  Asn Pro Ile Tyr Gly  Pro Asn Thr Ala Ser  Gln Asp Gln
    1550                 1555                 1560

Ile Lys  Leu Ala Leu Ser Ile  Cys Glu Tyr Ser Leu  Asp Leu Phe
    1565                 1570                 1575

Met Arg  Glu Trp Leu Asn Gly  Val Ser Leu Glu Ile  Tyr Ile Cys
    1580                 1585                 1590

Asp Ser  Asp Met Glu Val Ala  Asn Asp Arg Lys Gln  Ala Phe Ile
    1595                 1600                 1605

Ser Arg  His Leu Ser Phe Val  Cys Cys Leu Ala Glu  Ile Ala Ser
    1610                 1615                 1620

Phe Gly  Pro Asn Leu Leu Asn  Leu Thr Tyr Leu Glu  Arg Leu Asp
    1625                 1630                 1635
```

-continued

```
Leu Leu  Lys Gln Tyr Leu Glu  Leu Asn Ile Lys Glu  Asp Pro Thr
    1640                 1645                 1650

Leu Lys  Tyr Val Gln Ile Ser  Gly Leu Leu Ile Lys  Ser Phe Pro
    1655                 1660                 1665

Ser Thr  Val Thr Tyr Val Arg  Lys Thr Ala Ile Lys  Tyr Leu Arg
    1670                 1675                 1680

Ile Arg  Gly Ile Ser Pro Pro  Glu Val Ile Asp Asp  Trp Asp Pro
    1685                 1690                 1695

Val Glu  Asp Glu Asn Met Leu  Asp Asn Ile Val Lys  Thr Ile Asn
    1700                 1705                 1710

Asp Asn  Cys Asn Lys Asp Asn  Lys Gly Asn Lys Ile  Asn Asn Phe
    1715                 1720                 1725

Trp Gly  Leu Ala Leu Lys Asn  Tyr Gln Val Leu Lys  Ile Arg Ser
    1730                 1735                 1740

Ile Thr  Ser Asp Ser Asp Asp  Asn Asp Arg Leu Asp  Ala Asn Thr
    1745                 1750                 1755

Ser Gly  Leu Thr Leu Pro Gln  Gly Gly Asn Tyr Leu  Ser His Gln
    1760                 1765                 1770

Leu Arg  Leu Phe Gly Ile Asn  Ser Thr Ser Cys Leu  Lys Ala Leu
    1775                 1780                 1785

Glu Leu  Ser Gln Ile Leu Met  Lys Glu Val Asn Lys  Asp Lys Asp
    1790                 1795                 1800

Arg Leu  Phe Leu Gly Glu Gly  Ala Gly Ala Met Leu  Ala Cys Tyr
    1805                 1810                 1815

Asp Ala  Thr Leu Gly Pro Ala  Val Asn Tyr Tyr Asn  Ser Gly Leu
    1820                 1825                 1830

Asn Ile  Thr Asp Val Ile Gly  Gln Arg Glu Leu Lys  Ile Phe Pro
    1835                 1840                 1845

Ser Glu  Val Ser Leu Val Gly  Lys Lys Leu Gly Asn  Val Thr Gln
    1850                 1855                 1860

Ile Leu  Asn Arg Val Lys Val  Leu Phe Asn Gly Asn  Pro Asn Ser
    1865                 1870                 1875

Thr Trp  Ile Gly Asn Met Glu  Cys Glu Ser Leu Ile  Trp Ser Glu
    1880                 1885                 1890

Leu Asn  Asp Lys Ser Ile Gly  Leu Val His Cys Asp  Met Glu Gly
    1895                 1900                 1905

Ala Ile  Gly Lys Ser Glu Glu  Thr Val Leu His Glu  His Tyr Ser
    1910                 1915                 1920

Val Ile  Arg Ile Thr Tyr Leu  Ile Gly Asp Asp Asp  Val Val Leu
    1925                 1930                 1935

Val Ser  Lys Ile Ile Pro Thr  Ile Thr Pro Asn Trp  Ser Arg Ile
    1940                 1945                 1950

Leu Tyr  Leu Tyr Lys Leu Tyr  Trp Lys Asp Val Ser  Ile Ile Ser
    1955                 1960                 1965

Leu Lys  Thr Ser Asn Pro Ala  Ser Thr Glu Leu Tyr  Leu Ile Ser
    1970                 1975                 1980

Lys Asp  Ala Tyr Cys Thr Ile  Met Glu Pro Ser Glu  Ile Val Leu
    1985                 1990                 1995

Ser Lys  Leu Lys Arg Leu Ser  Leu Leu Glu Glu Asn  Asn Leu Leu
    2000                 2005                 2010

Lys Trp  Ile Ile Leu Ser Lys  Lys Arg Asn Asn Glu  Trp Leu His
    2015                 2020                 2025
```

-continued

His Glu Ile Lys Glu Gly Glu Arg Asp Tyr Gly Ile Met Arg Pro
2030 2035 2040

Tyr His Met Ala Leu Gln Ile Phe Gly Phe Gln Ile Asn Leu Asn
2045 2050 2055

His Leu Ala Lys Glu Phe Leu Ser Thr Pro Asp Leu Thr Asn Ile
2060 2065 2070

Asn Asn Ile Ile Gln Ser Phe Gln Arg Thr Ile Lys Asp Val Leu
2075 2080 2085

Phe Glu Trp Ile Asn Ile Thr His Asp Asp Lys Arg His Lys Leu
2090 2095 2100

Gly Gly Arg Tyr Asn Ile Phe Pro Leu Lys Asn Lys Gly Lys Leu
2105 2110 2115

Arg Leu Leu Ser Arg Arg Leu Val Leu Ser Trp Ile Ser Leu Ser
2120 2125 2130

Leu Ser Thr Arg Leu Leu Thr Gly Arg Phe Pro Asp Glu Lys Phe
2135 2140 2145

Glu His Arg Ala Gln Thr Gly Tyr Val Ser Leu Ala Asp Thr Asp
2150 2155 2160

Leu Glu Ser Leu Lys Leu Leu Ser Lys Asn Ile Ile Lys Asn Tyr
2165 2170 2175

Arg Glu Cys Ile Gly Ser Ile Ser Tyr Trp Phe Leu Thr Lys Glu
2180 2185 2190

Val Lys Ile Leu Met Lys Leu Ile Gly Gly Ala Lys Leu Leu Gly
2195 2200 2205

Ile Pro Arg Gln Tyr Lys Glu Pro Glu Asp Gln Leu Leu Glu Asn
2210 2215 2220

Tyr Asn Gln His Asp Glu Phe Asp Ile Asp
2225 2230

<210> SEQ ID NO 46
<211> LENGTH: 46
<212> TYPE: PRT
<213> ORGANISM: Human parainfluenza virus 3

<400> SEQUENCE: 46

Ile Ile Ile Ile Leu Ile Met Ile Ile Ile Leu Phe Ile Ile Asn Ile
1 5 10 15

Thr Ile Ile Thr Ile Ala Ile Lys Tyr Tyr Arg Ile Gln Lys Arg Asn
20 25 30

Arg Val Asp Gln Asn Asp Lys Pro Tyr Val Leu Thr Asn Lys
35 40 45

<210> SEQ ID NO 47
<211> LENGTH: 515
<212> TYPE: PRT
<213> ORGANISM: Bovine parainfluenza virus 3

<400> SEQUENCE: 47

Met Leu Ser Leu Phe Asp Thr Phe Ser Ala Arg Arg Gln Glu Asn Ile
1 5 10 15

Thr Lys Ser Ala Gly Gly Ala Val Ile Pro Gly Gln Lys Asn Thr Val
20 25 30

Ser Ile Phe Ala Leu Gly Pro Ser Ile Thr Asp Asp Asn Asp Lys Met
35 40 45

Thr Leu Ala Leu Leu Phe Leu Ser His Ser Leu Asp Asn Glu Lys Gln
50 55 60

-continued

His Ala Gln Arg Ala Gly Phe Leu Val Ser Leu Leu Ser Met Ala Tyr
65 70 75 80

Ala Asn Pro Glu Leu Tyr Leu Thr Ser Asn Gly Ser Asn Ala Asp Val
85 90 95

Lys Tyr Val Ile Tyr Met Ile Glu Lys Asp Pro Gly Arg Gln Lys Tyr
100 105 110

Gly Gly Phe Val Val Lys Thr Arg Glu Met Val Tyr Glu Lys Thr Thr
115 120 125

Asp Trp Met Phe Gly Ser Asp Leu Glu Tyr Asp Gln Asp Asn Met Leu
130 135 140

Gln Asn Gly Arg Ser Thr Ser Thr Ile Glu Asp Leu Val His Thr Phe
145 150 155 160

Gly Tyr Pro Ser Cys Leu Gly Ala Leu Ile Ile Gln Val Trp Ile Ile
165 170 175

Leu Val Lys Ala Ile Thr Ser Ile Ser Gly Leu Arg Lys Gly Phe Phe
180 185 190

Thr Arg Leu Glu Ala Phe Arg Gln Asp Gly Thr Val Lys Ser Ser Leu
195 200 205

Val Leu Ser Gly Asp Ala Val Glu Gln Ile Gly Ser Ile Met Arg Ser
210 215 220

Gln Gln Ser Leu Val Thr Leu Met Val Glu Thr Leu Ile Thr Met Asn
225 230 235 240

Thr Gly Arg Asn Asp Leu Thr Thr Ile Glu Lys Asn Ile Gln Ile Val
245 250 255

Gly Asn Tyr Ile Arg Asp Ala Gly Leu Ala Ser Phe Phe Asn Thr Ile
260 265 270

Arg Tyr Gly Ile Glu Thr Arg Met Ala Ala Leu Thr Leu Ser Thr Leu
275 280 285

Arg Pro Asp Ile Asn Arg Leu Lys Ala Leu Ile Glu Leu Tyr Leu Ser
290 295 300

Lys Gly Pro Arg Ala Pro Phe Ile Cys Ile Leu Arg Asp Pro Val His
305 310 315 320

Gly Glu Phe Ala Pro Gly Asn Tyr Pro Ala Leu Trp Ser Tyr Ala Met
325 330 335

Gly Val Ala Val Val Gln Asn Lys Ala Met Gln Gln Tyr Val Thr Gly
340 345 350

Arg Ser Tyr Leu Asp Ile Glu Met Phe Gln Leu Gly Gln Ala Val Ala
355 360 365

Arg Asp Ala Glu Ser Gln Met Ser Ser Ile Leu Glu Asp Glu Leu Gly
370 375 380

Val Thr Gln Glu Ala Lys Gln Ser Leu Lys Lys His Met Lys Asn Ile
385 390 395 400

Ser Ser Ser Asp Thr Thr Phe His Lys Pro Thr Gly Gly Ser Ala Ile
405 410 415

Glu Met Ala Ile Asp Glu Glu Ala Gly Gln Pro Glu Ser Arg Gly Asp
420 425 430

Gln Asp Gln Gly Asp Glu Pro Arg Ser Ser Ile Val Pro Tyr Ala Trp
435 440 445

Ala Asp Glu Thr Gly Asn Asp Asn Gln Thr Glu Ser Thr Thr Glu Ile
450 455 460

Asp Ser Ile Lys Thr Glu Gln Arg Asn Ile Arg Asp Arg Leu Asn Lys
465 470 475 480

```
Arg Leu Asn Glu Lys Arg Lys Gln Ser Asp Pro Arg Ser Thr Asp Ile
                485                 490                 495

Thr Asn Asn Thr Asn Gln Thr Glu Ile Asp Asp Leu Phe Ser Ala Phe
            500                 505                 510

Gly Ser Asn
        515


<210> SEQ ID NO 48
<211> LENGTH: 596
<212> TYPE: PRT
<213> ORGANISM: Bovine parainfluenza virus 3

<400> SEQUENCE: 48

Met Glu Asp Asn Val Gln Asn Asn Gln Ile Met Asp Ser Trp Glu Glu
1               5                   10                  15

Gly Ser Gly Asp Lys Ser Ser Asp Ile Ser Ser Ala Leu Asp Ile Ile
            20                  25                  30

Glu Phe Ile Leu Ser Thr Asp Ser Gln Glu Asn Thr Ala Asp Ser Asn
        35                  40                  45

Glu Ile Asn Thr Gly Thr Thr Arg Leu Ser Thr Thr Ile Tyr Gln Pro
    50                  55                  60

Glu Ser Lys Thr Thr Glu Thr Ser Lys Glu Asn Ser Gly Pro Ala Asn
65                  70                  75                  80

Lys Asn Arg Gln Phe Gly Ala Ser His Glu Arg Ala Thr Glu Thr Lys
                85                  90                  95

Asp Arg Asn Val Asn Gln Glu Thr Val Gln Gly Gly Tyr Arg Arg Gly
            100                 105                 110

Ser Ser Pro Asp Ser Arg Thr Glu Thr Met Val Thr Arg Arg Ile Ser
        115                 120                 125

Arg Ser Ser Pro Asp Pro Asn Asn Gly Thr Gln Ile Gln Glu Asp Ile
    130                 135                 140

Asp Tyr Asn Glu Val Gly Glu Met Asp Lys Asp Ser Thr Lys Arg Glu
145                 150                 155                 160

Met Arg Gln Phe Lys Asp Val Pro Val Lys Val Ser Gly Ser Asp Ala
                165                 170                 175

Ile Pro Pro Thr Lys Gln Asp Gly Asp Gly Asp Asp Gly Arg Gly Leu
            180                 185                 190

Glu Ser Ile Ser Thr Phe Asp Ser Gly Tyr Thr Ser Ile Val Thr Ala
        195                 200                 205

Ala Thr Leu Asp Asp Glu Glu Glu Leu Leu Met Lys Asn Asn Arg Pro
    210                 215                 220

Arg Lys Tyr Gln Ser Thr Pro Gln Asn Ser Asp Lys Gly Ile Lys Lys
225                 230                 235                 240

Gly Val Gly Arg Pro Lys Asp Thr Asp Lys Gln Ser Ser Ile Leu Asp
                245                 250                 255

Tyr Glu Leu Asn Phe Lys Gly Ser Lys Lys Ser Gln Lys Ile Leu Lys
            260                 265                 270

Ala Ser Thr Asn Thr Gly Glu Pro Thr Arg Pro Gln Asn Gly Ser Gln
        275                 280                 285

Gly Lys Arg Ile Thr Ser Trp Asn Ile Leu Asn Ser Glu Ser Gly Asn
    290                 295                 300

Arg Thr Glu Ser Thr Asn Gln Thr His Gln Thr Ser Thr Ser Gly Gln
305                 310                 315                 320
```

```
Asn His Thr Met Gly Pro Ser Arg Thr Thr Ser Glu Pro Arg Ile Lys
                325                 330                 335

Thr Gln Lys Thr Asp Gly Lys Glu Arg Glu Asp Thr Glu Glu Ser Thr
            340                 345                 350

Arg Phe Thr Glu Arg Ala Ile Thr Leu Leu Gln Asn Leu Gly Val Ile
        355                 360                 365

Gln Ser Ala Ala Lys Leu Asp Leu Tyr Gln Asp Lys Arg Val Val Cys
    370                 375                 380

Val Ala Asn Val Leu Asn Asn Ala Asp Thr Ala Ser Lys Ile Asp Phe
385                 390                 395                 400

Leu Ala Gly Leu Met Ile Gly Val Ser Met Asp His Asp Thr Lys Leu
                405                 410                 415

Asn Gln Ile Gln Asn Glu Ile Leu Ser Leu Lys Thr Asp Leu Lys Lys
            420                 425                 430

Met Asp Glu Ser His Arg Arg Leu Ile Glu Asn Gln Lys Glu Gln Leu
        435                 440                 445

Ser Leu Ile Thr Ser Leu Ile Ser Asn Leu Lys Ile Met Thr Glu Arg
    450                 455                 460

Gly Gly Lys Lys Asp Gln Pro Glu Pro Ser Gly Arg Thr Ser Met Ile
465                 470                 475                 480

Lys Thr Lys Ala Lys Glu Glu Lys Ile Lys Lys Val Arg Phe Asp Pro
                485                 490                 495

Leu Met Glu Thr Gln Gly Ile Glu Lys Asn Ile Pro Asp Leu Tyr Arg
            500                 505                 510

Ser Ile Glu Lys Thr Pro Glu Asn Asp Thr Gln Ile Lys Ser Glu Ile
        515                 520                 525

Asn Arg Leu Asn Asp Glu Ser Asn Ala Thr Arg Leu Val Pro Arg Arg
    530                 535                 540

Ile Ser Ser Thr Met Arg Ser Leu Ile Ile Ile Ile Asn Asn Ser Asn
545                 550                 555                 560

Leu Ser Ser Lys Ala Lys Gln Ser Tyr Ile Asn Glu Leu Lys Leu Cys
                565                 570                 575

Lys Ser Asp Glu Glu Val Ser Glu Leu Met Asp Met Phe Asn Glu Asp
            580                 585                 590

Val Ser Ser Gln
        595
```

<210> SEQ ID NO 49
<211> LENGTH: 351
<212> TYPE: PRT
<213> ORGANISM: Bovine parainfluenza virus 3

<400> SEQUENCE: 49

```
Met Ser Ile Thr Asn Ser Thr Ile Tyr Thr Phe Pro Glu Ser Ser Phe
1               5                   10                  15

Ser Glu Asn Gly Asn Ile Glu Pro Leu Pro Leu Lys Val Asn Glu Gln
            20                  25                  30

Arg Lys Ala Ile Pro His Ile Arg Val Val Lys Ile Gly Asp Pro Pro
        35                  40                  45

Lys His Gly Ser Arg Tyr Leu Asp Val Phe Leu Leu Gly Phe Phe Glu
    50                  55                  60

Met Glu Arg Ser Lys Asp Arg Tyr Gly Ser Ile Ser Asp Leu Asp Asp
65                  70                  75                  80
```

Asp Pro Ser Tyr Lys Val Cys Gly Ser Gly Ser Leu Pro Leu Gly Leu
85 90 95

Ala Arg Tyr Thr Gly Asn Asp Gln Glu Leu Leu Gln Ala Ala Thr Lys
100 105 110

Leu Asp Ile Glu Val Arg Arg Thr Val Lys Ala Thr Glu Met Ile Val
115 120 125

Tyr Thr Val Gln Asn Ile Lys Pro Glu Leu Tyr Pro Trp Ser Ser Arg
130 135 140

Leu Arg Lys Gly Met Leu Phe Asp Ala Asn Lys Val Ala Leu Ala Pro
145 150 155 160

Gln Cys Leu Pro Leu Asp Arg Gly Ile Lys Phe Arg Val Ile Phe Val
165 170 175

Asn Cys Thr Ala Ile Gly Ser Ile Thr Leu Phe Lys Ile Pro Lys Ser
180 185 190

Met Ala Leu Leu Ser Leu Pro Asn Thr Ile Ser Ile Asn Leu Gln Val
195 200 205

His Ile Lys Thr Gly Val Gln Thr Asp Ser Lys Gly Val Val Gln Ile
210 215 220

Leu Asp Glu Lys Gly Glu Lys Ser Leu Asn Phe Met Val His Leu Gly
225 230 235 240

Leu Ile Lys Arg Lys Met Gly Arg Met Tyr Ser Val Glu Tyr Cys Lys
245 250 255

Gln Lys Ile Glu Lys Met Arg Leu Leu Phe Ser Leu Gly Leu Val Gly
260 265 270

Gly Ile Ser Phe His Val Asn Ala Thr Gly Ser Ile Ser Lys Thr Leu
275 280 285

Ala Ser Gln Leu Ala Phe Lys Arg Glu Ile Cys Tyr Pro Leu Met Asp
290 295 300

Leu Asn Pro His Leu Asn Ser Val Ile Trp Ala Ser Ser Val Glu Ile
305 310 315 320

Thr Arg Val Asp Ala Val Leu Gln Pro Ser Leu Pro Gly Glu Phe Arg
325 330 335

Tyr Tyr Pro Asn Ile Ile Ala Lys Gly Val Gly Lys Ile Arg Gln
340 345 350

<210> SEQ ID NO 50
<211> LENGTH: 540
<212> TYPE: PRT
<213> ORGANISM: Bovine parainfluenza virus 3

<400> SEQUENCE: 50

Met Thr Ile Thr Thr Thr Ile Ile Ala Ile Leu Leu Ile Pro Pro Ser
1 5 10 15

Phe Cys Gln Ile Asp Ile Thr Lys Leu Gln Arg Val Gly Val Leu Val
20 25 30

Asn Asn Pro Lys Gly Met Lys Ile Ser Gln Asn Phe Glu Thr Arg Tyr
35 40 45

Leu Ile Leu Ser Leu Ile Pro Lys Ile Glu Asn Ser His Ser Cys Gly
50 55 60

Asp Gln Gln Ile Asn Gln Tyr Lys Lys Leu Leu Asp Arg Leu Ile Ile
65 70 75 80

Pro Leu Tyr Asp Gly Leu Lys Leu Gln Lys Asp Val Ile Val Val Ser
85 90 95

-continued

```
His Glu Thr His Asn Asn Thr Asn Leu Arg Thr Lys Arg Phe Phe Gly
            100                 105                 110

Glu Ile Ile Gly Thr Ile Ala Ile Gly Ile Ala Thr Ser Ala Gln Ile
        115                 120                 125

Thr Ala Ala Val Ala Leu Val Glu Ala Lys Gln Ala Lys Ser Asp Ile
    130                 135                 140

Glu Lys Leu Lys Glu Ala Ile Arg Asp Thr Asn Lys Ala Val Gln Ser
145                 150                 155                 160

Ile Gln Ser Ser Val Gly Asn Leu Ile Val Ala Val Lys Ser Val Gln
                165                 170                 175

Asp Tyr Val Asn Asn Glu Ile Ile Pro Ser Ile Thr Arg Leu Gly Cys
            180                 185                 190

Glu Ala Ala Gly Leu Gln Leu Gly Ile Ala Leu Thr Gln His Tyr Ser
        195                 200                 205

Glu Leu Thr Asn Ile Phe Gly Asp Asn Ile Gly Thr Leu Lys Glu Lys
    210                 215                 220

Gly Ile Lys Leu Gln Gly Ile Ala Ser Leu Tyr His Thr Asn Ile Thr
225                 230                 235                 240

Glu Ile Phe Thr Thr Ser Thr Val Asp Gln Tyr Asp Ile Tyr Asp Leu
                245                 250                 255

Leu Phe Thr Glu Ser Ile Lys Met Arg Val Ile Asp Val Asp Leu Ser
            260                 265                 270

Asp Tyr Ser Ile Thr Leu Gln Val Arg Leu Pro Leu Leu Thr Lys Leu
        275                 280                 285

Ser Asn Thr Gln Ile Tyr Lys Val Asp Ser Ile Ser Tyr Asn Ile Gln
    290                 295                 300

Gly Lys Glu Trp Tyr Ile Pro Leu Pro Asn His Ile Met Thr Lys Gly
305                 310                 315                 320

Ala Phe Leu Gly Gly Ala Asp Ile Lys Glu Cys Ile Glu Ala Phe Ser
                325                 330                 335

Ser Tyr Ile Cys Pro Ser Asp Pro Gly Tyr Ile Leu Asn His Glu Ile
            340                 345                 350

Glu Asn Cys Leu Ser Gly Asn Ile Thr Gln Cys Pro Lys Thr Val Val
        355                 360                 365

Thr Ser Asp Val Val Pro Arg Tyr Ala Phe Val Asn Gly Gly Leu Ile
    370                 375                 380

Ala Asn Cys Ile Thr Thr Thr Cys Thr Cys Asn Gly Ile Asp Asn Arg
385                 390                 395                 400

Ile Asn Gln Ser Pro Asp Gln Gly Ile Lys Ile Ile Thr His Lys Glu
                405                 410                 415

Cys Gln Val Ile Gly Ile Asn Gly Met Leu Phe Asn Thr Asn Arg Glu
            420                 425                 430

Gly Thr Leu Ala Thr Tyr Thr Phe Asp Asp Ile Ile Leu Asn Asn Ser
        435                 440                 445

Val Ala Leu Asn Pro Ile Asp Ile Ser Met Glu Leu Asn Lys Ala Lys
    450                 455                 460

Leu Glu Leu Glu Glu Ser Lys Glu Trp Ile Lys Lys Ser Asn Gln Lys
465                 470                 475                 480

Leu Asp Ser Val Gly Ser Trp Tyr Gln Ser Ser Ala Thr Ile Thr Ile
                485                 490                 495

Ile Ile Val Met Ile Ile Ile Leu Val Ile Ile Asn Ile Thr Ile Ile
            500                 505                 510
```

```
Val Val Ile Ile Lys Phe His Arg Ile Gln Gly Lys Asp Gln Asn Asp
        515                 520                 525

Lys Asn Ser Glu Pro Tyr Ile Leu Thr Asn Arg Gln
    530                 535                 540


<210> SEQ ID NO 51
<211> LENGTH: 572
<212> TYPE: PRT
<213> ORGANISM: Bovine parainfluenza virus 3

<400> SEQUENCE: 51

Met Glu Tyr Trp Lys His Thr Asn Ser Ile Asn Asn Thr Asn Asn Glu
1               5                   10                  15

Thr Glu Thr Ala Arg Gly Lys His Ser Ser Lys Val Thr Asn Ile Ile
            20                  25                  30

Met Tyr Thr Phe Trp Thr Ile Thr Leu Thr Ile Leu Ser Val Ile Phe
        35                  40                  45

Ile Met Ile Leu Thr Asn Leu Ile Gln Glu Asn Asn His Asn Lys Leu
    50                  55                  60

Met Leu Gln Glu Ile Arg Lys Glu Phe Ala Ala Ile Asp Thr Lys Ile
65                  70                  75                  80

Gln Arg Thr Ser Asp Asp Ile Gly Thr Ser Ile Gln Ser Gly Ile Asn
                85                  90                  95

Thr Arg Leu Leu Thr Ile Gln Ser His Val Gln Asn Tyr Ile Pro Leu
            100                 105                 110

Ser Leu Thr Gln Gln Met Ser Asp Leu Arg Lys Phe Ile Asn Asp Leu
        115                 120                 125

Thr Asn Lys Arg Glu His Gln Glu Val Pro Ile Gln Arg Met Thr His
    130                 135                 140

Asp Arg Gly Ile Glu Pro Leu Asn Pro Asn Lys Phe Trp Arg Cys Thr
145                 150                 155                 160

Ser Gly Asn Pro Ser Leu Thr Ser Ser Pro Lys Ile Arg Leu Ile Pro
                165                 170                 175

Gly Pro Gly Leu Leu Ala Thr Ser Thr Thr Val Asn Gly Cys Ile Arg
            180                 185                 190

Ile Pro Ser Leu Val Ile Asn His Leu Ile Tyr Ala Tyr Thr Ser Asn
        195                 200                 205

Leu Ile Thr Gln Gly Cys Gln Asp Ile Gly Lys Ser Tyr Gln Val Leu
    210                 215                 220

Gln Ile Gly Ile Ile Thr Ile Asn Ser Asp Leu Val Pro Asp Leu Asn
225                 230                 235                 240

Pro Arg Val Thr His Thr Phe Asn Ile Asp Asp Asn Arg Arg Ser Cys
                245                 250                 255

Ser Leu Ala Leu Leu Asn Thr Asp Val Tyr Gln Leu Cys Ser Thr Pro
            260                 265                 270

Lys Val Asp Glu Arg Ser Asp Tyr Ala Ser Thr Gly Ile Glu Asp Ile
        275                 280                 285

Val Leu Asp Ile Val Thr Asn Asn Gly Leu Ile Ile Thr Thr Arg Phe
    290                 295                 300

Thr Asn Asn Asn Ile Thr Phe Asp Lys Pro Tyr Ala Ala Leu Tyr Pro
305                 310                 315                 320

Ser Val Gly Pro Gly Ile Tyr Tyr Lys Asp Lys Val Ile Phe Leu Gly
                325                 330                 335

Tyr Gly Gly Leu Glu His Glu Glu Asn Gly Asp Val Ile Cys Asn Thr
            340                 345                 350
```

```
Thr Gly Cys Pro Gly Lys Thr Gln Arg Asp Cys Asn Gln Ala Ser Tyr
        355                 360                 365

Ser Pro Trp Phe Ser Asn Arg Arg Met Val Asn Ser Ile Ile Val Val
    370                 375                 380

Asp Lys Gly Ile Asp Ala Thr Phe Ser Leu Arg Val Trp Thr Ile Pro
385                 390                 395                 400

Met Ser Gln Asn Tyr Trp Gly Ser Glu Gly Arg Leu Leu Leu Leu Gly
                405                 410                 415

Asp Arg Ile Tyr Ile Tyr Thr Arg Ser Thr Ser Trp His Ser Lys Leu
            420                 425                 430

Gln Leu Gly Val Ile Asp Ile Ser Asp Tyr Thr Asn Ile Arg Ile Asn
        435                 440                 445

Trp Thr Trp His Asn Val Leu Ser Arg Pro Gly Asn Asp Glu Cys Pro
    450                 455                 460

Trp Gly His Ser Cys Pro Asp Gly Cys Ile Thr Gly Val Tyr Thr Asp
465                 470                 475                 480

Ala Tyr Pro Leu Asn Pro Ser Gly Ser Val Val Ser Ser Val Ile Leu
                485                 490                 495

Asp Ser Gln Lys Ser Arg Glu Asn Pro Ile Ile Thr Tyr Ser Thr Ala
            500                 505                 510

Thr Asn Arg Ile Asn Glu Leu Ala Ile Tyr Asn Arg Thr Leu Pro Ala
        515                 520                 525

Ala Tyr Thr Thr Thr Asn Cys Ile Thr His Tyr Asp Lys Gly Tyr Cys
    530                 535                 540

Phe His Ile Val Glu Ile Asn His Arg Ser Leu Asn Thr Phe Gln Pro
545                 550                 555                 560

Met Leu Phe Lys Thr Glu Val Pro Lys Asn Cys Ser
                565                 570


<210> SEQ ID NO 52
<211> LENGTH: 2233
<212> TYPE: PRT
<213> ORGANISM: Bovine parainfluenza virus 3

<400> SEQUENCE: 52

Met Asp Thr Glu Ser His Ser Gly Thr Thr Ser Asp Ile Leu Tyr Pro
1               5                   10                  15

Glu Cys His Leu Asn Ser Pro Ile Val Lys Gly Lys Ile Ala Gln Leu
            20                  25                  30

His Thr Ile Met Ser Leu Pro Gln Pro Tyr Asp Met Asp Asp Asp Ser
        35                  40                  45

Ile Leu Ile Ile Thr Arg Gln Lys Ile Lys Leu Asn Lys Leu Asp Lys
    50                  55                  60

Arg Gln Arg Ser Ile Arg Lys Leu Arg Ser Val Leu Met Glu Arg Val
65                  70                  75                  80

Ser Asp Leu Gly Lys Tyr Thr Phe Ile Arg Tyr Pro Glu Met Ser Ser
                85                  90                  95

Glu Met Phe Gln Leu Cys Ile Pro Gly Ile Asn Asn Lys Ile Asn Glu
            100                 105                 110

Leu Leu Ser Lys Ala Ser Lys Thr Tyr Asn Gln Met Thr Asp Gly Leu
        115                 120                 125

Arg Asp Leu Trp Val Thr Ile Leu Ser Lys Leu Ala Ser Lys Asn Asp
    130                 135                 140
```

```
Gly Ser Asn Tyr Asp Ile Asn Glu Asp Ile Ser Asn Ile Ser Asn Val
145                 150                 155                 160

His Met Thr Tyr Gln Ser Asp Lys Trp Tyr Asn Pro Phe Lys Thr Trp
                165                 170                 175

Phe Thr Ile Lys Tyr Asp Met Arg Arg Leu Gln Lys Ala Lys Asn Glu
            180                 185                 190

Ile Thr Phe Asn Arg His Lys Asp Tyr Asn Leu Leu Glu Asp Gln Lys
        195                 200                 205

Asn Ile Leu Leu Ile His Pro Glu Leu Val Leu Ile Leu Asp Lys Gln
    210                 215                 220

Asn Tyr Asn Gly Tyr Ile Met Thr Pro Glu Leu Val Leu Met Tyr Cys
225                 230                 235                 240

Asp Val Val Glu Gly Arg Trp Asn Ile Ser Ser Cys Ala Lys Leu Asp
                245                 250                 255

Pro Lys Leu Gln Ser Met Tyr Tyr Lys Gly Asn Asn Leu Trp Glu Ile
            260                 265                 270

Ile Asp Gly Leu Phe Ser Thr Leu Gly Glu Arg Thr Phe Asp Ile Ile
        275                 280                 285

Ser Leu Leu Glu Pro Leu Ala Leu Ser Leu Ile Gln Thr Tyr Asp Pro
    290                 295                 300

Val Lys Gln Leu Arg Gly Ala Phe Leu Asn His Val Leu Ser Glu Met
305                 310                 315                 320

Glu Leu Ile Phe Ala Ala Glu Cys Thr Thr Glu Glu Ile Pro Asn Val
                325                 330                 335

Asp Tyr Ile Asp Lys Ile Leu Asp Val Phe Lys Glu Ser Thr Ile Asp
            340                 345                 350

Glu Ile Ala Glu Ile Phe Ser Phe Phe Arg Thr Phe Gly His Pro Pro
        355                 360                 365

Leu Glu Ala Ser Ile Ala Ala Glu Lys Val Arg Lys Tyr Met Tyr Thr
    370                 375                 380

Glu Lys Cys Leu Lys Phe Asp Thr Ile Asn Lys Cys His Ala Ile Phe
385                 390                 395                 400

Cys Thr Ile Ile Ile Asn Gly Tyr Arg Glu Arg His Gly Gly Gln Trp
                405                 410                 415

Pro Pro Val Thr Leu Pro Val His Ala His Glu Phe Ile Ile Asn Ala
            420                 425                 430

Tyr Gly Ser Asn Ser Ala Ile Ser Tyr Glu Asn Ala Val Asp Tyr Tyr
        435                 440                 445

Lys Ser Phe Ile Gly Ile Lys Phe Asp Lys Phe Ile Glu Pro Gln Leu
    450                 455                 460

Asp Glu Asp Leu Thr Ile Tyr Met Lys Asp Lys Ala Leu Ser Pro Lys
465                 470                 475                 480

Lys Ser Asn Trp Asp Thr Val Tyr Pro Ala Ser Asn Leu Leu Tyr Arg
                485                 490                 495

Thr Asn Val Ser His Asp Ser Arg Arg Leu Val Glu Val Phe Ile Ala
            500                 505                 510

Asp Ser Lys Phe Asp Pro His Gln Val Leu Asp Tyr Val Glu Ser Gly
        515                 520                 525

Tyr Trp Leu Asp Asp Pro Glu Phe Asn Ile Ser Tyr Ser Leu Lys Glu
    530                 535                 540

Lys Glu Ile Lys Gln Glu Gly Arg Leu Phe Ala Lys Met Thr Tyr Lys
545                 550                 555                 560
```

-continued

```
Met Arg Ala Thr Gln Val Leu Ser Glu Thr Leu Leu Ala Asn Asn Ile
                565                 570                 575

Gly Lys Phe Phe Gln Glu Asn Gly Met Val Lys Gly Glu Ile Glu Leu
            580                 585                 590

Leu Lys Arg Leu Thr Thr Ile Ser Met Ser Gly Val Pro Arg Tyr Asn
        595                 600                 605

Glu Val Tyr Asn Asn Ser Lys Ser His Thr Glu Glu Leu Gln Ala Tyr
    610                 615                 620

Asn Ala Ile Ser Ser Ser Asn Leu Ser Ser Asn Gln Lys Ser Lys Lys
625                 630                 635                 640

Phe Glu Phe Lys Ser Thr Asp Ile Tyr Asn Asp Gly Tyr Glu Thr Val
                645                 650                 655

Ser Cys Phe Leu Thr Thr Asp Leu Lys Lys Tyr Cys Leu Asn Trp Arg
            660                 665                 670

Tyr Glu Ser Thr Ala Leu Phe Gly Asp Thr Cys Asn Gln Ile Phe Gly
        675                 680                 685

Leu Lys Glu Leu Phe Asn Trp Leu His Pro Arg Leu Glu Lys Ser Thr
    690                 695                 700

Ile Tyr Val Gly Asp Pro Tyr Cys Pro Pro Ser Asp Ile Glu His Leu
705                 710                 715                 720

Pro Leu Asp Asp His Pro Asp Ser Gly Phe Tyr Val His Asn Pro Lys
                725                 730                 735

Gly Gly Ile Glu Gly Phe Cys Gln Lys Leu Trp Thr Leu Ile Ser Ile
            740                 745                 750

Ser Ala Ile His Leu Ala Ala Val Lys Ile Gly Val Arg Val Thr Ala
        755                 760                 765

Met Val Gln Gly Asp Asn Gln Ala Ile Ala Val Thr Thr Arg Val Pro
    770                 775                 780

Asn Asn Tyr Asp Tyr Lys Val Lys Lys Glu Ile Val Tyr Lys Asp Val
785                 790                 795                 800

Val Arg Phe Phe Asp Ser Leu Arg Glu Val Met Asp Asp Leu Gly His
                805                 810                 815

Glu Leu Lys Leu Asn Glu Thr Ile Ile Ser Ser Lys Met Phe Ile Tyr
            820                 825                 830

Ser Lys Arg Ile Tyr Tyr Asp Gly Arg Ile Leu Pro Gln Ala Leu Lys
        835                 840                 845

Ala Leu Ser Arg Cys Val Phe Trp Ser Glu Thr Ile Ile Asp Glu Thr
    850                 855                 860

Arg Ser Ala Ser Ser Asn Leu Ala Thr Ser Phe Ala Lys Ala Ile Glu
865                 870                 875                 880

Asn Gly Tyr Ser Pro Val Leu Gly Tyr Val Cys Ser Ile Phe Lys Asn
                885                 890                 895

Ile Gln Gln Leu Tyr Ile Ala Leu Gly Met Asn Ile Asn Pro Thr Ile
            900                 905                 910

Thr Gln Asn Ile Lys Asp Gln Tyr Phe Arg Asn Ile His Trp Met Gln
        915                 920                 925

Tyr Ala Ser Leu Ile Pro Ala Ser Val Gly Gly Phe Asn Tyr Met Ala
    930                 935                 940

Met Ser Arg Cys Phe Val Arg Asn Ile Gly Asp Pro Thr Val Ala Ala
945                 950                 955                 960

Leu Ala Asp Ile Lys Arg Phe Ile Lys Ala Asn Leu Leu Asp Arg Gly
                965                 970                 975
```

-continued

```
Val Leu Tyr Arg Ile Met Asn Gln Glu Pro Gly Glu Ser Ser Phe Leu
            980                 985                 990

Asp Trp Ala Ser Asp Pro Tyr Ser  Cys Asn Leu Pro Gln  Ser Gln Asn
        995                 1000                1005

Ile Thr  Thr Met Ile Lys Asn  Ile Thr Ala Arg Asn  Val Leu Gln
    1010                 1015                 1020

Asp Ser  Pro Asn Pro Leu Leu  Ser Gly Leu Phe Thr  Ser Thr Met
    1025                 1030                 1035

Ile Glu  Glu Asp Glu Glu Leu  Ala Glu Phe Leu Met  Asp Arg Arg
    1040                 1045                 1050

Ile Ile  Leu Pro Arg Val Ala  His Asp Ile Leu Asp  Asn Ser Leu
    1055                 1060                 1065

Thr Gly  Ile Arg Asn Ala Ile  Ala Gly Met Leu Asp  Thr Thr Lys
    1070                 1075                 1080

Ser Leu  Ile Arg Val Gly Ile  Ser Arg Gly Gly Leu  Thr Tyr Asn
    1085                 1090                 1095

Leu Leu  Arg Lys Ile Ser Asn  Tyr Asp Leu Val Gln  Tyr Glu Thr
    1100                 1105                 1110

Leu Ser  Lys Thr Leu Arg Leu  Ile Val Ser Asp Lys  Ile Lys Tyr
    1115                 1120                 1125

Glu Asp  Met Cys Ser Val Asp  Leu Ala Ile Ser Leu  Arg Gln Lys
    1130                 1135                 1140

Met Trp  Met His Leu Ser Gly  Gly Arg Met Ile Asn  Gly Leu Glu
    1145                 1150                 1155

Thr Pro  Asp Pro Leu Glu Leu  Leu Ser Gly Val Ile  Ile Thr Gly
    1160                 1165                 1170

Ser Glu  His Cys Arg Ile Cys  Tyr Ser Thr Glu Gly  Glu Ser Pro
    1175                 1180                 1185

Tyr Thr  Trp Met Tyr Leu Pro  Gly Asn Leu Asn Ile  Gly Ser Ala
    1190                 1195                 1200

Glu Thr  Gly Ile Ala Ser Leu  Arg Val Pro Tyr Phe  Gly Ser Val
    1205                 1210                 1215

Thr Asp  Glu Arg Ser Glu Ala  Gln Leu Gly Tyr Ile  Lys Asn Leu
    1220                 1225                 1230

Ser Lys  Pro Ala Lys Ala Ala  Ile Arg Ile Ala Met  Ile Tyr Thr
    1235                 1240                 1245

Trp Ala  Phe Gly Asn Asp Glu  Ile Ser Trp Met Glu  Ala Ser Gln
    1250                 1255                 1260

Ile Ala  Gln Thr Arg Ala Asn  Phe Thr Leu Asp Ser  Leu Lys Ile
    1265                 1270                 1275

Leu Thr  Pro Val Thr Thr Ser  Thr Asn Leu Ser His  Arg Leu Lys
    1280                 1285                 1290

Asp Thr  Ala Thr Gln Met Lys  Phe Ser Ser Thr Ser  Leu Ile Arg
    1295                 1300                 1305

Val Ser  Arg Phe Ile Thr Ile  Ser Asn Asp Asn Met  Ser Ile Lys
    1310                 1315                 1320

Glu Ala  Asn Glu Thr Lys Asp  Thr Asn Leu Ile Tyr  Gln Gln Val
    1325                 1330                 1335

Met Leu  Thr Gly Leu Ser Val  Phe Glu Tyr Leu Phe  Arg Leu Glu
    1340                 1345                 1350

Glu Ser  Thr Gly His Asn Pro  Met Val Met His Leu  His Ile Glu
    1355                 1360                 1365
```

-continued

```
Asp Gly  Cys Cys Ile Lys Glu  Ser Tyr Asn Asp Glu  His Ile Asn
    1370                 1375                 1380

Pro Glu  Ser Thr Leu Glu Leu  Ile Lys Tyr Pro Glu  Ser Asn Glu
    1385                 1390                 1395

Phe Ile  Tyr Asp Lys Asp Pro  Leu Lys Asp Ile Asp  Leu Ser Lys
    1400                 1405                 1410

Leu Met  Val Ile Arg Asp His  Ser Tyr Thr Ile Asp  Met Asn Tyr
    1415                 1420                 1425

Trp Asp  Asp Thr Asp Ile Val  His Ala Ile Ser Ile  Cys Thr Ala
    1430                 1435                 1440

Val Thr  Ile Ala Asp Thr Met  Ser Gln Leu Asp Arg  Asp Asn Leu
    1445                 1450                 1455

Lys Glu  Leu Val Val Ile Ala  Asn Asp Asp Asp Ile  Asn Ser Leu
    1460                 1465                 1470

Ile Thr  Glu Phe Leu Thr Leu  Asp Ile Leu Val Phe  Leu Lys Thr
    1475                 1480                 1485

Phe Gly  Gly Leu Leu Val Asn  Gln Phe Ala Tyr Thr  Leu Tyr Gly
    1490                 1495                 1500

Leu Lys  Ile Glu Gly Arg Asp  Pro Ile Trp Asp Tyr  Ile Met Arg
    1505                 1510                 1515

Thr Leu  Lys Asp Thr Ser His  Ser Val Leu Lys Val  Leu Ser Asn
    1520                 1525                 1530

Ala Leu  Ser His Pro Lys Val  Phe Lys Arg Phe Trp  Asp Cys Gly
    1535                 1540                 1545

Val Leu  Asn Pro Ile Tyr Gly  Pro Asn Thr Ala Ser  Gln Asp Gln
    1550                 1555                 1560

Val Lys  Leu Ala Leu Ser Ile  Cys Glu Tyr Ser Leu  Asp Leu Phe
    1565                 1570                 1575

Met Arg  Glu Trp Leu Asn Gly  Ala Ser Leu Glu Ile  Tyr Ile Cys
    1580                 1585                 1590

Asp Ser  Asp Met Glu Ile Ala  Asn Asp Arg Arg Gln  Ala Phe Leu
    1595                 1600                 1605

Ser Arg  His Leu Ala Phe Val  Cys Cys Leu Ala Glu  Ile Ala Ser
    1610                 1615                 1620

Phe Gly  Pro Asn Leu Leu Asn  Leu Thr Tyr Leu Glu  Arg Leu Asp
    1625                 1630                 1635

Glu Leu  Lys Gln Tyr Leu Asp  Leu Asn Ile Lys Glu  Asp Pro Thr
    1640                 1645                 1650

Leu Lys  Tyr Val Gln Val Ser  Gly Leu Leu Ile Lys  Ser Phe Pro
    1655                 1660                 1665

Ser Thr  Val Thr Tyr Val Arg  Lys Thr Ala Ile Lys  Tyr Leu Arg
    1670                 1675                 1680

Ile Arg  Gly Ile Asn Pro Pro  Glu Thr Ile Glu Asp  Trp Asp Pro
    1685                 1690                 1695

Ile Glu  Asp Glu Asn Ile Leu  Asp Asn Ile Val Lys  Thr Val Asn
    1700                 1705                 1710

Asp Asn  Cys Ser Asp Asn Gln  Lys Arg Asn Lys Ser  Ser Tyr Phe
    1715                 1720                 1725

Trp Gly  Leu Ala Leu Lys Asn  Tyr Gln Val Val Lys  Ile Arg Ser
    1730                 1735                 1740

Ile Thr  Ser Asp Ser Glu Val  Asn Glu Ala Ser Asn  Val Thr Thr
    1745                 1750                 1755
```

```
His Gly  Met Thr Leu Pro Gln  Gly Gly Ser Tyr Leu  Ser His Gln
    1760                 1765                 1770

Leu Arg  Leu Phe Gly Val Asn  Ser Thr Ser Cys Leu  Lys Ala Leu
    1775                 1780                 1785

Glu Leu  Ser Gln Ile Leu Met  Arg Glu Val Lys Lys  Asp Lys Asp
    1790                 1795                 1800

Arg Leu  Phe Leu Gly Glu Gly  Ala Gly Ala Met Leu  Ala Cys Tyr
    1805                 1810                 1815

Asp Ala  Thr Leu Gly Pro Ala  Ile Asn Tyr Tyr Asn  Ser Gly Leu
    1820                 1825                 1830

Asn Ile  Thr Asp Val Ile Gly  Gln Arg Glu Leu Lys  Ile Phe Pro
    1835                 1840                 1845

Ser Glu  Val Ser Leu Val Gly  Lys Lys Leu Gly Asn  Val Thr Gln
    1850                 1855                 1860

Ile Leu  Asn Arg Val Arg Val  Leu Phe Asn Gly Asn  Pro Asn Ser
    1865                 1870                 1875

Thr Trp  Ile Gly Asn Met Glu  Cys Glu Ser Leu Ile  Trp Ser Glu
    1880                 1885                 1890

Leu Asn  Asp Lys Ser Ile Gly  Leu Val His Cys Asp  Met Glu Gly
    1895                 1900                 1905

Ala Ile  Gly Lys Ser Glu Glu  Thr Val Leu His Glu  His Tyr Ser
    1910                 1915                 1920

Ile Ile  Arg Ile Thr Tyr Leu  Ile Gly Asp Asp Asp  Val Val Leu
    1925                 1930                 1935

Val Ser  Lys Ile Ile Pro Thr  Ile Thr Pro Asn Trp  Ser Lys Ile
    1940                 1945                 1950

Leu Tyr  Leu Tyr Lys Leu Tyr  Trp Lys Asp Val Ser  Val Val Ser
    1955                 1960                 1965

Leu Lys  Thr Ser Asn Pro Ala  Ser Thr Glu Leu Tyr  Leu Ile Ser
    1970                 1975                 1980

Lys Asp  Ala Tyr Cys Thr Val  Met Glu Pro Ser Asn  Leu Val Leu
    1985                 1990                 1995

Ser Lys  Leu Lys Arg Ile Ser  Ser Ile Glu Glu Asn  Asn Leu Leu
    2000                 2005                 2010

Lys Trp  Ile Ile Leu Ser Lys  Arg Lys Asn Asn Glu  Trp Leu Gln
    2015                 2020                 2025

His Glu  Ile Lys Glu Gly Glu  Arg Asp Tyr Gly Ile  Met Arg Pro
    2030                 2035                 2040

Tyr His  Thr Ala Leu Gln Ile  Phe Gly Phe Gln Ile  Asn Leu Asn
    2045                 2050                 2055

His Leu  Ala Arg Glu Phe Leu  Ser Thr Pro Asp Leu  Thr Asn Ile
    2060                 2065                 2070

Asn Asn  Ile Ile Gln Ser Phe  Thr Arg Thr Ile Lys  Asp Val Met
    2075                 2080                 2085

Phe Glu  Trp Val Asn Ile Thr  His Asp Asn Lys Arg  His Lys Leu
    2090                 2095                 2100

Gly Gly  Arg Tyr Asn Leu Phe  Pro Leu Lys Asn Lys  Gly Lys Leu
    2105                 2110                 2115

Arg Leu  Leu Ser Arg Arg Leu  Val Leu Ser Trp Ile  Ser Leu Ser
    2120                 2125                 2130

Leu Ser  Thr Arg Leu Leu Thr  Gly Arg Phe Pro Asp  Glu Lys Phe
    2135                 2140                 2145
```

```
Glu Asn  Arg Ala Gln Thr Gly  Tyr Val Ser Leu Ala  Asp Ile Asp
    2150                 2155                 2160

Leu Glu  Ser Leu Lys Leu Leu  Ser Arg Asn Ile Val  Lys Asn Tyr
    2165                 2170                 2175

Lys Glu  His Ile Gly Leu Ile  Ser Tyr Trp Phe Leu  Thr Lys Glu
    2180                 2185                 2190

Val Lys  Ile Leu Met Lys Leu  Ile Gly Gly Val Lys  Leu Leu Gly
    2195                 2200                 2205

Ile Pro  Lys Gln Tyr Lys Glu  Leu Glu Asp Arg Ser  Ser Gln Gly
    2210                 2215                 2220

Tyr Glu  Tyr Asp Asn Glu Phe  Asp Ile Asp
    2225                 2230
```

<210> SEQ ID NO 53
<211> LENGTH: 47
<212> TYPE: PRT
<213> ORGANISM: Bovine parainfluenza virus 3

<400> SEQUENCE: 53

```
Ile Thr Ile Ile Ile Val Met Ile Ile Ile Leu Val Ile Ile Asn Ile
1               5                   10                  15

Thr Ile Ile Val Val Ile Ile Lys Phe His Arg Ile Gln Gly Lys Asp
            20                  25                  30

Gln Asn Asp Lys Asn Ser Glu Pro Tyr Ile Leu Thr Asn Arg Gln
        35                  40                  45
```

<210> SEQ ID NO 54
<211> LENGTH: 10
<212> TYPE: DNA
<213> ORGANISM: Human parainfluenza virus 1

<400> SEQUENCE: 54
agggttaaag 10

<210> SEQ ID NO 55
<211> LENGTH: 12
<212> TYPE: DNA
<213> ORGANISM: Human parainfluenza virus 1

<400> SEQUENCE: 55
aagtaagaaa aa 12

<210> SEQ ID NO 56
<211> LENGTH: 10
<212> TYPE: DNA
<213> ORGANISM: Human parainfluenza virus 1

<400> SEQUENCE: 56
agggtgaatg 10

<210> SEQ ID NO 57
<211> LENGTH: 12
<212> TYPE: DNA
<213> ORGANISM: Human parainfluenza virus 1

<400> SEQUENCE: 57
aattaagaaa aa 12

<210> SEQ ID NO 58
<211> LENGTH: 10
<212> TYPE: DNA

<213> ORGANISM: Human parainfluenza virus 1

<400> SEQUENCE: 58
agggtcaaag 10

<210> SEQ ID NO 59
<211> LENGTH: 12
<212> TYPE: DNA
<213> ORGANISM: Human parainfluenza virus 1

<400> SEQUENCE: 59
aaataagaaa aa 12

<210> SEQ ID NO 60
<211> LENGTH: 10
<212> TYPE: DNA
<213> ORGANISM: Human parainfluenza virus 1

<400> SEQUENCE: 60
agggacaaag 10

<210> SEQ ID NO 61
<211> LENGTH: 10
<212> TYPE: DNA
<213> ORGANISM: Human parainfluenza virus 1

<400> SEQUENCE: 61
agggttaaag 10

<210> SEQ ID NO 62
<211> LENGTH: 12
<212> TYPE: DNA
<213> ORGANISM: Human parainfluenza virus 1

<400> SEQUENCE: 62
gaataagaaa aa 12

<210> SEQ ID NO 63
<211> LENGTH: 10
<212> TYPE: DNA
<213> ORGANISM: Human parainfluenza virus 1

<400> SEQUENCE: 63
agggttaatg 10

<210> SEQ ID NO 64
<211> LENGTH: 12
<212> TYPE: DNA
<213> ORGANISM: Human parainfluenza virus 1

<400> SEQUENCE: 64
tagtaagaaa aa 12

<210> SEQ ID NO 65
<211> LENGTH: 14
<212> TYPE: DNA
<213> ORGANISM: Human parainfluenza virus 2

<400> SEQUENCE: 65
agattccggt gccg 14

<210> SEQ ID NO 66
<211> LENGTH: 14

<212> TYPE: DNA
<213> ORGANISM: Human parainfluenza virus 2

<400> SEQUENCE: 66
aatttaagaa aaaa 14

<210> SEQ ID NO 67
<211> LENGTH: 17
<212> TYPE: DNA
<213> ORGANISM: Human parainfluenza virus 2

<400> SEQUENCE: 67
aggcccggac gggttag 17

<210> SEQ ID NO 68
<211> LENGTH: 14
<212> TYPE: DNA
<213> ORGANISM: Human parainfluenza virus 2

<400> SEQUENCE: 68
aatttaataa aaaa 14

<210> SEQ ID NO 69
<211> LENGTH: 12
<212> TYPE: DNA
<213> ORGANISM: Human parainfluenza virus 2

<400> SEQUENCE: 69
aggtccgaaa gc 12

<210> SEQ ID NO 70
<211> LENGTH: 15
<212> TYPE: DNA
<213> ORGANISM: Human parainfluenza virus 2

<400> SEQUENCE: 70
aatctaacaa aaaaa 15

<210> SEQ ID NO 71
<211> LENGTH: 12
<212> TYPE: DNA
<213> ORGANISM: Human parainfluenza virus 2

<400> SEQUENCE: 71
aggccaaatt at 12

<210> SEQ ID NO 72
<211> LENGTH: 14
<212> TYPE: DNA
<213> ORGANISM: Human parainfluenza virus 2

<400> SEQUENCE: 72
aatttaagaa aaaa 14

<210> SEQ ID NO 73
<211> LENGTH: 12
<212> TYPE: DNA
<213> ORGANISM: Human parainfluenza virus 2

<400> SEQUENCE: 73
aagcacgaac cc 12

<210> SEQ ID NO 74

<211> LENGTH: 14
<212> TYPE: DNA
<213> ORGANISM: Human parainfluenza virus 2

<400> SEQUENCE: 74
tatttaagaa aaaa 14

<210> SEQ ID NO 75
<211> LENGTH: 8
<212> TYPE: DNA
<213> ORGANISM: Human parainfluenza virus 2

<400> SEQUENCE: 75 aggccaga 8

<210> SEQ ID NO 76
<211> LENGTH: 13
<212> TYPE: DNA
<213> ORGANISM: Human parainfluenza virus 2

<400> SEQUENCE: 76
tatttaagaa aaa 13

<210> SEQ ID NO 77
<211> LENGTH: 12
<212> TYPE: DNA
<213> ORGANISM: Human parainfluenza virus 3

<400> SEQUENCE: 77
aggattaaag ac 12

<210> SEQ ID NO 78
<211> LENGTH: 12
<212> TYPE: DNA
<213> ORGANISM: Human parainfluenza virus 3

<400> SEQUENCE: 78
aaataagaaa aa 12

<210> SEQ ID NO 79
<211> LENGTH: 10
<212> TYPE: DNA
<213> ORGANISM: Human parainfluenza virus 3

<400> SEQUENCE: 79
aggattaaag 10

<210> SEQ ID NO 80
<211> LENGTH: 12
<212> TYPE: DNA
<213> ORGANISM: Human parainfluenza virus 3

<400> SEQUENCE: 80
aaataagaaa aa 12

<210> SEQ ID NO 81
<211> LENGTH: 10
<212> TYPE: DNA
<213> ORGANISM: Human parainfluenza virus 3

<400> SEQUENCE: 81
aggattaaag 10

-continued

<210> SEQ ID NO 82
<211> LENGTH: 20
<212> TYPE: DNA
<213> ORGANISM: Human parainfluenza virus 3

<400> SEQUENCE: 82
aaataaagga taatcaaaaa 20

<210> SEQ ID NO 83
<211> LENGTH: 10
<212> TYPE: DNA
<213> ORGANISM: Human parainfluenza virus 3

<400> SEQUENCE: 83
aggacaaaag 10

<210> SEQ ID NO 84
<211> LENGTH: 12
<212> TYPE: DNA
<213> ORGANISM: Human parainfluenza virus 3

<400> SEQUENCE: 84
aattataaaa aa 12

<210> SEQ ID NO 85
<211> LENGTH: 10
<212> TYPE: DNA
<213> ORGANISM: Human parainfluenza virus 3

<400> SEQUENCE: 85
aggagtaaag 10

<210> SEQ ID NO 86
<211> LENGTH: 12
<212> TYPE: DNA
<213> ORGANISM: Human parainfluenza virus 3

<400> SEQUENCE: 86
aaatataaaa aa 12

<210> SEQ ID NO 87
<211> LENGTH: 10
<212> TYPE: DNA
<213> ORGANISM: Human parainfluenza virus 3

<400> SEQUENCE: 87
aggagcaaag 10

<210> SEQ ID NO 88
<211> LENGTH: 13
<212> TYPE: DNA
<213> ORGANISM: Human parainfluenza virus 3

<400> SEQUENCE: 88
aaagtaagaa aaa 13

<210> SEQ ID NO 89
<211> LENGTH: 12
<212> TYPE: PRT
<213> ORGANISM: Bovine parainfluenza virus 3

<400> SEQUENCE: 89

Ala Gly Gly Ala Thr Thr Ala Ala Ala Gly Ala Ala
1 5 10

```
<210> SEQ ID NO 90
<211> LENGTH: 13
<212> TYPE: PRT
<213> ORGANISM: Bovine parainfluenza virus 3

<400> SEQUENCE: 90

Cys Ala Ala Gly Thr Ala Ala Gly Ala Ala Ala Ala Ala
1               5                   10


<210> SEQ ID NO 91
<211> LENGTH: 12
<212> TYPE: PRT
<213> ORGANISM: Bovine parainfluenza virus 3

<400> SEQUENCE: 91

Ala Gly Gly Ala Thr Thr Ala Ala Thr Gly Gly Ala
1               5                   10


<210> SEQ ID NO 92
<211> LENGTH: 13
<212> TYPE: PRT
<213> ORGANISM: Bovine parainfluenza virus 3

<400> SEQUENCE: 92

Thr Gly Ala Thr Thr Ala Ala Gly Ala Ala Ala Ala Ala
1               5                   10


<210> SEQ ID NO 93
<211> LENGTH: 12
<212> TYPE: PRT
<213> ORGANISM: Bovine parainfluenza virus 3

<400> SEQUENCE: 93

Ala Gly Gly Ala Thr Gly Ala Ala Ala Gly Gly Ala
1               5                   10


<210> SEQ ID NO 94
<211> LENGTH: 13
<212> TYPE: PRT
<213> ORGANISM: Bovine parainfluenza virus 3

<400> SEQUENCE: 94

Gly Ala Ala Ala Ala Ala Thr Cys Ala Ala Ala Ala Ala
1               5                   10


<210> SEQ ID NO 95
<211> LENGTH: 12
<212> TYPE: PRT
<213> ORGANISM: Bovine parainfluenza virus 3

<400> SEQUENCE: 95

Ala Gly Gly Ala Thr Cys Ala Ala Ala Gly Gly Gly
1               5                   10


<210> SEQ ID NO 96
<211> LENGTH: 14
<212> TYPE: PRT
<213> ORGANISM: Bovine parainfluenza virus 3

<400> SEQUENCE: 96

Ala Ala Ala Ala Gly Thr Ala Cys Ala Ala Ala Ala Ala Ala
1               5                   10
```

-continued

<210> SEQ ID NO 97
<211> LENGTH: 12
<212> TYPE: PRT
<213> ORGANISM: Bovine parainfluenza virus 3

<400> SEQUENCE: 97

```
Ala Gly Gly Ala Ala Cys Ala Ala Ala Gly Thr Thr
1               5                   10
```

<210> SEQ ID NO 98
<211> LENGTH: 14
<212> TYPE: PRT
<213> ORGANISM: Bovine parainfluenza virus 3

<400> SEQUENCE: 98

```
Gly Ala Ala Ala Thr Ala Ala Thr Ala Ala Ala Ala Ala Ala
1               5                   10
```

<210> SEQ ID NO 99
<211> LENGTH: 12
<212> TYPE: PRT
<213> ORGANISM: Bovine parainfluenza virus 3

<400> SEQUENCE: 99

```
Ala Gly Gly Ala Gly Ala Ala Ala Ala Gly Thr Gly
1               5                   10
```

<210> SEQ ID NO 100
<211> LENGTH: 13
<212> TYPE: PRT
<213> ORGANISM: Bovine parainfluenza virus 3

<400> SEQUENCE: 100

```
Ala Ala Ala Gly Thr Ala Ala Gly Ala Ala Ala Ala Ala
1               5                   10
```

<210> SEQ ID NO 101
<211> LENGTH: 572
<212> TYPE: PRT
<213> ORGANISM: Human parainfluenza virus 3

<400> SEQUENCE: 101

```
Met Glu Tyr Trp Lys His Thr Asn His Gly Lys Asp Ala Gly Asn Glu
1               5                   10                  15

Leu Glu Thr Ser Met Ala Thr His Gly Asn Lys Leu Thr Asn Lys Ile
            20                  25                  30

Ile Tyr Ile Leu Trp Thr Ile Ile Leu Val Leu Leu Ser Ile Val Phe
        35                  40                  45

Ile Ile Val Leu Ile Asn Ser Ile Lys Ser Glu Lys Ala His Glu Ser
    50                  55                  60

Leu Leu Gln Asp Ile Asn Asn Glu Phe Met Glu Ile Thr Glu Lys Ile
65                  70                  75                  80

Gln Met Ala Ser Asp Asn Thr Asn Asp Leu Ile Gln Ser Gly Val Asn
                85                  90                  95

Thr Arg Leu Leu Thr Ile Gln Ser His Val Gln Asn Tyr Ile Pro Ile
            100                 105                 110

Ser Leu Thr Gln Gln Met Ser Asp Leu Arg Lys Phe Ile Ser Glu Ile
        115                 120                 125

Thr Ile Arg Asn Asp Asn Gln Glu Val Leu Pro Gln Arg Ile Thr His
    130                 135                 140
```

```
Asp Val Gly Ile Lys Pro Leu Asn Pro Asp Asp Phe Trp Arg Cys Thr
145                 150                 155                 160

Ser Gly Leu Pro Ser Leu Met Lys Thr Pro Lys Ile Arg Leu Met Pro
                165                 170                 175

Gly Pro Gly Leu Leu Ala Met Pro Thr Thr Val Asp Gly Cys Val Arg
            180                 185                 190

Thr Pro Ser Leu Val Ile Asn Asp Leu Ile Tyr Ala Tyr Thr Ser Asn
        195                 200                 205

Leu Ile Thr Arg Gly Cys Gln Asp Ile Gly Lys Ser Tyr Gln Val Leu
    210                 215                 220

Gln Ile Gly Ile Ile Thr Val Asn Ser Asp Leu Val Pro Asp Leu Asn
225                 230                 235                 240

Pro Arg Ile Ser His Thr Phe Asn Ile Asn Asp Asn Arg Lys Ser Cys
                245                 250                 255

Ser Leu Ala Leu Leu Asn Ile Asp Val Tyr Gln Leu Cys Ser Thr Pro
            260                 265                 270

Lys Val Asp Glu Arg Ser Asp Tyr Ala Ser Ser Gly Ile Glu Asp Ile
        275                 280                 285

Val Leu Asp Ile Val Asn Tyr Asp Gly Ser Ile Ser Thr Thr Arg Phe
    290                 295                 300

Lys Asn Asn Asn Ile Ser Phe Asp Gln Pro Tyr Ala Ala Leu Tyr Pro
305                 310                 315                 320

Ser Val Gly Pro Gly Ile Tyr Tyr Lys Gly Lys Ile Ile Phe Leu Gly
                325                 330                 335

Tyr Gly Gly Leu Glu His Pro Ile Asn Glu Asn Val Ile Cys Asn Thr
            340                 345                 350

Thr Gly Cys Pro Gly Lys Thr Gln Arg Asp Cys Asn Gln Ala Ser His
        355                 360                 365

Ser Thr Trp Phe Ser Asp Arg Arg Met Val Asn Ser Ile Ile Val Val
    370                 375                 380

Asp Lys Gly Leu Asn Ser Ile Pro Lys Leu Lys Val Trp Thr Ile Ser
385                 390                 395                 400

Met Arg Gln Asn Tyr Trp Gly Ser Glu Gly Arg Leu Leu Leu Leu Gly
                405                 410                 415

Asn Lys Ile Tyr Ile Tyr Thr Arg Ser Thr Ser Trp His Ser Lys Leu
            420                 425                 430

Gln Leu Gly Ile Ile Asp Ile Thr Asp Tyr Ser Asp Ile Arg Ile Lys
        435                 440                 445

Trp Thr Trp His Asn Val Leu Ser Arg Pro Gly Asn Asn Glu Cys Pro
    450                 455                 460

Trp Gly His Ser Cys Pro Asp Gly Cys Ile Thr Gly Val Tyr Thr Asp
465                 470                 475                 480

Ala Tyr Pro Leu Asn Pro Thr Gly Ser Ile Val Ser Ser Val Ile Leu
                485                 490                 495

Asp Ser Gln Lys Ser Arg Val Asn Pro Val Ile Thr Tyr Ser Thr Ala
            500                 505                 510

Thr Glu Arg Val Asn Glu Leu Ala Ile Leu Asn Arg Thr Leu Ser Ala
        515                 520                 525

Gly Tyr Thr Thr Thr Ser Cys Ile Thr His Tyr Asn Lys Gly Tyr Cys
    530                 535                 540

Phe His Ile Val Glu Ile Asn His Lys Ser Leu Asn Thr Phe Gln Pro
545                 550                 555                 560
```

```
Met Leu Phe Lys Thr Glu Ile Pro Lys Ser Cys Ser
                565                 570


<210> SEQ ID NO 102
<211> LENGTH: 1719
<212> TYPE: PRT
<213> ORGANISM: Human parainfluenza virus 3

<400> SEQUENCE: 102

Ala Thr Gly Gly Ala Ala Thr Ala Cys Thr Gly Gly Ala Ala Gly Cys
1               5                   10                  15

Ala Thr Ala Cys Cys Ala Ala Thr Cys Ala Cys Gly Gly Ala Ala Ala
            20                  25                  30

Gly Gly Ala Thr Gly Cys Thr Gly Gly Thr Ala Ala Thr Gly Ala Gly
        35                  40                  45

Cys Thr Gly Gly Ala Gly Ala Cys Gly Thr Cys Thr Ala Thr Gly Gly
    50                  55                  60

Cys Thr Ala Cys Thr Cys Ala Thr Gly Gly Cys Ala Ala Cys Ala Ala
65                  70                  75                  80

Gly Cys Thr Cys Ala Cys Thr Ala Ala Thr Ala Ala Gly Ala Thr Ala
                85                  90                  95

Ala Thr Ala Thr Ala Cys Ala Thr Ala Thr Thr Ala Thr Gly Gly Ala
            100                 105                 110

Cys Ala Ala Thr Ala Ala Thr Cys Cys Thr Gly Gly Thr Gly Thr Thr
        115                 120                 125

Ala Thr Thr Ala Thr Cys Ala Ala Thr Ala Gly Thr Cys Thr Thr Cys
    130                 135                 140

Ala Thr Cys Ala Thr Ala Gly Thr Gly Cys Thr Ala Ala Thr Thr Ala
145                 150                 155                 160

Ala Thr Thr Cys Cys Ala Thr Cys Ala Ala Ala Ala Gly Thr Gly Ala
                165                 170                 175

Ala Ala Ala Gly Gly Cys Cys Cys Ala Cys Gly Ala Ala Thr Cys Ala
            180                 185                 190

Thr Thr Gly Cys Thr Gly Cys Ala Ala Gly Ala Cys Ala Thr Ala Ala
        195                 200                 205

Ala Thr Ala Ala Thr Gly Ala Gly Thr Thr Thr Ala Thr Gly Gly Ala
    210                 215                 220

Ala Ala Thr Thr Ala Cys Ala Gly Ala Ala Ala Ala Gly Ala Thr Cys
225                 230                 235                 240

Cys Ala Ala Ala Thr Gly Gly Cys Ala Thr Cys Gly Gly Ala Thr Ala
                245                 250                 255

Ala Thr Ala Cys Cys Ala Ala Thr Gly Ala Thr Cys Thr Ala Ala Thr
            260                 265                 270

Ala Cys Ala Gly Thr Cys Ala Gly Gly Ala Gly Thr Gly Ala Ala Thr
        275                 280                 285

Ala Cys Ala Ala Gly Gly Cys Thr Thr Cys Thr Thr Ala Cys Ala Ala
    290                 295                 300

Thr Thr Cys Ala Gly Ala Gly Thr Cys Ala Thr Gly Thr Cys Cys Ala
305                 310                 315                 320

Gly Ala Ala Thr Thr Ala Cys Ala Thr Ala Cys Cys Ala Ala Thr Ala
                325                 330                 335

Thr Cys Ala Thr Thr Gly Ala Cys Ala Cys Ala Ala Cys Ala Gly Ala
            340                 345                 350

Thr Gly Thr Cys Ala Gly Ala Thr Cys Thr Thr Ala Gly Gly Ala Ala
        355                 360                 365
```

-continued

```
Ala Thr Thr Cys Ala Thr Thr Ala Gly Thr Gly Ala Ala Ala Thr Thr
    370                 375                 380

Ala Cys Ala Ala Thr Thr Ala Gly Ala Ala Ala Thr Gly Ala Thr Ala
385                 390                 395                 400

Ala Thr Cys Ala Ala Gly Ala Ala Gly Thr Gly Cys Thr Gly Cys Cys
                405                 410                 415

Ala Cys Ala Ala Ala Gly Ala Ala Thr Ala Ala Cys Ala Cys Ala Thr
            420                 425                 430

Gly Ala Thr Gly Thr Ala Gly Gly Thr Ala Thr Ala Ala Ala Ala Cys
        435                 440                 445

Cys Thr Thr Thr Ala Ala Ala Thr Cys Cys Ala Gly Ala Thr Gly Ala
    450                 455                 460

Thr Thr Thr Thr Thr Gly Gly Ala Gly Ala Thr Gly Cys Ala Cys Gly
465                 470                 475                 480

Thr Cys Thr Gly Gly Thr Cys Thr Thr Cys Cys Ala Thr Cys Thr Thr
                485                 490                 495

Thr Ala Ala Thr Gly Ala Ala Ala Ala Cys Thr Cys Cys Ala Ala Ala
            500                 505                 510

Ala Ala Thr Ala Ala Gly Gly Thr Thr Ala Ala Thr Gly Cys Cys Ala
        515                 520                 525

Gly Gly Gly Cys Cys Gly Gly Gly Ala Thr Thr Ala Thr Thr Ala Gly
    530                 535                 540

Cys Thr Ala Thr Gly Cys Cys Ala Ala Cys Gly Ala Cys Thr Gly Thr
545                 550                 555                 560

Thr Gly Ala Thr Gly Gly Cys Thr Gly Thr Gly Thr Thr Ala Gly Ala
                565                 570                 575

Ala Cys Thr Cys Cys Gly Thr Cys Thr Thr Thr Ala Gly Thr Thr Ala
            580                 585                 590

Thr Ala Ala Ala Thr Gly Ala Thr Cys Thr Gly Ala Thr Thr Thr Ala
        595                 600                 605

Thr Gly Cys Thr Thr Ala Thr Ala Cys Cys Thr Cys Ala Ala Ala Thr
    610                 615                 620

Cys Thr Ala Ala Thr Thr Ala Cys Thr Cys Gly Ala Gly Gly Thr Thr
625                 630                 635                 640

Gly Thr Cys Ala Gly Gly Ala Thr Ala Thr Ala Gly Gly Ala Ala Ala
                645                 650                 655

Ala Thr Cys Ala Thr Ala Thr Cys Ala Ala Gly Thr Cys Thr Thr Ala
            660                 665                 670

Cys Ala Gly Ala Thr Ala Gly Gly Gly Ala Thr Ala Ala Thr Ala Ala
        675                 680                 685

Cys Thr Gly Thr Ala Ala Ala Cys Thr Cys Ala Gly Ala Cys Thr Thr
    690                 695                 700

Gly Gly Thr Ala Cys Cys Thr Gly Ala Cys Thr Thr Ala Ala Ala Thr
705                 710                 715                 720

Cys Cys Thr Ala Gly Gly Ala Thr Cys Thr Cys Thr Cys Ala Thr Ala
                725                 730                 735

Cys Cys Thr Thr Thr Ala Ala Cys Ala Thr Ala Ala Ala Thr Gly Ala
            740                 745                 750

Cys Ala Ala Thr Ala Gly Gly Ala Ala Gly Thr Cys Ala Thr Gly Thr
        755                 760                 765

Thr Cys Thr Cys Thr Ala Gly Cys Ala Cys Thr Cys Cys Thr Ala Ala
    770                 775                 780
```

```
Ala Thr Ala Thr Ala Gly Ala Thr Gly Thr Ala Thr Ala Thr Cys Ala
785                 790                 795                 800

Ala Cys Thr Gly Thr Gly Thr Thr Cys Ala Ala Cys Thr Cys Cys Cys
                805                 810                 815

Ala Ala Ala Gly Thr Thr Gly Ala Thr Gly Ala Ala Ala Gly Ala Thr
            820                 825                 830

Cys Ala Gly Ala Thr Thr Ala Thr Gly Cys Ala Thr Cys Ala Thr Cys
        835                 840                 845

Ala Gly Gly Cys Ala Thr Ala Gly Ala Ala Gly Ala Thr Ala Thr Thr
    850                 855                 860

Gly Thr Ala Cys Thr Thr Gly Ala Thr Ala Thr Thr Gly Thr Cys Ala
865                 870                 875                 880

Ala Thr Thr Ala Thr Gly Ala Thr Gly Gly Thr Thr Cys Ala Ala Thr
                885                 890                 895

Cys Thr Cys Ala Ala Cys Ala Ala Cys Ala Ala Gly Ala Thr Thr Thr
            900                 905                 910

Ala Ala Gly Ala Ala Thr Ala Ala Thr Ala Ala Cys Ala Thr Ala Ala
        915                 920                 925

Gly Cys Thr Thr Thr Gly Ala Thr Cys Ala Ala Cys Cys Ala Thr Ala
    930                 935                 940

Thr Gly Cys Thr Gly Cys Ala Cys Thr Ala Thr Ala Cys Cys Cys Ala
945                 950                 955                 960

Thr Cys Thr Gly Thr Thr Gly Gly Ala Cys Cys Ala Gly Gly Gly Ala
                965                 970                 975

Thr Ala Thr Ala Cys Thr Ala Cys Ala Ala Ala Gly Gly Cys Ala Ala
            980                 985                 990

Ala Ala Thr Ala Ala Thr Ala Thr  Thr Thr Cys Thr Cys  Gly Gly Gly
        995                 1000                1005

Thr Ala  Thr Gly Gly Ala Gly  Gly Thr Cys Thr Thr  Gly Ala Ala
    1010                1015                1020

Cys Ala  Thr Cys Cys Ala Ala  Thr Ala Ala Ala Thr  Gly Ala Gly
    1025                1030                1035

Ala Ala  Thr Gly Thr Ala Ala  Thr Cys Thr Gly Cys  Ala Ala Cys
    1040                1045                1050

Ala Cys  Ala Ala Cys Thr Gly  Gly Gly Thr Gly Cys  Cys Cys Cys
    1055                1060                1065

Gly Gly  Gly Ala Ala Ala Ala  Cys Ala Cys Ala Gly  Ala Gly Ala
    1070                1075                1080

Gly Ala  Cys Thr Gly Thr Ala  Ala Thr Cys Ala Ala  Gly Cys Ala
    1085                1090                1095

Thr Cys  Thr Cys Ala Thr Ala  Gly Thr Ala Cys Thr  Thr Gly Gly
    1100                1105                1110

Thr Thr  Thr Thr Cys Ala Gly  Ala Thr Ala Gly Gly  Ala Gly Gly
    1115                1120                1125

Ala Thr  Gly Gly Thr Cys Ala  Ala Cys Thr Cys Cys  Ala Thr Cys
    1130                1135                1140

Ala Thr  Thr Gly Thr Thr Gly  Thr Thr Gly Ala Cys  Ala Ala Ala
    1145                1150                1155

Gly Gly  Cys Thr Thr Ala Ala  Ala Cys Thr Cys Ala  Ala Thr Thr
    1160                1165                1170

Cys Cys  Ala Ala Ala Ala Thr  Thr Gly Ala Ala Ala  Gly Thr Ala
    1175                1180                1185
```

-continued

```
Thr Gly  Gly Ala Cys Gly Ala  Thr Ala Thr Cys Thr  Ala Thr Gly
    1190                 1195                 1200

Cys Gly  Ala Cys Ala Ala Ala  Ala Thr Thr Ala Cys  Thr Gly Gly
    1205                 1210                 1215

Gly Gly  Gly Thr Cys Ala Gly  Ala Ala Gly Gly Ala  Ala Gly Gly
    1220                 1225                 1230

Thr Thr  Ala Cys Thr Thr Cys  Thr Ala Cys Thr Ala  Gly Gly Thr
    1235                 1240                 1245

Ala Ala  Cys Ala Ala Gly Ala  Thr Cys Thr Ala Thr  Ala Thr Ala
    1250                 1255                 1260

Thr Ala  Thr Ala Cys Ala Ala  Gly Ala Thr Cys Thr  Ala Cys Ala
    1265                 1270                 1275

Ala Gly  Thr Thr Gly Gly Cys  Ala Thr Ala Gly Cys  Ala Ala Gly
    1280                 1285                 1290

Thr Thr  Ala Cys Ala Ala Thr  Thr Ala Gly Gly Ala  Ala Thr Ala
    1295                 1300                 1305

Ala Thr  Thr Gly Ala Thr Ala  Thr Thr Ala Cys Thr  Gly Ala Thr
    1310                 1315                 1320

Thr Ala  Cys Ala Gly Thr Gly  Ala Thr Ala Thr Ala  Ala Gly Gly
    1325                 1330                 1335

Ala Thr  Ala Ala Ala Ala Thr  Gly Gly Ala Cys Ala  Thr Gly Gly
    1340                 1345                 1350

Cys Ala  Thr Ala Ala Thr Gly  Thr Gly Cys Thr Ala  Thr Cys Ala
    1355                 1360                 1365

Ala Gly  Ala Cys Cys Ala Gly  Gly Ala Ala Ala Cys  Ala Ala Thr
    1370                 1375                 1380

Gly Ala  Ala Thr Gly Thr Cys  Cys Ala Thr Gly Gly  Gly Gly Ala
    1385                 1390                 1395

Cys Ala  Thr Thr Cys Ala Thr  Gly Thr Cys Cys Ala  Gly Ala Thr
    1400                 1405                 1410

Gly Gly  Ala Thr Gly Thr Ala  Thr Ala Ala Cys Ala  Gly Gly Ala
    1415                 1420                 1425

Gly Thr  Ala Thr Ala Thr Ala  Cys Thr Gly Ala Thr  Gly Cys Ala
    1430                 1435                 1440

Thr Ala  Thr Cys Cys Ala Cys  Thr Cys Ala Ala Thr  Cys Cys Cys
    1445                 1450                 1455

Ala Cys  Ala Gly Gly Gly Ala  Gly Cys Ala Thr Thr  Gly Thr Gly
    1460                 1465                 1470

Thr Cys  Ala Thr Cys Thr Gly  Thr Cys Ala Thr Ala  Thr Thr Ala
    1475                 1480                 1485

Gly Ala  Cys Thr Cys Ala Cys  Ala Ala Ala Ala Ala  Thr Cys Gly
    1490                 1495                 1500

Ala Gly  Ala Gly Thr Gly Ala  Ala Cys Cys Cys Ala  Gly Thr Cys
    1505                 1510                 1515

Ala Thr  Ala Ala Cys Thr Thr  Ala Cys Thr Cys Ala  Ala Cys Ala
    1520                 1525                 1530

Gly Cys  Ala Ala Cys Cys Gly  Ala Ala Ala Gly Ala  Gly Thr Ala
    1535                 1540                 1545

Ala Ala  Cys Gly Ala Gly Cys  Thr Gly Gly Cys Cys  Ala Thr Cys
    1550                 1555                 1560

Cys Thr  Ala Ala Ala Cys Ala  Gly Ala Ala Cys Ala  Cys Thr Cys
    1565                 1570                 1575
```

```
Thr Cys  Ala Gly Cys Thr Gly  Gly Ala Thr Ala Thr  Ala Cys Ala
    1580                1585                1590

Ala Cys  Ala Ala Cys Ala Ala  Gly Cys Thr Gly Cys  Ala Thr Thr
    1595                1600                1605

Ala Cys  Ala Cys Ala Cys Thr  Ala Thr Ala Ala Cys  Ala Ala Ala
    1610                1615                1620

Gly Gly  Ala Thr Ala Thr Thr  Gly Thr Thr Thr Thr  Cys Ala Thr
    1625                1630                1635

Ala Thr  Ala Gly Thr Ala Gly  Ala Ala Ala Thr Ala  Ala Ala Thr
    1640                1645                1650

Cys Ala  Thr Ala Ala Ala Ala  Gly Cys Thr Thr Ala  Ala Ala Cys
    1655                1660                1665

Ala Cys  Ala Thr Thr Thr Cys  Ala Ala Cys Cys Cys  Ala Thr Gly
    1670                1675                1680

Thr Thr  Gly Thr Thr Cys Ala  Ala Ala Ala Cys Ala  Gly Ala Gly
    1685                1690                1695

Ala Thr  Thr Cys Cys Ala Ala  Ala Ala Ala Gly Cys  Thr Gly Cys
    1700                1705                1710

Ala Gly  Thr Thr Ala Ala
    1715


<210> SEQ ID NO 103
<211> LENGTH: 65
<212> TYPE: PRT
<213> ORGANISM: Sendai virus

<400> SEQUENCE: 103

Val Ile Thr Ile Ile Val Val Met Val Val Ile Leu Val Val Ile Ile
1               5                   10                  15

Val Ile Ile Ile Val Leu Tyr Arg Leu Arg Arg Ser Met Leu Met Gly
            20                  25                  30

Asn Pro Asp Asp Arg Ile Pro Arg Asp Thr Tyr Thr Leu Glu Pro Lys
        35                  40                  45

Ile Arg His Met Tyr Thr Asn Gly Gly Phe Asp Ala Met Ala Glu Lys
    50                  55                  60

Arg
65


<210> SEQ ID NO 104
<211> LENGTH: 49
<212> TYPE: PRT
<213> ORGANISM: Newcastle disease virus

<400> SEQUENCE: 104

Ile Val Leu Thr Ile Ile Ser Leu Val Phe Gly Ile Leu Ser Leu Ile
1               5                   10                  15

Leu Ala Cys Tyr Leu Met Tyr Lys Gln Lys Ala Gln Gln Lys Thr Leu
            20                  25                  30

Leu Trp Leu Gly Asn Asn Thr Leu Asp Gln Met Arg Ala Thr Thr Lys
        35                  40                  45

Met


<210> SEQ ID NO 105
<211> LENGTH: 594
<212> TYPE: PRT
<213> ORGANISM: Artificial sequence
<220> FEATURE:
<223> OTHER INFORMATION: Recombinant RSV F
```

<400> SEQUENCE: 105

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400
```

Asp Val Ser Ser Ser Val Ile Thr Ser Leu Gly Ala Ile Val Ser Cys
405 410 415

Tyr Gly Lys Thr Lys Cys Thr Ala Ser Asn Lys Asn Arg Gly Ile Ile
420 425 430

Lys Thr Phe Ser Asn Gly Cys Asp Tyr Val Ser Asn Lys Gly Val Asp
435 440 445

Thr Val Ser Val Gly Asn Thr Leu Tyr Tyr Val Asn Lys Gln Glu Gly
450 455 460

Lys Ser Leu Tyr Val Lys Gly Glu Pro Ile Ile Asn Phe Tyr Asp Pro
465 470 475 480

Leu Val Phe Pro Ser Asp Glu Phe Asp Ala Ser Ile Ser Gln Val Asn
485 490 495

Glu Lys Ile Asn Gln Ser Leu Ala Phe Ile Arg Lys Ser Asp Glu Leu
500 505 510

Leu His Asn Val Asn Ala Gly Lys Ser Thr Thr Asn Ile Met Ile Thr
515 520 525

Thr Ile Ile Ile Val Ile Ile Val Ile Leu Leu Ser Leu Ile Ala Val
530 535 540

Gly Leu Leu Leu Tyr Cys Leu Tyr Arg Leu Arg Arg Ser Met Leu Met
545 550 555 560

Gly Asn Pro Asp Asp Arg Ile Pro Arg Asp Thr Tyr Thr Leu Glu Pro
565 570 575

Lys Ile Arg His Met Tyr Thr Asn Gly Gly Phe Asp Ala Met Ala Glu
580 585 590

Lys Arg

<210> SEQ ID NO 106
<211> LENGTH: 594
<212> TYPE: PRT
<213> ORGANISM: Artificial sequence
<220> FEATURE:
<223> OTHER INFORMATION: Recombinant RSV F

<400> SEQUENCE: 106

Met Glu Leu Leu Ile Leu Lys Ala Asn Ala Ile Thr Thr Ile Leu Thr
1 5 10 15

Ala Val Thr Phe Cys Phe Ala Ser Gly Gln Asn Ile Thr Glu Glu Phe
20 25 30

Tyr Gln Ser Thr Cys Ser Ala Val Ser Lys Gly Tyr Leu Ser Ala Leu
35 40 45

Arg Thr Gly Trp Tyr Thr Ser Val Ile Thr Ile Glu Leu Ser Asn Ile
50 55 60

Lys Glu Asn Lys Cys Asn Gly Thr Asp Ala Lys Val Lys Leu Ile Lys
65 70 75 80

Gln Glu Leu Asp Lys Tyr Lys Asn Ala Val Thr Glu Leu Gln Leu Leu
85 90 95

Met Gln Ser Thr Pro Ala Thr Asn Asn Arg Ala Arg Arg Glu Leu Pro
100 105 110

Arg Phe Met Asn Tyr Thr Leu Asn Asn Ala Lys Lys Thr Asn Val Thr
115 120 125

Leu Ser Lys Lys Arg Lys Arg Arg Phe Leu Gly Phe Leu Leu Gly Val
130 135 140

Gly Ser Ala Ile Ala Ser Gly Val Ala Val Ser Lys Val Leu His Leu
145 150 155 160

-continued

```
Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu His Asn Val Asn Ala Gly Lys Ser Thr Thr Asn Ile Met Ile Thr
        515                 520                 525

Thr Val Ile Thr Ile Ile Val Val Met Val Val Ile Leu Val Val Ile
    530                 535                 540

Ile Val Ile Ile Ile Val Leu Tyr Arg Leu Arg Arg Ser Met Leu Met
545                 550                 555                 560

Gly Asn Pro Asp Asp Arg Ile Pro Arg Asp Thr Tyr Thr Leu Glu Pro
                565                 570                 575
```

```
Lys Ile Arg His Met Tyr Thr Asn Gly Gly Phe Asp Ala Met Ala Glu
            580                 585                 590

Lys Arg


<210> SEQ ID NO 107
<211> LENGTH: 594
<212> TYPE: PRT
<213> ORGANISM: Artificial sequence
<220> FEATURE:
<223> OTHER INFORMATION: Recombinant RSV F

<400> SEQUENCE: 107

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Cys Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Phe Lys Val
            180                 185                 190

Leu Asp Leu Lys Asn Tyr Ile Asp Lys Gln Leu Leu Pro Ile Leu Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Cys Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335
```

```
Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu His Asn Val Asn Ala Gly Lys Ser Thr Thr Asn Ile Met Ile Thr
        515                 520                 525

Thr Ile Ile Ile Val Ile Ile Val Ile Leu Leu Ser Leu Ile Ala Val
    530                 535                 540

Gly Leu Leu Leu Tyr Cys Leu Tyr Arg Leu Arg Arg Ser Met Leu Met
545                 550                 555                 560

Gly Asn Pro Asp Asp Arg Ile Pro Arg Asp Thr Tyr Thr Leu Glu Pro
                565                 570                 575

Lys Ile Arg His Met Tyr Thr Asn Gly Gly Phe Asp Ala Met Ala Glu
            580                 585                 590

Lys Arg


<210> SEQ ID NO 108
<211> LENGTH: 594
<212> TYPE: PRT
<213> ORGANISM: Artificial sequence
<220> FEATURE:
<223> OTHER INFORMATION: Recombinant RSV F

<400> SEQUENCE: 108

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95
```

-continued

```
Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Cys Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Phe Lys Val
            180                 185                 190

Leu Asp Leu Lys Asn Tyr Ile Asp Lys Gln Leu Leu Pro Ile Leu Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Cys Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510
```

```
Leu His Asn Val Asn Ala Gly Lys Ser Thr Thr Asn Ile Met Ile Thr
        515                 520                 525

Thr Val Ile Thr Ile Ile Val Val Met Val Val Ile Leu Val Val Ile
    530                 535                 540

Ile Val Ile Ile Ile Val Leu Tyr Arg Leu Arg Arg Ser Met Leu Met
545                 550                 555                 560

Gly Asn Pro Asp Asp Arg Ile Pro Arg Asp Thr Tyr Thr Leu Glu Pro
                565                 570                 575

Lys Ile Arg His Met Tyr Thr Asn Gly Gly Phe Asp Ala Met Ala Glu
            580                 585                 590

Lys Arg


<210> SEQ ID NO 109
<211> LENGTH: 578
<212> TYPE: PRT
<213> ORGANISM: Artificial sequence
<220> FEATURE:
<223> OTHER INFORMATION: Recombinant RSV F

<400> SEQUENCE: 109

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270
```

Leu Met Ser Asn Asn Val Gln Ile Val Arg Gln Gln Ser Tyr Ser Ile
275 280 285

Met Ser Ile Ile Lys Glu Glu Val Leu Ala Tyr Val Val Gln Leu Pro
290 295 300

Leu Tyr Gly Val Ile Asp Thr Pro Cys Trp Lys Leu His Thr Ser Pro
305 310 315 320

Leu Cys Thr Thr Asn Thr Lys Glu Gly Ser Asn Ile Cys Leu Thr Arg
325 330 335

Thr Asp Arg Gly Trp Tyr Cys Asp Asn Ala Gly Ser Val Ser Phe Phe
340 345 350

Pro Gln Ala Glu Thr Cys Lys Val Gln Ser Asn Arg Val Phe Cys Asp
355 360 365

Thr Met Asn Ser Leu Thr Leu Pro Ser Glu Val Asn Leu Cys Asn Val
370 375 380

Asp Ile Phe Asn Pro Lys Tyr Asp Cys Lys Ile Met Thr Ser Lys Thr
385 390 395 400

Asp Val Ser Ser Ser Val Ile Thr Ser Leu Gly Ala Ile Val Ser Cys
405 410 415

Tyr Gly Lys Thr Lys Cys Thr Ala Ser Asn Lys Asn Arg Gly Ile Ile
420 425 430

Lys Thr Phe Ser Asn Gly Cys Asp Tyr Val Ser Asn Lys Gly Val Asp
435 440 445

Thr Val Ser Val Gly Asn Thr Leu Tyr Tyr Val Asn Lys Gln Glu Gly
450 455 460

Lys Ser Leu Tyr Val Lys Gly Glu Pro Ile Ile Asn Phe Tyr Asp Pro
465 470 475 480

Leu Val Phe Pro Ser Asp Glu Phe Asp Ala Ser Ile Ser Gln Val Asn
485 490 495

Glu Lys Ile Asn Gln Ser Leu Ala Phe Ile Arg Lys Ser Asp Glu Leu
500 505 510

Leu His Asn Val Asn Ala Gly Lys Ser Thr Thr Asn Ile Met Ile Thr
515 520 525

Thr Ile Ile Ile Val Ile Ile Val Ile Leu Leu Ser Leu Ile Ala Val
530 535 540

Gly Leu Leu Leu Tyr Cys Met Tyr Lys Gln Lys Ala Gln Gln Lys Thr
545 550 555 560

Leu Leu Trp Leu Gly Asn Asn Thr Leu Asp Gln Met Arg Ala Thr Thr
565 570 575

Lys Met

<210> SEQ ID NO 110
<211> LENGTH: 578
<212> TYPE: PRT
<213> ORGANISM: Artificial sequence
<220> FEATURE:
<223> OTHER INFORMATION: Recombinant RSV F

<400> SEQUENCE: 110

Met Glu Leu Leu Ile Leu Lys Ala Asn Ala Ile Thr Thr Ile Leu Thr
1 5 10 15

Ala Val Thr Phe Cys Phe Ala Ser Gly Gln Asn Ile Thr Glu Glu Phe
20 25 30

Tyr Gln Ser Thr Cys Ser Ala Val Ser Lys Gly Tyr Leu Ser Ala Leu
35 40 45

-continued

```
Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
    450                 455                 460
```

```
Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu His Asn Val Asn Ala Gly Lys Ser Thr Thr Asn Ile Met Ile Thr
        515                 520                 525

Thr Ile Val Leu Thr Ile Ile Ser Leu Val Phe Gly Ile Leu Ser Leu
    530                 535                 540

Ile Leu Ala Cys Tyr Leu Met Tyr Lys Gln Lys Ala Gln Gln Lys Thr
545                 550                 555                 560

Leu Leu Trp Leu Gly Asn Asn Thr Leu Asp Gln Met Arg Ala Thr Thr
                565                 570                 575

Lys Met


<210> SEQ ID NO 111
<211> LENGTH: 49
<212> TYPE: DNA
<213> ORGANISM: Artificial sequence
<220> FEATURE:
<223> OTHER INFORMATION: Oligonucleotide primer

<400> SEQUENCE: 111

gcggccgccg tacgctatca gttggagaag gcgatattgt tgatgccgg                 49


<210> SEQ ID NO 112
<211> LENGTH: 578
<212> TYPE: PRT
<213> ORGANISM: Artificial sequence
<220> FEATURE:
<223> OTHER INFORMATION: Recombinant RSV F

<400> SEQUENCE: 112

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Cys Lys Val Leu His Leu
145                 150                 155                 160

Glu Gly Glu Val Asn Lys Ile Lys Ser Ala Leu Leu Ser Thr Asn Lys
                165                 170                 175
```

-continued

```
Ala Val Val Ser Leu Ser Asn Gly Val Ser Val Leu Thr Phe Lys Val
            180                 185                 190

Leu Asp Leu Lys Asn Tyr Ile Asp Lys Gln Leu Leu Pro Ile Leu Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Cys Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu His Asn Val Asn Ala Gly Lys Ser Thr Thr Asn Ile Met Ile Thr
        515                 520                 525

Thr Ile Ile Ile Val Ile Ile Val Ile Leu Leu Ser Leu Ile Ala Val
    530                 535                 540

Gly Leu Leu Leu Tyr Cys Met Tyr Lys Gln Lys Ala Gln Gln Lys Thr
545                 550                 555                 560

Leu Leu Trp Leu Gly Asn Asn Thr Leu Asp Gln Met Arg Ala Thr Thr
                565                 570                 575

Lys Met
```

<210> SEQ ID NO 113

<211> LENGTH: 594
<212> TYPE: PRT
<213> ORGANISM: Artificial sequence
<220> FEATURE:
<223> OTHER INFORMATION: Recombinant RSV F

<400> SEQUENCE: 113

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Cys Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Phe Lys Val
            180                 185                 190

Leu Asp Leu Lys Asn Tyr Ile Asp Lys Gln Leu Leu Pro Ile Leu Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Cys Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
    370                 375                 380
```

```
Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu His Asn Val Asn Ala Gly Lys Ser Thr Thr Asn Ile Met Ile Thr
        515                 520                 525

Thr Val Ile Thr Ile Ile Val Val Met Val Val Ile Leu Val Val Ile
    530                 535                 540

Ile Val Ile Ile Ile Val Leu Tyr Arg Leu Arg Arg Ser Met Leu Met
545                 550                 555                 560

Gly Asn Pro Asp Asp Arg Ile Pro Arg Asp Thr Tyr Thr Leu Glu Pro
                565                 570                 575

Lys Ile Arg His Met Tyr Thr Asn Gly Gly Phe Asp Ala Met Ala Glu
            580                 585                 590

Lys Arg


<210> SEQ ID NO 114
<211> LENGTH: 199
<212> TYPE: PRT
<213> ORGANISM: Human parainfluenza virus 3

<400> SEQUENCE: 114

Met Leu Lys Thr Ile Lys Ser Trp Ile Leu Gly Lys Arg Asn Gln Glu
1               5                   10                  15

Ile Asn Gln Leu Ile Ser Pro Arg Pro Ser Thr Ser Leu Asn Ser Tyr
            20                  25                  30

Ser Ala Pro Thr Pro Lys Lys Thr Tyr Arg Lys Thr Thr Gln Ser Thr
        35                  40                  45

Gln Glu Pro Ser Asn Ser Val Pro Pro Ser Val Asn Gln Lys Ser Asn
    50                  55                  60

Gln Gln Lys Gln Val Arg Lys Ile Val Asp Gln Leu Thr Lys Ile Asp
65                  70                  75                  80

Ser Pro Gly His His Thr Asn Val Gln Gln Lys Gln Lys Ile Glu Ile
                85                  90                  95

Leu Ile Arg Lys Leu Tyr Arg Glu Asp Leu Gly Glu Glu Ala Ala Gln
            100                 105                 110

Ile Val Glu Leu Arg Leu Trp Ser Leu Glu Glu Ser Pro Glu Ala Ser
        115                 120                 125

Gln Ile Leu Lys Met Glu Pro Lys Thr Arg Arg Ile Leu Ile Ser Met
    130                 135                 140

Lys Leu Glu Arg Trp Ile Arg Thr Leu Leu Arg Gly Lys Cys Asp Asn
145                 150                 155                 160
```

```
Leu Gln Met Phe Gln Ala Arg Tyr Gln Glu Val Met Thr Tyr Leu Gln
                165                 170                 175

Gln Asn Lys Val Glu Thr Val Ile Met Glu Glu Ala Trp Asn Leu Ser
            180                 185                 190

Val His Leu Ile Gln Asp Gln
        195


<210> SEQ ID NO 115
<211> LENGTH: 201
<212> TYPE: PRT
<213> ORGANISM: Bovine parainfluenza virus 3

<400> SEQUENCE: 115

Met Phe Lys Thr Ile Lys Ser Trp Ile Leu Gly Lys Arg Asp Gln Glu
1               5                   10                  15

Ile Asn His Leu Thr Ser His Arg Pro Ser Thr Ser Leu Asn Ser Tyr
            20                  25                  30

Ser Ala Pro Thr Pro Lys Arg Thr Arg Gln Thr Ala Met Lys Ser Thr
        35                  40                  45

Gln Glu Pro Gln Asp Leu Ala Arg Gln Ser Thr Asn Leu Asn Pro Lys
    50                  55                  60

Gln Gln Lys Gln Ala Arg Lys Ile Val Asp Gln Leu Thr Lys Ile Asp
65                  70                  75                  80

Ser Leu Gly His His Thr Asn Val Pro Gln Arg Gln Lys Ile Glu Met
                85                  90                  95

Leu Ile Arg Arg Leu Tyr Arg Glu Asp Ile Gly Glu Glu Ala Ala Gln
            100                 105                 110

Ile Val Glu Leu Arg Leu Trp Ser Leu Glu Glu Ser Pro Glu Ala Ala
        115                 120                 125

Gln Ile Leu Thr Met Glu Pro Lys Ser Arg Lys Ile Leu Ile Thr Met
    130                 135                 140

Lys Leu Glu Arg Trp Ile Arg Thr Leu Leu Arg Gly Lys Cys Asp Asn
145                 150                 155                 160

Leu Lys Met Phe Gln Ser Arg Tyr Gln Glu Val Met Pro Phe Leu Gln
                165                 170                 175

Gln Asn Lys Met Glu Thr Val Met Met Glu Glu Ala Trp Asn Leu Ser
            180                 185                 190

Val His Leu Ile Gln Asp Ile Pro Val
        195                 200


<210> SEQ ID NO 116
<211> LENGTH: 412
<212> TYPE: PRT
<213> ORGANISM: Bovine parainfluenza virus 3

<400> SEQUENCE: 116

Met Glu Asp Asn Val Gln Asn Asn Gln Ile Met Asp Ser Trp Glu Glu
1               5                   10                  15

Gly Ser Gly Asp Lys Ser Ser Asp Ile Ser Ser Ala Leu Asp Ile Ile
            20                  25                  30

Glu Phe Ile Leu Ser Thr Asp Ser Gln Glu Asn Thr Ala Asp Ser Asn
        35                  40                  45

Glu Ile Asn Thr Gly Thr Thr Arg Leu Ser Thr Thr Ile Tyr Gln Pro
    50                  55                  60

Glu Ser Lys Thr Thr Glu Thr Ser Lys Glu Asn Ser Gly Pro Ala Asn
65                  70                  75                  80
```

```
Lys Asn Arg Gln Phe Gly Ala Ser His Glu Arg Ala Thr Glu Thr Lys
                85                  90                  95

Asp Arg Asn Val Asn Gln Glu Thr Val Gln Gly Gly Tyr Arg Arg Gly
            100                 105                 110

Ser Ser Pro Asp Ser Arg Thr Glu Thr Met Val Thr Arg Arg Ile Ser
        115                 120                 125

Arg Ser Ser Pro Asp Pro Asn Asn Gly Thr Gln Ile Gln Glu Asp Ile
    130                 135                 140

Asp Tyr Asn Glu Val Gly Glu Met Asp Lys Asp Ser Thr Lys Arg Glu
145                 150                 155                 160

Met Arg Gln Phe Lys Asp Val Pro Val Lys Val Ser Gly Ser Asp Ala
                165                 170                 175

Ile Pro Pro Thr Lys Gln Asp Gly Asp Gly Asp Asp Gly Arg Gly Leu
            180                 185                 190

Glu Ser Ile Ser Thr Phe Asp Ser Gly Tyr Thr Ser Ile Val Thr Ala
        195                 200                 205

Ala Thr Leu Asp Asp Glu Glu Glu Leu Leu Met Lys Asn Asn Arg Pro
    210                 215                 220

Arg Lys Tyr Gln Ser Thr Pro Gln Asn Ser Asp Lys Gly Ile Lys Lys
225                 230                 235                 240

Gly Gly Trp Lys Ala Lys Arg His Arg Gln Thr Ile Ile Asn Ile Gly
                245                 250                 255

Leu Arg Thr Gln Leu Gln Arg Ile Glu Glu Glu Pro Glu Asn Pro Gln
            260                 265                 270

Ser Gln His Glu Tyr Arg Arg Thr Asn Lys Thr Thr Glu Trp Ile Pro
        275                 280                 285

Gly Glu Glu Asn His Ile Leu Glu His Pro Gln Gln Arg Glu Arg Gln
    290                 295                 300

Ser Asn Arg Ile Asn Lys Pro Asn Pro Ser Asp Ile Asn Leu Gly Thr
305                 310                 315                 320

Glu Pro His Asn Gly Thr Lys Gln Asn Asn Leu Arg Thr Lys Asp Gln
                325                 330                 335

Asp Thr Lys Asp Gly Trp Lys Gly Lys Arg Gly His Arg Arg Glu His
            340                 345                 350

Ser Ile Tyr Arg Lys Gly Asp Tyr Ile Ile Thr Glu Ser Trp Cys Asn
        355                 360                 365

Pro Ile Cys Ser Lys Ile Arg Pro Ile Pro Arg Gln Glu Ser Cys Val
    370                 375                 380

Cys Gly Glu Cys Pro Lys Gln Cys Arg Tyr Cys Ile Lys Asp Arg Leu
385                 390                 395                 400

Pro Ser Arg Phe Asp Asp Arg Ser Val Asn Gly Ser
                405                 410
```

<210> SEQ ID NO 117
<211> LENGTH: 46
<212> TYPE: DNA
<213> ORGANISM: human parainfluenza virus 2

<400> SEQUENCE: 117
ttaaaagaag ttaagtaaaa tttaaagaac acaatagaga aaacct 46

<210> SEQ ID NO 118
<211> LENGTH: 28
<212> TYPE: DNA
<213> ORGANISM: human parainfluenza virus 2

<400> SEQUENCE: 118
ctaaacattc aataataaat caaagttc 28

<210> SEQ ID NO 119
<211> LENGTH: 8
<212> TYPE: DNA
<213> ORGANISM: human parainfluenza virus 2

<400> SEQUENCE: 119 cctaaaat 8

<210> SEQ ID NO 120
<211> LENGTH: 42
<212> TYPE: DNA
<213> ORGANISM: human parainfluenza virus 2

<400> SEQUENCE: 120
taatctttat ataatgtaac aatactacta agattataat at 42

<210> SEQ ID NO 121
<211> LENGTH: 34
<212> TYPE: DNA
<213> ORGANISM: Artificial sequence
<220> FEATURE:
<223> OTHER INFORMATION: Oligonucleotide primer

<400> SEQUENCE: 121
aagaagacca agttgagcca gaagaggtac gaag 34

<210> SEQ ID NO 122
<211> LENGTH: 34
<212> TYPE: DNA
<213> ORGANISM: Artificial sequence
<220> FEATURE:
<223> OTHER INFORMATION: Oligonucleotide primer

<400> SEQUENCE: 122
cttcgtacct cttctggctc aacttggtct tctt 34

<210> SEQ ID NO 123
<211> LENGTH: 51
<212> TYPE: DNA
<213> ORGANISM: Artificial sequence
<220> FEATURE:
<223> OTHER INFORMATION: Oligonucleotide primer

<400> SEQUENCE: 123
ccagctaaca taggagggtt caacgcgatg tctacagcta gatgttttgt c 51

<210> SEQ ID NO 124
<211> LENGTH: 51
<212> TYPE: DNA
<213> ORGANISM: Artificial sequence
<220> FEATURE:
<223> OTHER INFORMATION: Oligonucleotide primer

<400> SEQUENCE: 124
gacaaaacat ctagctgtag acatcgcgtt gaaccctcct atgttagctg g 51

<210> SEQ ID NO 125
<211> LENGTH: 12
<212> TYPE: DNA
<213> ORGANISM: Human parainfluenza virus 1

<400> SEQUENCE: 125
aagtaagaaa aa 12

<210> SEQ ID NO 126
<211> LENGTH: 10
<212> TYPE: DNA
<213> ORGANISM: Human parainfluenza virus 1

<400> SEQUENCE: 126
agggtgaatg 10

<210> SEQ ID NO 127
<211> LENGTH: 46
<212> TYPE: DNA
<213> ORGANISM: Artificial sequence
<220> FEATURE:
<223> OTHER INFORMATION: Oligonucleotide primer

<400> SEQUENCE: 127
acgcgtcccg ggaacaatgg aactgctgat cctgaaggcc aacgcc 46

<210> SEQ ID NO 128
<211> LENGTH: 73
<212> TYPE: DNA
<213> ORGANISM: Artificial sequence
<220> FEATURE:
<223> OTHER INFORMATION: Oligonucleotide primer

<400> SEQUENCE: 128
acgcgtcgta cgcattcacc ctaagttttt cttactttct atcagttgga gaaggcgata 60
ttgttgatgc cgg 73

<210> SEQ ID NO 129
<211> LENGTH: 48
<212> TYPE: DNA
<213> ORGANISM: Artificial sequence
<220> FEATURE:
<223> OTHER INFORMATION: Oligonucleotide primer

<400> SEQUENCE: 129
ggcgcgcccc cgggaacaat ggaactgctg atcctgaagg ccaacgcc 48

<210> SEQ ID NO 130
<211> LENGTH: 79
<212> TYPE: DNA
<213> ORGANISM: Artificial sequence
<220> FEATURE:
<223> OTHER INFORMATION: Oligonucleotide primer

<400> SEQUENCE: 130
ggcgcgcccg tacgccattc accctaagtt tttcttactt gattctatca gttggagaag 60
gcgatattgt tgatgccgg 79

<210> SEQ ID NO 131
<211> LENGTH: 72
<212> TYPE: DNA
<213> ORGANISM: Artificial sequence
<220> FEATURE:
<223> OTHER INFORMATION: Oligonucleotide primer

<400> SEQUENCE: 131
gcggccgccc gggaagtaag aaaaacttag ggtgaatgaa caatggaact gctgatcctg 60
aaggccaacg cc 72

<210> SEQ ID NO 132
<211> LENGTH: 31
<212> TYPE: PRT
<213> ORGANISM: Artificial sequence
<220> FEATURE:
<223> OTHER INFORMATION: linker and foldon domain

<400> SEQUENCE: 132

```
Ser Ala Ile Gly Gly Tyr Ile Pro Glu Ala Pro Arg Asp Gly Gln Ala
1               5                   10                  15

Tyr Val Arg Lys Asp Gly Glu Trp Val Leu Leu Ser Thr Phe Leu
            20                  25                  30
```

<210> SEQ ID NO 133
<211> LENGTH: 586
<212> TYPE: PRT
<213> ORGANISM: Artificial sequence
<220> FEATURE:
<223> OTHER INFORMATION: Recombinant RSV F

<400> SEQUENCE: 133

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Cys Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Phe Lys Val
            180                 185                 190

Leu Asp Leu Lys Asn Tyr Ile Asp Lys Gln Leu Leu Pro Ile Leu Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270
```

-continued

Leu Met Ser Asn Asn Val Gln Ile Val Arg Gln Gln Ser Tyr Ser Ile
        275                 280                 285

Met Cys Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu His Asn Val Asn Ala Gly Lys Ser Thr Thr Asn Ile Met Ile Thr
        515                 520                 525

Thr Ile Ile Ile Val Ile Ile Val Ile Leu Leu Ser Leu Ile Ala Val
    530                 535                 540

Gly Leu Leu Leu Tyr Cys Arg Val Arg Arg Leu Leu Val Met Ile Asn
545                 550                 555                 560

Ser Thr His Asn Ser Pro Val Asn Ala Tyr Thr Leu Glu Ser Arg Met
                565                 570                 575

Arg Asn Pro Tyr Met Gly Asn Asn Ser Asn
            580                 585

<210> SEQ ID NO 134
<211> LENGTH: 1764
<212> TYPE: DNA
<213> ORGANISM: Artificial sequence
<220> FEATURE:
<223> OTHER INFORMATION: recombinant RSV F

<400> SEQUENCE: 134
atggaactgc tgatcctgaa agccaacgct attactacta tcctgaccgc cgtgacattt 60
tgcttcgcat ctggacagaa cattactgag gaattctacc agtcaacatg cagcgccgtg 120
tccaaaggat acctgagcgc cctgcggacc ggctggtata catcagtgat tactatcgag 180
ctgtccaaca tcaaggaaaa caaatgtaat gggaccgacg caaaggtgaa actgatcaag 240

-continued

```
caggagctgg ataagtacaa aaatgccgtg acagaactgc agctgctgat gcagtccaca    300

ccagcaacta acaatcgcgc ccggagagag ctgccccggt tcatgaacta taccctgaac    360

aatgctaaga aaaccaatgt gacactgtcc aagaaacgca agaggcgctt cctgggattt    420

ctgctgggcg tggggtctgc catcgctagt ggagtggccg tctgcaaagt cctgcacctg    480

gagggcgaag tgaacaagat caaaagcgcc ctgctgtcca ctaacaaggc agtggtcagt    540

ctgtcaaatg gcgtgtccgt cctgaccttc aaggtgctgg acctgaaaaa ttatattgat    600

aagcagctgc tgcctatcct gaacaaacag agctgctcca tttctaatat cgagacagtg    660

atcgaattcc agcagaagaa caatagactg ctggagatta ccagagagtt cagcgtgaac    720

gccggcgtca ccacacccgt gtccacctac atgctgacaa atagtgagct gctgtcactg    780

attaacgaca tgcctatcac caatgatcag aagaaactga tgtccaacaa tgtgcagatc    840

gtcagacagc agagttactc aatcatgtgc atcattaagg aggaagtcct ggcctacgtg    900

gtccagctgc cactgtatgg cgtgatcgac accccctgct ggaaactgca tacatctcct    960

ctgtgcacta ccaacacaaa ggaaggaagt aatatctgcc tgactcgaac cgaccgggga   1020

tggtactgtg ataacgcagg cagcgtgtcc ttctttccac aggccgagac ctgcaaggtc   1080

cagagcaaca gggtgttctg tgacactatg aatagcctga ccctgccttc cgaagtcaac   1140

ctgtgcaatg tggacatctt taatccaaag tacgattgta agatcatgac tagcaagacc   1200

gatgtcagct cctctgtgat tacttctctg gggggccatcg tgagttgcta cggaaagaca  1260

aaatgtactg ccagcaacaa aaatcgcggc atcattaaga ccttctccaa cgggtgcgac   1320

tatgtctcta acaagggcgt ggatacagtg agtgtcggga acactctgta ctatgtcaat   1380

aagcaggagg gaaaaagcct gtacgtgaag ggcgaaccca tcattaactt ctatgacccc   1440

ctggtgttcc cttccgacga gtttgatgca tctattagtc aggtgaacga aaaaatcaat   1500

cagagtctgg cctttattcg gaagtcagat gagctgctgc acaacgtgaa tgctggcaaa   1560

tctacaacta acatcatgat caccacaatc atcatcgtga ttatcgtcat tctgctgtca   1620

ctgatcgctg tggggctgct gctgtactgt cgagtgcgga gactgctggt catgattaac   1680

agcacccaca attcccccgt caacgcctac acactggagt ctaggatgcg caatccttat   1740

atggggaaca atagcaactg atag                                          1764
```

<210> SEQ ID NO 135
<211> LENGTH: 588
<212> TYPE: PRT
<213> ORGANISM: Artificial sequence
<220> FEATURE:
<223> OTHER INFORMATION: recombinant RSV F

<400> SEQUENCE: 135

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95
```

```
Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Cys Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Phe Lys Val
            180                 185                 190

Leu Asp Leu Lys Asn Tyr Ile Asp Lys Gln Leu Leu Pro Ile Leu Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Cys Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510
```

-continued

```
Leu His Asn Val Asn Ala Gly Lys Ser Thr Thr Asn Ile Met Ile Thr
        515                 520                 525

Thr Gln Ile Ile Met Ile Ile Ile Val Cys Ile Leu Ile Ile Ile Ile
    530                 535                 540

Cys Gly Ile Leu Tyr Tyr Leu Tyr Arg Val Arg Arg Leu Leu Val Met
545                 550                 555                 560

Ile Asn Ser Thr His Asn Ser Pro Val Asn Ala Tyr Thr Leu Glu Ser
                565                 570                 575

Arg Met Arg Asn Pro Tyr Met Gly Asn Asn Ser Asn
            580                 585
```

<210> SEQ ID NO 136
<211> LENGTH: 1770
<212> TYPE: DNA
<213> ORGANISM: Artificial sequence
<220> FEATURE:
<223> OTHER INFORMATION: recombinant RSV F

<400> SEQUENCE: 136

```
atggaactgc tgatcctgaa agccaacgct attactacta tcctgaccgc cgtgacattt     60

tgcttcgcat ctggacagaa cattactgag gaattctacc agtcaacatg cagcgccgtg    120

tccaaaggat acctgagcgc cctgcggacc ggctggtata catcagtgat tactatcgag    180

ctgtccaaca tcaaggaaaa caaatgtaat gggaccgacg caaaggtgaa actgatcaag    240

caggagctgg ataagtacaa aaatgccgtg acagaactgc agctgctgat gcagtccaca    300

ccagcaacta acaatcgcgc ccggagagag ctgccccggt tcatgaacta taccctgaac    360

aatgctaaga aaaccaatgt gacactgtcc aagaaacgca agaggcgctt cctgggattt    420

ctgctgggcg tggggtctgc catcgctagt ggagtggccg tctgcaaagt cctgcacctg    480

gagggcgaag tgaacaagat caaaagcgcc ctgctgtcca ctaacaaggc agtggtcagt    540

ctgtcaaatg gcgtgtccgt cctgaccttc aaggtgctgg acctgaaaaa ttatattgat    600

aagcagctgc tgcctatcct gaacaaacag agctgctcca tttctaatat cgagacagtg    660

atcgaattcc agcagaagaa caatagactg ctggagatta ccagagagtt cagcgtgaac    720

gccggcgtca ccacacccgt gtccacctac atgctgacaa atagtgagct gctgtcactg    780

attaacgaca tgcctatcac caatgatcag aagaaactga tgtccaacaa tgtgcagatc    840

gtcagacagc agagttactc aatcatgtgc atcattaagg aggaagtcct ggcctacgtg    900

gtccagctgc cactgtatgg cgtgatcgac accccctgct ggaaactgca tacatctcct    960

ctgtgcacta ccaacacaaa ggaaggaagt aatatctgcc tgactcgaac cgaccgggga   1020

tggtactgtg ataacgcagg cagcgtgtcc ttctttccac aggccgagac ctgcaaggtc   1080

cagagcaaca gggtgttctg tgacactatg aatagcctga ccctgccttc cgaagtcaac   1140

ctgtgcaatg tggacatctt taatccaaag tacgattgta agatcatgac tagcaagacc   1200

gatgtcagct cctctgtgat tacttctctg gggggccatcg tgagttgcta cggaaagaca   1260

aaatgtactg ccagcaacaa aaatcgcggc atcattaaga ccttctccaa cgggtgcgac   1320

tatgtctcta acaagggcgt ggatacagtg agtgtcggga acactctgta ctatgtcaat   1380

aagcaggagg gaaaaagcct gtacgtgaag ggcgaaccca tcattaactt ctatgacccc   1440

ctggtgttcc cttccgacga gtttgatgca tctattagtc aggtgaacga aaaaatcaat   1500

cagagtctgg cctttattcg gaagtcagat gagctgctgc acaacgtgaa tgctggcaaa   1560

tctacaacta acatcatgat caccacacag atcattatga tcattatcgt gtgcattctg   1620
```

-continued attatcatta tctgtggcat cctgtactat ctgtaccgag tgcggagact gctggtcatg 1680
attaacagca cccacaattc ccccgtcaac gcctacacac tggagtctag gatgcgcaat 1740
ccttatatgg ggaacaatag caactgatag 1770

<210> SEQ ID NO 137
<211> LENGTH: 1731
<212> TYPE: DNA
<213> ORGANISM: Artificial sequence
<220> FEATURE:
<223> OTHER INFORMATION: recombinant RSV F

<400> SEQUENCE: 137
atggaactgc tgatcctgaa agccaacgct attactacta tcctgaccgc cgtgacattt 60
tgcttcgcat ctggacagaa cattactgag gaattctacc agtcaacatg cagcgccgtg 120
tccaaaggat acctgagcgc cctgcggacc ggctggtata catcagtgat tactatcgag 180
ctgtccaaca tcaaggaaaa caaatgtaat gggaccgacg caaaggtgaa actgatcaag 240
caggagctgg ataagtacaa aaatgccgtg acagaactgc agctgctgat gcagtccaca 300
ccagcaacta acaatcgcgc ccggagagag ctgccccggt tcatgaacta taccctgaac 360
aatgctaaga aaaccaatgt gacactgtcc aagaaacgca agaggcgctt cctgggattt 420
ctgctgggcg tggggtctgc catcgctagt ggagtggccg tctgcaaagt cctgcacctg 480
gagggcgaag tgaacaagat caaaagcgcc ctgctgtcca ctaacaaggc agtggtcagt 540
ctgtcaaatg gcgtgtccgt cctgacctcc aaggtgctgg acctgaaaaa ttatattgat 600
aagcagctgc tgcctatcgt caacaaacag agctgctcca tttctaatat cgagacagtg 660
atcgaattcc agcagaagaa caatagactg ctggagatta ccagagagtt cagcgtgaac 720
gccggcgtca ccacacccgt gtccacctac atgctgacaa atagtgagct gctgtcactg 780
attaacgaca tgcctatcac caatgatcag aagaaactga tgtccaacaa tgtgcagatc 840
gtcagacagc agagttactc aatcatgtgc atcattaagg aggaagtcct ggcctacgtg 900
gtccagctgc cactgtatgg cgtgatcgac accccctgct ggaaactgca tacatctcct 960
ctgtgcacta ccaacacaaa ggaaggaagt aatatctgcc tgactcgaac cgaccgggga 1020
tggtactgtg ataacgcagg cagcgtgtcc ttctttccac aggccgagac ctgcaaggtc 1080
cagagcaaca gggtgttctg tgacactatg aatagcctga ccctgccttc cgaagtcaac 1140
ctgtgcaatg tggacatctt taatccaaag tacgattgta agatcatgac tagcaagacc 1200
gatgtcagct cctctgtgat tacttctctg gggggccatcg tgagttgcta cggaaagaca 1260
aaatgtactg ccagcaacaa aaatcgcggc atcattaaga ccttctccaa cgggtgcgac 1320
tatgtctcta acaagggcgt ggatacagtg agtgtcggga acactctgta ctatgtcaat 1380
aagcaggagg gaaaaagcct gtacgtgaag ggcgaaccca tcattaactt ctatgacccc 1440
ctggtgttcc cttccgacga gtttgatgca tctattagtc aggtgaacga aaaaatcaat 1500
cagagtctgg cctttattcg gaagtcagat gagctgctgc acaacgtgaa tgctggcaaa 1560
tctacaacta acatcatgat caccacaatc accatcatta tcgtgatgat tatcattctg 1620
gtcatcatta acatcacaat cattgtggtc atcattaagt tccaccggat tcagggcaag 1680
gaccagaacg ataaaaatag cgagccctac atcctgacca atagacagtg a 1731

<210> SEQ ID NO 138
<211> LENGTH: 15
<212> TYPE: DNA
<213> ORGANISM: Human parainfluenza virus 1

<400> SEQUENCE: 138
agggttaaag taata 15

<210> SEQ ID NO 139
<211> LENGTH: 21
<212> TYPE: DNA
<213> ORGANISM: Human parainfluenza virus 1

<400> SEQUENCE: 139
taaatacgcg tcccgggaac a 21

<210> SEQ ID NO 140
<211> LENGTH: 38
<212> TYPE: DNA
<213> ORGANISM: Human parainfluenza virus 1

<400> SEQUENCE: 140
aaagtaagaa aaacttaggg tgaatgcgta cgacgcgt 38

<210> SEQ ID NO 141
<211> LENGTH: 14
<212> TYPE: DNA
<213> ORGANISM: Human parainfluenza virus 1

<400> SEQUENCE: 141
agggtgaatg acaa 14

<210> SEQ ID NO 142
<211> LENGTH: 21
<212> TYPE: DNA
<213> ORGANISM: Human parainfluenza virus 1

<400> SEQUENCE: 142
cagggcgcgc ccccgggaac a 21

<210> SEQ ID NO 143
<211> LENGTH: 44
<212> TYPE: DNA
<213> ORGANISM: Human parainfluenza virus 1

<400> SEQUENCE: 143
aatcaagtaa gaaaaactta gggtgaatgg cgtacgggcg cgcc 44

<210> SEQ ID NO 144
<211> LENGTH: 42
<212> TYPE: DNA
<213> ORGANISM: Human parainfluenza virus 1

<400> SEQUENCE: 144
gcggccgccc gggaagtaag aaaaacttag ggtgaatgaa ca 42

<210> SEQ ID NO 145
<211> LENGTH: 31
<212> TYPE: DNA
<213> ORGANISM: Human parainfluenza virus 1

<400> SEQUENCE: 145
cgtacggcgg ccgcaaaaca attaagaaaa a 31

<210> SEQ ID NO 146
<211> LENGTH: 15
<212> TYPE: DNA

<213> ORGANISM: Human parainfluenza virus 1

<400> SEQUENCE: 146
acgcgtgccg ccacc 15

<210> SEQ ID NO 147
<211> LENGTH: 37
<212> TYPE: DNA
<213> ORGANISM: Human parainfluenza virus 1

<400> SEQUENCE: 147
aaaagtaaga aaaacttagg gtgaatgacg cgtaatg 37

<210> SEQ ID NO 148
<211> LENGTH: 64
<212> TYPE: DNA
<213> ORGANISM: Human parainfluenza virus 3

<400> SEQUENCE: 148
cttaggatta aagacattga ctagaaggtc aagaaaaggg aactctataa tttcaaaaat 60
gttg 64

<210> SEQ ID NO 149
<211> LENGTH: 20
<212> TYPE: DNA
<213> ORGANISM: Human parainfluenza virus 3

<400> SEQUENCE: 149
gcttagcgcc gccaccatgg 20

<210> SEQ ID NO 150
<211> LENGTH: 49
<212> TYPE: DNA
<213> ORGANISM: Human parainfluenza virus 3

<400> SEQUENCE: 150
tgatagataa taaataagaa aaacttagga ttaaagaagc ttagcaatg 49

<210> SEQ ID NO 151
<211> LENGTH: 63
<212> TYPE: PRT
<213> ORGANISM: Bovine parainfluenza virus 3

<400> SEQUENCE: 151

Asn Gln Lys Leu Asp Ser Val Gly Ser Trp Tyr Gln Ser Ser Ala Thr
1 5 10 15

Ile Thr Ile Ile Ile Val Met Ile Ile Ile Leu Val Ile Ile Asn Ile
20 25 30

Thr Ile Ile Val Val Ile Ile Lys Phe His Arg Ile Gln Gly Lys Asp
35 40 45

Gln Asn Asp Lys Asn Ser Glu Pro Tyr Ile Leu Thr Asn Arg Gln
50 55 60

<210> SEQ ID NO 152
<211> LENGTH: 79
<212> TYPE: PRT
<213> ORGANISM: Human parainfluenza virus 1

<400> SEQUENCE: 152

Leu Met Lys Ala Arg Ala Ile Ile Ser Ala Val Gly Gly Trp His Asn
1 5 10 15

-continued

```
Thr Glu Ser Thr Gln Ile Ile Met Ile Ile Ile Val Cys Ile Leu Ile
            20                  25                  30

Ile Ile Ile Cys Gly Ile Leu Tyr Tyr Leu Tyr Arg Val Arg Arg Leu
        35                  40                  45

Leu Val Met Ile Asn Ser Thr His Asn Ser Pro Val Asn Ala Tyr Thr
    50                  55                  60

Leu Glu Ser Arg Met Arg Asn Pro Tyr Met Gly Asn Asn Ser Asn
65                  70                  75


<210> SEQ ID NO 153
<211> LENGTH: 66
<212> TYPE: PRT
<213> ORGANISM: Human parainfluenza virus 3

<400> SEQUENCE: 153

Ile Arg Arg Ser Asn Gln Lys Leu Asp Ser Ile Gly Asn Trp His Gln
1               5                   10                  15

Ser Ser Thr Thr Ile Ile Ile Ile Leu Ile Met Ile Ile Ile Leu Phe
            20                  25                  30

Ile Ile Asn Ile Thr Ile Ile Thr Ile Ala Ile Lys Tyr Tyr Arg Ile
        35                  40                  45

Gln Lys Arg Asn Arg Val Asp Gln Asn Asp Lys Pro Tyr Val Leu Thr
    50                  55                  60

Asn Lys
65
```